United States Patent
Takahashi et al.

(10) Patent No.: US 12,262,634 B2
(45) Date of Patent: *Mar. 25, 2025

(54) ORGANIC ELECTROLUMINESCENCE DEVICE AND NOVEL COMPOUND

(71) Applicant: IDEMITSU KOSAN CO., LTD., Tokyo (JP)

(72) Inventors: Ryota Takahashi, Sodegaura (JP); Hidetsugu Ikeda, Sodegaura (JP); Keita Seda, Sodegaura (JP); Yuki Nakano, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 135 days.

This patent is subject to a terminal disclaimer.

(21) Appl. No.: 18/079,612

(22) Filed: Dec. 12, 2022

(65) Prior Publication Data

US 2023/0128708 A1    Apr. 27, 2023

Related U.S. Application Data

(63) Continuation of application No. 16/345,213, filed as application No. PCT/JP2018/044792 on Dec. 5, 2018, (Continued)

(30) Foreign Application Priority Data

Dec. 6, 2017  (JP) ................................. 2017-234331
Jun. 15, 2018  (JP) ................................. 2018-114580

(51) Int. Cl.
*H10K 85/60*   (2023.01)
*C07D 487/22*   (2006.01)
(Continued)

(52) U.S. Cl.
CPC ......... *H10K 85/636* (2023.02); *C07D 487/22* (2013.01); *C07D 491/22* (2013.01);
(Continued)

(58) Field of Classification Search
None
See application file for complete search history.

(56) References Cited

U.S. PATENT DOCUMENTS 5,843,607 A    12/1998   Hu et al.
5,942,340 A    8/1999    Hu et al.
(Continued)

FOREIGN PATENT DOCUMENTS

CN    103664950 A    3/2014
CN    104119347 A    10/2014
(Continued)

OTHER PUBLICATIONS

Brigitte Wex et al., "Perspective on carbazole-based organic compounds as emitters and hosts in TADF applications", J. Mater. Chem. C, 2017, 5, 8622-8653.
(Continued)

*Primary Examiner* — Vu A Nguyen
(74) *Attorney, Agent, or Firm* — Foley & Lardner LLP

(57) ABSTRACT

An organic electroluminescence device comprising:
a cathode,
an anode, and
at least one organic layer disposed between the cathode and the anode, wherein
at least one layer of the at least one organic layer comprises a compound represented by the following formulas (1-1) and (1-3) or a compound represented by the following formulas (1-2) and (1-3).
(Continued)

(1-1)

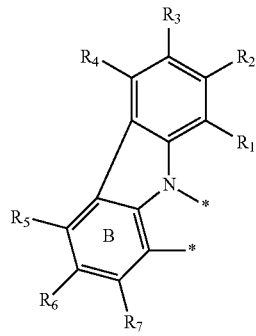

(1-2)

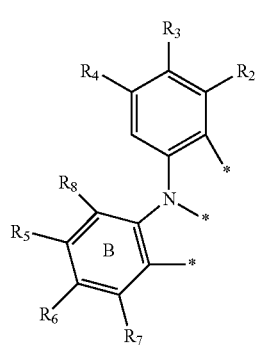

(1-3)

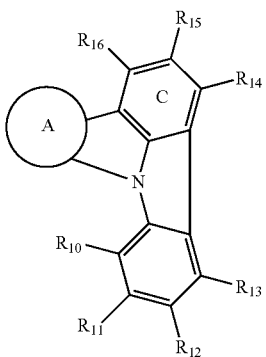

13 Claims, 1 Drawing Sheet

Related U.S. Application Data now Pat. No. 11,569,449, which is a continuation of application No. 16/201,984, filed on Nov. 27, 2018, now Pat. No. 10,672,989, and a continuation of application No. 16/043,074, filed on Jul. 23, 2018, now Pat. No. 10,249,832.

(51) Int. Cl.
| | | |
|---|---|---|
| *C07D 491/22* | (2006.01) | |
| *C09K 11/06* | (2006.01) | |
| *H10K 50/11* | (2023.01) | |
| *H10K 50/15* | (2023.01) | |
| *H10K 50/16* | (2023.01) | |
| *H10K 50/17* | (2023.01) | |
| *H10K 50/81* | (2023.01) | |
| *H10K 50/82* | (2023.01) | |
| *H10K 71/00* | (2023.01) | |
| *H10K 71/16* | (2023.01) | |
| *H10K 101/10* | (2023.01) | |
| *H10K 102/00* | (2023.01) | |
| *H10K 102/10* | (2023.01) | |

(52) U.S. Cl.
CPC .............. *C09K 11/06* (2013.01); *H10K 50/11* (2023.02); *H10K 85/615* (2023.02); *H10K 85/626* (2023.02); *H10K 85/633* (2023.02); *H10K 85/6572* (2023.02); *H10K 85/6574* (2023.02); *H10K 85/6576* (2023.02); *C09K 2211/1007* (2013.01); *C09K 2211/1018* (2013.01); *H10K 50/15* (2023.02); *H10K 50/16* (2023.02); *H10K 50/17* (2023.02); *H10K 50/171* (2023.02); *H10K 50/81* (2023.02); *H10K 50/82* (2023.02); *H10K 71/00* (2023.02); *H10K 71/164* (2023.02); *H10K 2101/10* (2023.02); *H10K 2102/00* (2023.02); *H10K 2102/103* (2023.02); *H10K 2102/351* (2023.02)

(56) References Cited

U.S. PATENT DOCUMENTS

| | | |
|---|---|---|
| 6,337,404 B1 | 1/2002 | Han et al. |
| 6,562,982 B1 | 5/2003 | Hu et al. |
| 6,649,772 B2 | 11/2003 | Lin et al. |
| 6,670,054 B1 | 12/2003 | Hu et al. |
| 7,227,027 B2 | 6/2007 | Qiu et al. |
| 8,227,801 B2 | 7/2012 | Xia et al. |
| 8,343,637 B2 | 1/2013 | Parham et al. |
| 8,405,070 B2 | 3/2013 | Iwaki et al. |
| 9,233,922 B2 | 1/2016 | Nakayama et al. |
| 9,530,969 B2 | 12/2016 | Mizuki et al. |
| 9,825,239 B2 | 11/2017 | Matsuki et al. |
| 10,177,316 B2 | 1/2019 | Zeng et al. |
| 10,249,832 B1 | 4/2019 | Takahashi et al. |
| 10,593,889 B1 | 3/2020 | Takahashi et al. |
| 2008/0220285 A1 | 9/2008 | Vestweber et al. |
| 2009/0036689 A1 | 2/2009 | Wu et al. |
| 2009/0066235 A1 | 3/2009 | Yabunouchi et al. |
| 2010/0051928 A1 | 3/2010 | Fukuzaki |
| 2011/0062429 A1 | 3/2011 | Kai et al. |
| 2012/0157689 A1 | 6/2012 | Wu et al. |
| 2012/0202997 A1 | 8/2012 | Parham et al. |
| 2012/0232241 A1 | 9/2012 | Stoessel et al. |
| 2012/0241732 A1 | 9/2012 | Endo et al. |
| 2012/0273764 A1 | 11/2012 | Yu et al. |
| 2012/0319052 A1 | 12/2012 | Brocke et al. |
| 2012/0326141 A1 | 12/2012 | Pflumm et al. |
| 2013/0026422 A1 | 1/2013 | Parham et al. |
| 2013/0112952 A1 | 5/2013 | Adamovich et al. |
| 2013/0168663 A1 | 7/2013 | Gerhard et al. |
| 2013/0248849 A1 | 9/2013 | Feldman et al. |
| 2013/0320839 A1 | 12/2013 | Watanabe |
| 2014/0299856 A1 | 10/2014 | Kitamura et al. |
| 2014/0319507 A1 | 10/2014 | Yamamoto et al. |
| 2014/0374711 A1 | 12/2014 | Cho et al. |
| 2015/0295184 A1 | 10/2015 | Kaiser et al. |
| 2015/0295186 A1 | 10/2015 | Parham et al. |
| 2015/0325798 A1 | 11/2015 | Cho et al. |
| 2015/0357579 A1 | 12/2015 | Itoi et al. |
| 2016/0126471 A1 | 5/2016 | Lui et al. |
| 2016/0181542 A1 | 6/2016 | Kawamura et al. |
| 2016/0233435 A1 | 8/2016 | Zeng et al. |
| 2016/0268516 A1 | 9/2016 | Tanaka et al. |
| 2017/0117485 A1 | 4/2017 | Cho et al. |
| 2017/0117486 A1 | 4/2017 | Cho et al. |
| 2017/0125697 A1 | 5/2017 | Cho et al. |
| 2017/0179406 A1 | 6/2017 | Kang et al. |
| 2017/0183360 A1 | 6/2017 | Ishii et al. |
| 2017/0186964 A1 | 6/2017 | Cho et al. |
| 2017/0186978 A1 | 6/2017 | Kim et al. |
| 2017/0194569 A1 | 7/2017 | Kim et al. |
| 2017/0213984 A1 | 7/2017 | Kim et al. |

(56) References Cited

U.S. PATENT DOCUMENTS

| | | |
|---|---|---|
| 2017/0294613 A1 | 10/2017 | Cho et al. |
| 2017/0324045 A1 | 11/2017 | Takahashi et al. |
| 2018/0083201 A1 | 3/2018 | Ogawa et al. |
| 2018/0114924 A1 | 4/2018 | Lee et al. |
| 2018/0179206 A1 | 6/2018 | Haketa et al. |
| 2018/0182974 A1 | 6/2018 | Haketa et al. |
| 2018/0198076 A1 | 7/2018 | Takahashi et al. |
| 2018/0240981 A1 | 8/2018 | Cho et al. |
| 2018/0269402 A1 | 9/2018 | Huh et al. |
| 2018/0287070 A1 | 10/2018 | Ji et al. |
| 2018/0315930 A1 | 11/2018 | Han et al. |
| 2018/0337345 A1 | 11/2018 | Li et al. |
| 2019/0055222 A1 | 2/2019 | Han et al. |
| 2019/0074446 A1 | 3/2019 | Xia |
| 2019/0097142 A1 | 3/2019 | Takahashi et al. |
| 2019/0148650 A1 | 5/2019 | Kwak et al. |
| 2019/0334098 A1 | 10/2019 | Watanabe |
| 2020/0052225 A1 | 2/2020 | Takahashi et al. |

FOREIGN PATENT DOCUMENTS

| | | |
|---|---|---|
| CN | 105492413 A | 4/2016 |
| CN | 107652295 A | 2/2018 |
| CN | 108026106 A | 5/2018 |
| DE | 19831427 A1 | 1/2000 |
| DE | 102016122122 A1 | 5/2017 |
| EP | 2 182 040 A2 | 5/2010 |
| EP | 2 927 234 A1 | 10/2015 |
| EP | 3 269 720 A1 | 1/2018 |
| JP | 2008227088 A * | 9/2008 |
| JP | 2012-191031 A | 10/2012 |
| JP | 2013-523847 A | 6/2013 |
| JP | 2013-147481 A | 8/2013 |
| JP | 2014-073965 A | 4/2014 |
| JP | 2015-153911 A | 8/2015 |
| JP | 2015-530357 A | 10/2015 |
| JP | 2017-141167 A | 8/2017 |
| JP | 2017-521525 A | 8/2017 |
| JP | 2018-108939 A | 7/2018 |
| KR | 2010-0131745 A | 12/2010 |
| KR | 2011-0016044 A | 2/2011 |
| KR | 2011-0016047 A | 2/2011 |
| KR | 2011-0079402 A | 7/2011 |
| KR | 2011-0111094 A | 10/2011 |
| KR | 2012-0013278 A | 2/2012 |
| KR | 2012-0034140 A | 4/2012 |
| KR | 2012-0130074 A | 11/2012 |
| KR | 2013-0106255 A | 9/2013 |
| KR | 2014-034710 A | 3/2014 |
| KR | 2015-0111271 A | 10/2015 |
| KR | 2015-0135125 A | 12/2015 |
| KR | 2016-0098064 A | 8/2016 |
| KR | 2017-103358 A | 9/2017 |
| KR | 2017-108895 A | 9/2017 |
| KR | 2017-113398 A | 10/2017 |
| KR | 2017-0116983 A | 3/2018 |
| KR | 2018-0078177 A | 7/2018 |
| WO | WO-2010/050778 A1 | 5/2010 |
| WO | WO-2013/077344 A1 | 5/2013 |
| WO | WO-2014/081131 A1 | 5/2014 |
| WO | WO-2015/099507 A1 | 7/2015 |
| WO | WO-2016/006925 A1 | 1/2016 |
| WO | WO-2017/074052 A1 | 5/2017 |
| WO | WO-2017/138755 A1 | 8/2017 |
| WO | WO-2017/142310 A1 | 8/2017 |
| WO | WO-2017/175690 A1 | 10/2017 |
| WO | WO-2018/026197 A1 | 2/2018 |
| WO | WO-2018/038544 A1 | 3/2018 |
| WO | WO-2018/138306 A1 | 8/2018 |
| WO | WO-2018/139662 A1 | 8/2018 |
| WO | WO-2018/151065 A1 | 8/2018 |
| WO | WO-2018/221930 A1 | 12/2018 |
| WO | WO-2019/022512 A1 | 1/2019 |
| WO | WO-2019/098766 A1 | 5/2019 |
| WO | WO-2019/111971 A1 | 6/2019 |

OTHER PUBLICATIONS

International Search Report dated Feb. 19, 2019 in corresponding application No. PCT/JP2018/044792.

J.V. Grazulevicius et al."Carbazole-containing polymers: synthesis, properties and applications", 2003,—Prog. Polym. Sci. 28 1297-1353.

Non-Final Office Action on U.S. Appl. No. 16/290,702 Dtd May 8, 2019.

Notice of Allowance on U.S. Appl. No. 16/043,074 Dtd Oct. 3, 2018.

International Search Report issued in the corresponding Japanese Patent Application Ser. No. PCT/JP2019/023611, dated Aug. 6, 2019.

Niebel, Claude et al., "Dibenzo[2,3:5,6]pyrrolizino[1,7-bc]indolo[1,2,3-lm]carbazole: a new electron donor", New Journal of Chemistry, 2010, vol. 34, pp. 1243-1246.

Database Registry [online] Chemical Abstract Service, US; Nov. 16, 1984 (Nov. 16, 1984), Retrieved from STN, Database accession No. RN: 14458-65-2, 1, 7b, 8, 14b-Tetraazabenz[a]indeno[1,2,4-hi]aceanthrylene [Nov. 21, 2019].

International Search Report dated Dec. 10, 2019 for corresponding Application No. PCT/JP2019/037865.

Moehrle, H., et al., Ring opening reactions of carbinolamine equivalents of the tetrahydro-B-carboline series. I, Archivder Pharmazie (Weinheim, Germany), 1986, 319(11), 1043-9.

Szantay, C. et al., Synthesis of substituted octahydroindolo [2,3-a]-quinolizines. The formation of a new type of ring system, Journal of Organic Chemistry, 1967, 32(2), 423-7.

Tsuge, O., et al., Polyazapentalenes. I. Preparation of 6-dehydroindazolo[1,2-a]benzotriazole, Journal of Heterocyclic Chemistry, 1971, 8(5), 707-10.

European Extended Search Report, dated Jul. 29, 2021, issued in corresponding European Patent Application No. 18886934.1, (7 pages).

International Preliminary Report on Patentability and Written Opinion dated Dec. 24, 2020 for corresponding International Patent Application No. PCT/JP2019/023611.

International Preliminary Report on Patentability and Written Opinion dated Apr. 8, 2021 for corresponding International Patent Application No. PCT/JP2019/037865.

Notice of References Cited in Office Action dated Nov. 16, 2023 in U.S. Appl. No. 17/278,419.

Wang et al., Journal of the Chinese Chemical Society, 1993, 40, 497-502.

Office Action issued in connection with Chinese Appl. No. 201980063600.3 dated Oct. 20, 2023.

* cited by examiner

ORGANIC ELECTROLUMINESCENCE DEVICE AND NOVEL COMPOUND

CROSS-REFERENCE TO RELATED APPLICATIONS

The present application is a Continuation of U.S. patent application Ser. No. 16/345,213, filed on Apr. 25, 2019, which is a U.S. National Stage Application claiming the benefit of International Application No. PCT/JP2018/044792, filed on Dec. 5, 2018, which is a Continuation of U.S. patent application Ser. No. 16/043,074, filed on Jul. 23, 2018 (now U.S. Pat. No. 10,249,832, issued on Apr. 2, 2019), and U.S. patent application Ser. No. 16/201,984, filed on Jul. 23, 2018 (now U.S. Pat. No. 10,672,989, issued on Jun. 2, 2020), which claims the benefit of priority to Japanese Patent Application No. 2018-114580, filed Jun. 15, 2018, and Japanese Patent Application No. 2017-234331, filed Dec. 6, 2017, the disclosures of which are hereby incorporated by reference.

TECHNICAL FIELD

The invention relates to an organic electroluminescence device and a novel compound.

BACKGROUND ART

When a voltage is applied to an organic electroluminescence device (hereinafter may be referred to as an organic EL device), holes are injected to an emitting layer from an anode and electrons are injected to an emitting layer from a cathode. In the emitting layer, injected holes and electrons are re-combined and excitons are formed.

An organic EL device comprises an emitting layer between the anode and the cathode. Further, there may be a case where it has a stacked layer structure comprising an organic layer such as a hole-injecting layer, a hole-transporting layer, an electron-injecting layer, an electron-transporting layer, etc.

Patent Documents 1 to 3 disclose a compound used as a material for an organic electroluminescence device.

RELATED ART DOCUMENTS

Patent Documents

Patent Document 1: WO2013/077344
Patent Document 2: U.S. Pat. No. 5,843,607
Patent Document 3: WO2017/175690

SUMMARY OF THE INVENTION

An object of the invention is to provide an organic electroluminescence device having a high luminous efficiency and a novel compound that can be used as a material for an organic electroluminescence device having a high luminous efficiency.

According to one aspect of the invention, an organic electroluminescence device comprising:
a cathode,
an anode, and
at least one organic layer disposed between the cathode and the anode, wherein
at least one layer of the at least one organic layer comprises a compound represented by the following formulas (1-1) and (1-3), or a compound represented by the following formulas (1-2) and (1-3):

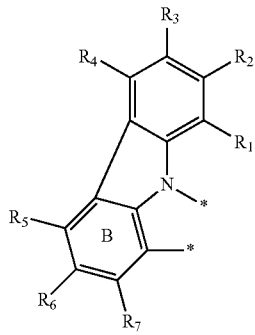

(1-1)

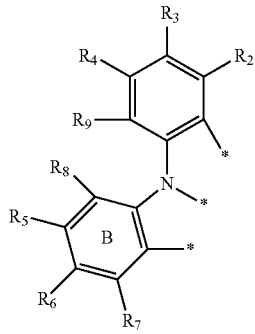

(1-2)

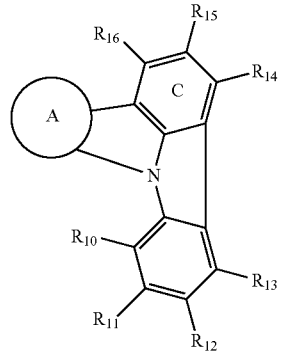

(1-3)

wherein in the formulas (1-1), (1-2) and (1-3),
ring A is a substituted or unsubstituted fused aryl ring including 10 to 50 ring carbon atoms, a substituted or unsubstituted fused heterocyclic ring including 8 to 50 ring atoms or a benzene ring represented by the following formula (2);
two atomic bondings * in the formula (1-1) are respectively bonded with a ring carbon atom of the fused aryl ring of the ring A, a ring atom of the fused heterocyclic ring of the ring A, or a ring carbon atom of the benzene ring represented by the formula (2) of the ring A;
three atomic bondings * in the formula (1-2) are respectively bonded with a ring carbon atom of the fused aryl ring of the ring A, a ring atom of the fused heterocyclic ring of the ring A, or a ring carbon atom of the benzene ring represented by the formula (2) of the ring A;
one or more pairs of adjacent two or more of $R_1$ to $R_{16}$ may form a substituted or unsubstituted, saturated or unsaturated ring;
$R_1$ to $R_{16}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms; and when each of $R_{31}$ to $R_{37}$ is present in plural, each of the plural $R_{31}$s to $R_{37}$s may be the same or different;

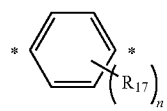

(2)

wherein in the formula (2), at one of the two ring carbon atoms indicated by * the atomic bonding extending from the benzene ring B in the formula (1-1) or the formula (1-2) is bonded, and at the other of the two ring carbon atoms indicated by *, the atomic bonding extending from the benzene ring C in the formula (1-3) is bonded;

$R_{17}$ is a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms;

when each of $R_{31}$ to $R_{37}$ is present in plural, each of the plural $R_{31}$s to $R_{37}$s may be the same or different; and n is an integer of 1 or 2, and when n is 2, two $R_{17}$s may be the same or different.

According to one aspect of the invention, an electronic apparatus provided with the organic electroluminescence device is provided.

According to one aspect of the invention, a compound represented by the following formulas (1-1) and (1-3), or a compound represented by the following formulas (1-2) and (1-3) is provided:

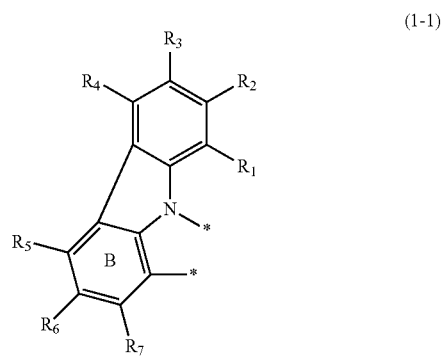

(1-1)

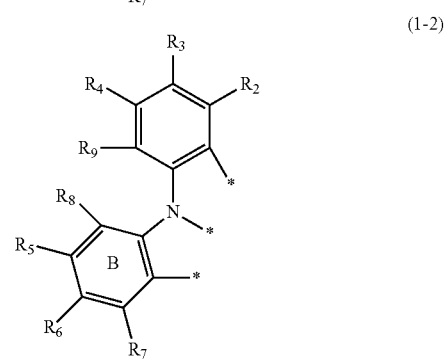

(1-2)

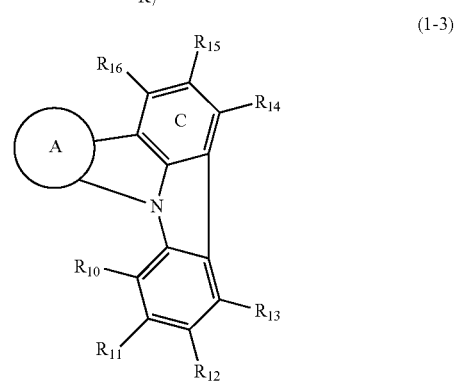

(1-3)

wherein in the formulas (1-1), (1-2) and (1-3),
ring A is a substituted or unsubstituted fused aryl ring including 10 to 50 ring carbon atoms, a substituted or unsubstituted fused heterocyclic ring including 8 to 50 ring atoms or a benzene ring represented by the following formula (2);

two atomic bondings * in the formula (1-1) are respectively bonded with a ring carbon atom of the fused aryl ring of the ring A, a ring atom of the fused heterocyclic ring of the ring A, or a ring carbon atom of the benzene ring represented by the formula (2) of the ring A;

three atomic bondings * in the formula (1-2) are respectively bonded with a ring carbon atom of the fused aryl ring of the ring A, a ring atom of the fused heterocyclic ring of the ring A, or a ring carbon atom of the benzene ring represented by the formula (2) of the ring A;

one or more pairs of adjacent two or more of $R_1$ to $R_{16}$ may form a substituted or unsubstituted, saturated or unsaturated ring;

$R_1$ to $R_{16}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si$(R_{31})(R_{32})(R_{33})$, —C(=O)$R_{34}$, —COO$R_{35}$, —N$(R_{36})(R_{37})$, a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms;

when each of $R_{31}$ to $R_{37}$ is present in plural, each of the plural $R_{31}$s to $R_{37}$s may be the same or different; and when the ring A is a benzene ring represented by the formula (2), at least one of $R_1$ to $R_{17}$ is a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms; or at least one pair of adjacent two or more of $R_1$ to $R_{16}$ forms a substituted or unsubstituted, saturated or unsaturated ring;

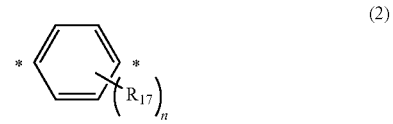

wherein in the formula (2), at one of the two ring carbon atoms indicated by * the atomic bonding extending from the benzene ring B in the formula (1-1) or the formula (1-2) is bonded, and at the other of the two ring carbon atoms indicated by *, the atomic bonding extending from the benzene ring C in the formula (1-3) is bonded;

$R_{17}$ is a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si$(R_{31})(R_{32})(R_{33})$, —C(=O)$R_{34}$, —COO$R_{35}$, —N$(R_{36})(R_{37})$, a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms;

when each of $R_{31}$ to $R_{37}$ is present in plural, each of the plural $R_{31}$s to $R_{37}$s may be the same or different; and n is an integer of 1 or 2, and when n is 2, two $R_{17}$s may be the same or different.

MODE FOR CARRYING OUT THE INVENTION

Figure 1:
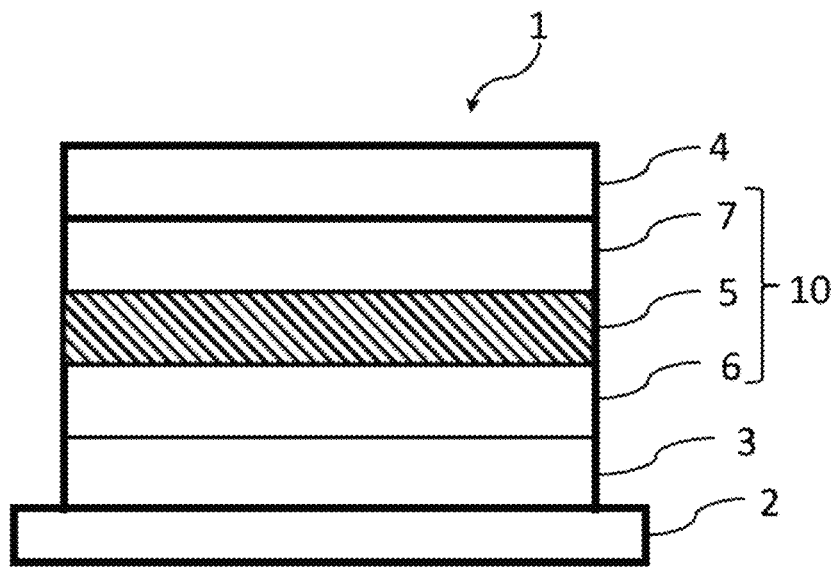
FIG. 1 is a view showing a schematic configuration of one embodiment of the organic EL device of the invention.

In the present specification, a hydrogen atom includes isomers differing in number of neutrons, i.e. protium, deuterium and tritium.

In the present specification, the number of "ring carbon atoms" means the number of carbon atoms among atoms constituting a ring itself of a compound in which atoms are bonded in the form of a ring (for example, a monocyclic compound, a fused ring compound, a cross-linked compound, a carbocyclic compound or a heterocyclic compound). When the ring is substituted by a substituent, the carbon contained in the substituent is not included in the number of ring carbon atoms. The same is applied to the "ring carbon atoms" mentioned below, unless otherwise indicated. For example, a benzene ring includes 6 ring carbon atoms, a naphthalene ring includes 10 ring carbon atoms, a pyridinyl group includes 5 ring carbon atoms, and a furanyl group includes 4 ring carbon atoms. When a benzene ring or a naphthalene ring is substituted by an alkyl group as a substituent, for example, the number of carbon atoms of the alkyl group is not included in the number of ring carbon atoms. When a fluorene ring is bonded with a fluorene ring as a substituent (including a spirofluorene ring), for example, the number of carbon atoms of the fluorene ring as the substituent is not included in the number of ring carbon atoms.

In the present specification, the number of "ring atoms" means the number of atoms constituting a ring itself of a compound having a structure in which atoms are bonded in the form of a ring (for example, monocycle, fused ring, ring assembly) (for example, a monocyclic compound, a fused ring compound, a cross-linked compound, a carbocyclic compound or a heterocyclic compound). It does not include atoms which do not form a ring (for example, a hydrogen atom which terminates the atomic bonding constituting a ring) or atoms contained in a substituent when the ring is substituted by the substituent. The same is applied to the "ring atoms" mentioned below, unless otherwise indicated. For example, a pyridine ring includes 6 ring atoms, a quinazoline ring includes 10 ring atoms, and a furan ring includes 5 ring atoms. Hydrogen atoms respectively bonded with a carbon atom of a pyridine ring or a quinazoline ring or atoms constituting a substituent are not included in the number of ring atoms. When a fluorene ring is bonded with a fluorene ring as a substituent (including a spirofluorene ring), for example, the number of atoms of the fluorene ring as a substituent is not included in the number of ring atoms.

In the present specification, the "XX to YY carbon atoms" in the "substituted or unsubstituted ZZ group including XX to YY carbon atoms" means the number of carbon atoms when the ZZ group is unsubstituted. The number of carbon atoms of a substituent when the group is substituted is not included. Here, "YY" is larger than "XX", and "XX" and "YY" independently mean an integer of 1 or more.

In the present specification, the "XX to YY atoms" in the "substituted or unsubstituted ZZ group including XX to YY atoms" means the number of atoms when the ZZ group is unsubstituted. The number of atoms of a substituent when the group is substituted is not included. Here, "YY" is larger than "XX", and "XX" and "YY" independently mean an integer of 1 or more.

In the present specification, the "unsubstituted" in the "substituted or unsubstituted" means bonding of a hydrogen atom, not substitution by the substituent mentioned above.

As specific examples of each substituent in the present specification, the following can be given.

As the unsubstituted alkyl group including 1 to 50 (preferably 1 to 30, more preferably 1 to 18, and further preferably 1 to 5) carbon atoms, a methyl group, an ethyl group, a propyl group, an isopropyl group, an n-butyl group, a s-butyl group, an isobutyl group, a t-butyl group, an n-pentyl group, an n-hexyl group, an n-heptyl group, an n-octyl group or the like can be given, for example.

As the substituted alkyl group including 1 to 50 (preferably 1 to 30, more preferably 1 to 18, and further preferably 1 to 5) carbon atoms, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a 1-pyrrolylmethyl group, a 2-(1-pyrrolyl)ethyl group, a 1-hydroxy-2-phenylisopropyl group, a 1-chloro-2-phenyl-isopropyl group or the like can be given.

The substituted or unsubstituted haloalkyl group including 1 to 50 carbon atoms is a group in which one or more of hydrogen atoms of the alkyl group is substituted by a halogen atom. As the substituted or unsubstituted haloalkyl group including 1 to 50 carbon atoms, a group obtained by substituting one or more halogen atoms in the above-mentioned substituted or unsubstituted alkyl group including 1 to 50 carbon atoms can be given.

As the unsubstituted alkenyl group including 2 to 50 (preferably 2 to 30, more preferably 2 to 18) carbon atoms, a vinyl group, an allyl group, a 1-butenyl group, a 2-butenyl group, a 3-butenyl group, a 1,3-butanedienyl group, a 1-methylvinyl group, a 1-methylallyl group, a 1,1-dimethylallyl group, a 2-methylally group, a 1,2-dimethylallyl group or the like can be given.

As the unsubstituted alkynyl group including 2 to 50 (preferably 2 to 30, more preferably 2 to 18) carbon atoms, an ethynyl group or the like can be given.

As the unsubstituted cycloalkyl group including 3 to 50 (preferably 3 to 30, more preferably 3 to 18, and further preferably 3 to 6) ring carbon atoms, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group or the like can be given.

The unsubstituted alkoxy group including 1 to 50 (preferably 1 to 30, more preferably 1 to 18) carbon atoms is represented by —OX. As examples of X, the alkyl group including 1 to 50 carbon atoms mentioned above can be given, for example.

The unsubstituted alkyl group including 1 to 50 (preferably 1 to 30, more preferably 1 to 18) carbon atoms is represented by —SX. As examples of X, the alkyl group including 1 to 50 carbon atoms mentioned above can be given, for example.

As the unsubstituted aryl group including 6 to 50 (preferably 6 to 30, more preferably 6 to 18) ring carbon atoms, a phenyl group, a 1-naphthyl group, a 2-naphthyl group, a 1-anthryl group, a 2-anthryl group, a 9-anthryl group, a 9-phenanthryl group, a 1-phenanthryl group, a 2-phenanthryl group, a 3-phenanthryl group, a 4-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, a fluorenyl group or the like can be given.

Among these, a phenyl group, a naphthyl group, a biphenylyl group, a terphenyl group, a pyrenyl group, a phenanthryl group and a fluorenyl group are preferable. A phenyl group, a naphthyl group, a biphenylyl group, a terphenyl group, a pyrenyl group and a fluorenyl group are more preferable.

As the substituted aryl group including 6 to 50 (preferably 6 to 30, more preferably 6 to 18) ring carbon atoms, an o-tolyl group, a m-tolyl group, a p-tolyl group, a para-isopropylphenyl group, a meta-isopropylphenyl group, an ortho-isopropylphenyl group, a p-t-butylphenyl group, a meta-t-butylphenyl group, an ortho-t-butylphenyl group, a 3,4,5-trimethylphenyl group, a 4-phenoxyphenyl group, a 4-methoxyphenyl group, a 3,4-dimethoxyphenyl group, a 3,4,5-trimethoxyphenyl group, a 4-(phenylsulfanyl) phenyl group, a 4-(methylsulfanyl)phenyl group, a N',N'-dimethyl-N-phenyl group, a, 2,6-dimethylphenyl group, a 2-(phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a 9,9-dimethylfluorenyl group, a 9,9-diphenylfluorenyl group, a 9,9'-spirobifluorenyl group, a 9,9-di(4-methylphenyl)fluorenyl group, a 9,9-di(4-isopropylphenyl)fluorenyl group, a 9,9-di(4-t-butylphenyl)fluorenyl group, a chrysenyl group, a fluoranthenyl group or the like can be given.

As the unsubstituted arylene group including 6 to 50 (preferably 6 to 30, more preferably 6 to 18) ring carbon atoms, a divalent group formed of an aromatic hydrocarbon ring constituting the aryl group including 6 to 50 ring carbon atoms exemplified above can be given.

The unsubstituted aryloxy group including 6 to 50 (preferably 6 to 30, more preferably 6 to 18) ring carbon atoms is represented by —OY As examples of Y, the aryl group including 6 to 50 ring carbon atoms mentioned above can be given.

The unsubstituted arylthio group including 6 to 50 (preferably 6 to 30, more preferably 6 to 18) ring carbon atoms is represented by —SY As examples of Y, the aryl group including 6 to 50 ring carbon atoms mentioned above can be given.

As the unsubstituted aralkyl group including 7 to 50 (preferably 7 to 30, more preferably 7 to 18) carbon atoms, a benzyl group, a 1-phenylethyl group, a 2-phenylethyl group, a 1-phenylisopropyl group, a 2-phenylisopropyl group, a phenyl-t-butyl group, a α-naphthylmethyl group, a 1-α-naphthylethyl group, a 2-α-naphthylethyl group, 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group or the like can be given.

As the substituted aralkyl group including 7 to 50 (preferably 7 to 30, more preferably 7 to 18) carbon atoms, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-nitrobenzyl group, a m-nitrobenzyl group, an o-nitrobenzyl group, a p-cyanobenzyl group, a m-cyanobenzyl group, an o-cyanobenzyl group or the like can be given, for example.

As the unsubstituted monovalent heterocyclic group including 5 to 50 (preferably 5 to 30, more preferably 5 to 18) ring atoms, a pyrrolyl group, a pyrazinyl group, a pyridinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, and a thienyl group or the like, and a monovalent group formed of a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzo[a]dibenzofuran ring, a benzo[b]dibenzofuran ring and benzo[c]dibenzofuran ring, a 1,3-benzodioxole ring, a 2,3-dihydro-1,4-benzodioxine ring, a phenanthro[4,5-bcd] furan ring, a benzophenoxazine ring or the like can be given.

As the hetero atom constituting the heterocyclic group, in addition to a hetero atom such as S, O, N or the like, a hetero atom such as Si, Ge and Se can be given.

As the unsubstituted divalent heterocyclic group including 5 to 50 (preferably 5 to 30, more preferably 5 to 18) ring carbon atoms, a divalent group formed of the above-exemplified groups and the monovalent heterocyclic group or the like can be given.

As the substituted or unsubstituted monovalent heterocyclic group including 5 to 50 ring atoms, the following groups are included. As the divalent heterocyclic group including 5 to 50 ring atoms, groups obtained by forming the following groups into divalent groups are also included.

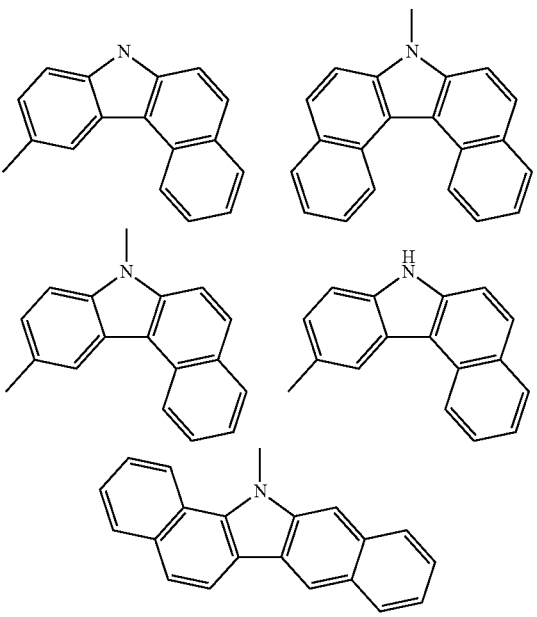

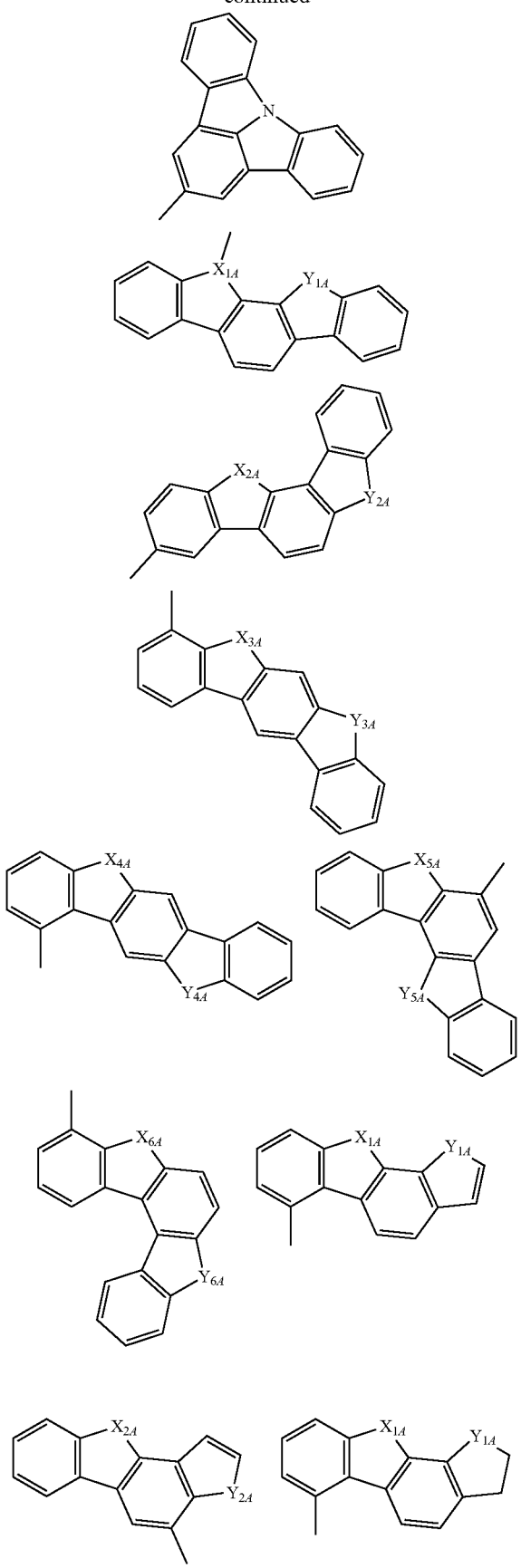
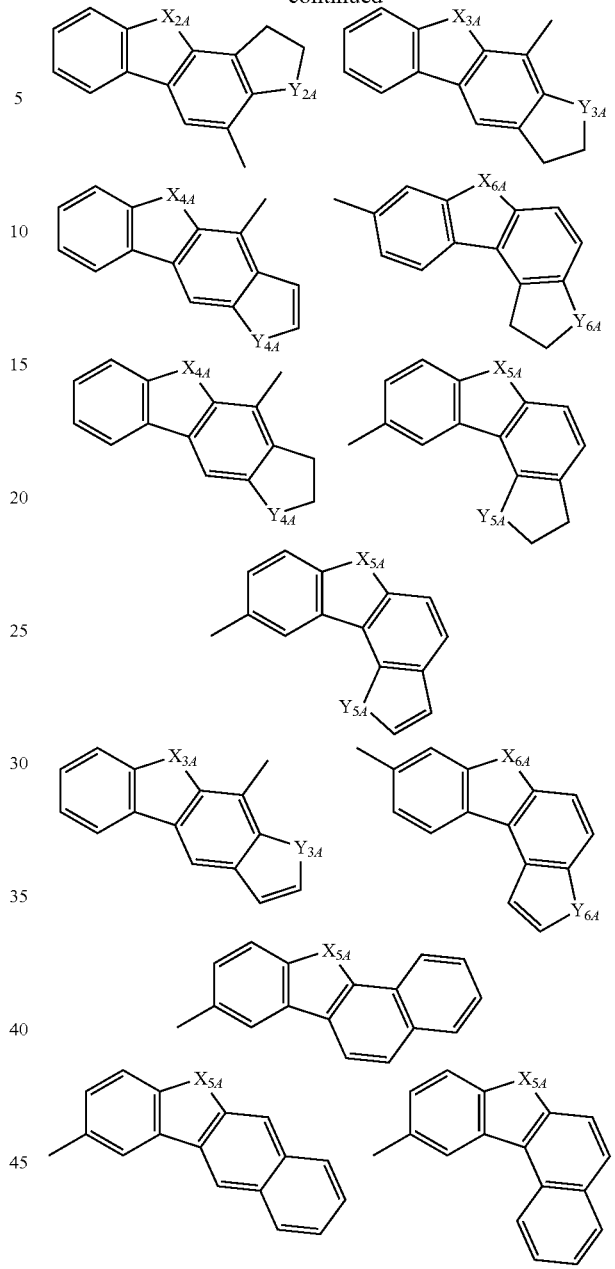

wherein $X_{1A}$ to $X_{6A}$ and $Y_{1A}$ to $Y_{6A}$ are independently an oxygen atom, a sulfur atom, a —NZ— group or a —NH-group. Z is a substituted or unsubstituted aryl group including 6 to 50 ring carbon atoms, a substituted or unsubstituted monovalent heterocyclic group including 5 to 50 ring atoms or a substituted or unsubstituted alkyl group including 1 to 50 carbon atoms. When two or more Zs are present, the two or more Zs may be the same or different.

As the halogen atom, a fluorine atom, a chlorine atom, a bromine atom, an iodine atom or the like can be given.

<Organic Electroluminescence Device>

The organic electroluminescence device according to one aspect of the invention comprises a cathode, an anode and at least one organic layer disposed between the cathode and the anode.

At least one layer of the at least one organic layer comprises the compound represented by the following formulas (1-1) and (1-3), or the compound represented by the following formulas (1-2) and (1-3):

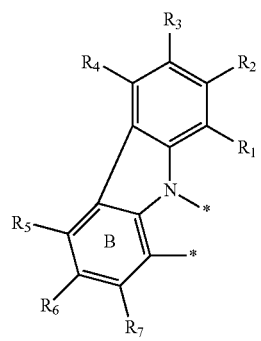

(1-1)

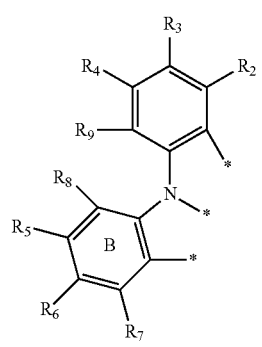

(1-2)

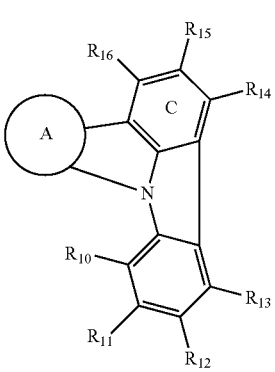

(1-3)

wherein in the formulas (1-1), (1-2) and (1-3),
ring A is a substituted or unsubstituted fused aryl ring including 10 to 50 ring carbon atoms, a substituted or unsubstituted fused heterocyclic ring including 8 to 50 ring atoms or a benzene ring represented by the following formula (2);
two atomic bondings * in the formula (1-1) are respectively bonded with a ring carbon atom of the fused aryl ring of the ring A, a ring atom of the fused heterocyclic ring of the ring A, or a ring carbon atom of the benzene ring represented by the formula (2) of the ring A;
three atomic bondings * in the formula (1-2) are respectively bonded with a ring carbon atom of the fused aryl ring of the ring A, a ring atom of the fused heterocyclic ring of the ring A, or a ring carbon atom of the benzene ring represented by the formula (2) of the ring A;
one or more pairs of adjacent two or more of $R_1$ to $R_{16}$ may form a substituted or unsubstituted, saturated or unsaturated ring;

$R_1$ to $R_{16}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;
$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms; and
when each of $R_{31}$ to $R_{37}$ is present in plural, each of the plural $R_{31}$s to $R_{37}$s may be the same or different;

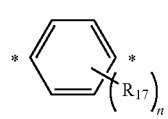

(2)

wherein in the formula (2), at one of the two ring carbon atoms indicated by * the atomic bonding extending from the benzene ring B in the formula (1-1) or the formula (1-2) is bonded, and at the other of the two ring carbon atoms indicated by *, the atomic bonding extending from the benzene ring C in the formula (1-3) is bonded;
$R_{17}$ is a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms;

when each of $R_{31}$ to $R_{37}$ is present in plural, each of the plural $R_{31}$s to $R_{37}$s may be the same or different; and n is an integer of 1 or 2, and when n is 2, two $R_{17}$s may be the same or different.

In the formulas (1-1), (1-2) and (1-3), the fused aryl ring is a ring obtained by fusion of plural aromatic rings. Therefore, biphenyl obtained by bonding of two aromatic rings through a single bond is not included in the fused aryl ring.

In the formulas (1-1), (1-2) and (1-3), the fused heterocyclic ring is a ring obtained by fusion of plural heterocyclic rings or a ring obtained by fusion of a heterocyclic ring and an aromatic ring.

An explanation will be given on "one or more pairs of two or more adjacent groups of $R_1$ to $R_{16}$ may form a substituted or unsubstituted, saturated or unsaturated ring".

The "one or more pairs of two or more adjacent groups of $R_1$ to $R_{16}$" is a combination of $R_1$ and $R_2$, $R_2$ and $R_3$, $R_3$ and $R_4$, $R_5$ and $R_6$, $R_6$ and $R_7$, $R_1$ and $R_2$, $R_3$ or the like, for example.

For the substituent when the "substituted or unsubstituted" saturated or unsaturated ring is "substituted", the same substituents as those for "substituted or unsubstituted" mentioned later can be given.

The "saturated or unsaturated ring" means, when $R_1$ and $R_2$ form a ring, a ring formed by a carbon atom with which $R_1$ is bonded, a carbon atom with which $R_2$ is bonded and one or more arbitrary elements. Specifically, when a ring is formed by $R_1$ and $R_2$, if an unsaturated ring is formed by a carbon atom with which $R_1$ is bonded, a carbon atom with which $R_2$ is bonded and 4 carbon atoms, a ring formed by $R_1$ and $R_2$ is a benzene ring.

The "arbitrary element" is preferably a C element, a N element, an O element and a S element. In an arbitrary element (for example, in the case of a C element or a N element), an atomic bonding that does not form a ring may be terminated with a hydrogen atom or the like.

The "one or more arbitrary elements" is preferably 2 or more and 15 or less, more preferably 3 or more and 12 or less, and further preferably 3 or more and 5 or less arbitrary elements.

Hereinbelow, the "one or more pairs of two or more adjacent groups of X to Y may form a substituted or unsubstituted, saturated or unsaturated ring" has the same meaning as the mentioned above, except that X is changed to $R_1$ and Y is changed to $R_{16}$.

Hereinbelow, an explanation is made on a compound represented by the formulas (1-1) and (1-3), and a compound represented by the formulas (1-2) and (1-3).

The "*" in the formula (1-1) is an atomic bonding that is bonded with the ring A in the formula (1-3). In the formula (1-1), there are two "*"s. The two "*"s are respectively bonded with a ring carbon atom in the fused aryl ring in the ring A, a ring atom in the fused heterocyclic ring, or a ring carbon atom of the benzene ring represented by the formula (2), and form a compound.

The "*" in the formula (1-2) is also an atomic bonding that is bonded with the ring A in the formula (1-3). In the formula (1-2), there are three "*"s. The three "*"s are respectively bonded with a ring carbon atom in the fused aryl ring in the ring A, a ring atom in the fused heterocyclic ring, or a ring carbon atom of the benzene ring represented by the formula (2), and form a compound.

The "*" in the formula (2) indicates a bonding position. At one of the ring carbon atoms indicated by the two *s, an atomic bonding extending from the benzene ring B in the formula (1-1) or (1-2) is bonded, and at the other of ring carbon atoms indicated by the two *s, an atomic bonding extending from the benzene ring C in the formula (1-3) is bonded.

In one embodiment, the compound represented by the formulas (1-1) and (1-3) or the compound represented by the formulas (1-2) and (1-3) are compounds represented by the following formula (3), (4) or (5).

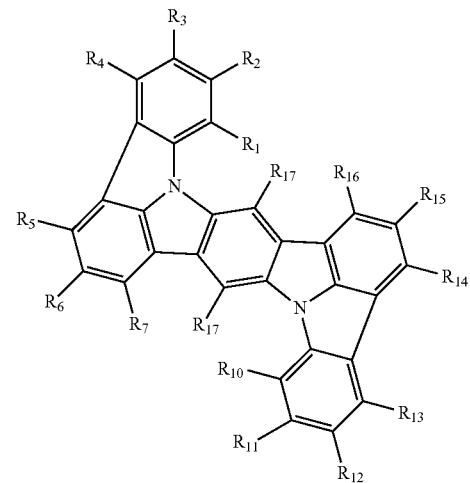

(3)

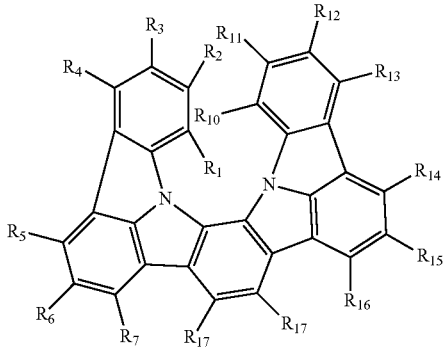

(4)

(5)

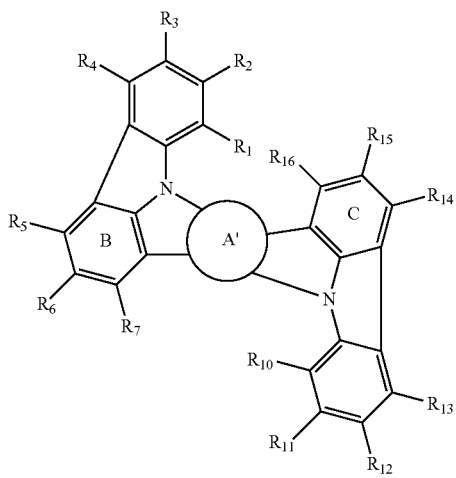

wherein in the formulas (3), (4) and (5),
the ring A' is a substituted or unsubstituted fused aryl ring including 10 to 50 ring carbon atoms or a substituted or unsubstituted fused heterocyclic ring including 8 to 50 ring atoms.

$R_1$ to $R_7$ and $R_{10}$ to $R_{17}$ are as defined in the formulas (1-1), (1-2), (1-3) and (2).

In one embodiment, the substituted or unsubstituted fused aryl ring including 10 to 50 ring carbon atoms in the ring A in the formula (1-3) or the ring A in the formula (5) is a substituted or unsubstituted naphthalene ring or a substituted or unsubstituted fluorene ring.

In one embodiment, the substituted or unsubstituted fused aryl ring including 10 to 50 ring carbon atoms in the ring A in the formula (1-3) or the ring A in the formula (5) may include, for example, 10 to 30, 10 to 20 or 10 to 14 ring carbon atoms. As the fused aryl ring, a substituted or unsubstituted naphthalene ring, a substituted or unsubstituted anthracene ring, or a substituted or unsubstituted fluorene ring can be given.

In one embodiment, the substituted or unsubstituted fused heterocyclic ring including 8 to 50 ring atoms in the ring A in the formula (1-3) or the ring A in the formula (5) is a substituted or unsubstituted dibenzofurane ring, a substituted or unsubstituted carbazole ring or a substituted or unsubstituted dibenzothiophene ring.

In one embodiment, the substituted or unsubstituted fused heterocyclic ring including 8 to 50 ring atoms in the ring A in the formula (1-3) or the ring A in the formula (5) is a substituted or unsubstituted dibenzofuran skeleton-containing structure (such as a substituted or unsubstituted dibenzofuran, a substituted or unsubstituted naphthobenzofuran, a substituted or unsubstituted dinaphthofuran, and the like), or a substituted or unsubstituted dibenzothiophene skeleton-containing structure (such as a substituted or unsubstituted dibenzothiophene, a substituted or unsubstituted naphthobenzothiophene, a substituted or unsubstituted dinaphthothiophene, and the like).

In one embodiment, the substituted or unsubstituted fused heterocyclic ring including 8 to 50 ring atoms in the ring A in the formula (1-3) or the ring A in the formula (5) is a substituted or unsubstituted dibenzofuran ring or a substituted or unsubstituted dibenzothiophene ring.

In one embodiment, the substituted or unsubstituted fused heterocyclic ring including 8 to 50 ring atoms in the ring A in the formula (1-3) or the ring A in the formula (5) is a substituted carbazole skeleton-containing structure (such as a substituted carbazole ring), and the substituent is a substituted or unsubstituted aryl group including 6 to 50 ring carbon atoms or a substituted or unsubstituted monovalent heterocyclic group including 5 to 50 ring atoms. The aryl group or monovalent heterocyclic group of the above substituent is not bonded to the carbazole ring.

In one embodiment, the substituted or unsubstituted fused heterocyclic ring including 8 to 50 ring atoms in the ring A in the formula (1-3) or the ring A in the formula (5) is a substituted carbazole skeleton-containing structure (such as a substituted carbazole ring), and the carbazole skeleton-containing structure has a substituent at 9-position of the carbazole ring, and the substituent is a substituted or unsubstituted aryl group including 6 to 50 ring carbon atoms or a substituted or unsubstituted monovalent heterocyclic group including 5 to 50 ring atoms. When the substituent is an unsubstituted phenyl group, the unsubstituted phenyl group is not bonded to the carbazole skeleton-containing structure.

In one embodiment, in the compound represented by the formula (5), at least one pair of $R_5$ and $R_6$, $R_6$ and $R_7$, $R_{14}$ and $R_{15}$, and $R_{15}$ and $R_{16}$ forms a substituted or unsubstituted, saturated or unsaturated ring. As the ring structure to be formed, a substituted or unsubstituted fluorene ring structure having ring B or ring C at one end, or a substituted or unsubstituted naphthalene ring structure having ring B or ring C at one end can be given.

In one embodiment, in the compound represented by the formula (5), at least one pair of $R_1$ and $R_2$, $R_2$ and $R_3$, $R_3$ and $R_4$, $R_{10}$ and $R_{11}$, $R_{11}$ and $R_{12}$, and $R_{12}$ and $R_{13}$ forms a substituted or unsubstituted, saturated or unsaturated ring. As the ring structure to be formed, a substituted or unsubstituted fluorene ring structure having a benzene ring, to which $R_1$ to $R_4$ is bonded or a benzene ring to which $R_{10}$ to $R_{13}$ are bonded, at one end, or a substituted or unsubstituted naphthalene ring structure having a benzene ring, to which $R_1$ to $R_4$ is bonded or a benzene ring to which $R_{10}$ to $R_{13}$ are bonded, at one end can be given.

In one embodiment, the compound represented by the formula (5) is a compound represented by any one of the following formulas (5-1) to (5-3):

(5-1)

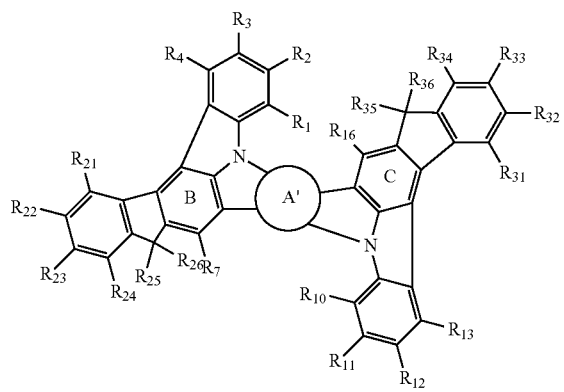

(5-2)

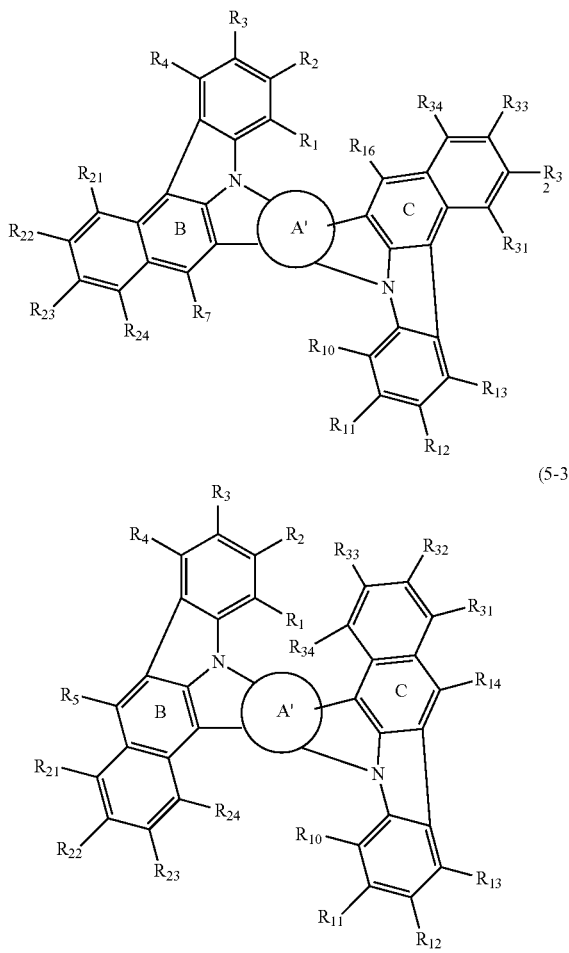

(5-3)

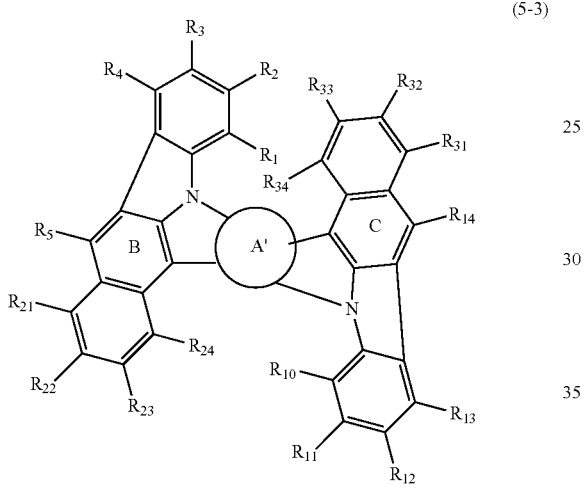

wherein in the formulas (5-1) to (5-3),
ring A is a substituted or unsubstituted fused aryl ring including 10 to 50 ring carbon atoms or a substituted or unsubstituted fused heterocyclic ring including 8 to 50 ring atoms;
$R_1$ to $R_5$, $R_7$, $R_{10}$ to $R_{14}$ and $R_{16}$ are as defined in the formulas (1-1), (1-2), (1-3) and (2);
$R_{21}$ to $R_{26}$ and $R_{31}$ to $R_{36}$ are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, $-Si(R_{31})(R_{32})(R_{33})$, $-C(=O)R_{34}$, $-COOR_{35}$, $-N(R_{36})(R_{37})$, a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{31}$ to $R_{37}$ are as defined in the formulas (1-1), (1-2), (1-3) and (2).

In one embodiment, the compound represented by the formulas (1-1) and (1-3) or the compound represented by the formulas (1-2) and (1-3) are selected from the group consisting of compounds represented by the following formulas (6-1) to (6-7):

(6-1)

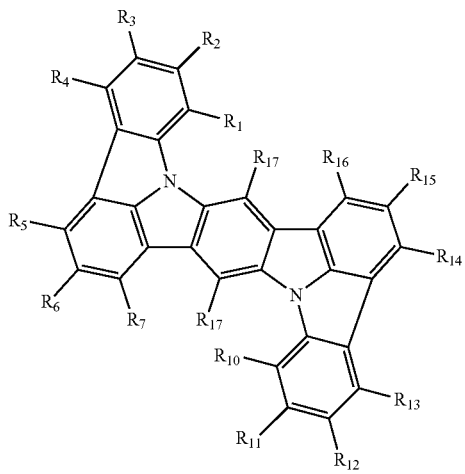

(6-2)

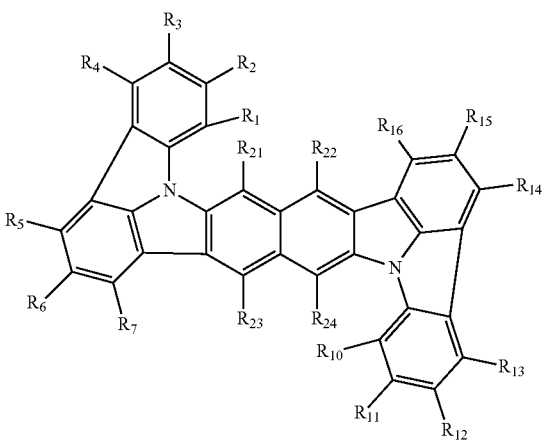

-continued (6-3)
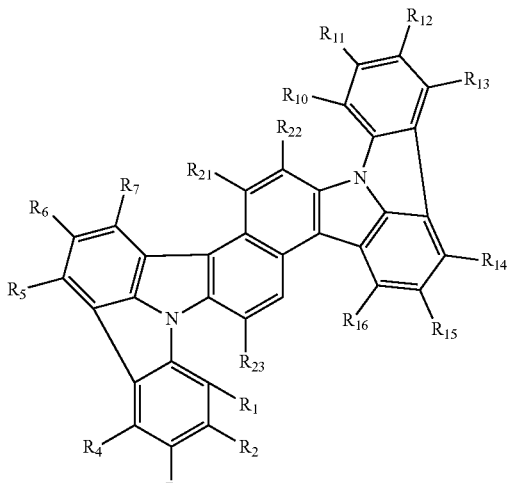

(6-4)
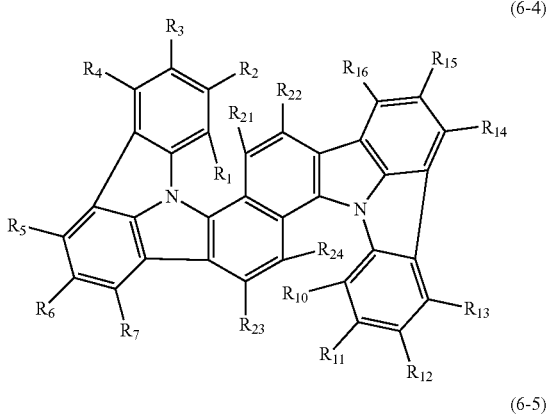

(6-5)
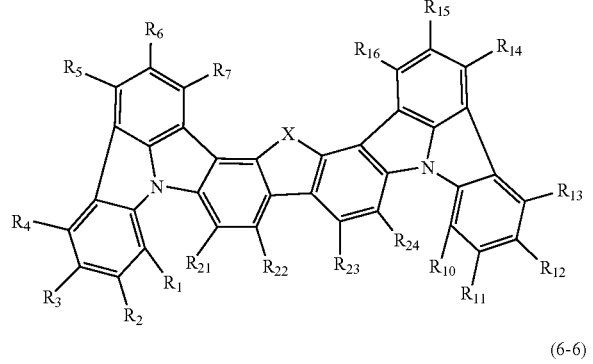

(6-6)
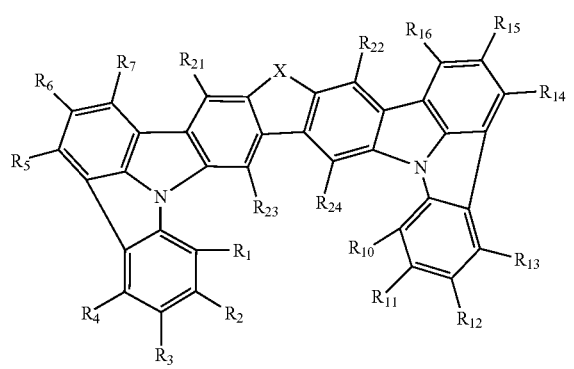

-continued (6-7)
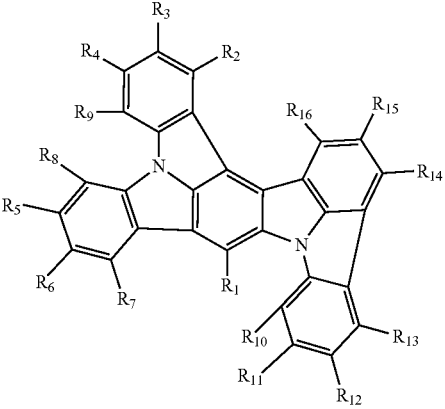

wherein in the formulas (6-1) to (6-7), $R_1$ to $R_{17}$ are as defined in the formulas (1-1), (1-2), (1-3) and (2);

X is O, $NR_{25}$ or $C(R_{26})(R_{27})$.

one or more pairs of adjacent two or more of $R_{21}$ to $R_{27}$ may form a substituted or unsubstituted, saturated or unsaturated ring;

$R_{21}$ to $R_{27}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si$(R_{31})(R_{32})(R_{33})$, —C(=O)$R_{34}$, —COOR$_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms; and when each of $R_{31}$ to $R_{37}$ is present in plural, each of the plural $R_{31}$ to $R_{37}$ may be the same or different.

In one embodiment, the compound represented by the formulas (1-1) and (1-3) or the compound represented by the formulas (1-2) and (1-3) are selected from the group consisting of compounds represented by the following formulas (6-8) to (6-10):

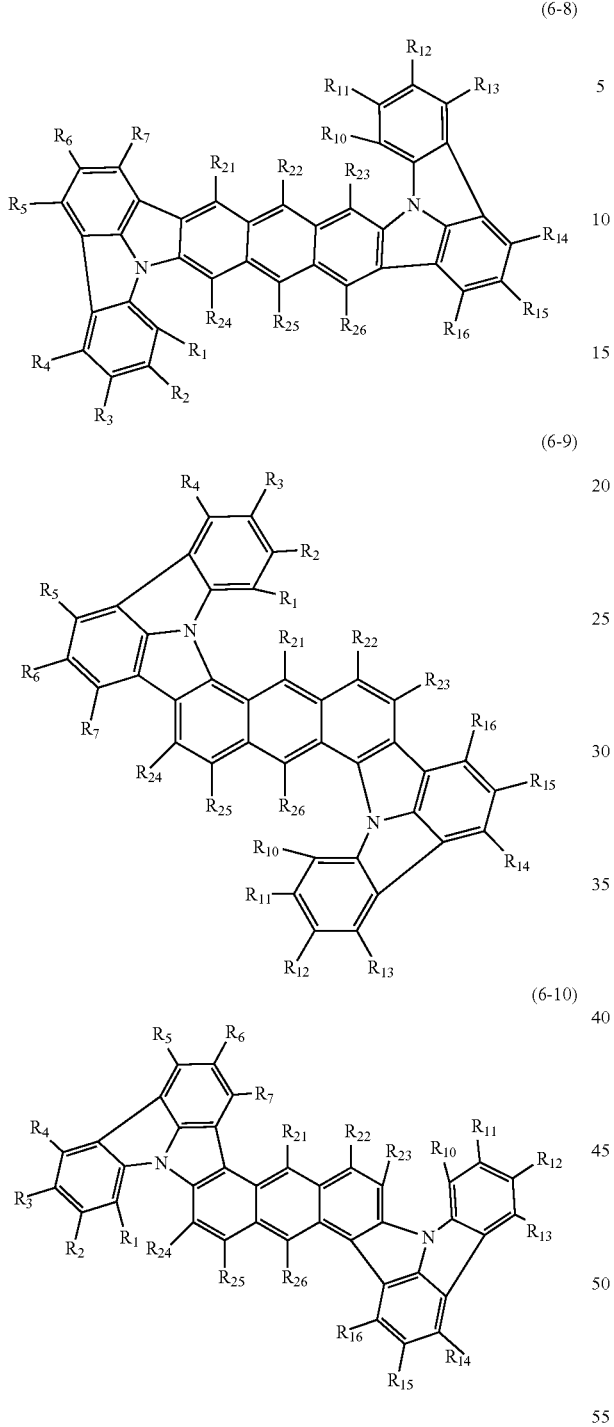

(6-8)

(6-9)

(6-10)

wherein in the formulas (6-8) to (6-10), $R_1$ to $R_7$ and $R_{10}$ to $R_{16}$ are as defined in the formulas (1-1), (1-2), (1-3) and (2); one or more pairs of adjacent two or more of $R_{21}$ to $R_{26}$ may form a substituted or unsubstituted, saturated or unsaturated ring;

$R_{21}$ to $R_{26}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms; and when each of $R_{31}$ to $R_{37}$ is present in plural, each of the plural $R_{31}$ to $R_{37}$ may be the same or different.

In one embodiment, the compound represented by the formulas (1-1) and (1-3) or the compound represented by the formulas (1-2) and (1-3) is a compound represented by the following formula (3-2):

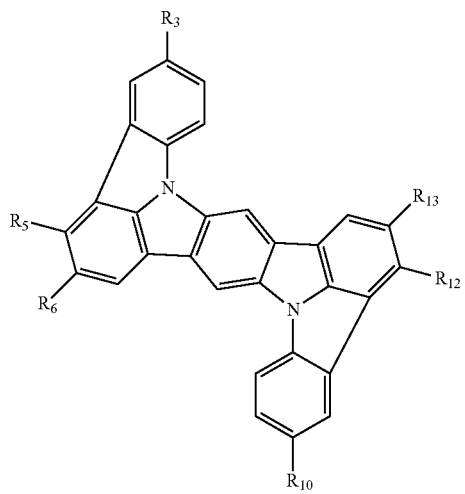

(3-2)

wherein in the formula (3-2), $R_3$, $R_5$, $R_6$, $R_{10}$, $R_{12}$ and $R_{13}$ are as defined in the formulas (1-1) and (1-3).

In one embodiment, the compound represented by the formulas (1-1) and (1-3) or the compound represented by the formulas (1-2) and (1-3) is a compound represented by the following formula (7):

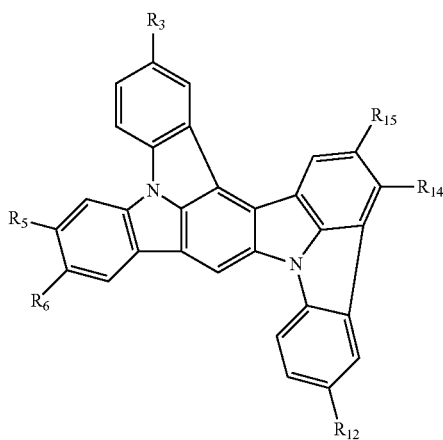

(7)

wherein in the formula (7), $R_3$, $R_5$, $R_6$, $R_{12}$, $R_{14}$ and $R_{15}$ are as defined in the formula (1-2) and the formula (1-3).

In one embodiment, $R_1$ to $R_{17}$ are independently selected from the group consisting of a hydrogen atom, a substituted or unsubstituted aryl group including 6 to 50 ring carbon atoms and a substituted or unsubstituted heterocyclic group including 5 to 50 ring atoms.

In one embodiment, $R_1$ to $R_{17}$ are independently selected from the group consisting of a hydrogen atom, a substituted or unsubstituted aryl group including 6 to 18 ring carbon atoms and a substituted or unsubstituted heterocyclic group including 5 to 18 ring atoms.

A substituent in the "substituted or unsubstituted" in the compound represented by the formula (1-1) and (1-3) and the compound represented by the formula (1-2) and (1-3) is selected from the group consisting of an alkyl group including 1 to 50 carbon atoms, a haloalkyl group including 1 to 50 carbon atoms, an alkenyl group including 2 to 50 carbon atoms, an alkynyl group including 2 to 50 carbon atoms, a cycloalkyl group including 3 to 50 ring carbon atoms, an alkoxy group including 1 to 50 carbon atoms, an alkylthio group including 1 to 50 carbon atoms, an aryloxy group including 6 to 50 ring carbon atoms, an arylthio group including 6 to 50 ring carbon atoms, an aralkyl group including 7 to 50 carbon atoms, —Si($R_{41}$)($R_{42}$)($R_{43}$), —C(=O)$R_{44}$, —COO$R_4$s, —S(=O)$_2R_{40}$, —P(=O)($R_{47}$)($R_{43}$), —Ge($R_{49}$)($R_{50}$)($R_{51}$), —N($R_{52}$)($R_{53}$) (wherein $R_{41}$ to $R_{53}$ are independently a hydrogen atom, an alkyl group including 1 to 50 carbon atoms, an aryl group including 6 to 50 ring carbon atoms or a heterocyclic group including 5 to 50 ring atoms. When each of $R_{41}$s to $R_{53}$s are present in plural, each of the plural $R_{41}$s to $R_{53}$s may be the same or different), a hydroxyl group, a halogen atom, a cyano group, a nitro group, an aryl group including 6 to 50 ring carbon atoms, and a monovalent heterocyclic group including 5 to 50 ring atoms.

In one embodiment, the substituent in the "substituted or unsubstituted" in the compound represented by the formulas (1-1) and (1-3) and the compound represented by the formulas (1-2) and (1-3) is an alkyl group including 1 to 50 carbon atoms, an aryl group including 6 to 50 ring carbon atoms and a monovalent heterocyclic group including 5 to 50 ring atoms.

In one embodiment, the substituent in the "substituted or unsubstituted" in the compound represented by the formulas (1-1) and (1-3) and the compound represented by the formulas (1-2) and (1-3) is selected from the group consisting of an alkyl group including 1 to 18 carbon atoms, an aryl group including 6 to 18 ring carbon atoms and a monovalent heterocyclic group including 5 to 18 ring atoms.

Specific examples of each substituent, substituents for "substituted or unsubstituted" and halogen atoms in the compound represented by the formulas (1-1) and (1-3), and the compound represented by the formulas (1-2) and (1-3) are the same as those mentioned above.

As specific example of the compound represented by the formulas (1-1) and (1-3) and the compound represented by the formulas (1-2) and (1-3), the following compounds can be given, for example.

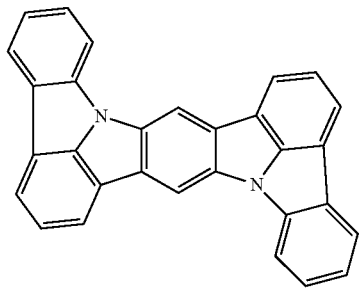
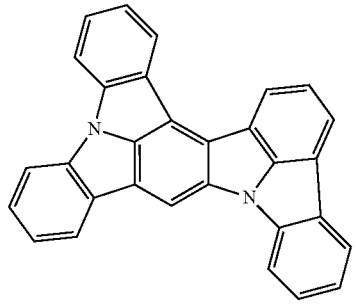
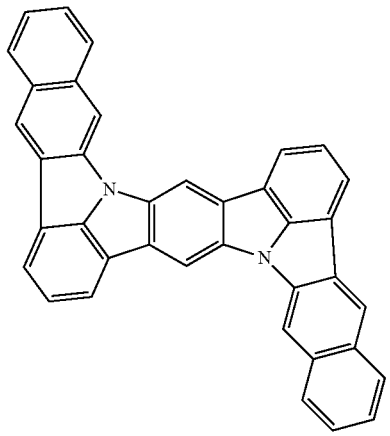
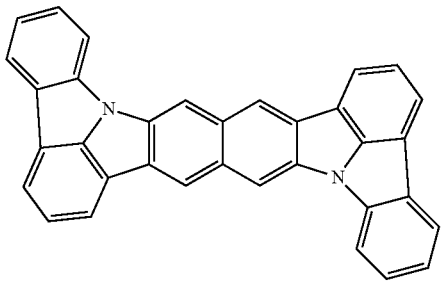

-continued
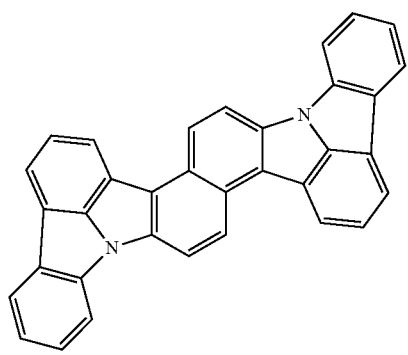
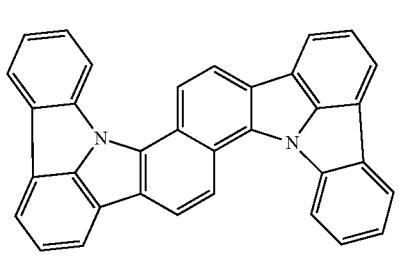
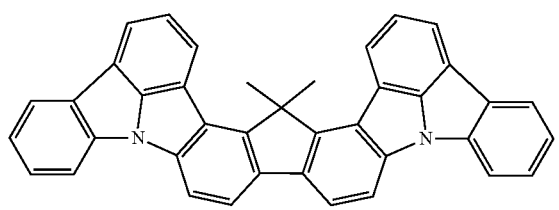
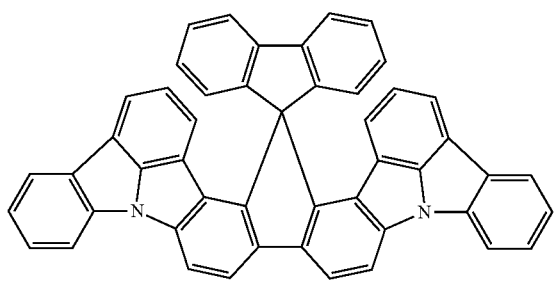
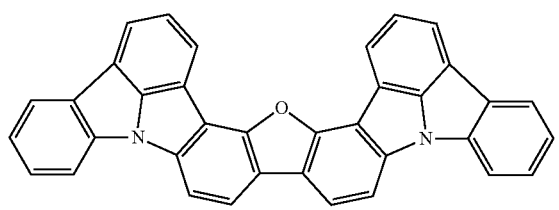
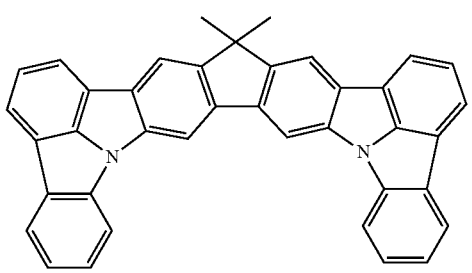
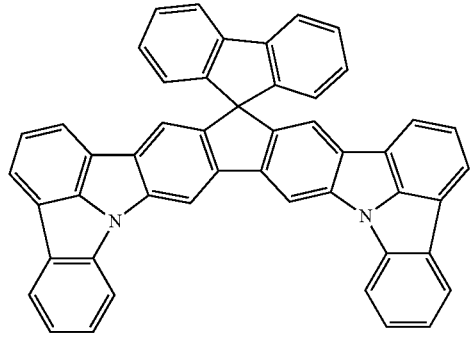
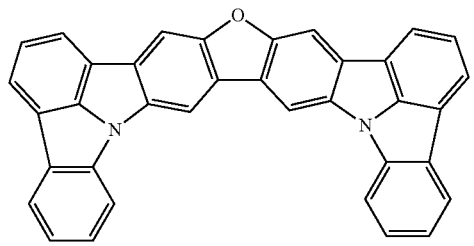
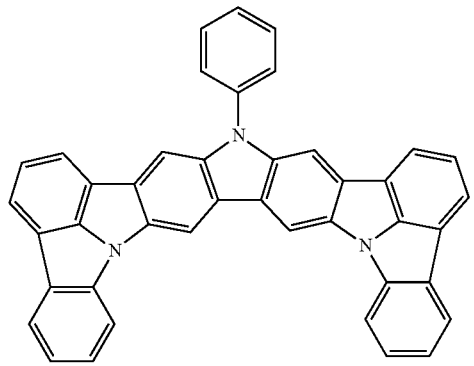
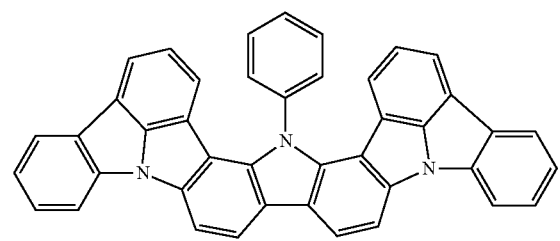

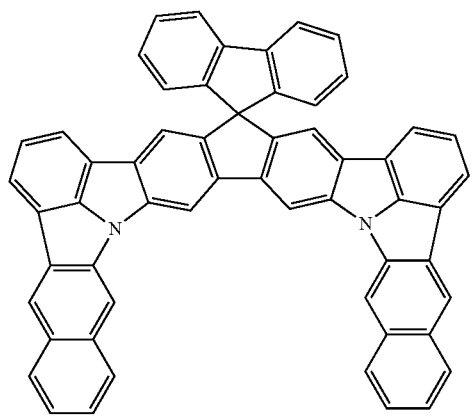
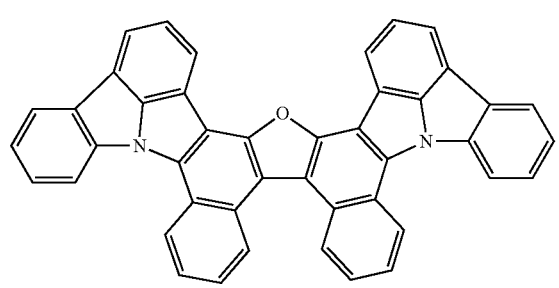
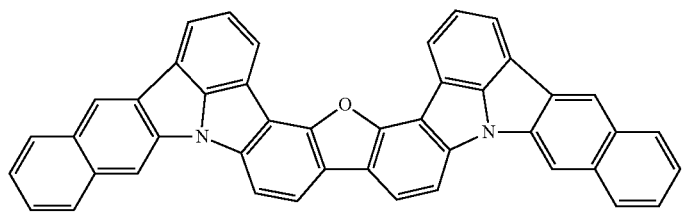
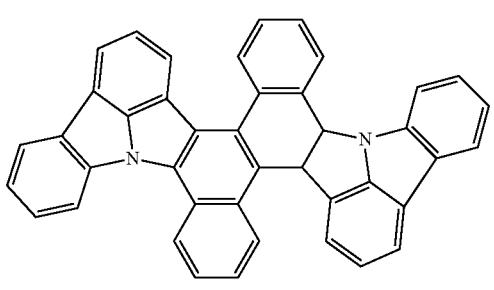
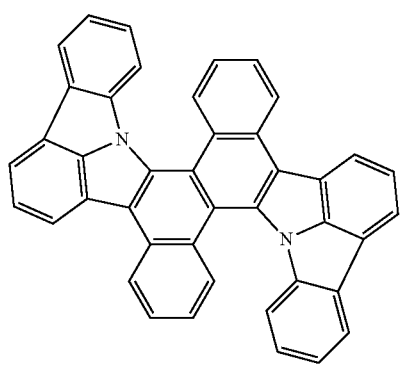
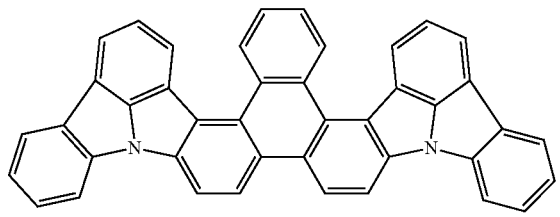
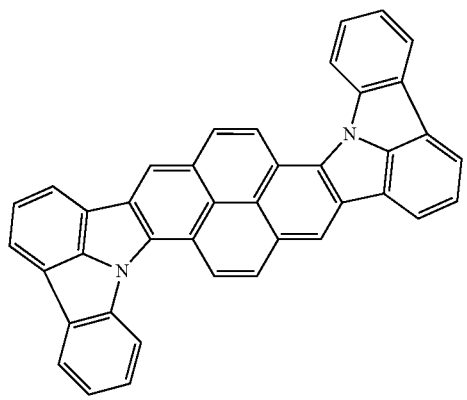
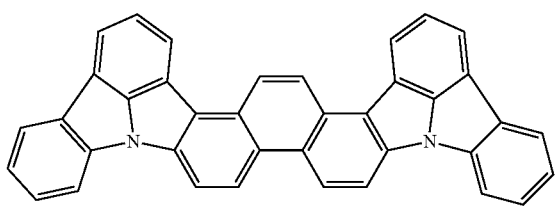

-continued
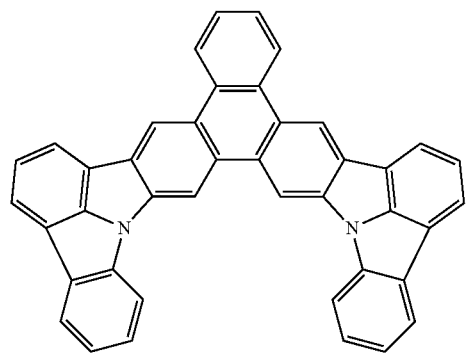
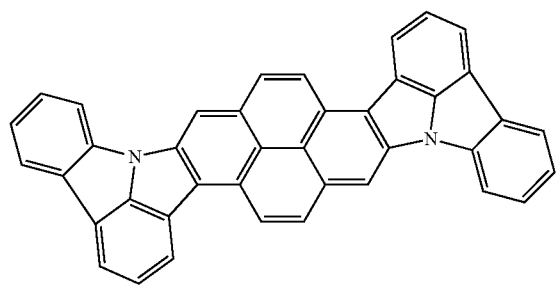
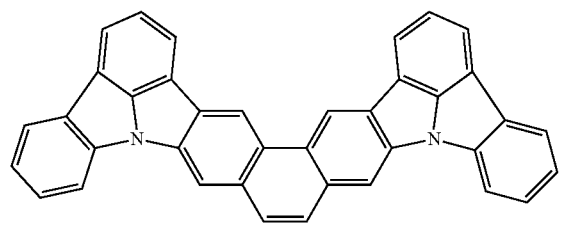
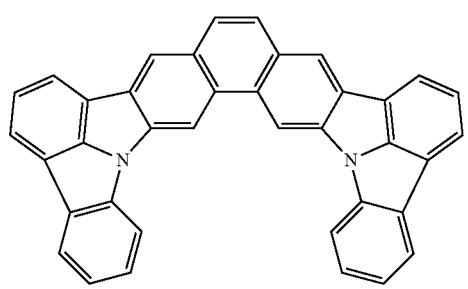
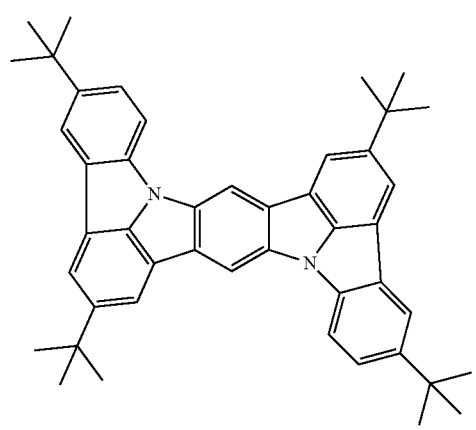
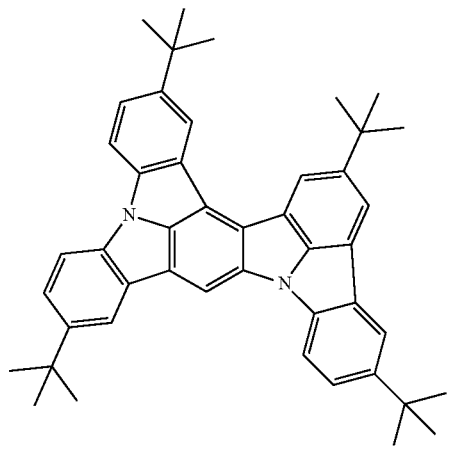
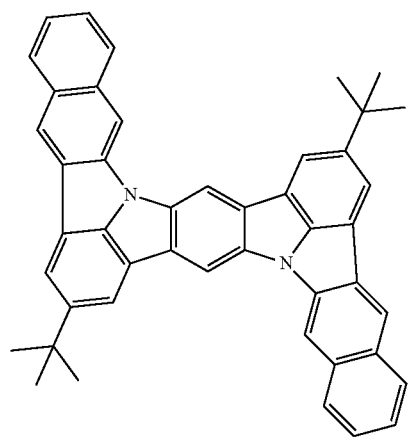
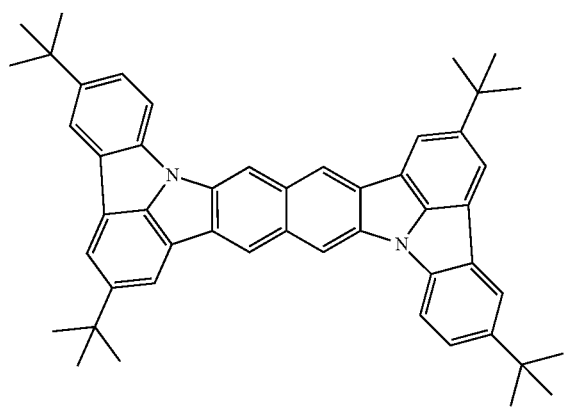

-continued
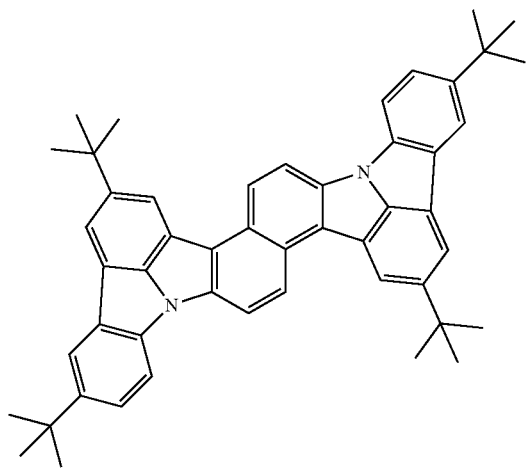
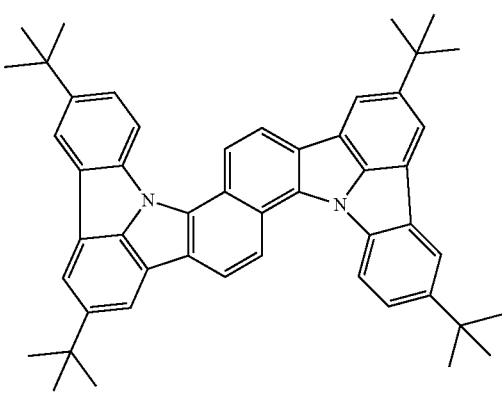
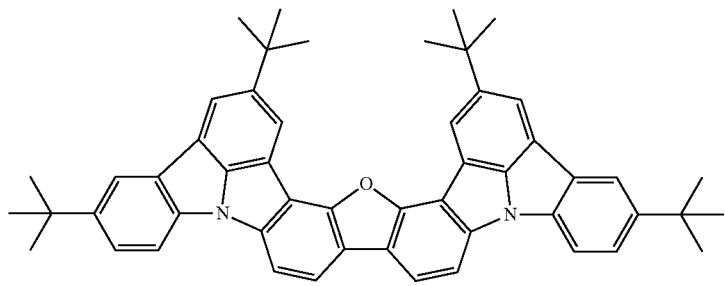
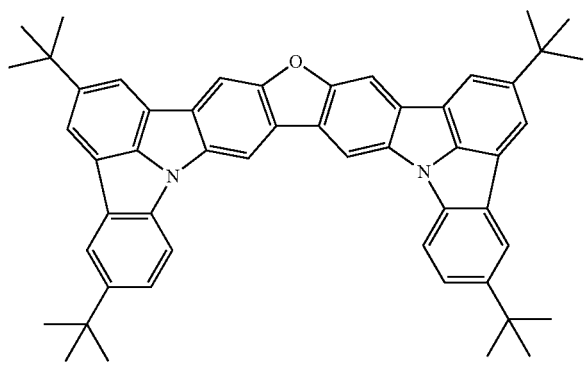
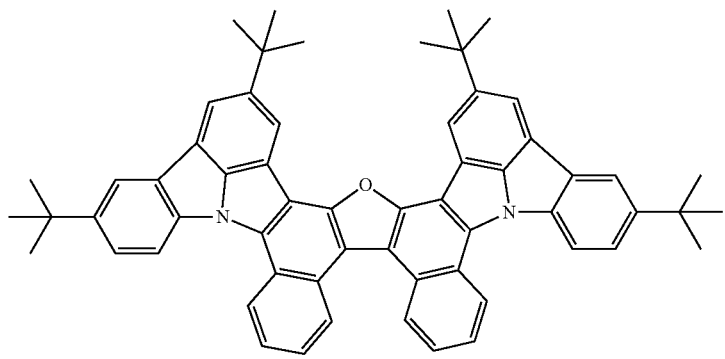

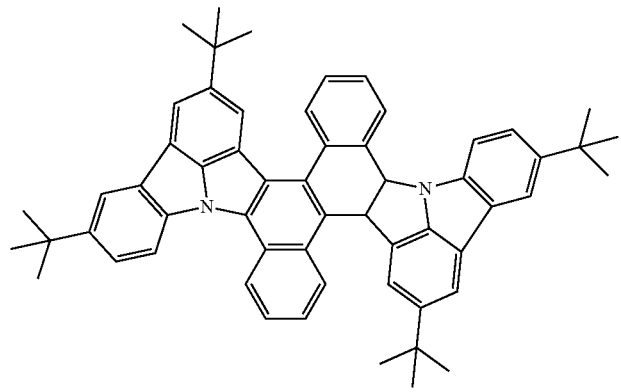
35
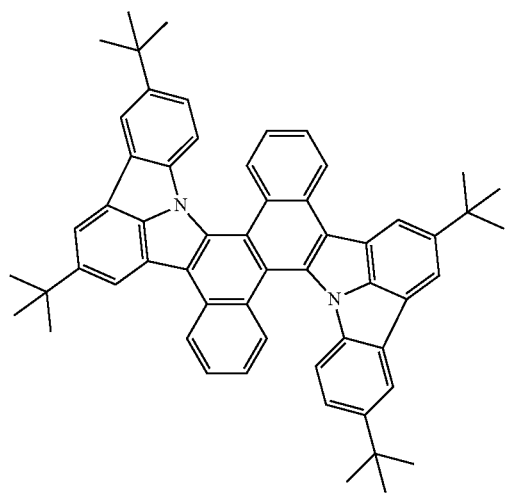
36
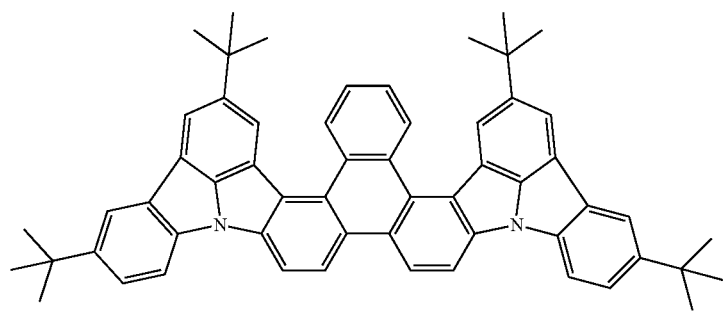
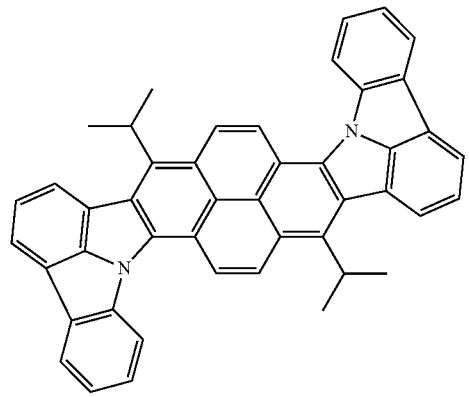
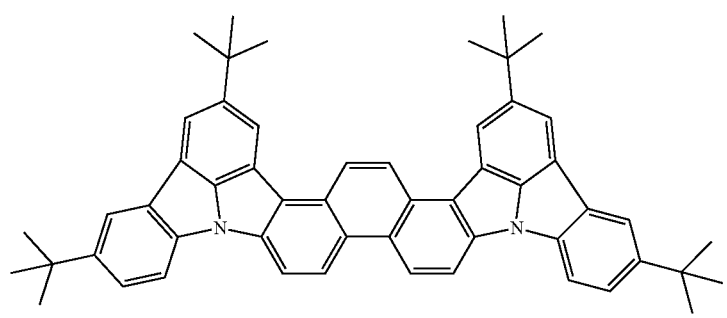

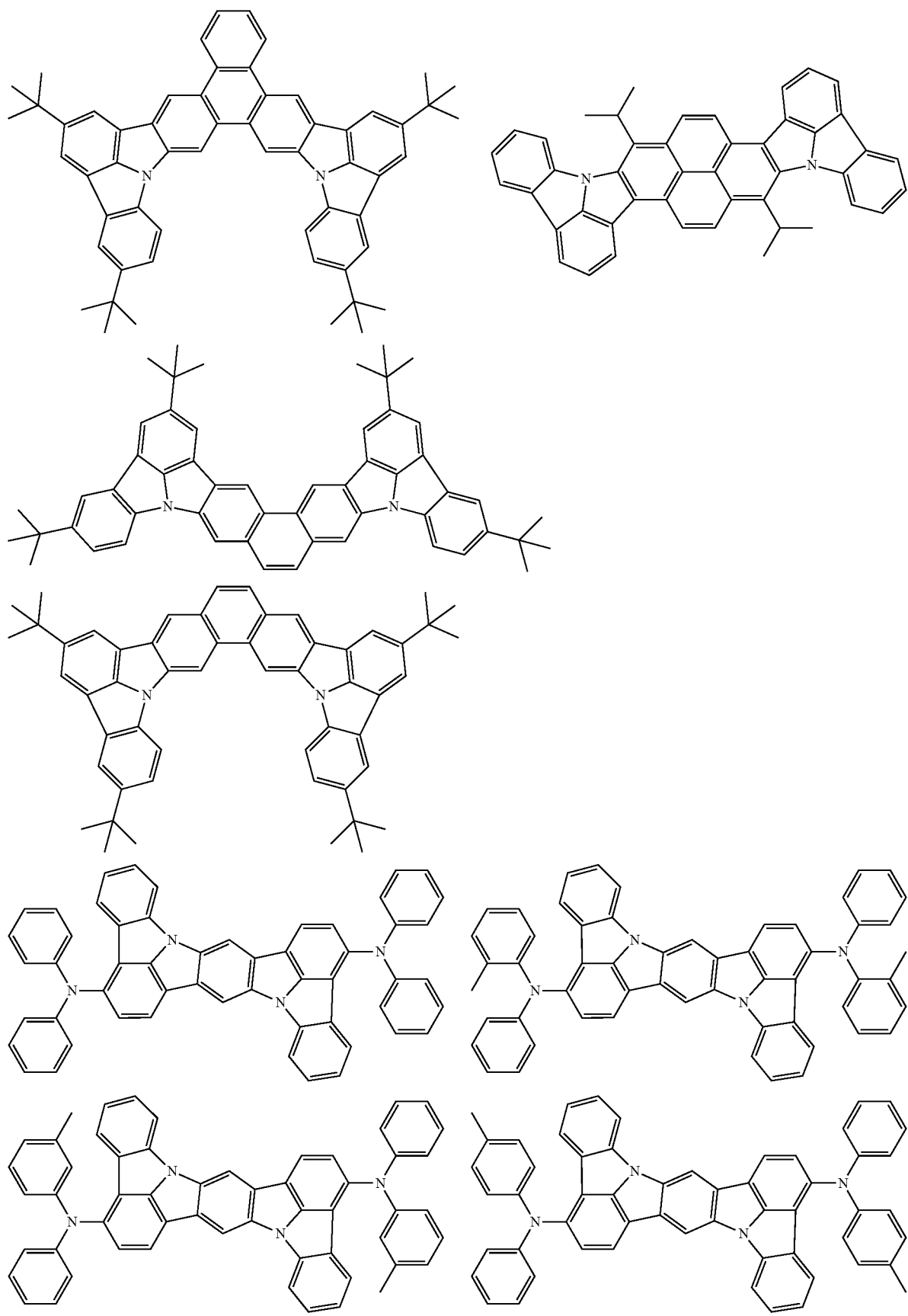

-continued
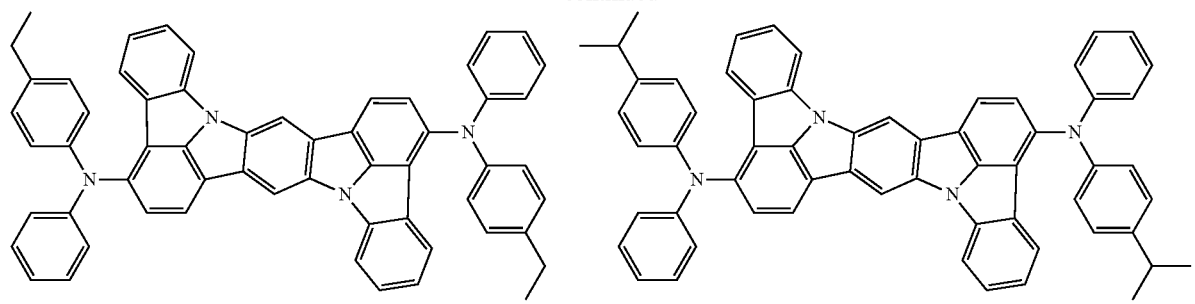
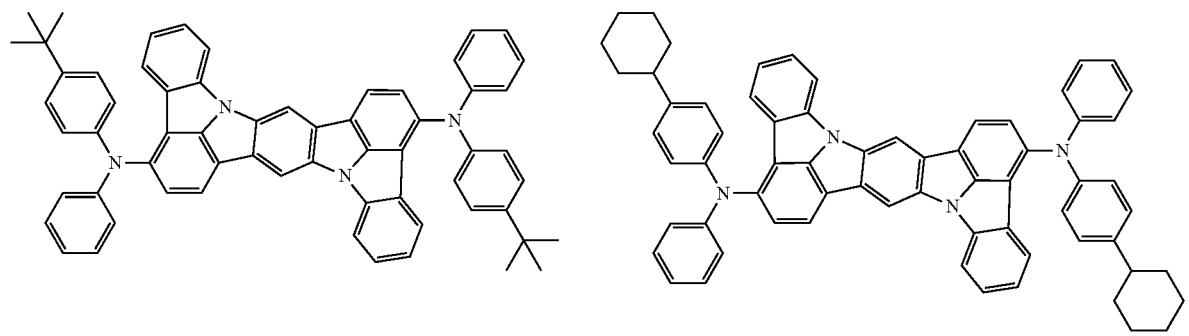
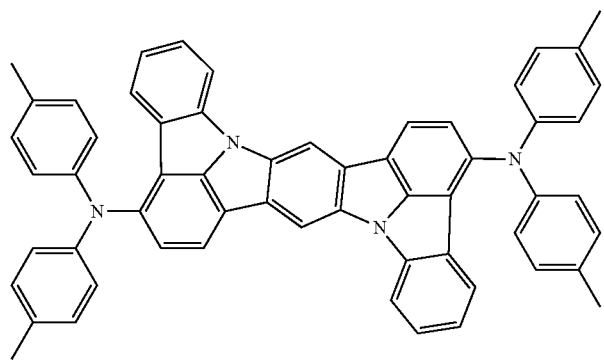
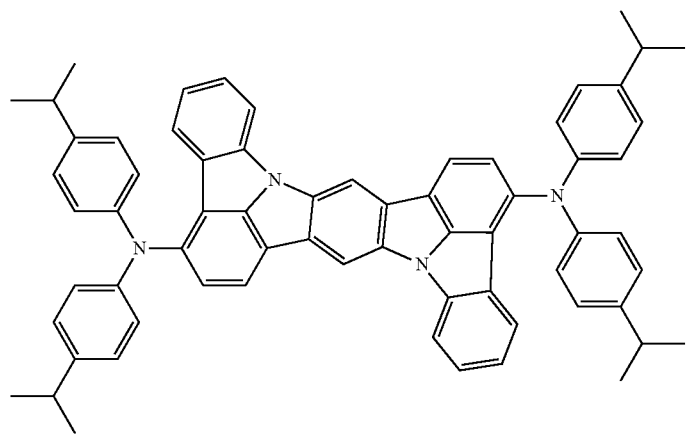

-continued
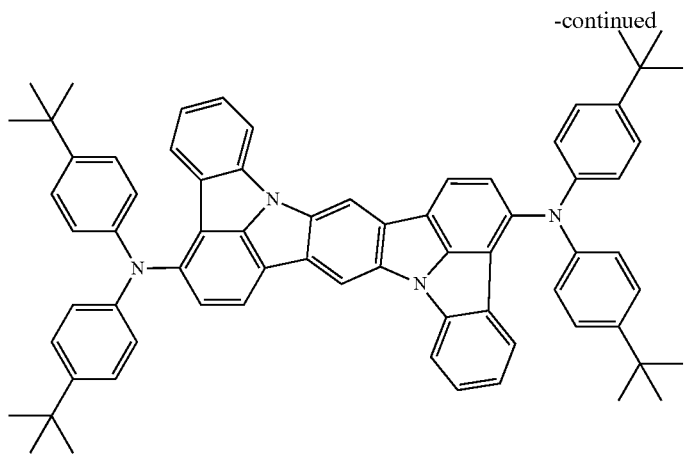
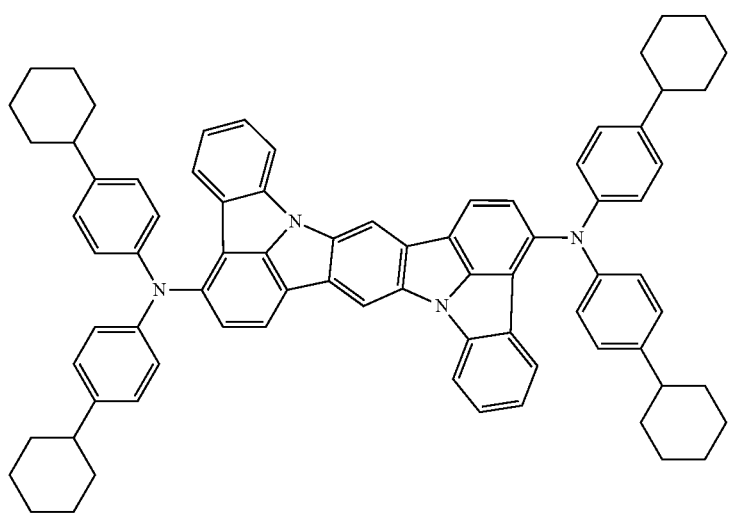
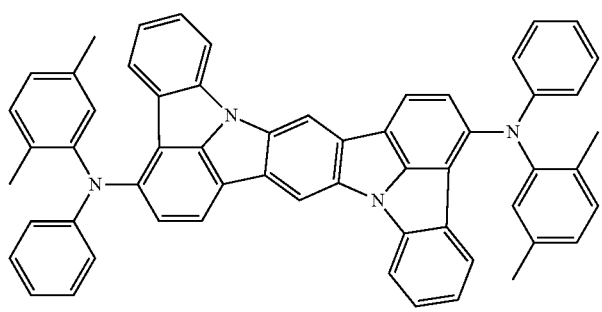
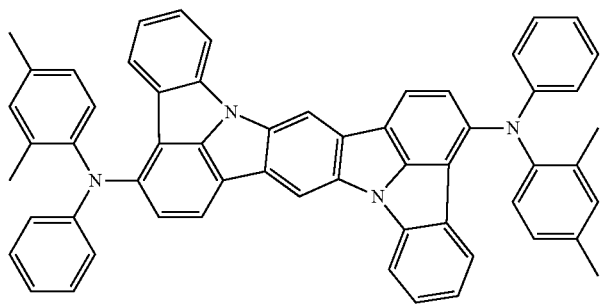

-continued
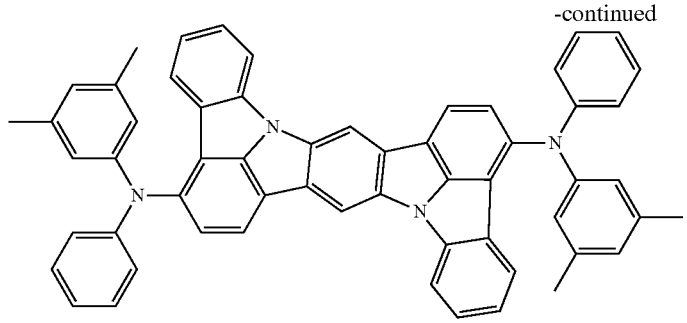
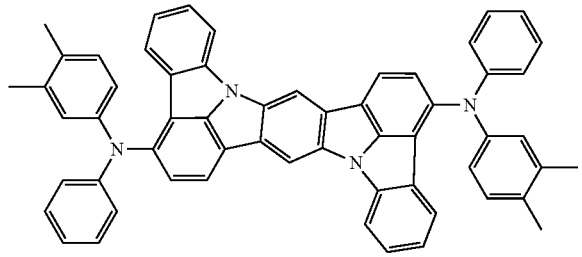
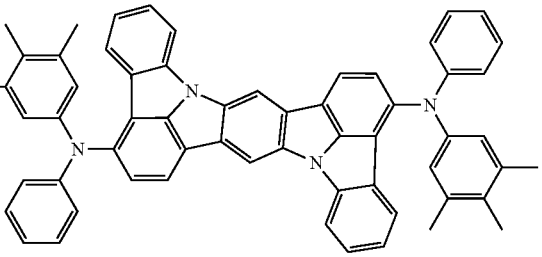
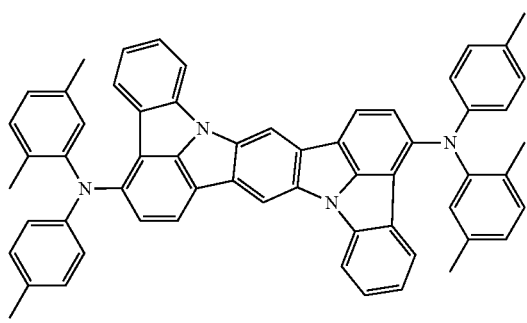
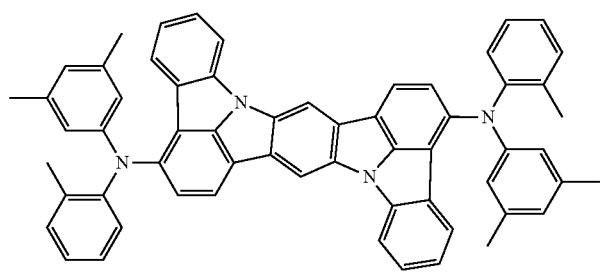
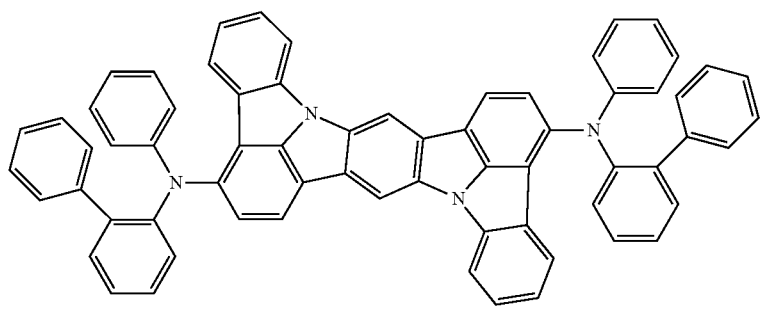
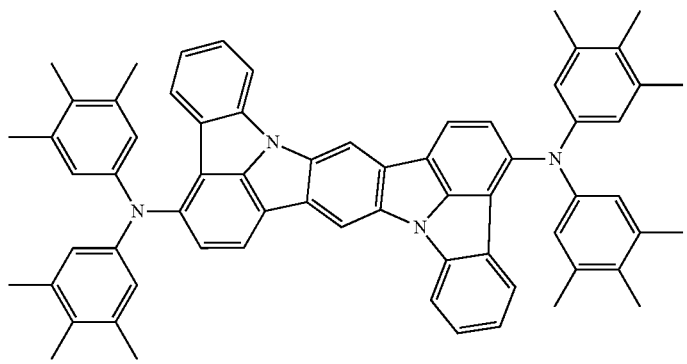

-continued
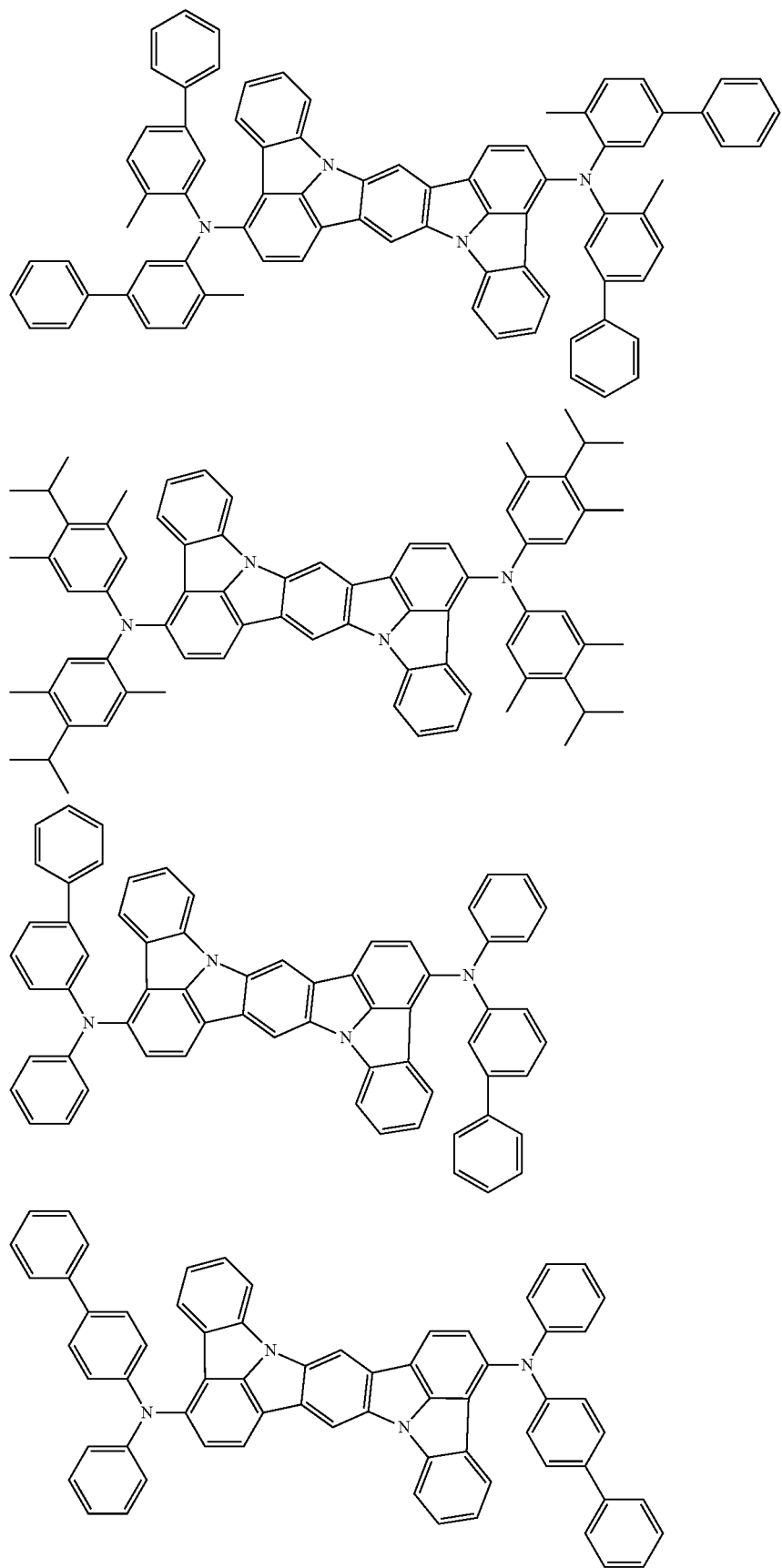

-continued
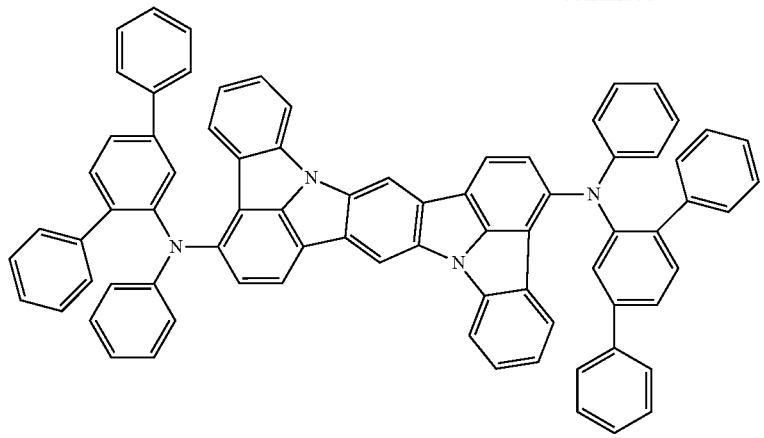
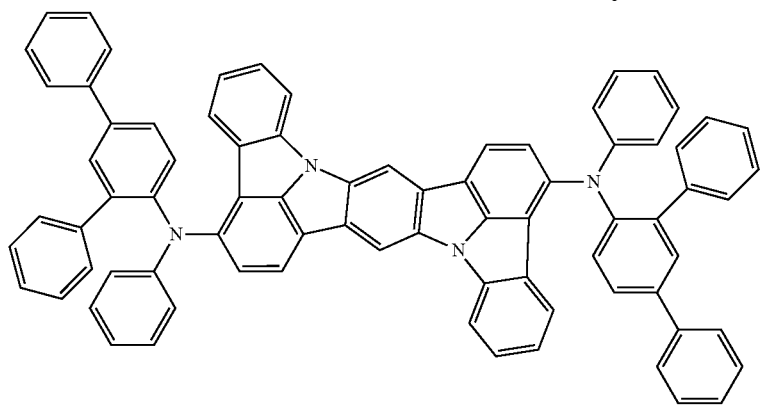
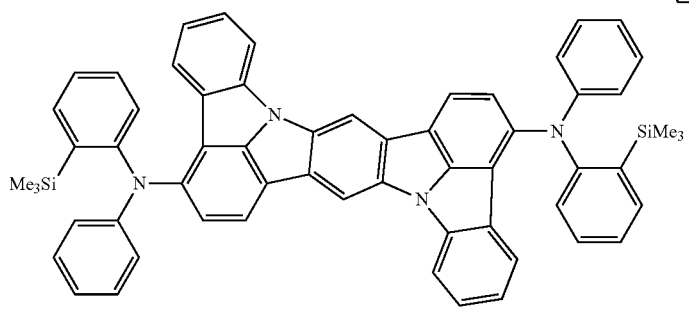
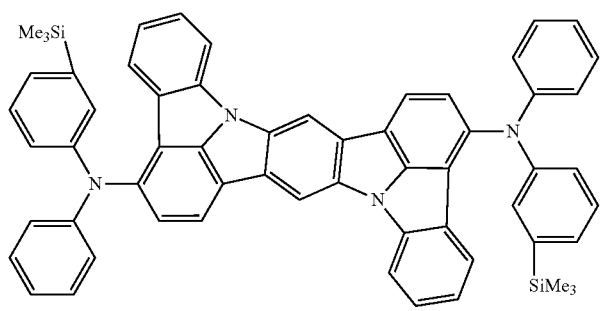
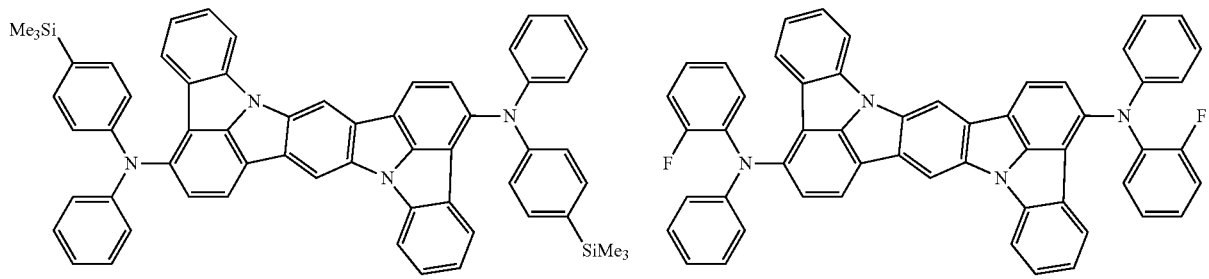

-continued
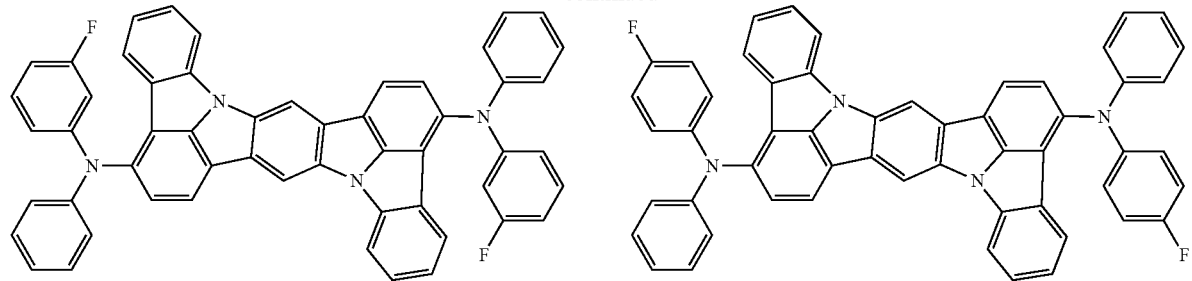
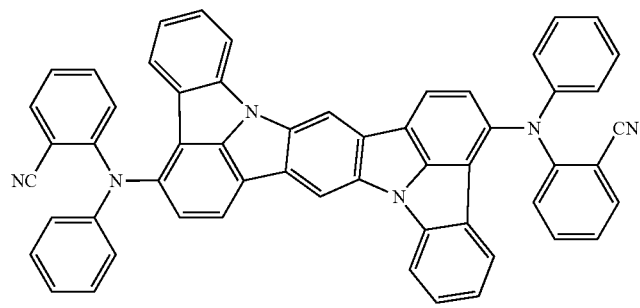
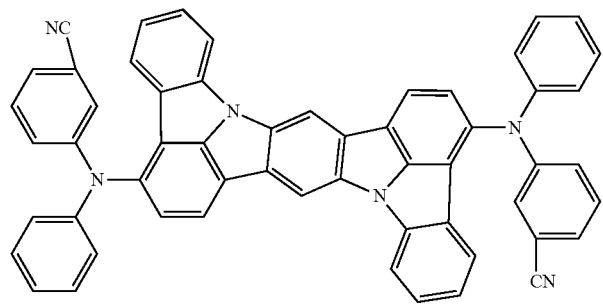
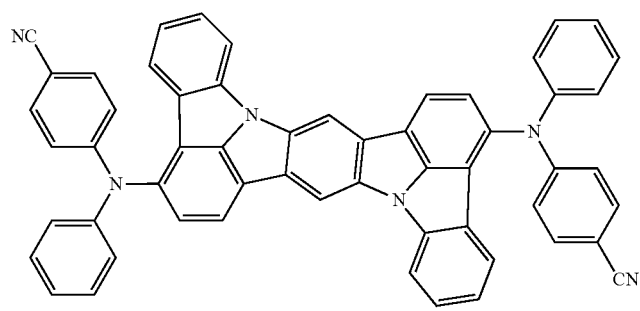
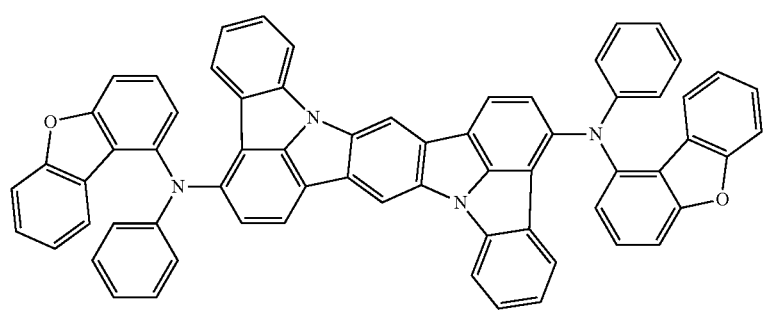

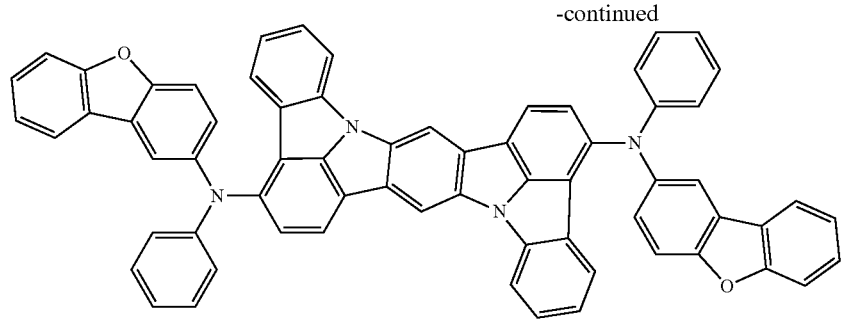
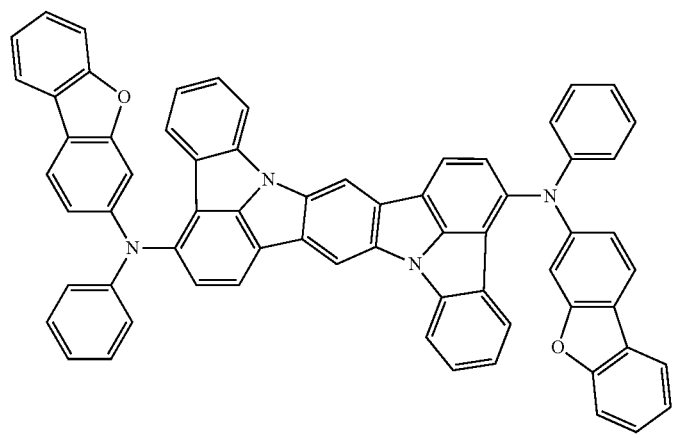
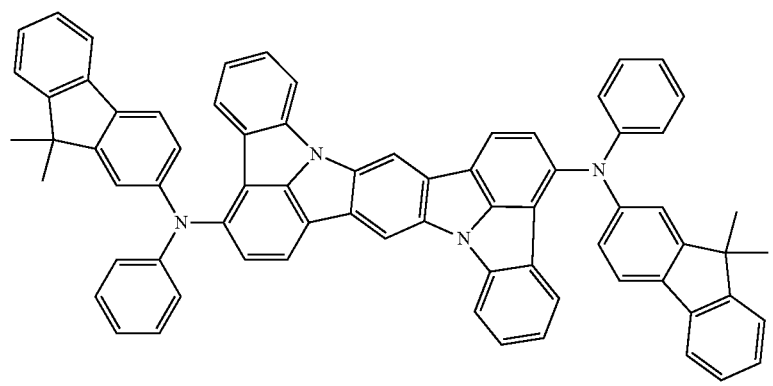
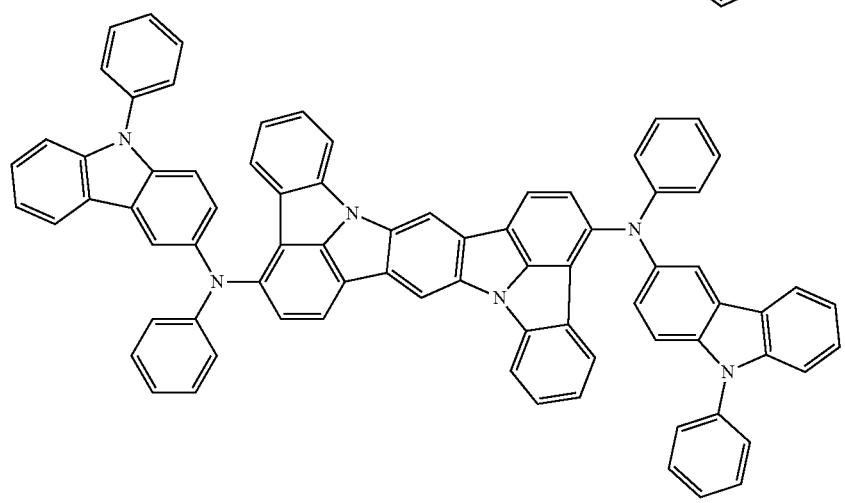

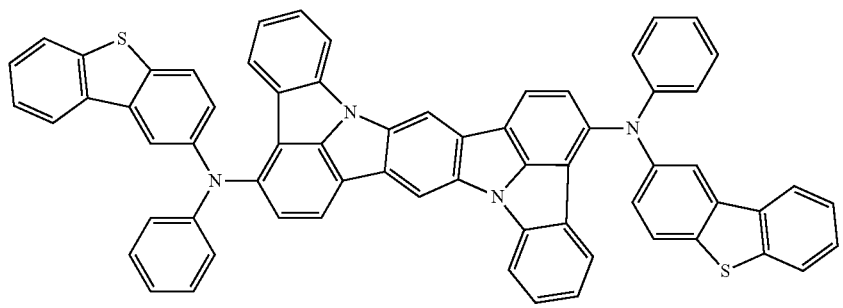
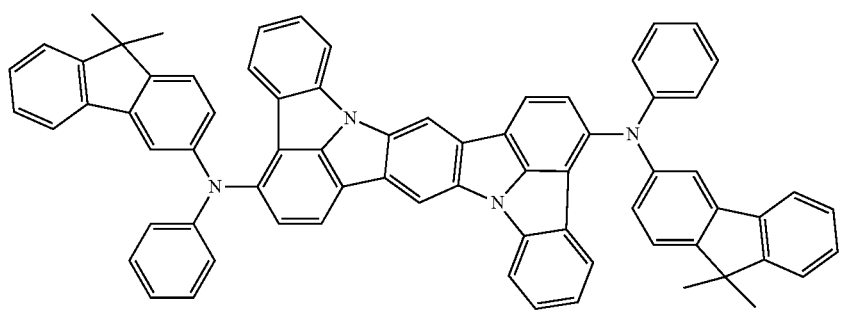
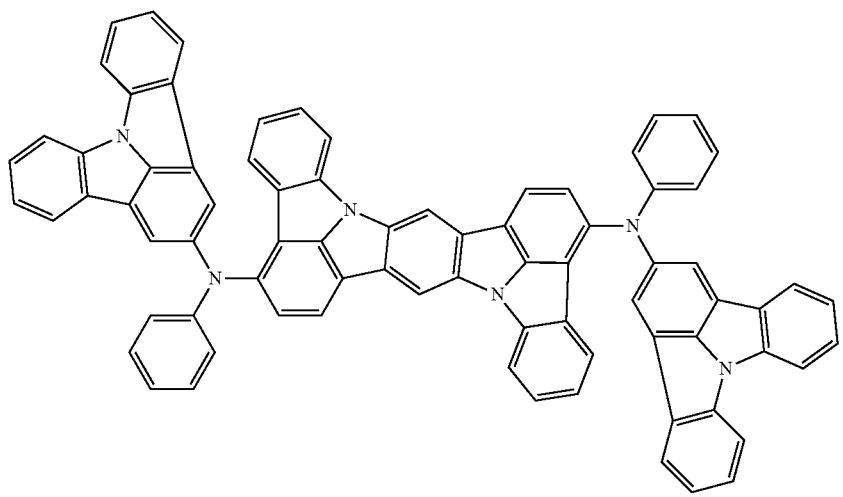
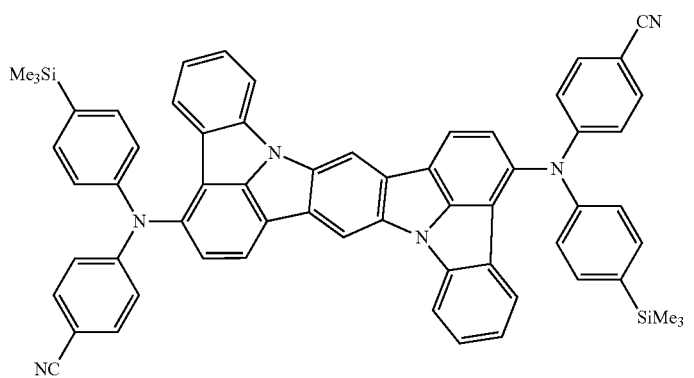

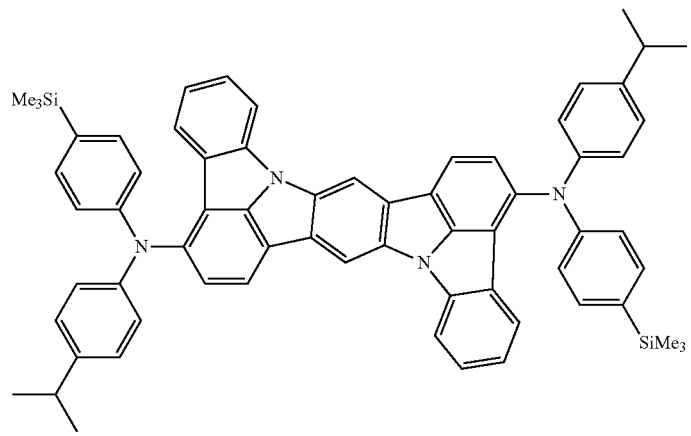
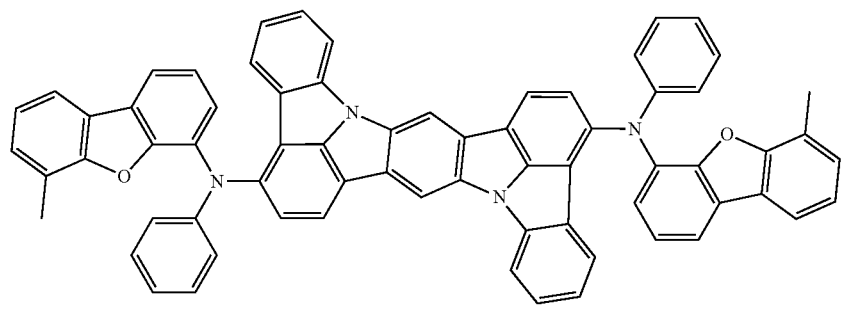
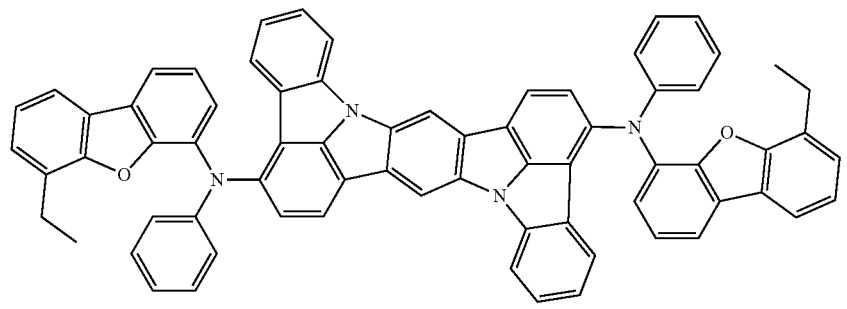
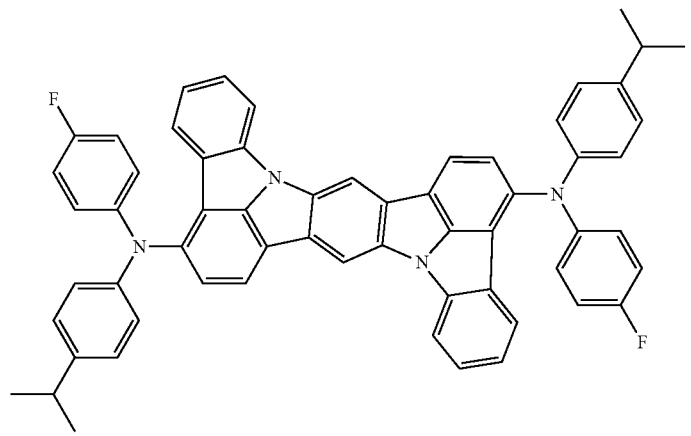

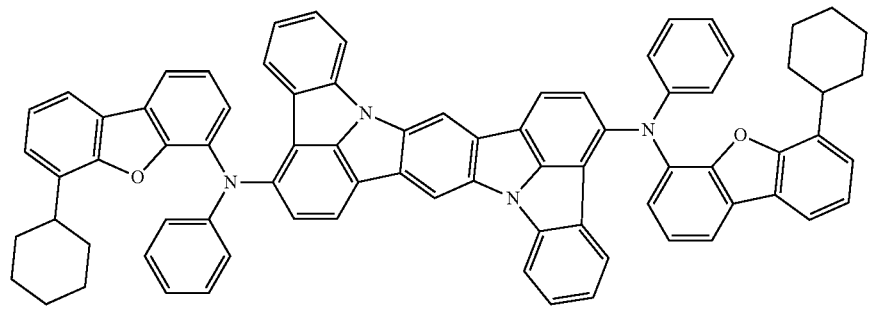
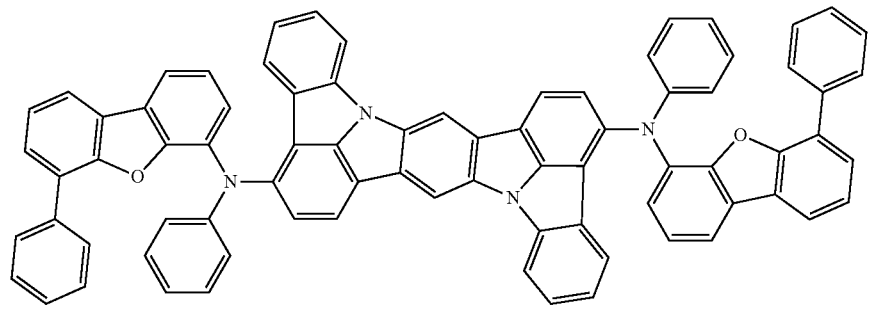
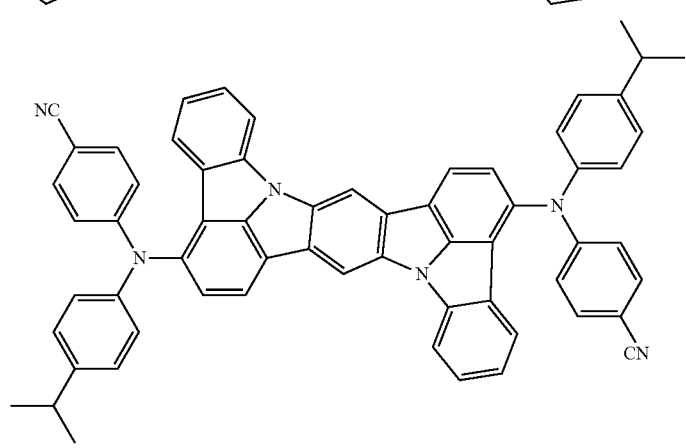
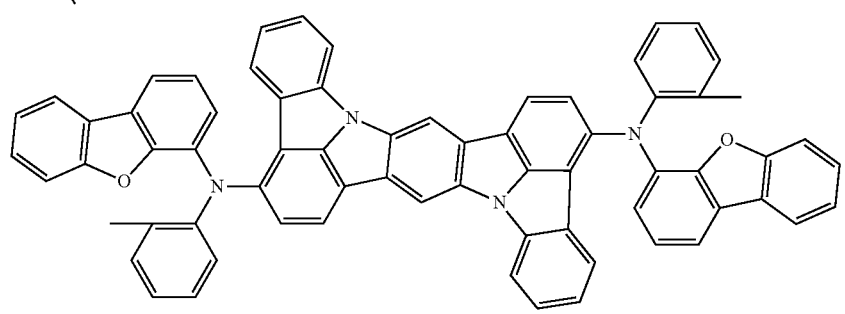
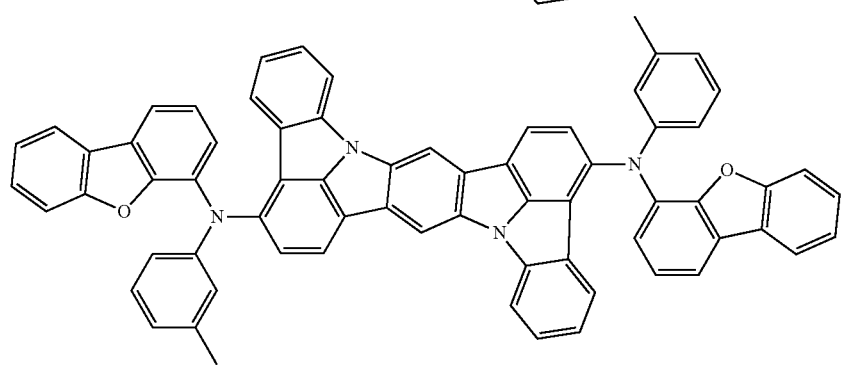

-continued
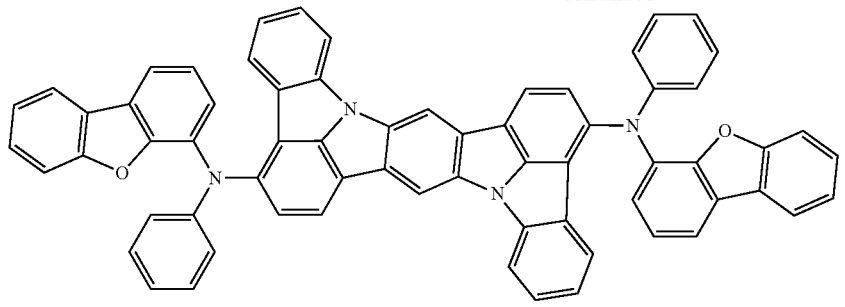
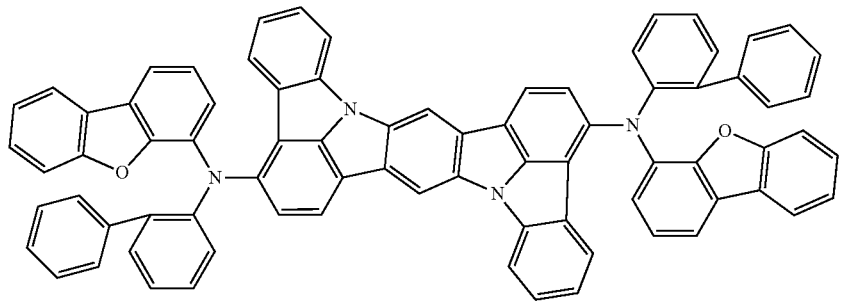
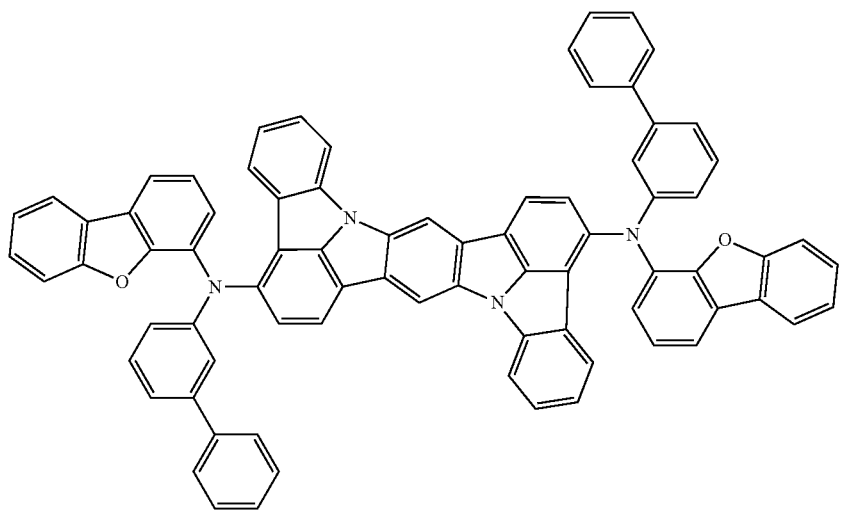
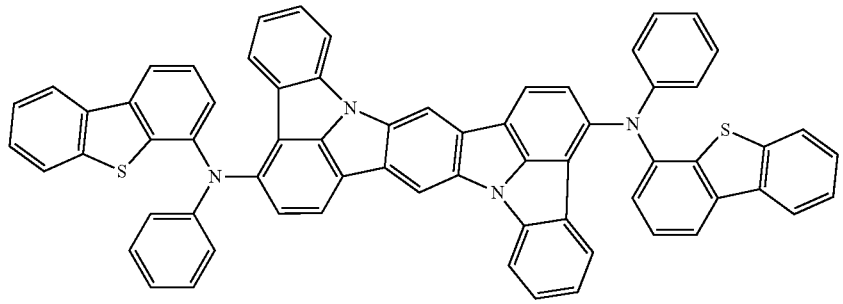
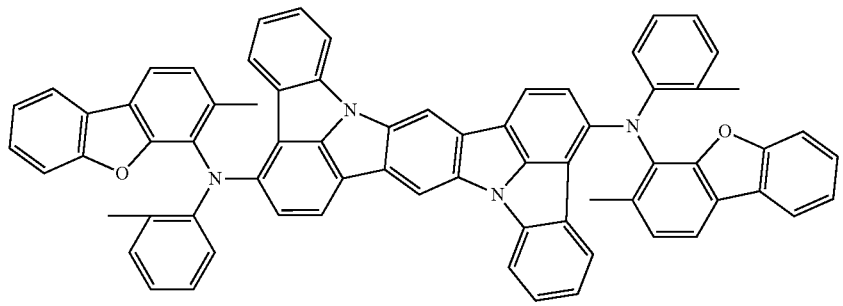

-continued
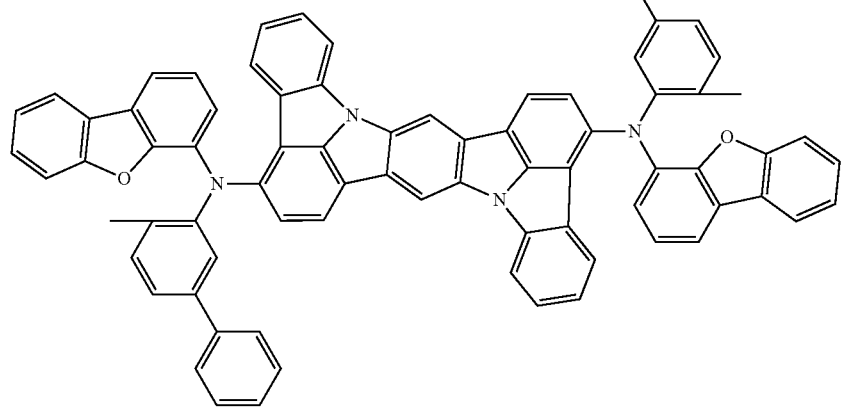
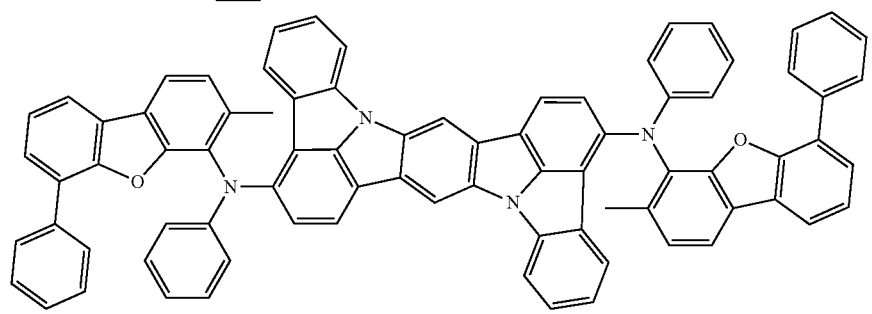
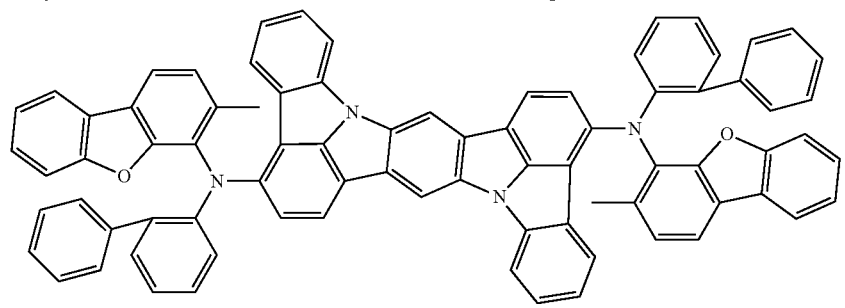
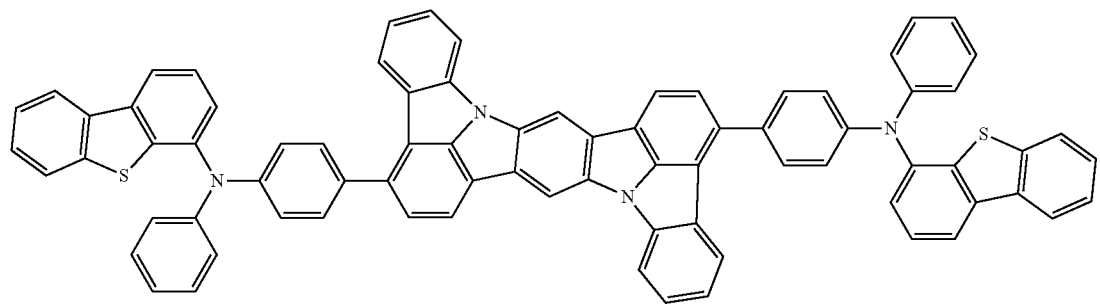
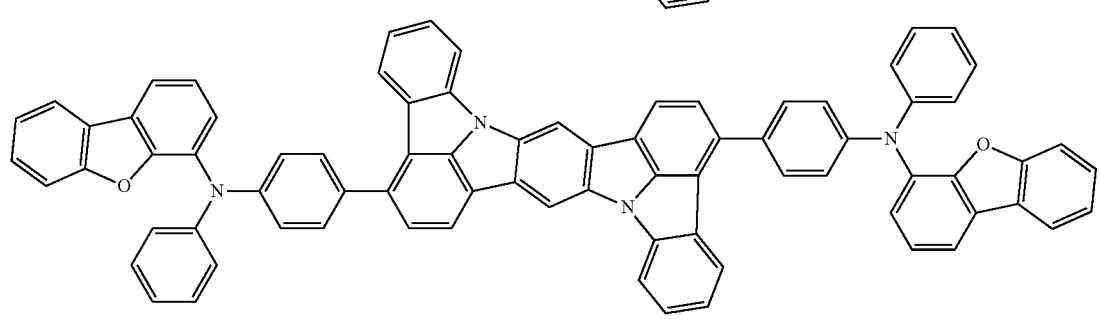

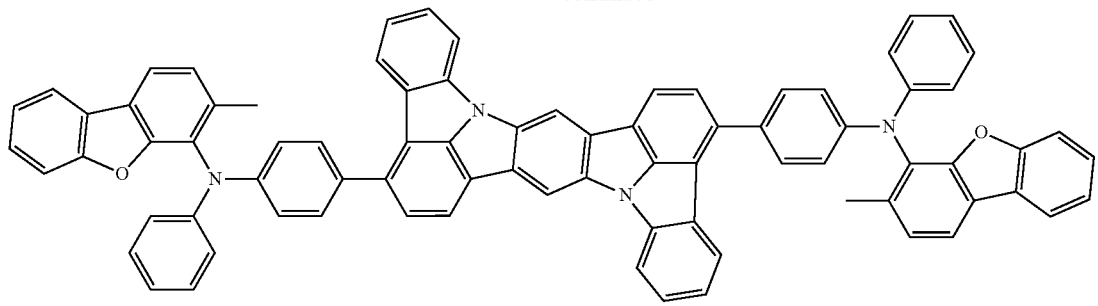
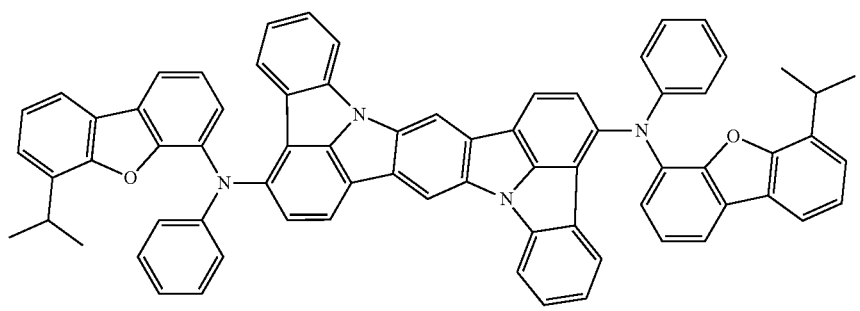
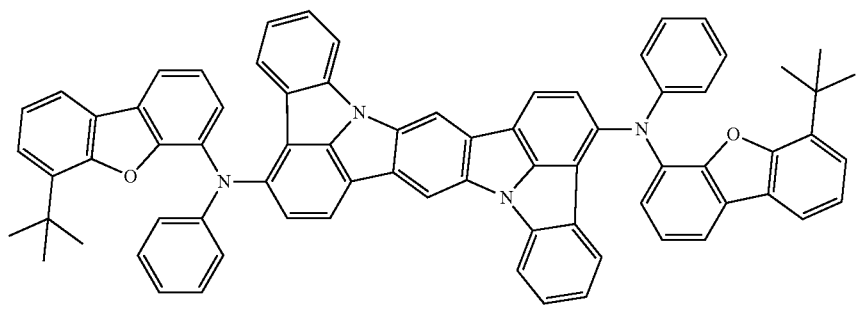
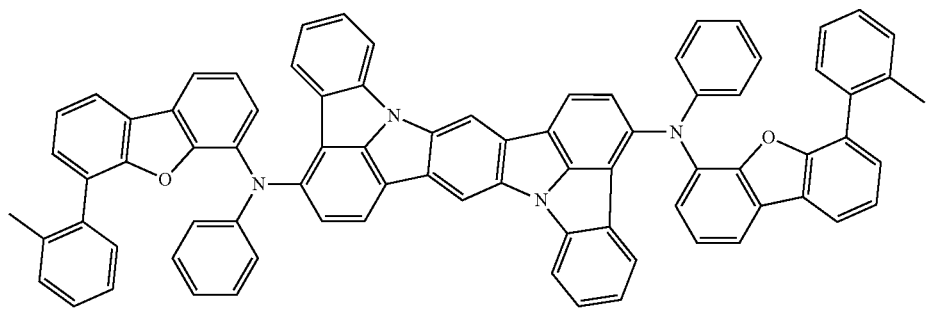
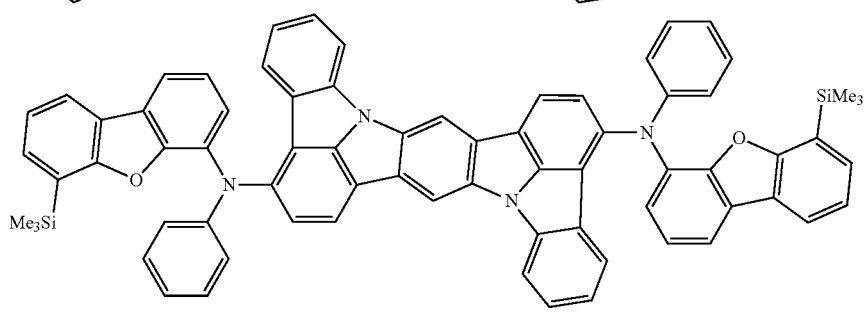

-continued
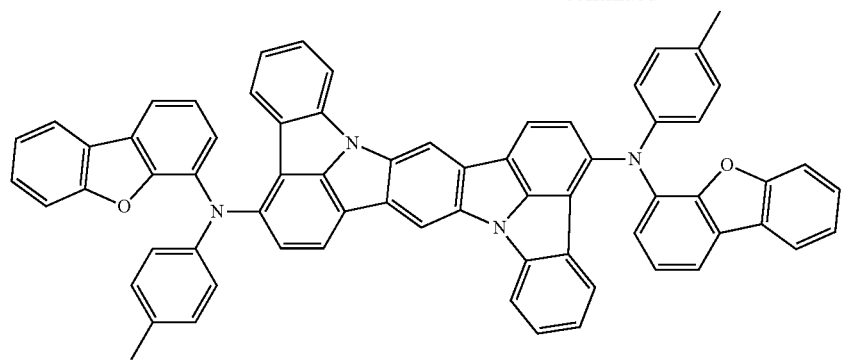
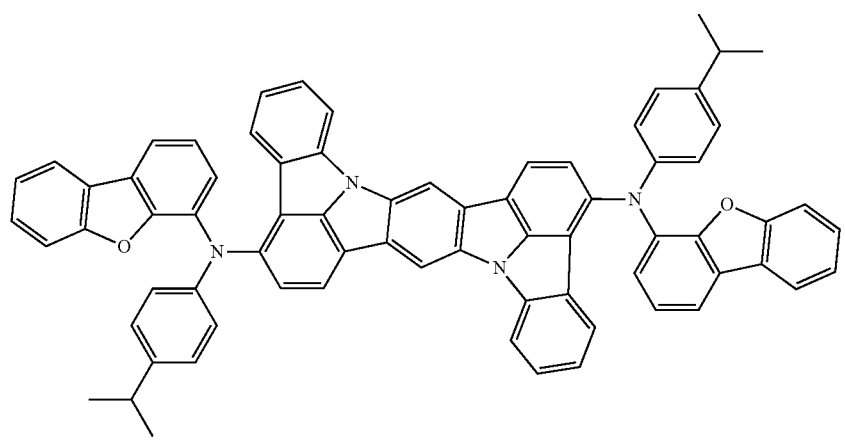
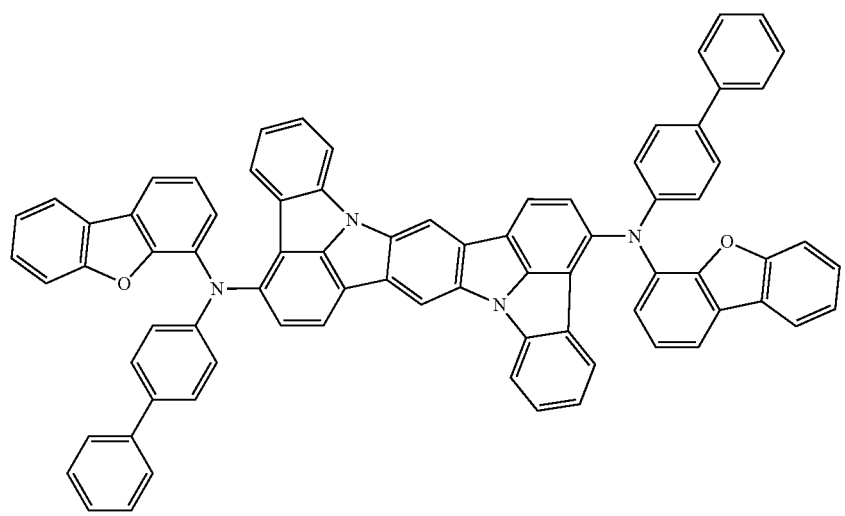
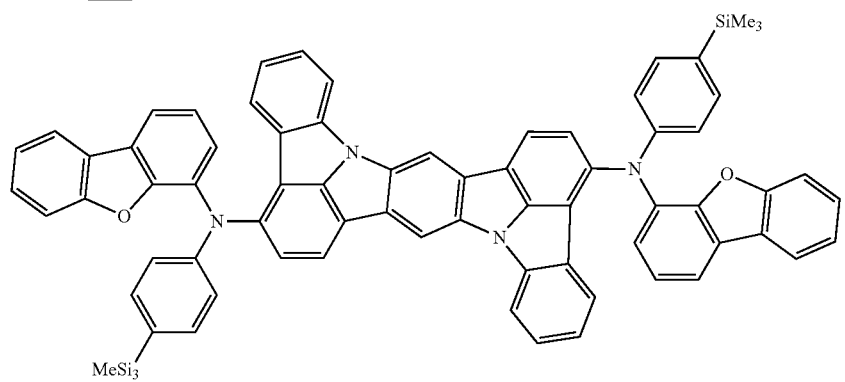

-continued
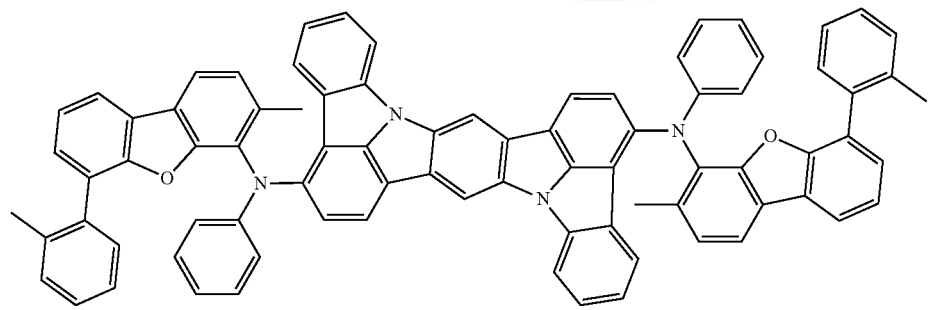
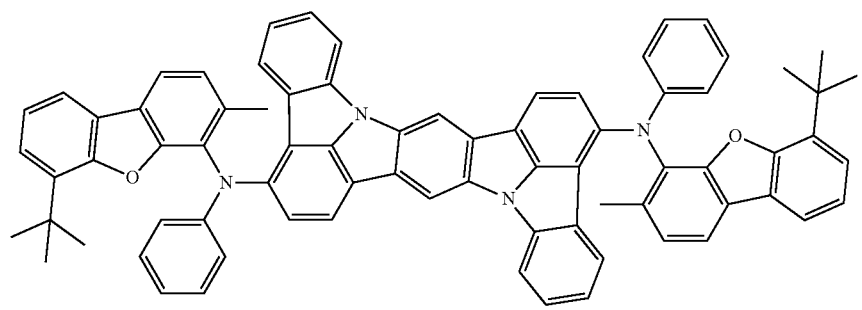
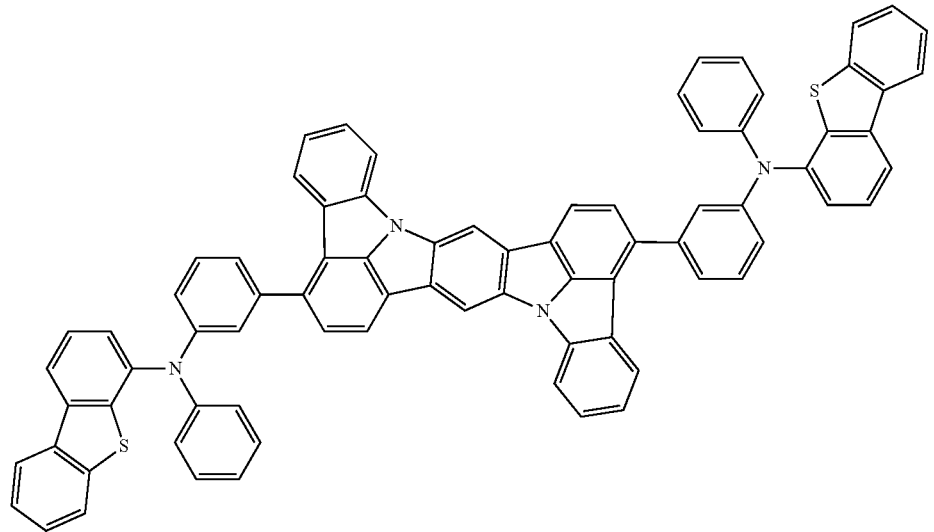
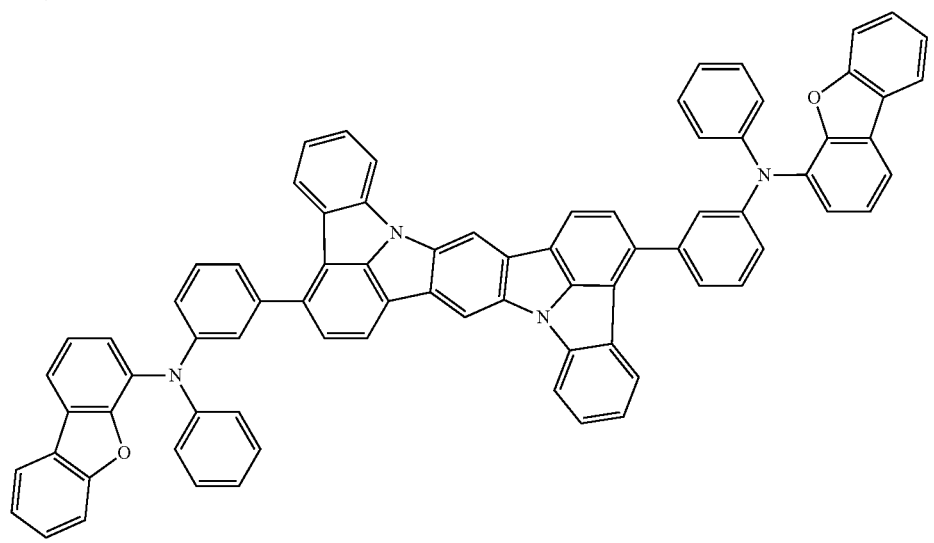

-continued
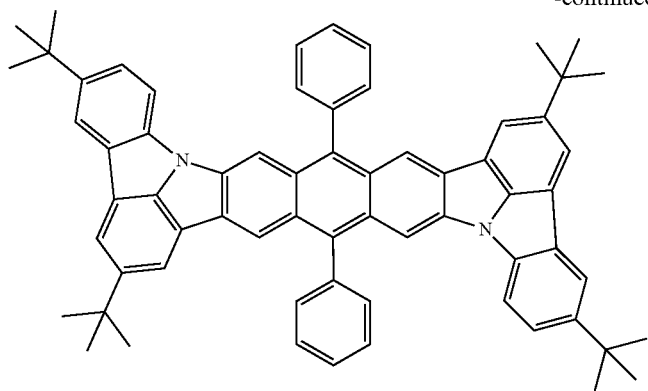
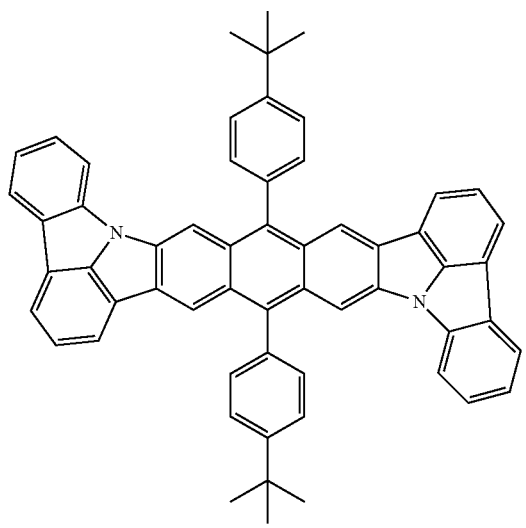
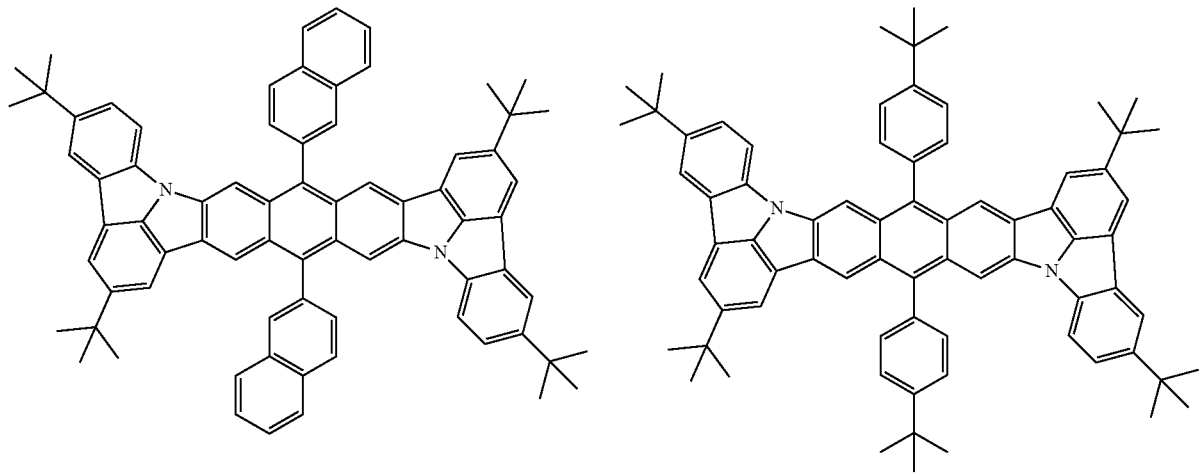

-continued
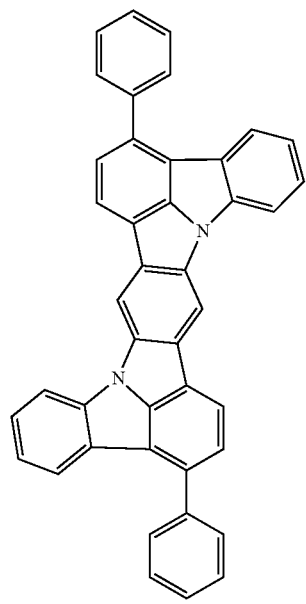
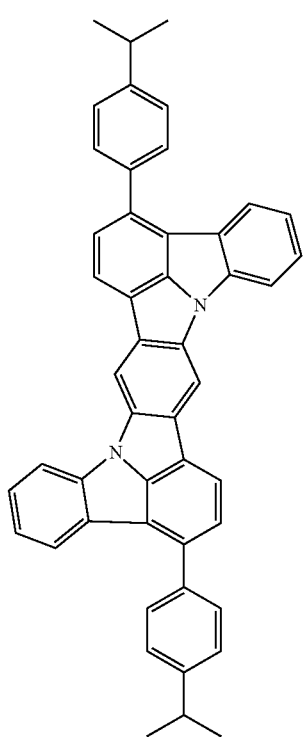
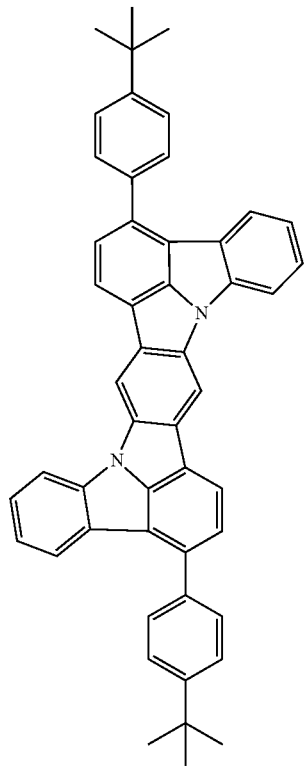
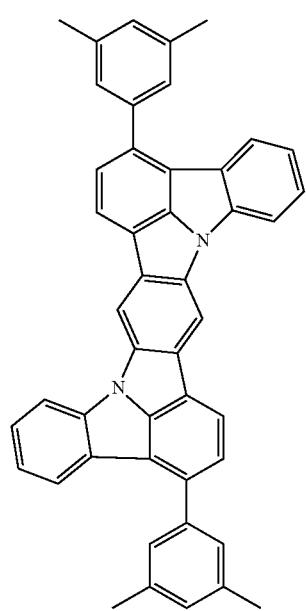
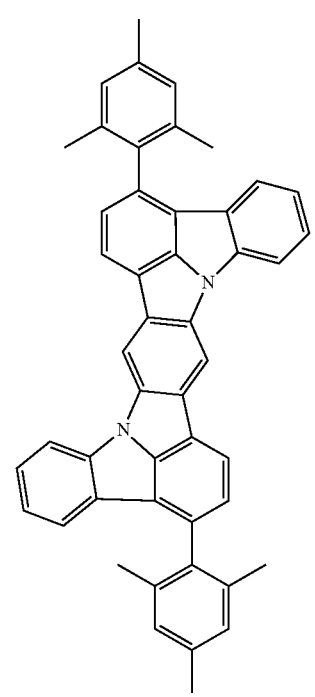
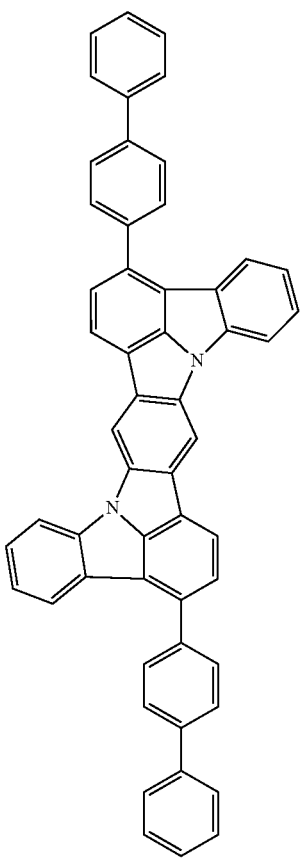

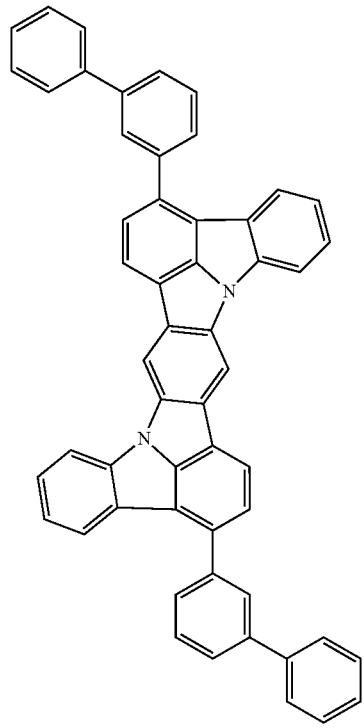
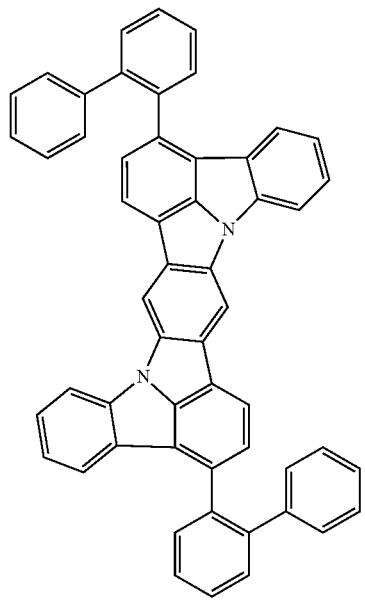
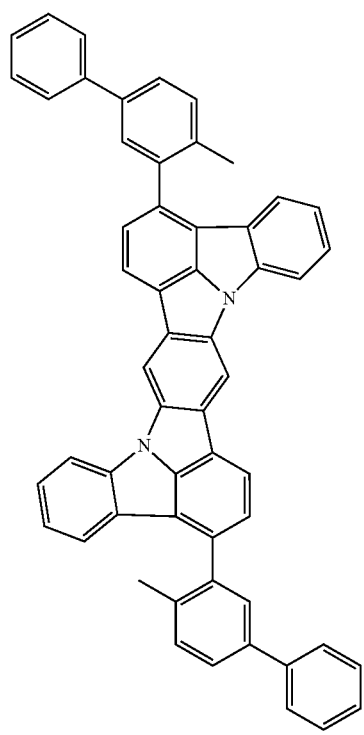
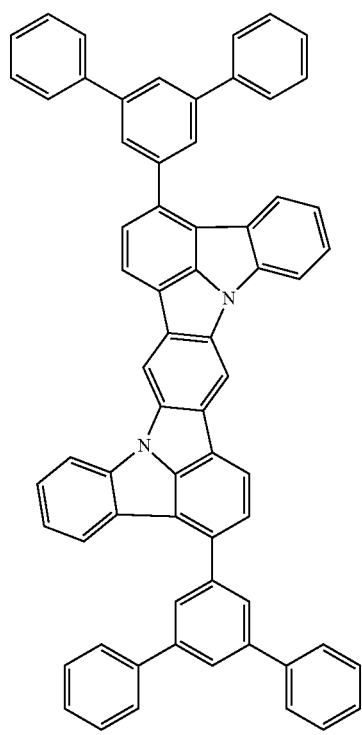

75 76
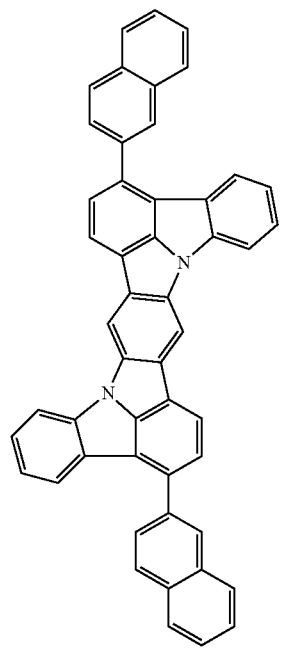 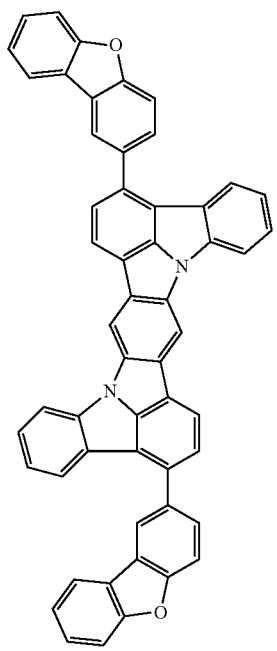 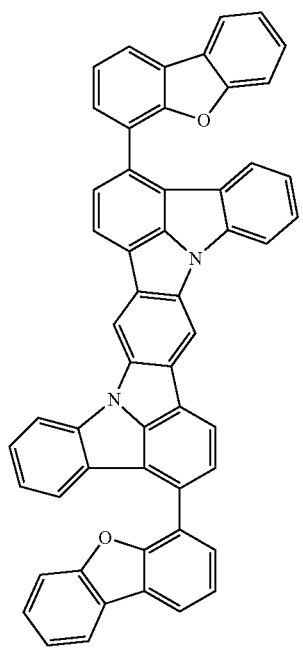
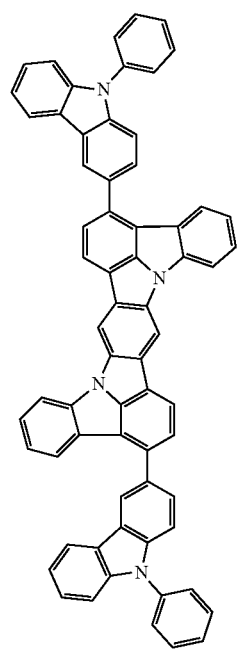 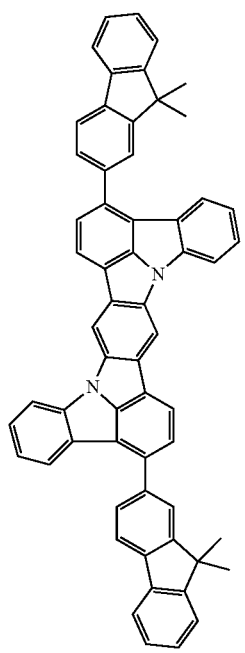 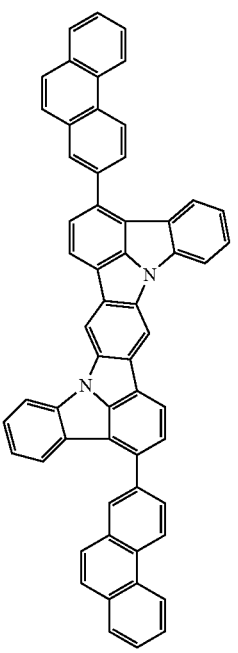 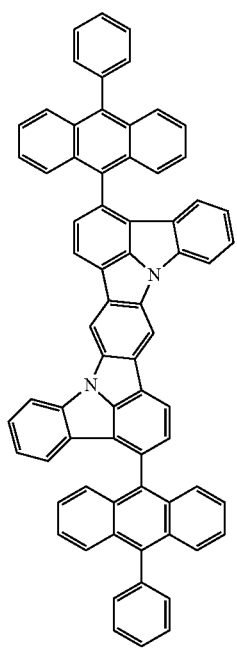

-continued
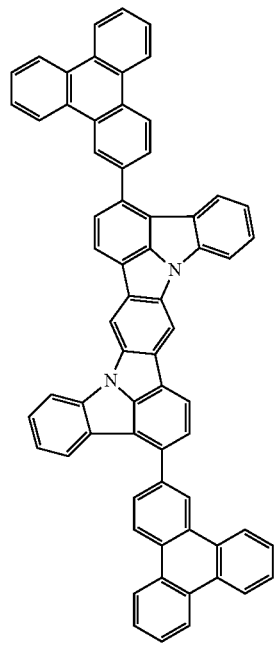
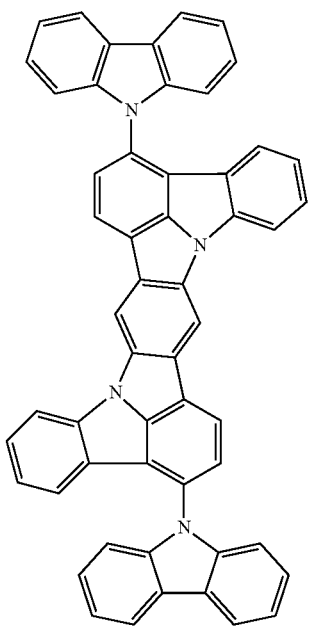
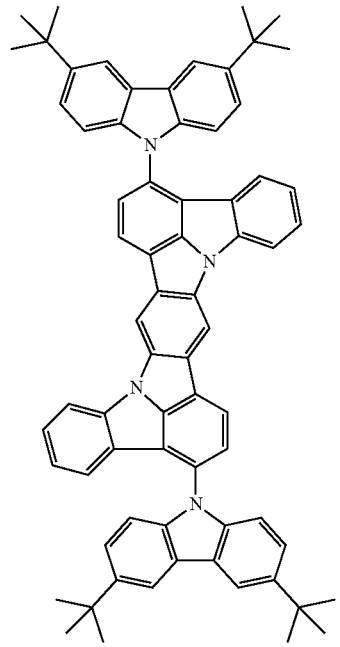
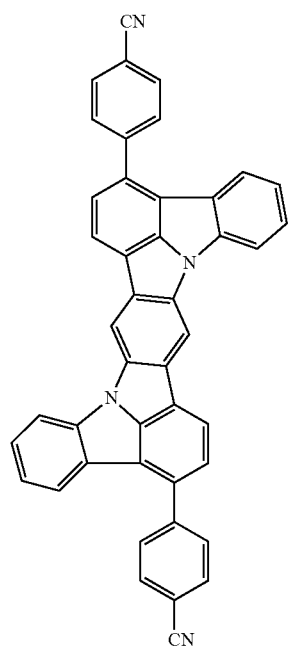
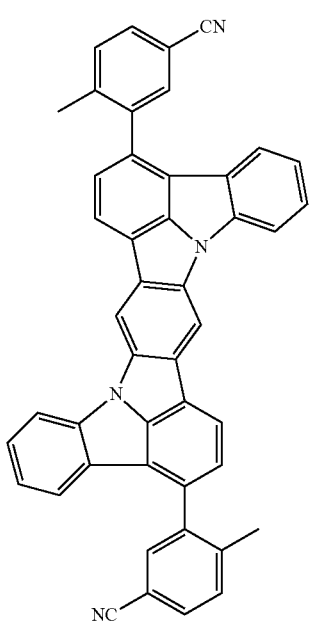
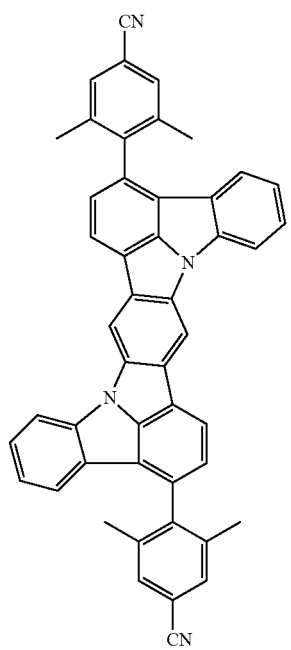

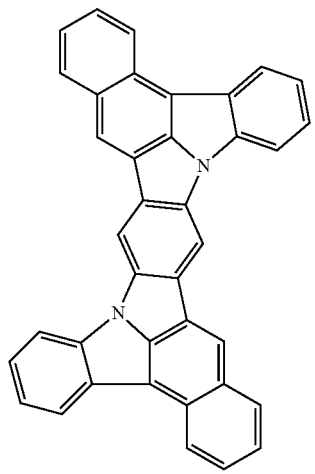 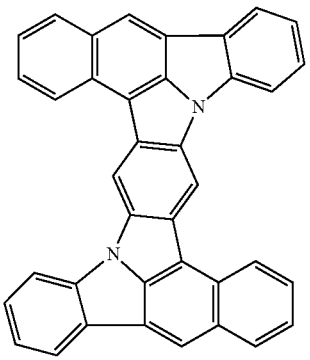 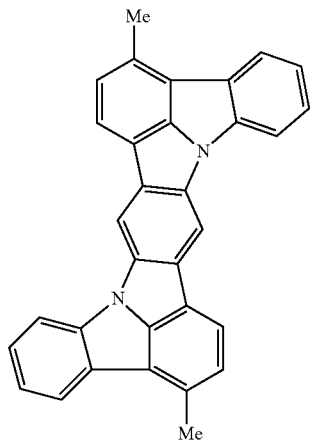
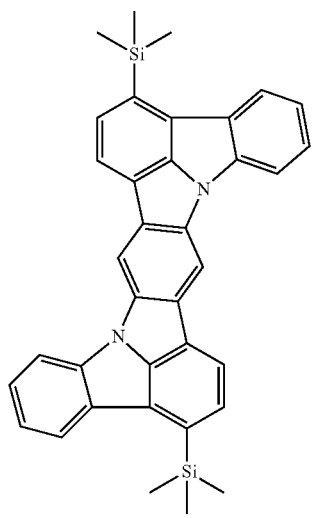 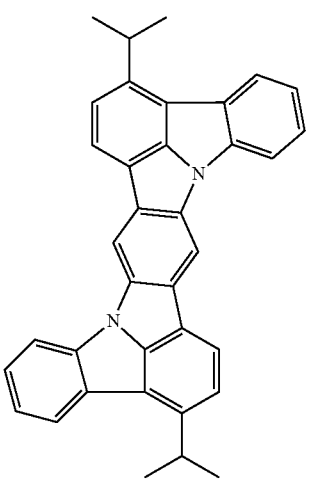 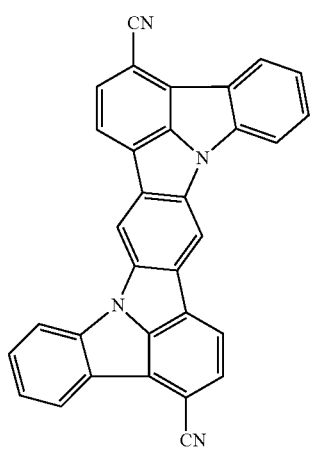
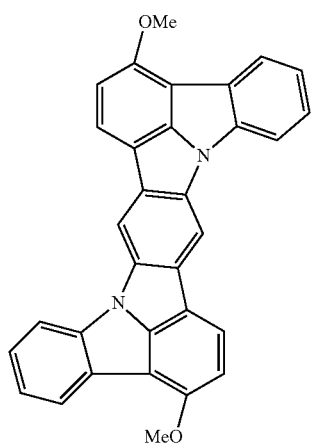 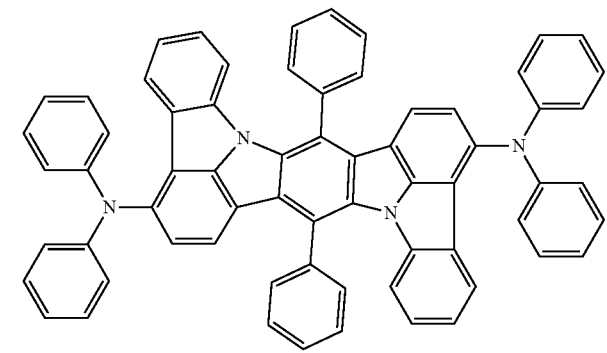

-continued
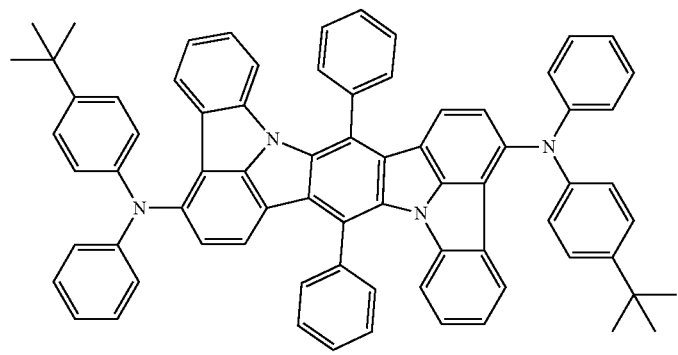
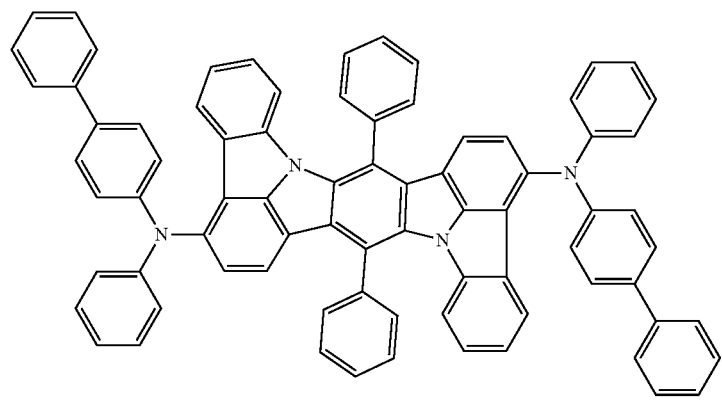
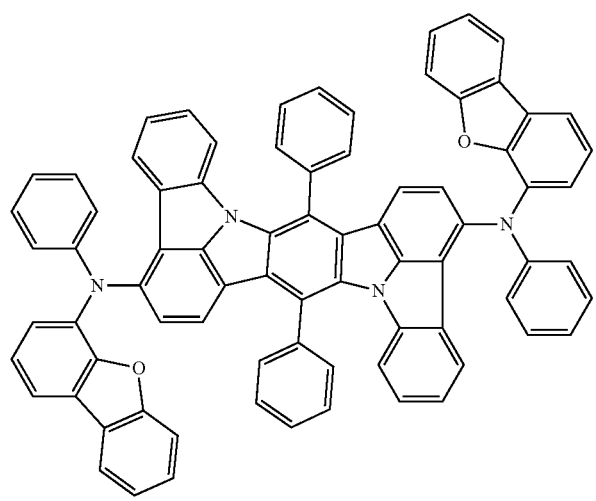

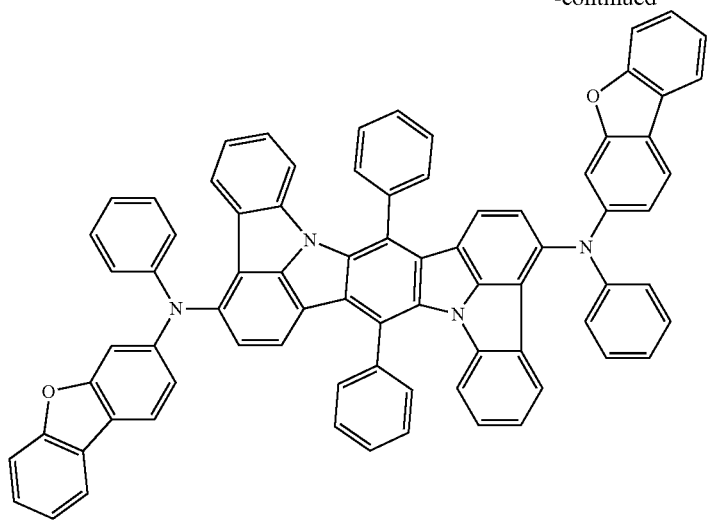
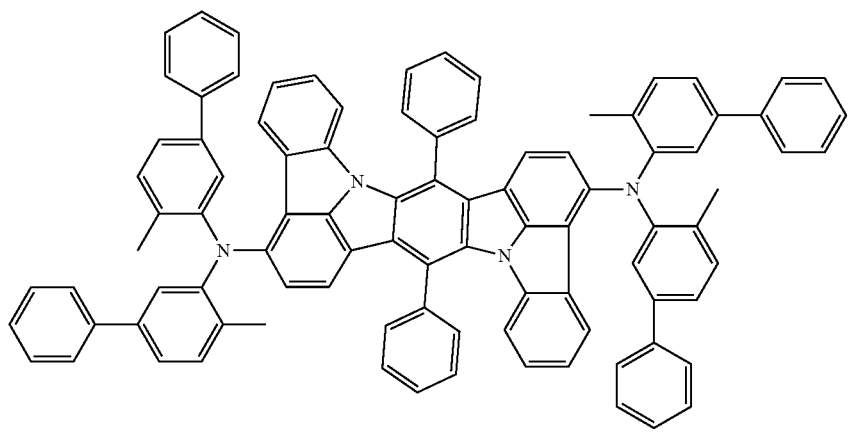
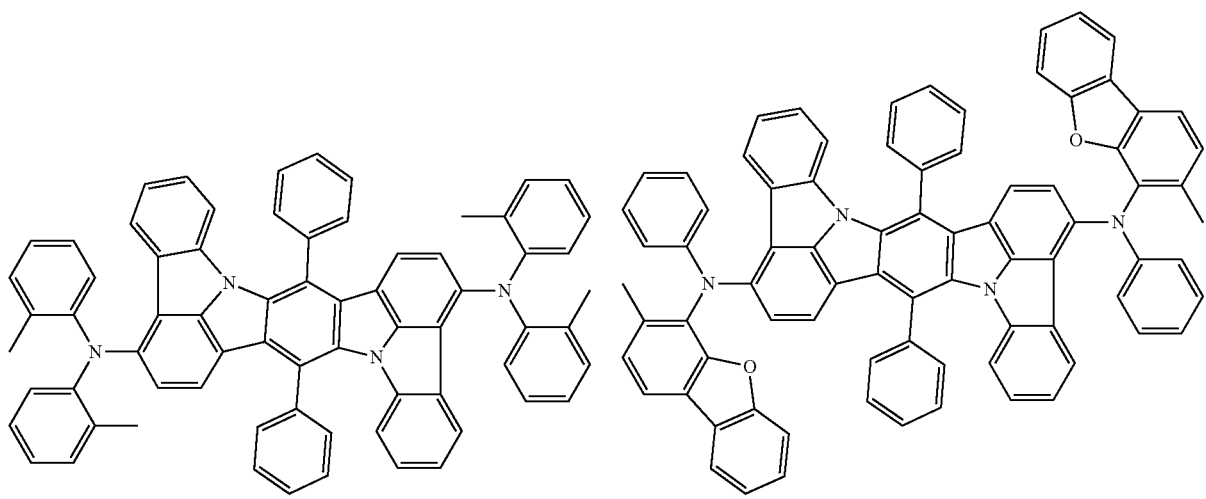

85
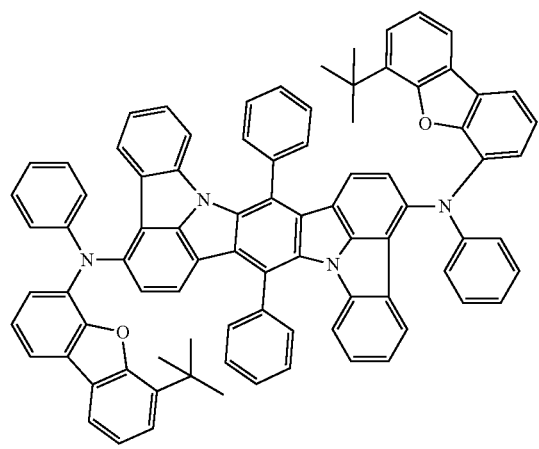
86
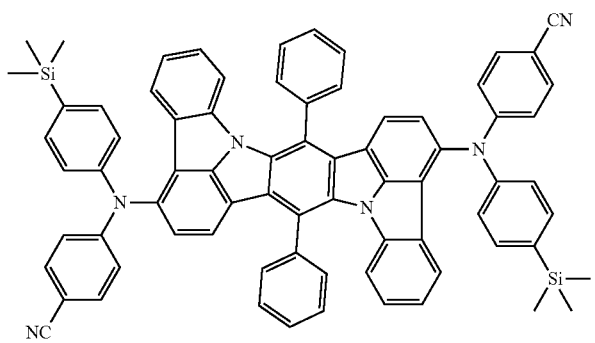
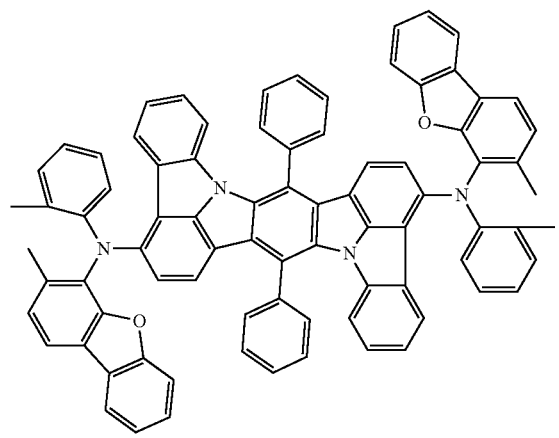
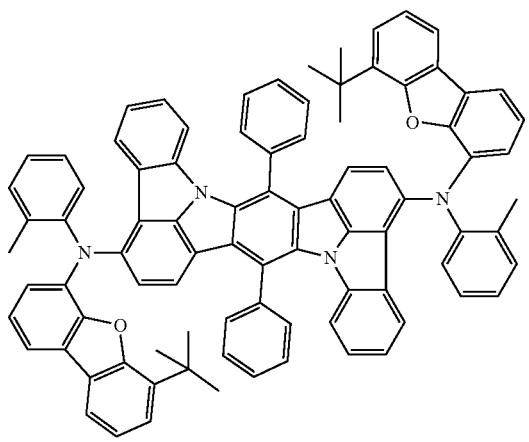
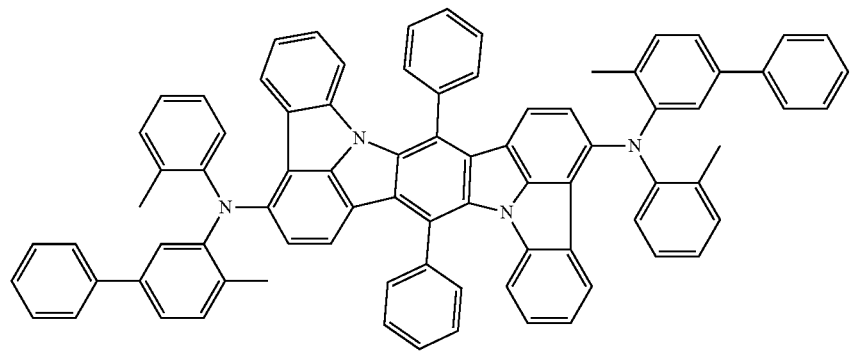

-continued
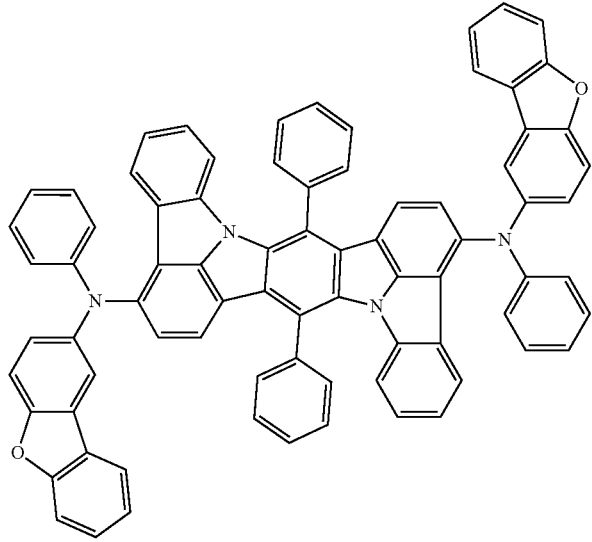
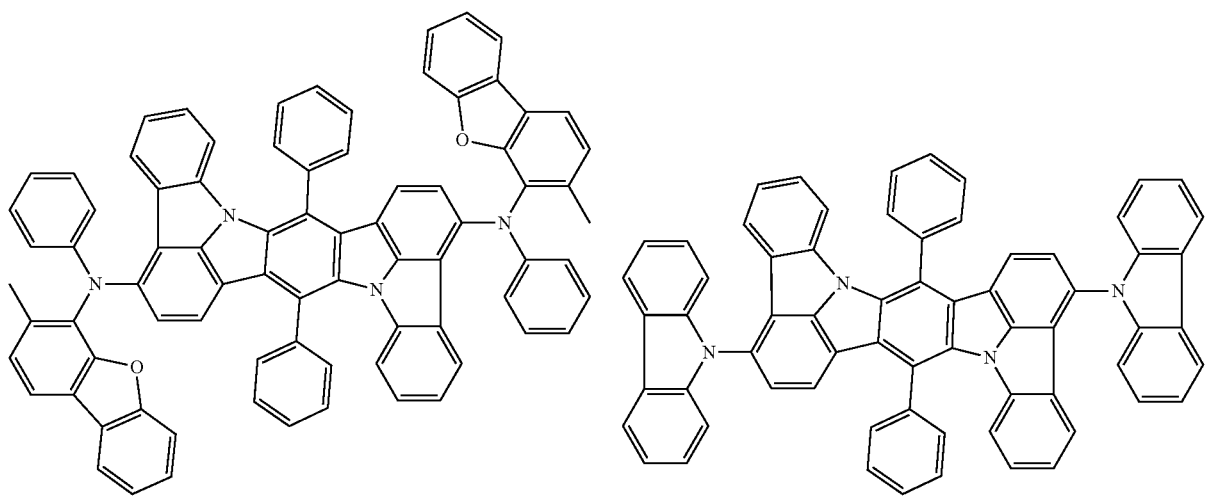
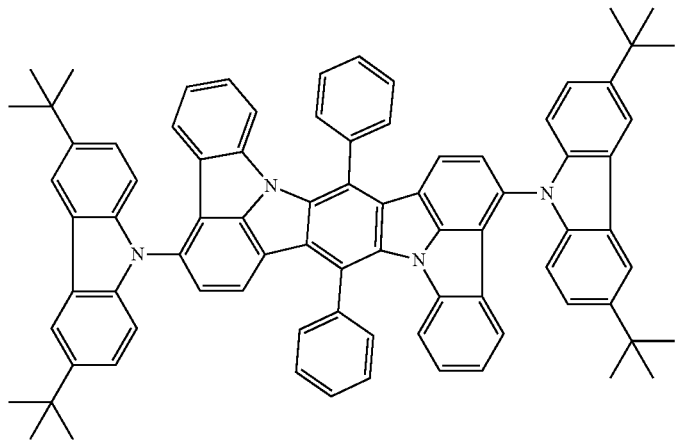

-continued
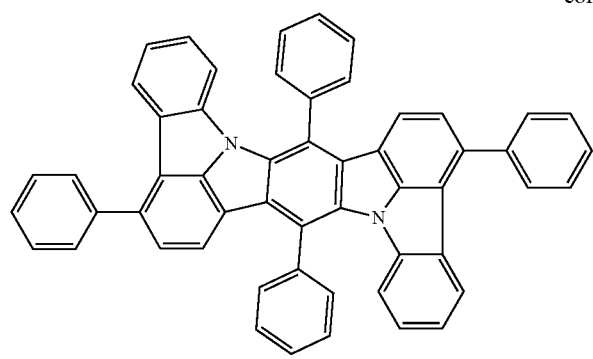
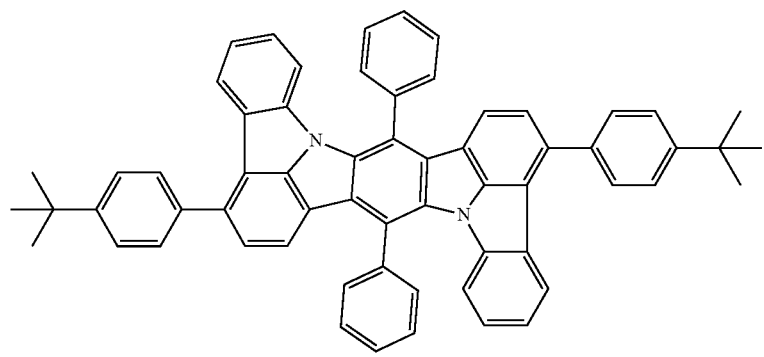
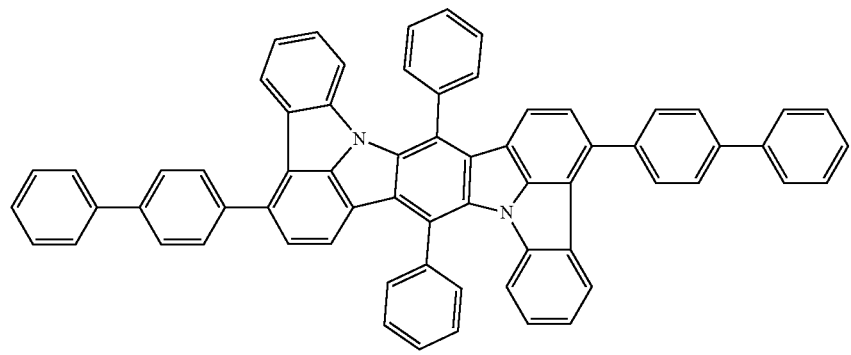
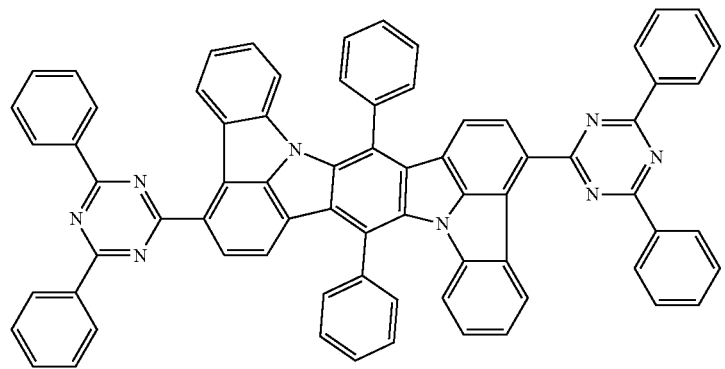

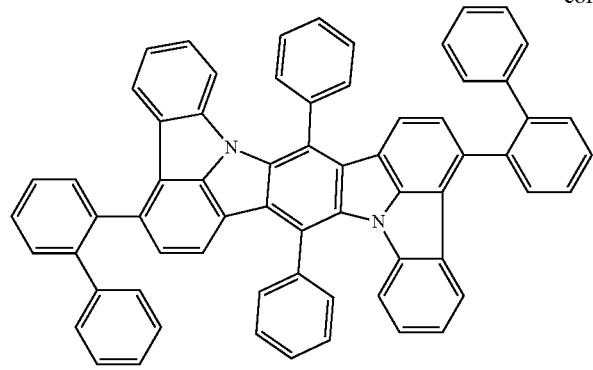
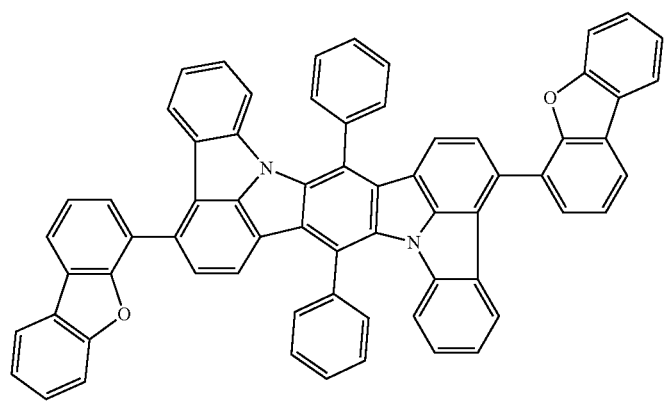
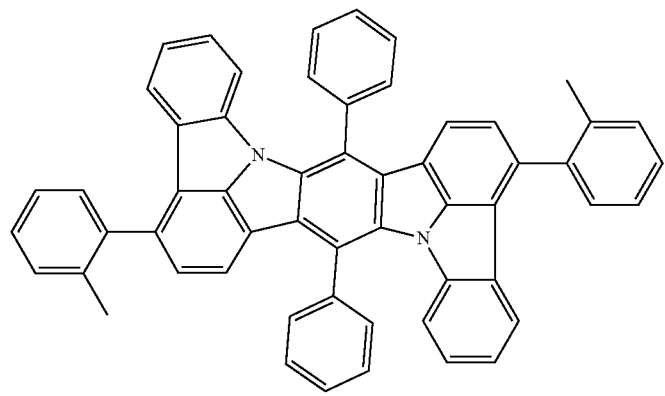
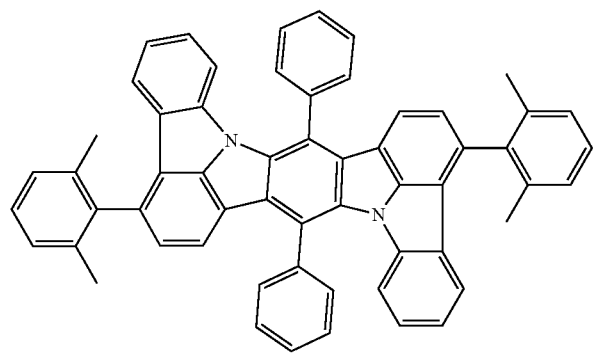

-continued
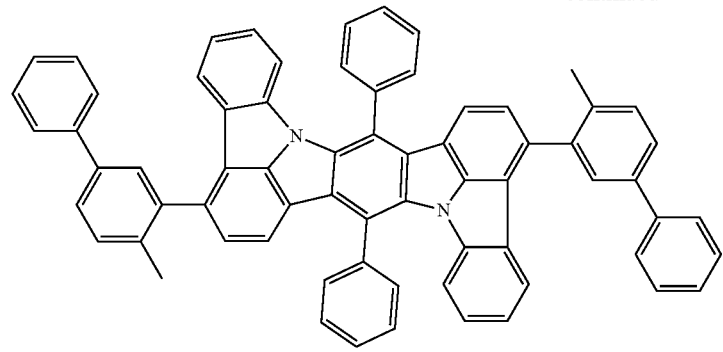
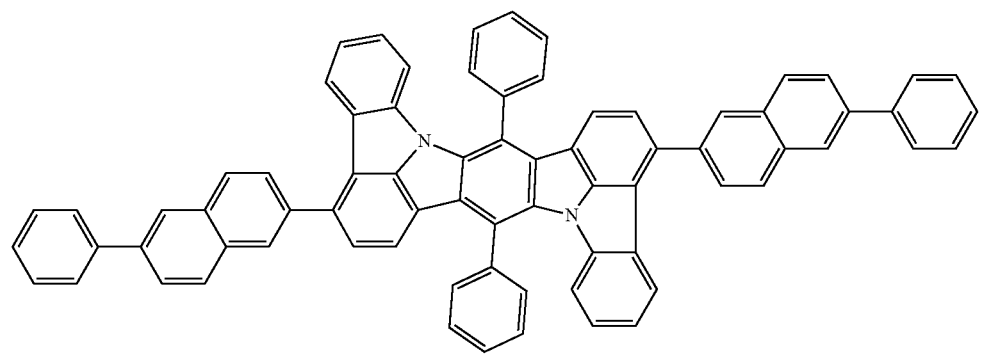
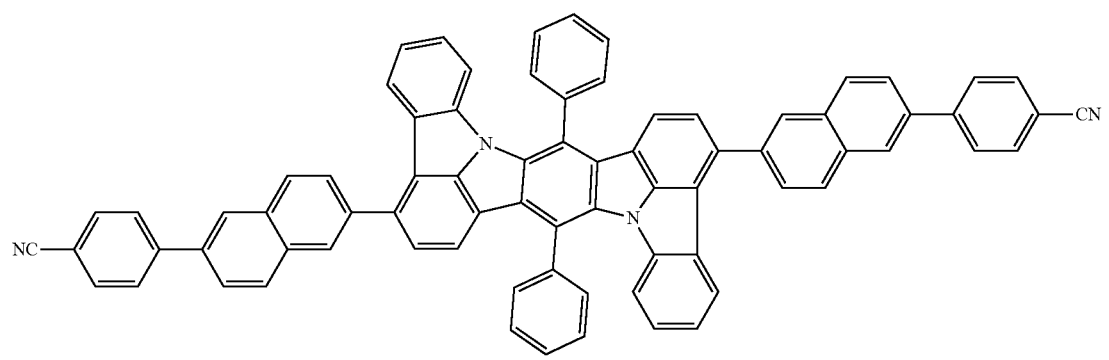
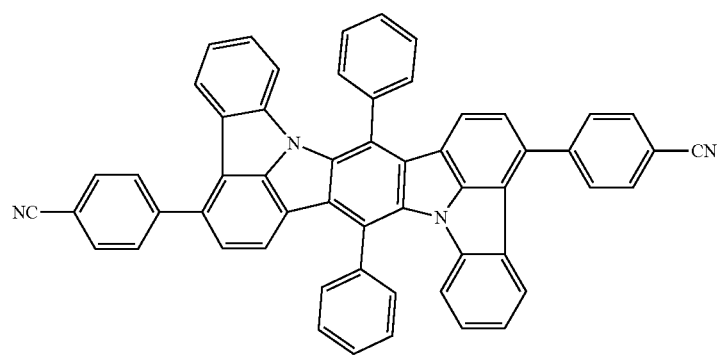

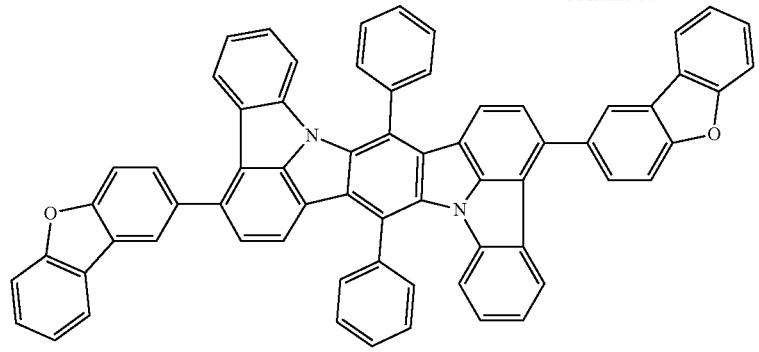
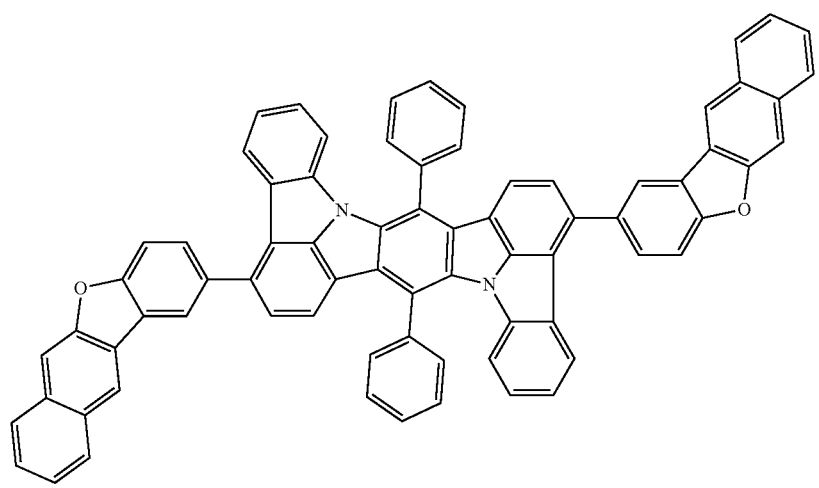
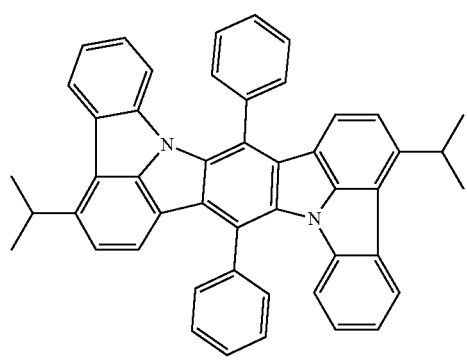
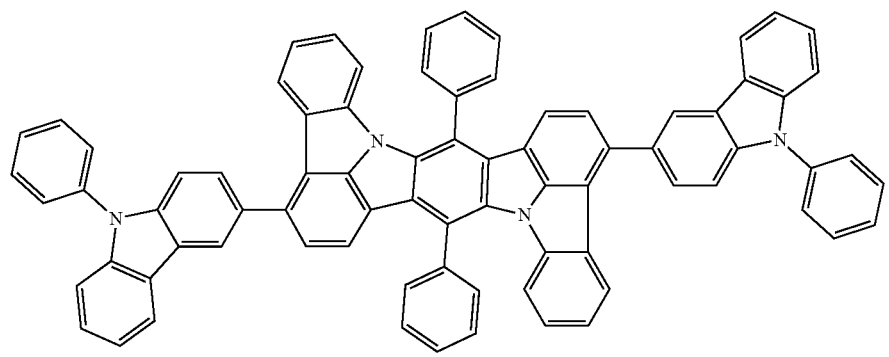

-continued
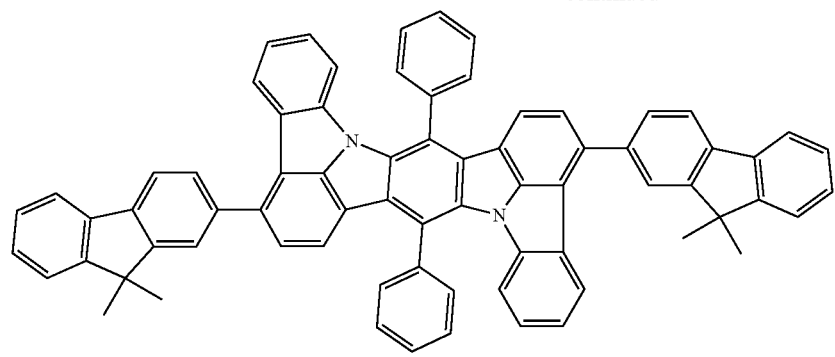
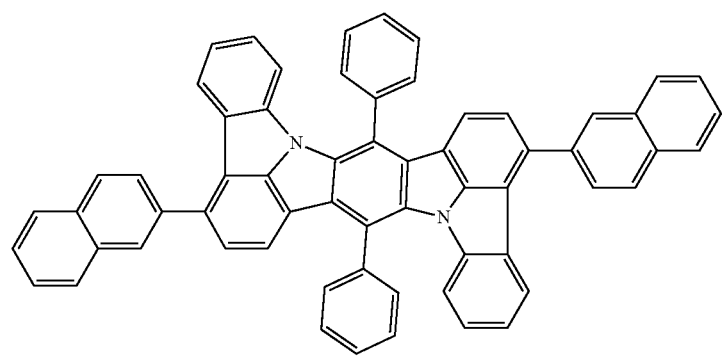
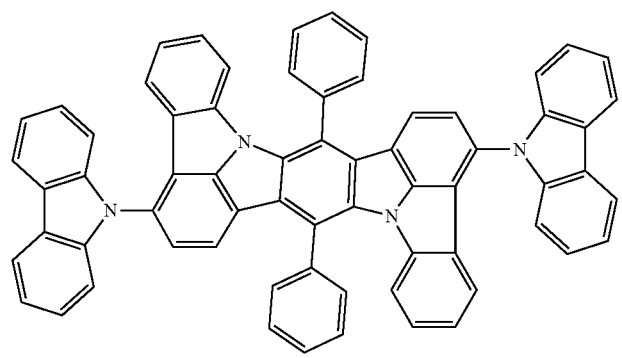
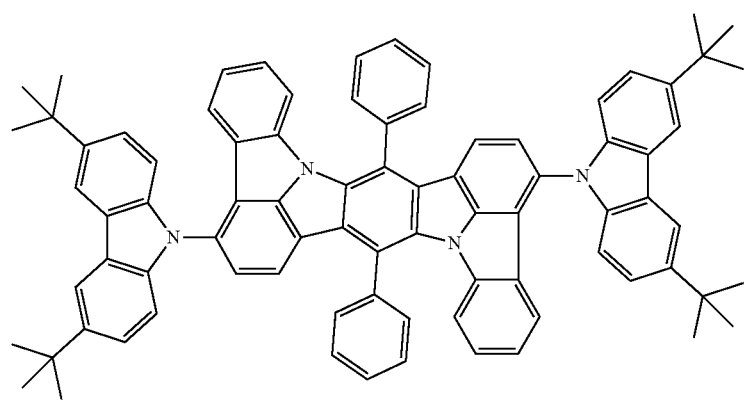

-continued
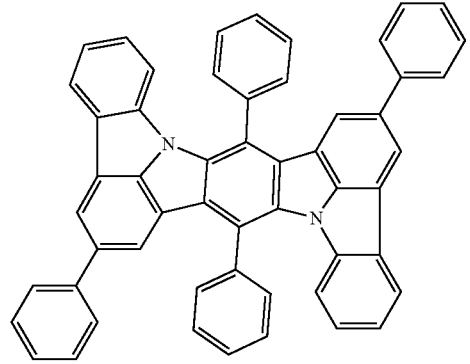
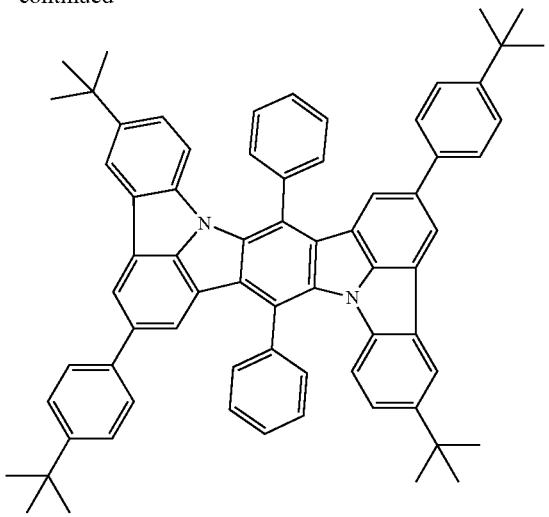
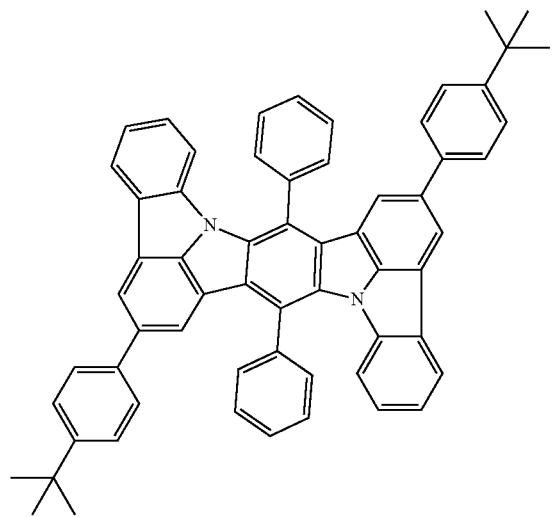
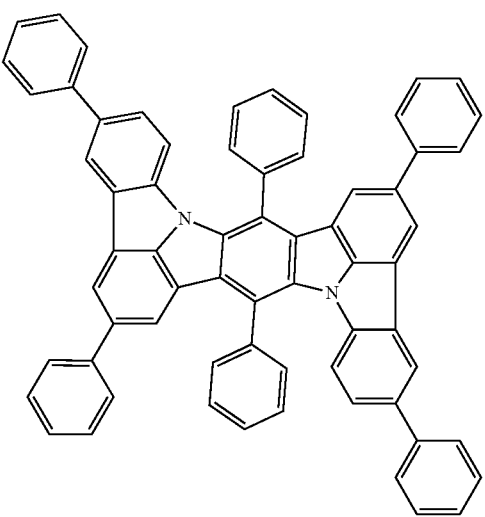
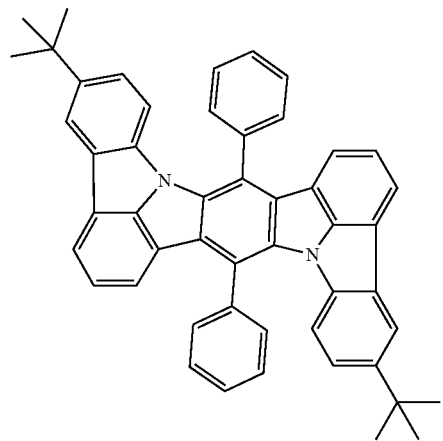
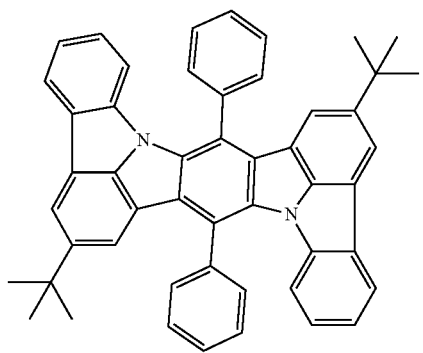

-continued
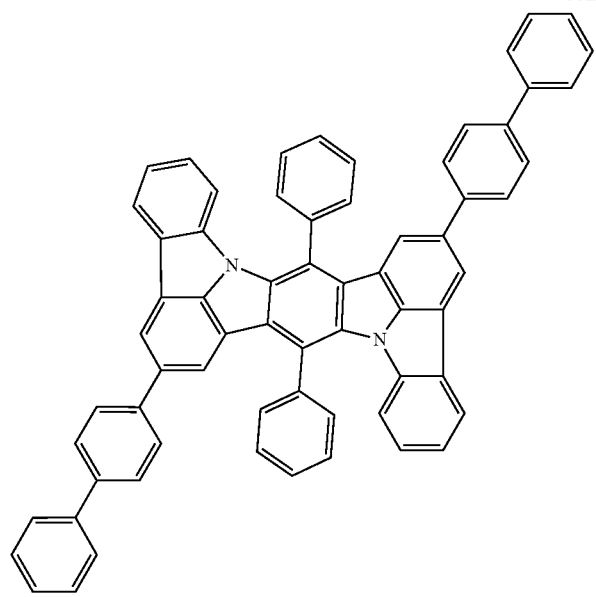
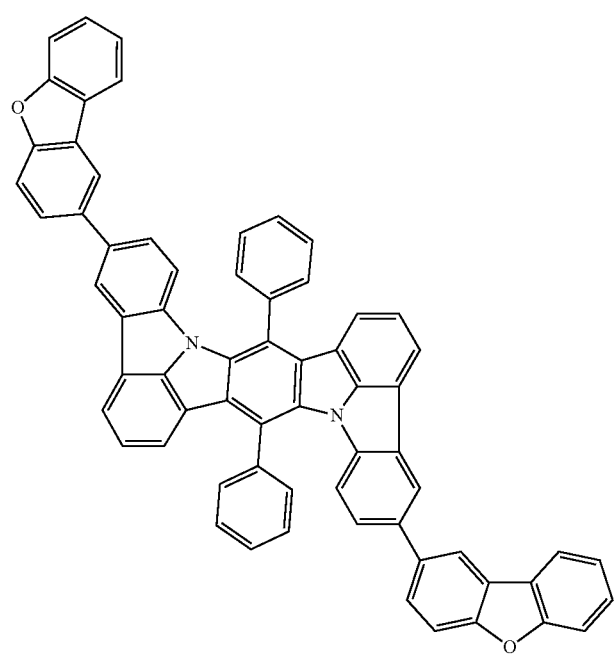

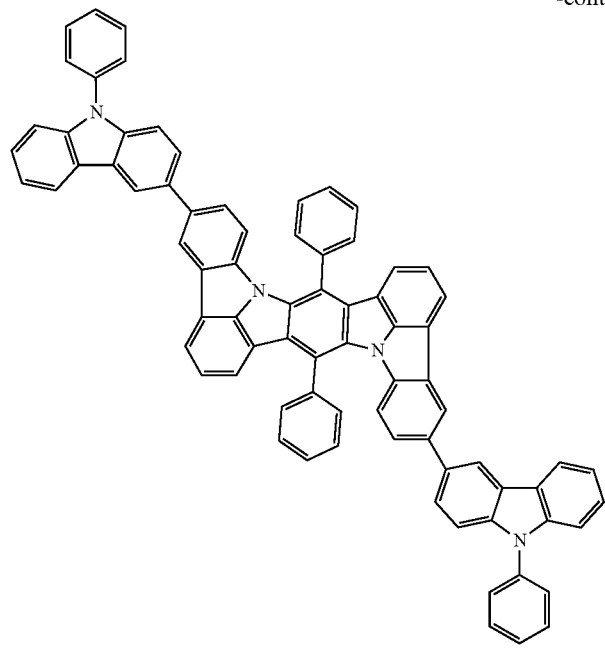
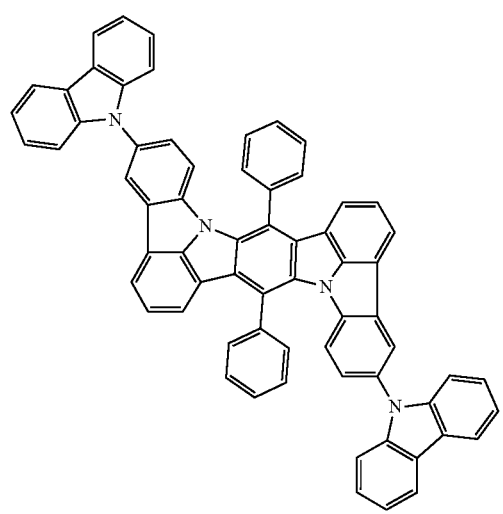
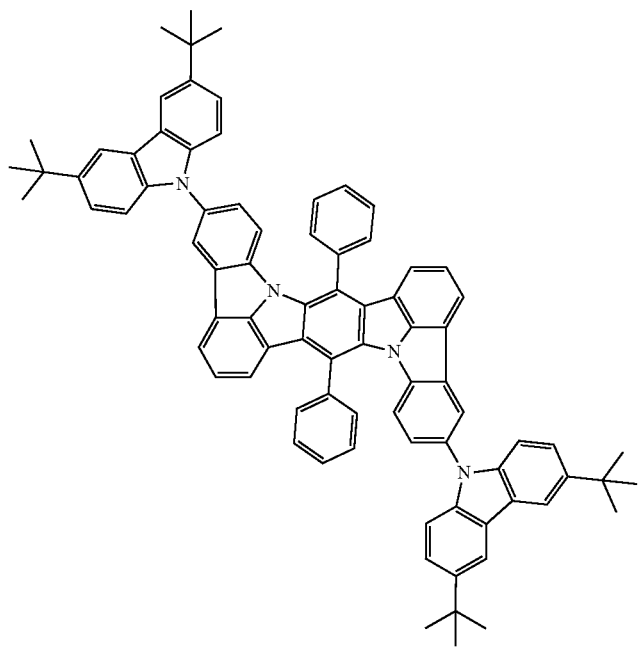

105
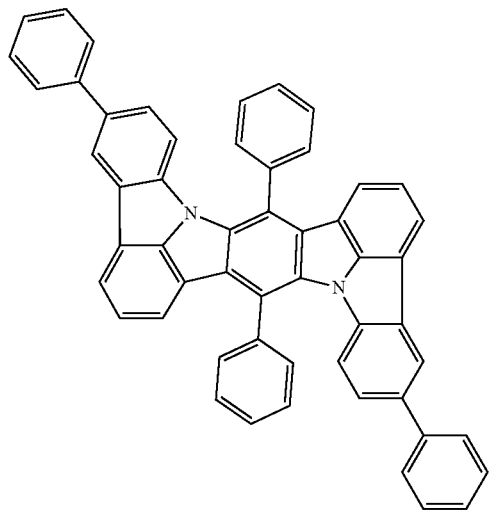
106
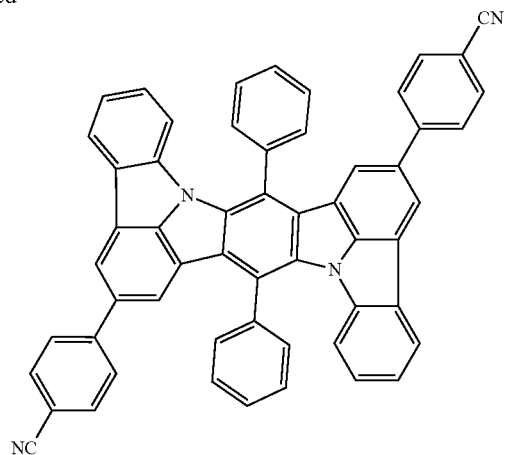
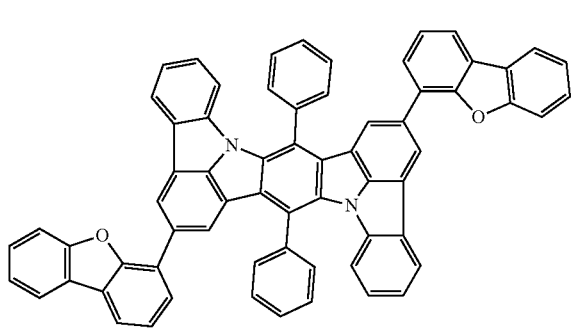
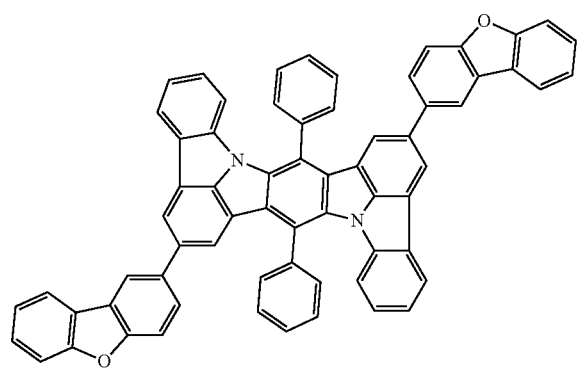
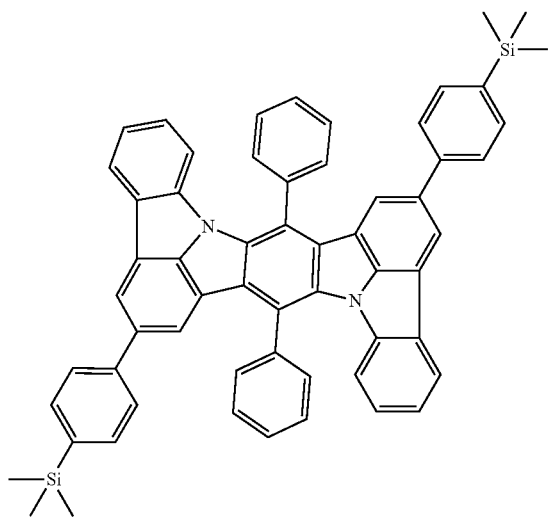
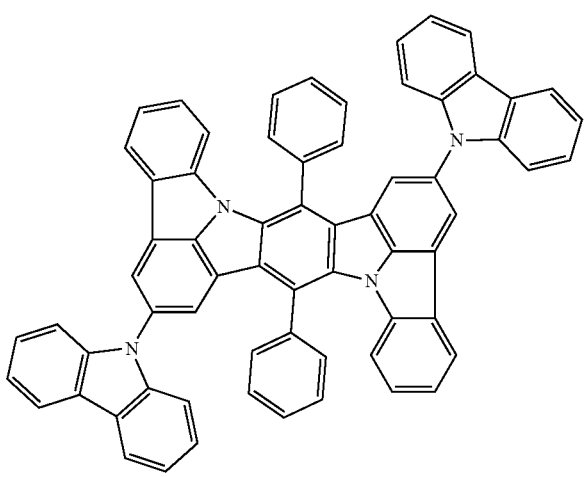

-continued
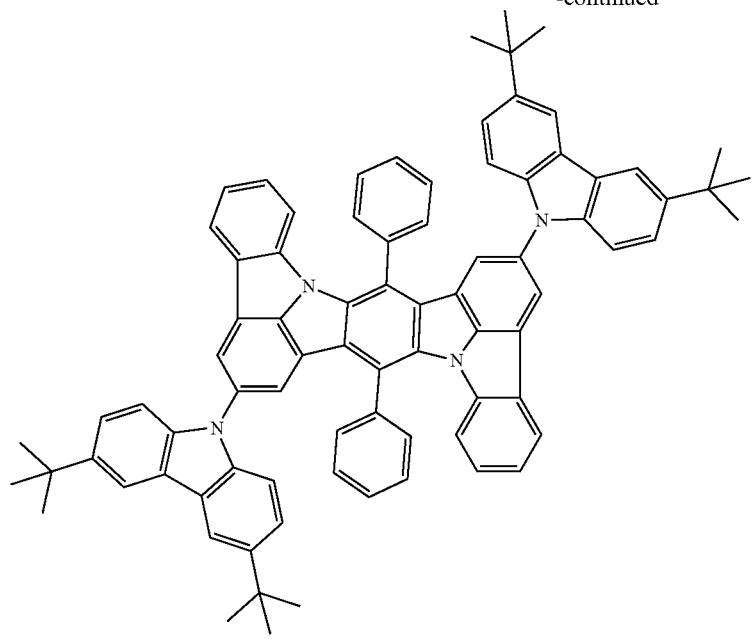
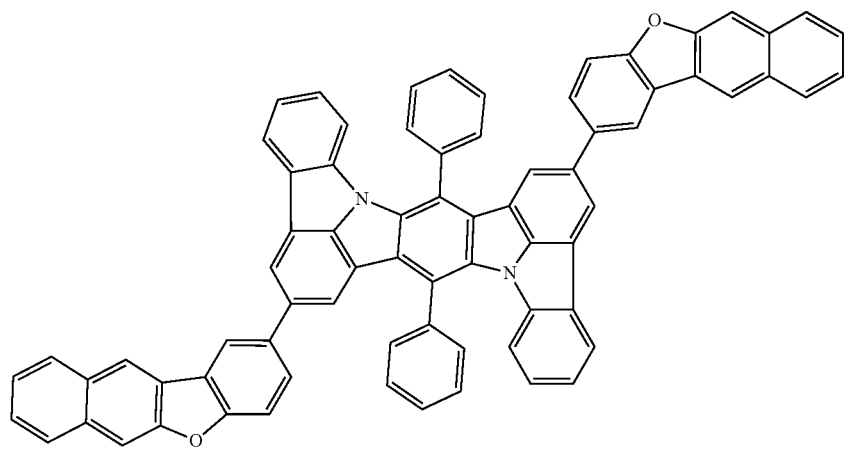
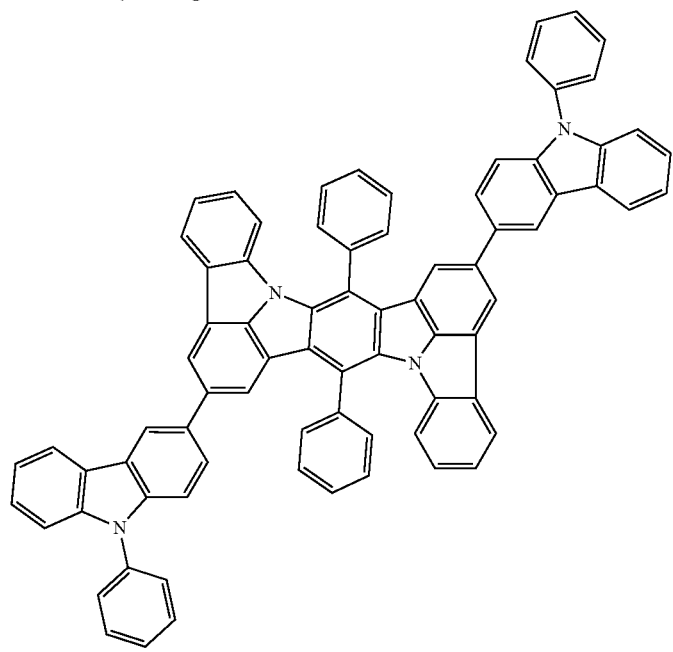

-continued
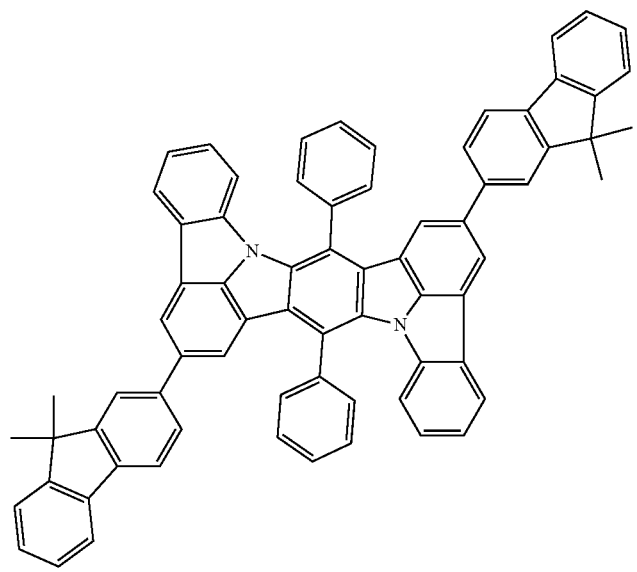
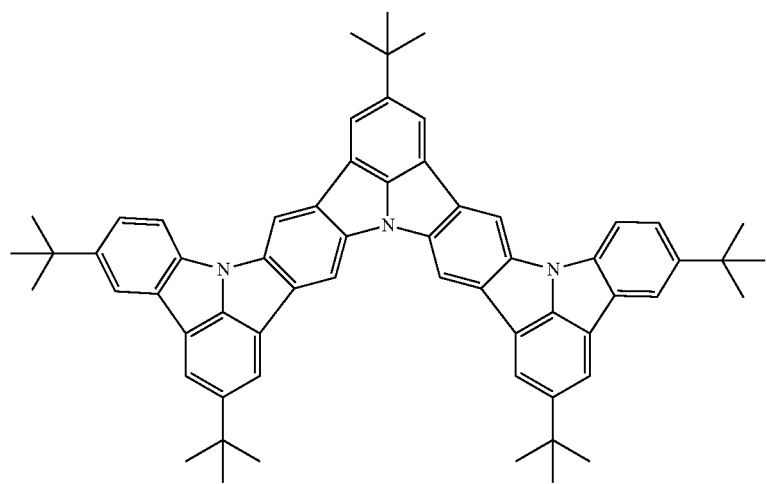
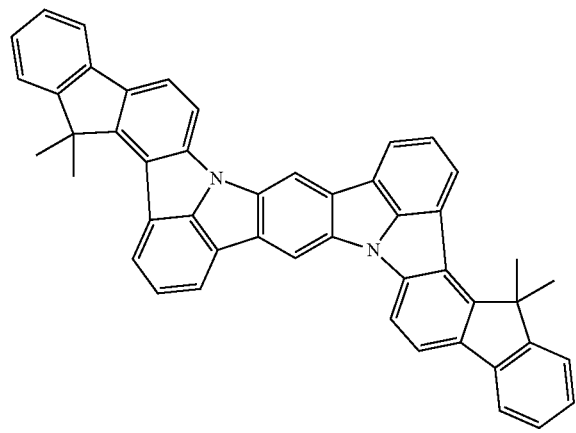
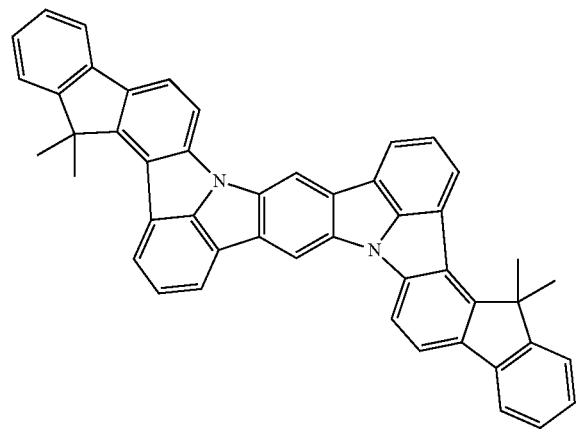

-continued
111
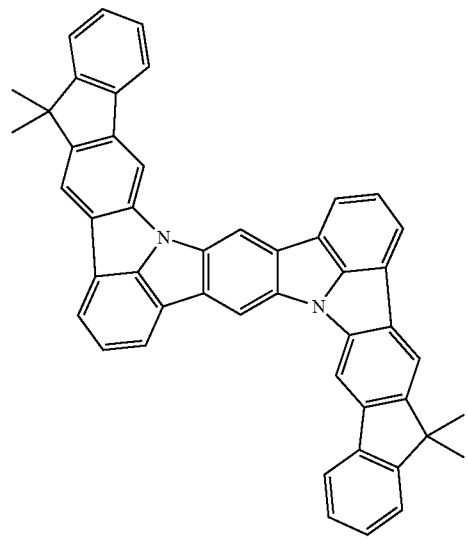
112
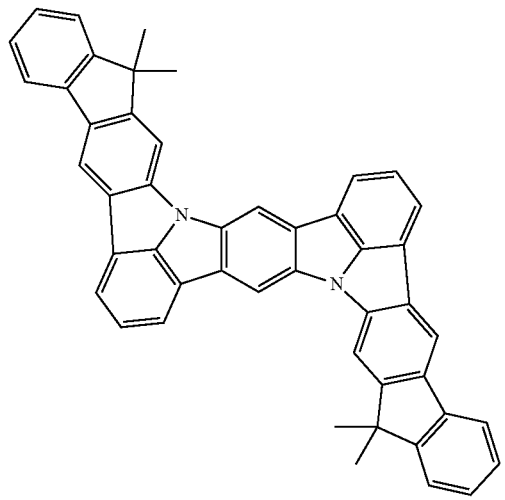
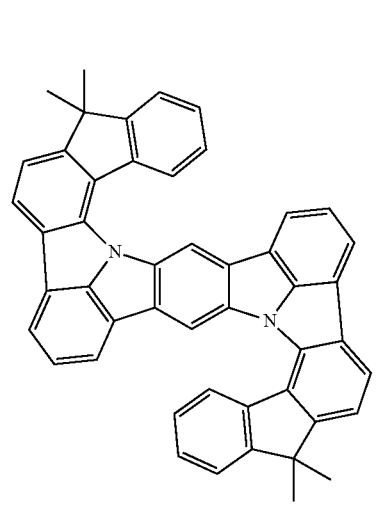
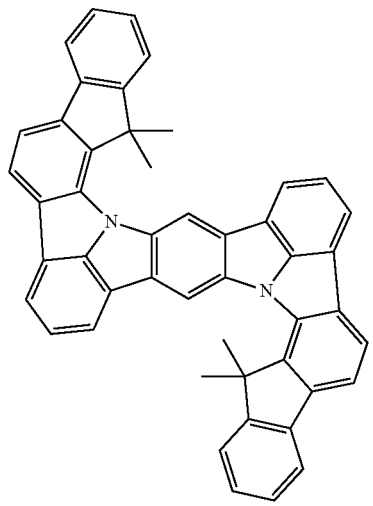
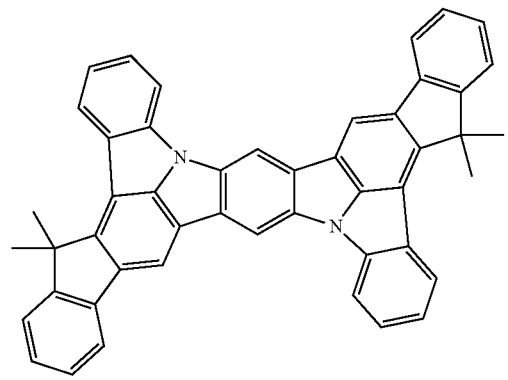
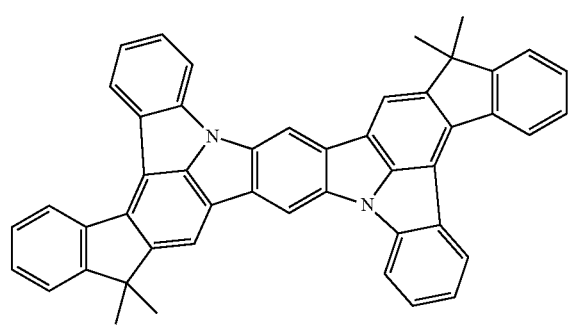

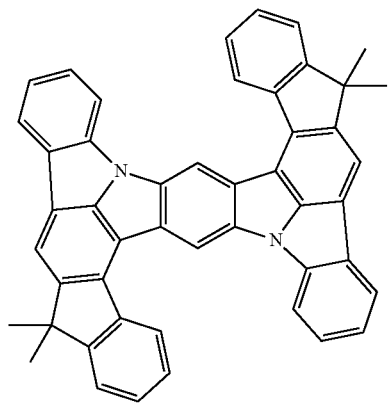
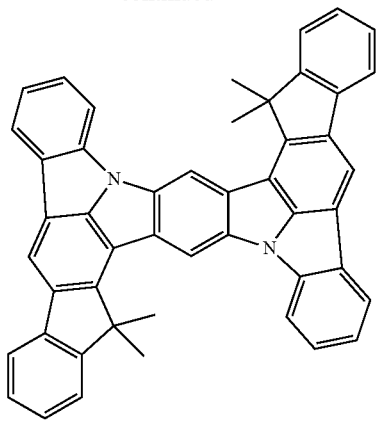
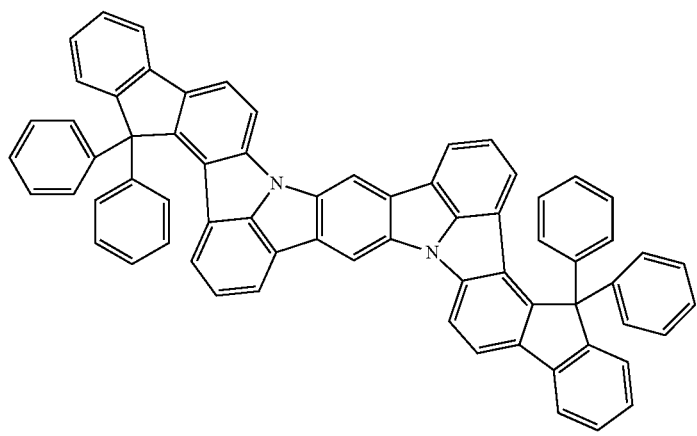
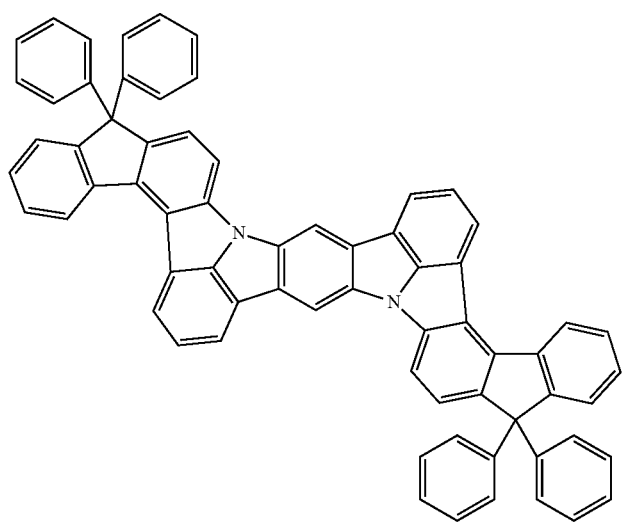

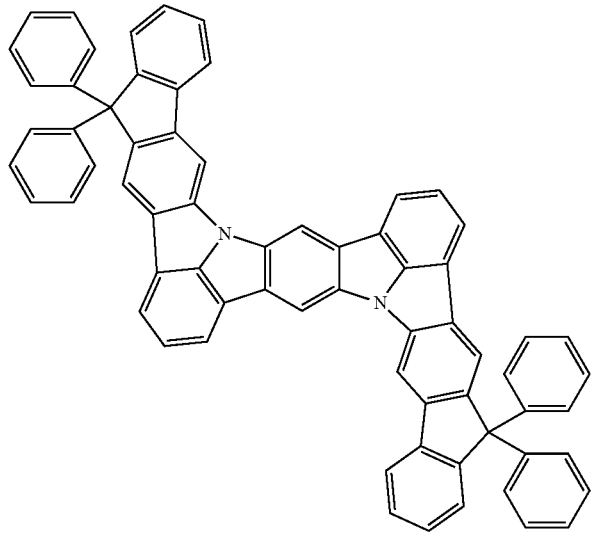
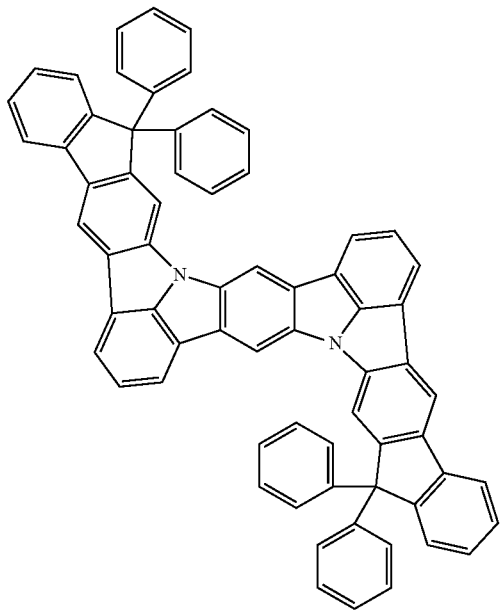
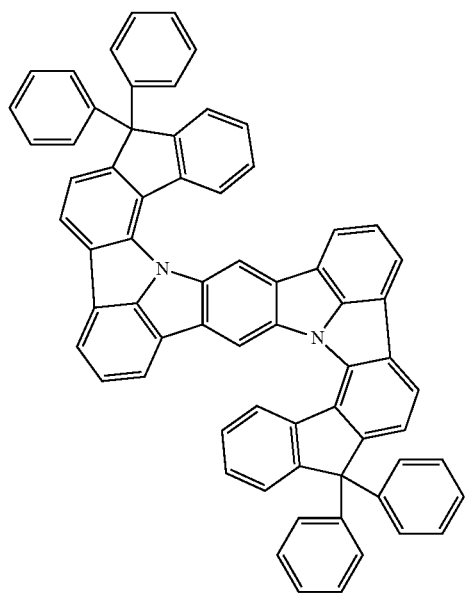
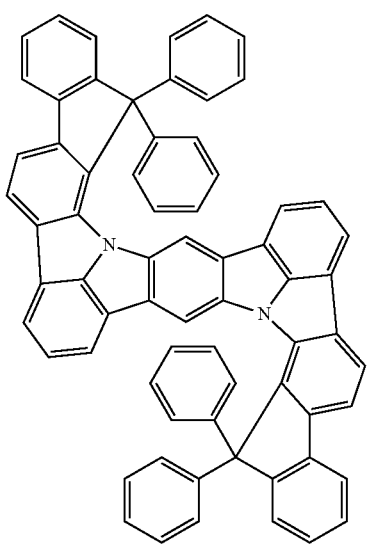
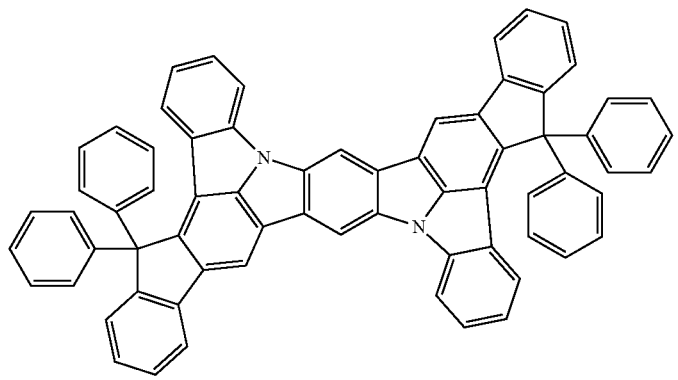

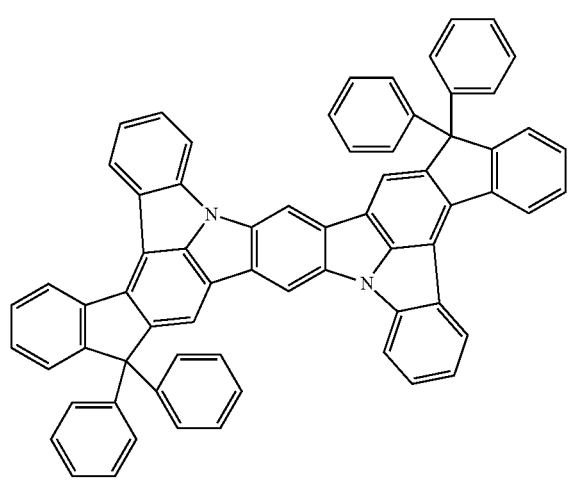
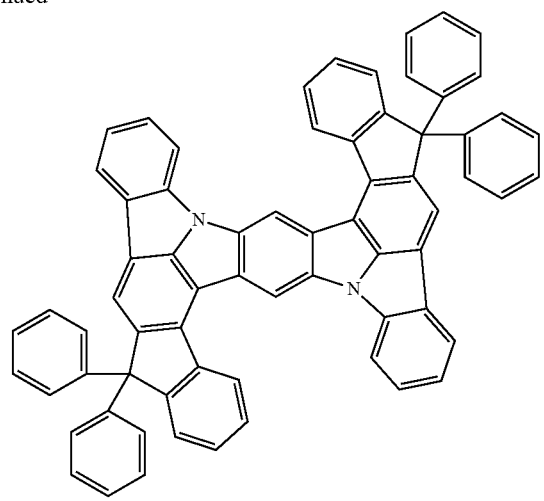
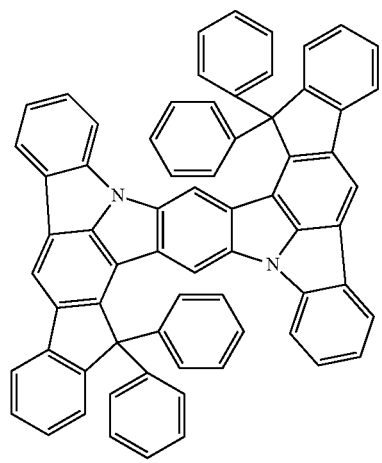
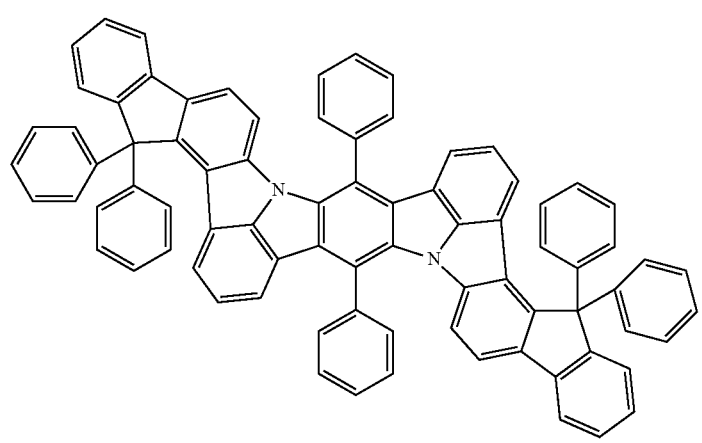
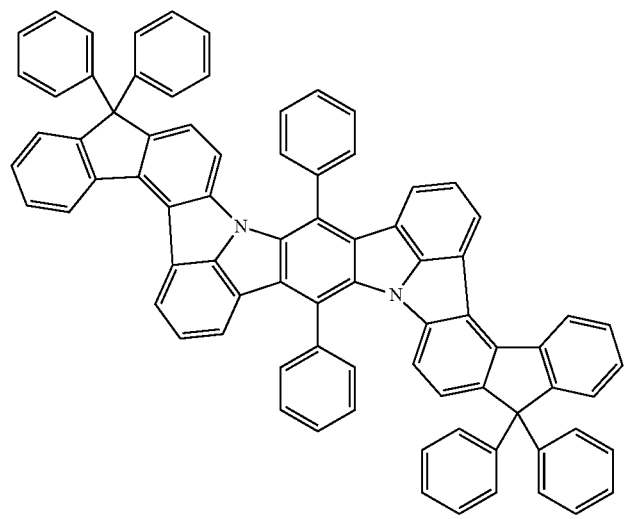

119
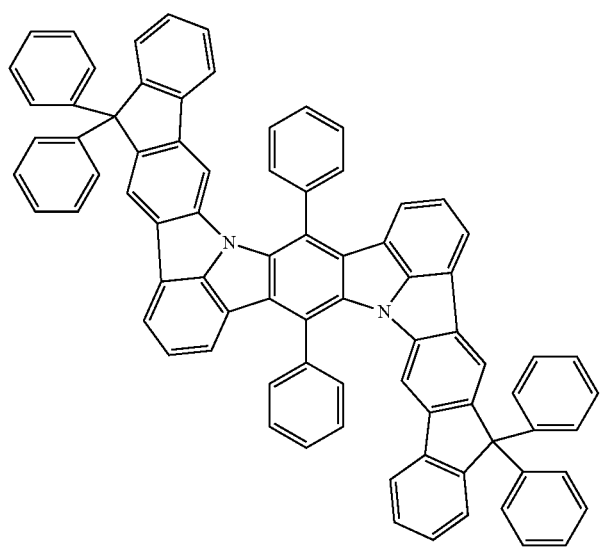
120
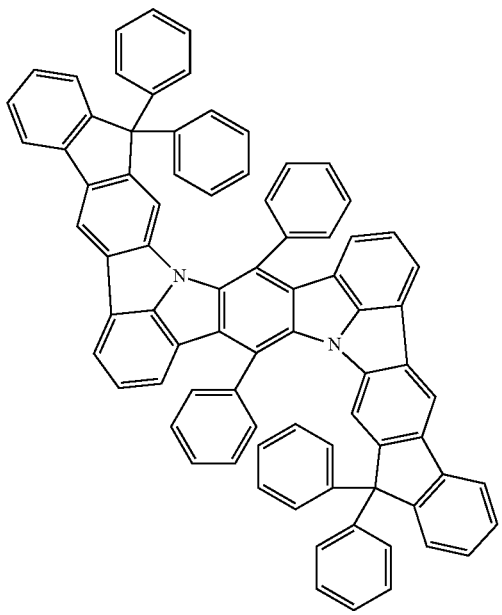
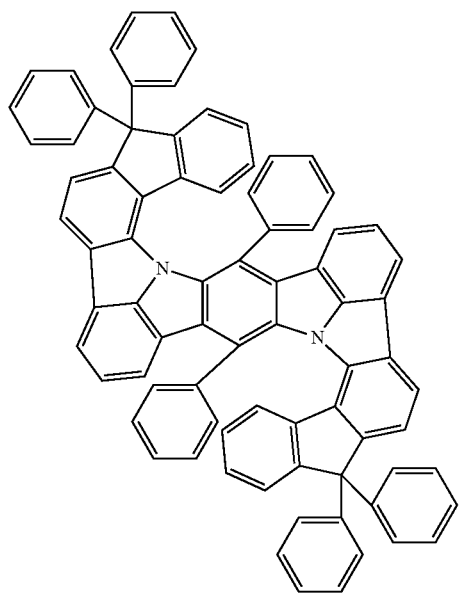
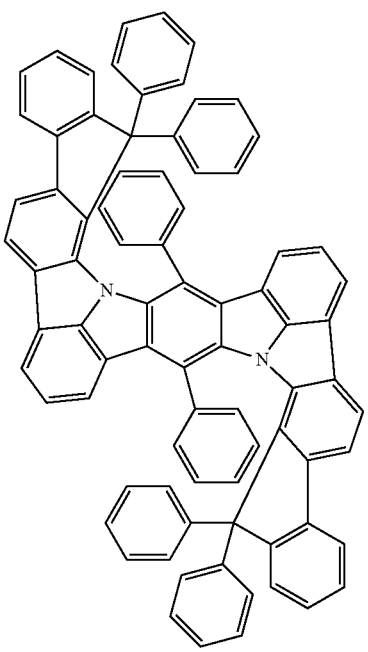
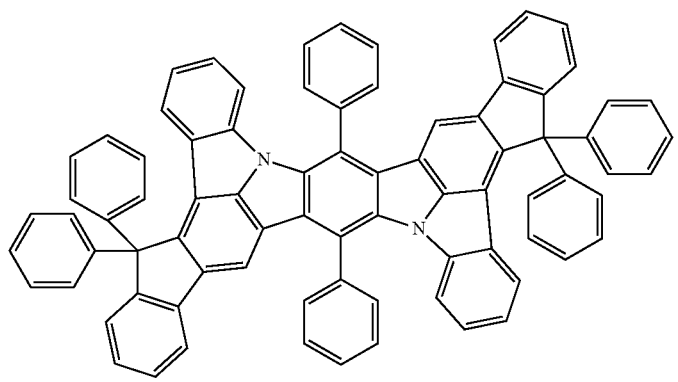

-continued
121 122
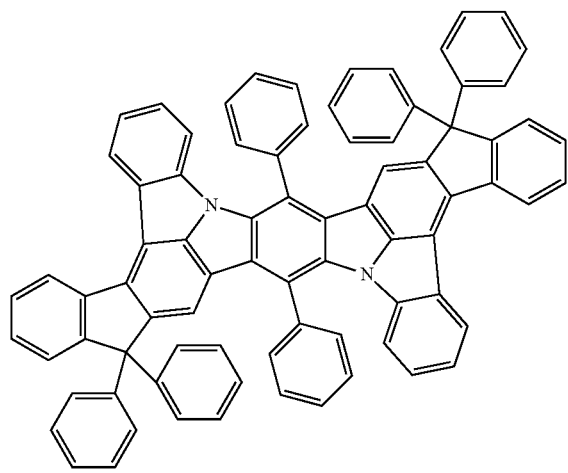
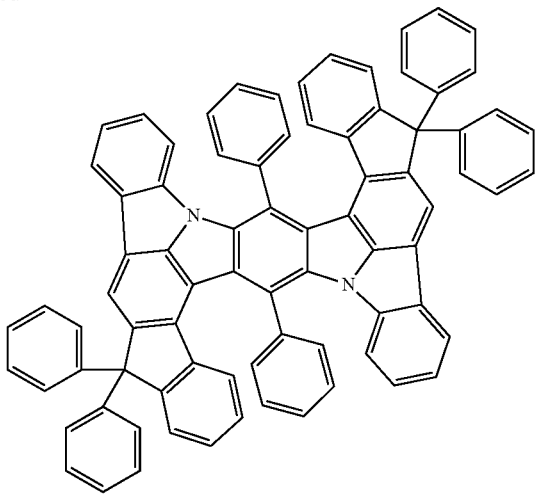
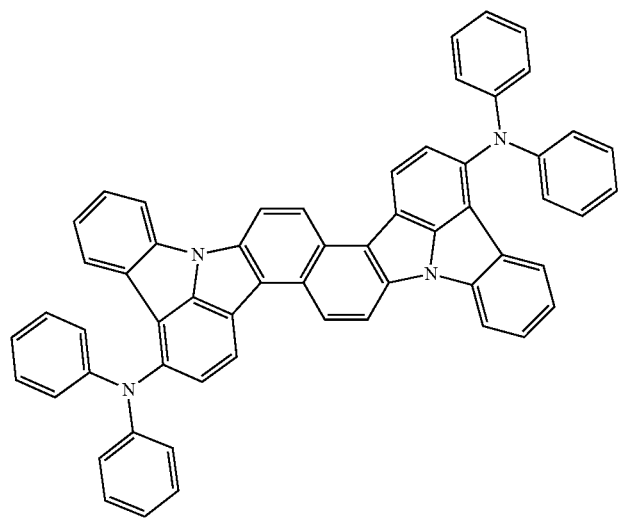
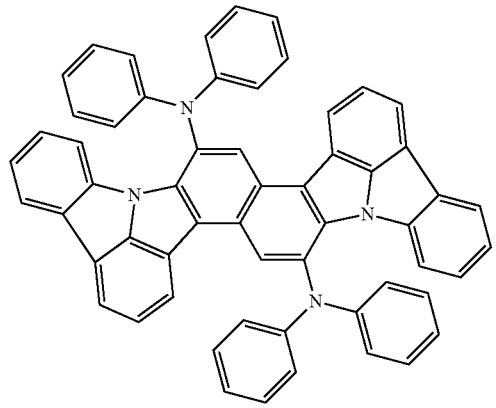
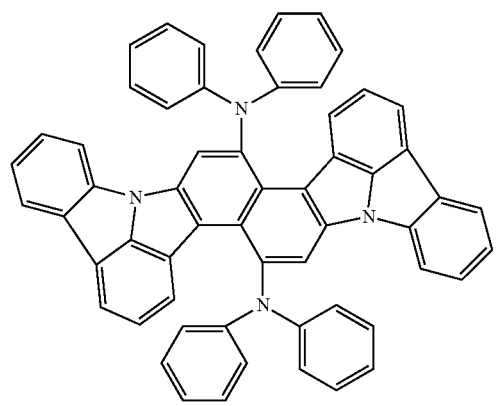

-continued
123
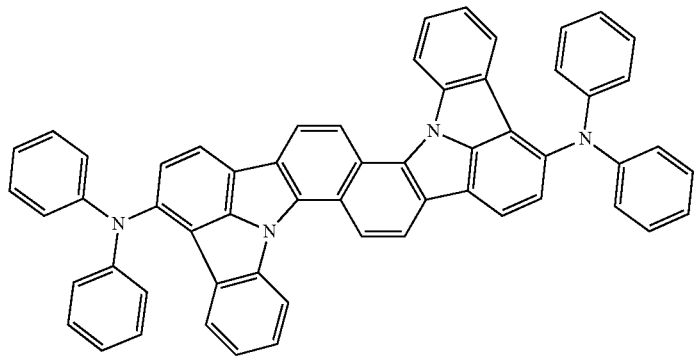
124
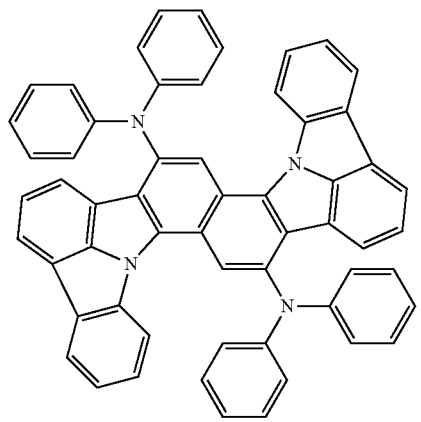
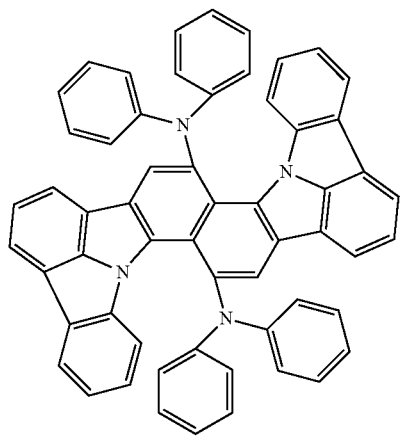
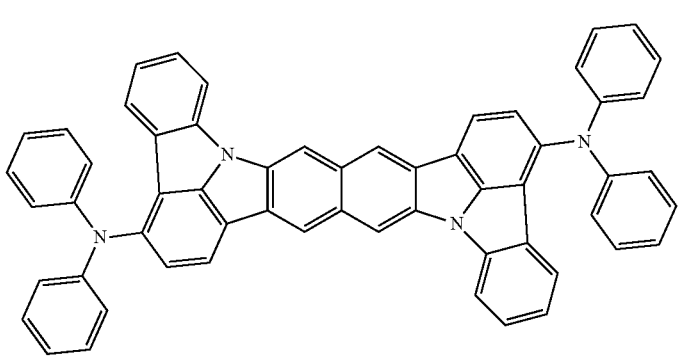
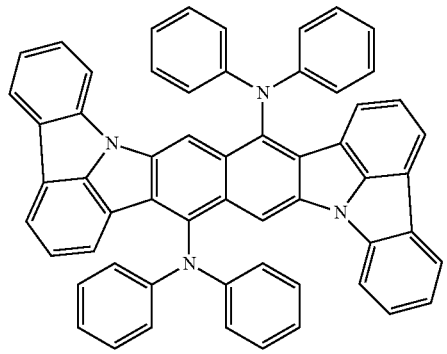
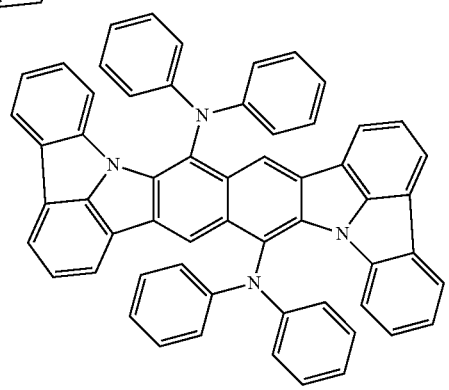
-continued
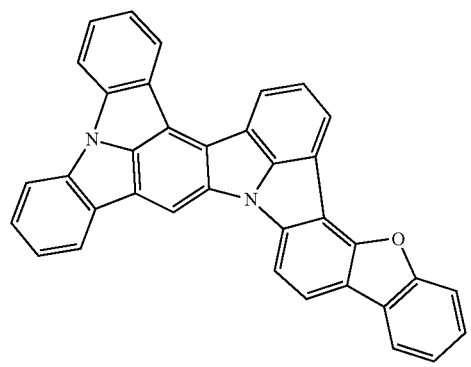
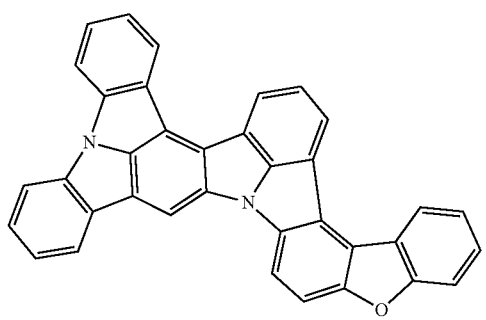

125
-continued
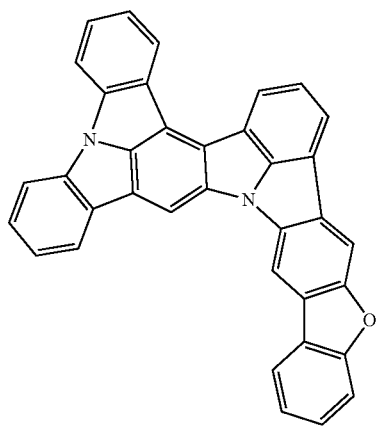
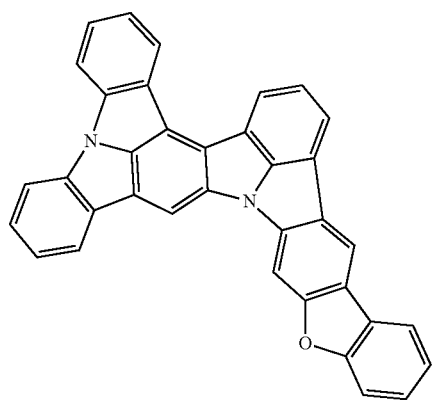
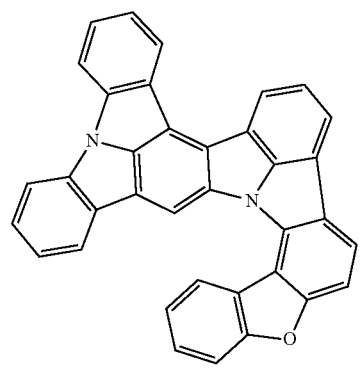
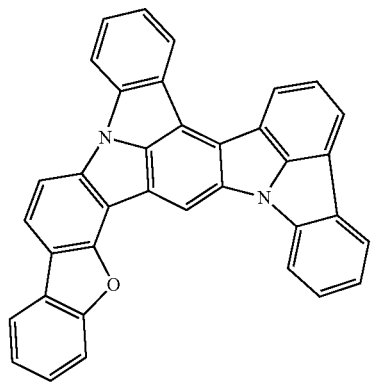
126
-continued
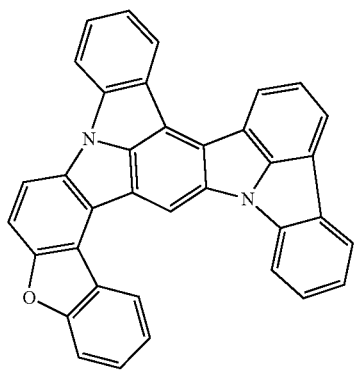
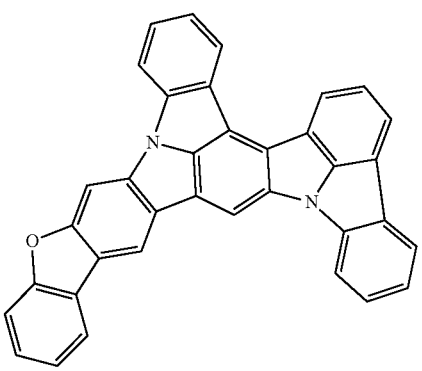
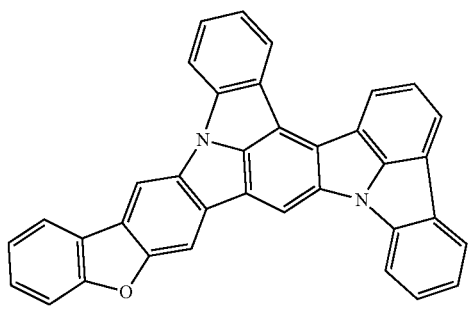
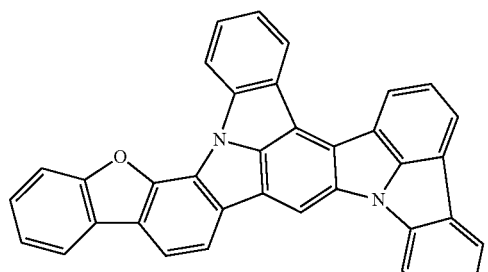
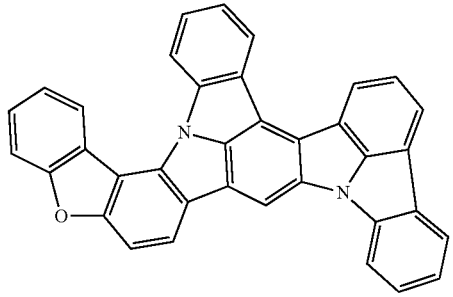

127
-continued
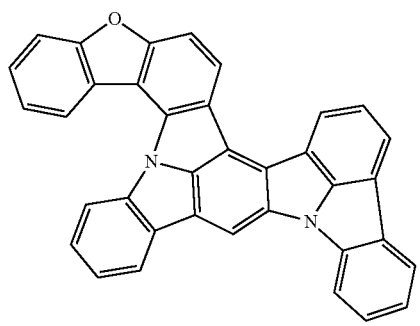
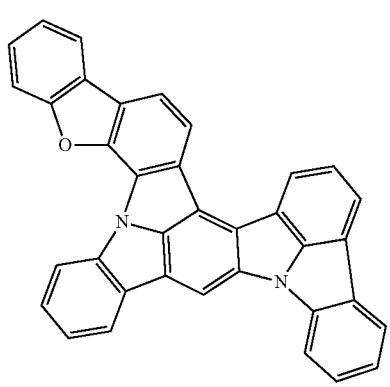
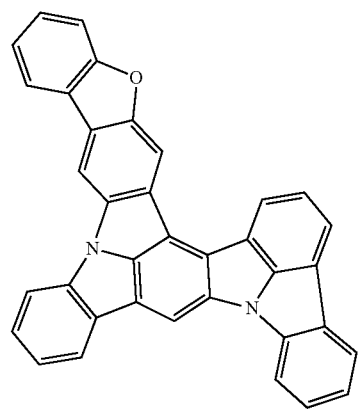
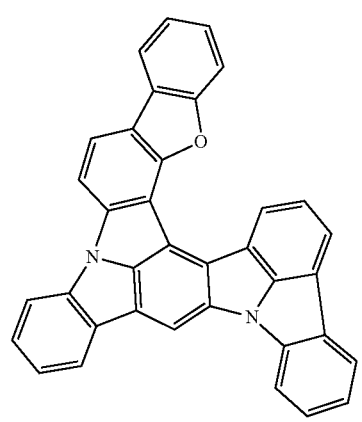
128
-continued
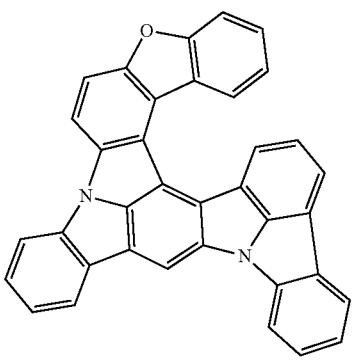
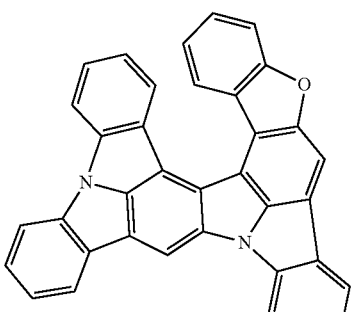
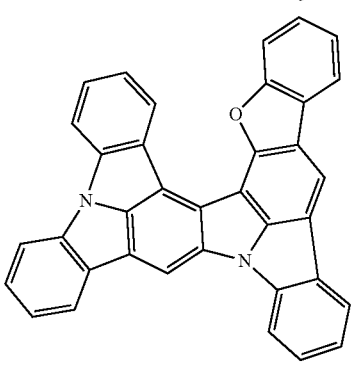
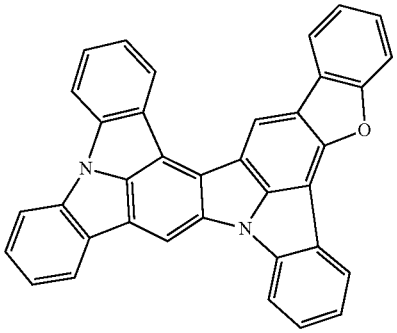
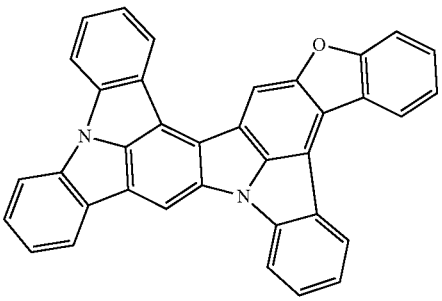

129
-continued
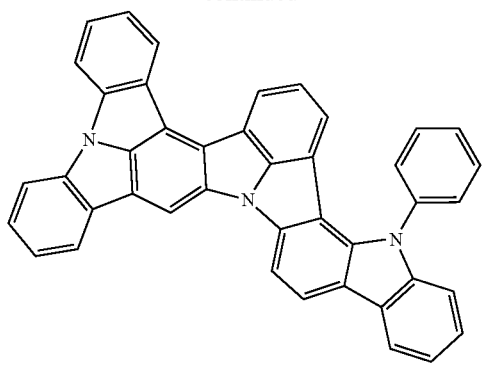
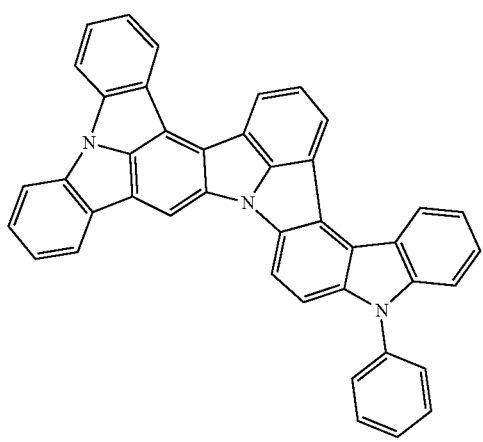
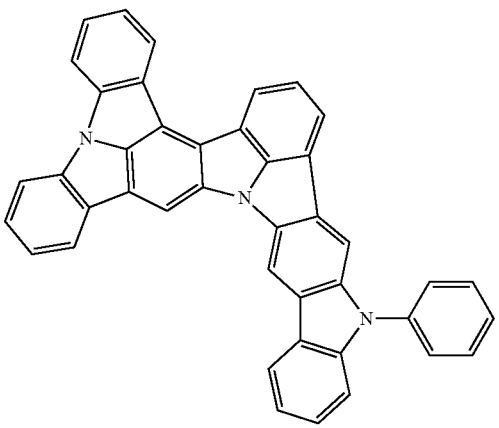
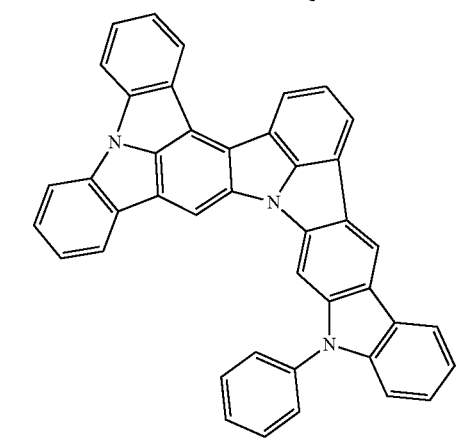
130
-continued
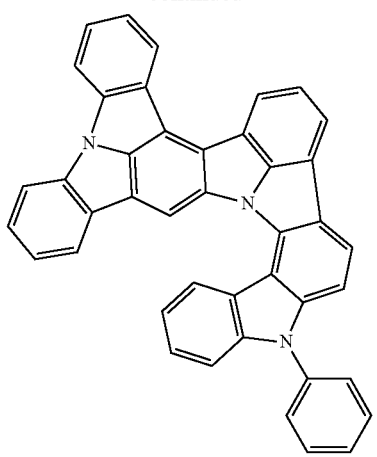
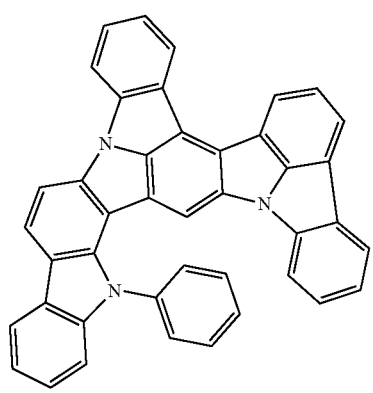
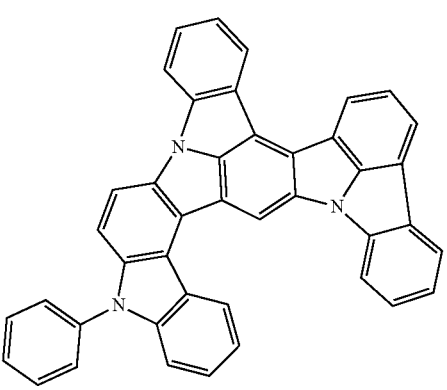
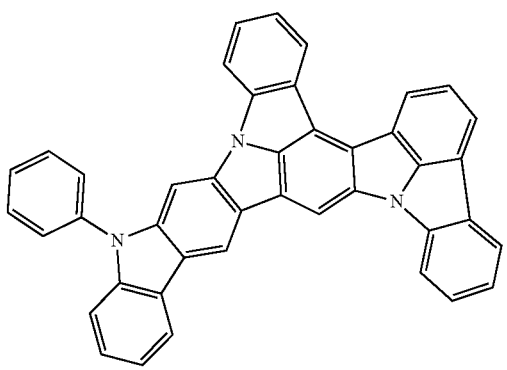

131
-continued
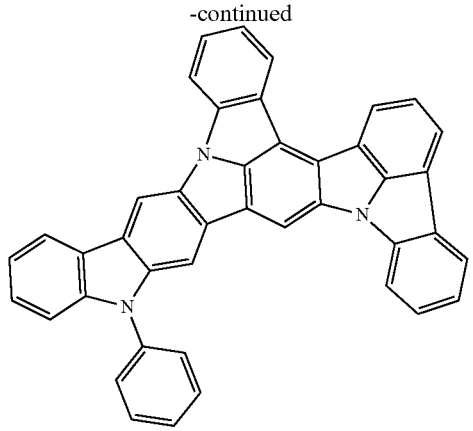
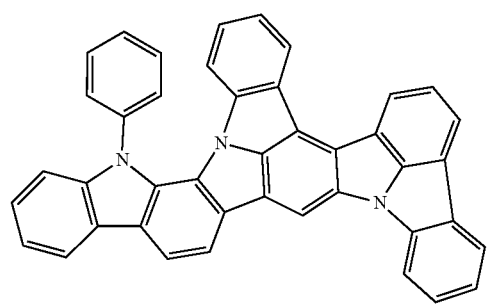
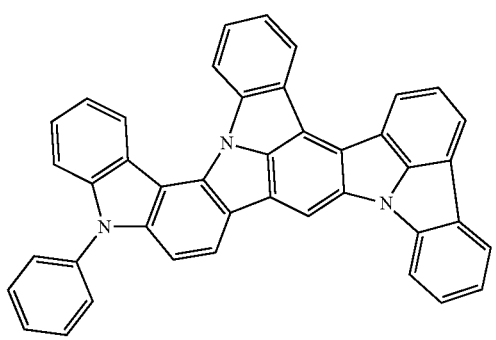
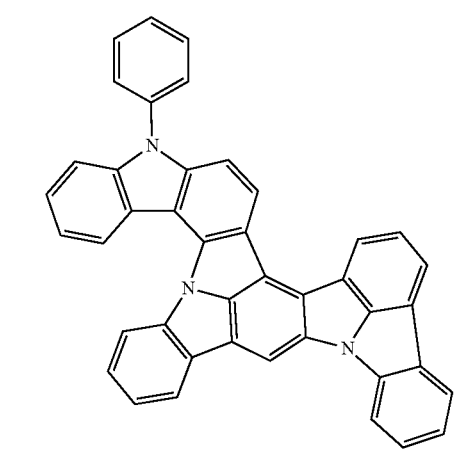
132
-continued
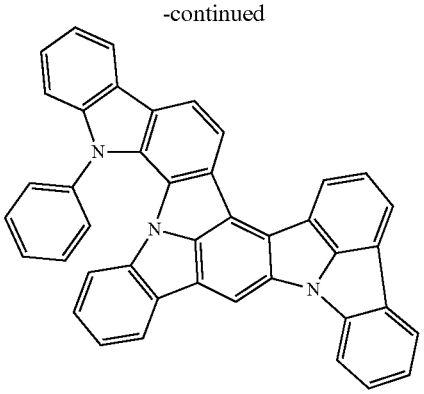
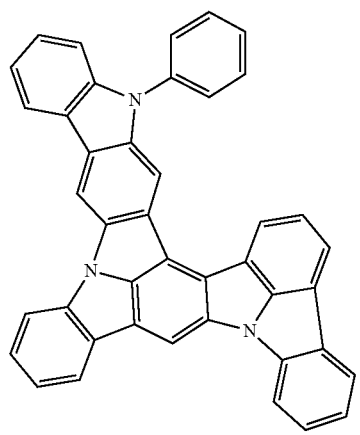
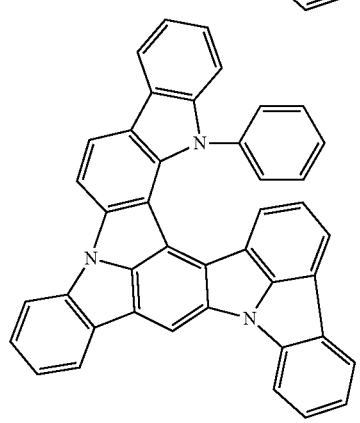
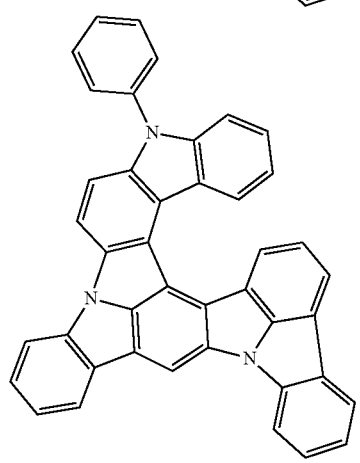

133
-continued
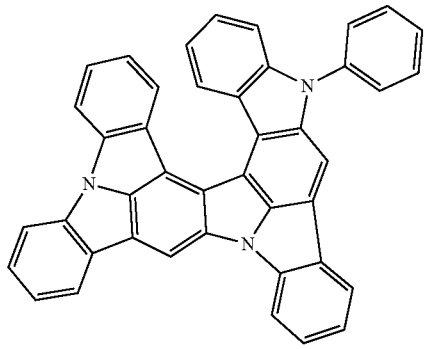
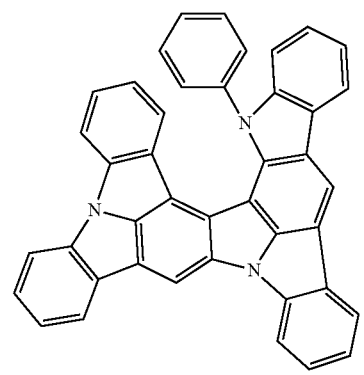
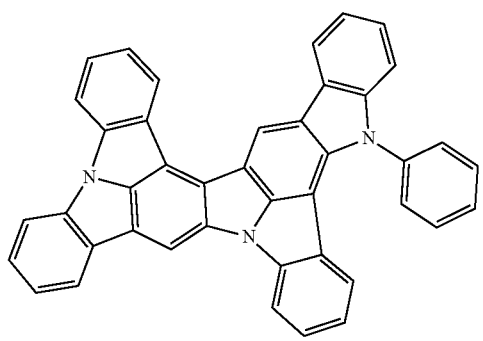
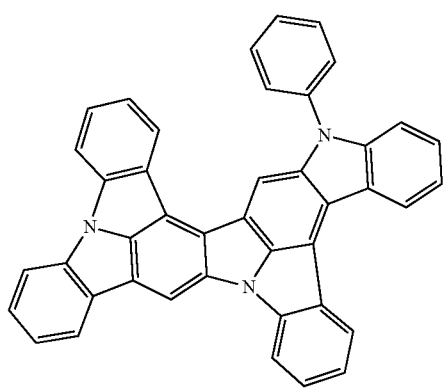
134
-continued
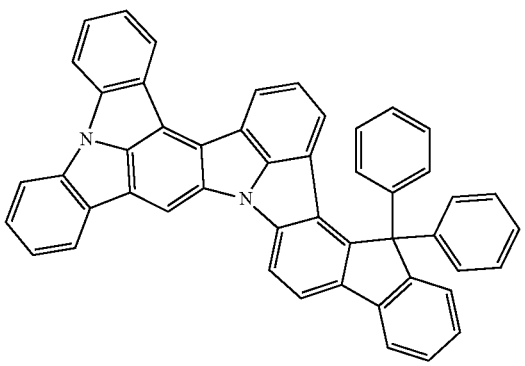
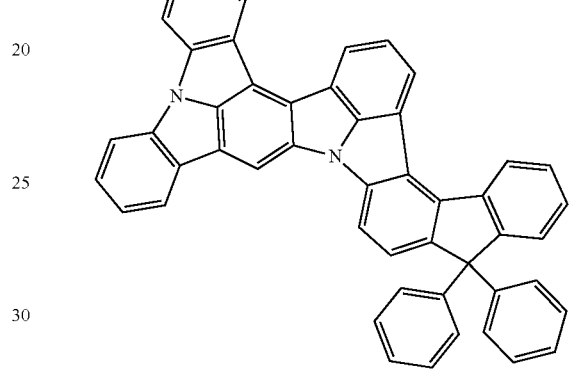
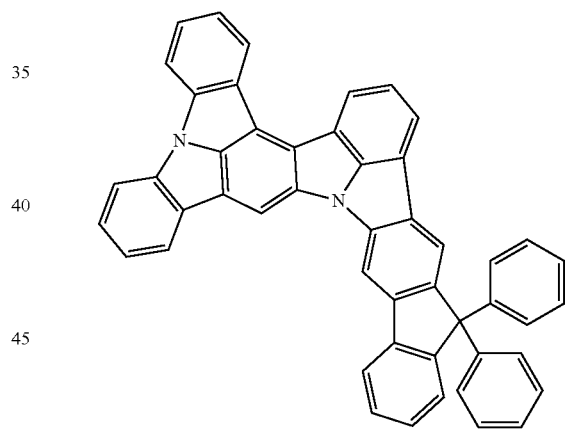
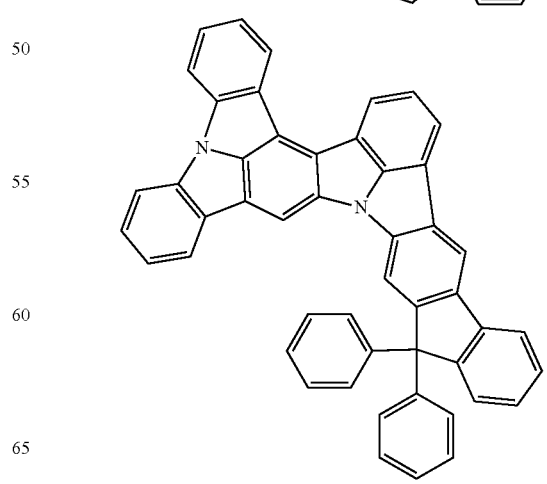

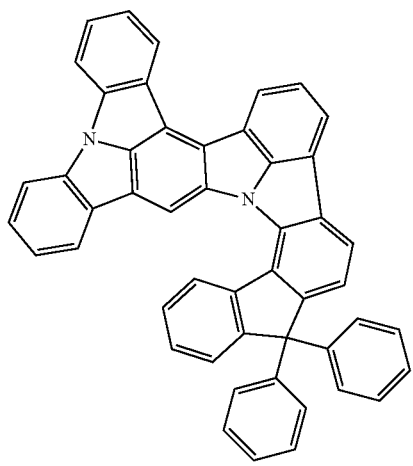
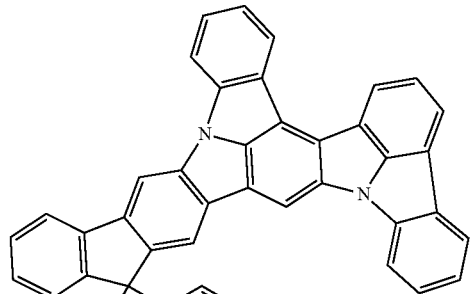
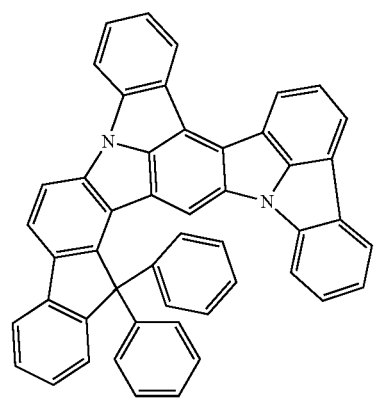
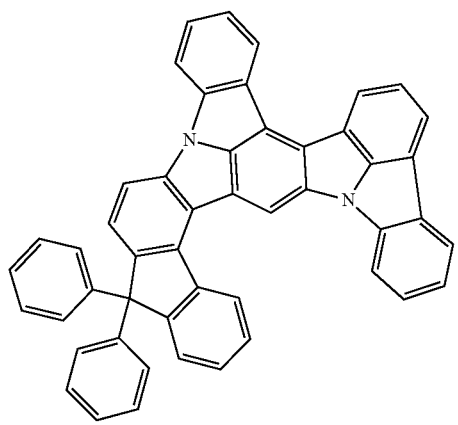
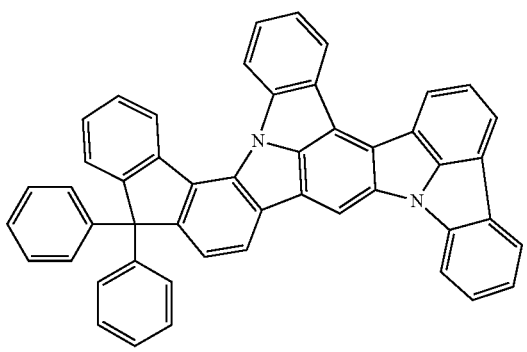
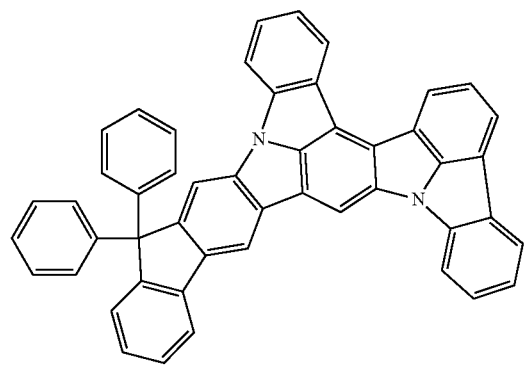
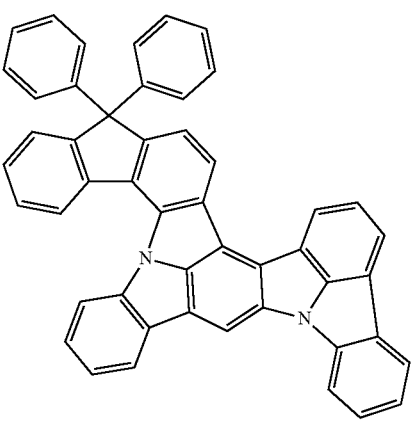

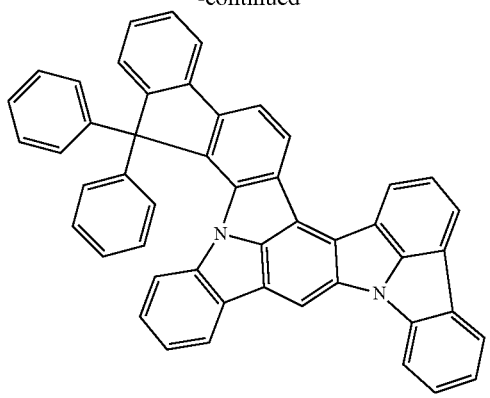
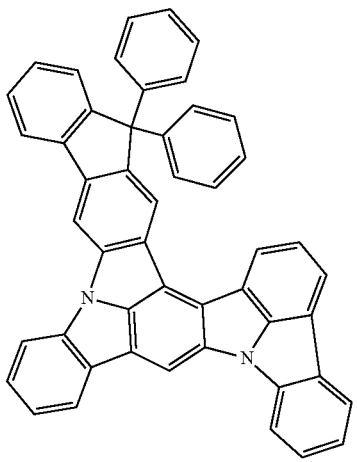
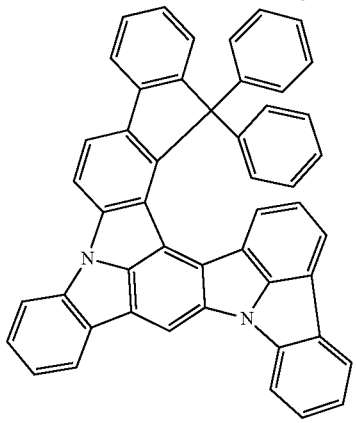
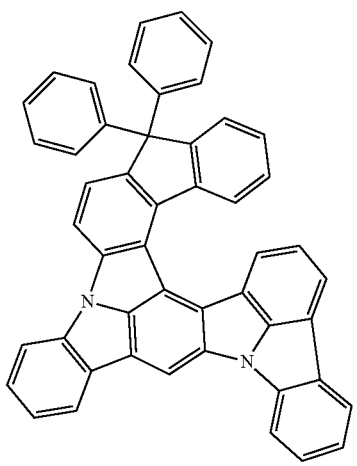
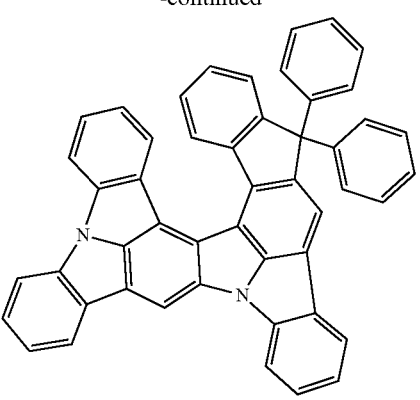
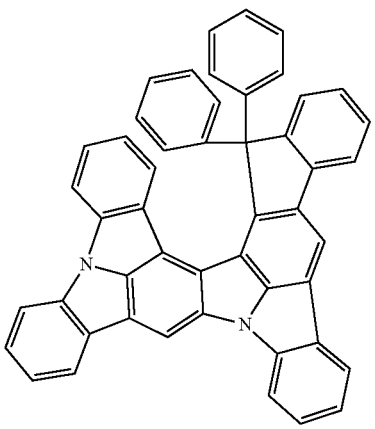
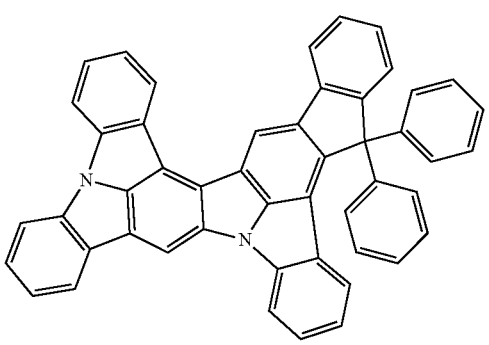
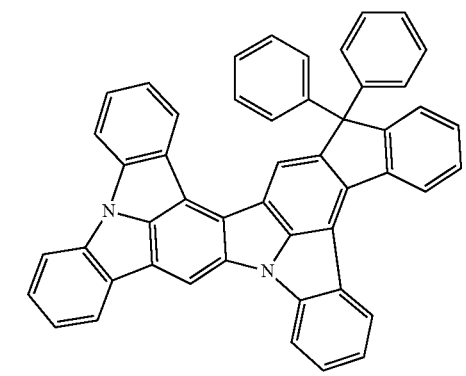

139
-continued
140
-continued
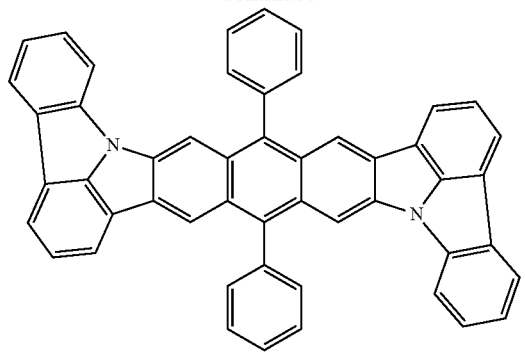
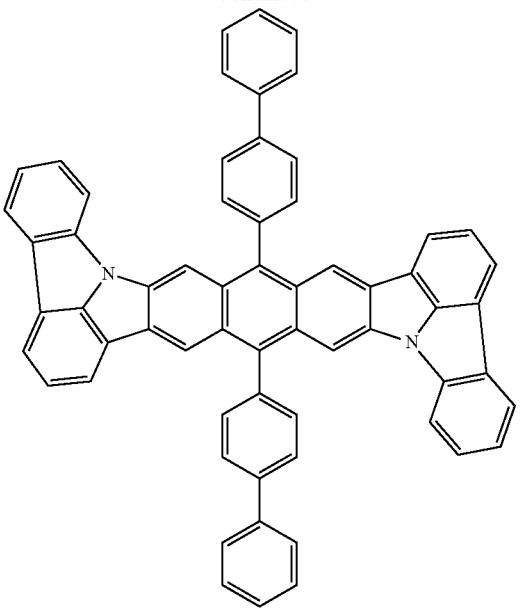
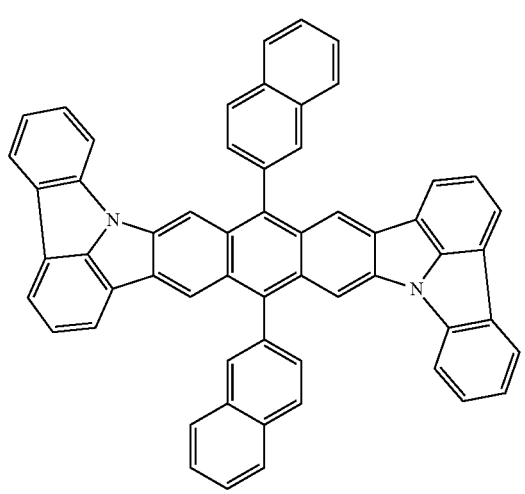
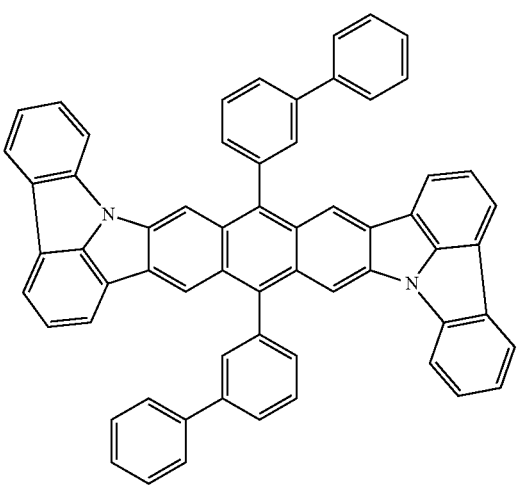
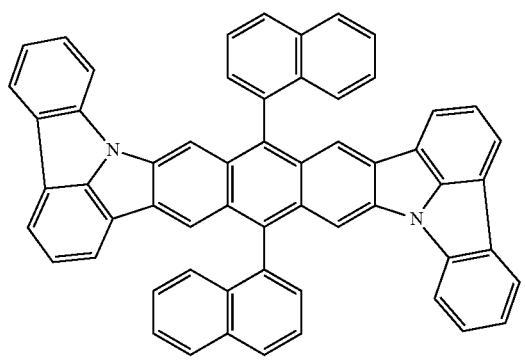
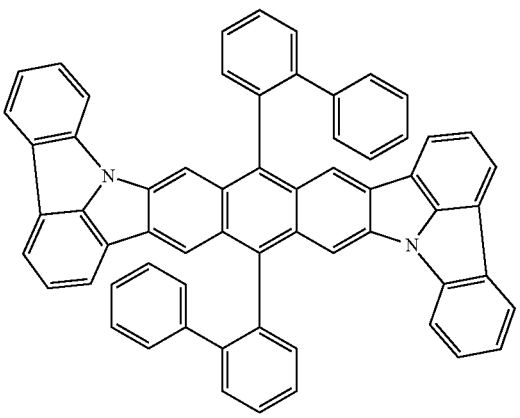

-continued
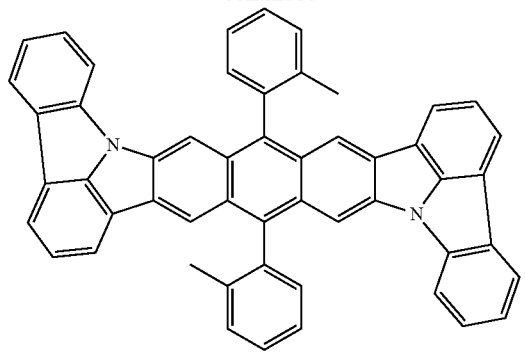
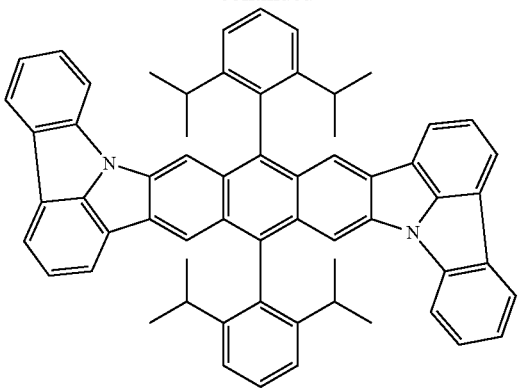
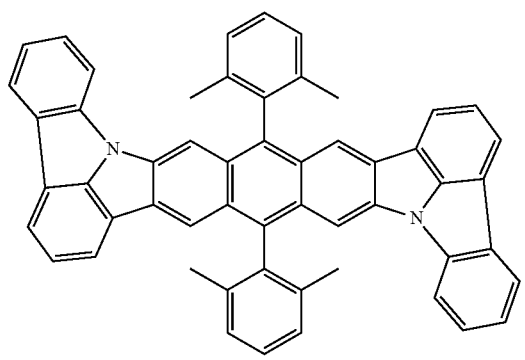
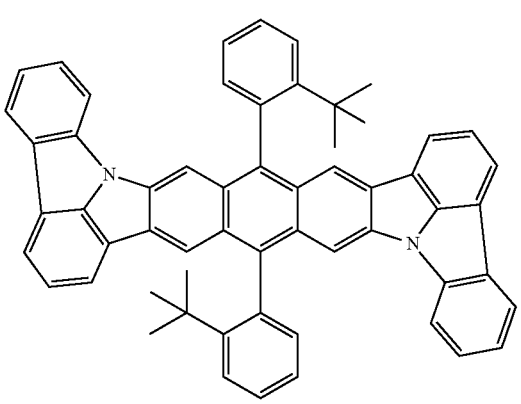
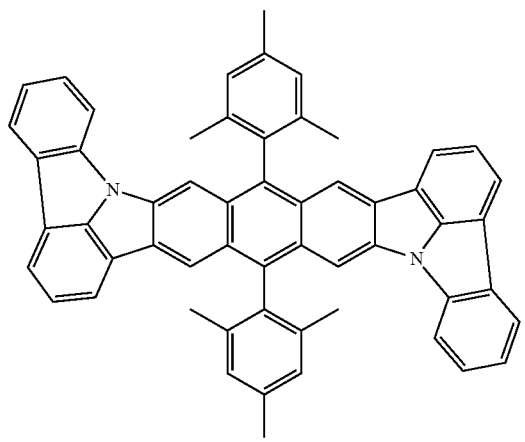
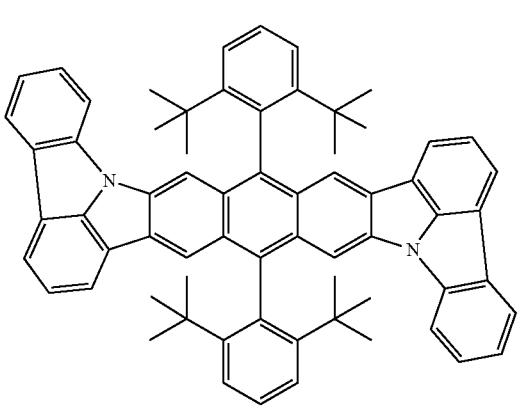
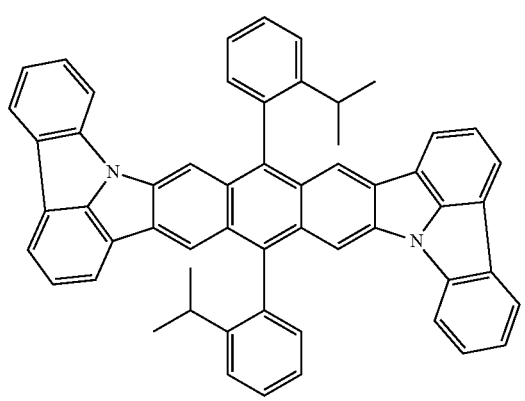
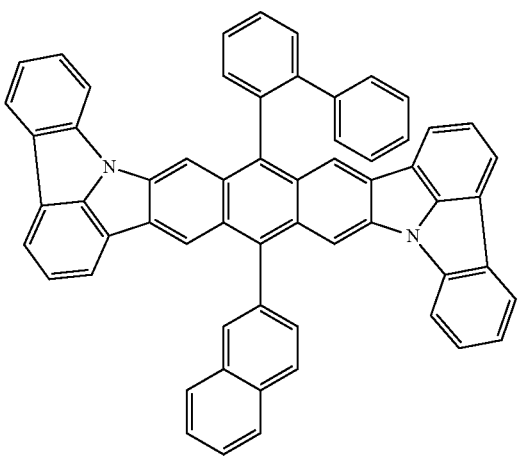

143
-continued
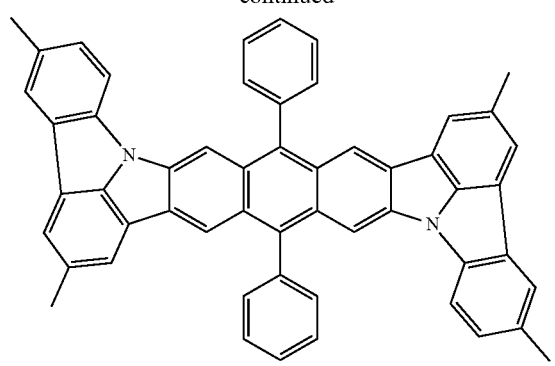
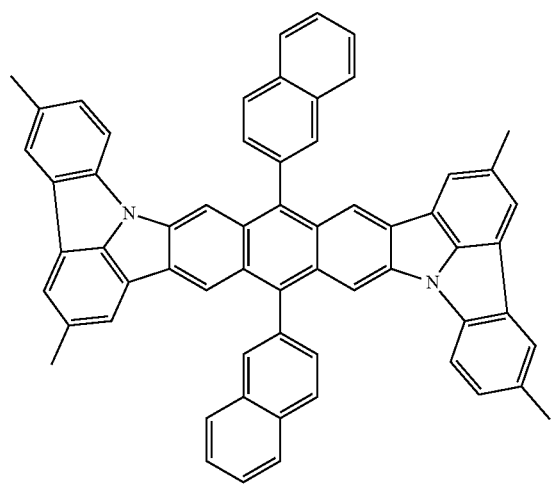
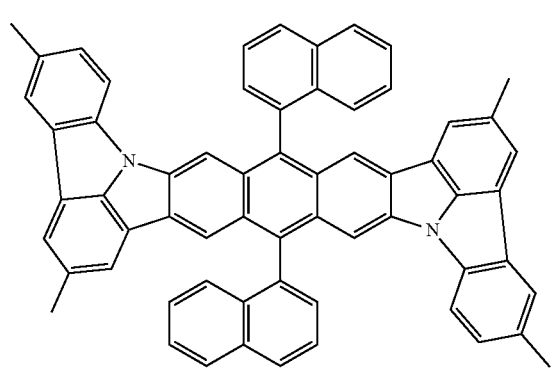
144
-continued
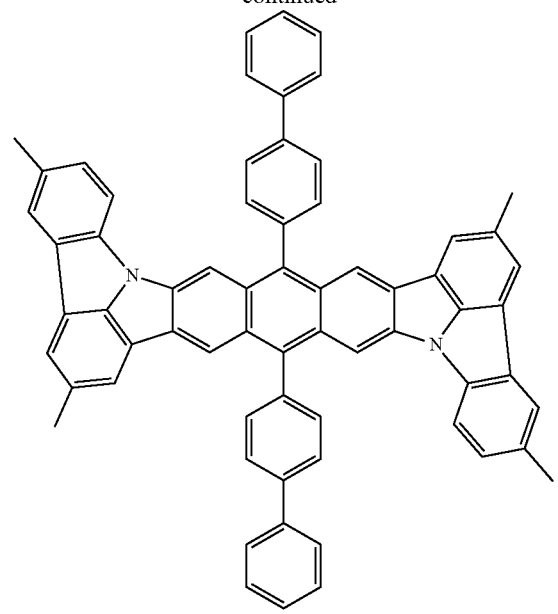
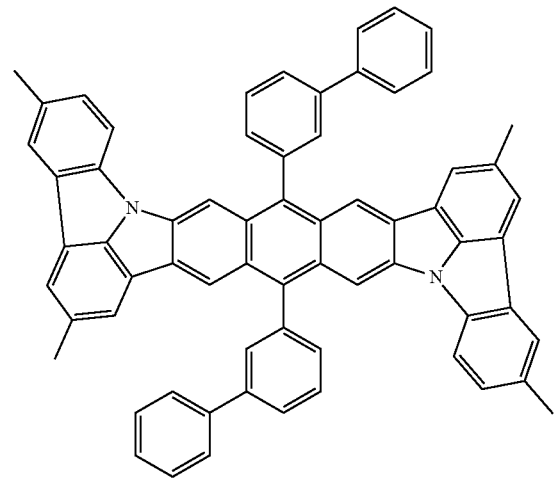
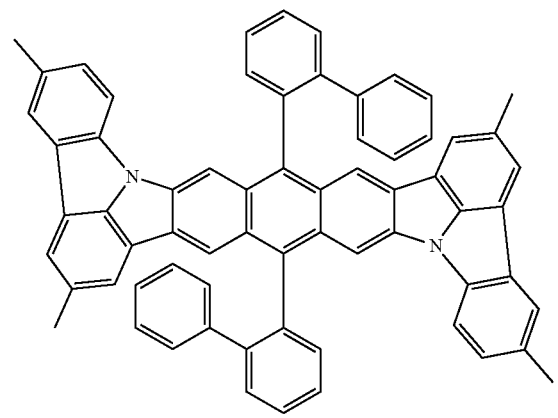

-continued
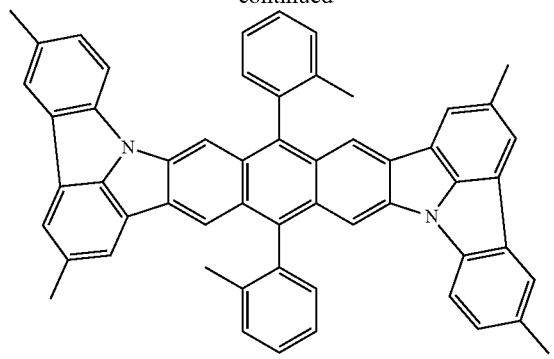
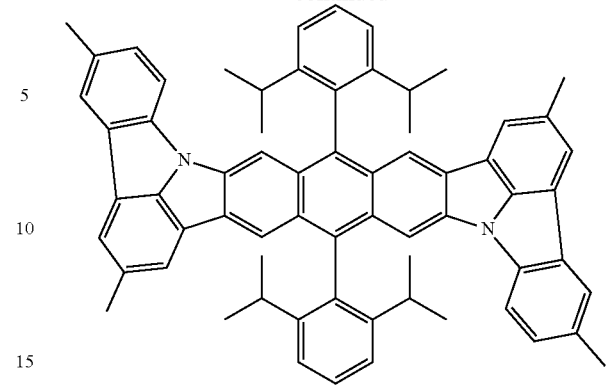
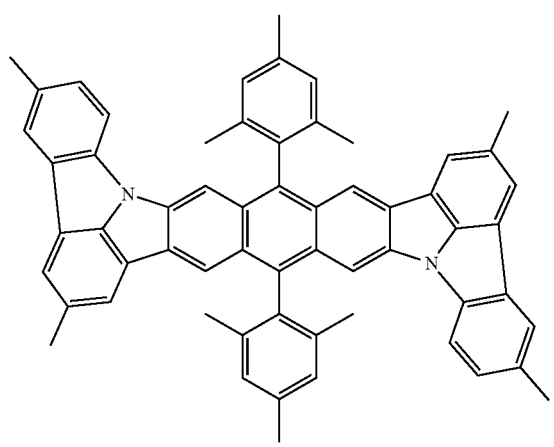

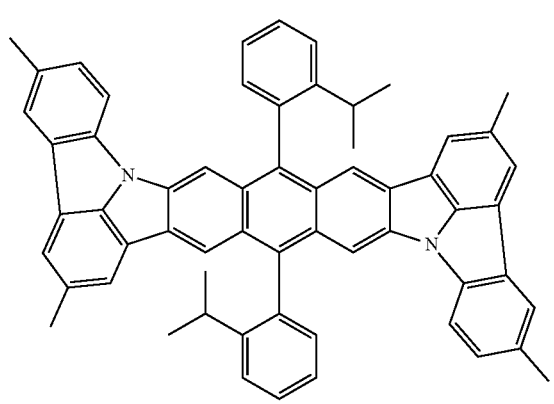
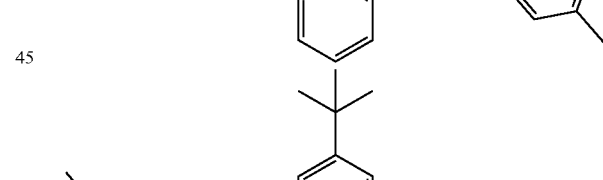
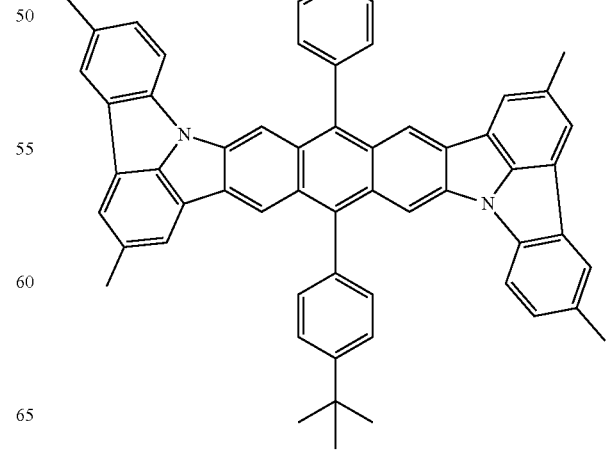

147
-continued
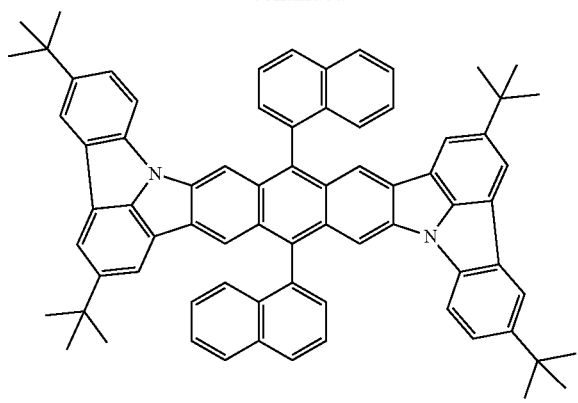
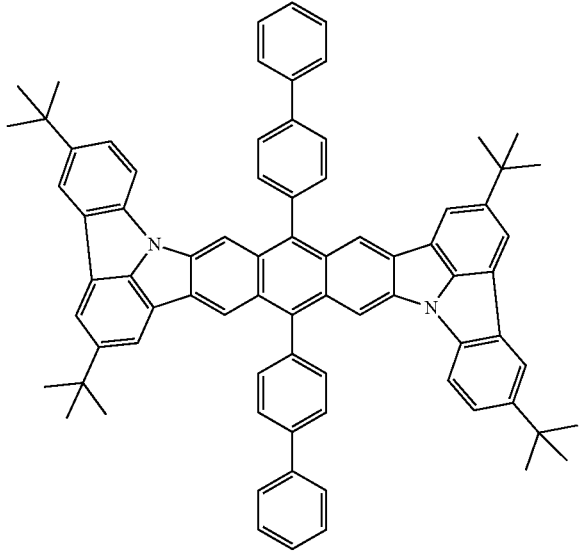
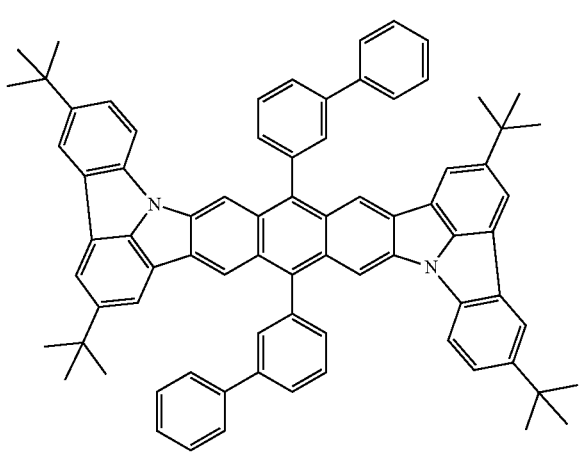
148
-continued
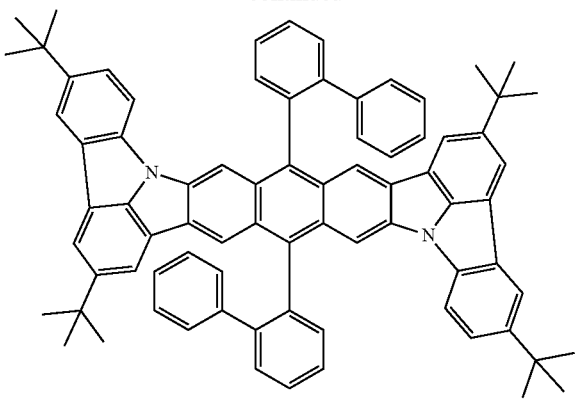
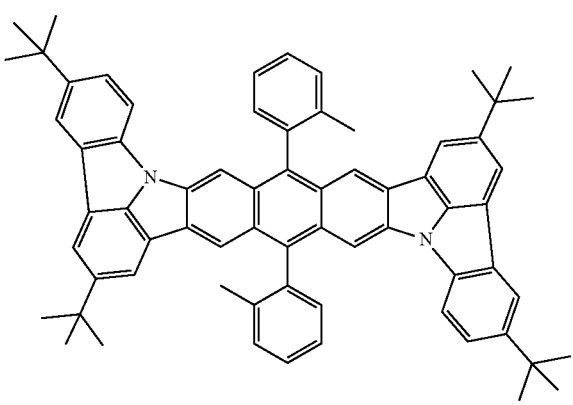
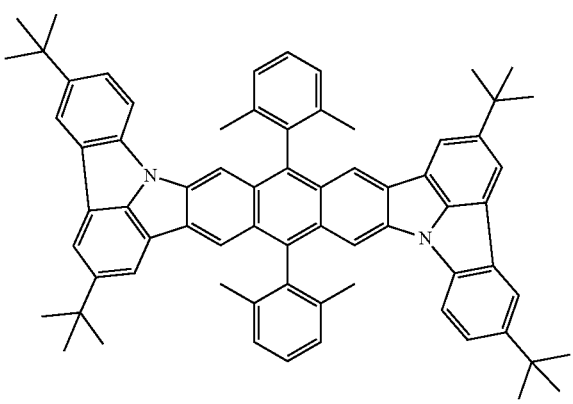
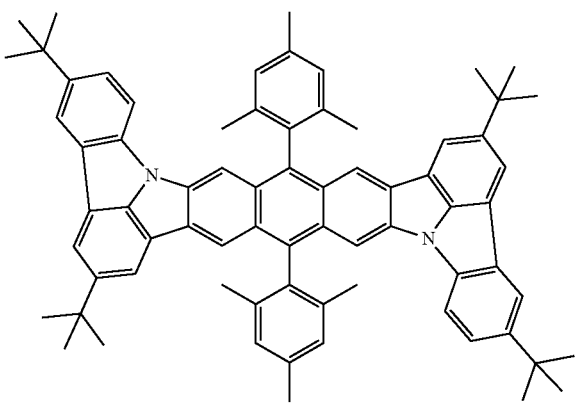

149
-continued
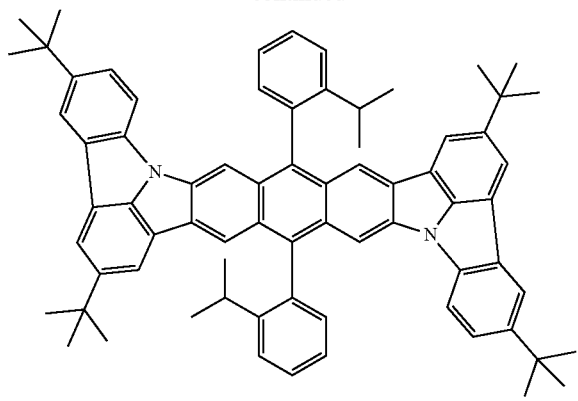
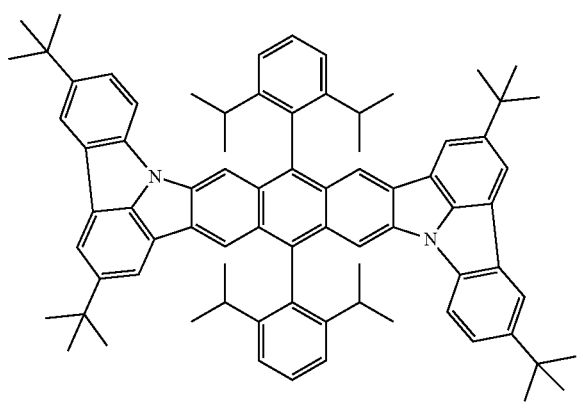
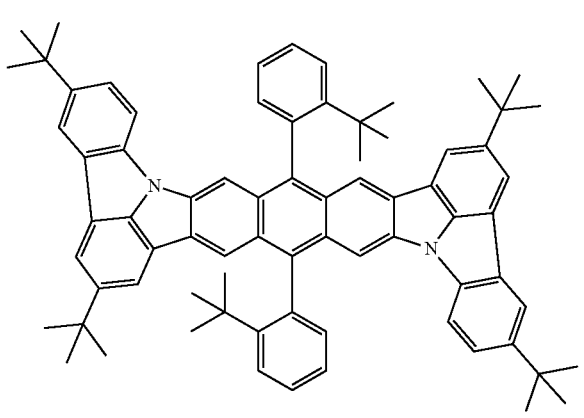
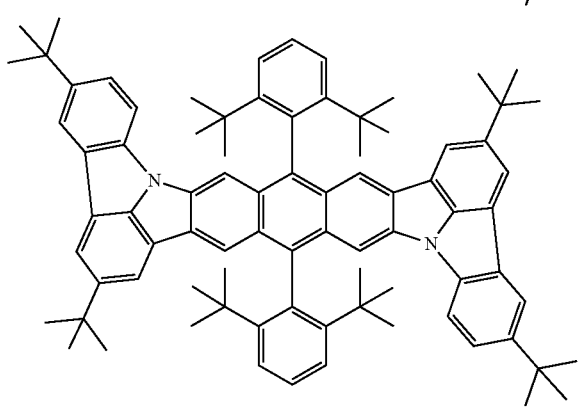
150
-continued
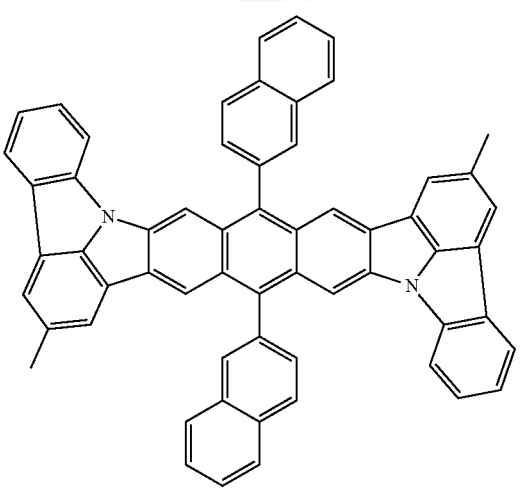
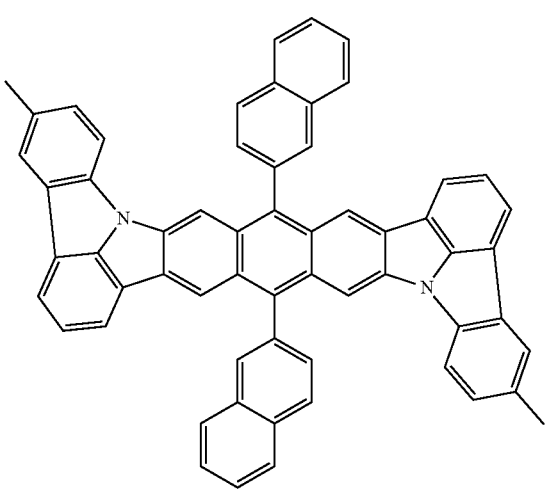
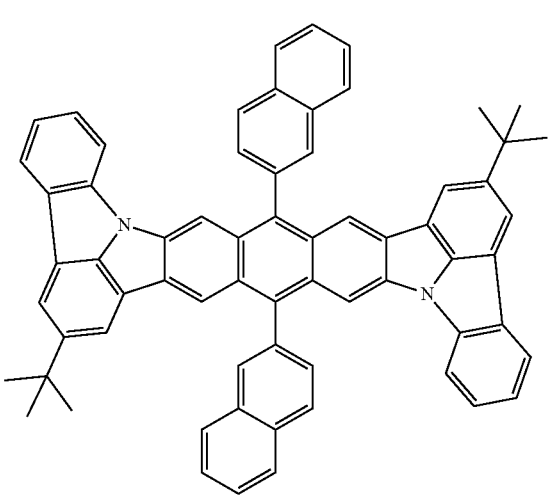

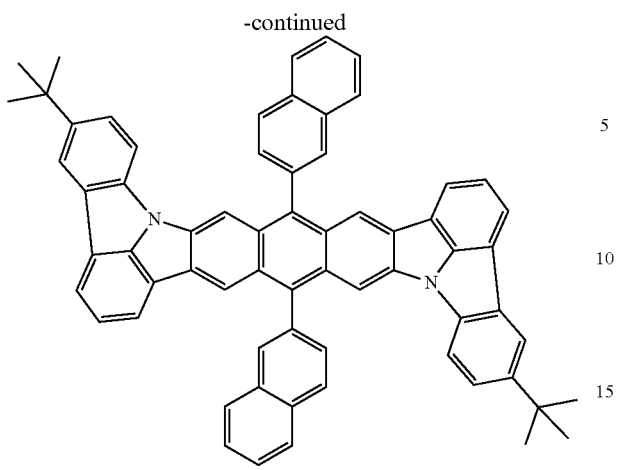

The compound represented by the formulas (1-1) and (1-3) and the compound represented by the formulas (1-2) and (1-3) can be synthesized in accordance with the reaction conducted in the Examples, and by using a known alternative reaction or raw materials suited to an intended product, for example.

In another aspect of the invention, an organic electroluminescence device has a cathode, an anode, and at least one organic layer disposed between the cathode and the anode.

The at least one layer of the at least one organic layer comprises a compound represented by the following formula (3-11):

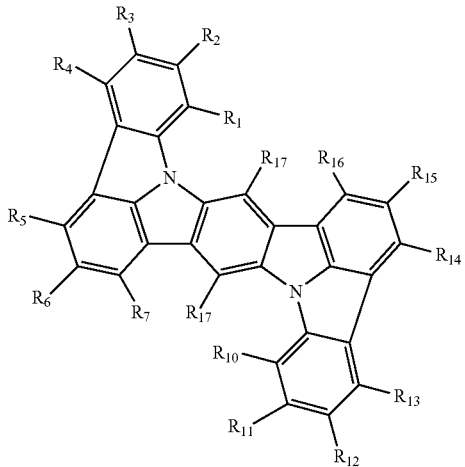

wherein in the formula (3-11),
one or more pairs of adjacent two or more of $R_1$ to $R_7$ and $R_{10}$ to $R_{16}$ may form a substituted or unsubstituted, saturated or unsaturated ring;
$R_1$ to $R_7$ and $R_{10}$ to $R_{16}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_3$,)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms, provided that at least one of $R_1$ to $R_7$ and $R_{10}$ to $R_{16}$ is —N($R_{36}$)($R_{37}$);
$R_{17}$ is a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;
two $R_{17}$s may be the same or different;
$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms;
when each of $R_{31}$ to $R_{37}$ is present in plural, each of the plural $R_{31}$s to $R_{37}$s may be the same or different.

An explanation will be given on the feature that "one or more pairs of two or more adjacent groups of $R_1$ to $R_7$ and $R_{10}$ to $R_{16}$ may form a substituted or unsubstituted, saturated or unsaturated ring."

The "one or more pairs of two or more adjacent groups of $R_1$ to $R_7$ and $R_{10}$ to $R_{16}$" is a combination of: for example, $R_1$ and $R_2$; $R_2$ and $R_3$; $R_3$ and $R_4$; $R_5$ and $R_6$; $R_6$ and $R_7$; $R_1$ and $R_2$ and $R_3$ or the like.

For the substituent when the "substituted or unsubstituted" saturated or unsaturated ring is "substituted", the same substituents as those for "substituted or unsubstituted" mentioned later can be given.

The "saturated or unsaturated ring" means, as an example when $R_1$ and $R_2$ form a ring, a ring formed by: a carbon atom with which $R_1$ is bonded; a carbon atom with which $R_2$ is bonded; and one or more arbitrary elements. Specifically, when a ring is formed by $R_1$ and $R_2$, if an unsaturated ring is formed by a carbon atom with which $R_1$ is bonded, a carbon atom with which $R_2$ is bonded and 4 carbon atoms, a ring formed by $R_1$ and $R_2$ is a benzene ring.

The "arbitrary element" is preferably a C element, a N element, an O element and a S element. For an arbitrary element (for example, in the case of a C element or a N element), an atomic bonding that does not form a ring may be terminated with a hydrogen atom or the like.

The "one or more arbitrary elements" are preferably 2 or more and 15 or less, more preferably 3 or more and 12 or less, and further preferably 3 or more and 5 or less arbitrary elements.

Hereinbelow, the expression "one or more pairs of two or more adjacent groups of X to Y may form a substituted or unsubstituted, saturated or unsaturated ring" has the same meaning as the mentioned above, except that X is changed to $R_1$ and Y is changed to $R_{16}$.

In one embodiment, the compound represented by the formula (3-11) is a compound represented by the following formula (3-12):

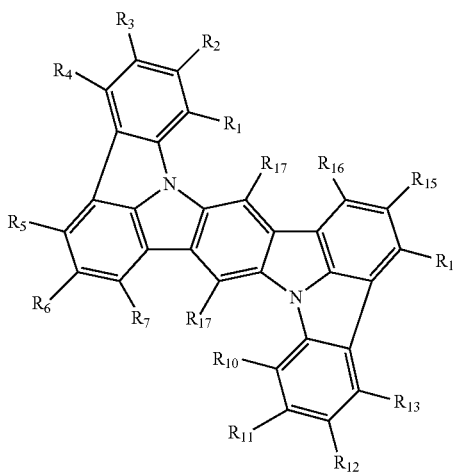

(3-12)

wherein in the formula (3-12),
$R_1$ to $R_7$ and $R_{10}$ to $R_{16}$ are as defined in the formula (3-11), provided that any two of $R_1$ to $R_7$ and $R_{10}$ to $R_{16}$ are —N($R_{36}$)($R_{37}$).

In one embodiment, $R_1$ to $R_7$ and $R_{10}$ to $R_{16}$ are independently selected from the group consisting of a hydrogen atom, a substituted or unsubstituted aryl group including 6 to 50 ring carbon atoms and a substituted or unsubstituted heterocyclic group including 5 to 50 ring atoms.

In one embodiment, $R_1$ to $R_7$ and $R_{10}$ to $R_{16}$ are independently selected from the group consisting of a hydrogen atom, a substituted or unsubstituted aryl group including 6 to 18 ring carbon atoms and a substituted or unsubstituted heterocyclic group including 5 to 18 ring atoms.

A substituent in the "substituted or unsubstituted" in the compound represented by the formula (3-11) is selected from the group consisting of an alkyl group including 1 to 50 carbon atoms, a haloalkyl group including 1 to 50 carbon atoms, an alkenyl group including 2 to 50 carbon atoms, an alkynyl group including 2 to 50 carbon atoms, a cycloalkyl group including 3 to 50 ring carbon atoms, an alkoxy group including 1 to 50 carbon atoms, an alkylthio group including 1 to 50 carbon atoms, an aryloxy group including 6 to 50 ring carbon atoms, an arylthio group including 6 to 50 ring carbon atoms, an aralkyl group including 7 to 50 carbon atoms, —Si($R_{41}$)($R_{42}$)($R_{43}$), —C(=O)$R_{44}$, —COO$R_{45}$, —S(=O)$_2R_{46}$, —P(=O)($R_{47}$)($R_{48}$), —Ge($R_{49}$)($R_{50}$)($R_{51}$), —N($R_{52}$)($R_{53}$) ($R_{41}$ to $R_{53}$ are independently a hydrogen atom, an alkyl group including 1 to 50 carbon atoms, an aryl group including 6 to 50 ring carbon atoms or a heterocyclic group including 5 to 50 ring atoms. When each of $R_{41}$ to $R_{53}$ is present in plural, each of the plural $R_{41}$s to $R_{53}$s may be the same or different.), a hydroxyl group, a halogen atom, a cyano group, a nitro group, an aryl group including 6 to 50 ring carbon atoms, and a monovalent heterocyclic group including 5 to 50 ring atoms.

In one embodiment, the substituent in the "substituted or unsubstituted" in the compound represented by the formula (3-11) is an alkyl group including 1 to 50 carbon atoms, an aryl group including 6 to 50 ring carbon atoms and a monovalent heterocyclic group including 5 to 50 ring atoms.

In one embodiment, the substituent in the "substituted or unsubstituted" in the compound represented by the formula (3-11) is selected from the group consisting of an alkyl group including 1 to 18 carbon atoms, an aryl group including 6 to 18 ring carbon atoms and a monovalent heterocyclic group including 5 to 18 ring atoms.

Specific examples of each substituent, substituents for "substituted or unsubstituted" and halogen atoms in the compound represented by the formula (3-11) are the same as those mentioned above.

In one embodiment, the compound represented by the formula (3-11) is a compound represented by the following formula (3-13):

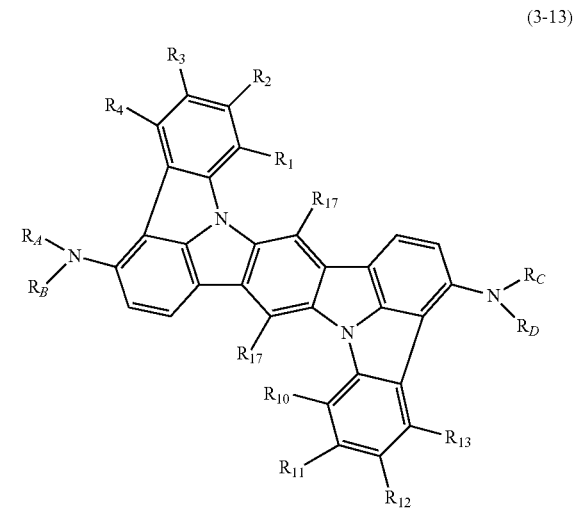

(3-13)

wherein in the formula (3-13),
one or more pairs of adjacent two or more of $R_1$ to $R_4$ and $R_{10}$ to $R_{13}$ may form a substituted or unsubstituted, saturated or unsaturated ring;
$R_1$ to $R_4$, $R_{10}$ to $R_{13}$, and $R_{17}$ that do not form the substituted or unsubstituted, saturated or unsaturated ring are independently a hydrogen atom, a substituted or unsubstituted aryl group including 6 to 18 ring carbon atoms or a substituted or unsubstituted monovalent heterocyclic group including 6 to 18 ring atoms;
two $R_{17}$s may be the same or different; and
$R_A$, $R_B$, $R_C$ and $R_D$ are independently a substituted or unsubstituted aryl group including 6 to 18 ring carbon atoms or a substituted or unsubstituted monovalent heterocyclic group including 6 to 18 ring atoms.

An explanation will be given on the feature that "one or more pairs of two or more adjacent groups of $R_1$ to $R_4$ and $R_{10}$ to $R_{13}$ may form a substituted or unsubstituted, saturated or unsaturated ring."

The "one or more pairs of two or more adjacent groups of $R_1$ to $R_4$ and $R_{10}$ to $R_{13}$" is a combination of: for example, $R_1$ and $R_2$; $R_2$ and $R_3$; $R_3$ and $R_4$; $R_1$ and $R_2$ and $R_3$ or the like.

For the substituent when the "substituted or unsubstituted" saturated or unsaturated ring is "substituted", the same substituents as those for "substituted or unsubstituted" mentioned later can be given.

The "saturated or unsaturated ring" means the same as explained in the above formula (3-11).

In the compound represented by the formula (3-13), one or more pairs of adjacent two or more of $R_1$ to $R_4$, $R_{10}$ to $R_{13}$ and $R_{17}$ may form a substituted or unsubstituted, saturated or unsaturated ring and may not form a substituted or unsubstituted, saturated or unsaturated ring. In the compound represented by formula (3-13), it is preferable that one or more pairs of adjacent two or more of $R_1$ to $R_4$, $R_{10}$ to $R_{13}$ and $R_{17}$ do not form a substituted or unsubstituted, saturated or unsaturated ring.

In one embodiment, the compound represented by the formula (3-13) is a compound represented by the following formula (3-14):

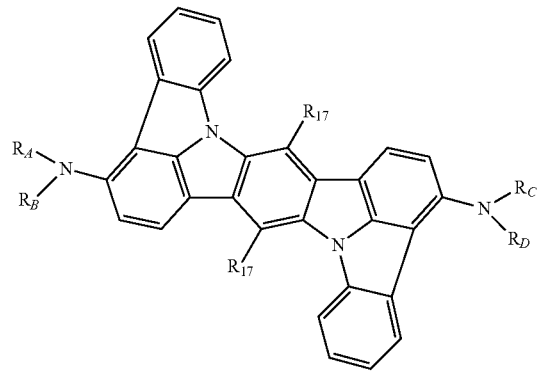

(3-14)

wherein in the formula (3-14),
$R_{17}$, $R_A$, $R_B$, $R_C$ and $R_D$ are as defined in the formula (3-13).

In one embodiment, $R_A$, $R_B$, $R_C$ and $R_D$ of the compound represented by formula (3-13) and the compound represented by formula (3-14) are independently a substituted or unsubstituted aryl group including 6 to 18 ring carbon atoms.

In one embodiment, $R_A$, $R_B$, $R_C$ and $R_D$ of the compound represented by formula (3-13) and the compound represented by formula (3-14) are independently a substituted or unsubstituted phenyl group.

In one embodiment, two $R_{17}$s of the compound represented by formula (3-13) and the compound represented by formula (3-14) are independently a hydrogen atom.

A substituent in the "substituted or unsubstituted" in the compound represented by the formula (3-13) and the compound represented by the formula (3-14) is selected from the group consisting of an alkyl group including 1 to 18 carbon atoms, an aryl group including 6 to 18 ring carbon atoms, and a monovalent heterocyclic group including 5 to 18 ring atoms.

In one embodiment, a substituent in the "substituted or unsubstituted" in the compound represented by the formula (3-13) and the compound represented by the formula (3-14) is an alkyl group including 1 to 5 carbon atoms.

Specific examples of each substituent and substituents for "substituted or unsubstituted" in the compound represented by the formulas (3-13) and (3-14) are the same as those mentioned above.

In another aspect of the invention, an organic electroluminescence device has a cathode, an anode, and at least one organic layer disposed between the cathode and the anode.

The at least one layer of the at least one organic layer comprises a compound represented by the following formula (3-21):

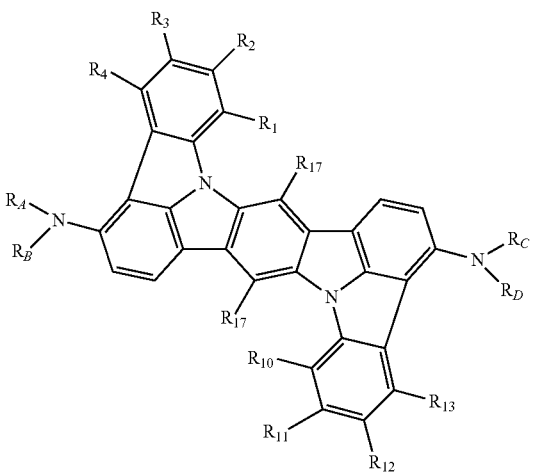

(3-21)

wherein in the formula (3-21),
one or more pairs of adjacent two or more of $R_1$ to $R_4$ and $R_{10}$ to $R_{13}$ may form a substituted or unsubstituted, saturated or unsaturated ring;
$R_1$ to $R_4$, $R_{10}$ to $R_{13}$, and $R_{17}$ that do not form the substituted or unsubstituted, saturated or unsaturated ring are independently a hydrogen atom, a substituted or unsubstituted aryl group including 6 to 20 ring carbon atoms or a substituted or unsubstituted monovalent heterocyclic group including 5 to 20 ring atoms;
two $R_{17}$s may be the same or different; and
$R_A$, $R_B$, $R_C$ and $R_D$ are independently a substituted or unsubstituted aryl group including 6 to 20 ring carbon atoms.

The "one or more pairs of adjacent two or more of $R_1$ to $R_4$ and $R_{10}$ to $R_{13}$ may form a substituted or unsubstituted, saturated or unsaturated ring" means the same as explained in the above formula (3-13).

For the substituent when the "substituted or unsubstituted" saturated or unsaturated ring is "substituted", the same substituents as those for "substituted or unsubstituted" mentioned later can be given.

The "saturated or unsaturated ring" means the same as explained in the above formula (3-11).

In the compound represented by the formula (3-21), one or more pairs of adjacent two or more of $R_1$ to $R_4$, $R_{10}$ to $R_{13}$ and $R_{17}$ may form a substituted or unsubstituted, saturated or unsaturated ring and may not form a substituted or unsubstituted, saturated or unsaturated ring. In the compound represented by formula (3-21), it is preferable that one or more pairs of adjacent two or more of $R_1$ to $R_4$, $R_{10}$ to $R_{13}$ and $R_{17}$ do not form a substituted or unsubstituted, saturated or unsaturated ring.

In one embodiment, the compound represented by the formula (3-21) is a compound represented by the following formula (3-22):

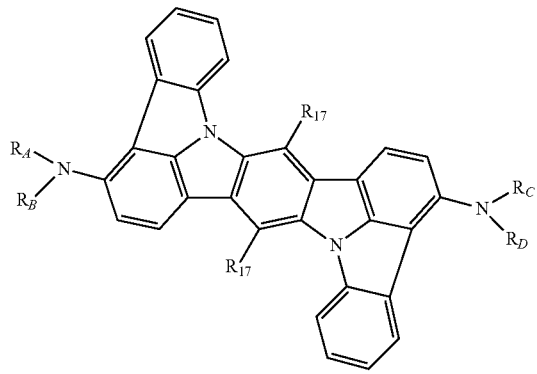
(3-22)

wherein in the formula (3-22), $R_{17}$, $R_A$, $R_B$, $R_C$ and $R_D$ are as defined in the formula (3-21).

In one embodiment, in the compound represented by the formulas (3-21) and (3-22), $R_A$, $R_B$, $R_C$ and $R_D$ are independently a substituted or unsubstituted phenyl group.

In one embodiment, in the compound represented by the formulas (3-21) and (3-22), two $R_{17}$s are independently a hydrogen atom.

In one embodiment, in the compound represented by the formulas (3-21) and (3-22), a substituent in the "substituted or unsubstituted" is selected from the group consisting of an alkyl group including 1 to 20 carbon atoms, an aryl group including 6 to 20 ring carbon atoms, and a monovalent heterocyclic group including 5 to 20 ring atoms.

In one embodiment, in the compound represented by the formulas (3-21) and (3-22), a substituent in the "substituted or unsubstituted" is an alkyl group including 1 to 5 carbon atoms.

In one embodiment, in the compound represented by the formulas (3-21) and (3-22), $R_A$, $R_B$, $R_C$ and $R_D$ are independently a substituted or unsubstituted phenyl group; and two $R_{17}$s are independently a hydrogen atom.

In one embodiment, in the compound represented by the formulas (3-21) and (3-22), $R_A$, $R_B$, $R_C$ and $R_D$ are independently a substituted or unsubstituted phenyl group; two $R_{17}$s are independently a hydrogen atom; and a substituent in the "substituted or unsubstituted" is selected from the group consisting of an alkyl group including 1 to 20 carbon atoms, an aryl group including 6 to 20 ring carbon atoms, and a monovalent heterocyclic group including 5 to 20 ring atoms.

In one embodiment, in the compound represented by the formulas (3-21) and (3-22), $R_A$, $R_B$, $R_C$ and $R_D$ are independently a substituted or unsubstituted phenyl group; two $R_{17}$s are independently a hydrogen atom; and a substituent in the "substituted or unsubstituted" is an alkyl group including 1 to 5 carbon atoms.

In another aspect of the invention, an organic electroluminescence device has a cathode, an anode, and at least one organic layer disposed between the cathode and the anode.

The at least one layer of the at least one organic layer comprises a compound represented by the following formulas (3-31) or (3-32):

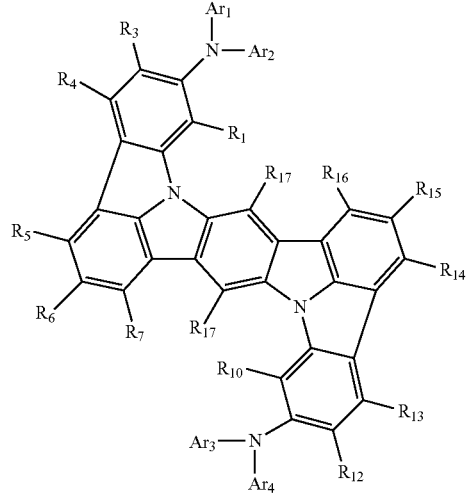
(3-31)

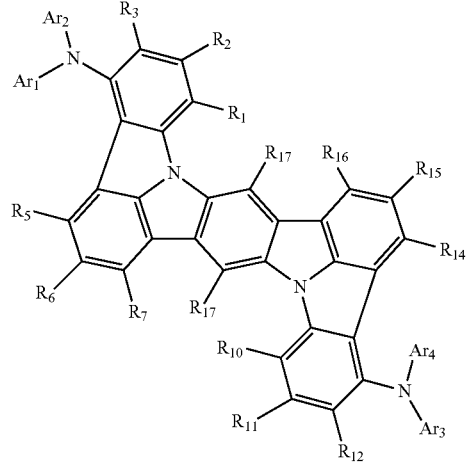
(3-32)

wherein in the formulas (3-31) and (3-32),
one or more pairs of adjacent two or more of $R_1$ to $R_7$ and $R_{10}$ to $R_{16}$ may form a substituted or unsubstituted, saturated or unsaturated ring;
$R_{17}$, and $R_1$ to $R_7$ and $R_{10}$ to $R_{16}$ that do not form the substituted or unsubstituted, saturated or unsaturated ring are independently a hydrogen atom, a substituted or unsubstituted aryl group including 6 to 20 ring carbon atoms or a substituted or unsubstituted monovalent heterocyclic group including 5 to 20 ring atoms;
two $R_{17}$s may be the same or different; and
$Ar_1$ to $Ar_4$ are independently a substituted or unsubstituted aryl group including 6 to 20 ring carbon atoms.

An explanation will be given on the feature that "one or more pairs of two or more adjacent groups of $R_1$ to $R_7$ and $R_{10}$ to $R_{16}$ may form a substituted or unsubstituted, saturated or unsaturated ring."

The "one or more pairs of to or more adjacent groups of $R_1$ to $R_7$ and $R_{10}$ to $R_{16}$" is a combination of: for example, $R_3$ and $R_4$; $R_5$ and $R_6$; $R_6$ and $R_7$; $R_5$ and $R_6$ and $R_7$ or the like in the formula (3-31), and $R_1$ and $R_2$; $R_2$ and $R_3$; $R_5$ and $R_6$; $R_6$ and $R_7$; $R_1$ and $R_2$ and $R_3$ or the like in the formula (3-32).

For the substituent when the "substituted or unsubstituted" saturated or unsaturated ring is "substituted", the same substituents as those for "substituted or unsubstituted" mentioned later can be given.

The "saturated or unsaturated ring" means the same as explained in the above formula (3-11).

In the formulas (3-31) and (3-32), one or more pairs of adjacent two or more of $R_1$ to $R_7$ and $R_{10}$ to $R_{16}$ may not form a substituted or unsubstituted, saturated or unsaturated ring;

In one embodiment, the compound represented by the following formula (3-31) or (3-32) is a compound represented by the following formula (3-33) or (3-34):

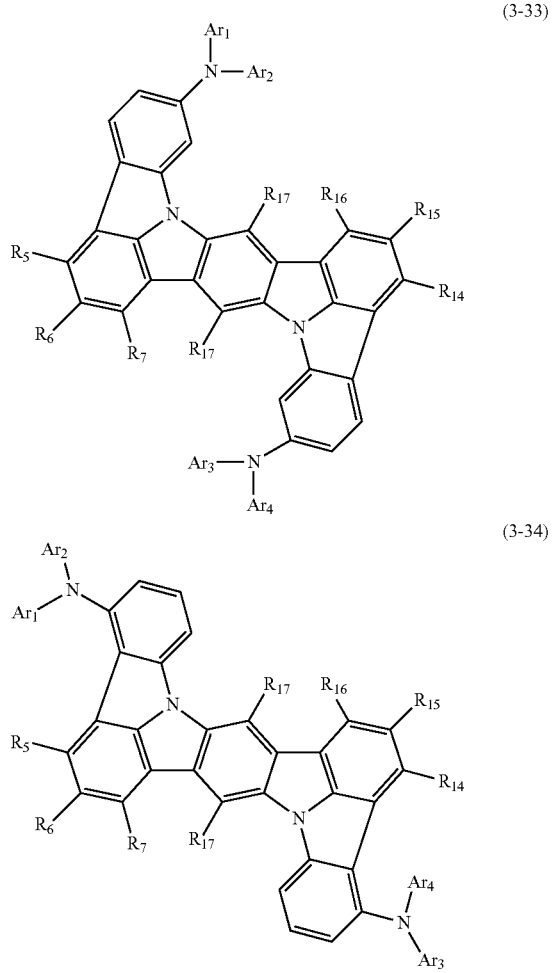

wherein in the formulas (3-33) and (3-34), $R_5$ to $R_7$, $R_{14}$ to $R_{17}$ and $Ar_1$ to $Ar_4$ are as defined in the formulas (3-31) and (3-32).

In one embodiment, in the compound represented by the formulas (3-31) to (3-34), $Ar_1$ to $Ar_4$ are independently a substituted or unsubstituted phenyl group.

In one embodiment, in the compound represented by the formulas (3-31) to (3-34), two $R_{17}$s are independently a substituted or unsubstituted aryl group including 6 to 20 ring carbon atoms.

In one embodiment, in the compound represented by the formulas (3-31) to (3-34), two $R_{17}$s are independently a substituted or unsubstituted phenyl group.

In one embodiment, in the compound represented by the formulas (3-31) to (3-34), two $R_{17}$s are hydrogen atoms.

In one embodiment, in the compound represented by the formulas (3-31) to (3-34), $R_5$ to $R_7$ and $R_{14}$ to $R_{16}$ are hydrogen atoms.

In one embodiment, in the compound represented by the formulas (3-31) to (3-34), a substituent in the "substituted or unsubstituted" is selected from the group consisting of an alkyl group including 1 to 20 carbon atoms, an aryl group including 6 to 20 ring carbon atoms, and a monovalent heterocyclic group including 5 to 20 ring atoms.

In one embodiment, in the compound represented by the formulas (3-31) to (3-34), a substituent in the "substituted or unsubstituted" is an alkyl group including 1 to 5 carbon atoms.

In one embodiment, in the compound represented by the formulas (3-31) to (3-34), $Ar_1$ to $Ar_4$ are independently a substituted or unsubstituted phenyl group; and two $R_{17}$s are hydrogen atoms.

In one embodiment, in the compound represented by the formulas (3-31) to (3-34), $Ar_1$ to $Ar_4$ are independently a substituted or unsubstituted phenyl group; two $R_{17}$s are independently a substituted or unsubstituted aryl group including 6 to 20 ring carbon atoms; $R_5$ to $R_7$ and $R_{14}$ to $R_{16}$ are hydrogen atoms; and a substituent in the "substituted or unsubstituted" is selected from the group consisting of an alkyl group including 1 to 20 carbon atoms, an aryl group including 6 to 20 ring carbon atoms, and a monovalent heterocyclic group including 5 to 20 ring atoms.

In one embodiment, in the compound represented by the formulas (3-31) to (3-34), $Ar_1$ to $Ar_4$ are independently a substituted or unsubstituted phenyl group; two $R_{17}$s are independently a substituted or unsubstituted phenyl group; $R_5$ to $R_7$ and $R_{14}$ to $R_{16}$ are hydrogen atoms; and a substituent in the "substituted or unsubstituted" is an alkyl group including 1 to 5 carbon atoms.

Specific examples of each substituent and substituents for "substituted or unsubstituted" in the compound represented by the formulas (3-31) to (3-34) are the same as those mentioned above.

As a specific example of the compound represented by the formulas (3-11) to (3-14), (3-21), (3-22) and (3-31) to (3-34), the following compounds can be given, for example.

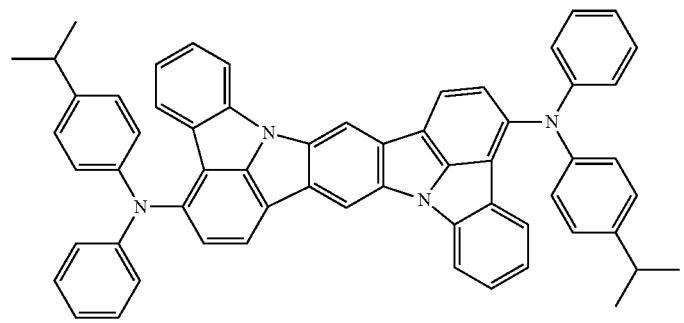
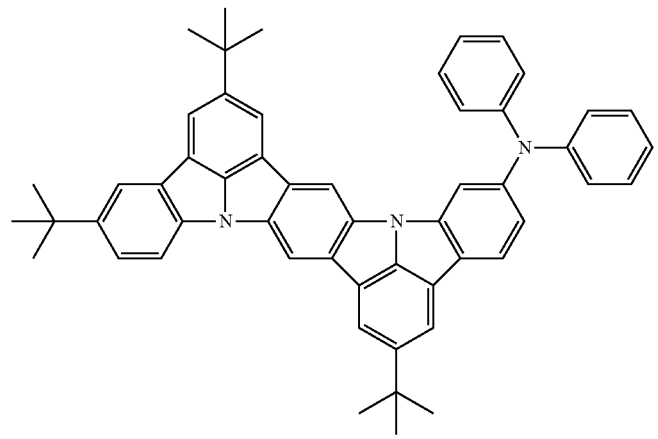
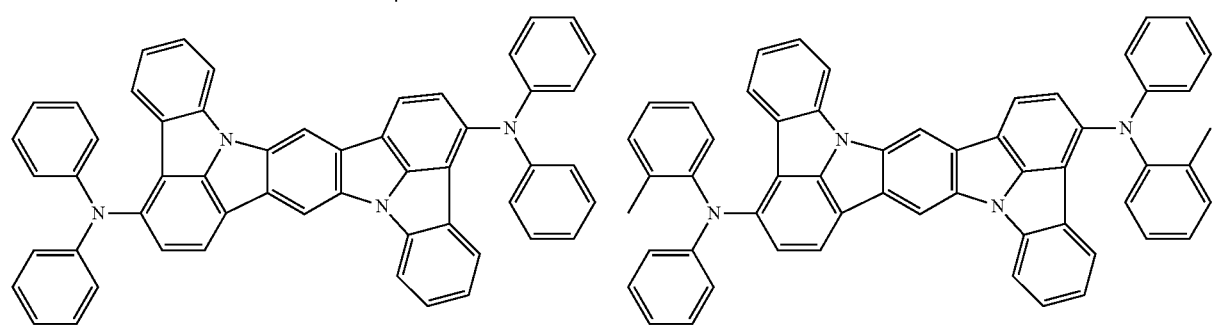
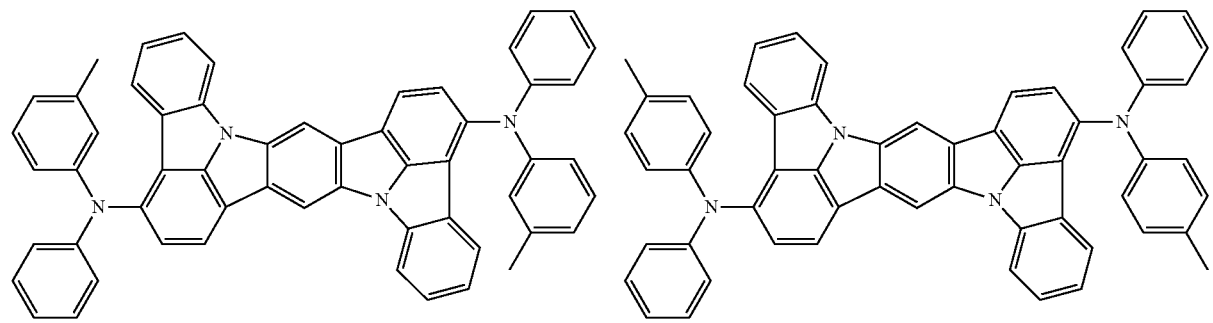
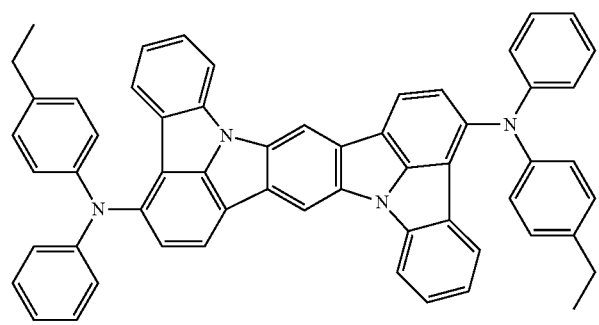

163 164
-continued
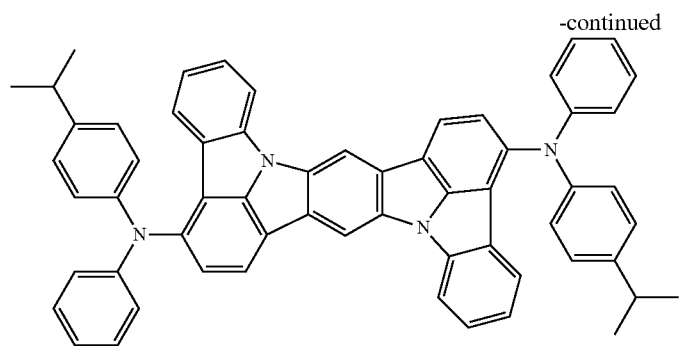

-continued
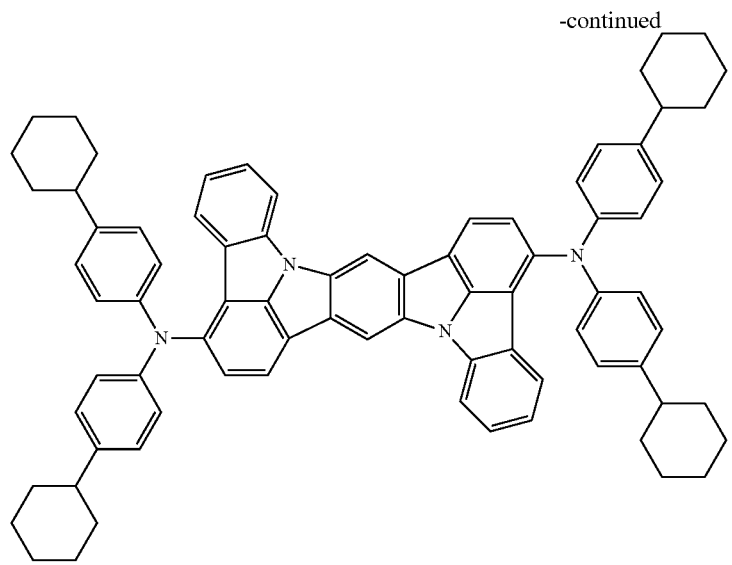
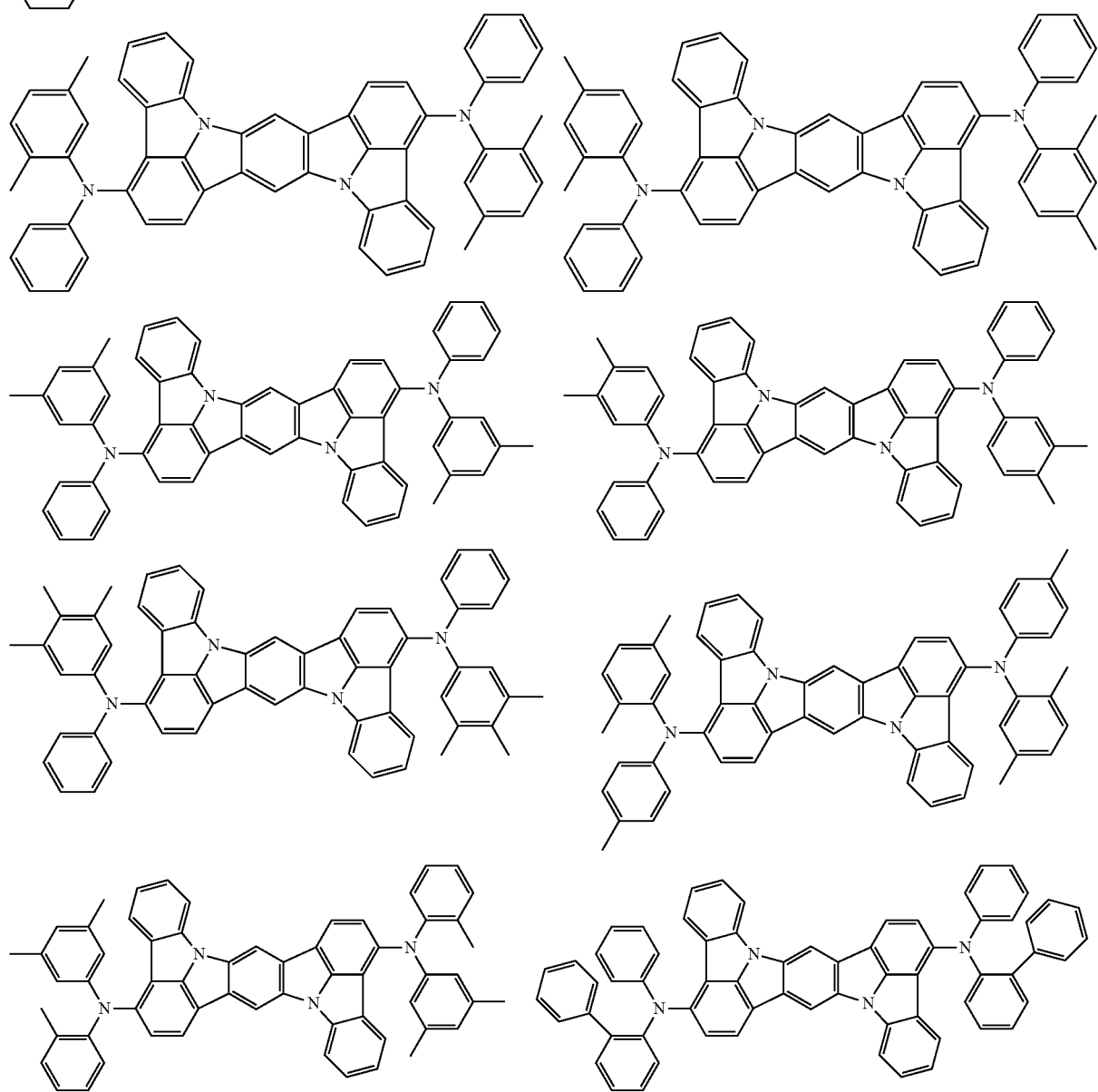

-continued
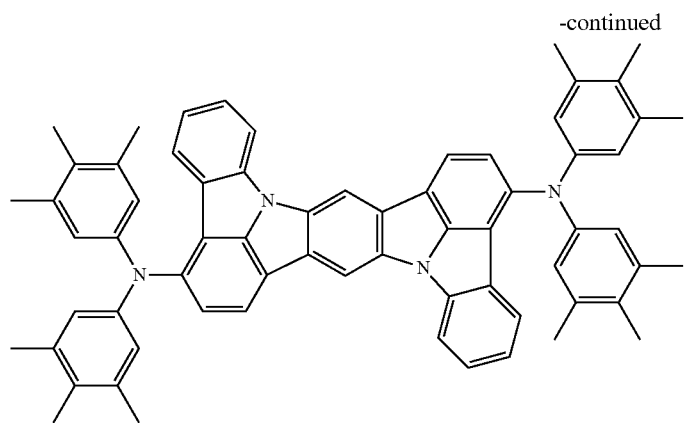
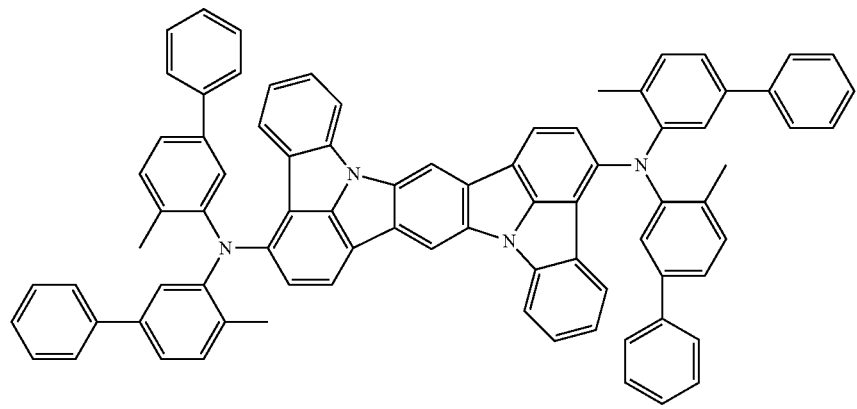
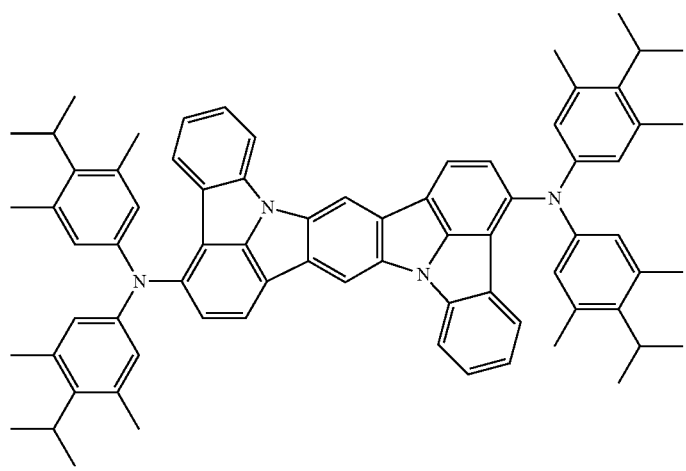
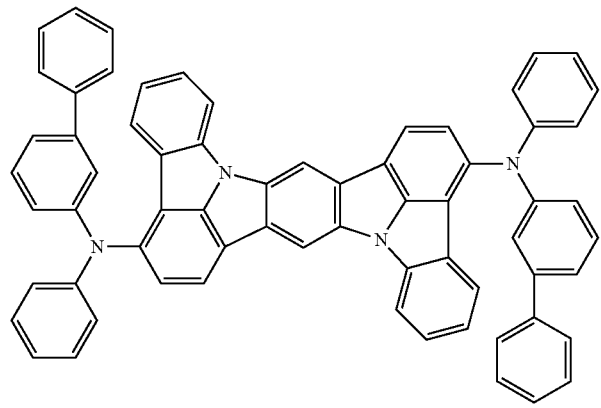

-continued
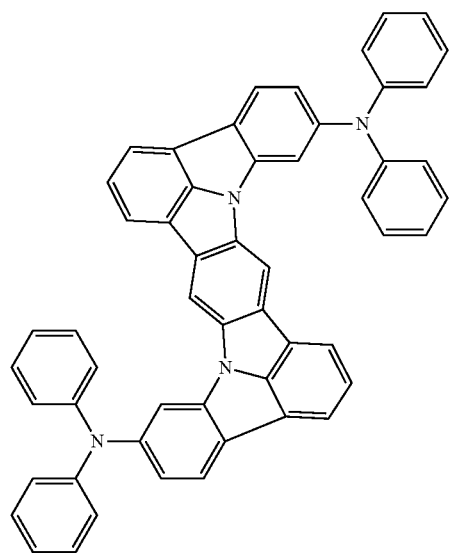
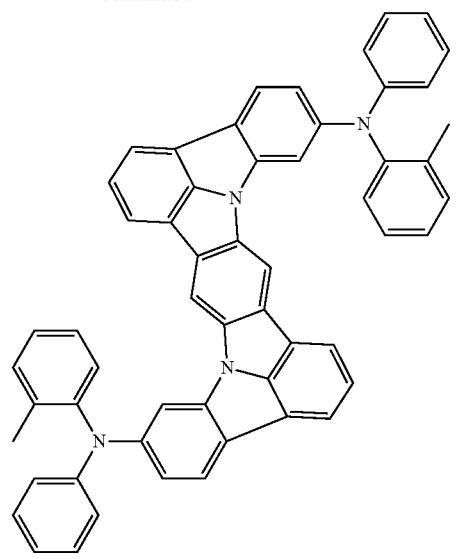
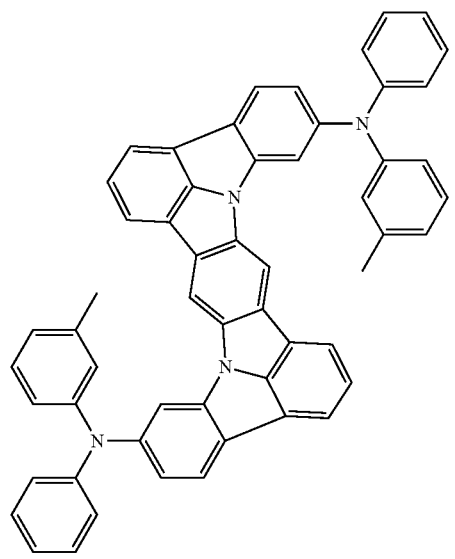
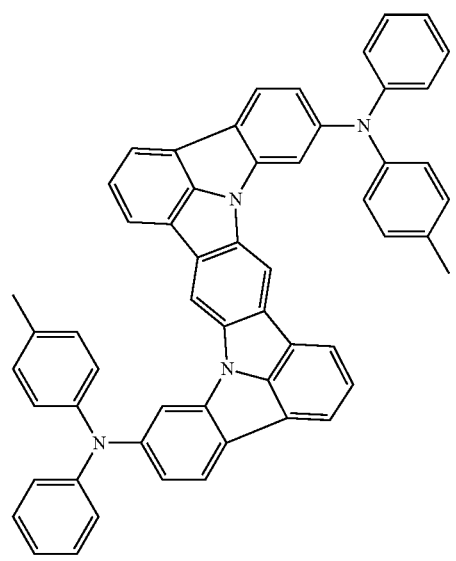
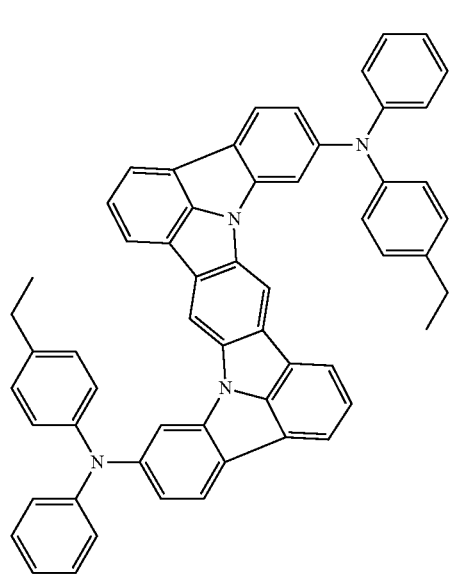
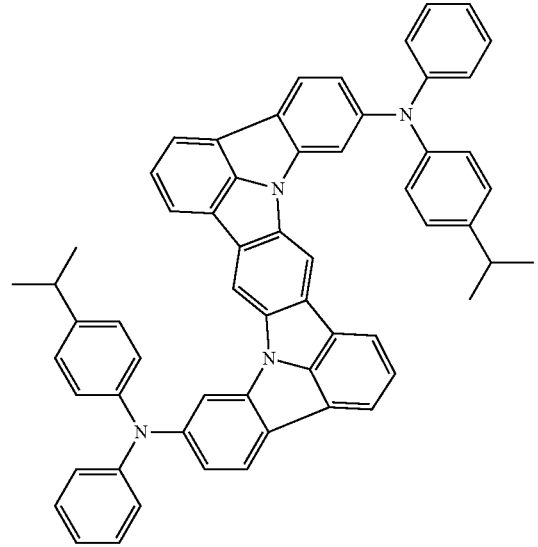

171
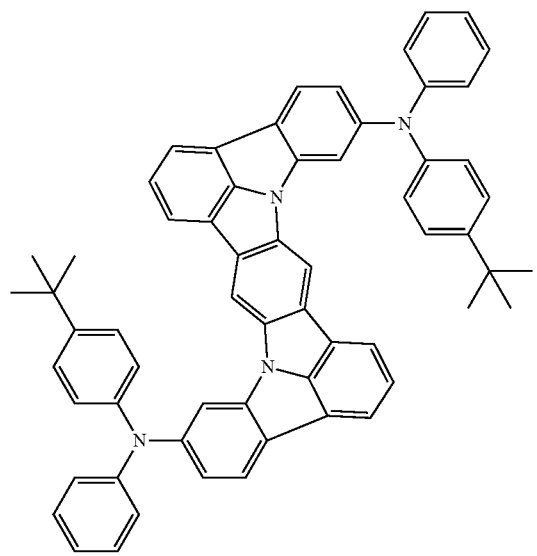
172
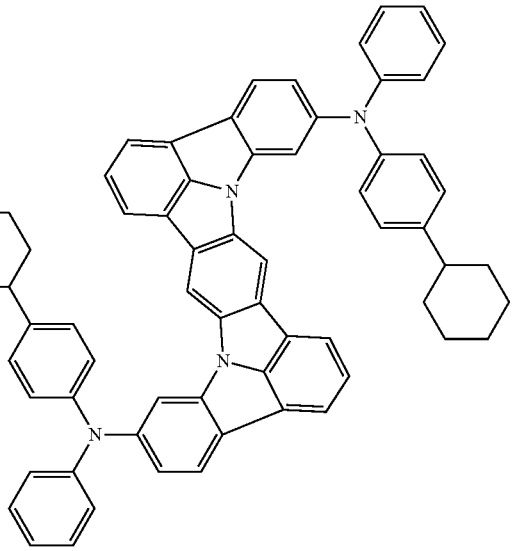
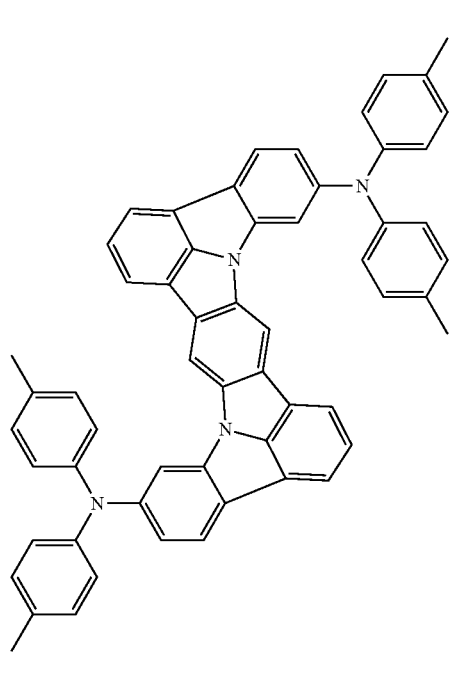
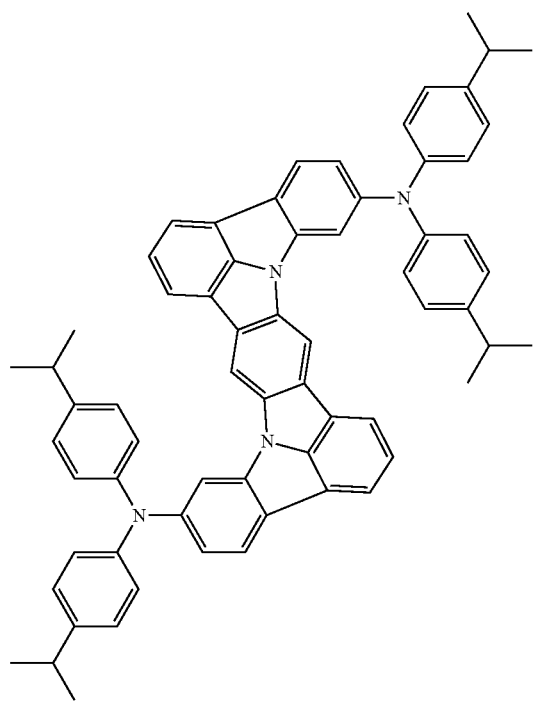

173 174
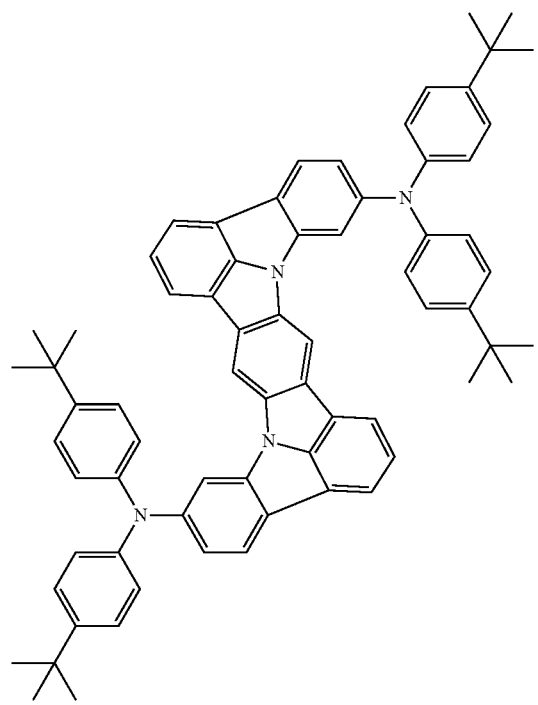
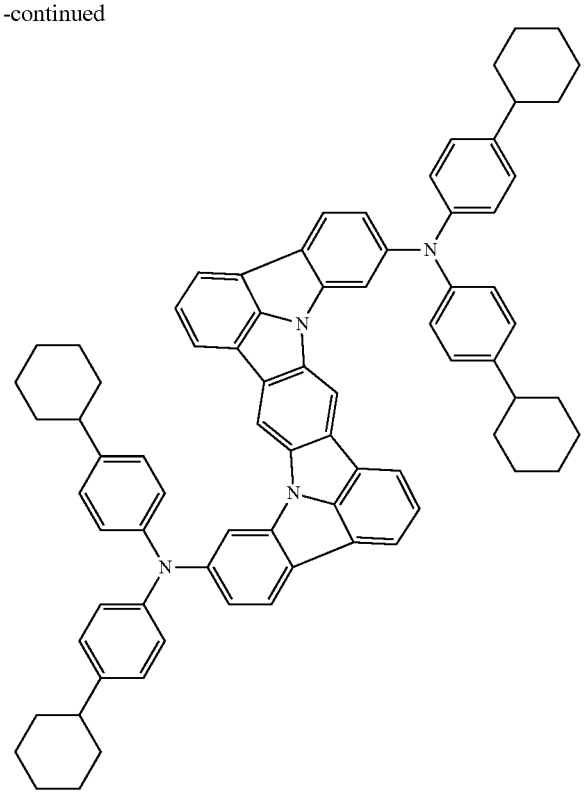
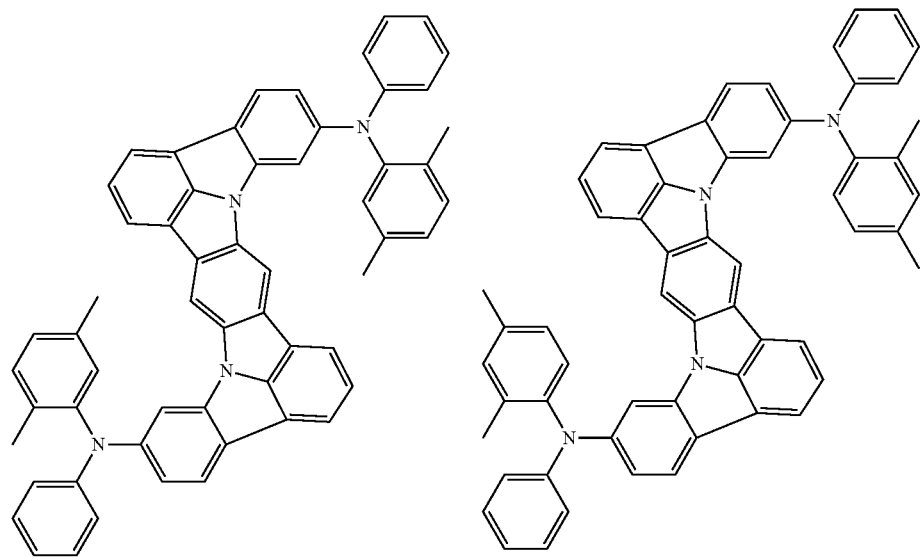

-continued
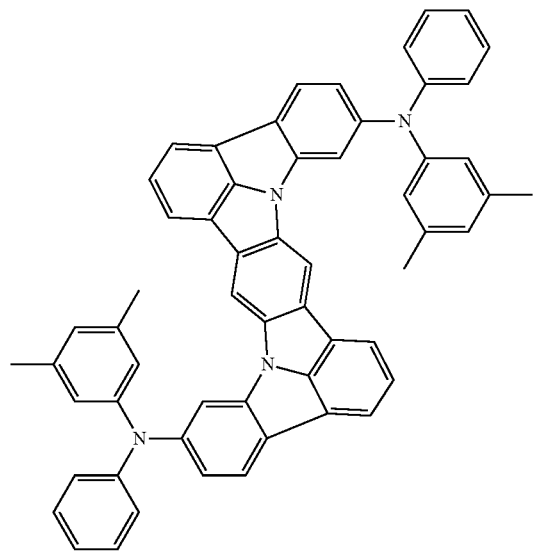
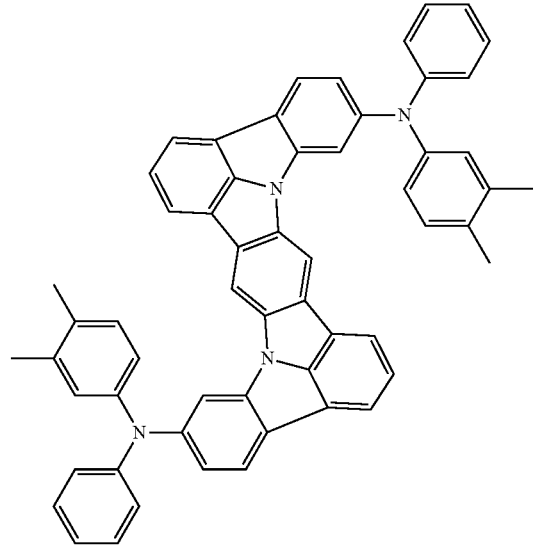
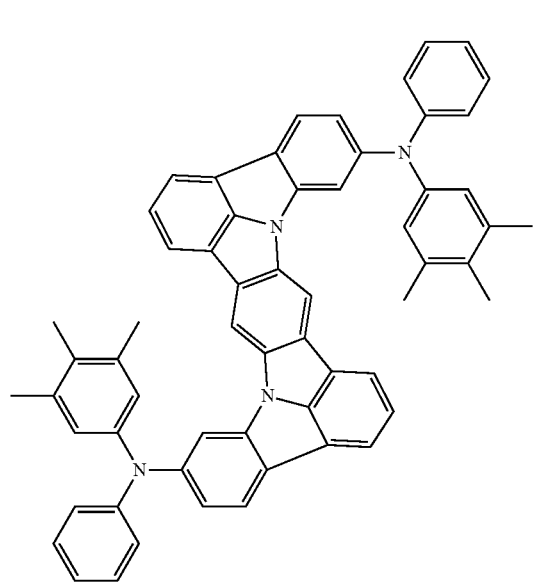
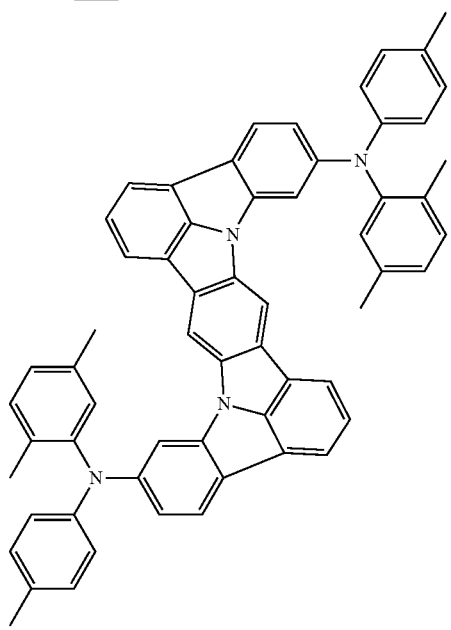
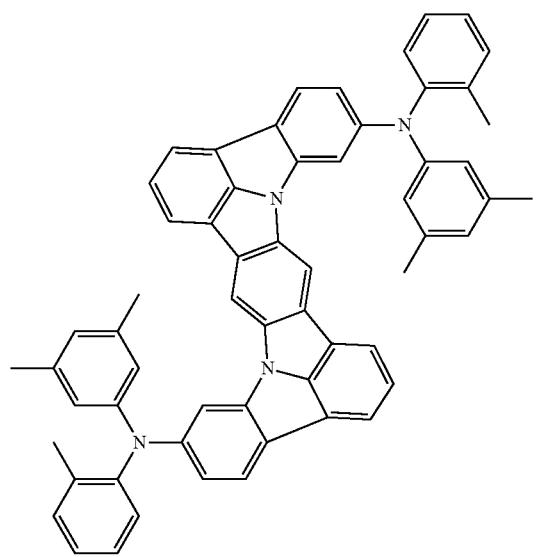
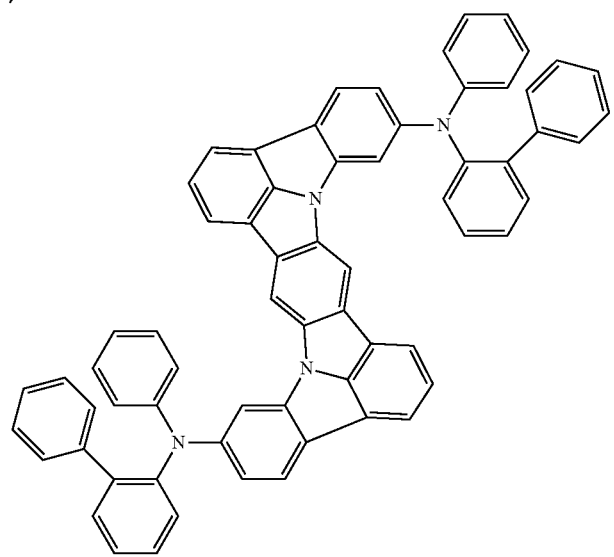

-continued
177
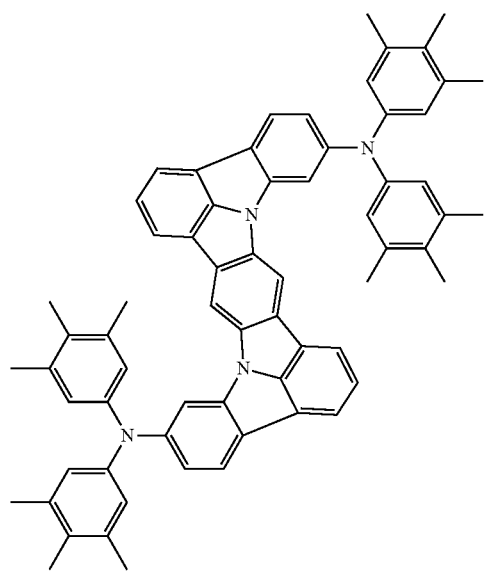
178
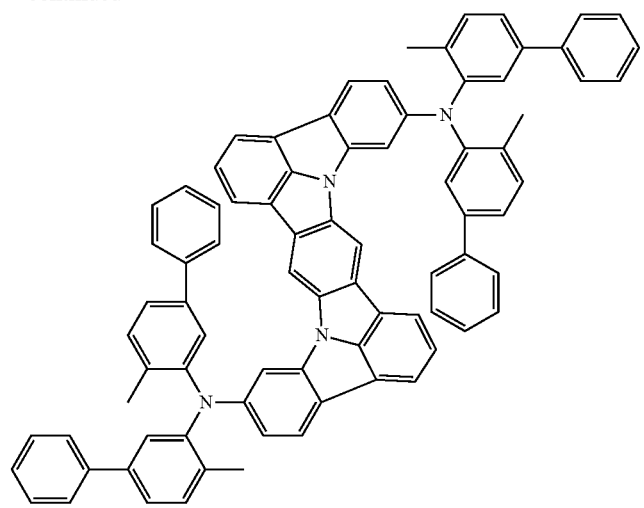
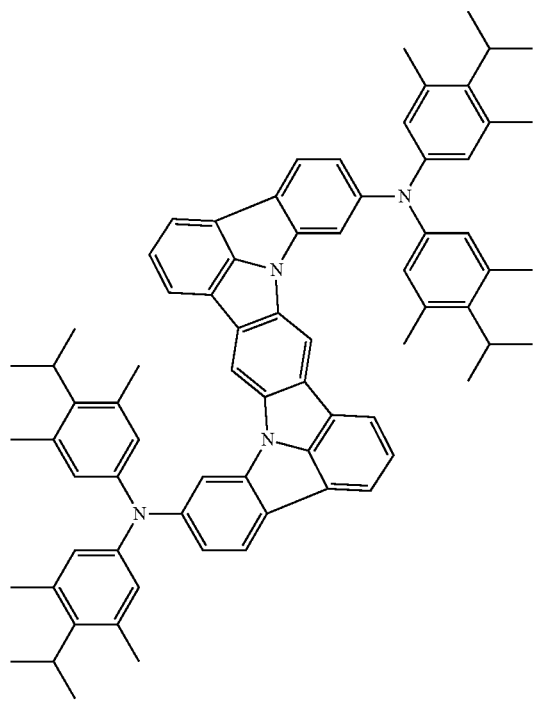
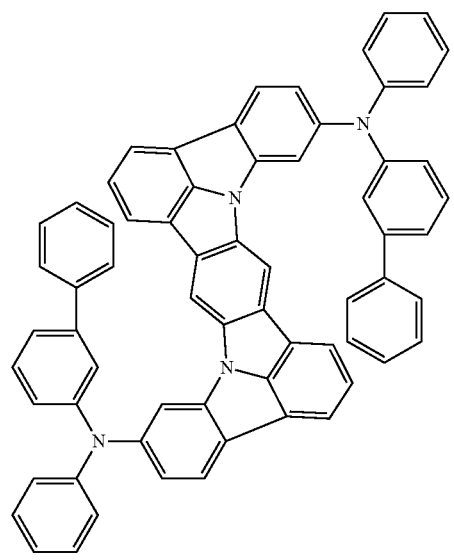

-continued
179
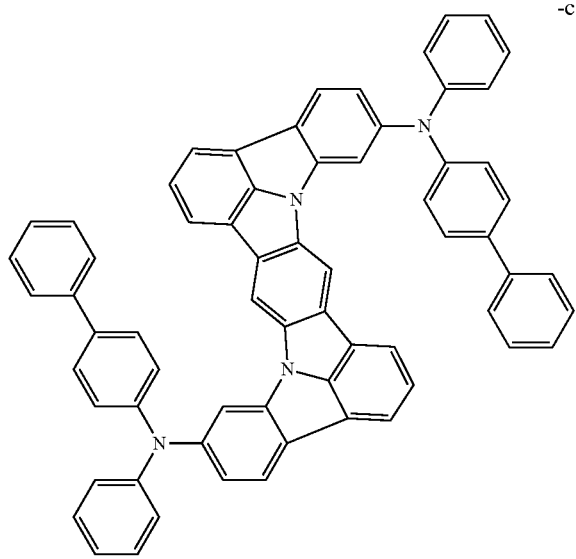
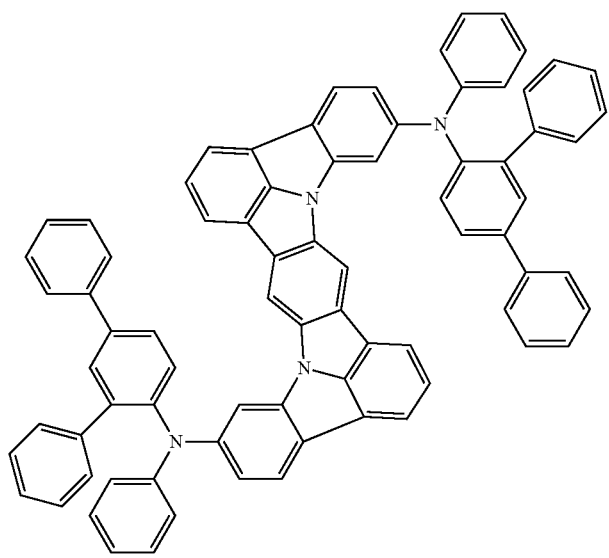
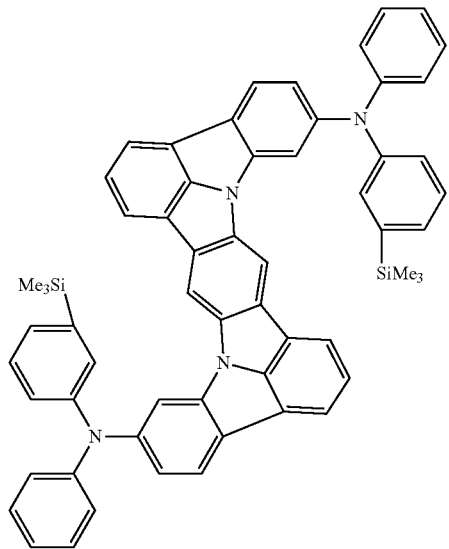
180
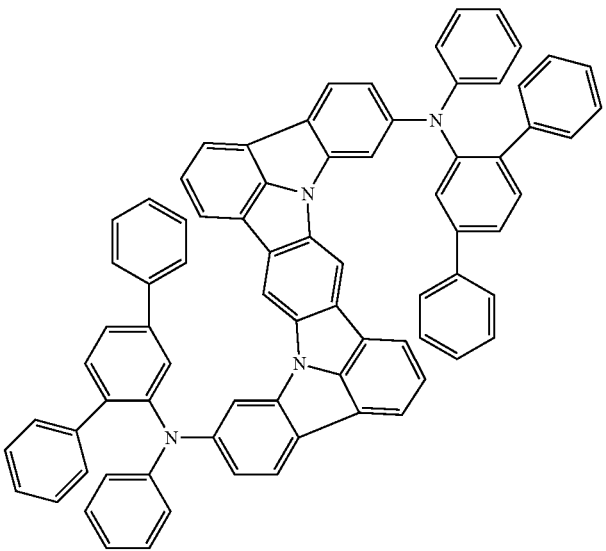
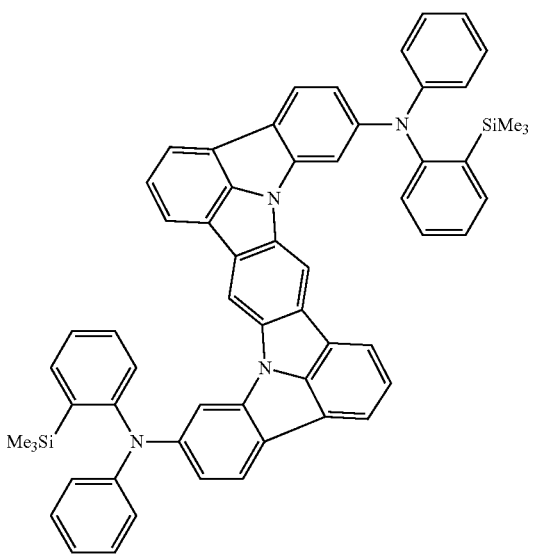
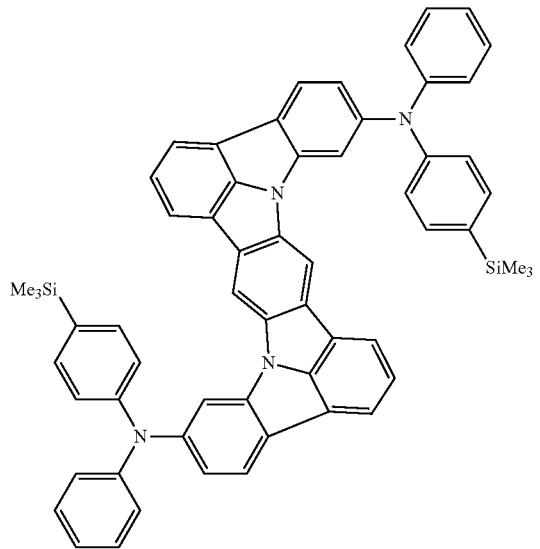

-continued
181
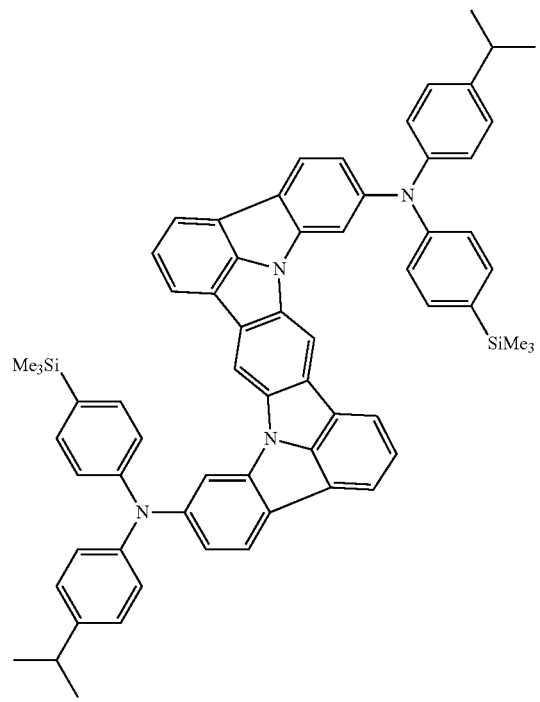
182
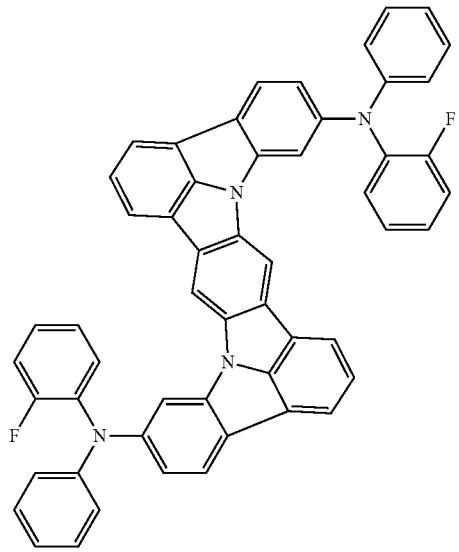
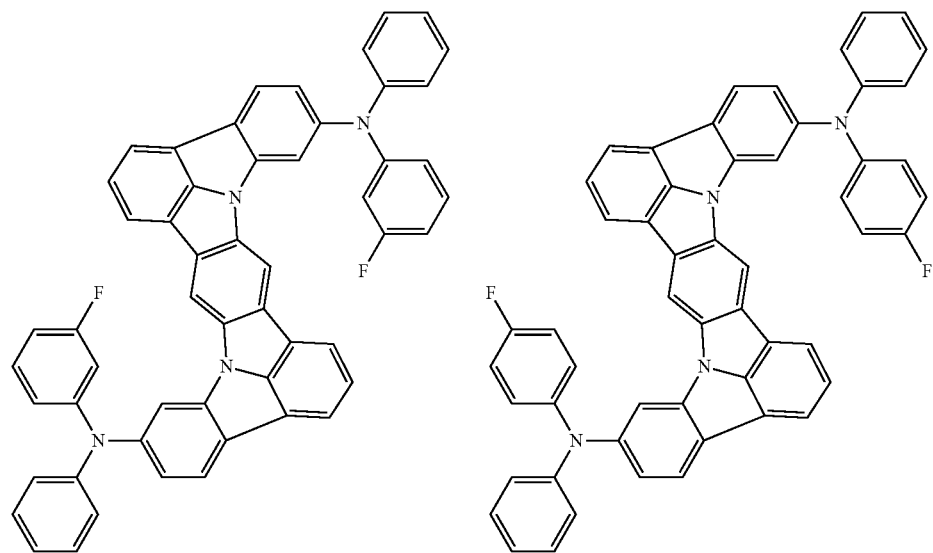

-continued
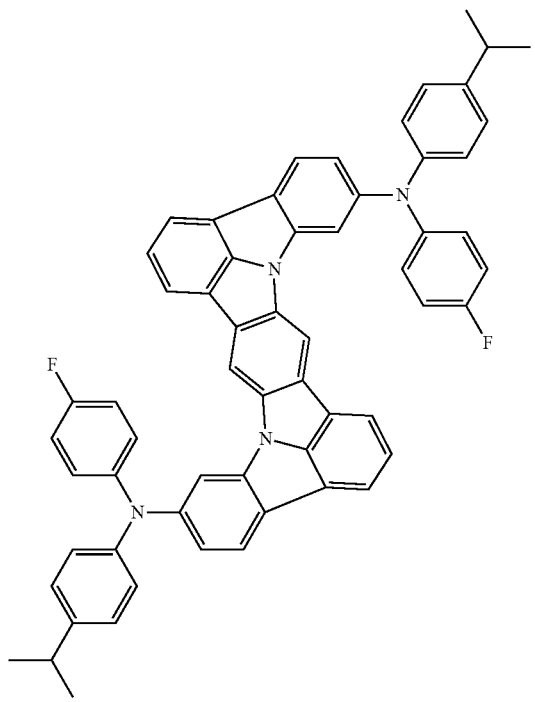
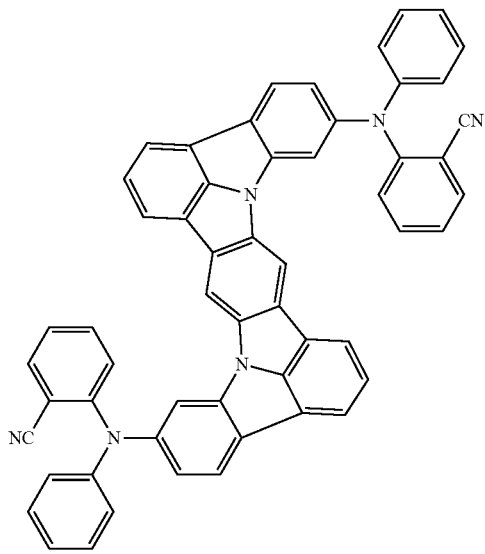
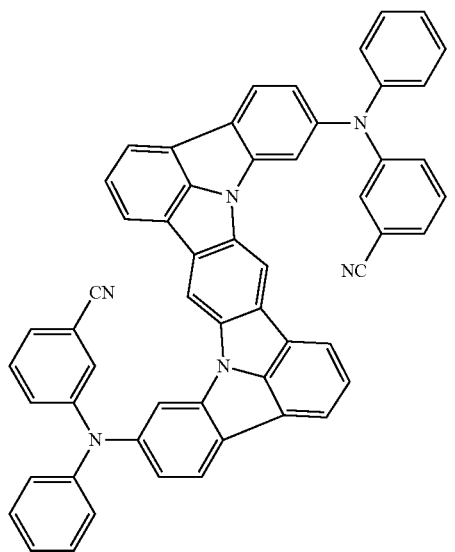
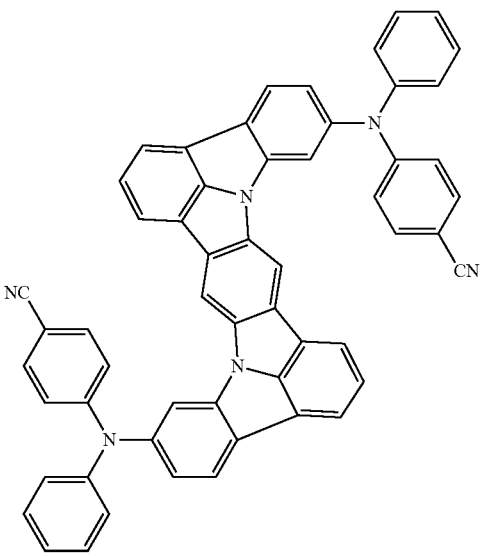

-continued
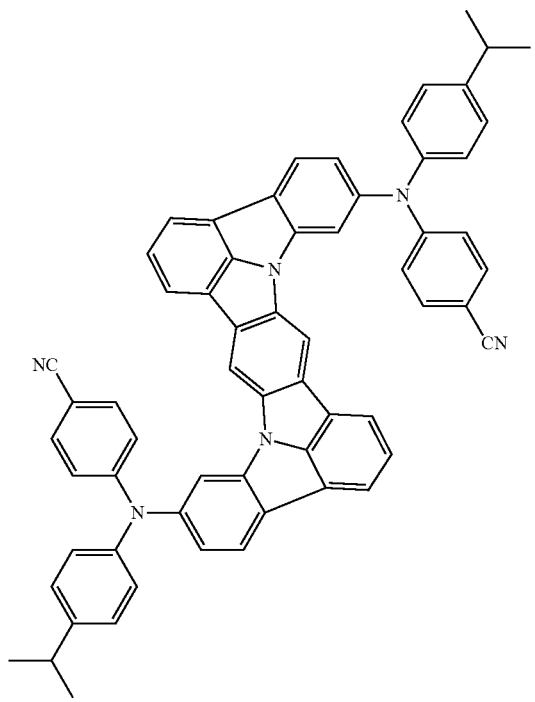
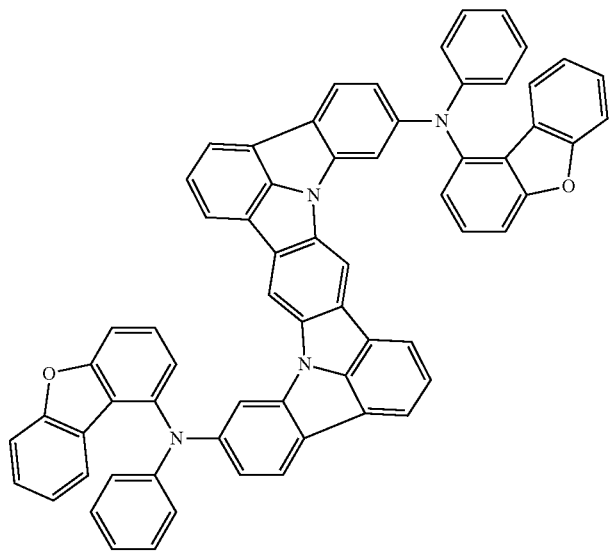
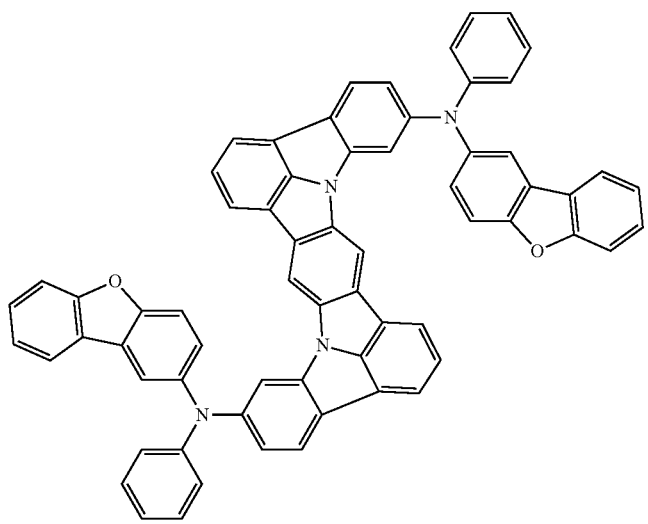
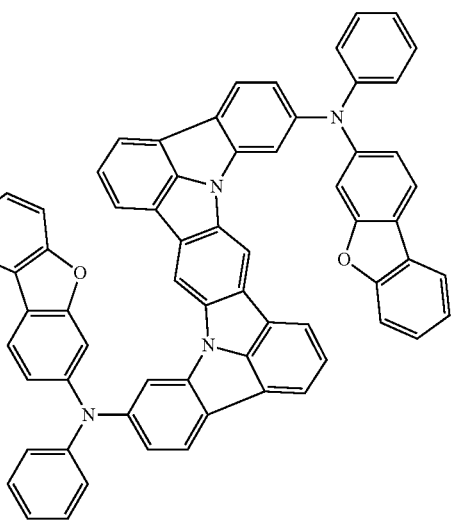
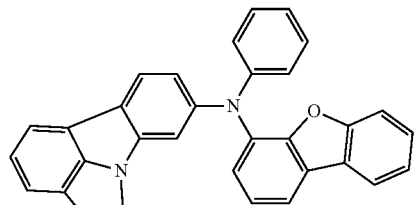
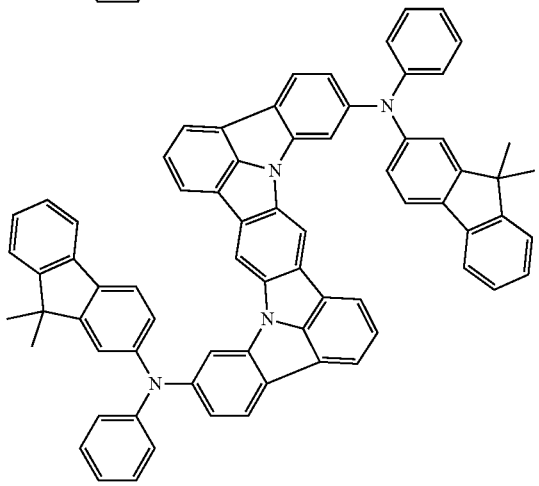
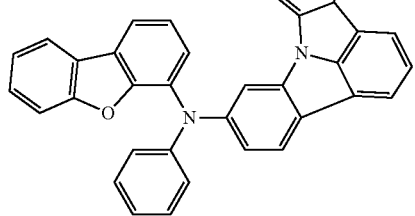

187
188
-continued
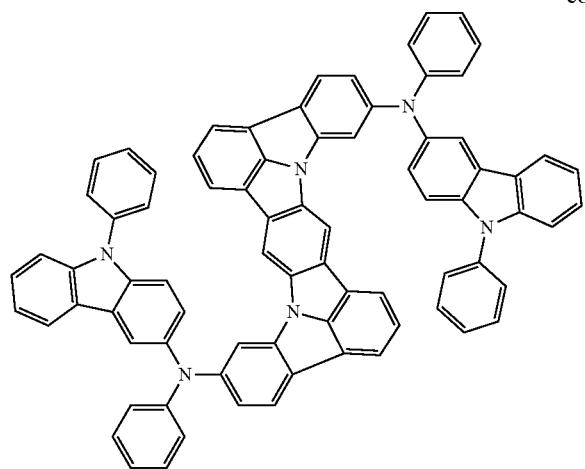
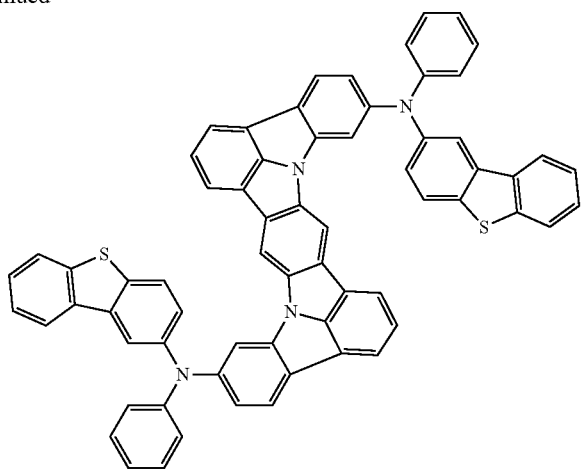
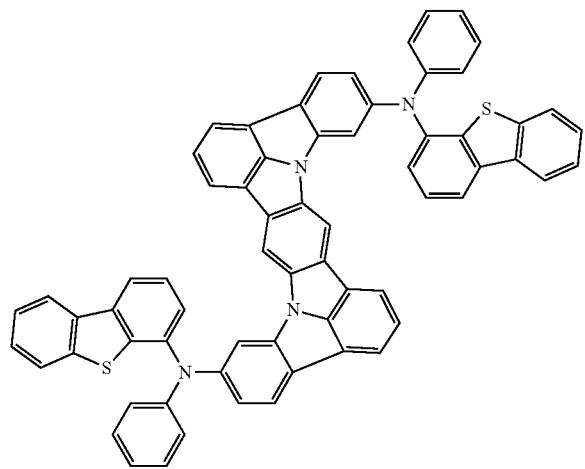
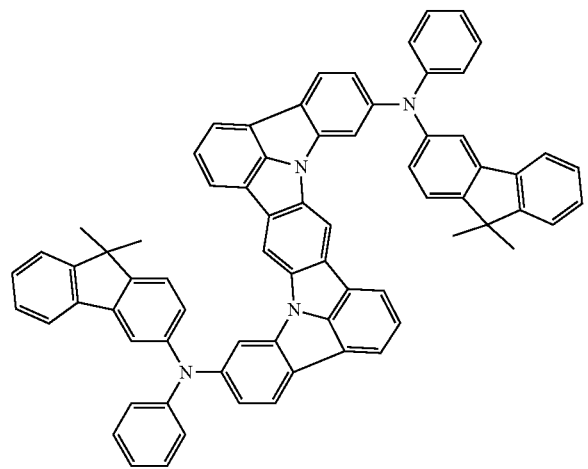
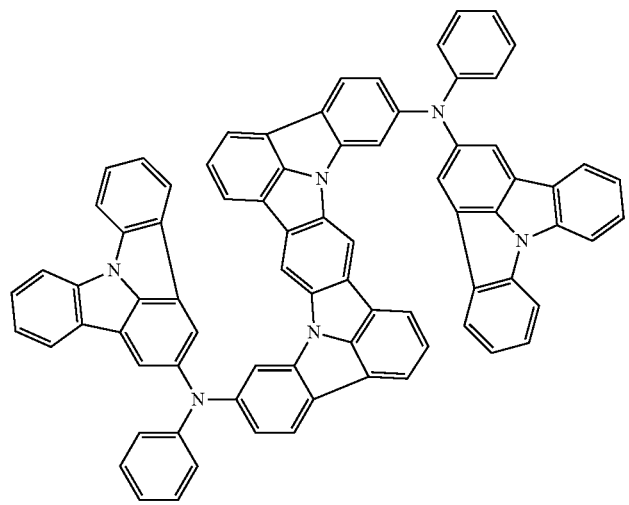
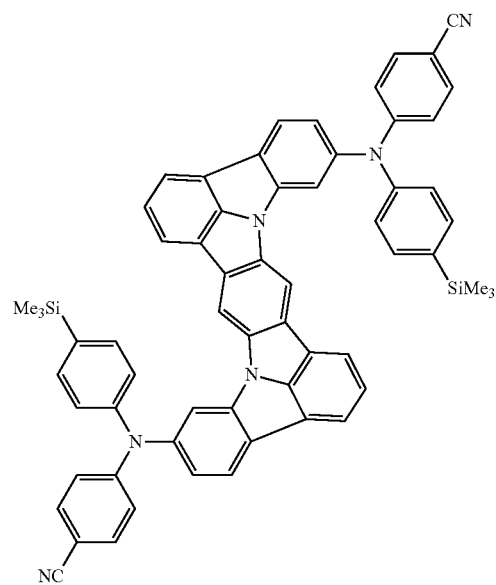

-continued
| 189 | 190 |
|---|---|
| 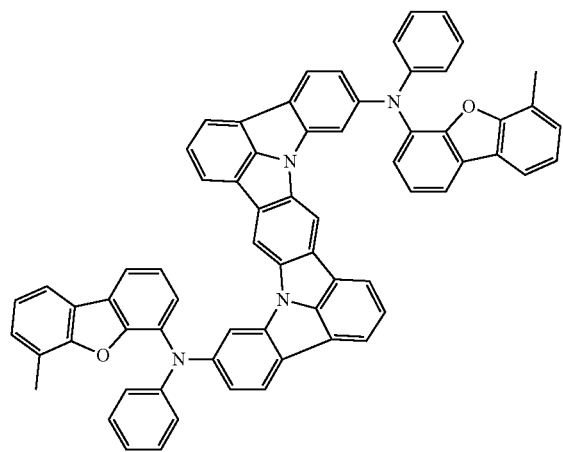 | 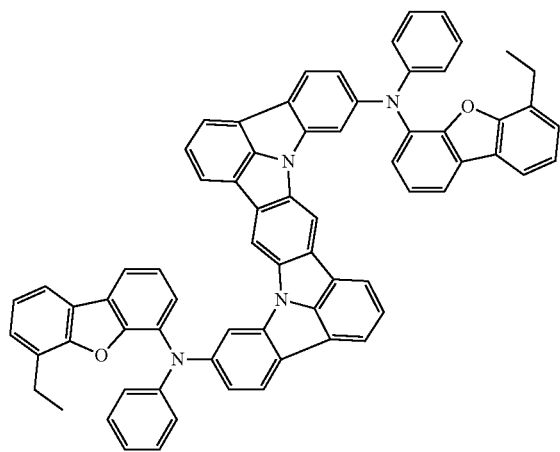 |
| 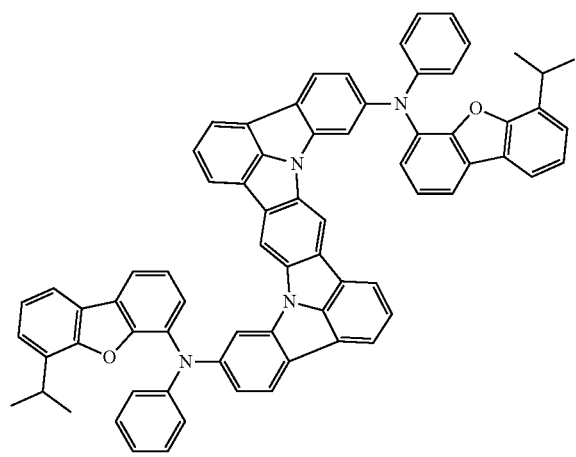 | 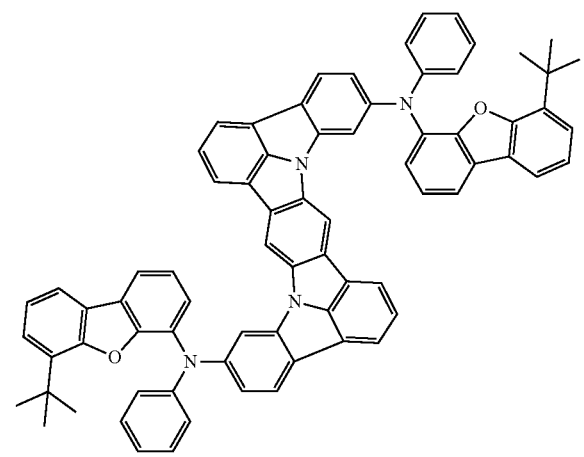 |
| 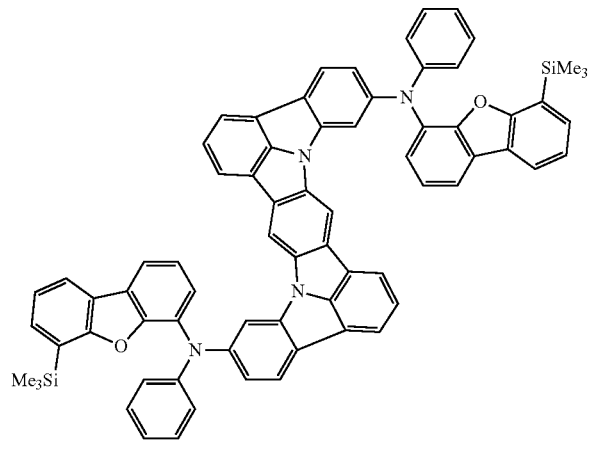 | 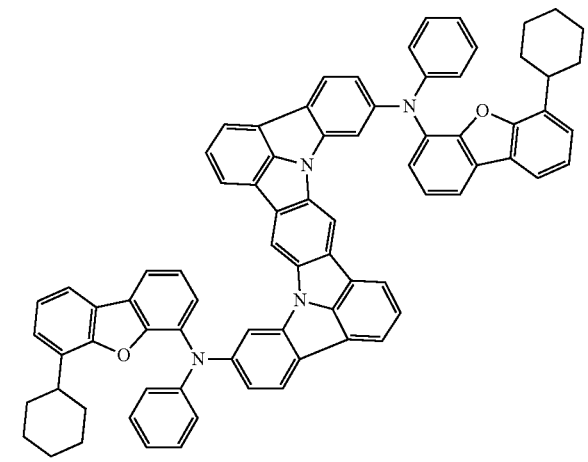 |

-continued
191
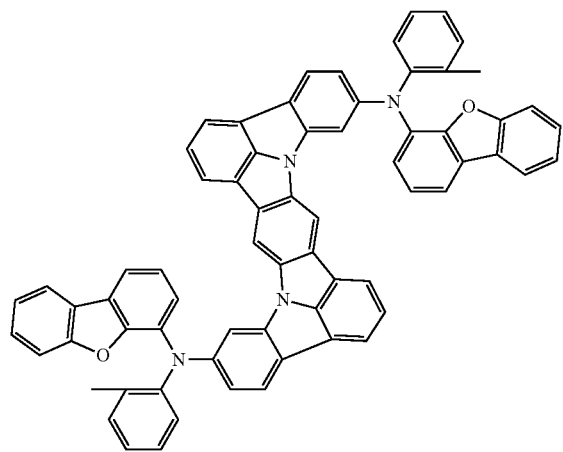
192
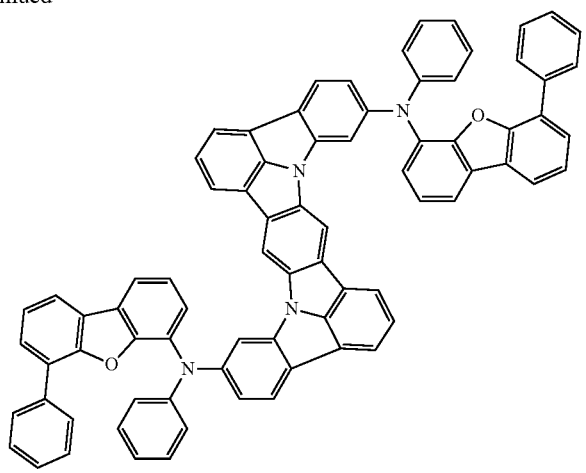
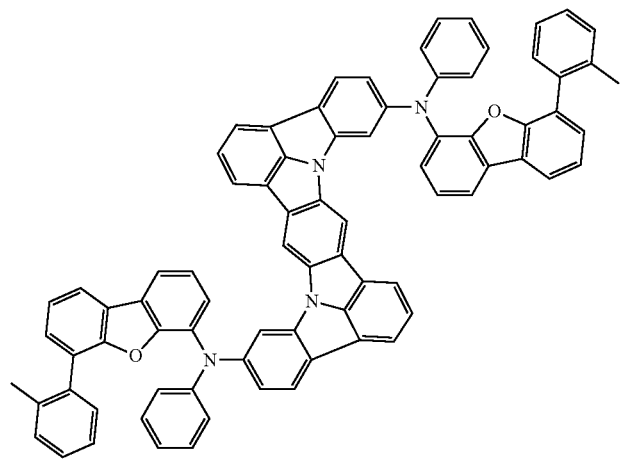
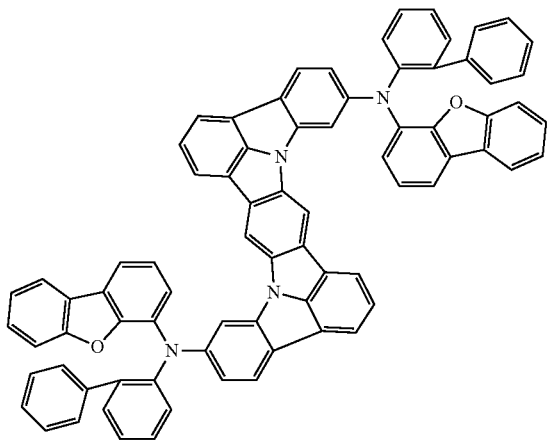
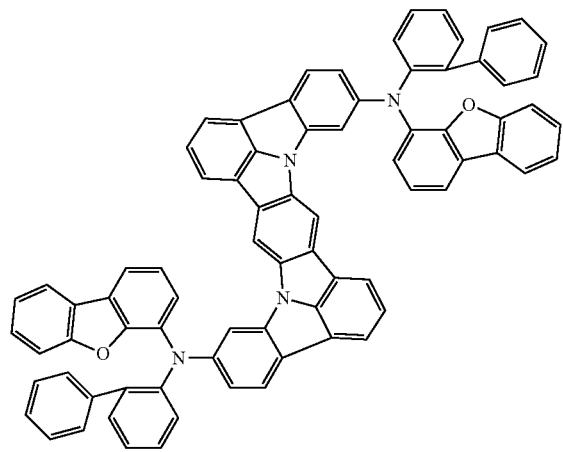
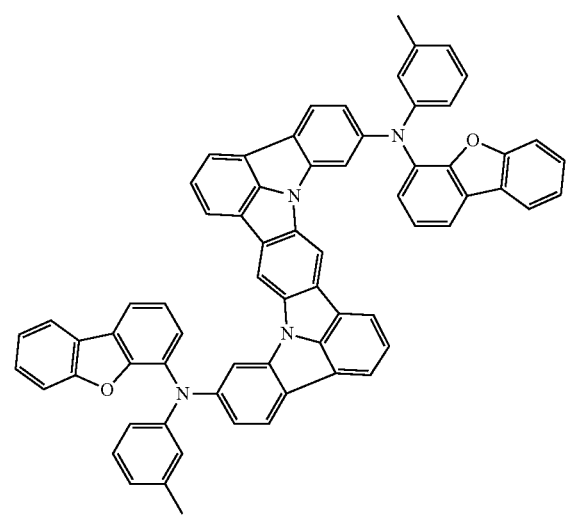

193 194
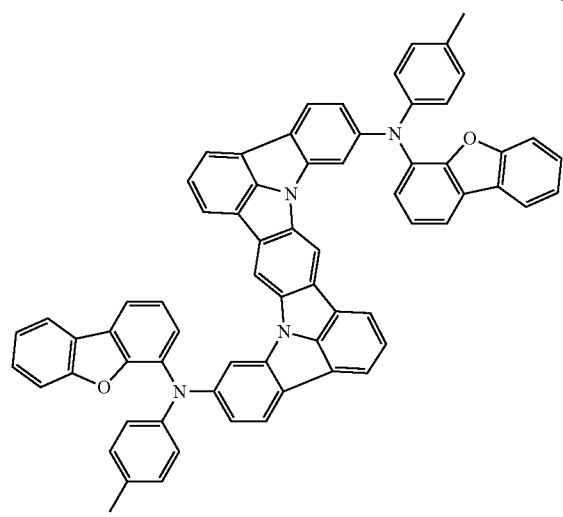 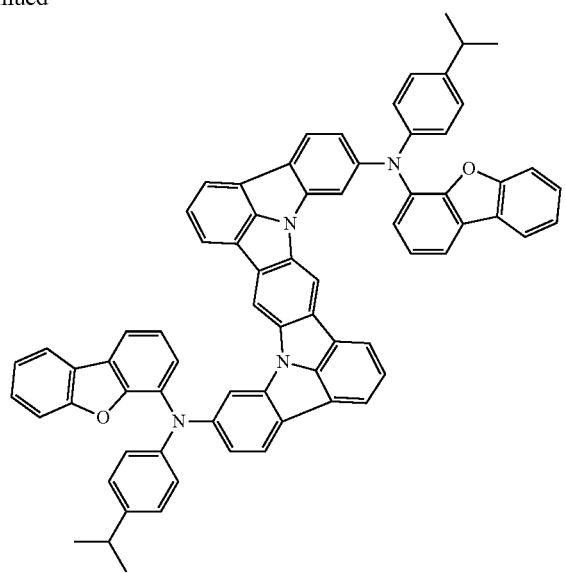
-continued
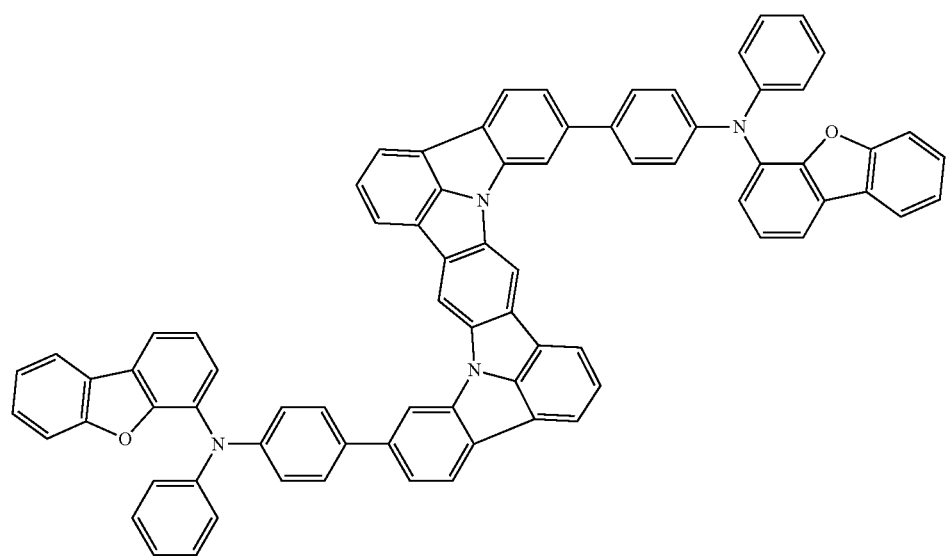

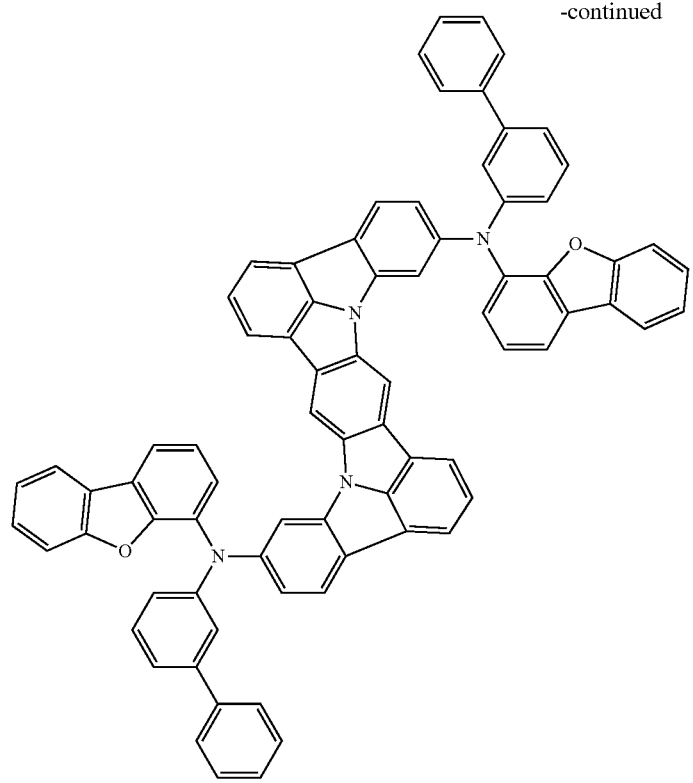
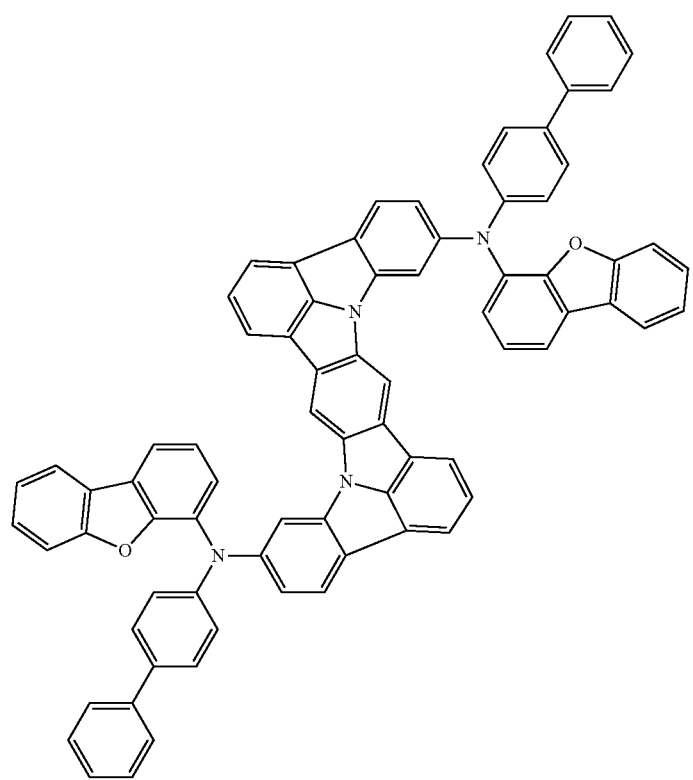

-continued
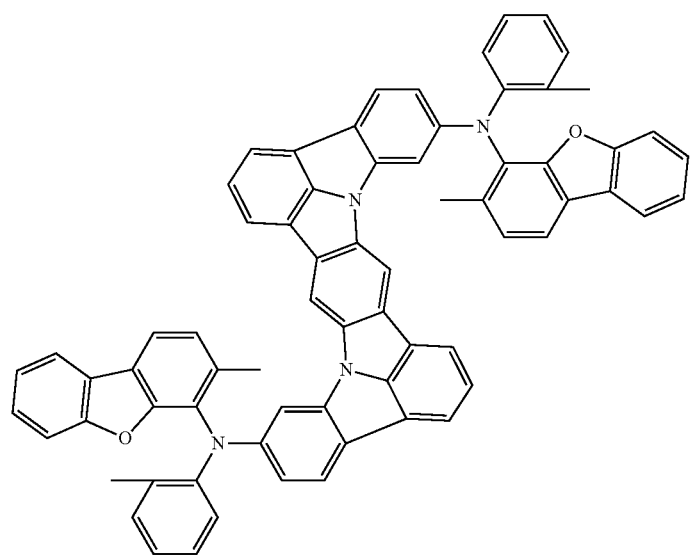

-continued
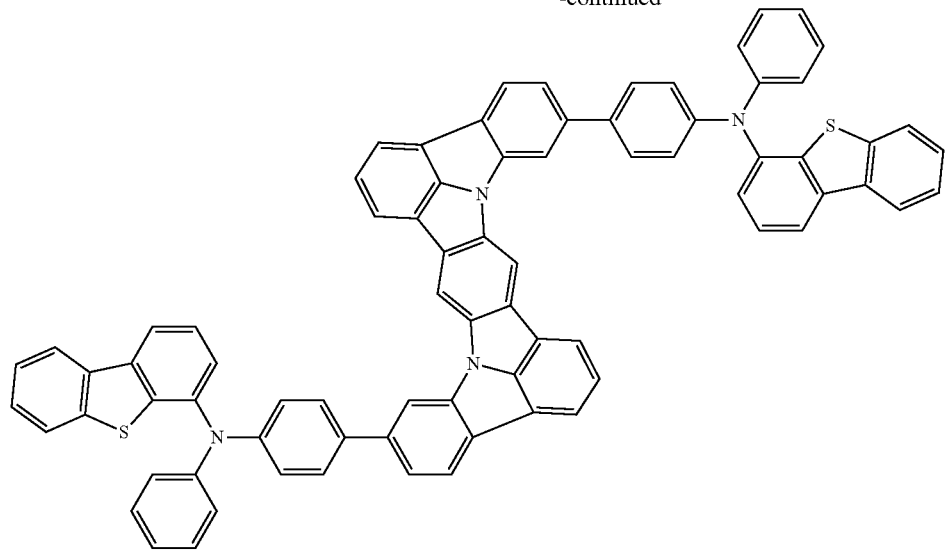
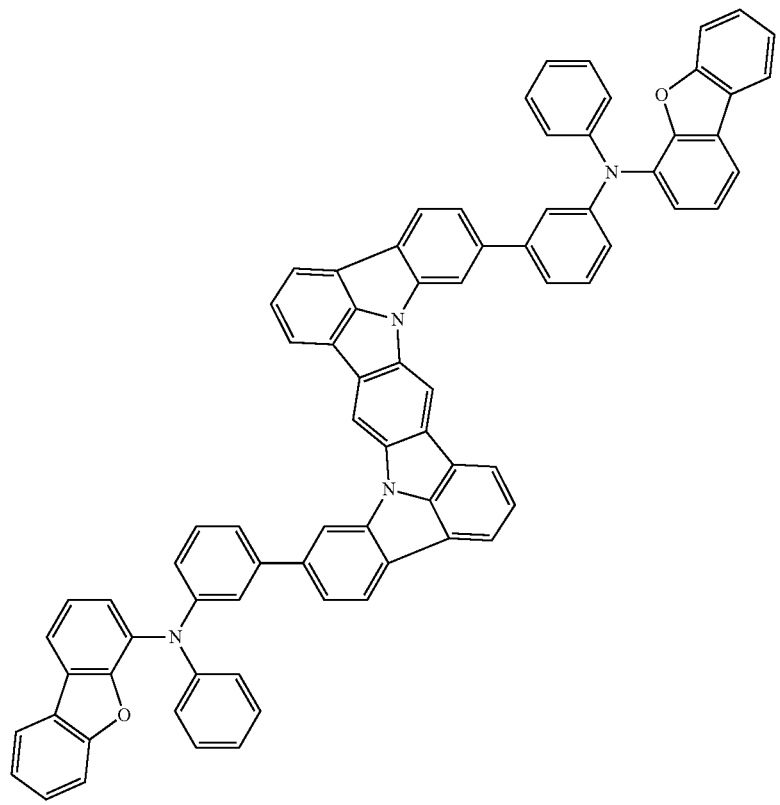

-continued
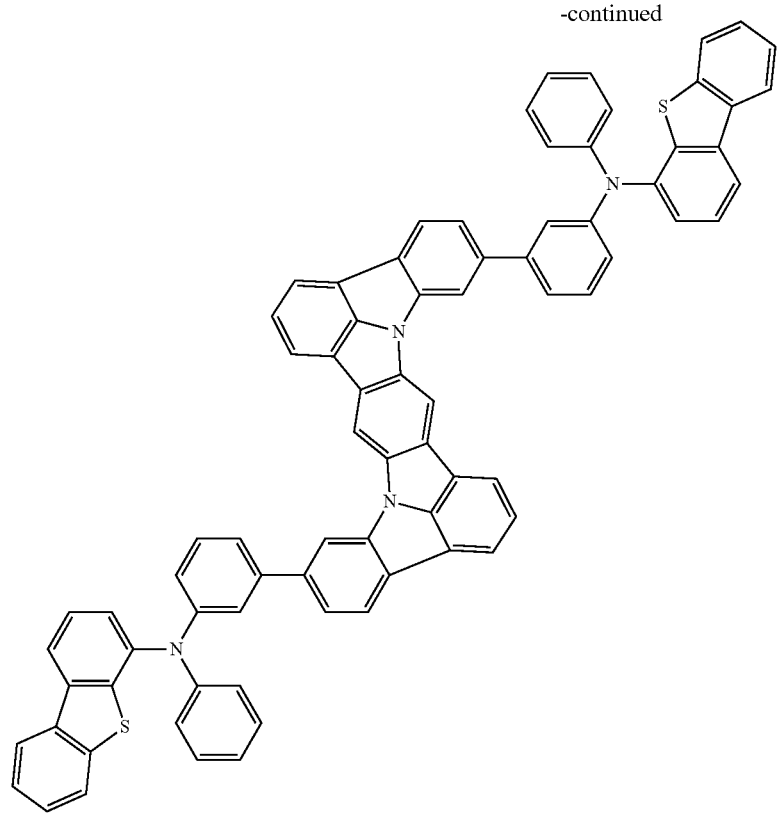
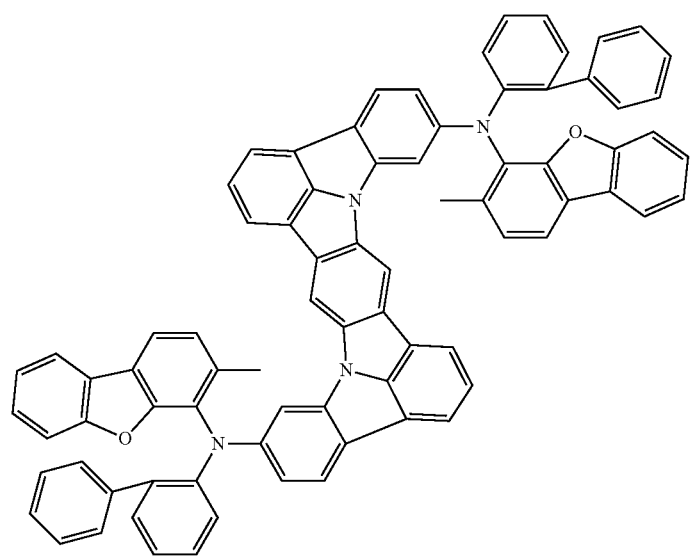

-continued
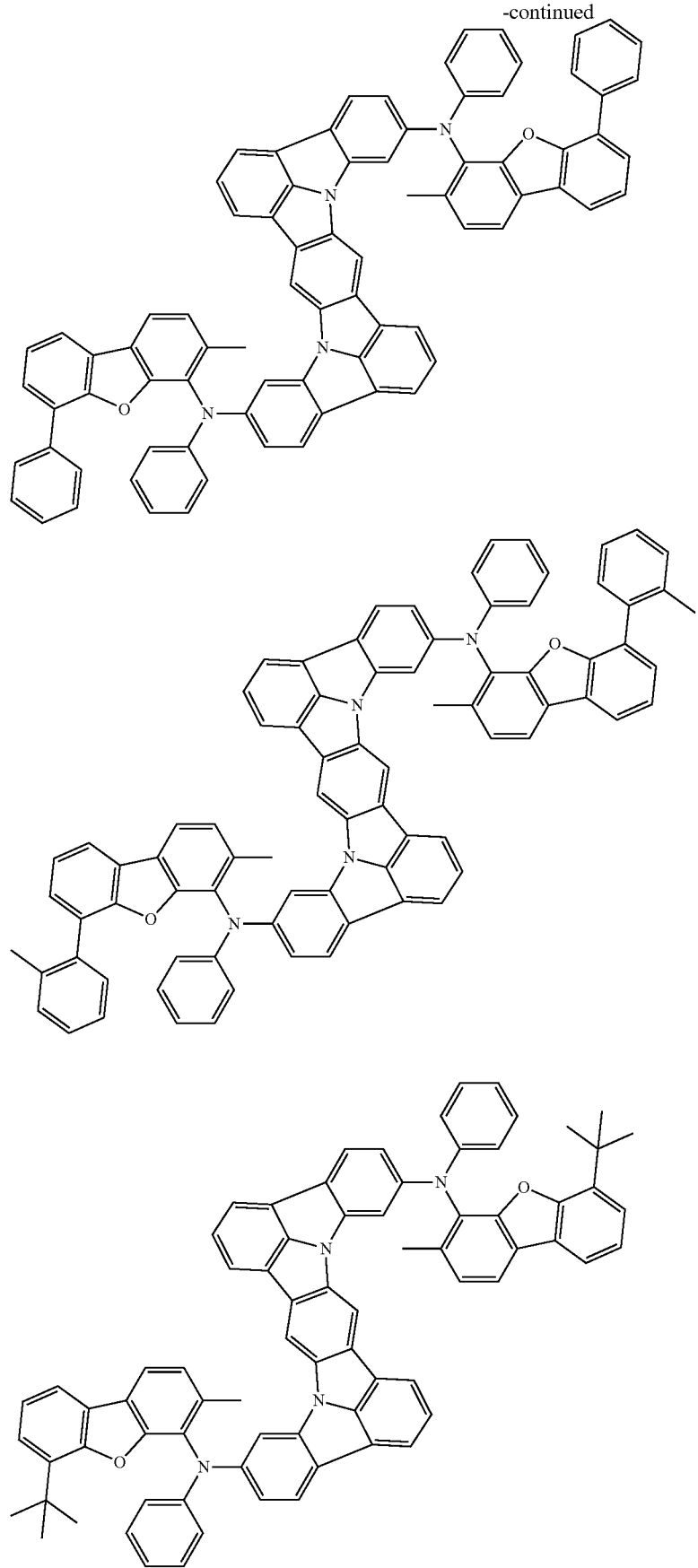

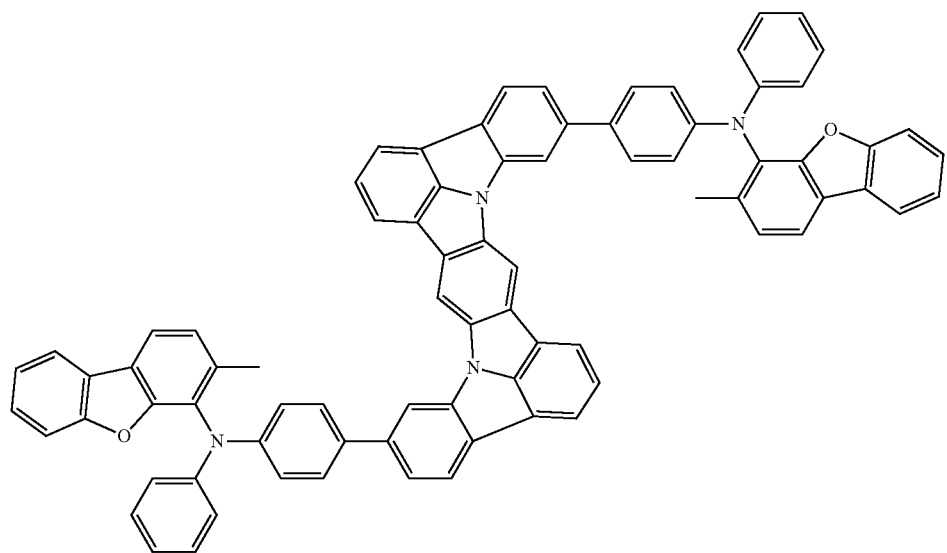
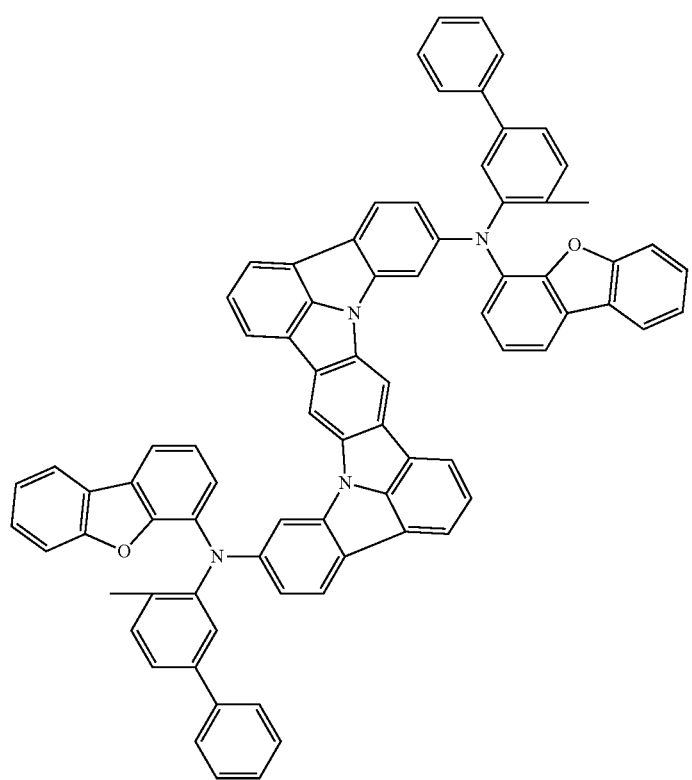

207
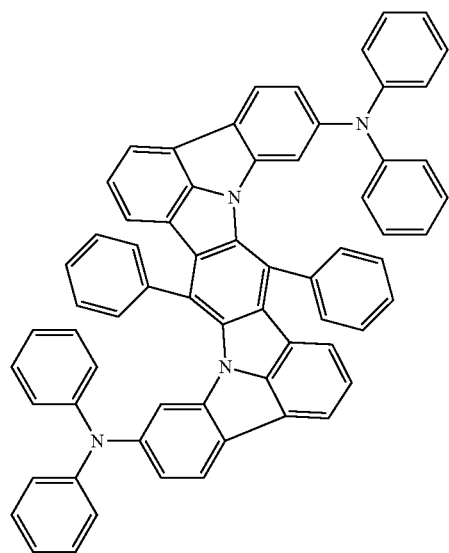
208
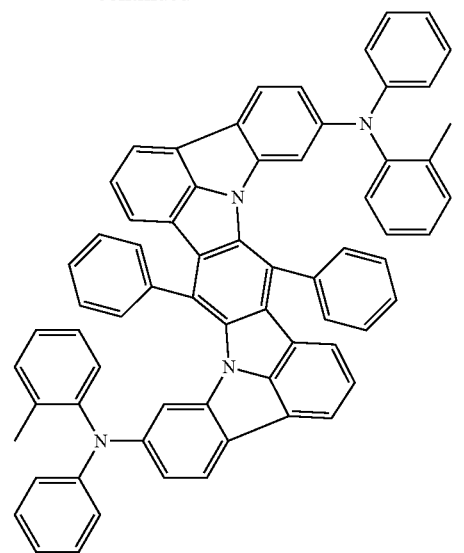
-continued
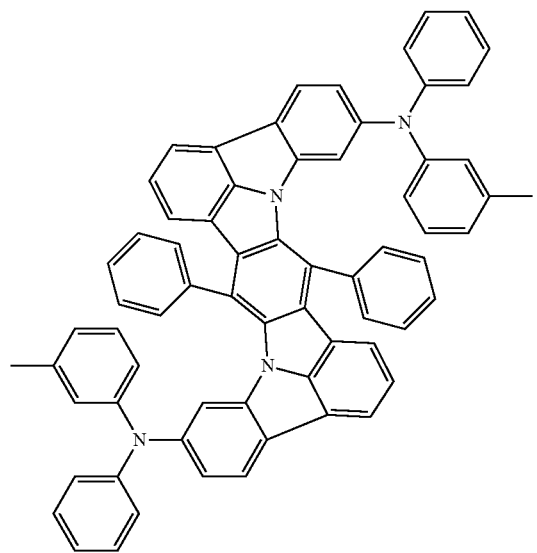
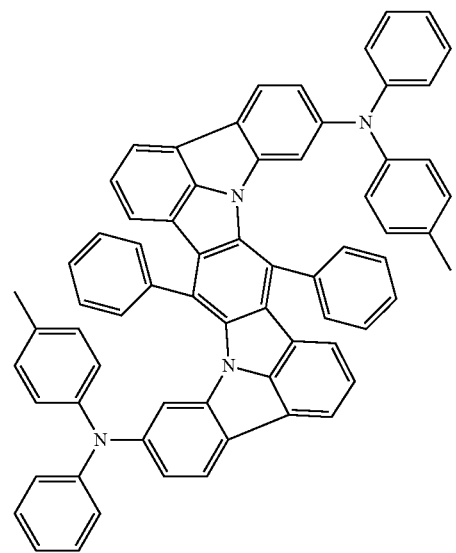
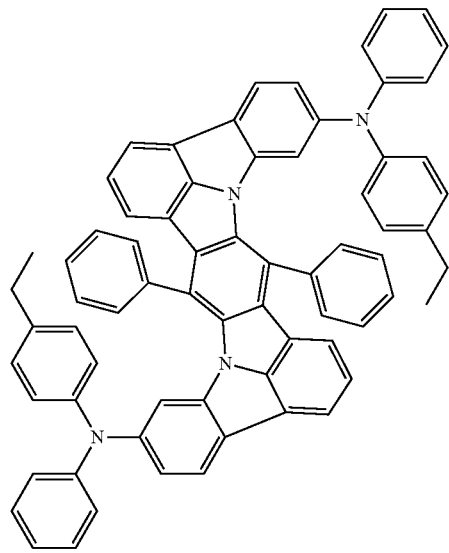
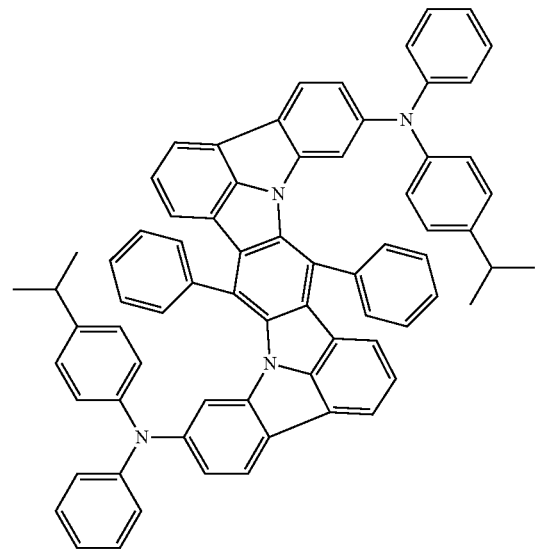

209 210
-continued
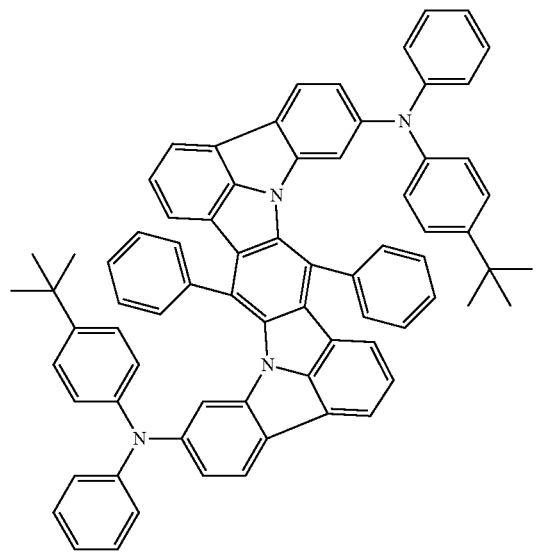 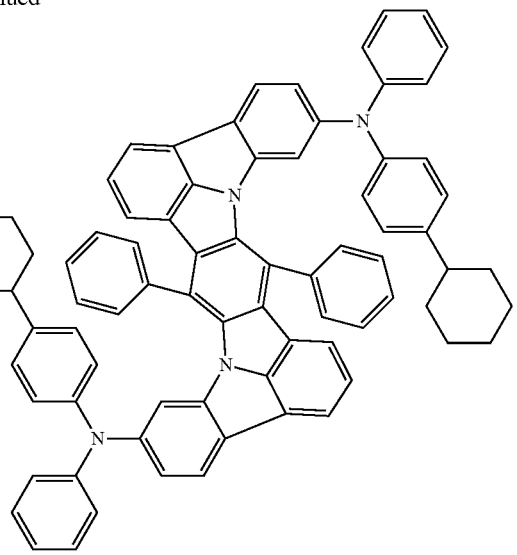
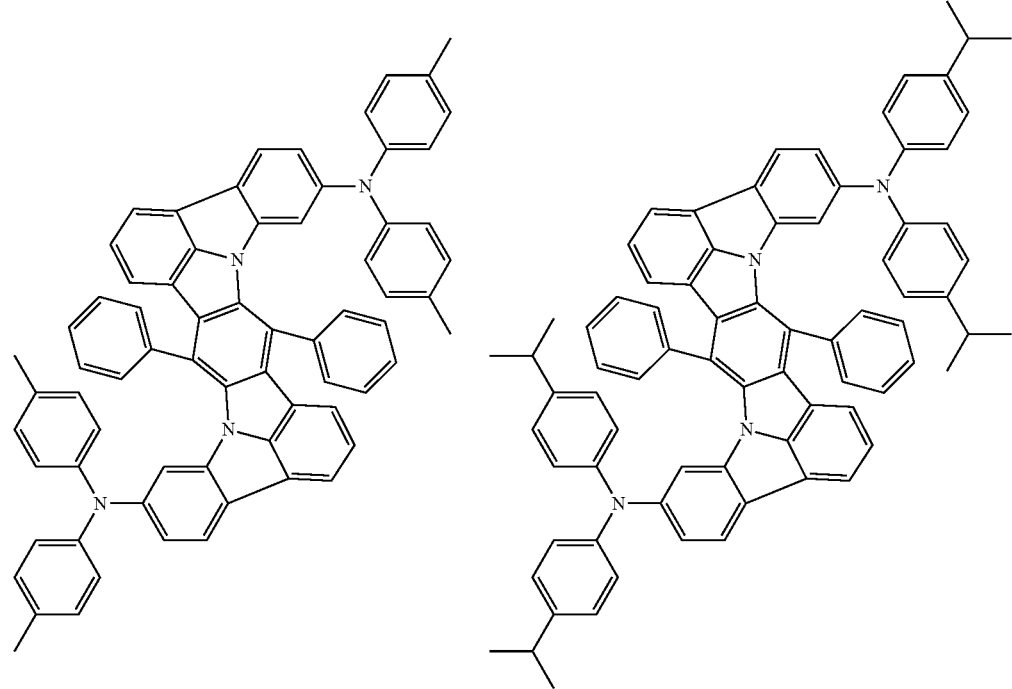

-continued
211
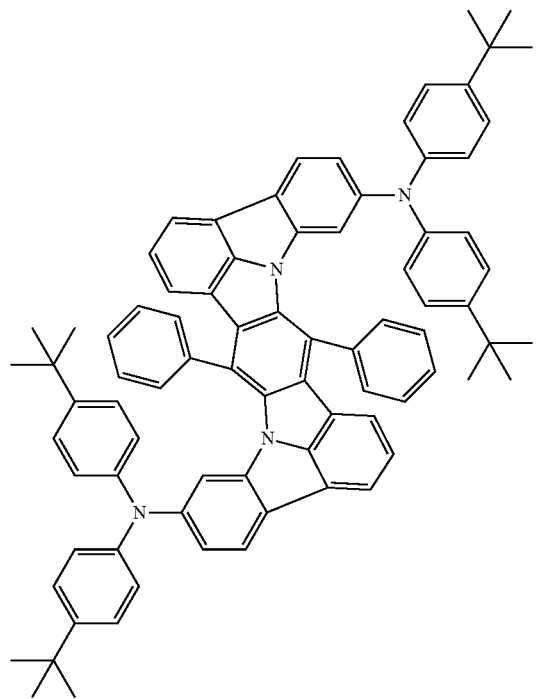
212
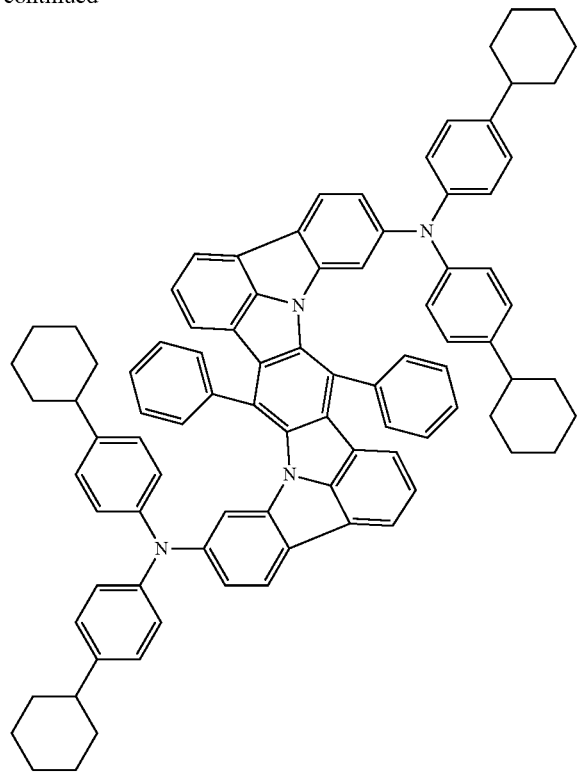
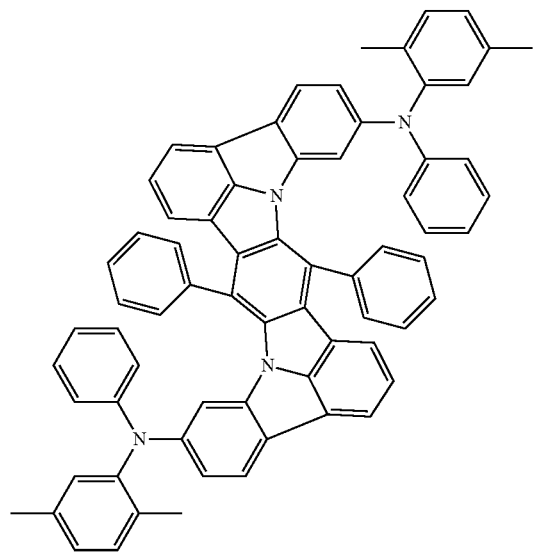
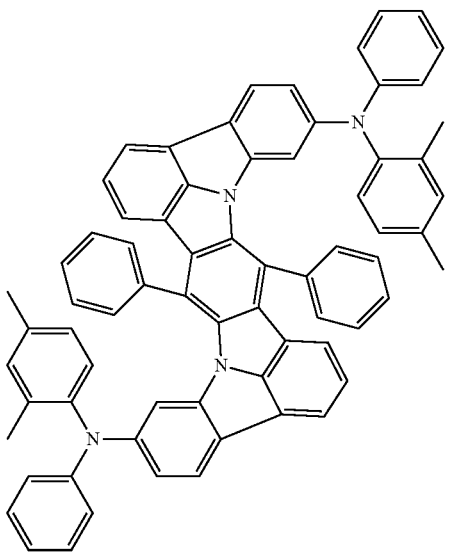

-continued
213
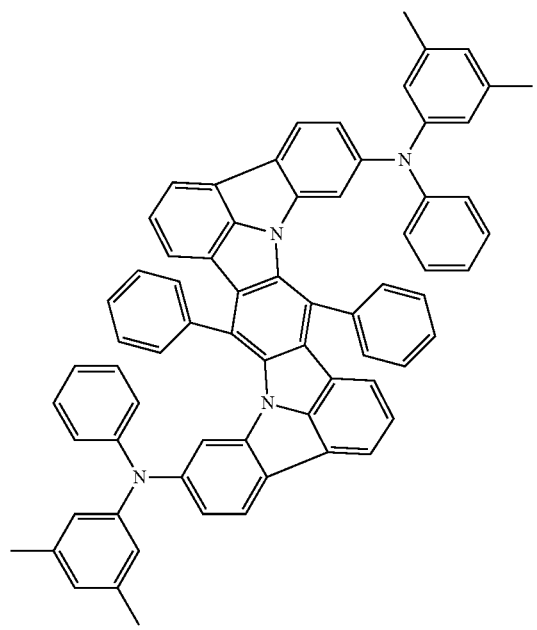
214
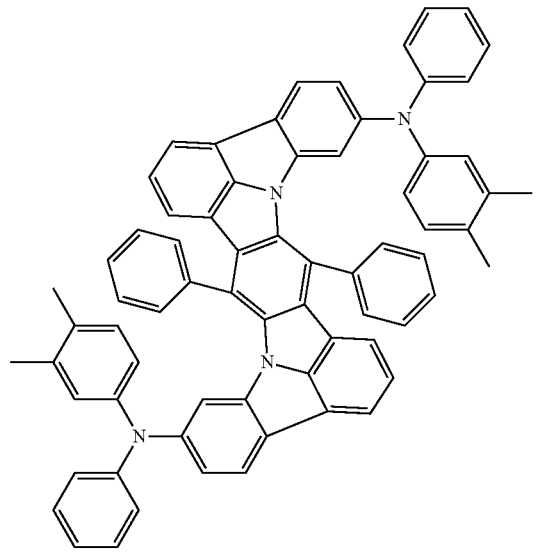
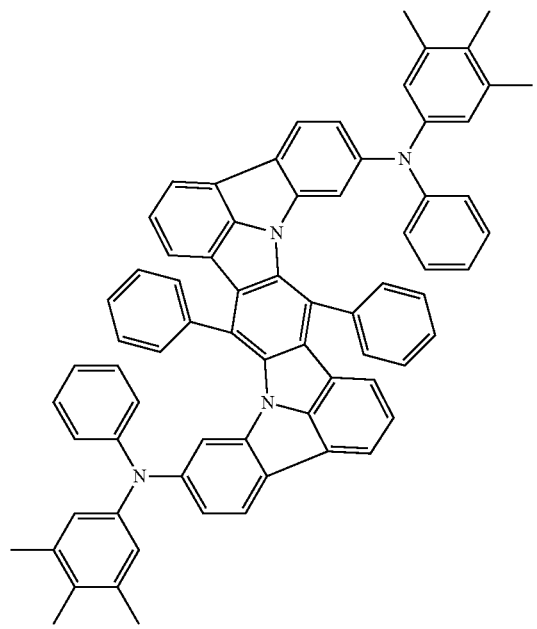
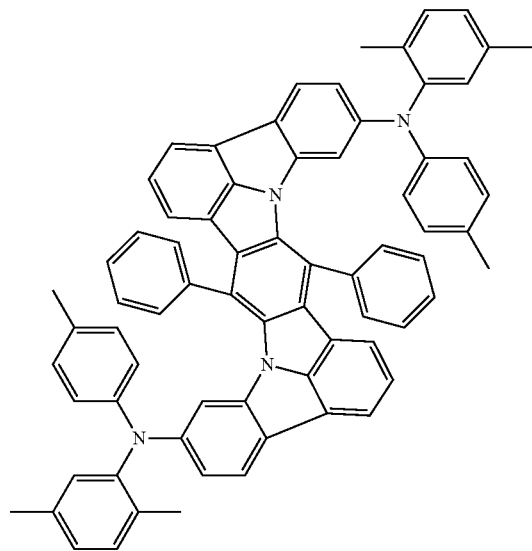

215
216
-continued
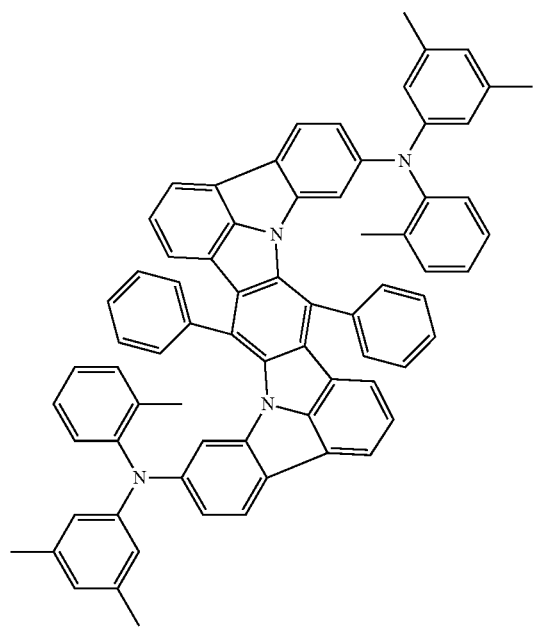
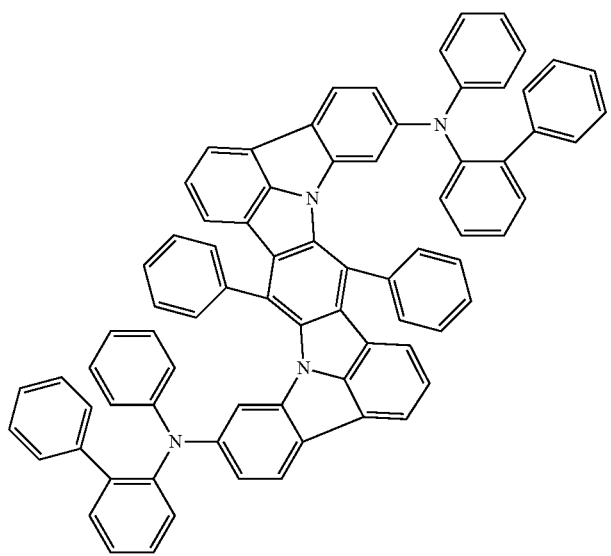
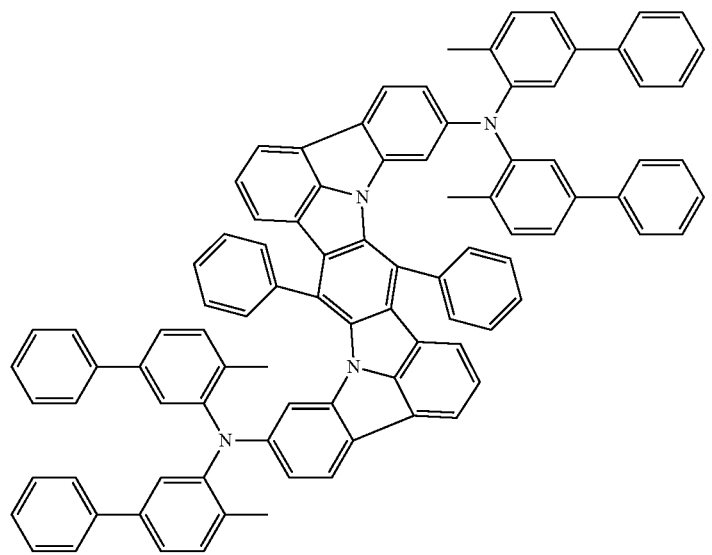

217 218
-continued
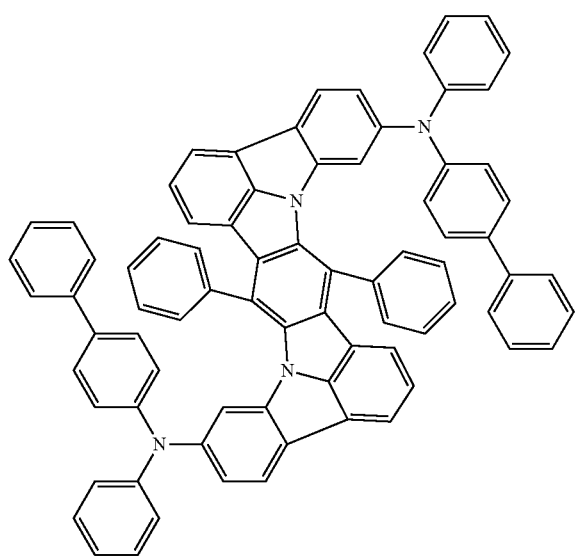 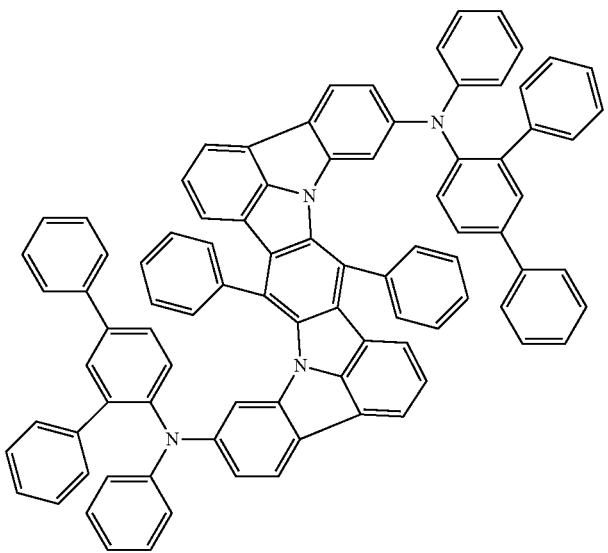
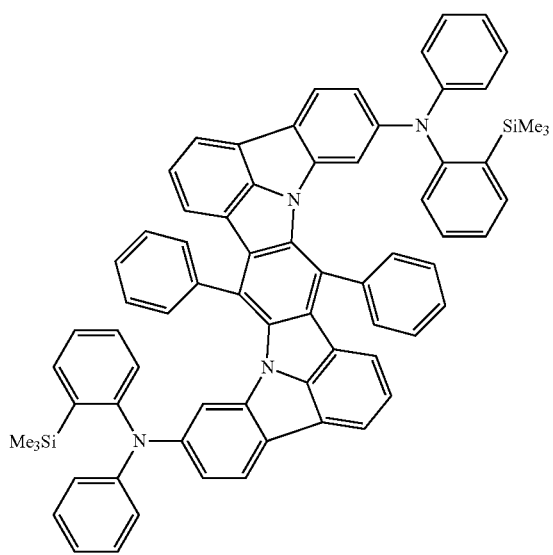
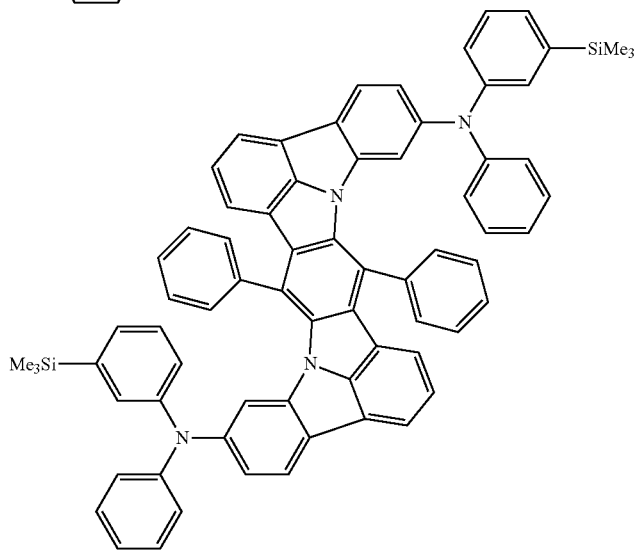

-continued
| 219 | 220 |
|---|---|
| 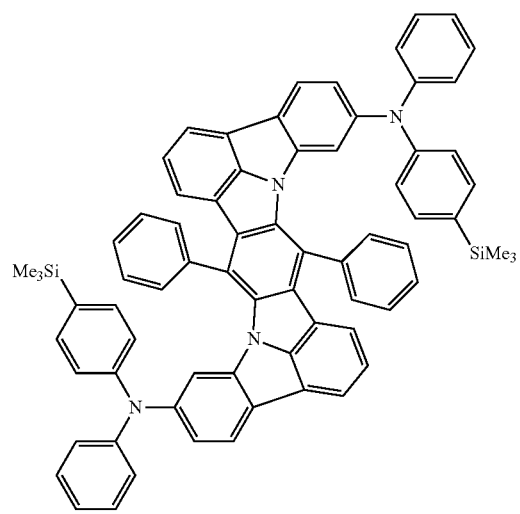 | 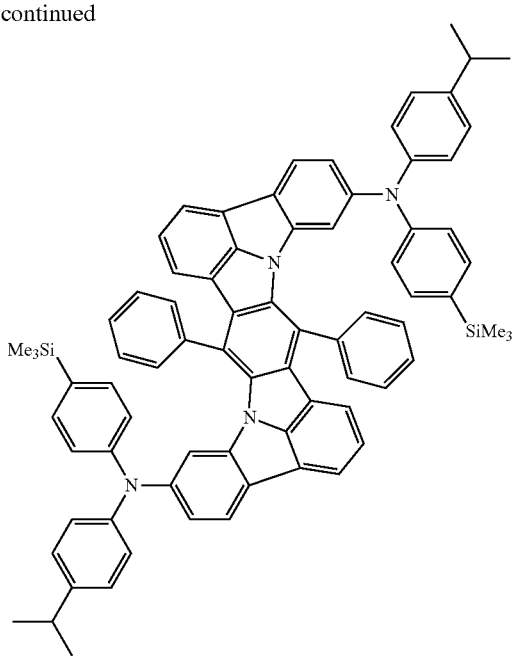 |
| 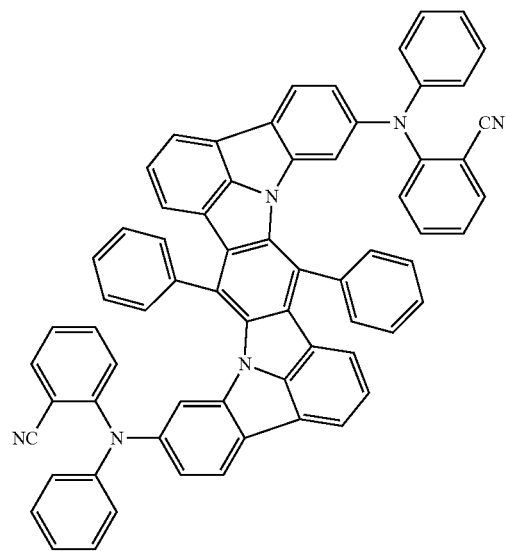 | 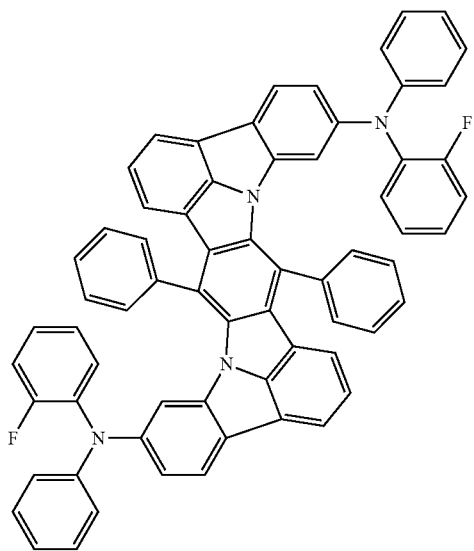 |

-continued
221
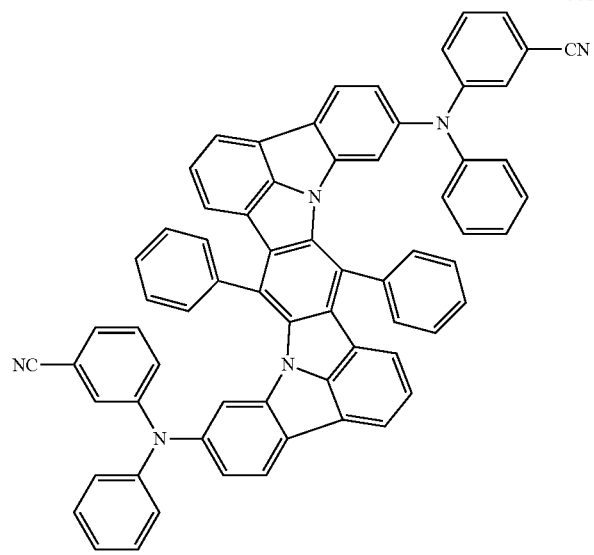
222
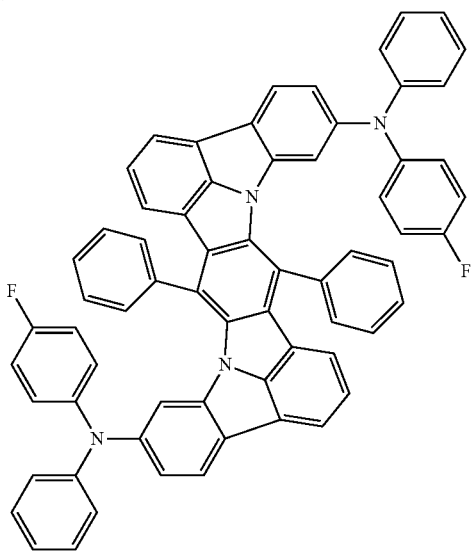
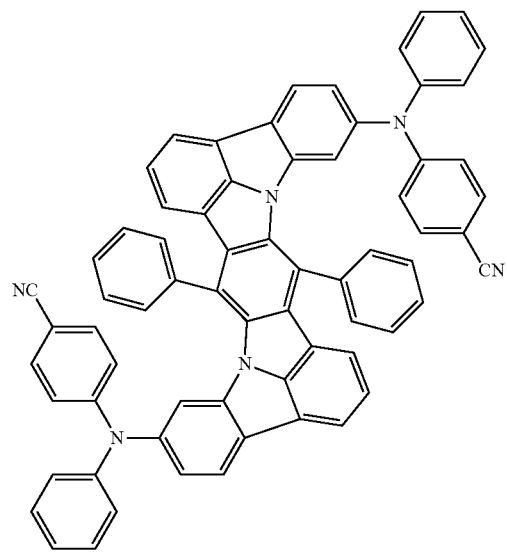
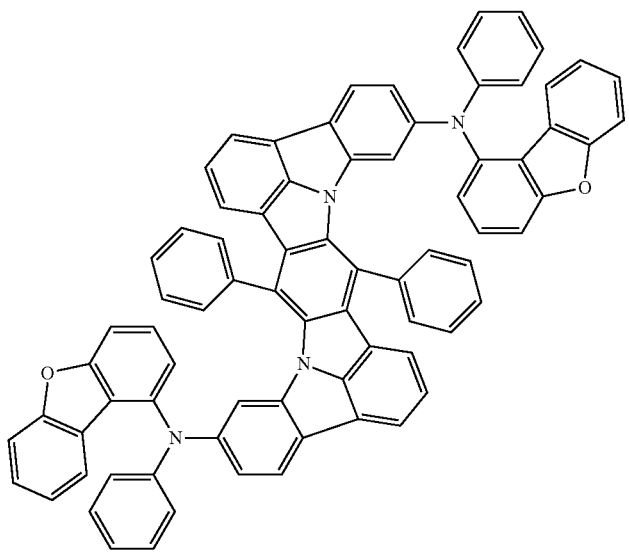
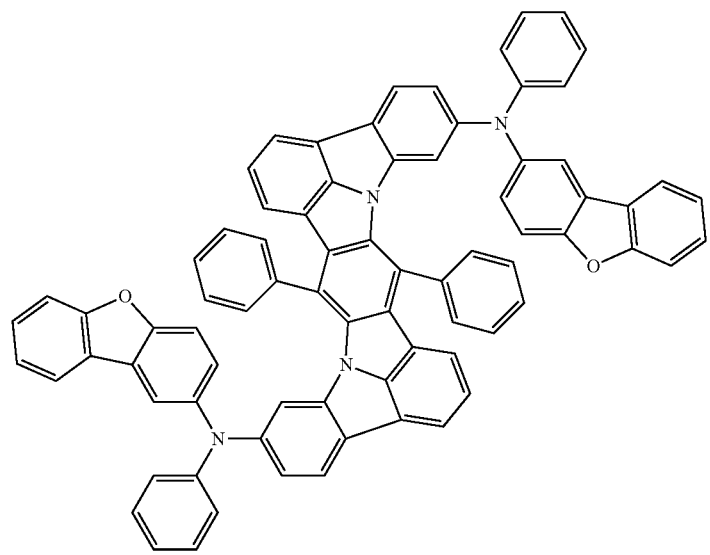

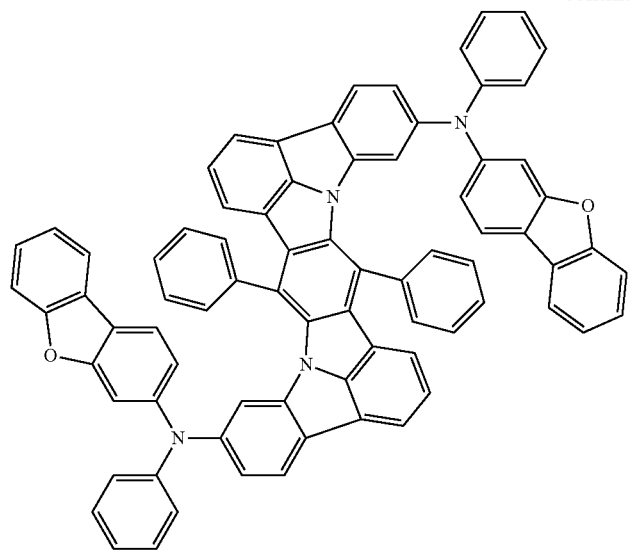
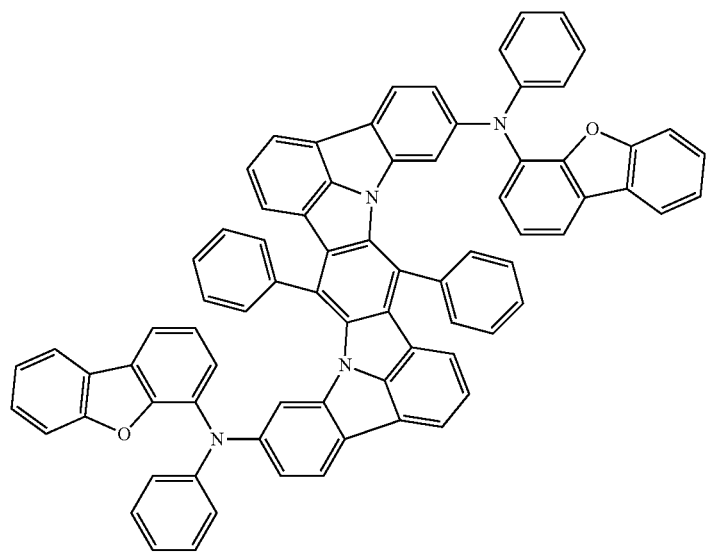
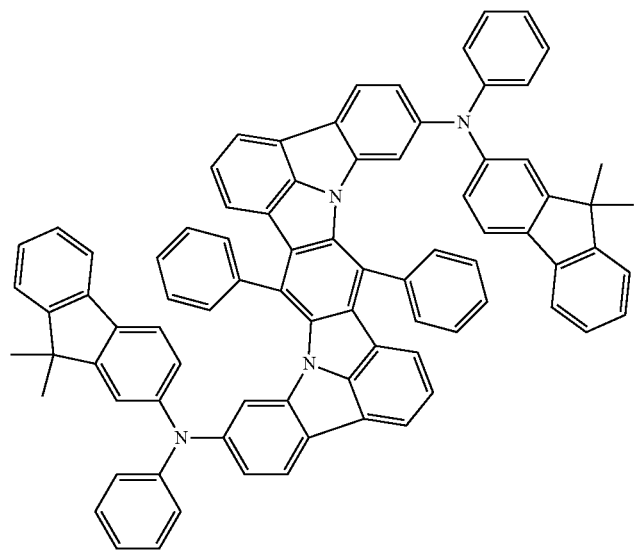

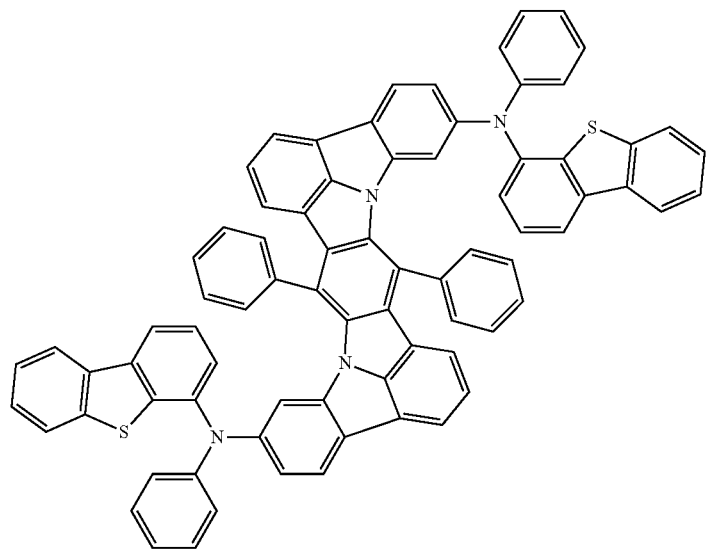

-continued
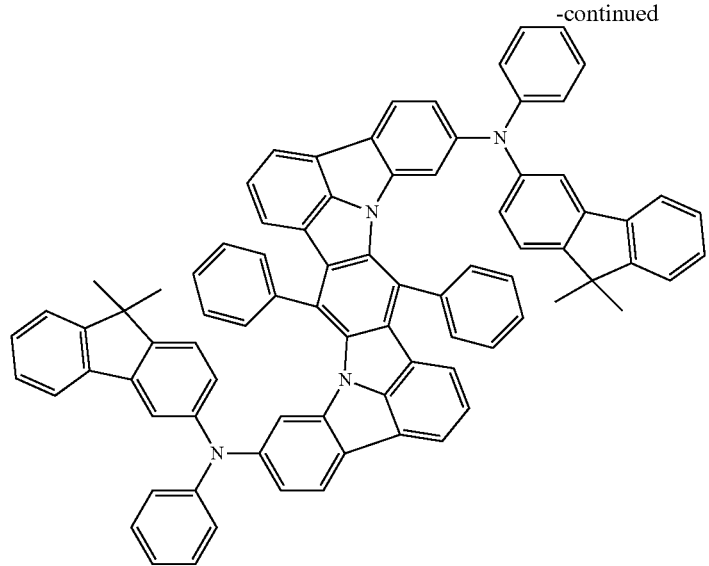
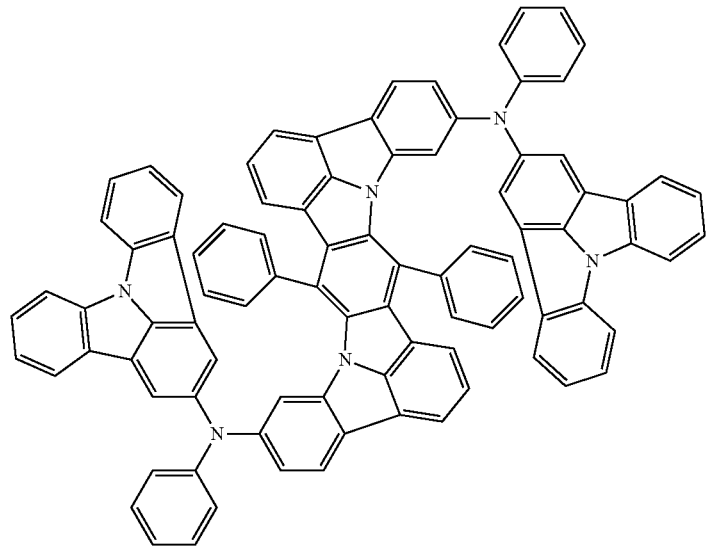
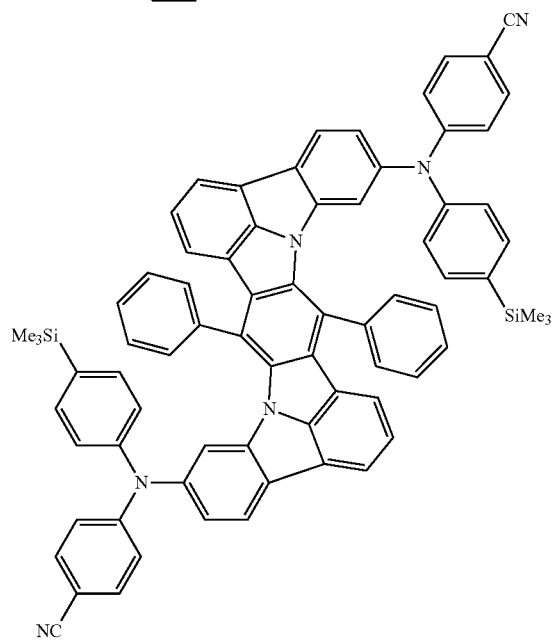

-continued
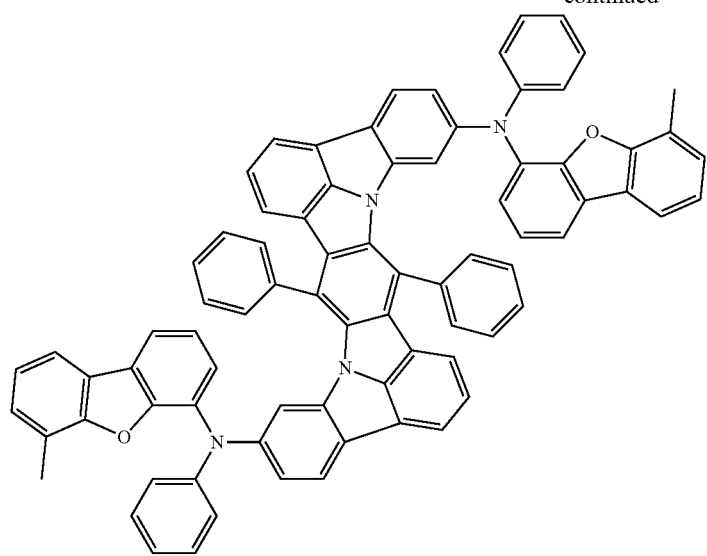
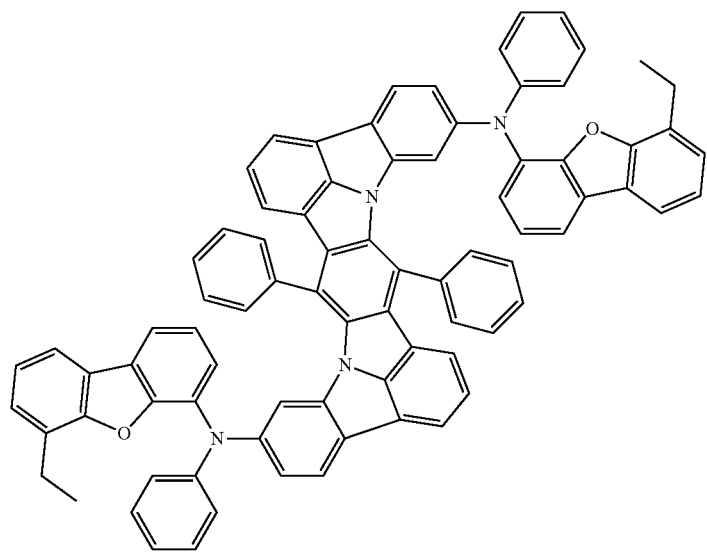
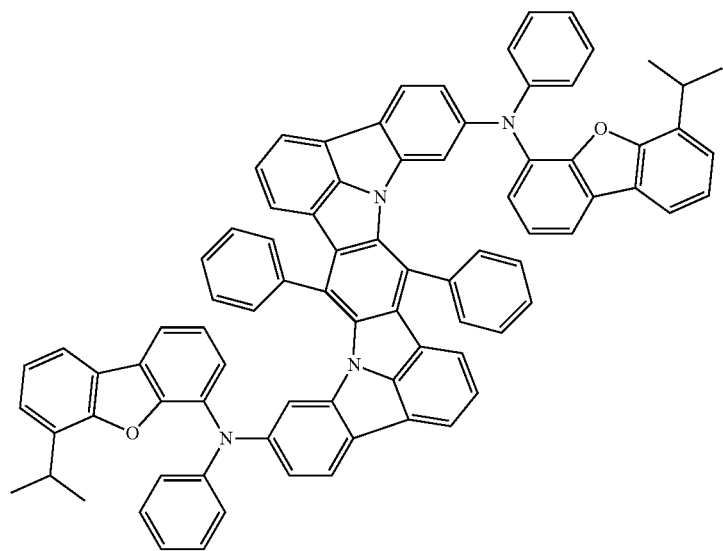

-continued
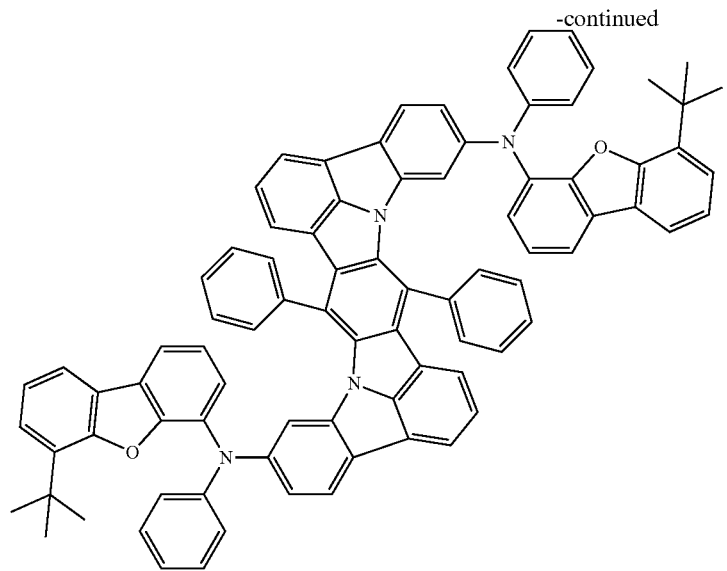
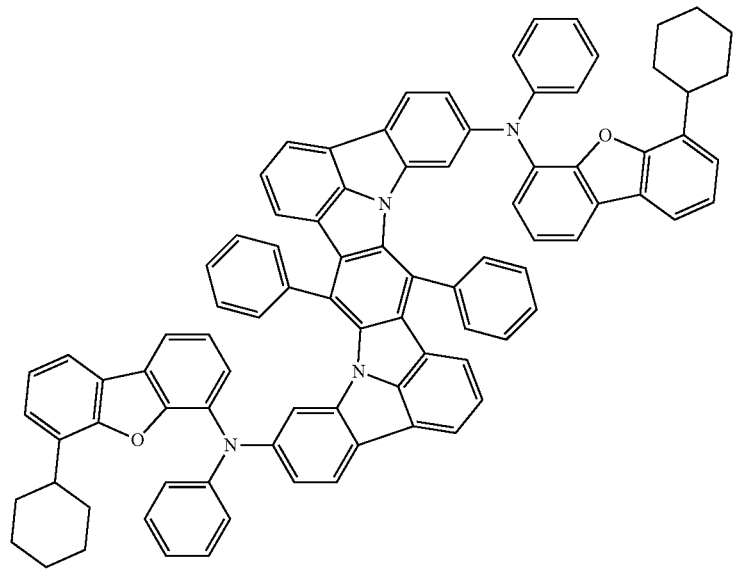
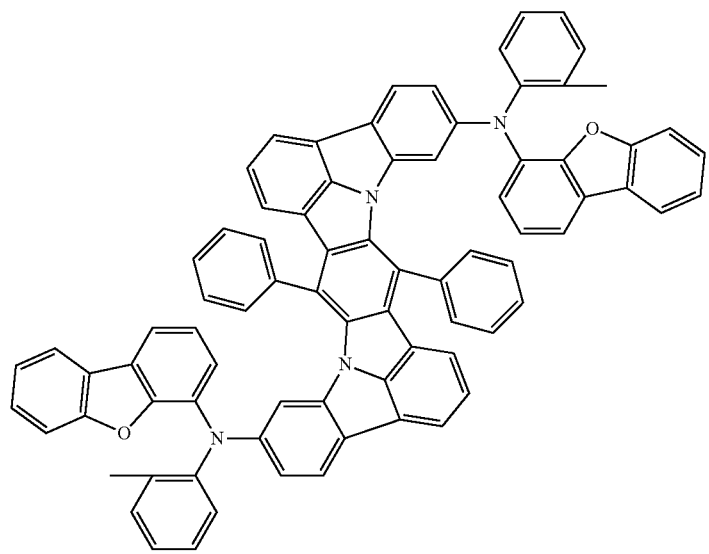

-continued
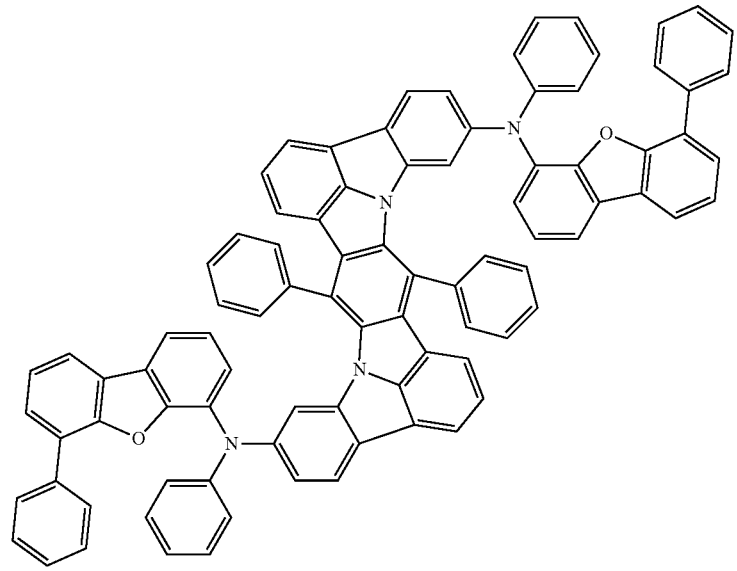
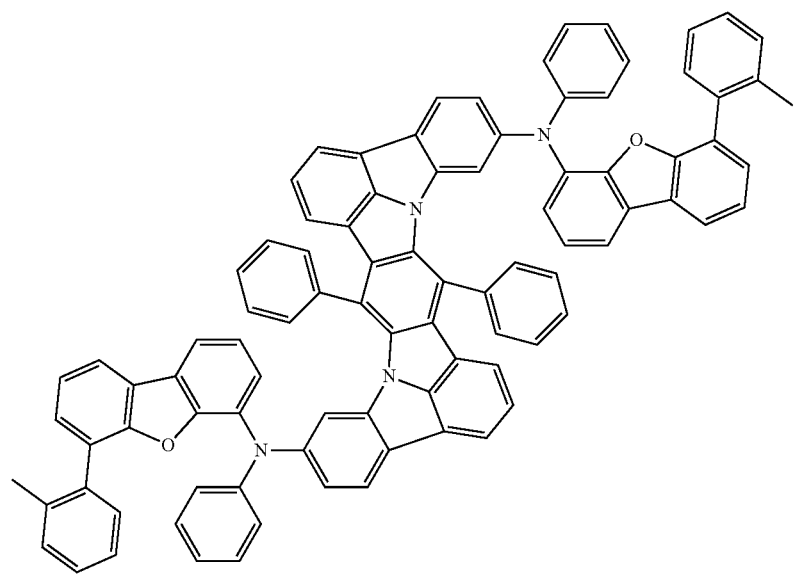
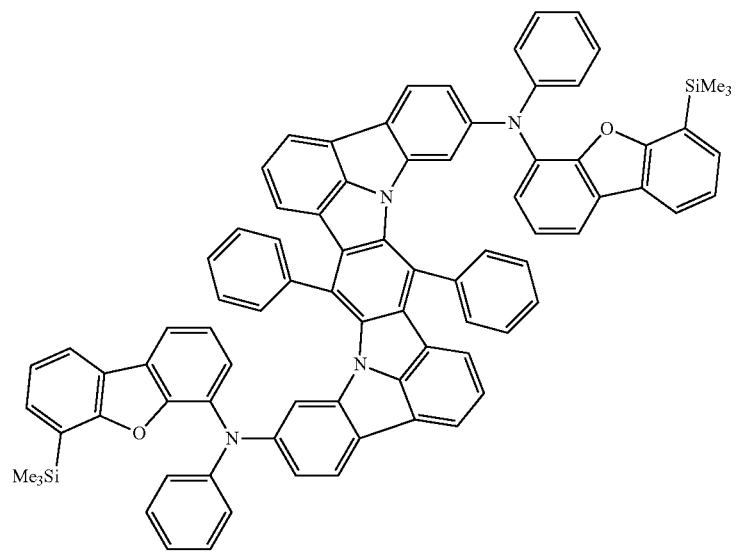

-continued
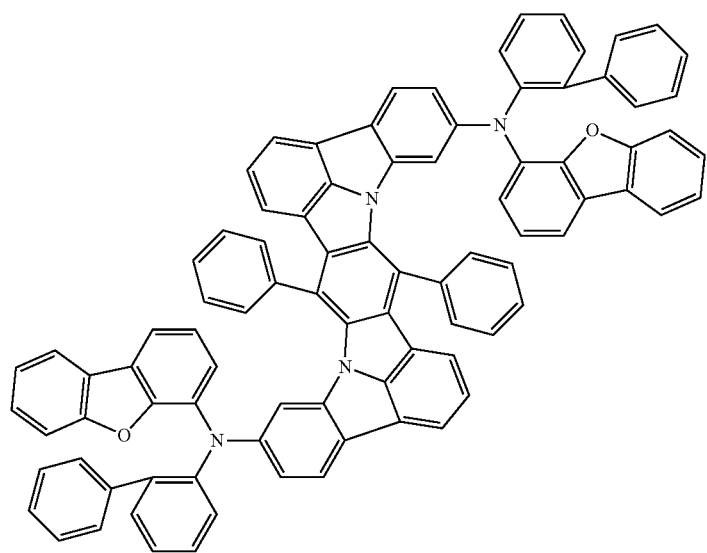
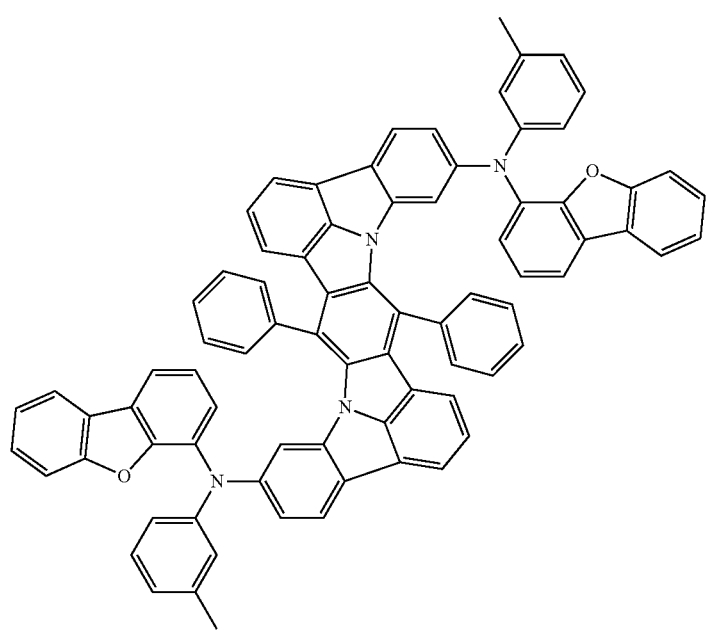

-continued
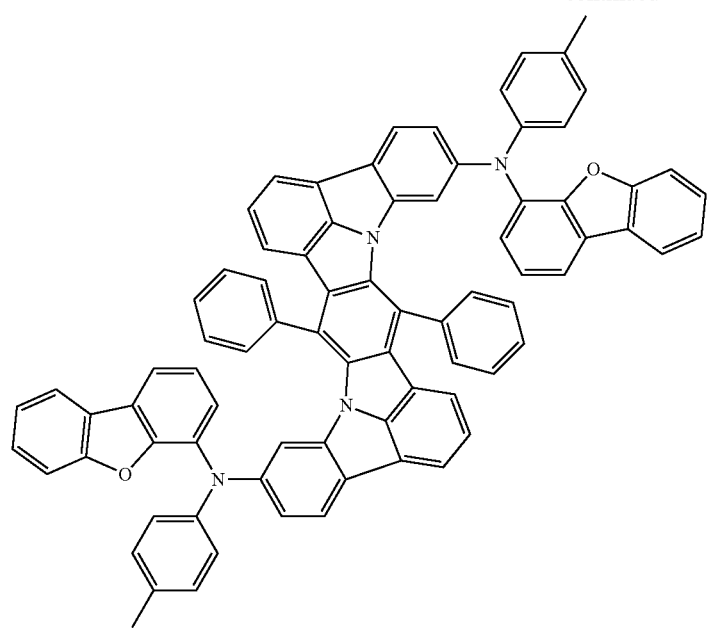
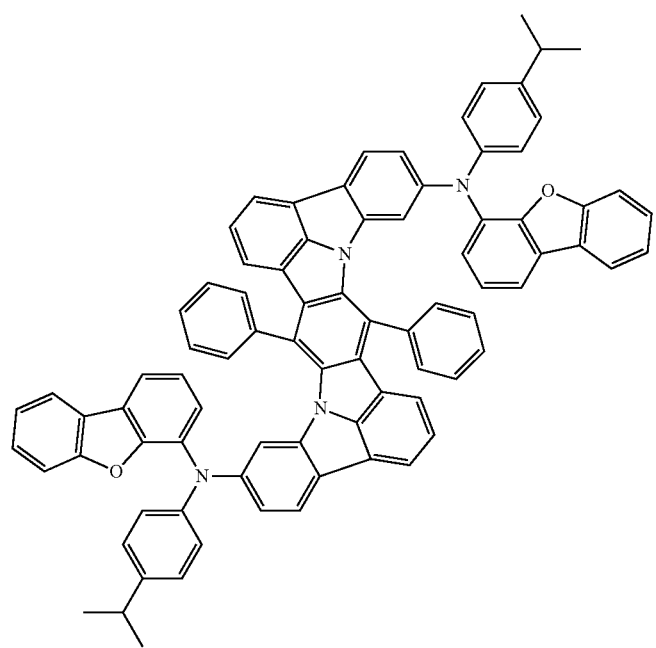

-continued
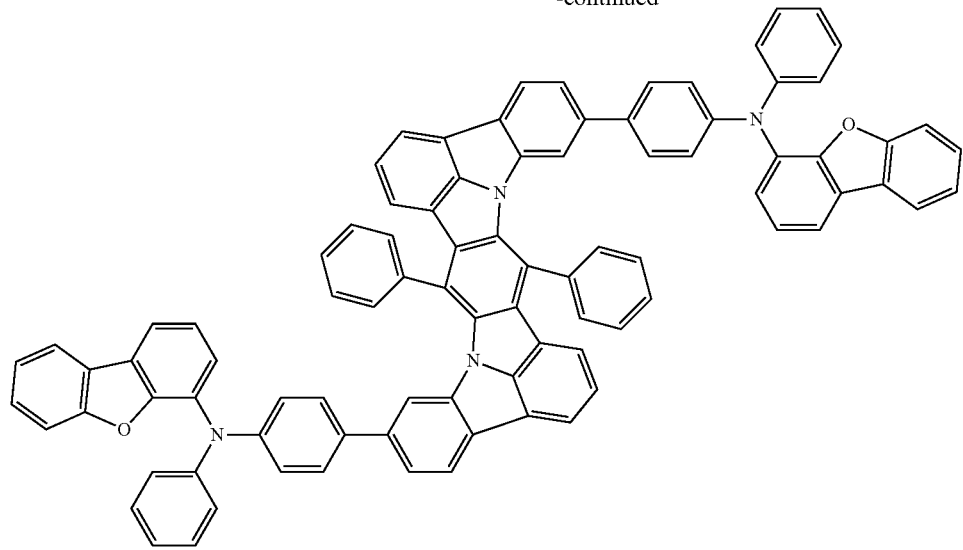
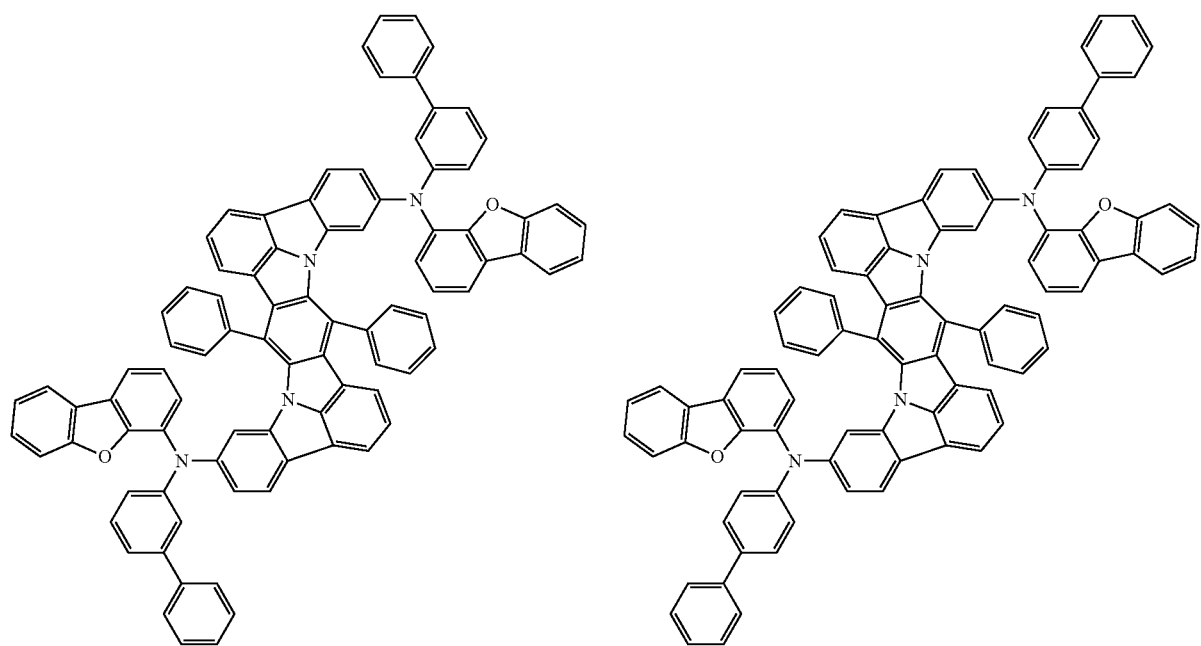

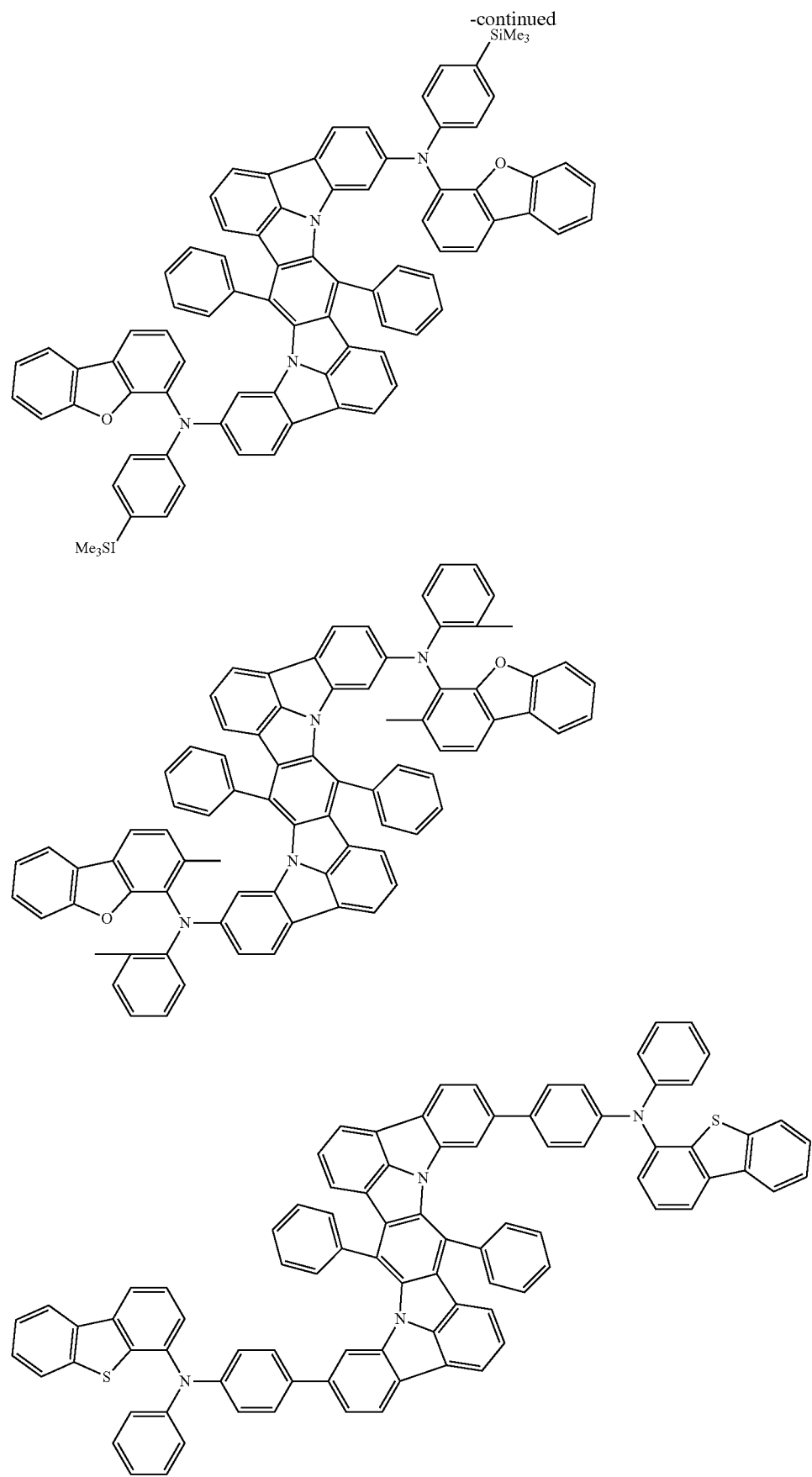

-continued
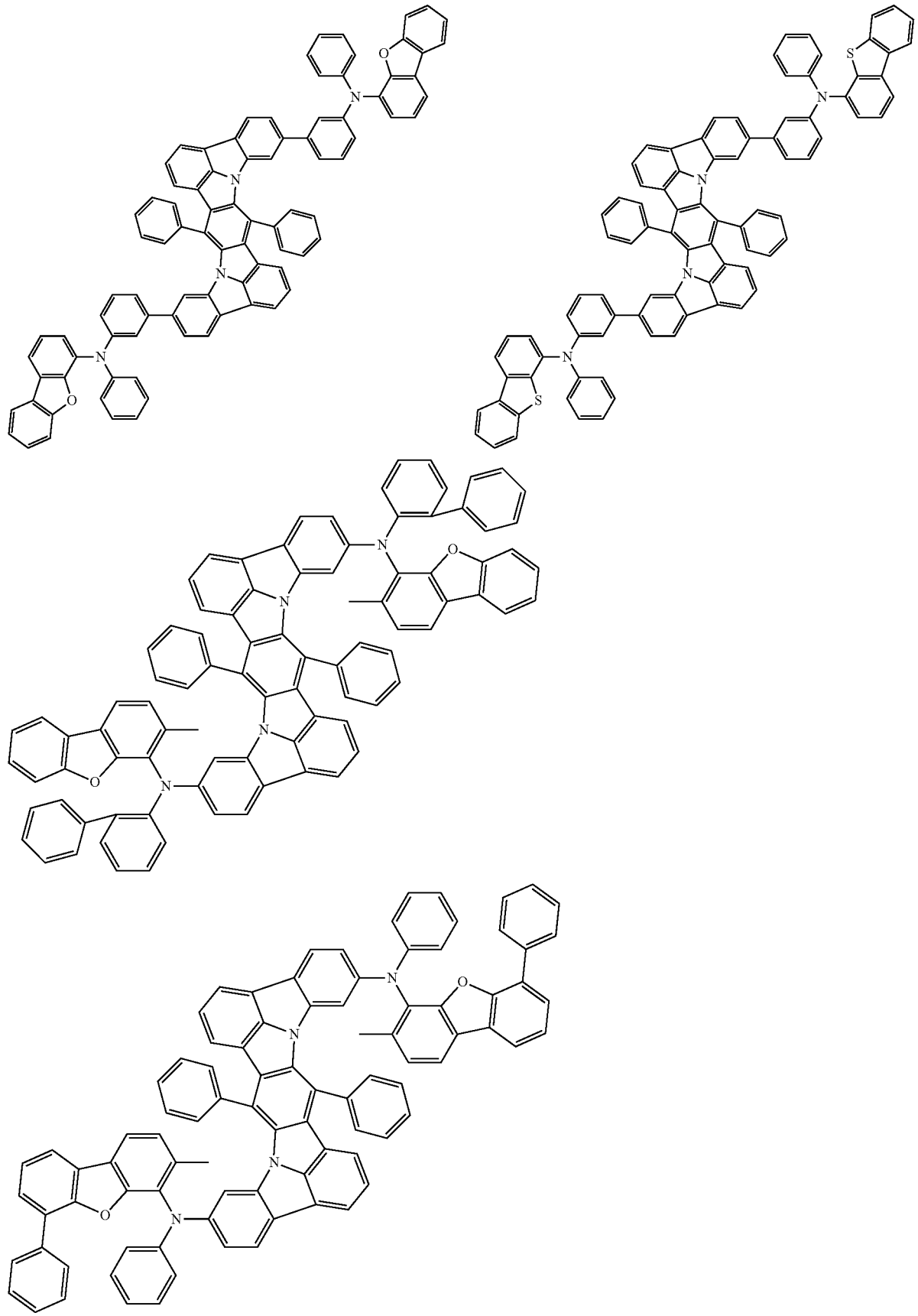

-continued
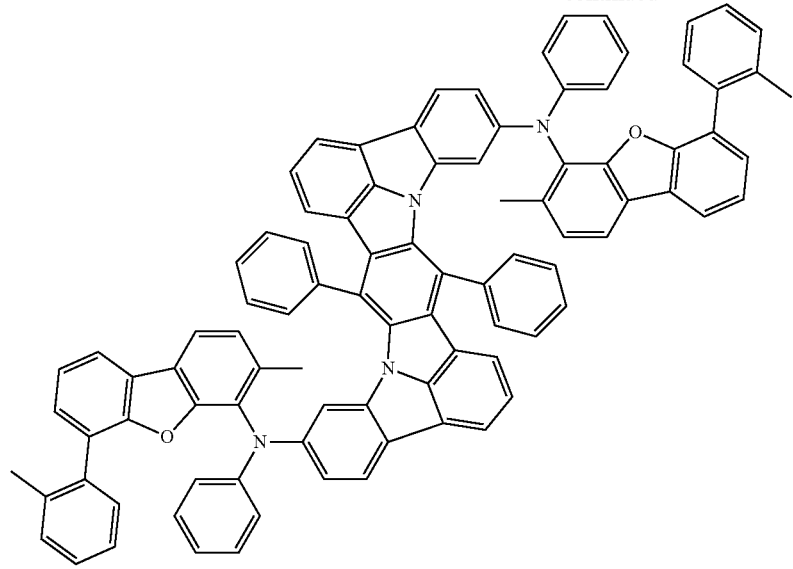
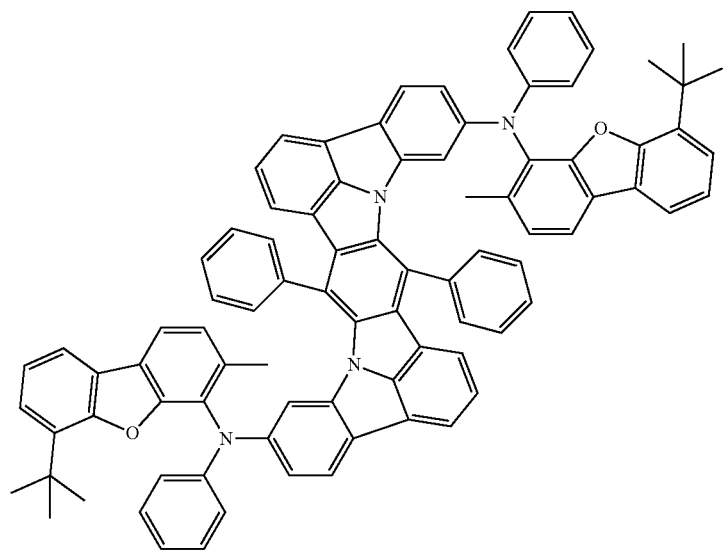
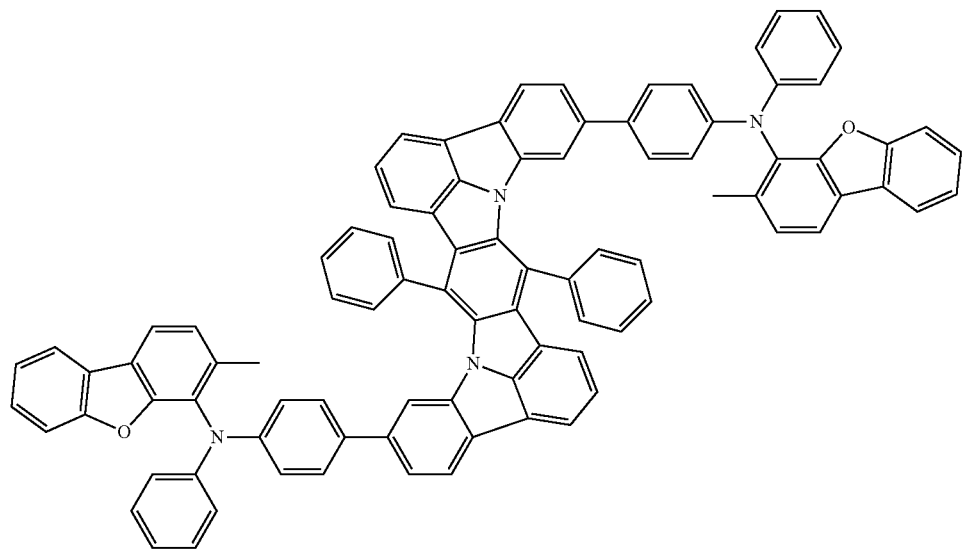

-continued
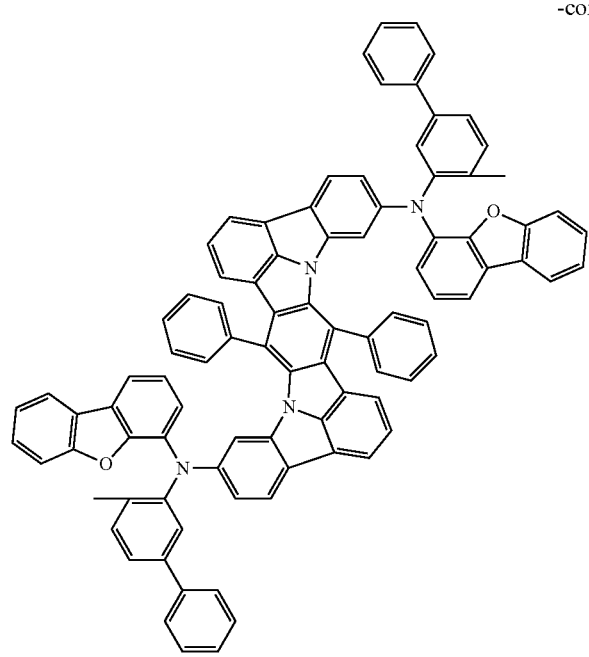
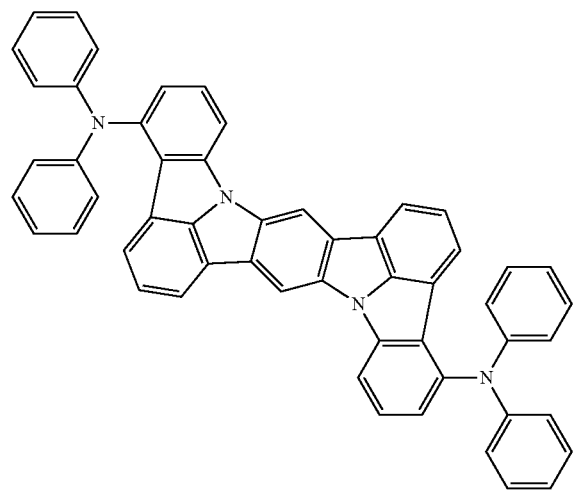
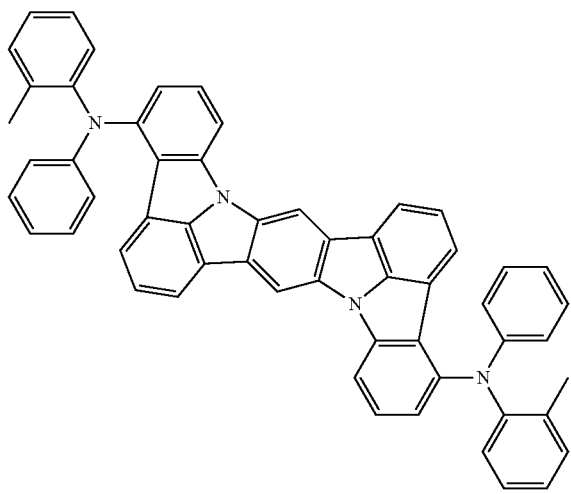
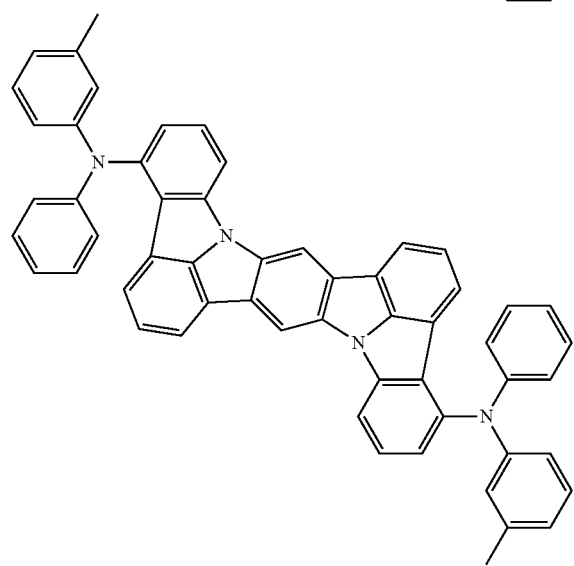
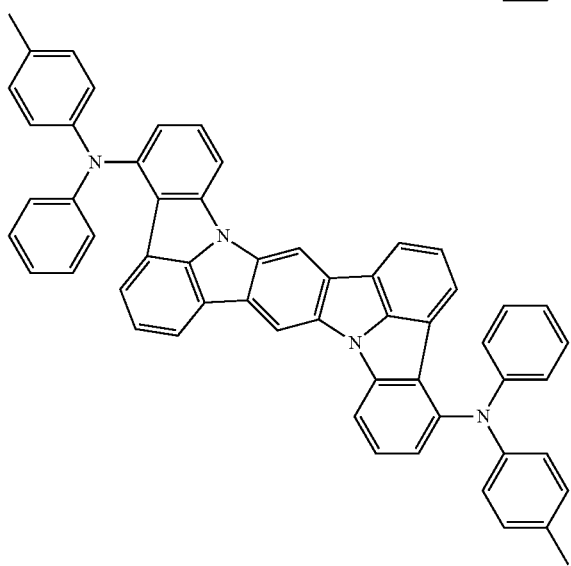

249
250
-continued
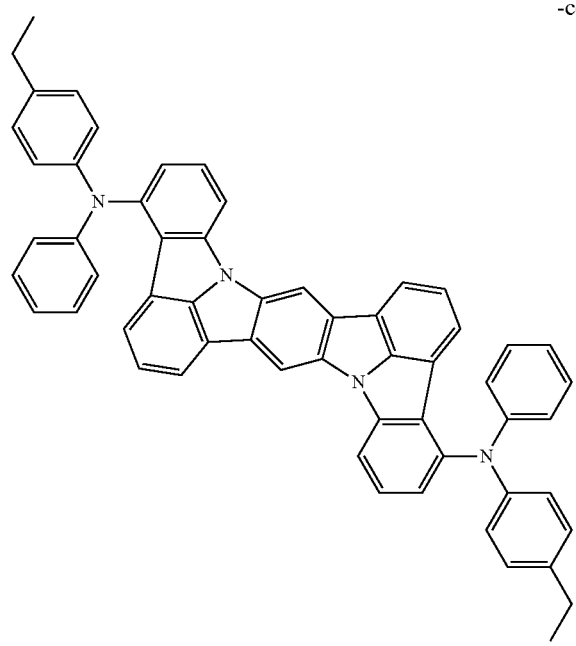
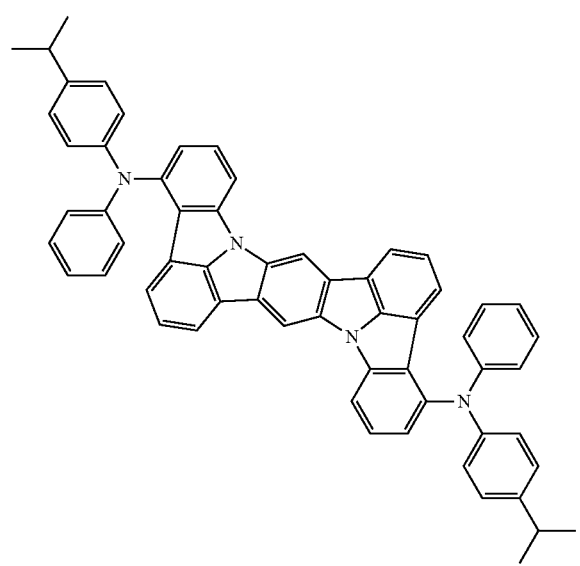
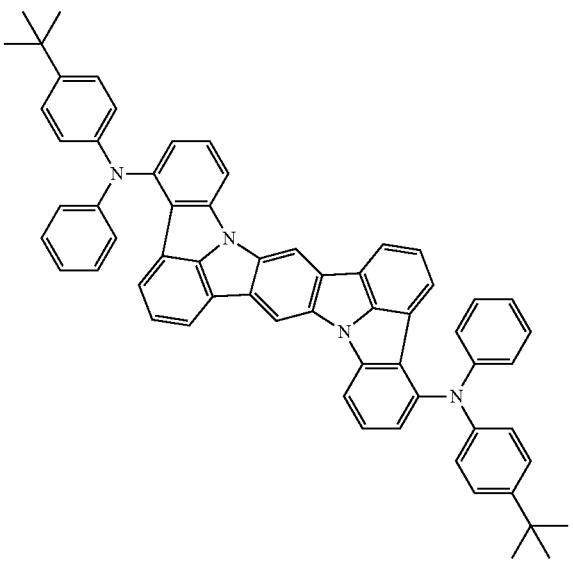

251
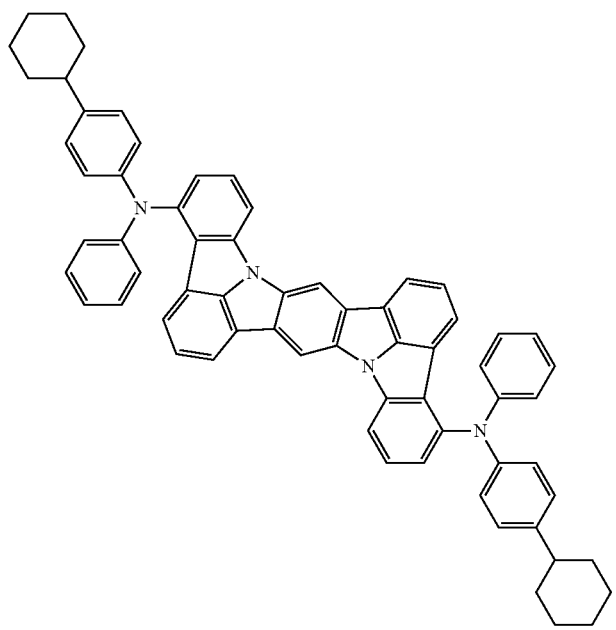
252
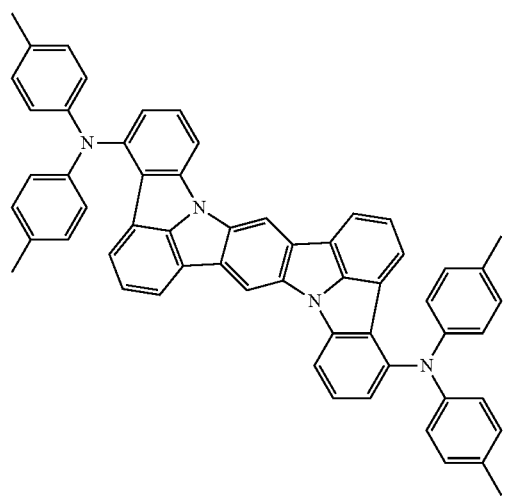
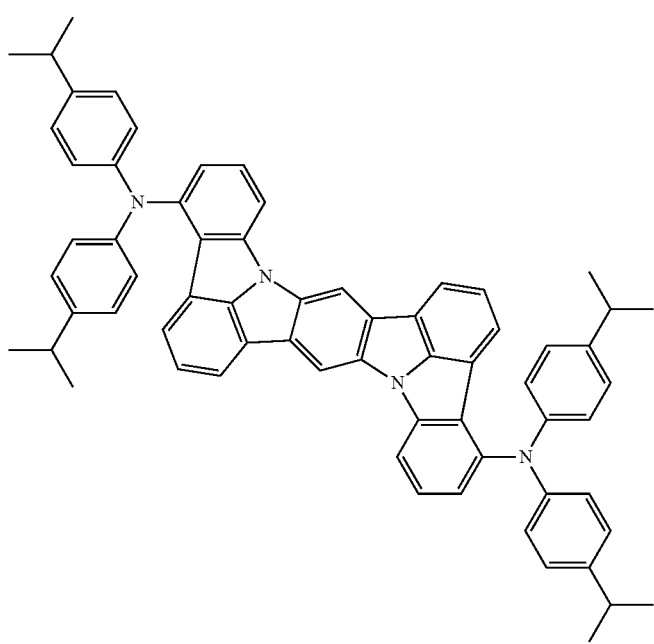

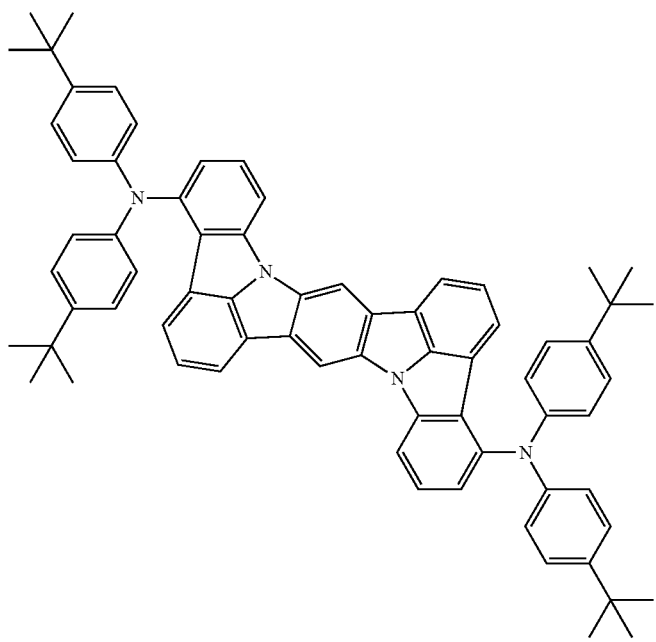
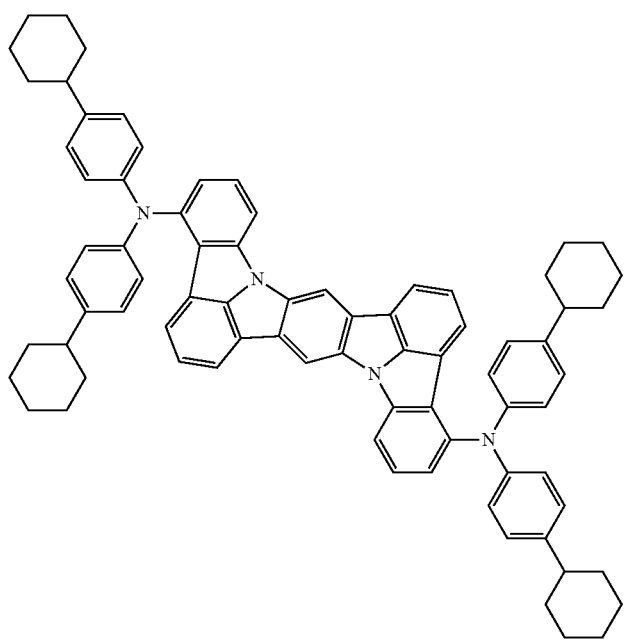

-continued
| 255 | 256 |
|---|---|
| 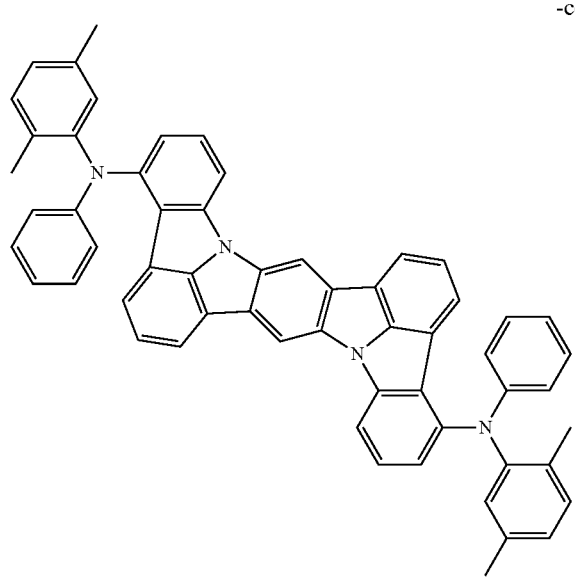 | 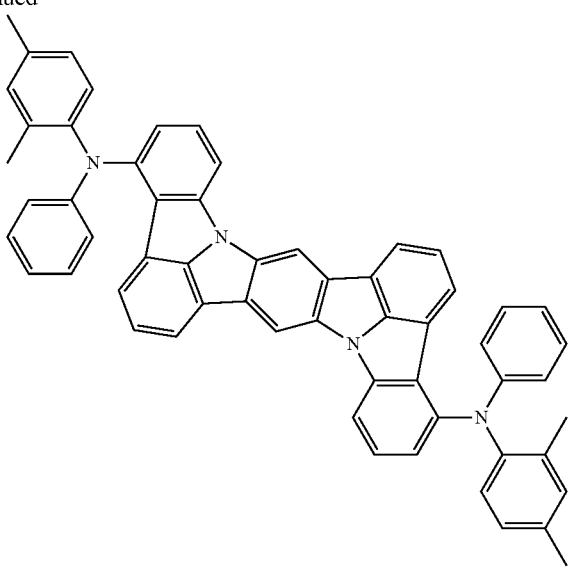 |
| 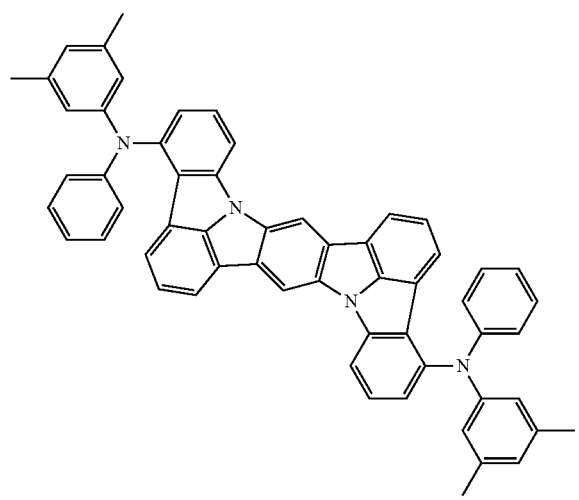 | 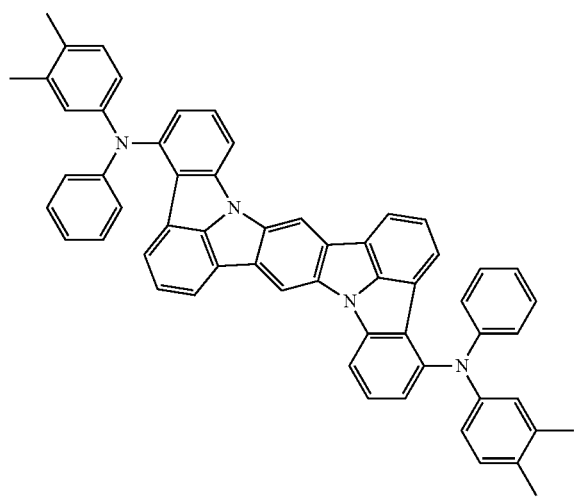 |
| 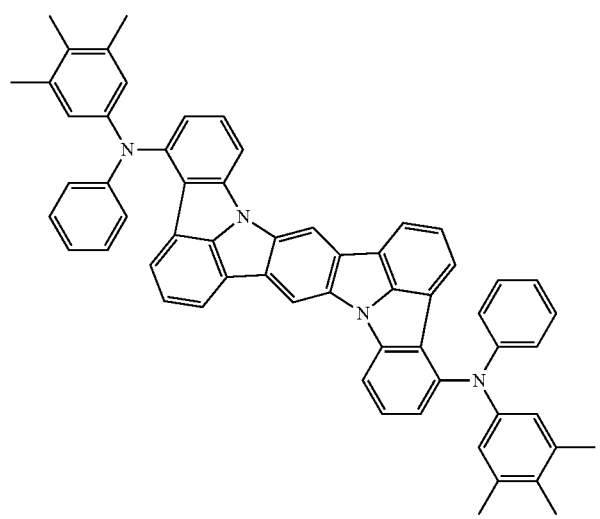 | 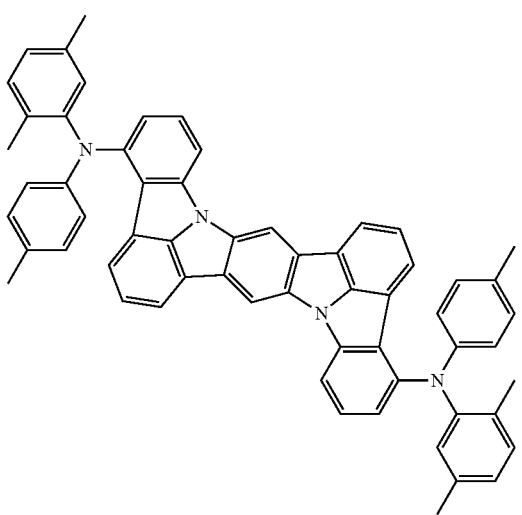 |

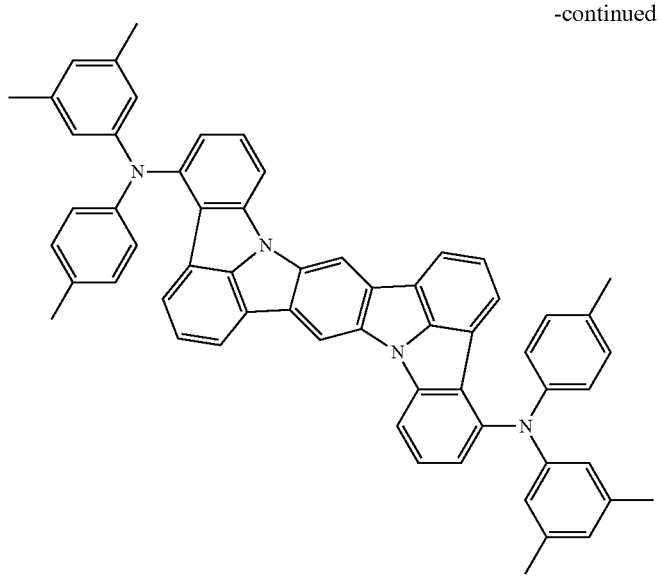
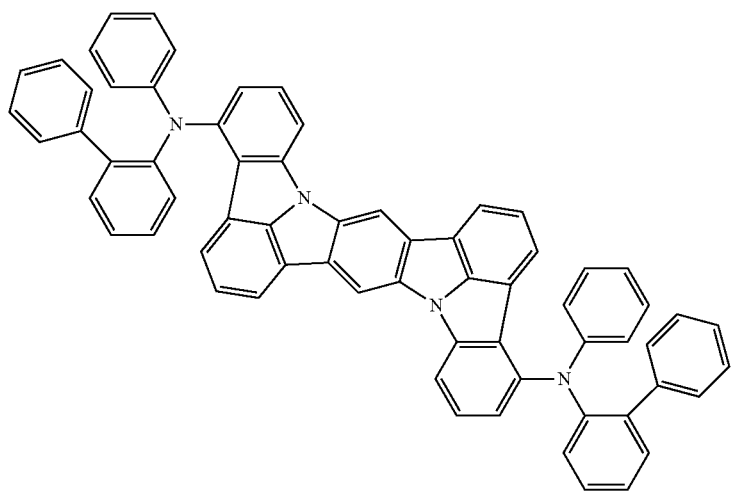
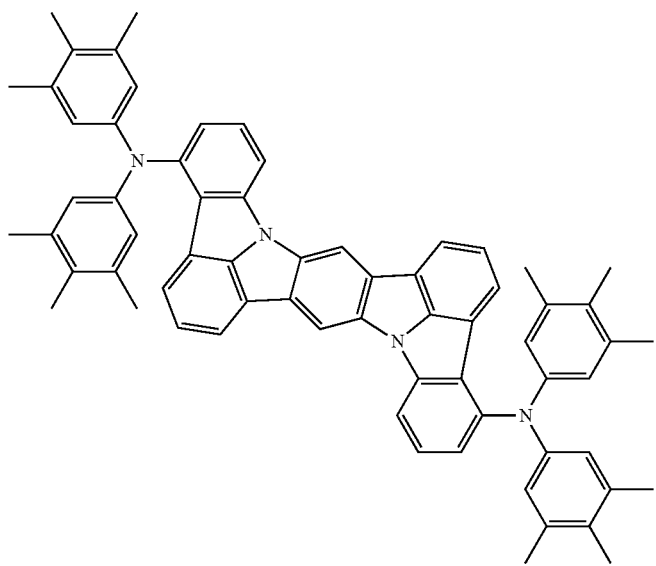

-continued
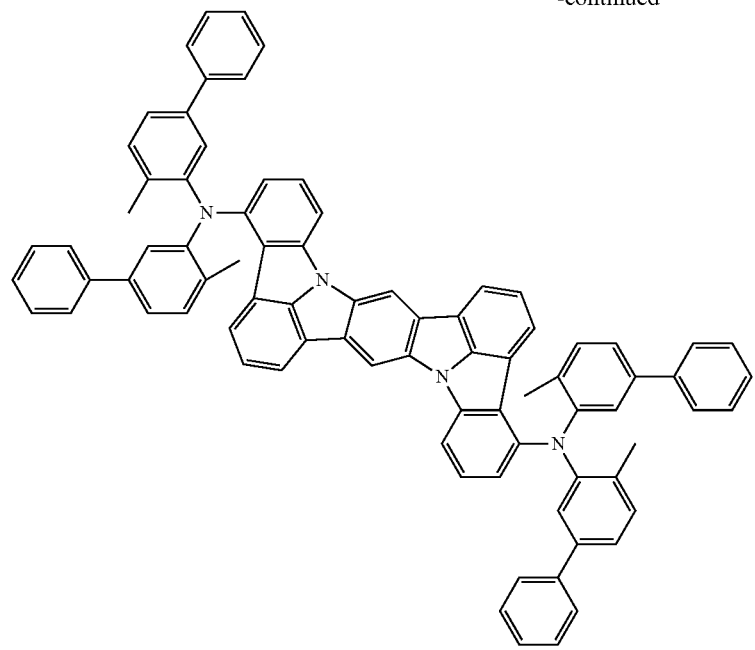
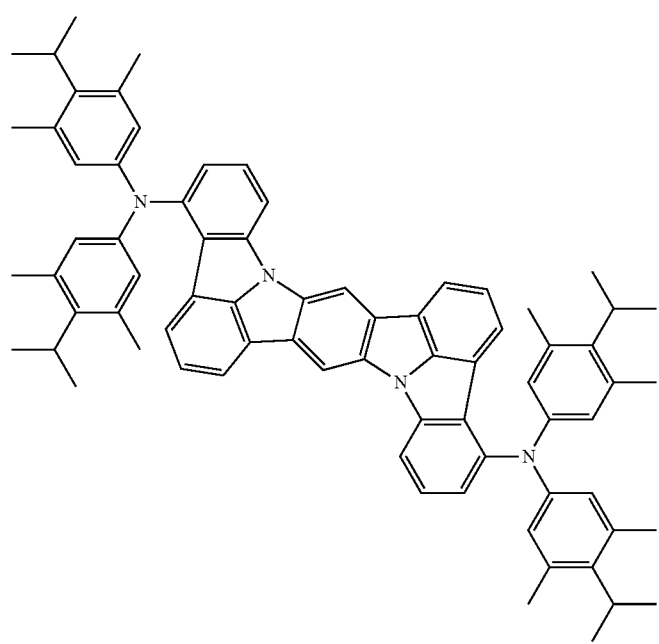

261
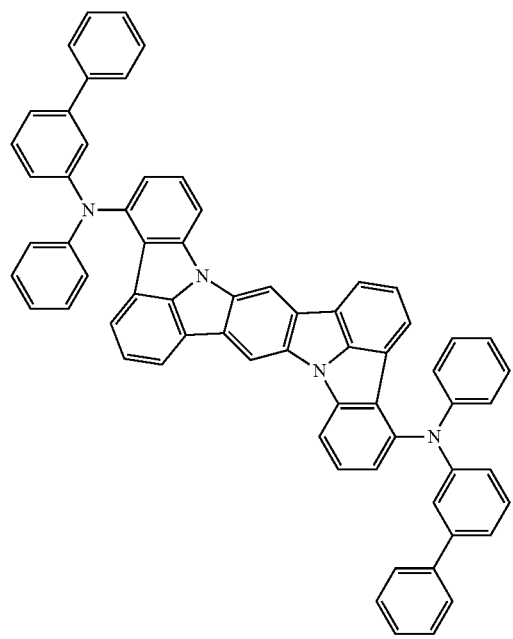
262
-continued
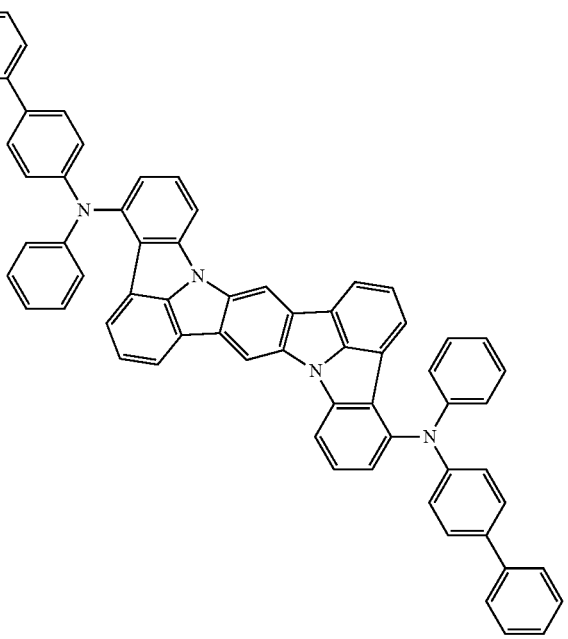
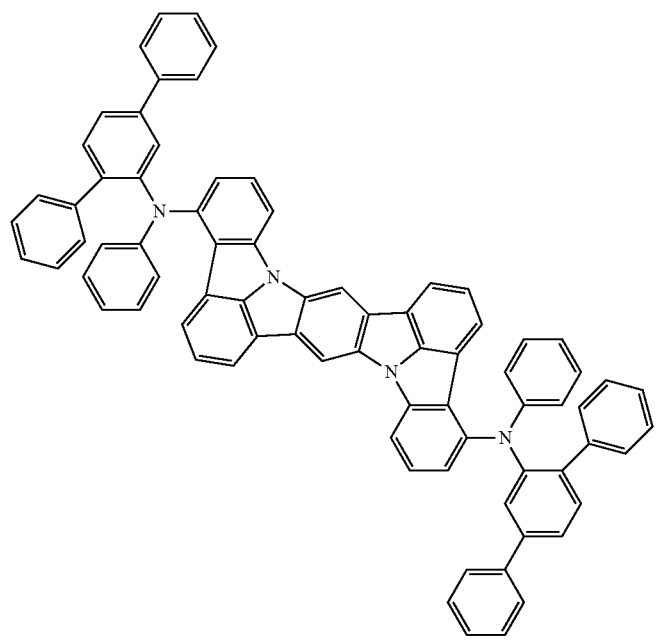 [SMILES: c1ccc(-c2ccc(-c3ccccc3)c(N(c3ccccc3)c3cccc4c3c3cccc5c6cc7c(cc6n4c53)c3cccc4c5c(N(c6ccccc6)c6cc(-c8ccccc8)ccc6-c6ccccc6)cccc5n7c34)c2)cc1]

-continued
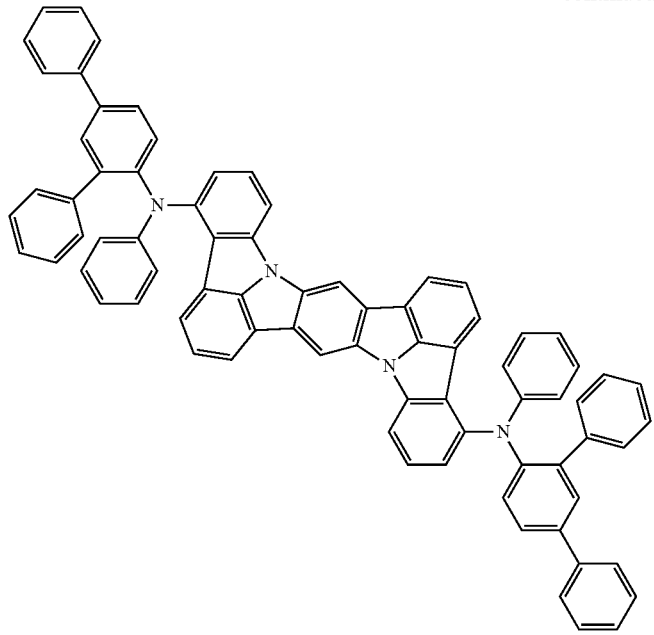
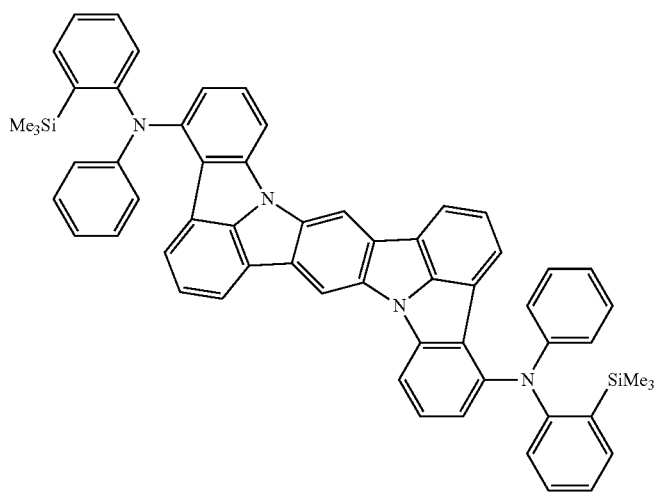
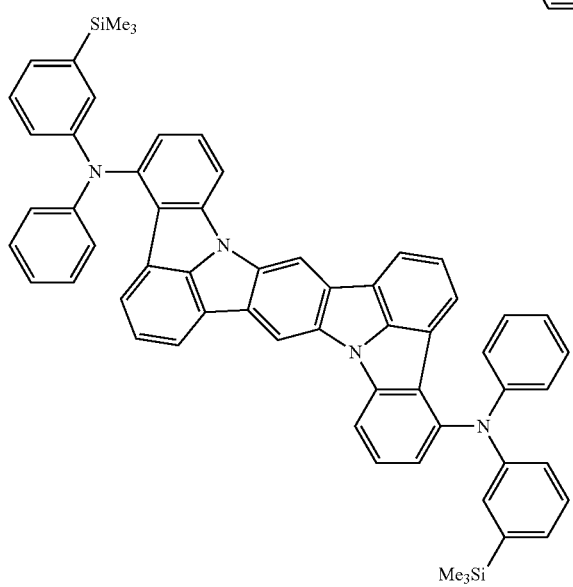

265
266
-continued
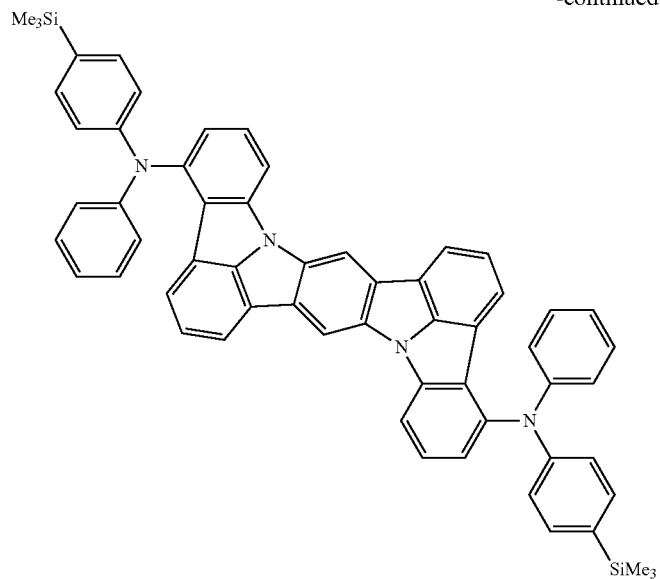
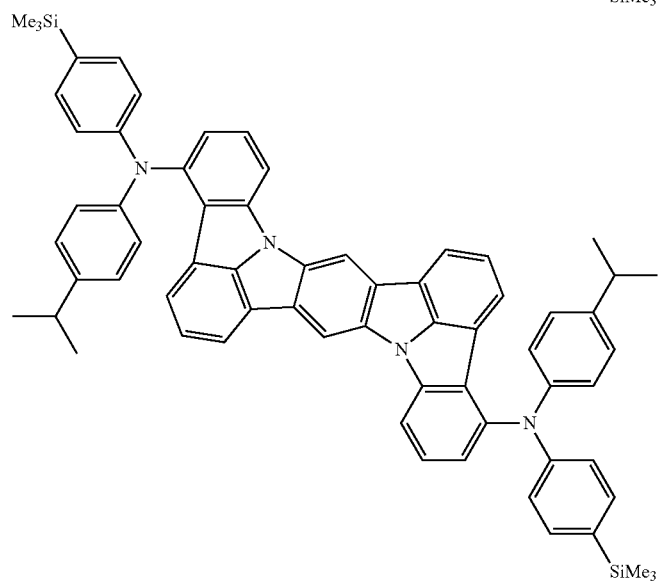
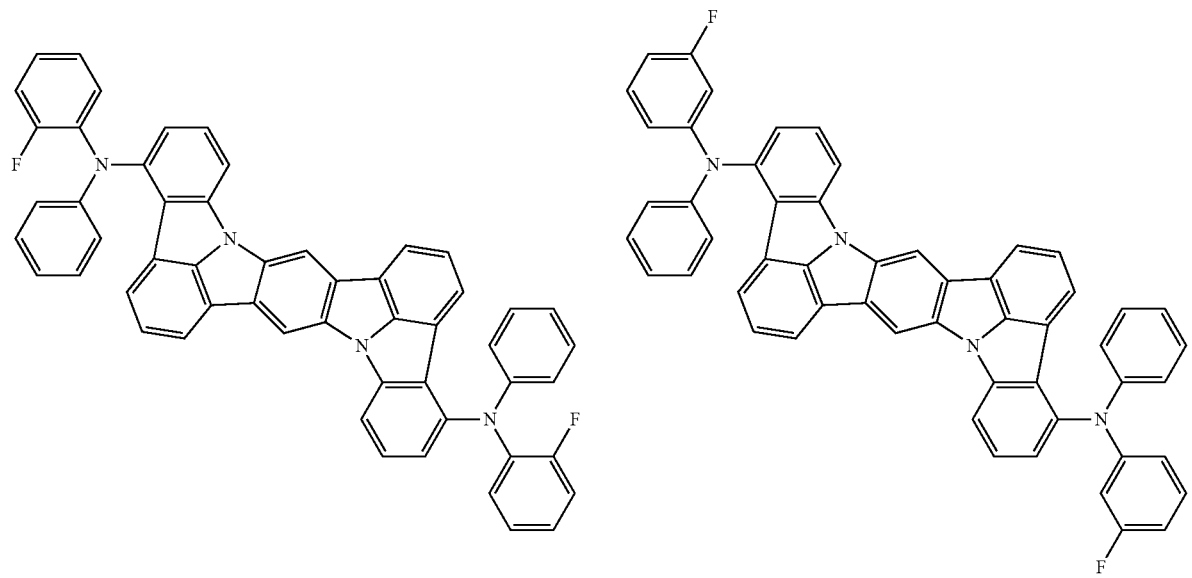

-continued
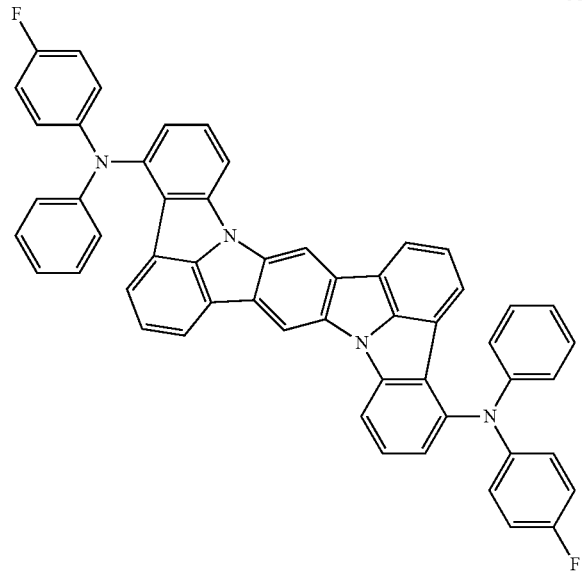
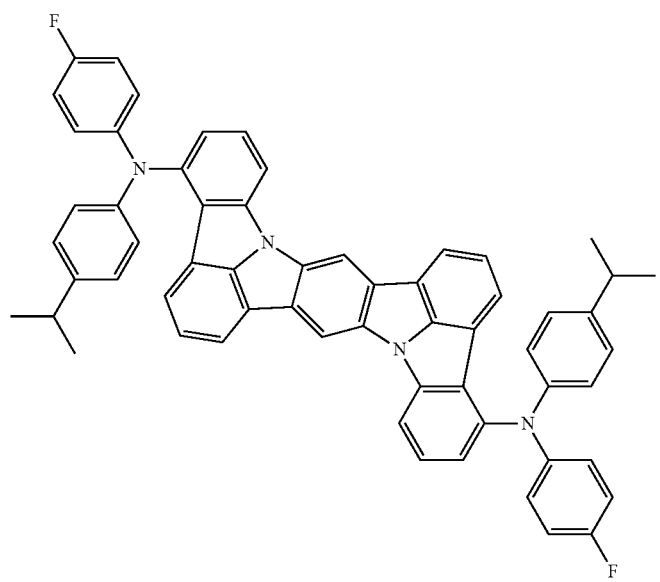
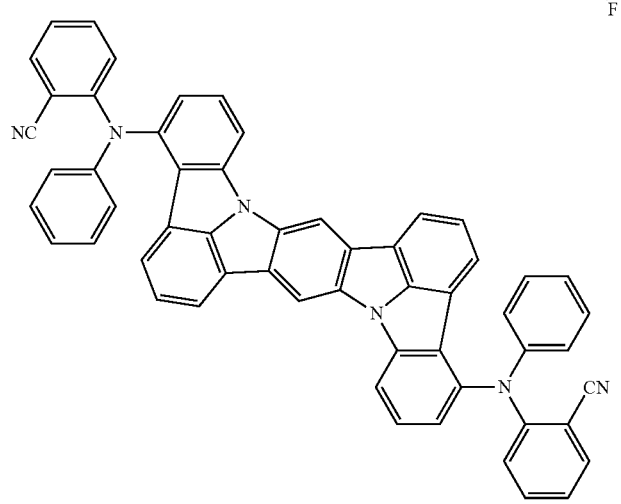

269
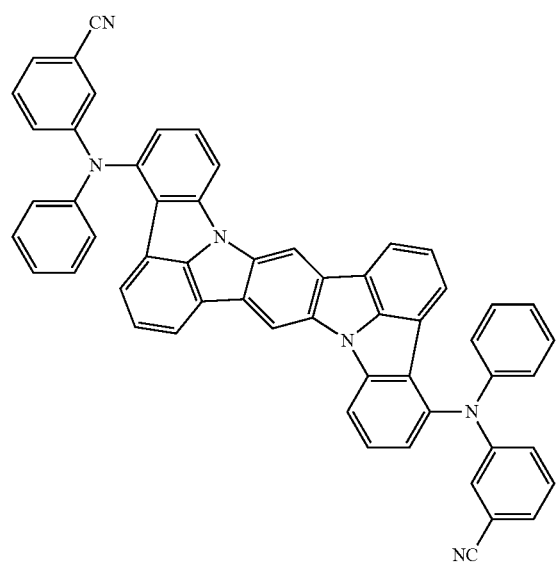
270
-continued
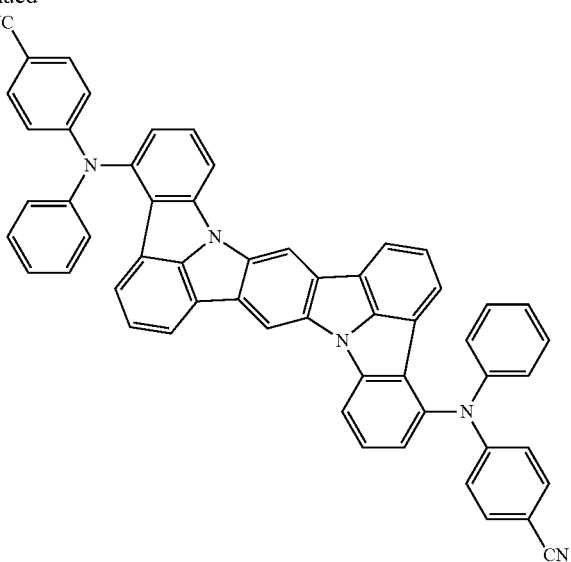
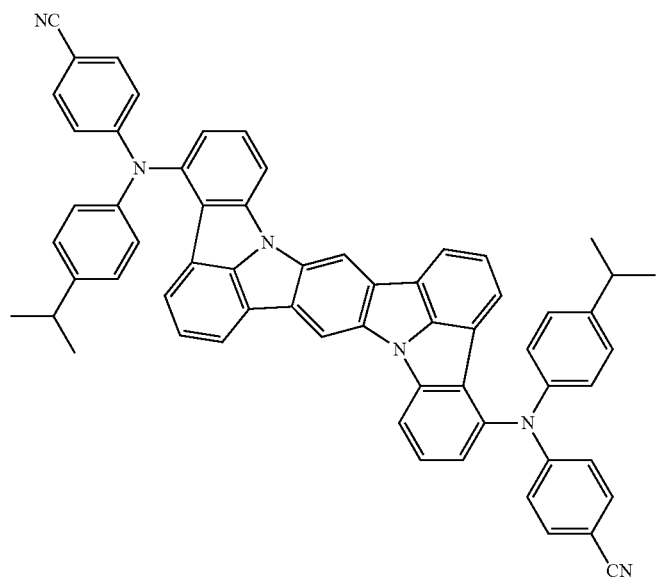
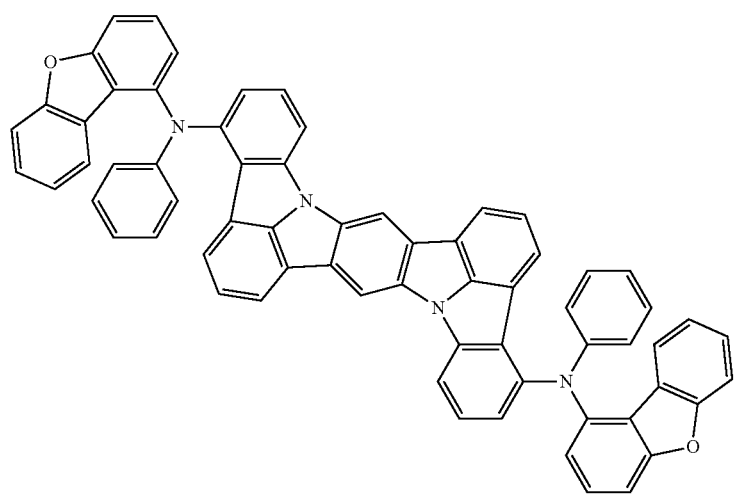

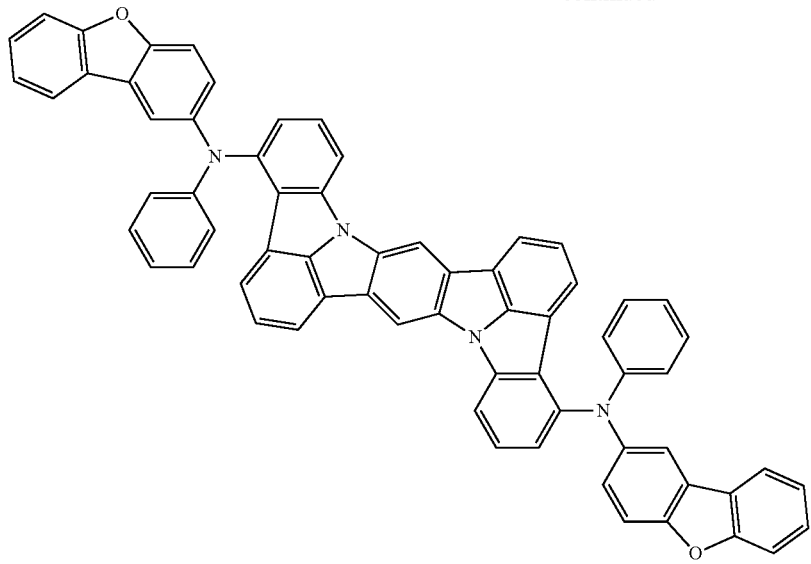
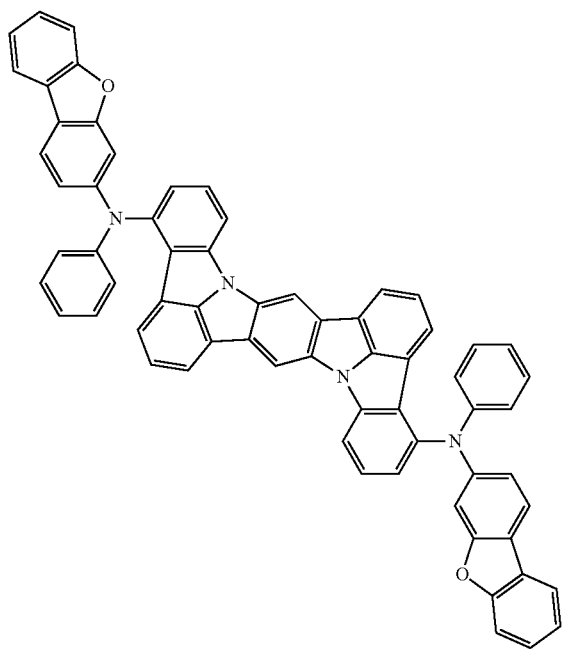
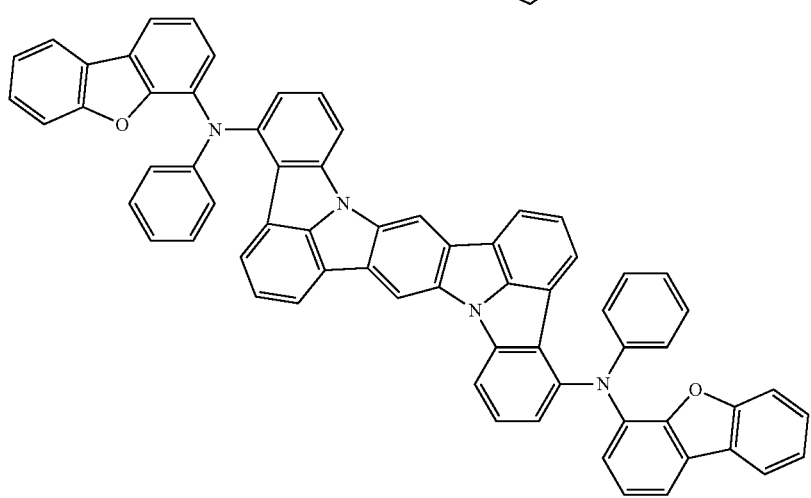

-continued
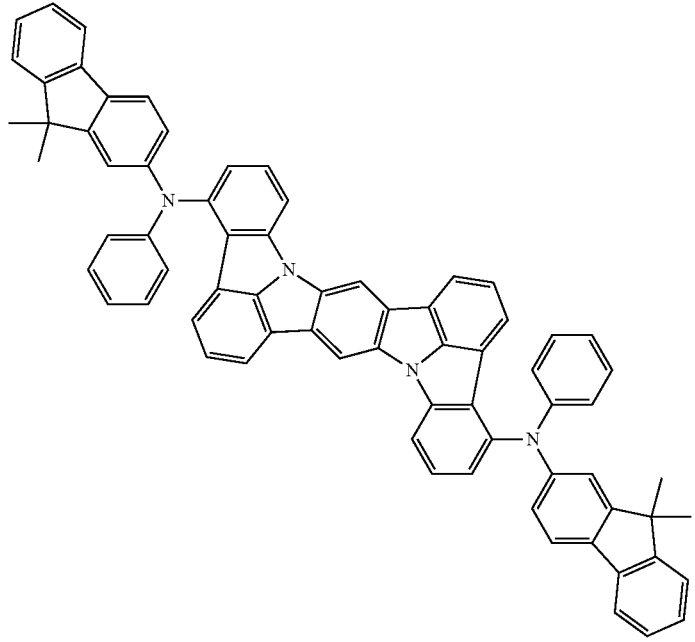
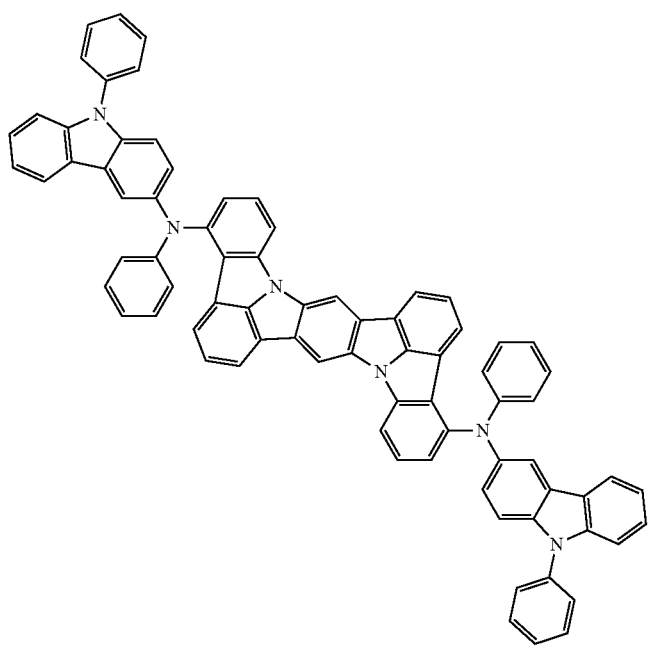

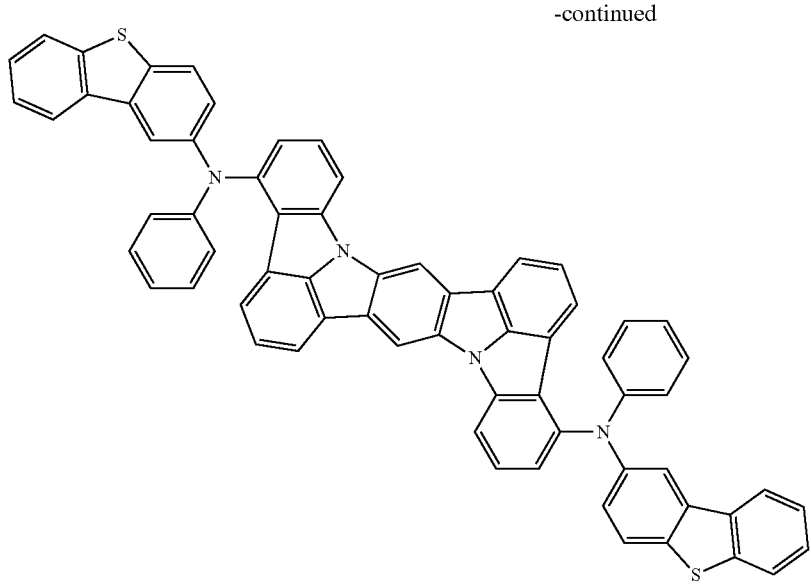
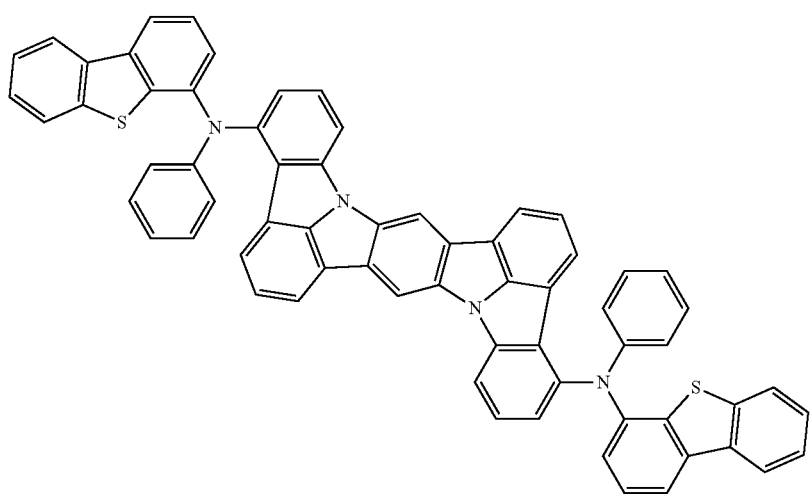
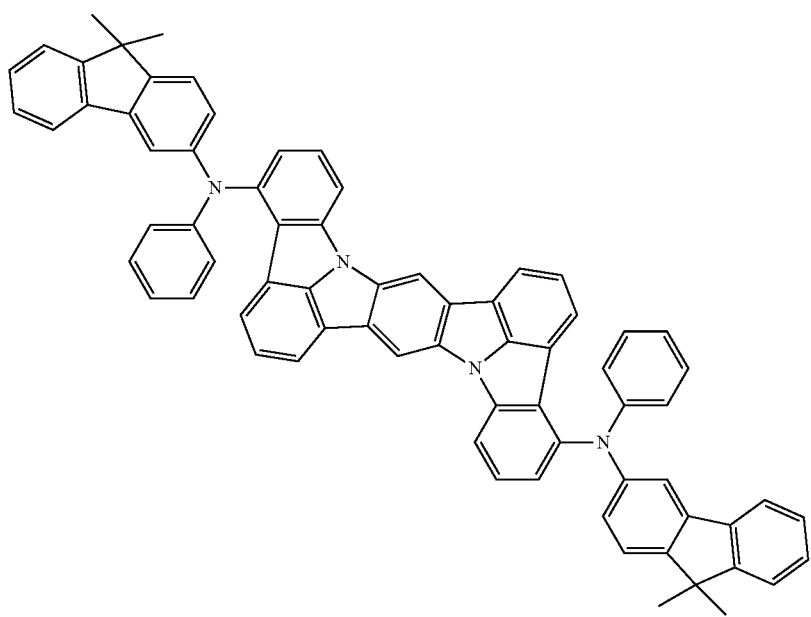

-continued
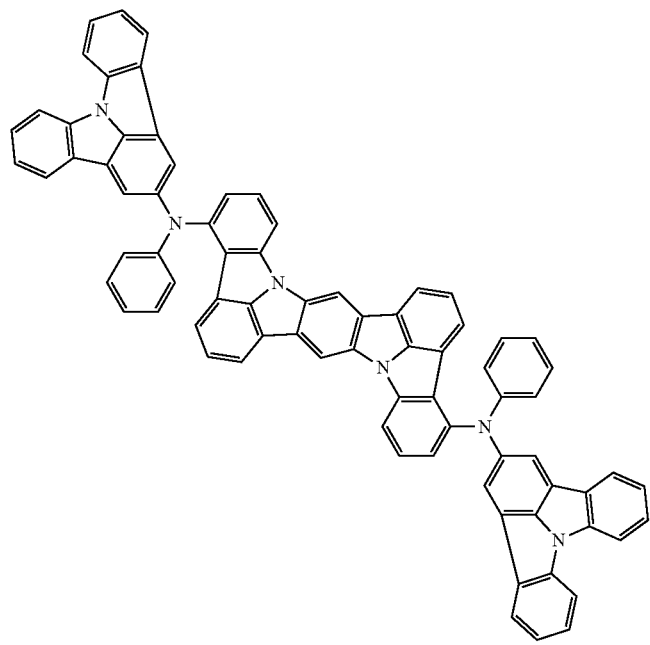
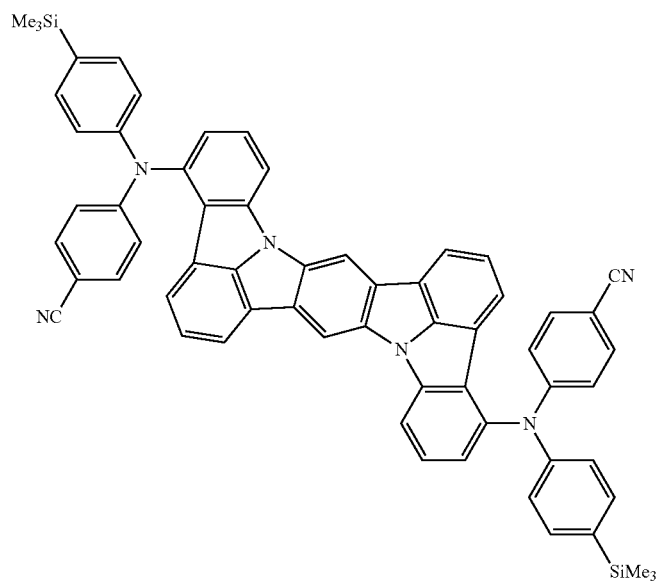
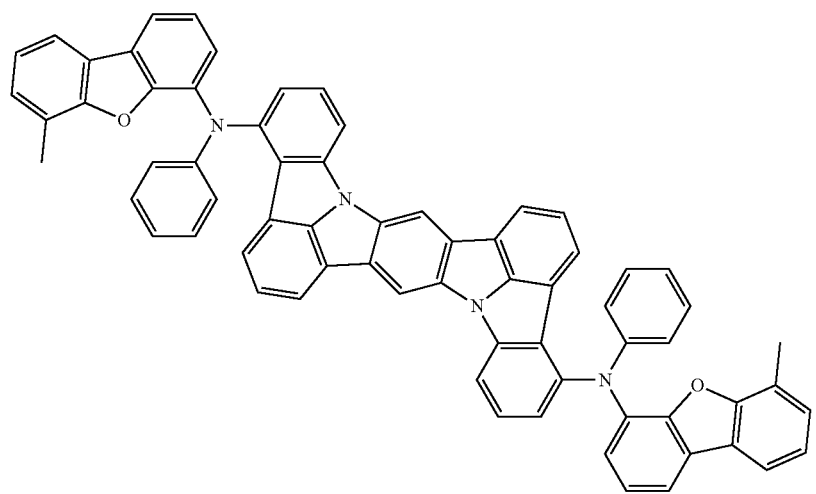

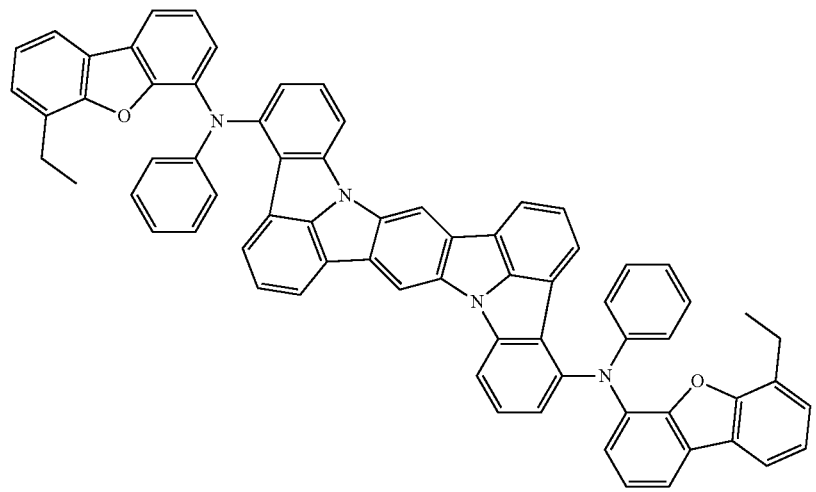
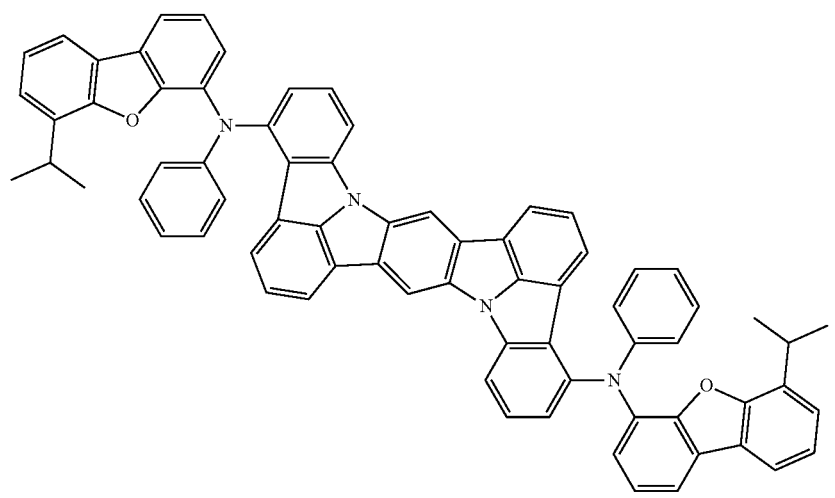
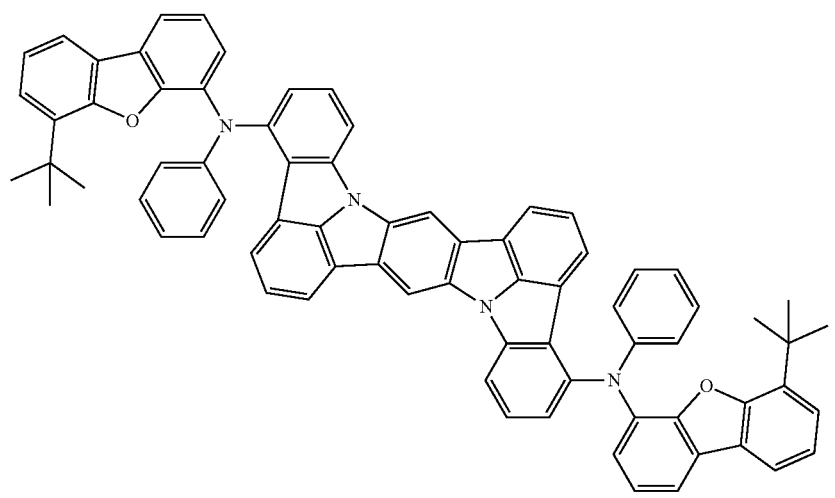

-continued
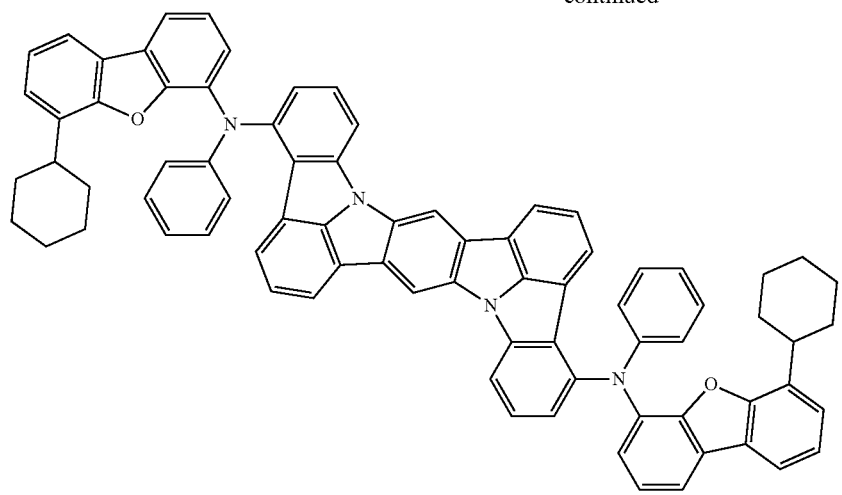
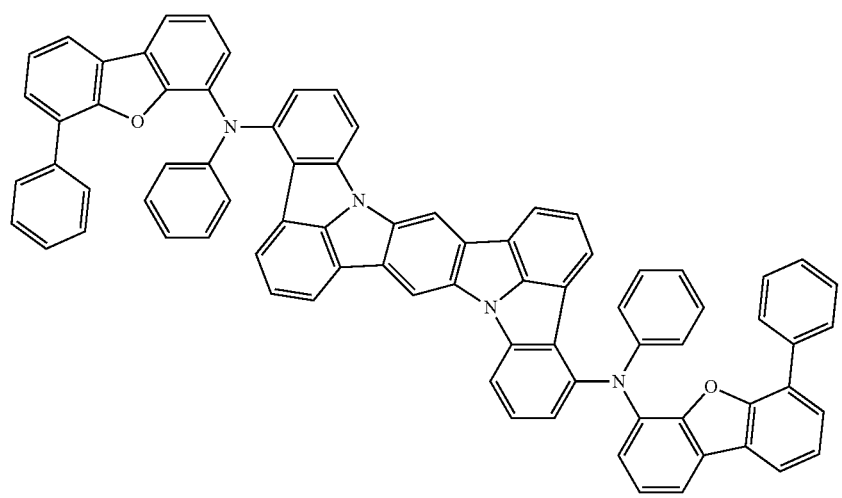
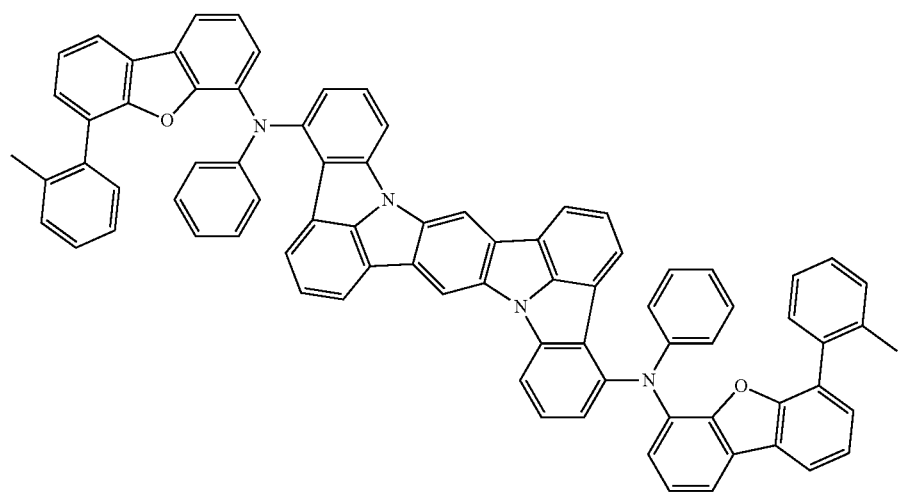

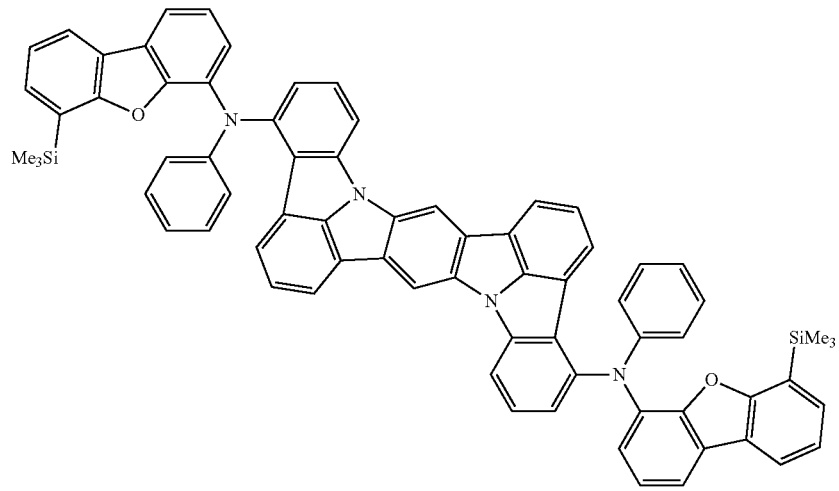
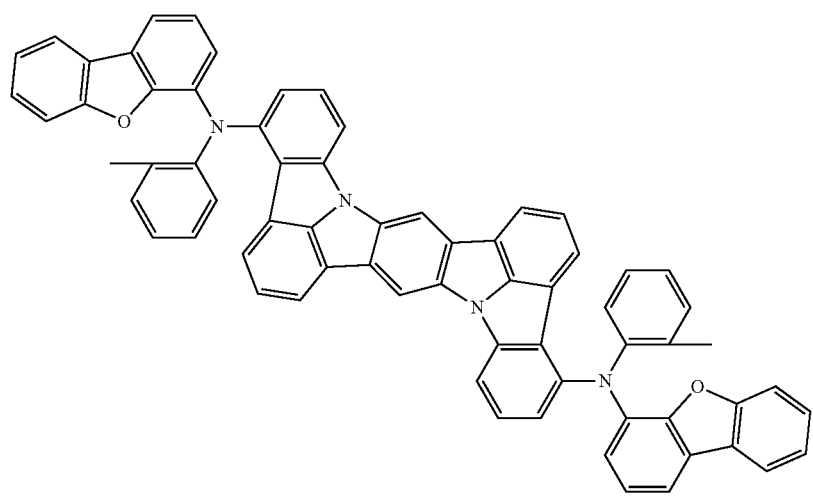
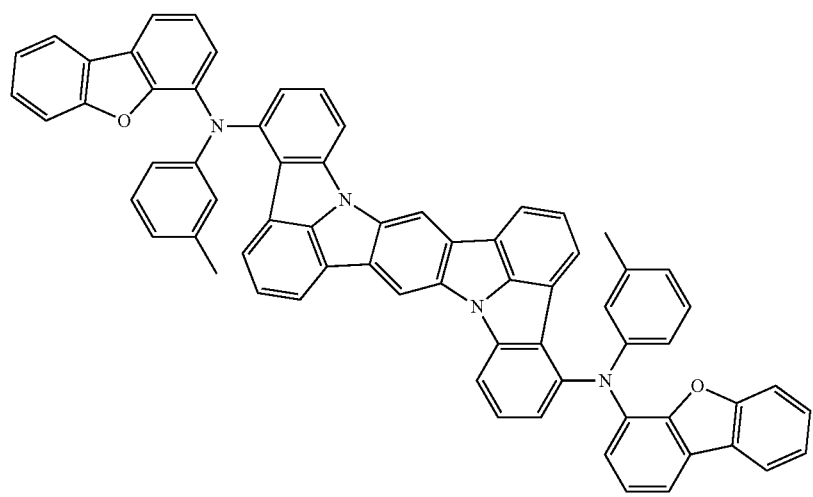

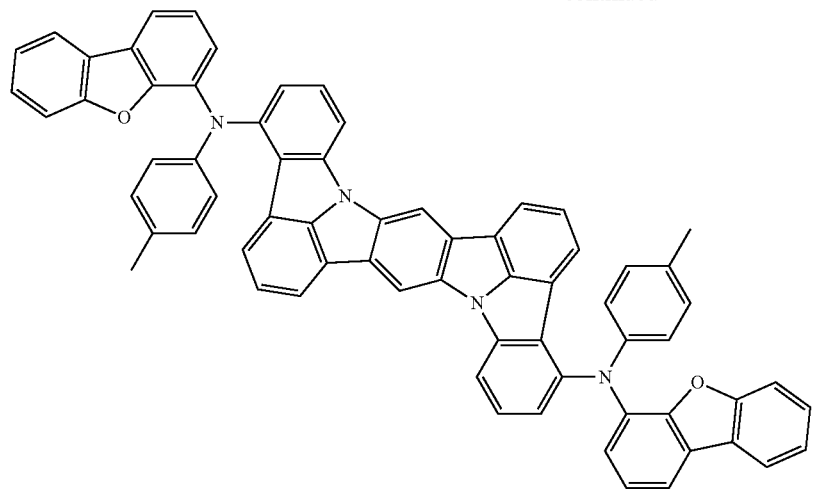
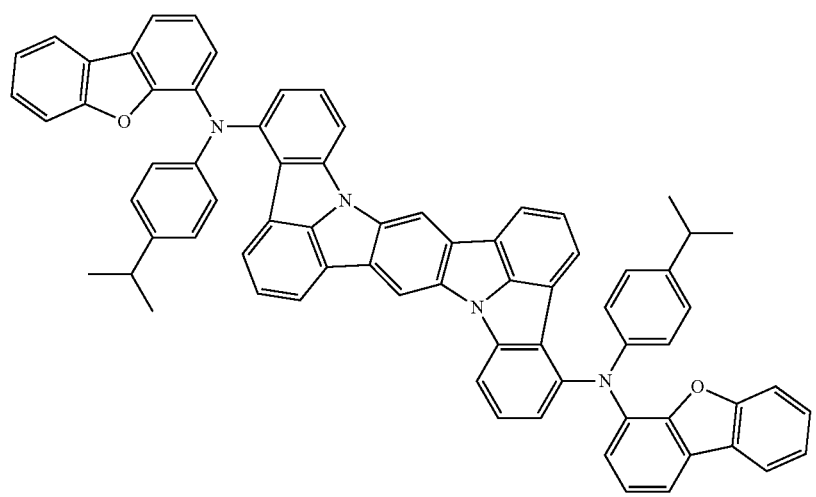
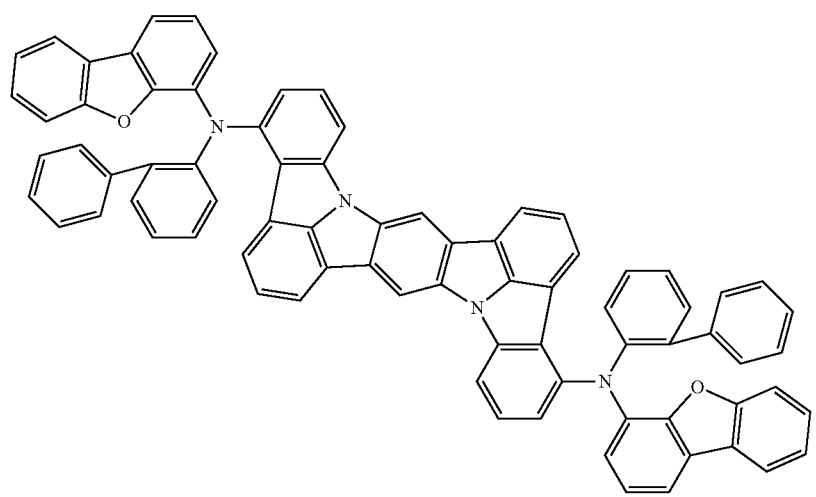

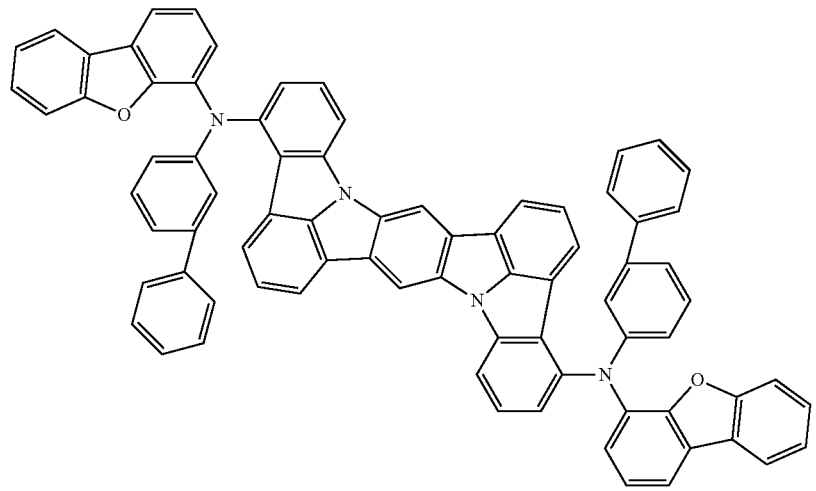
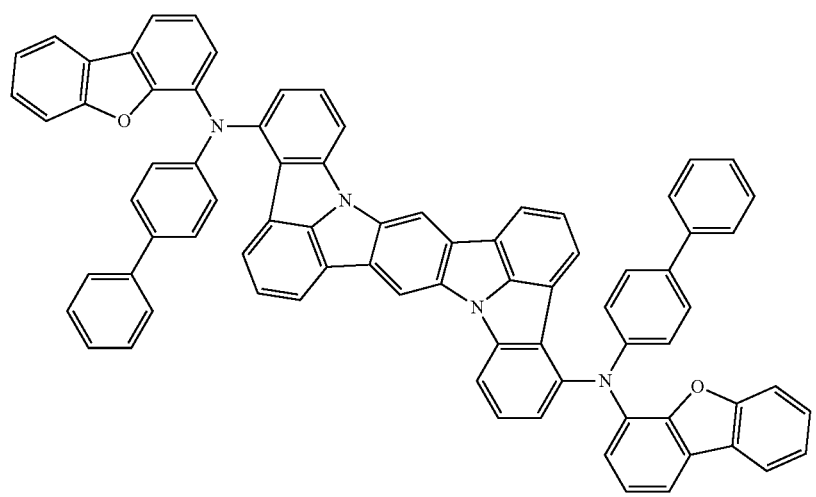
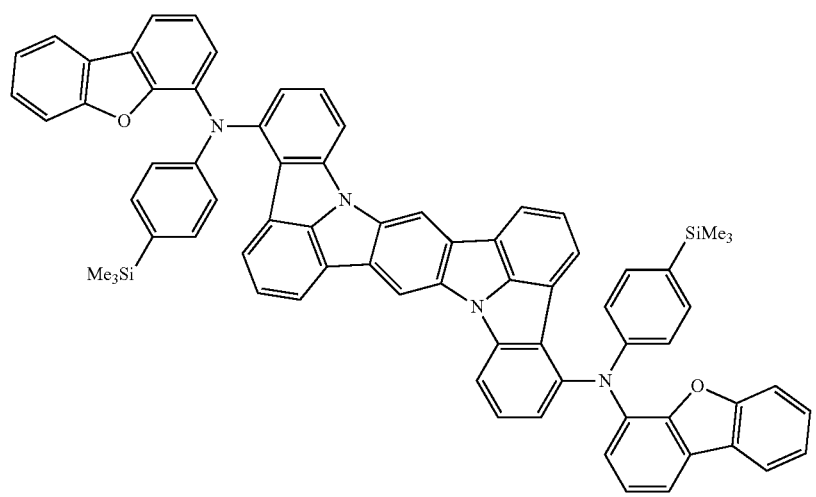

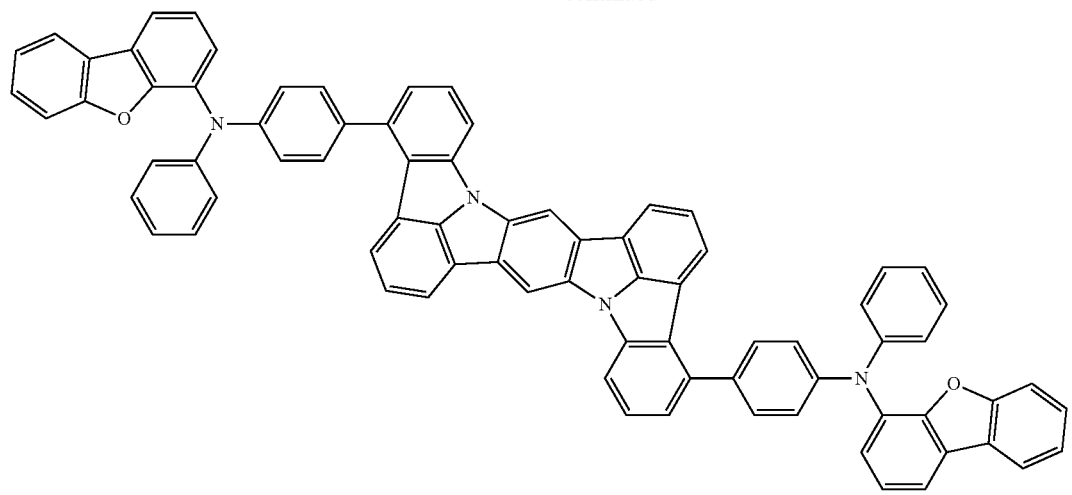
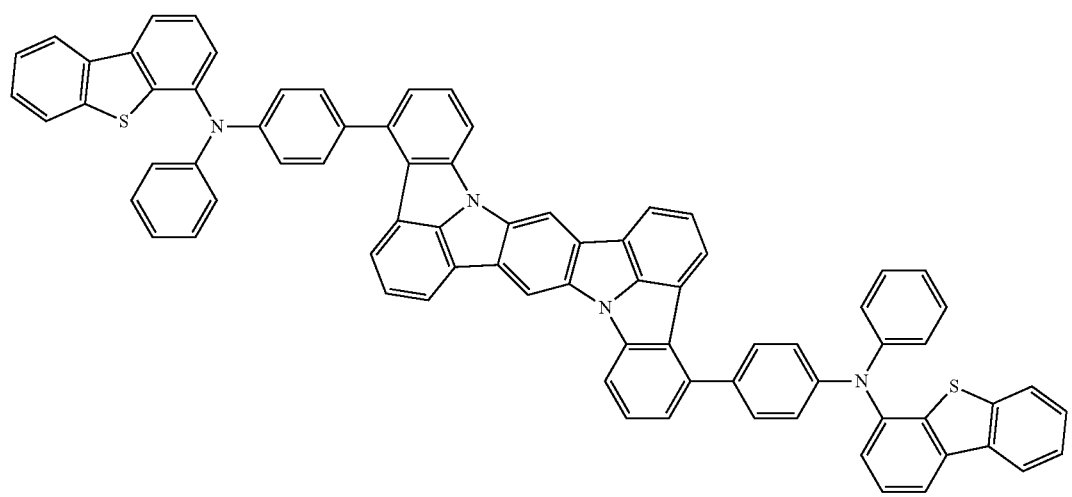
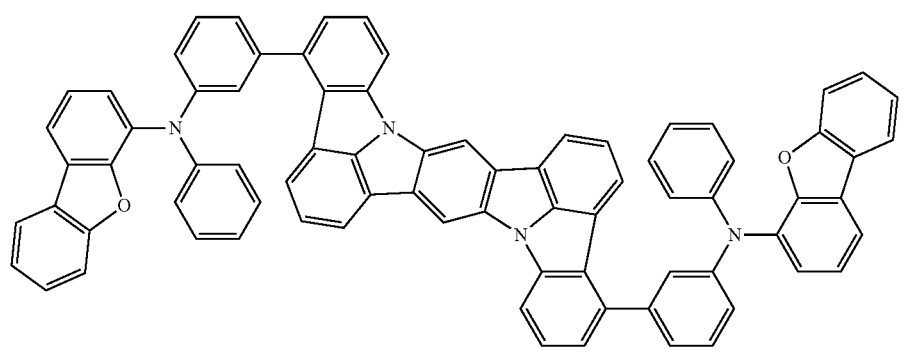
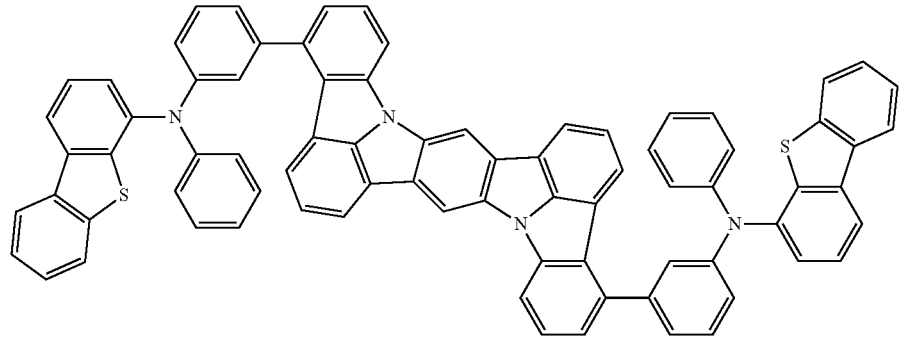

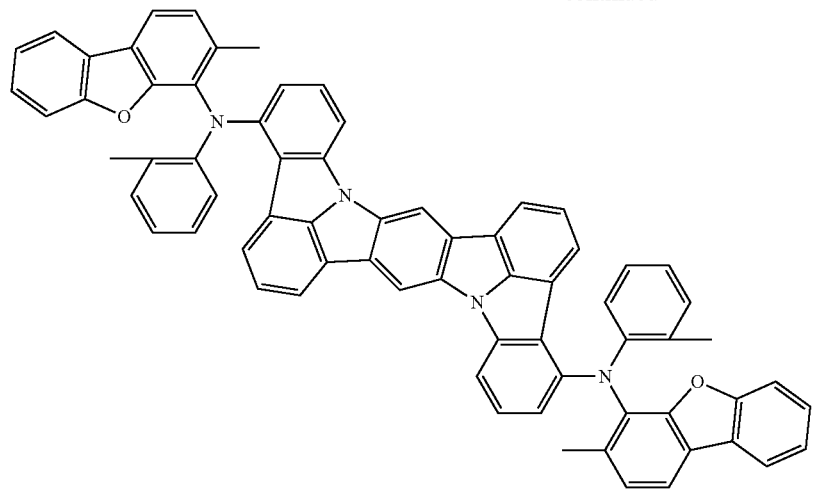
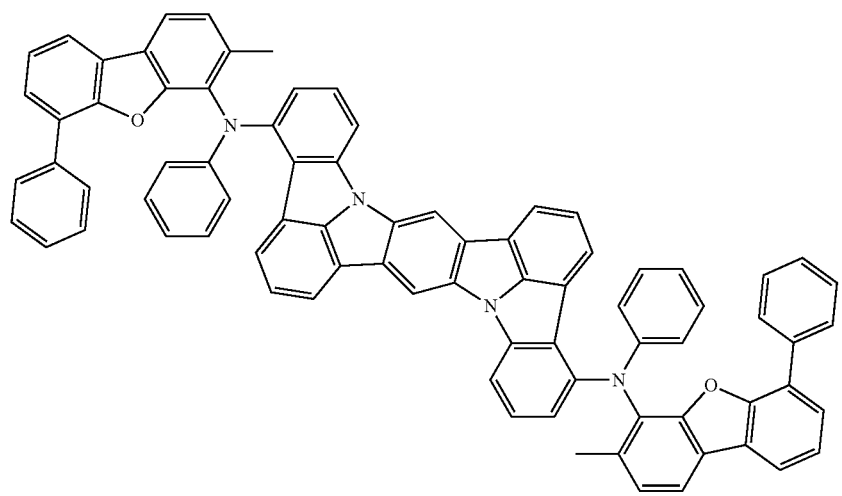
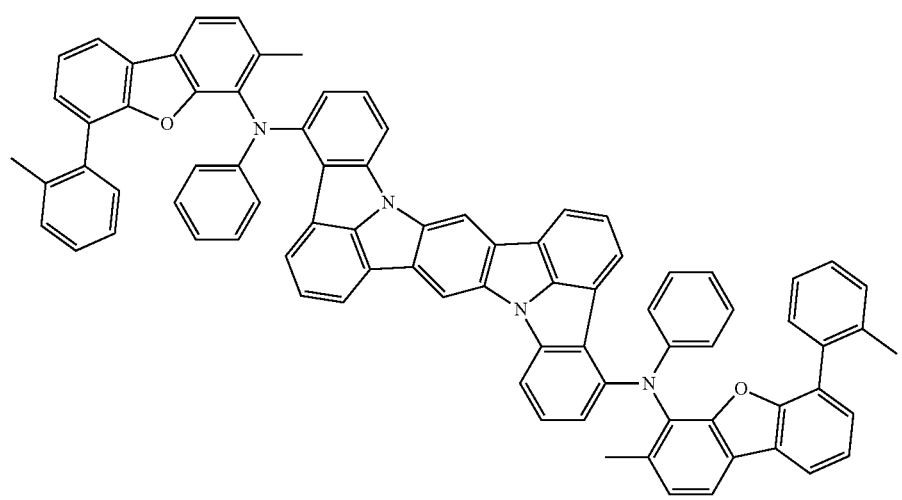

-continued
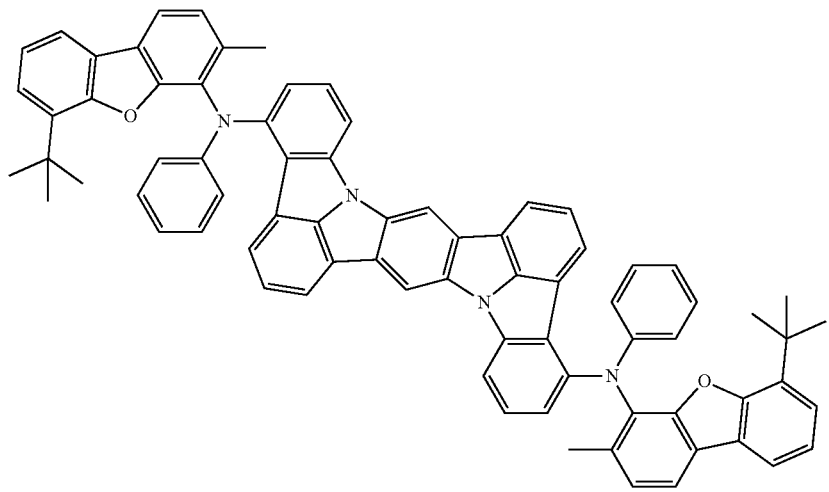
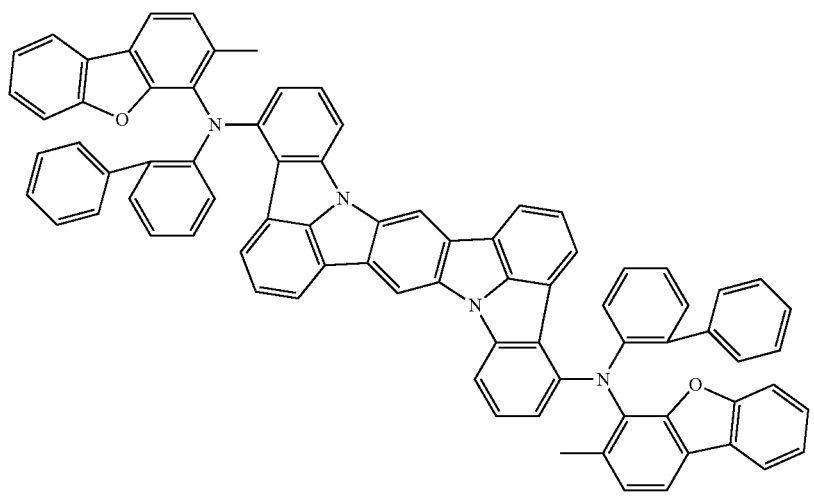
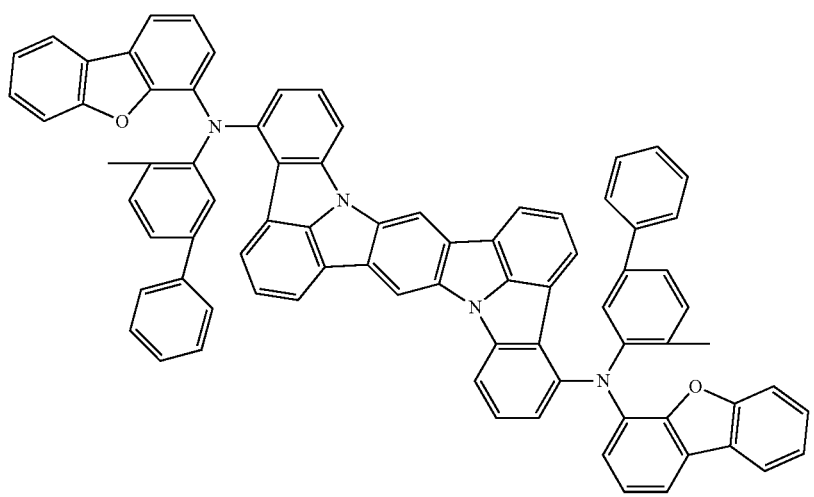

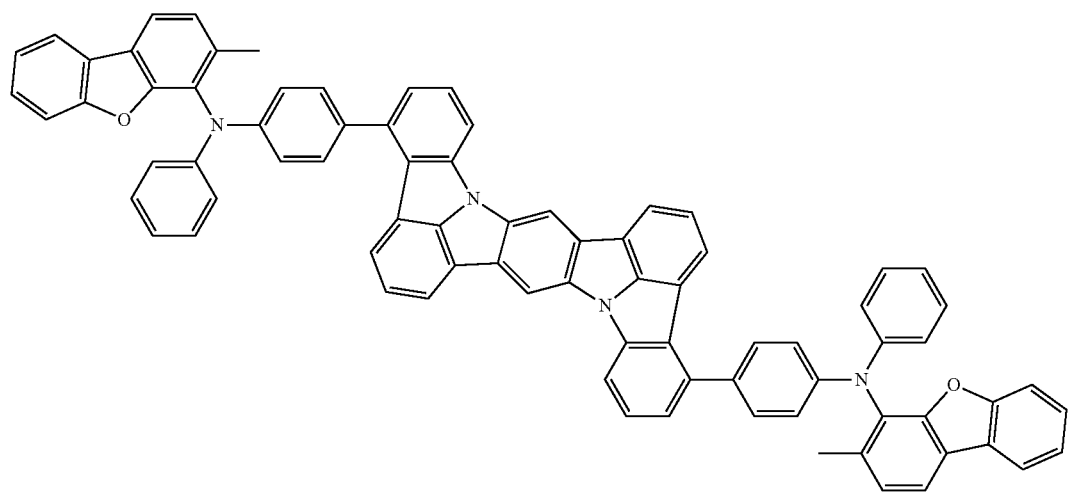 [SMILES: Cc1ccc2c(oc3ccccc32)c1N(c1ccccc1)c1ccc(-c2cccc3c2c2cccc4c5cc6c(cc5n3c42)c2cccc3c4c(-c5ccc(N(c7ccccc7)c7c(C)ccc8c7oc7ccccc78)cc5)cccc4n6c23)cc1]
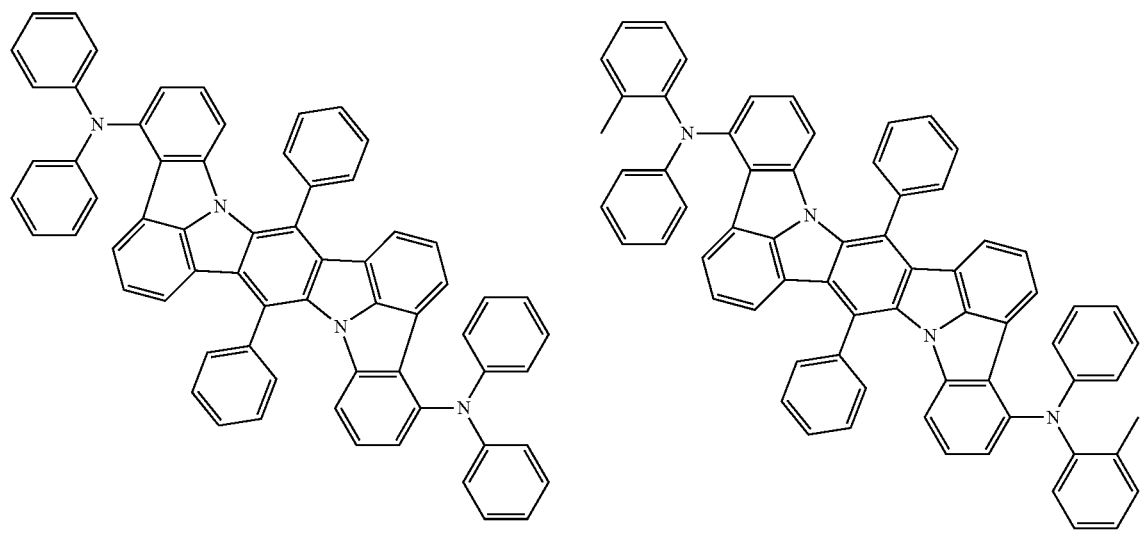
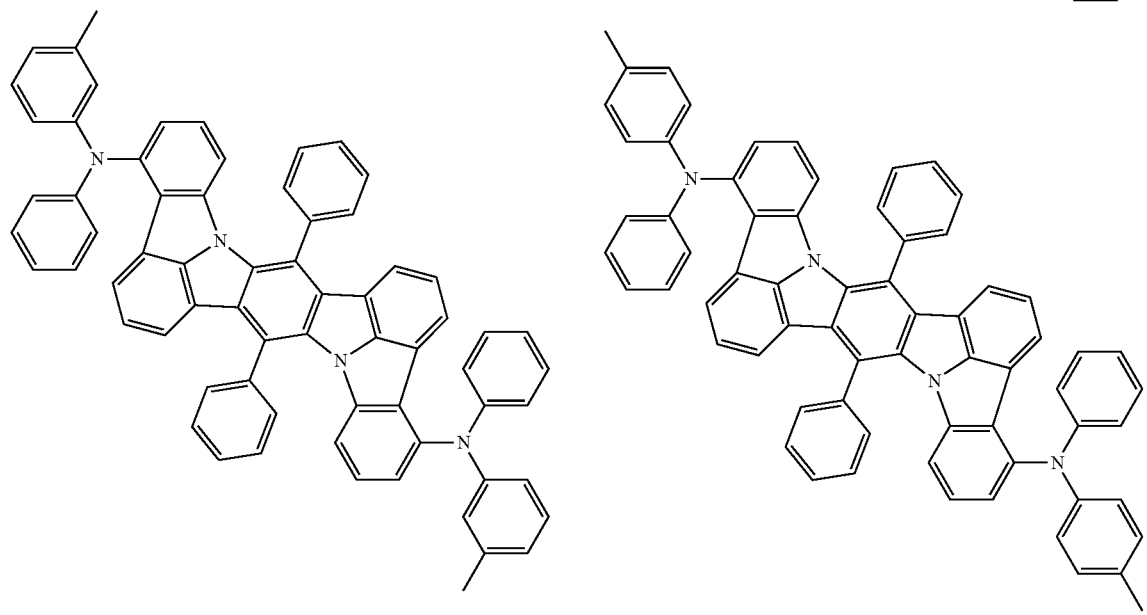

297 298
-continued
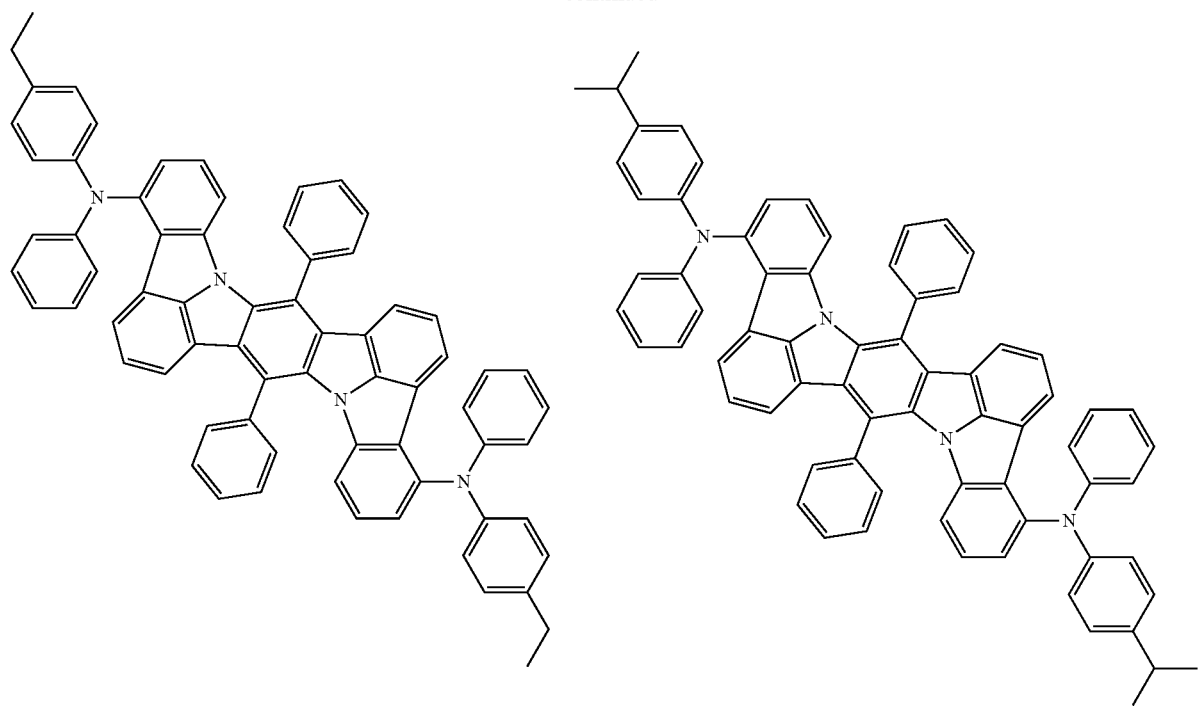
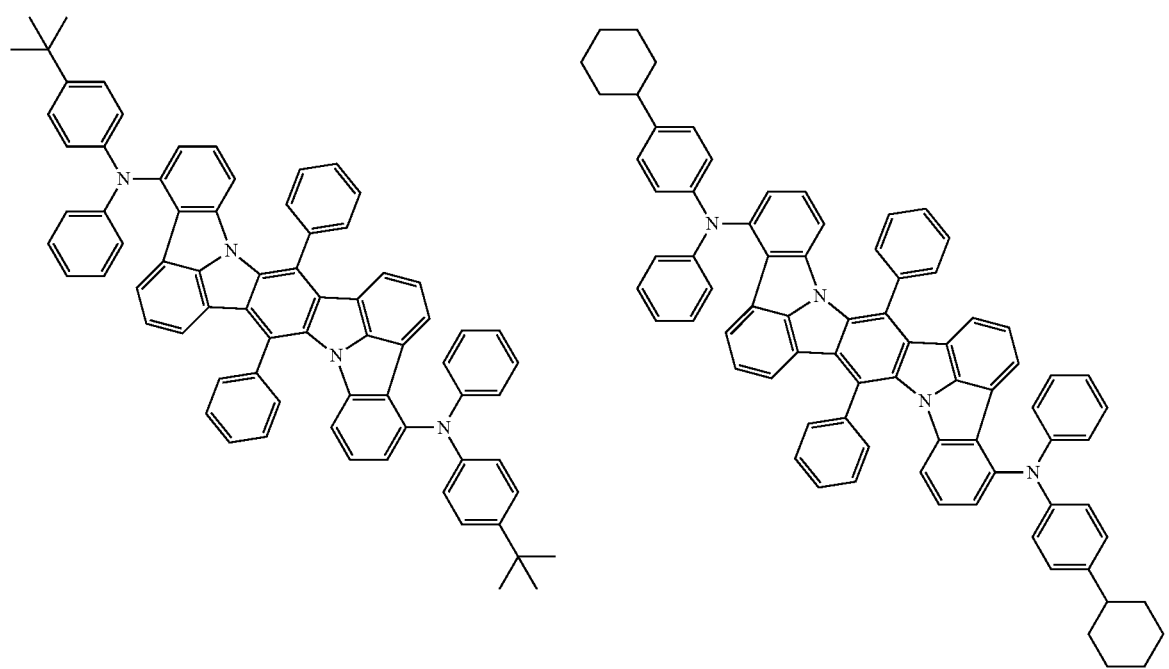 [SMILES: CC(C)(C)c1ccc(N(c2ccccc2)c2cccc3c2c2cccc4c5c(-c6ccccc6)c6c(c(-c7ccccc7)c5n3c24)c2cccc3c4c(N(c5ccccc5)c5ccc(C(C)(C)C)cc5)cccc4n6c32)cc1 ; c1ccc(-c2c3c4cccc5c6c(N(c7ccccc7)c7ccc(C8CCCCC8)cc7)cccc6n(c3c(-c3ccccc3)c3c6cccc7c8c(N(c9ccccc9)c9ccc(C%10CCCCC%10)cc9)cccc8n(c23)c76)c54)cc1]

| 299 | 300 |
|---|---|
| 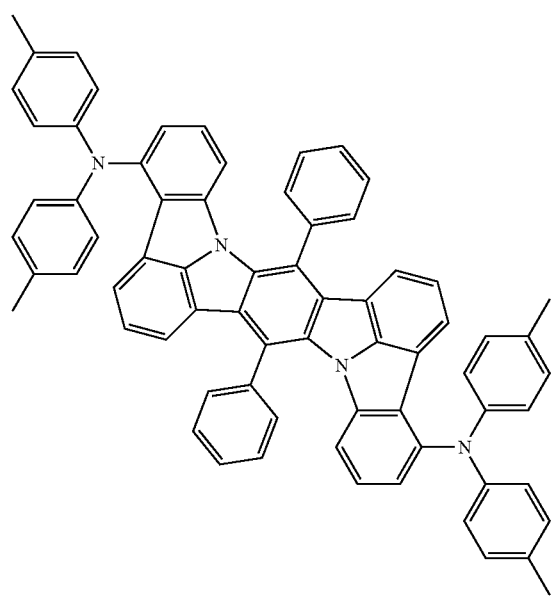 | 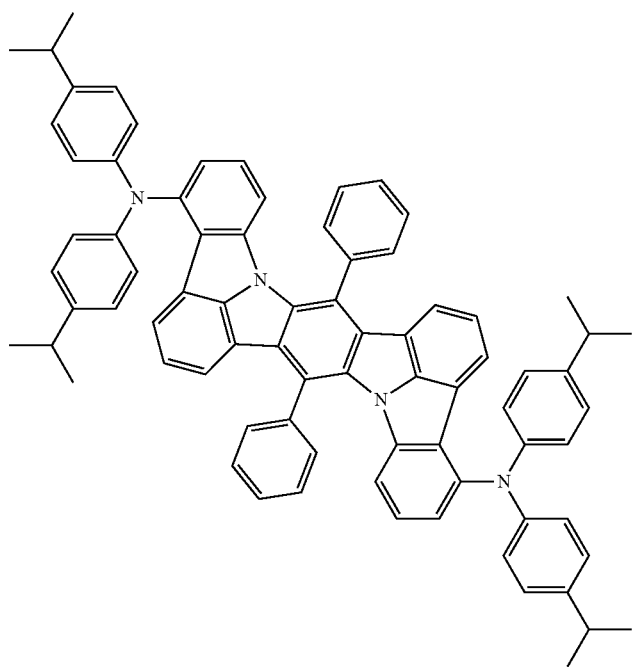 |
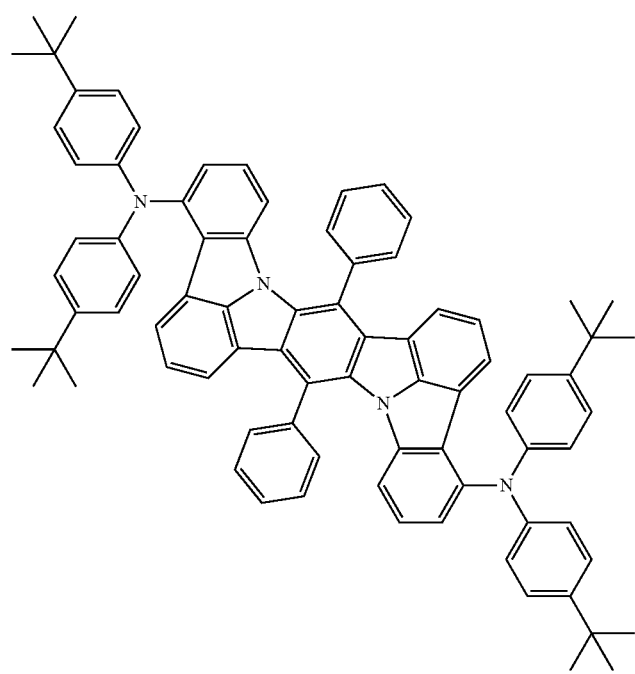

301 302
-continued
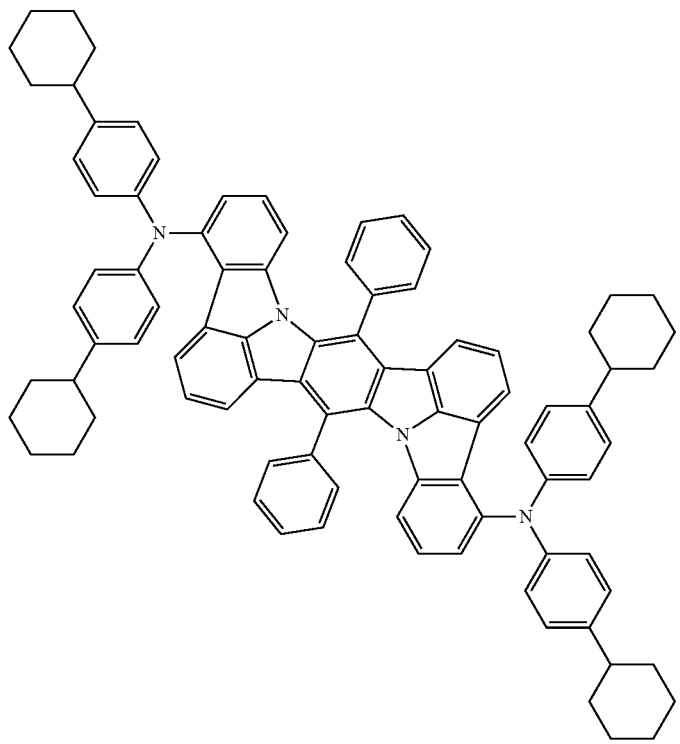
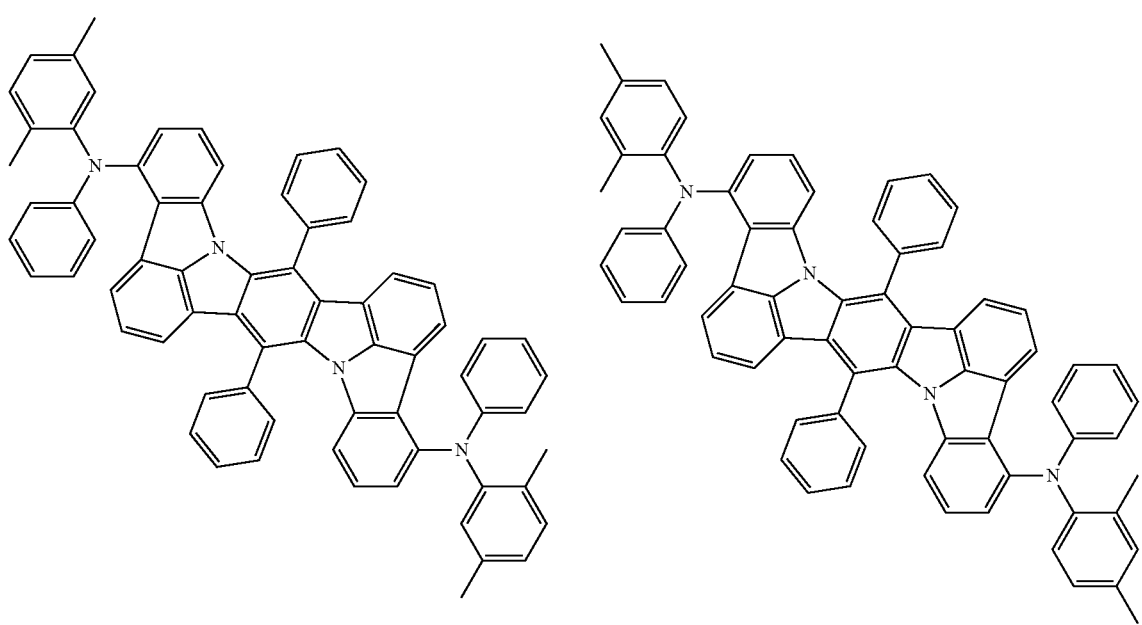

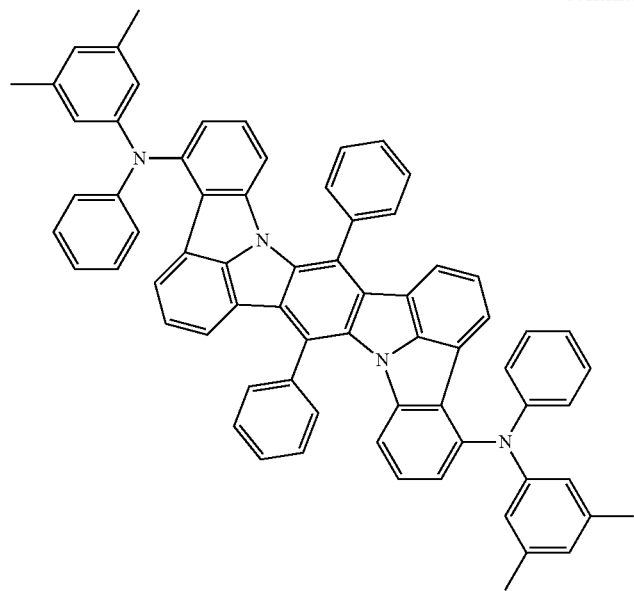
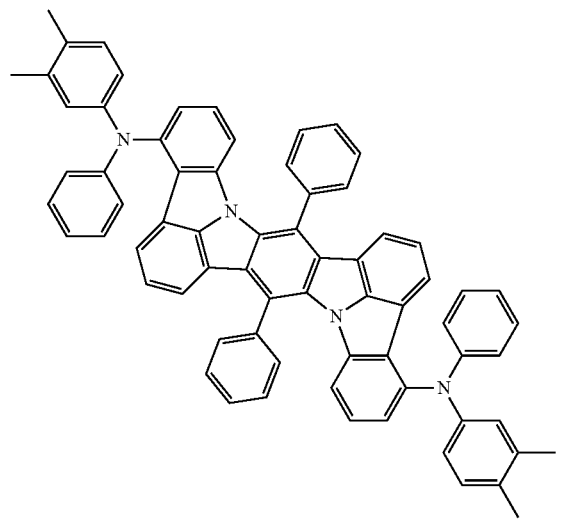
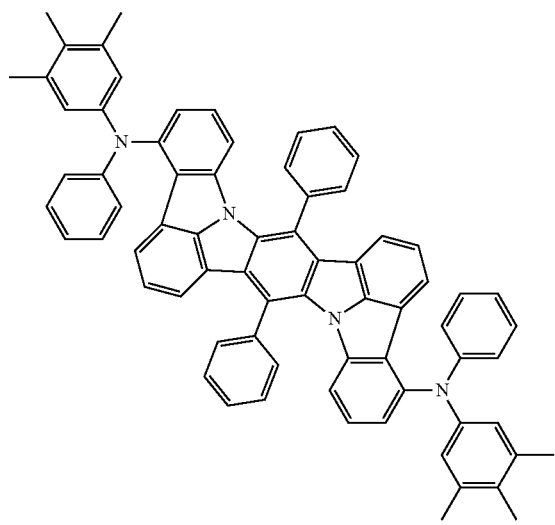
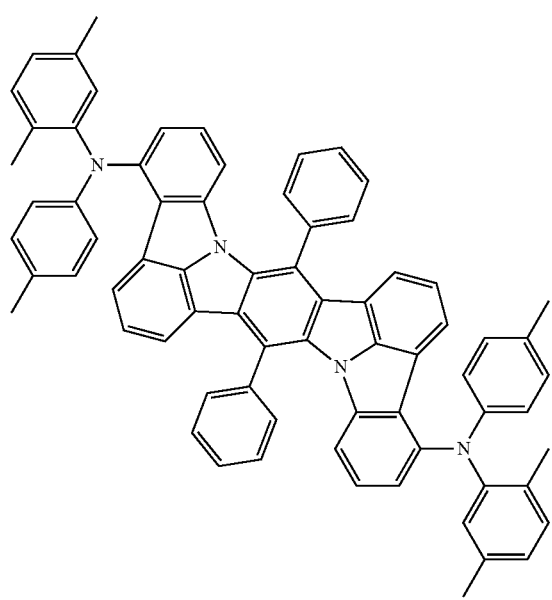
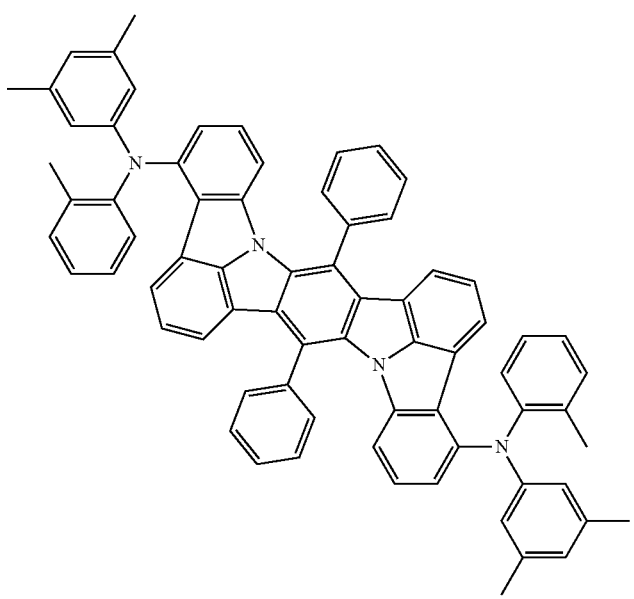

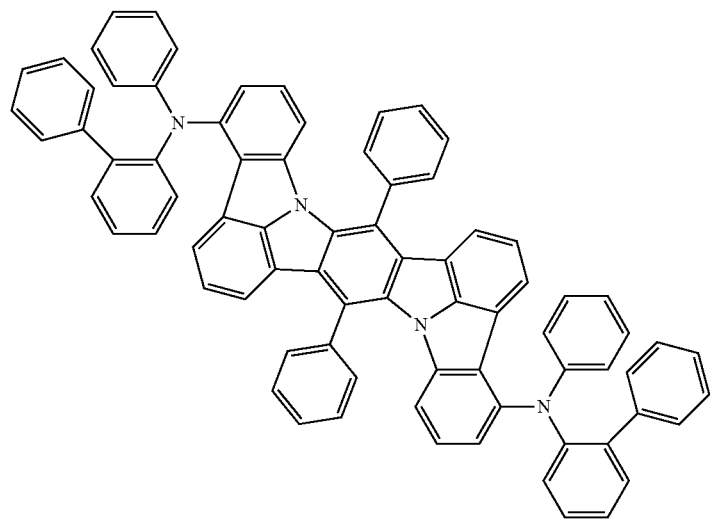

307 308
-continued
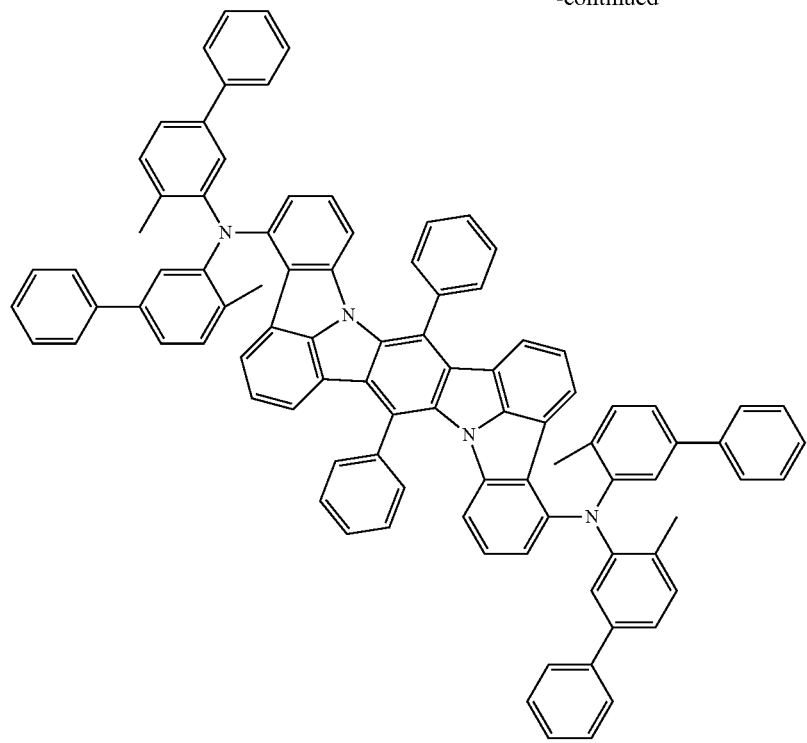
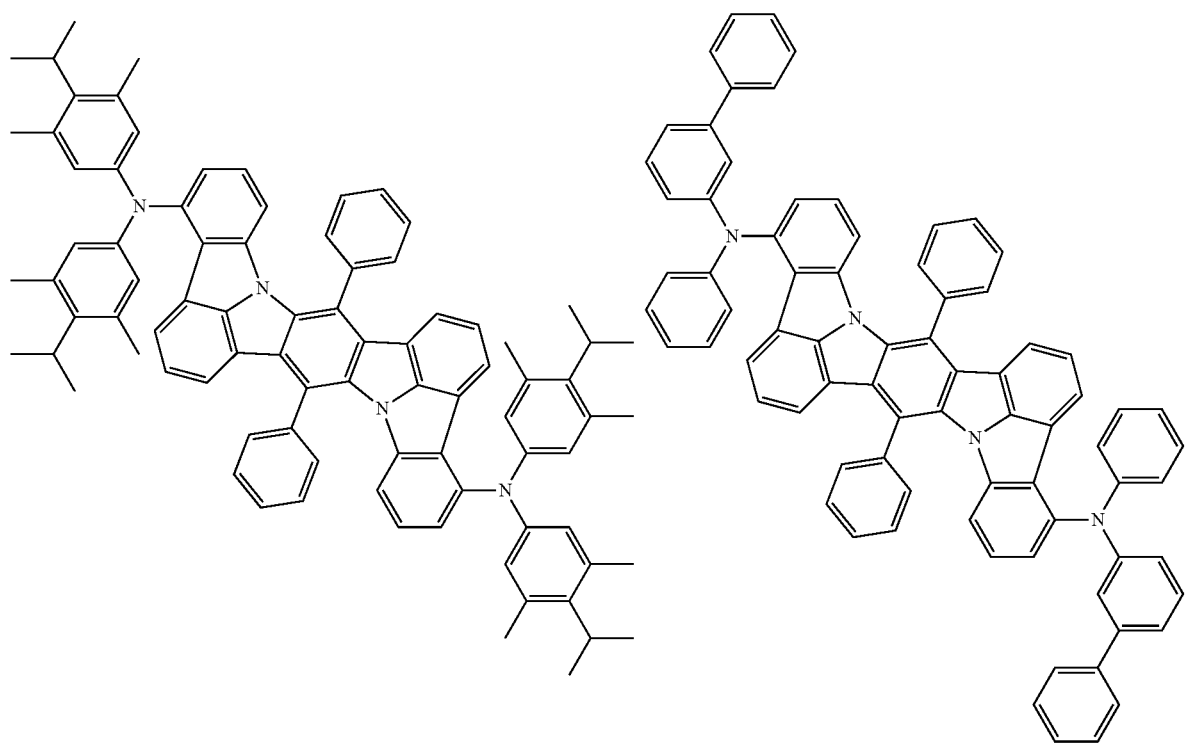

309
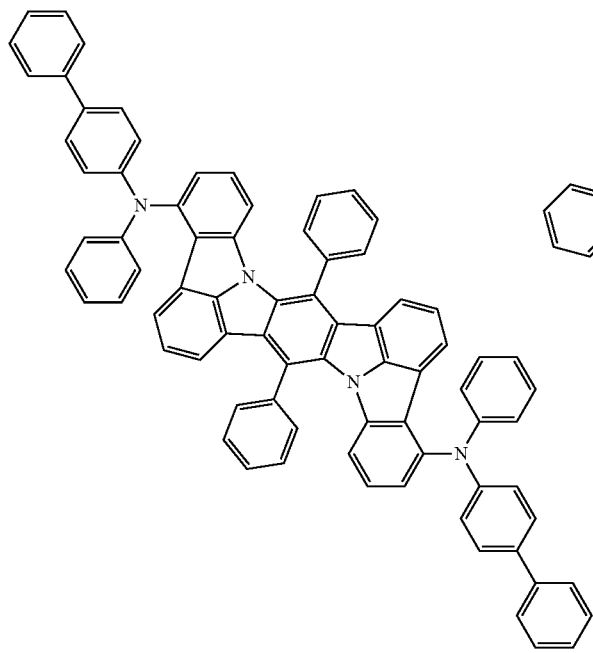
310
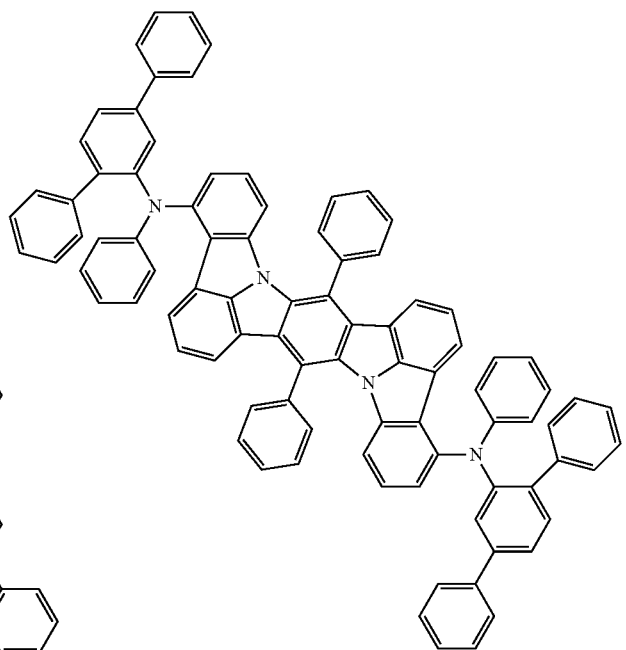
-continued
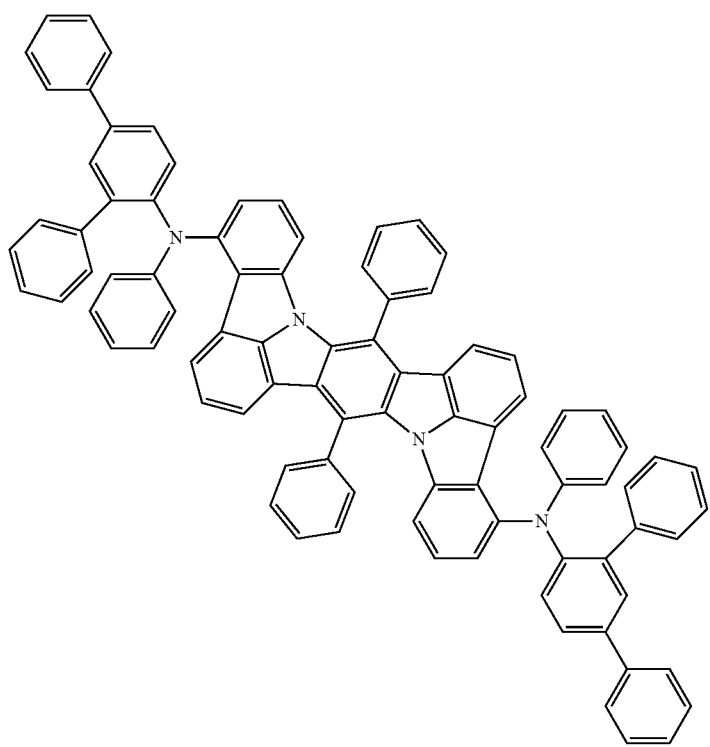

-continued
311
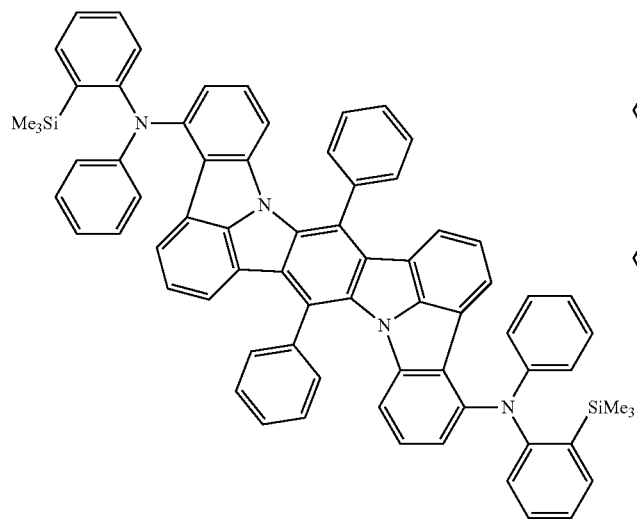
312
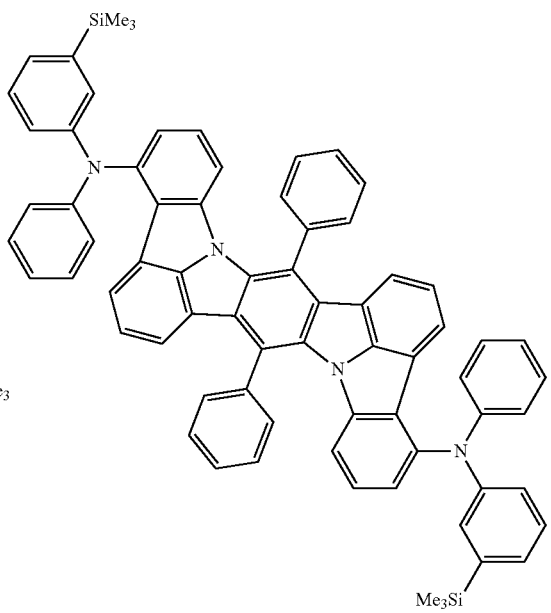
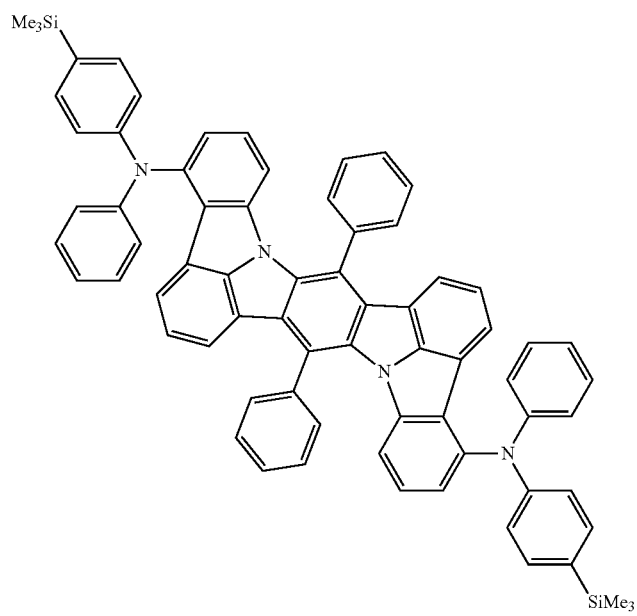

313 314
-continued
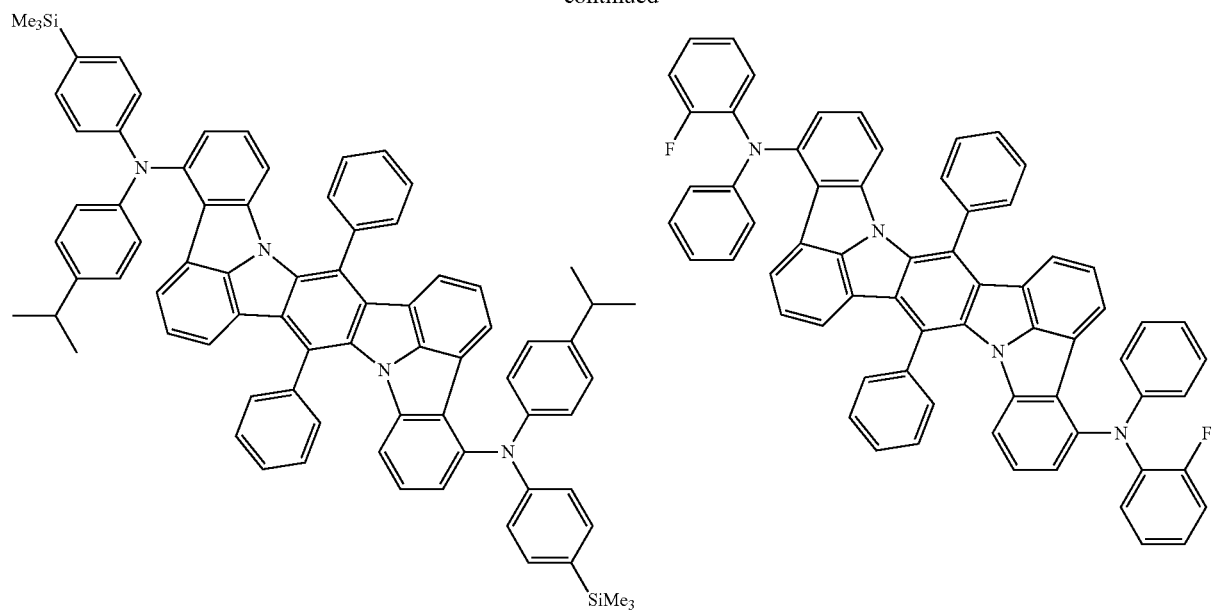
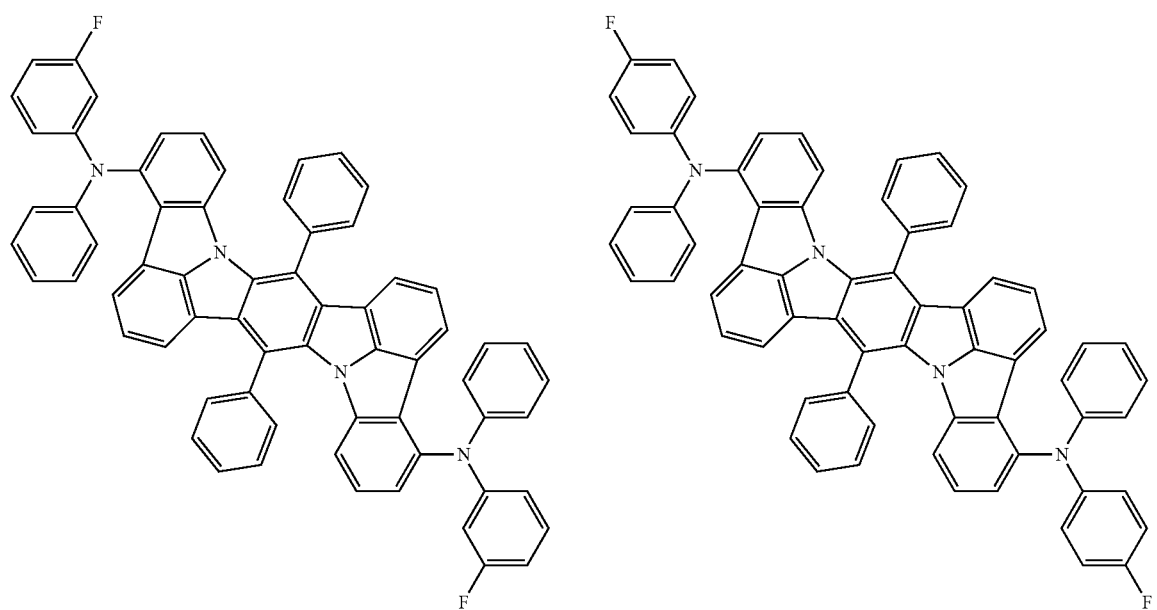

315
316
-continued
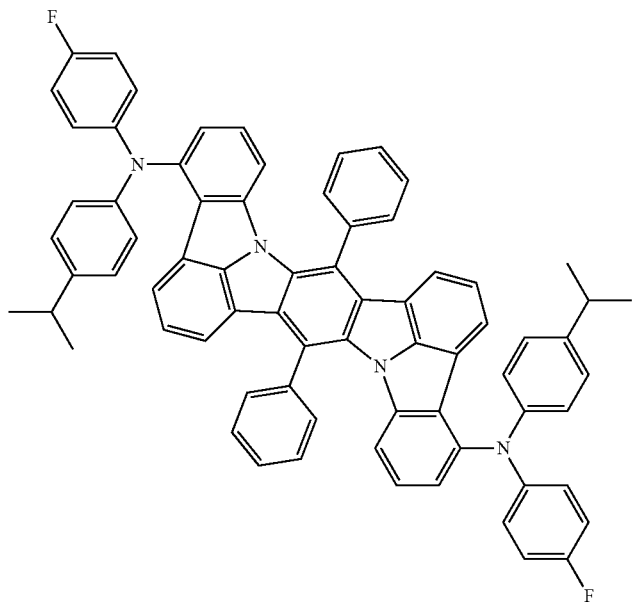
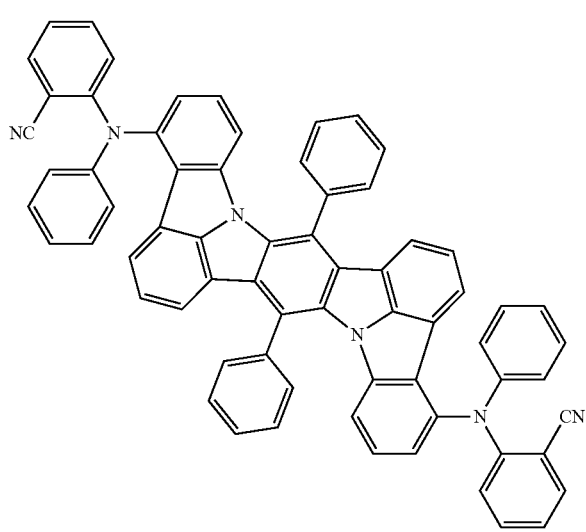
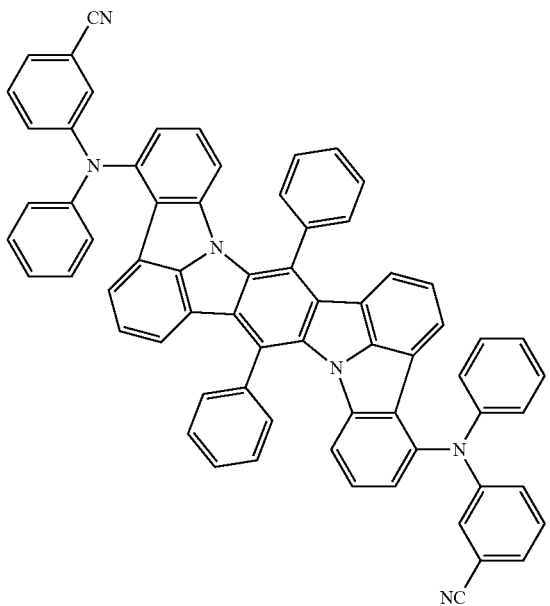

-continued
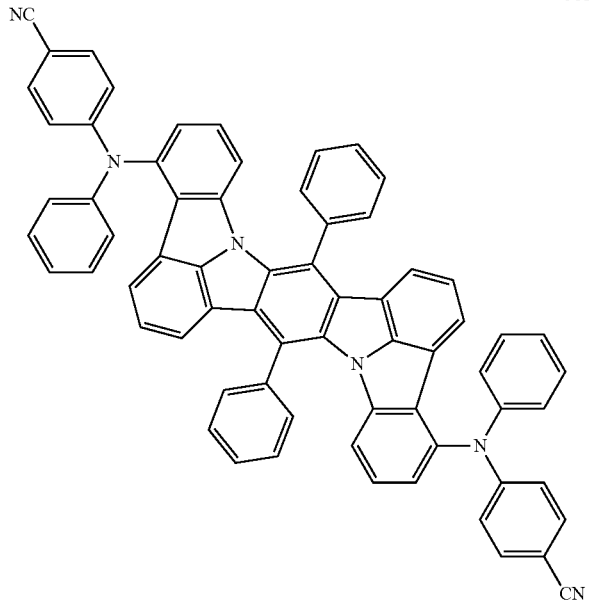
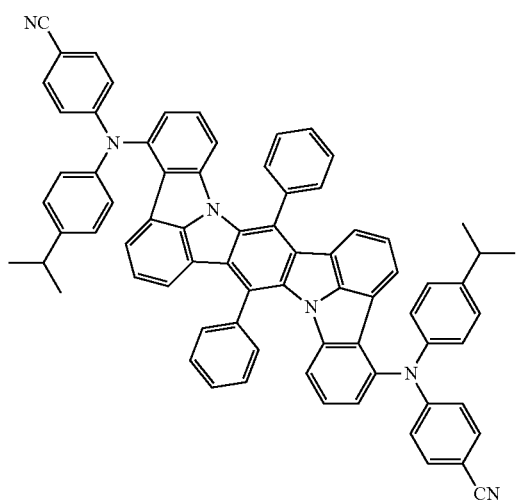
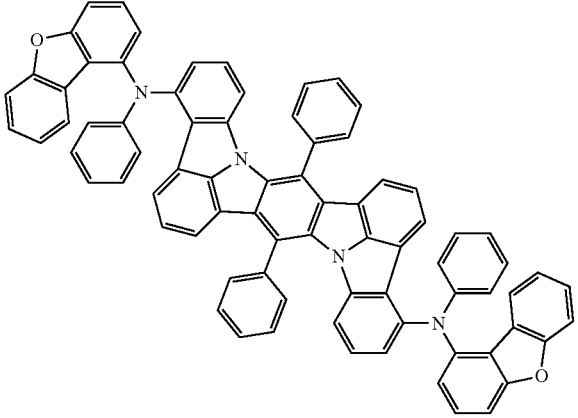
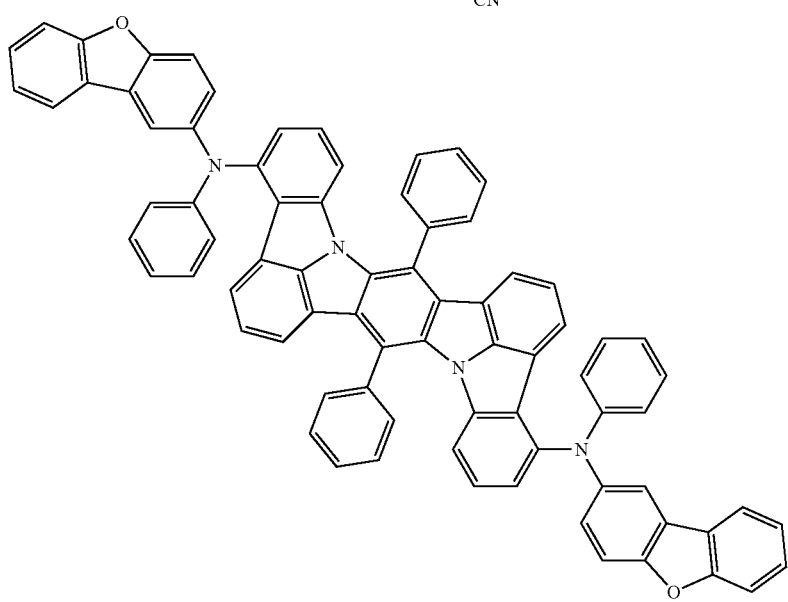

-continued
319
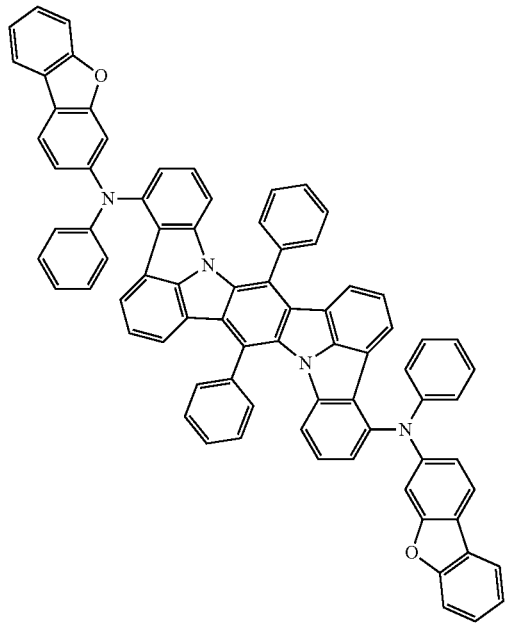
320
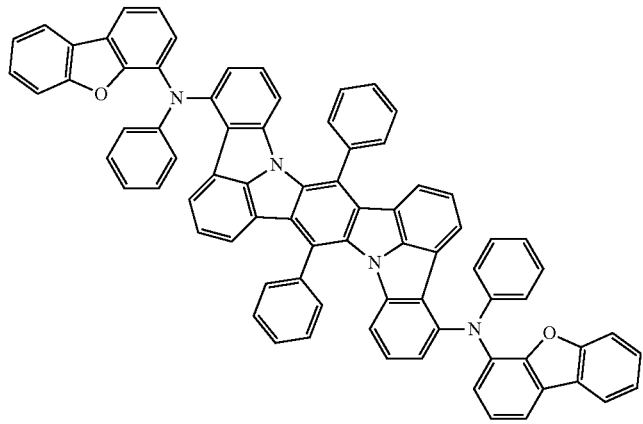
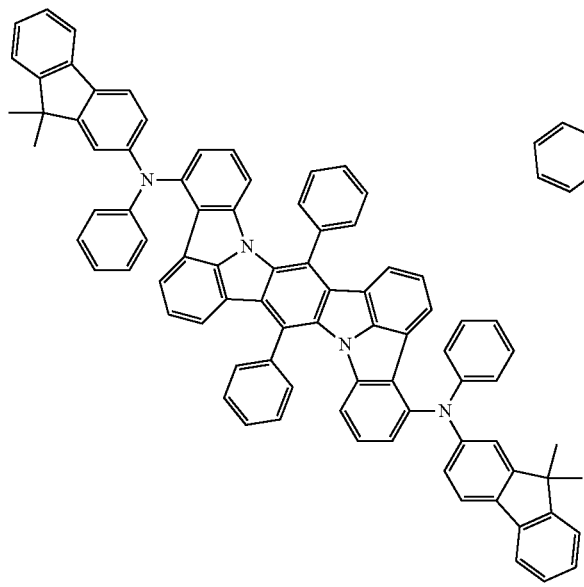
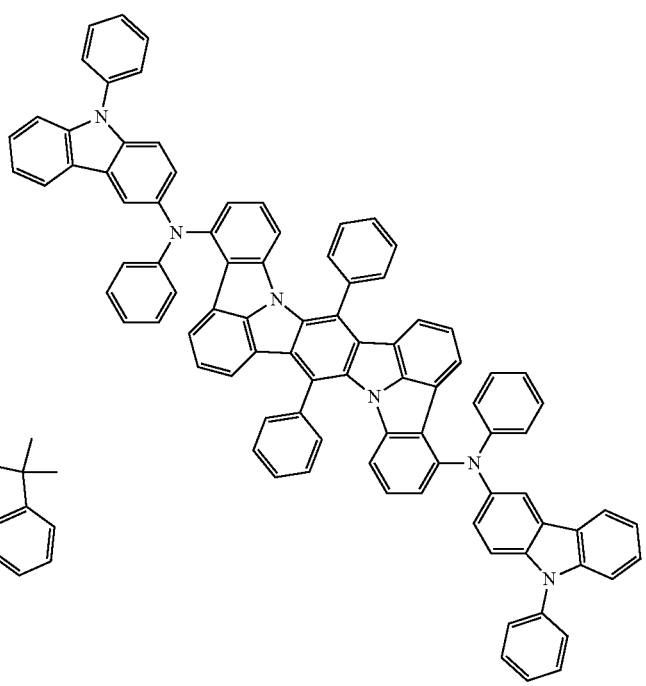

-continued
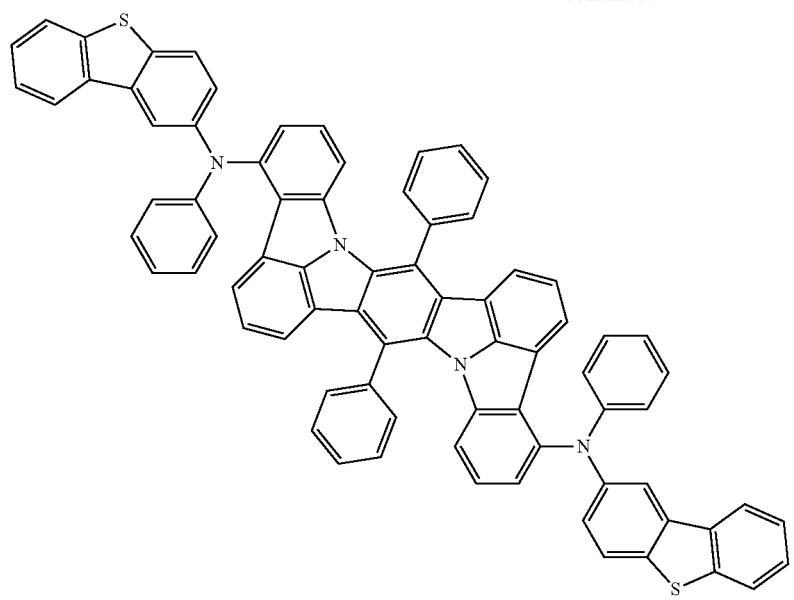
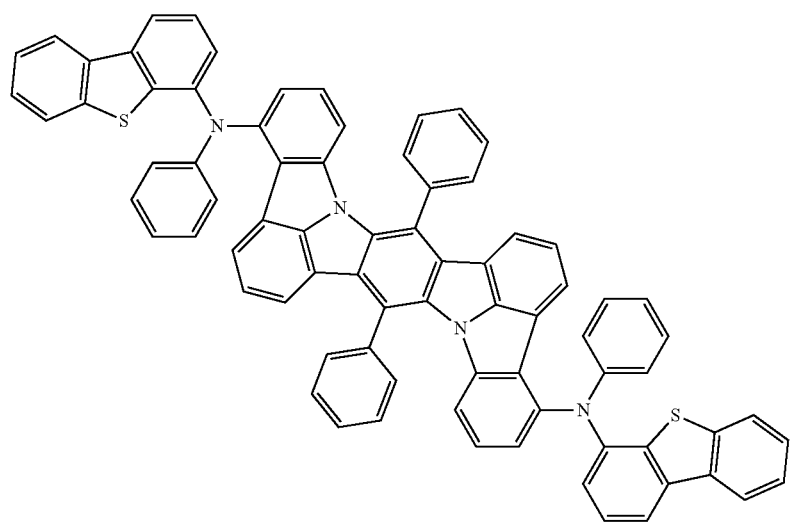

-continued
323
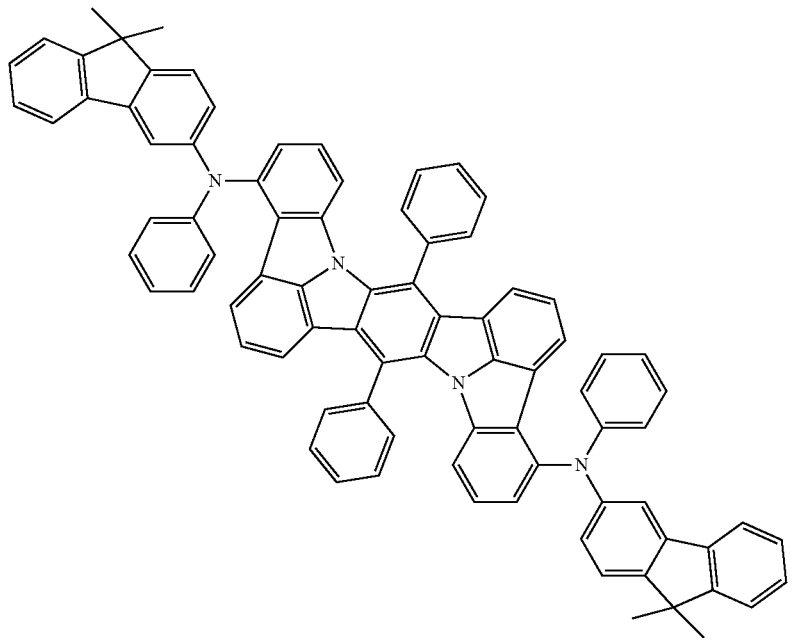
324
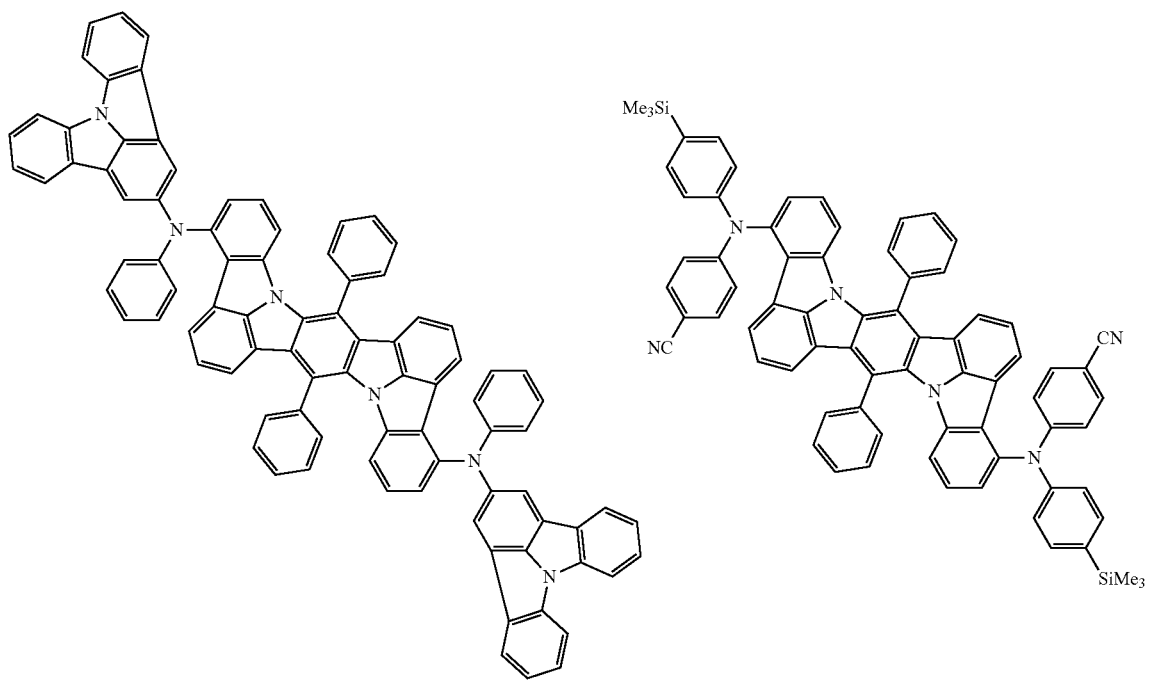 [SMILES: c1ccc(-c2c3c4cccc5c6c(N(c7ccccc7)c7cc8c9ccccc9n9c%10ccccc%10c(c7)c89)cccc6n(c3c(-c3ccccc3)c3c6cccc7c8c(N(c9ccccc9)c9cc%10c%11ccccc%11n%11c%12ccccc%12c(c9)c%10%11)cccc8n(c23)c76)c54)cc1 ; C[Si](C)(C)c1ccc(N(c2ccc(C#N)cc2)c2cccc3c2c2cccc4c5c(-c6ccccc6)c6c(c(-c7ccccc7)c5n3c24)c2cccc3c4c(N(c5ccc(C#N)cc5)c5ccc([Si](C)(C)C)cc5)cccc4n6c32)cc1]
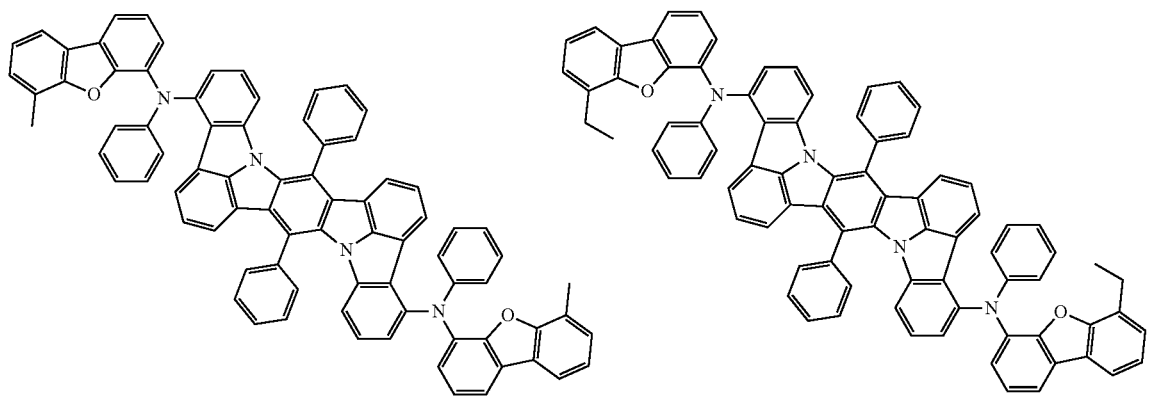

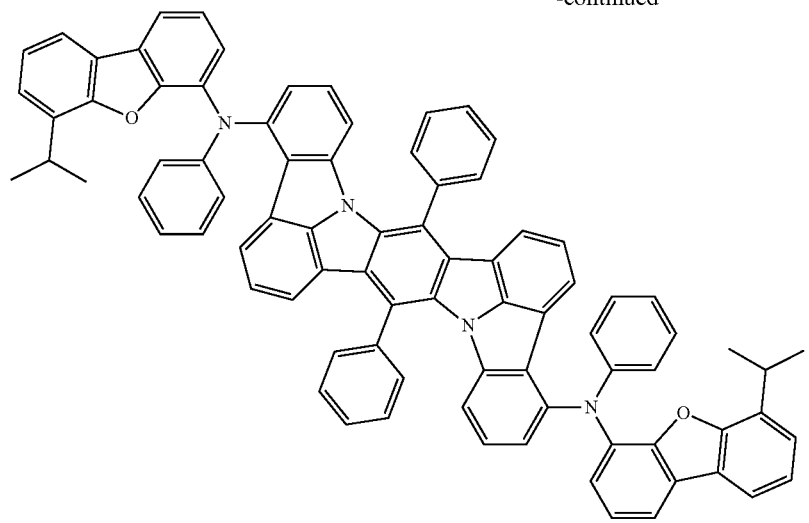
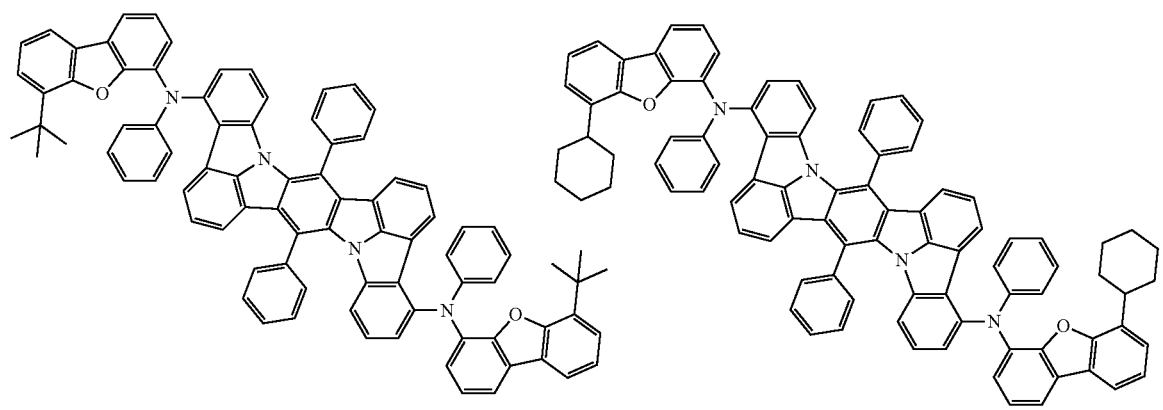
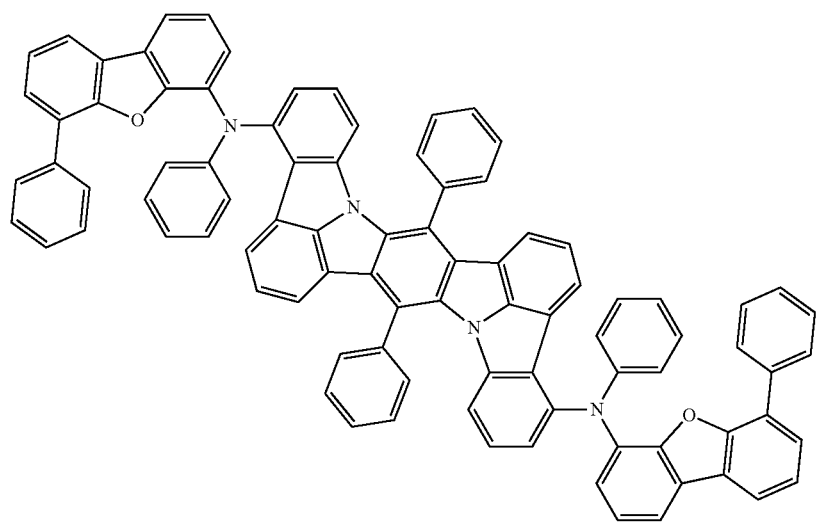

-continued
327
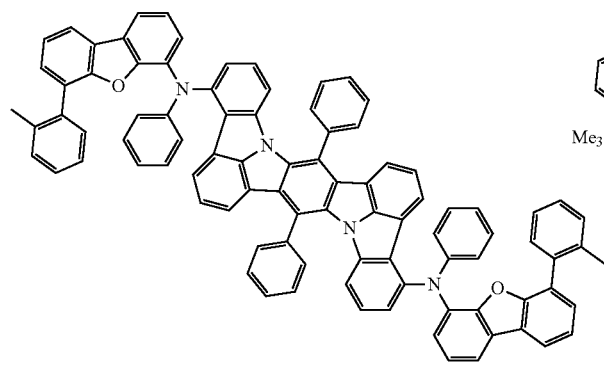
328
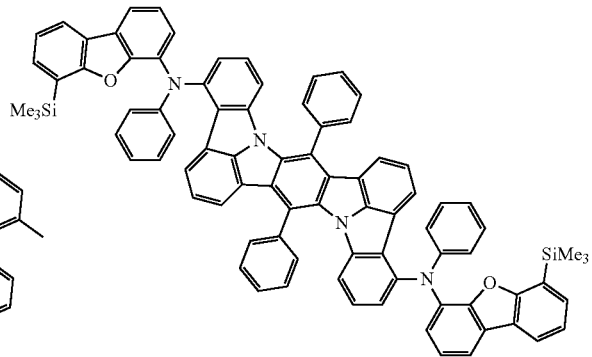
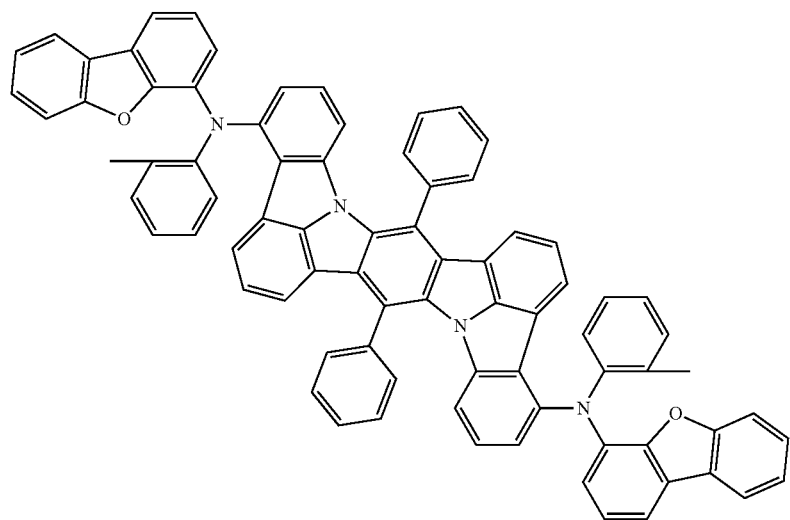
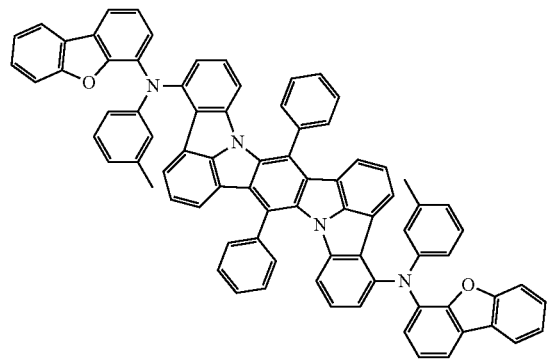
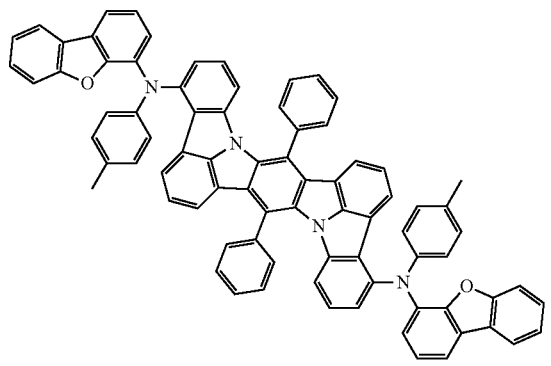

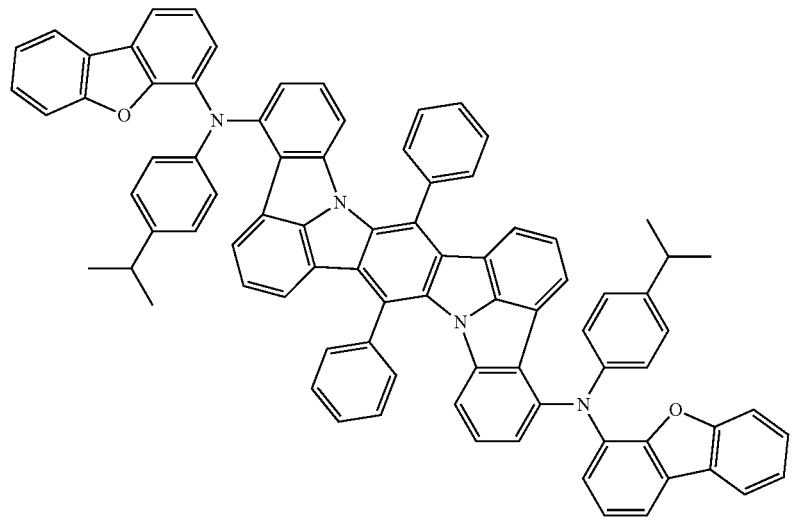
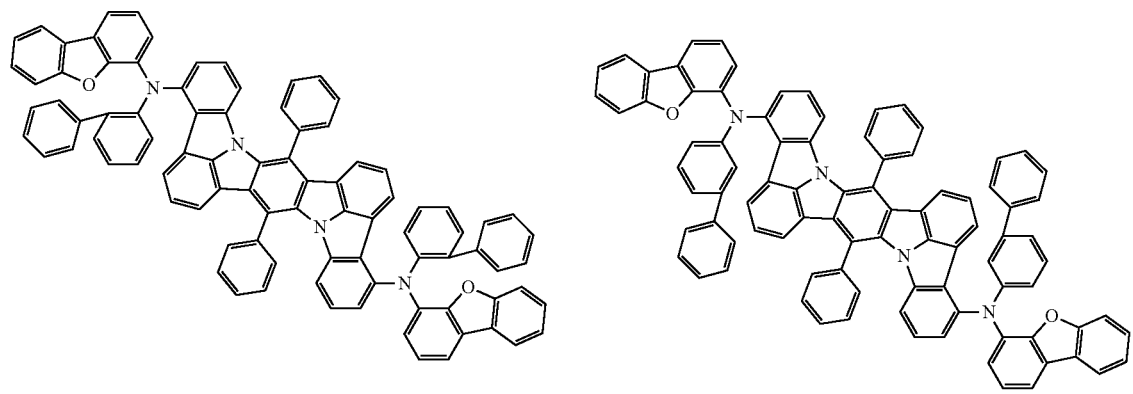
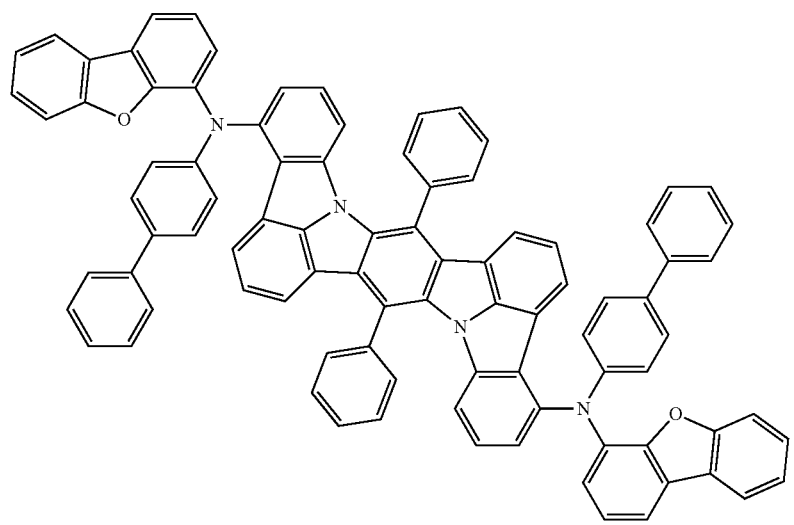

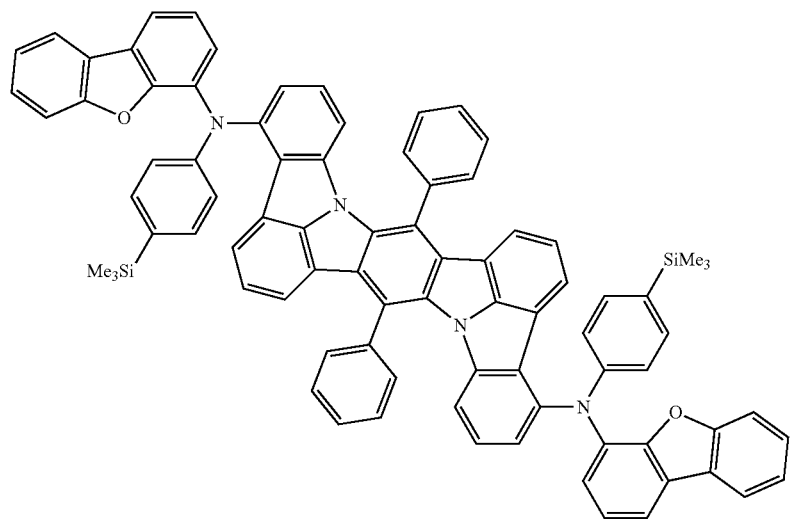
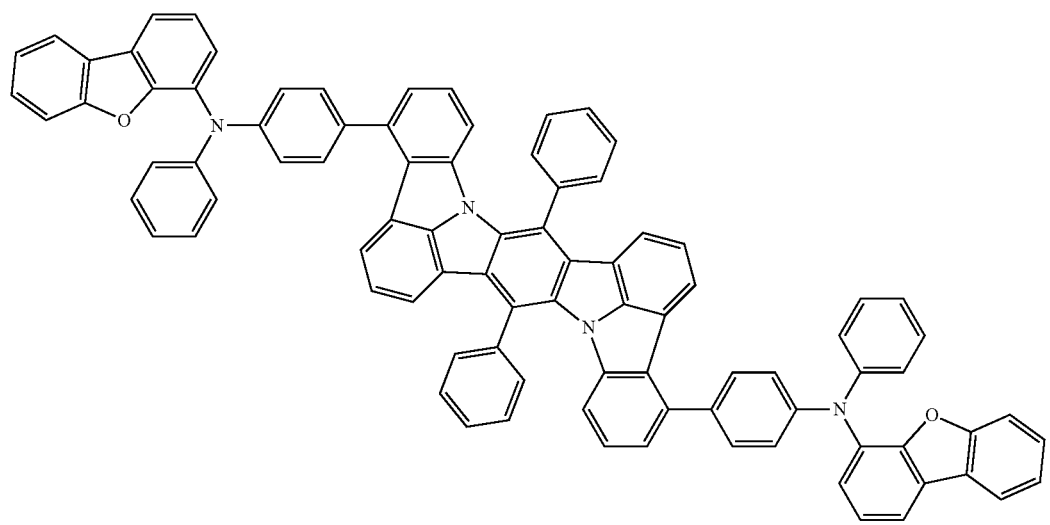
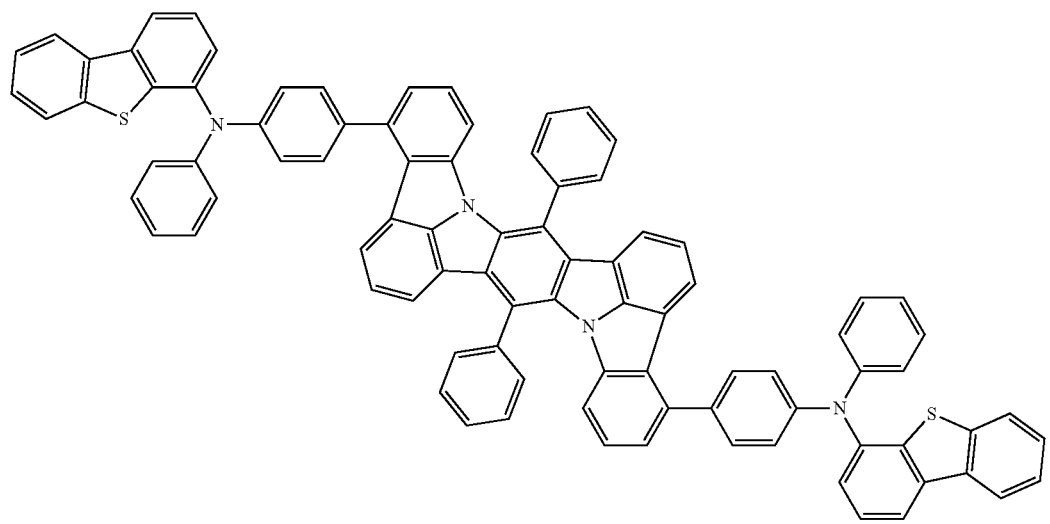

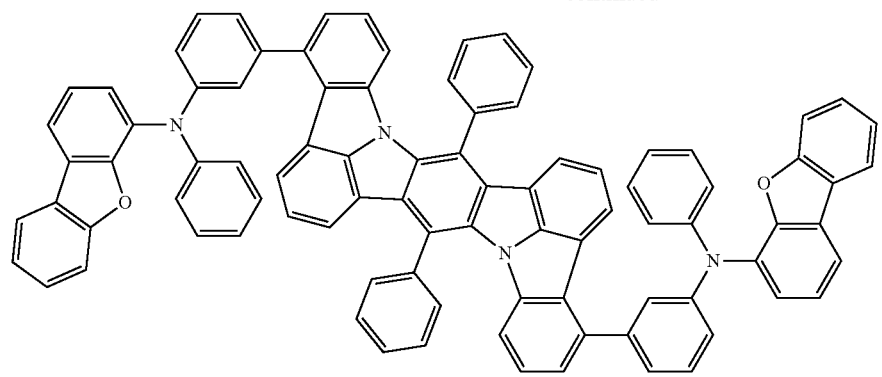
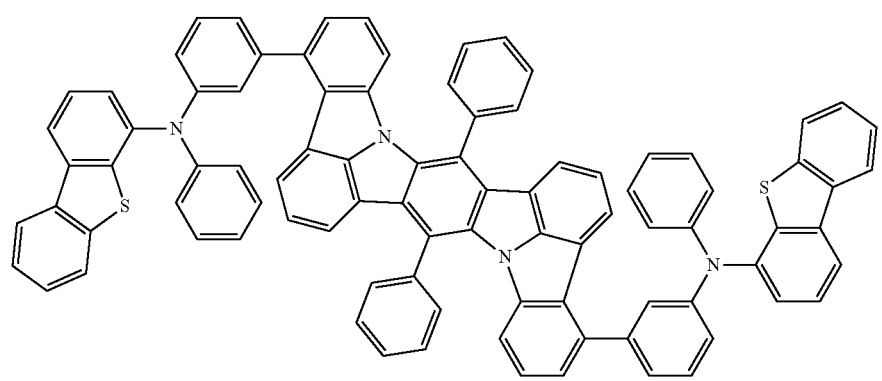
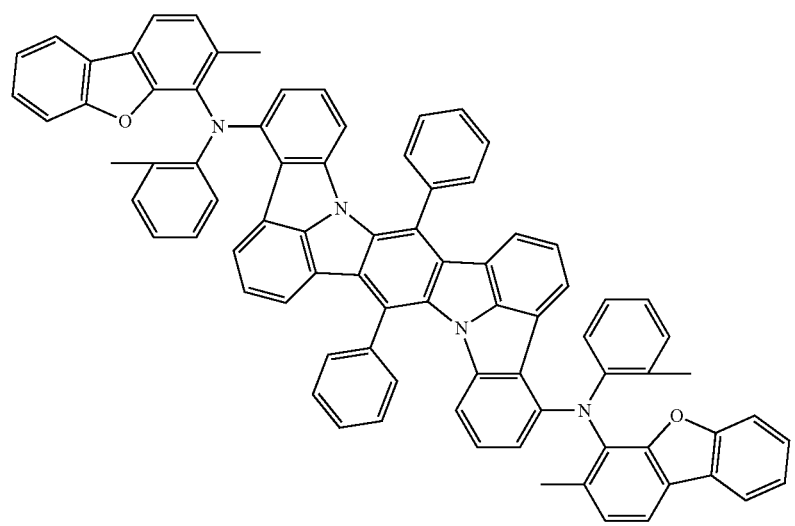

-continued
335
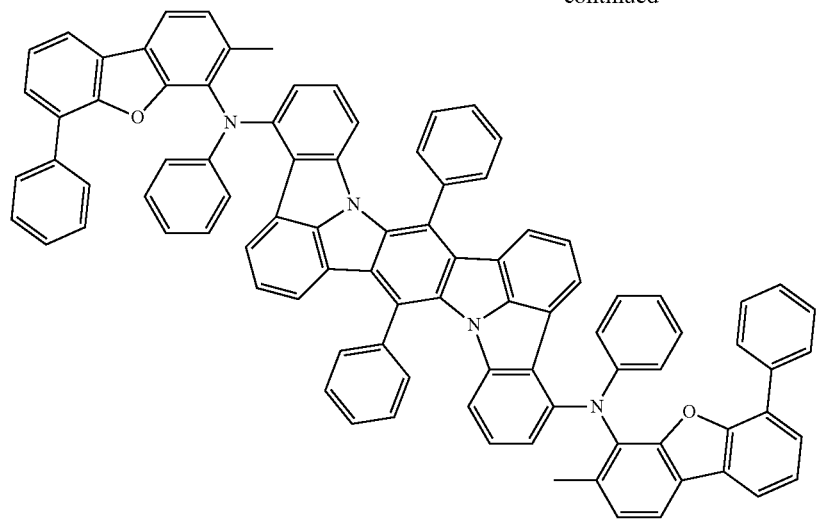
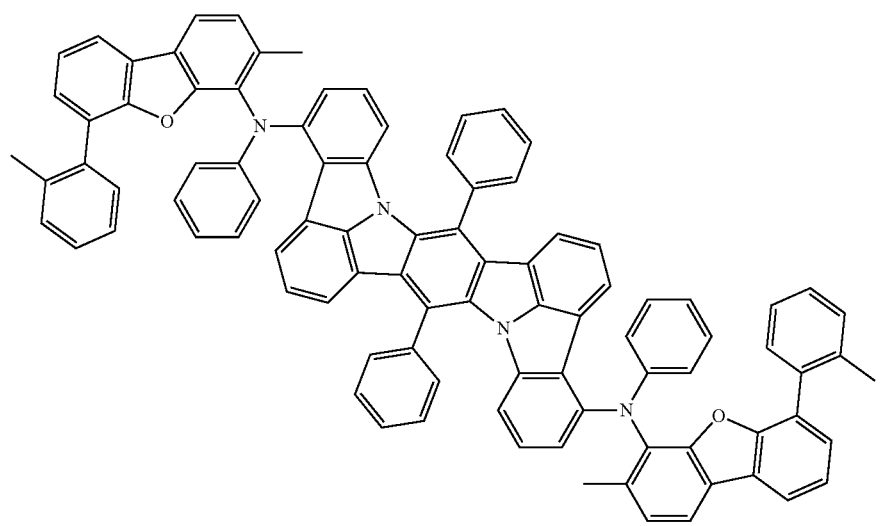
336
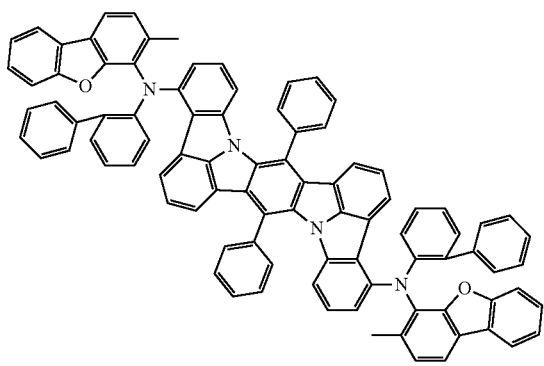

-continued
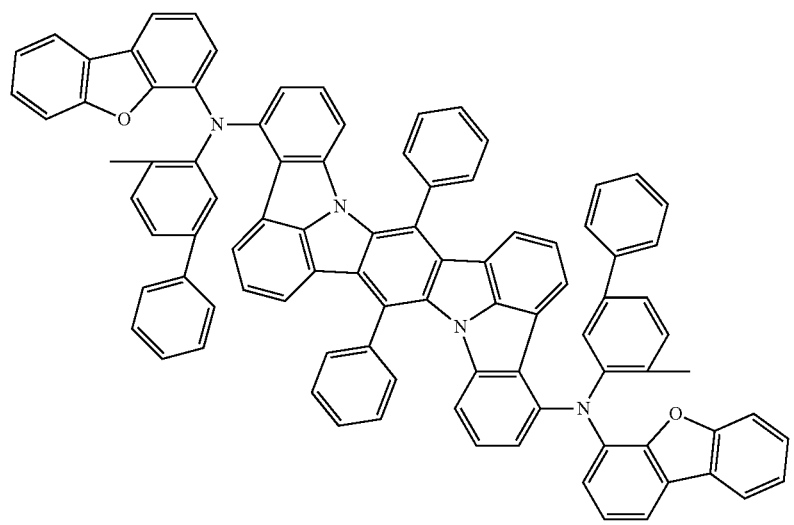
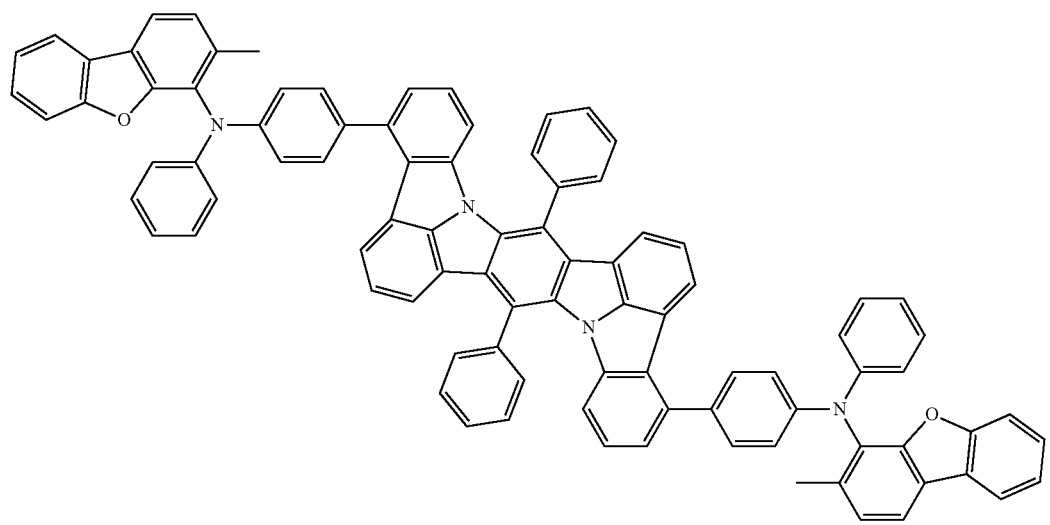
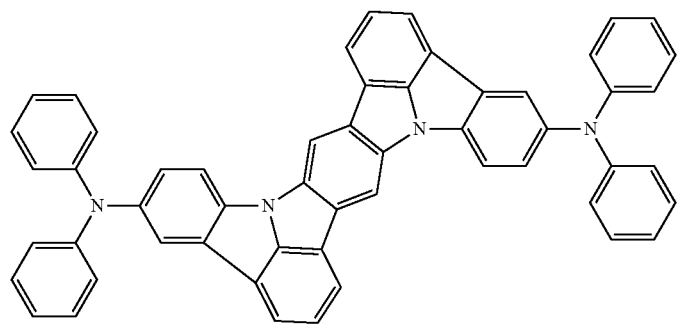
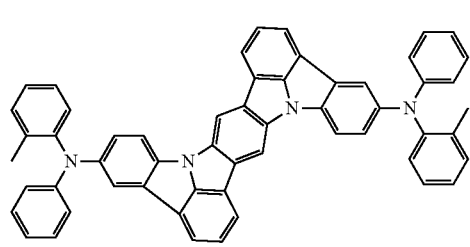
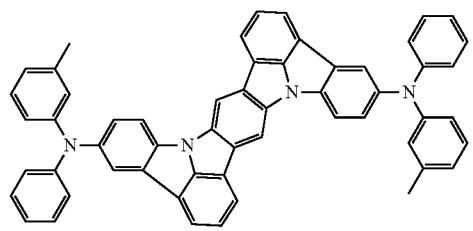

-continued
| 339 | 340 |
|---|---|
| 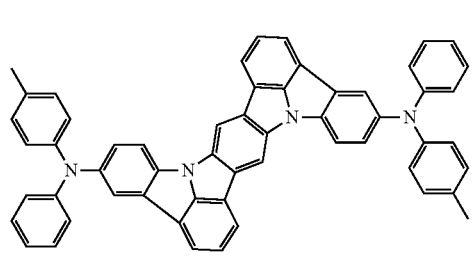 | 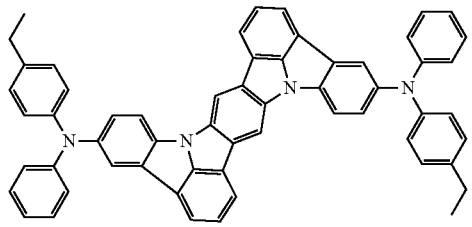 |
| 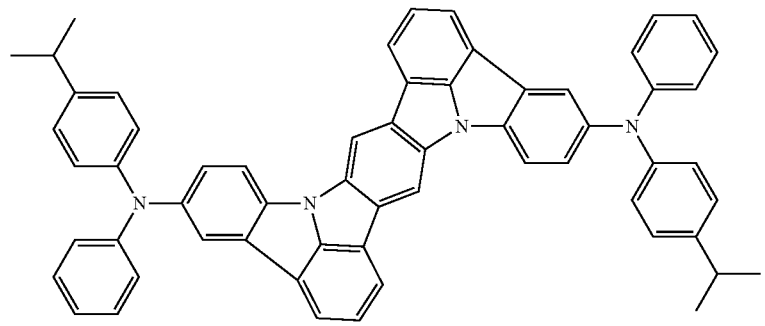 | 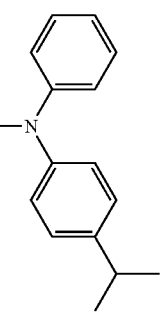 |
| 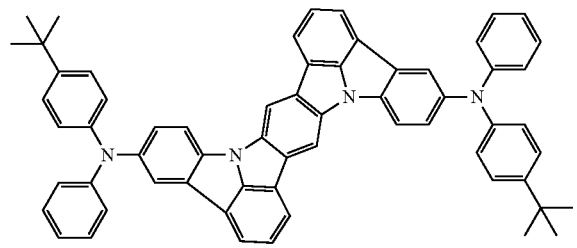 | 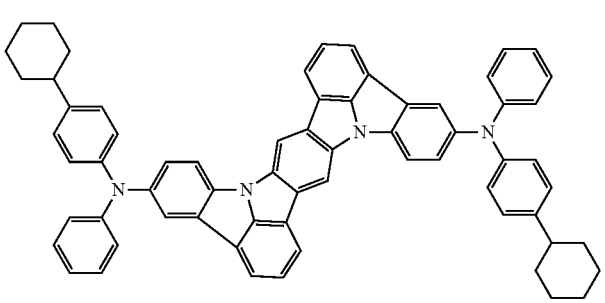 |
| 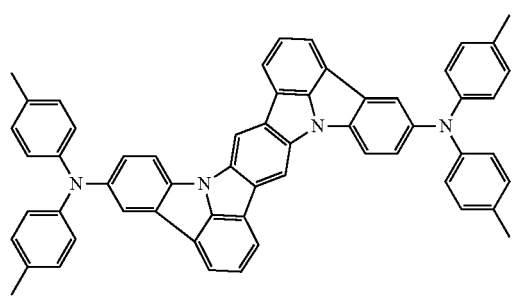 | 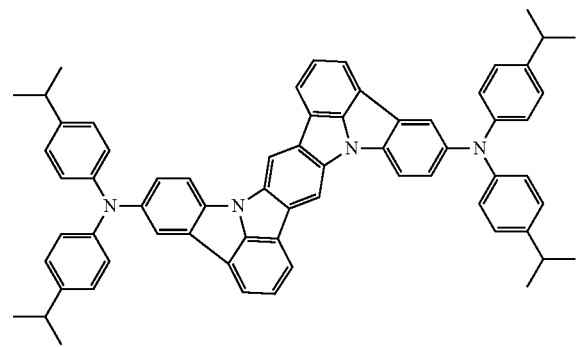 |
| 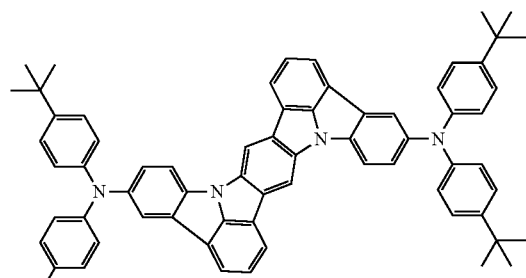 | 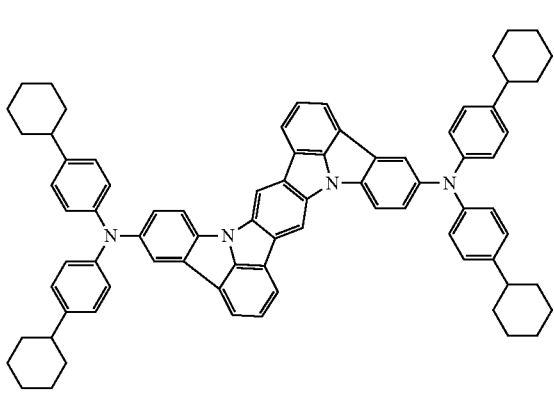 |

-continued
| 341 | 342 |
|---|---|
| 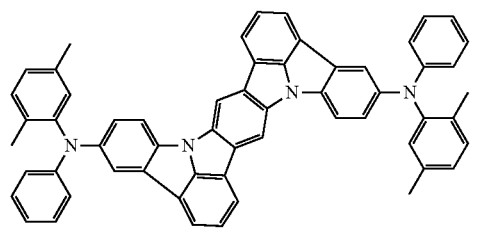 | 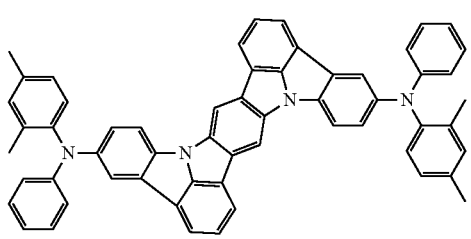 |
| 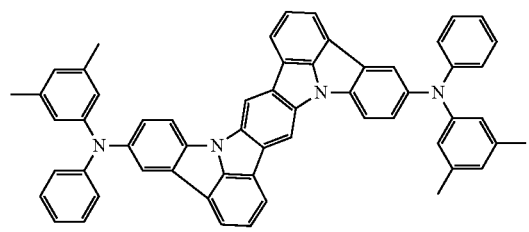 | 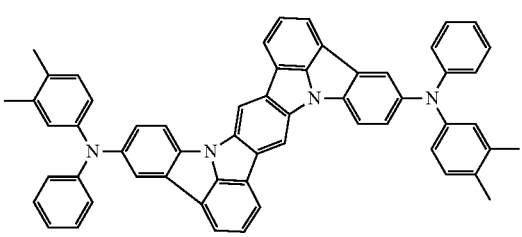 |
| 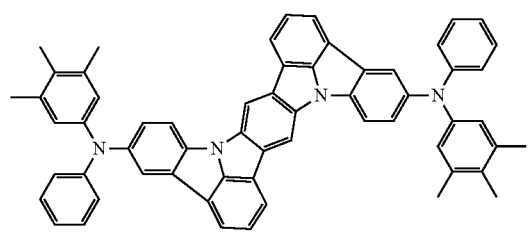 | 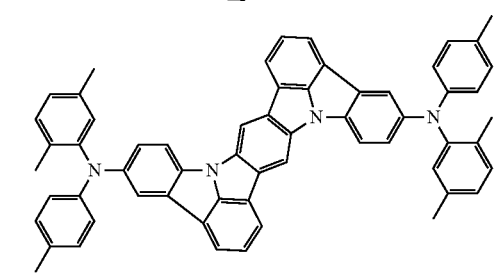 |
| 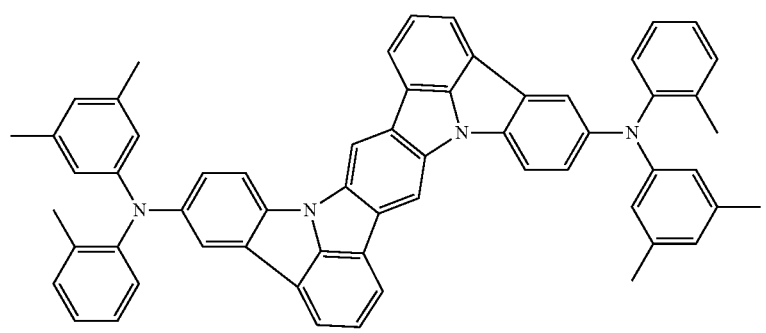 | |
| 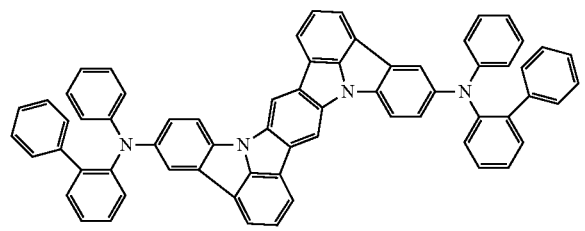 | 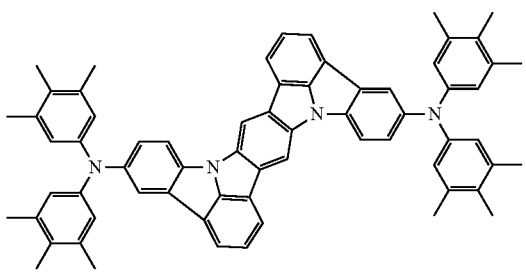 |
| 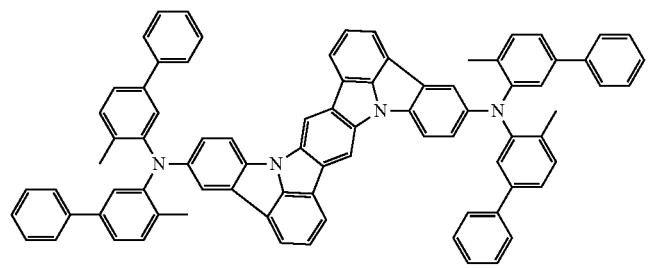 | 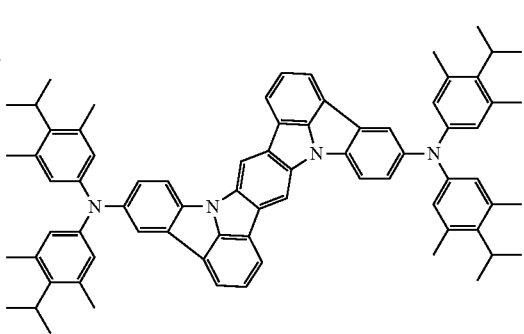 |

343
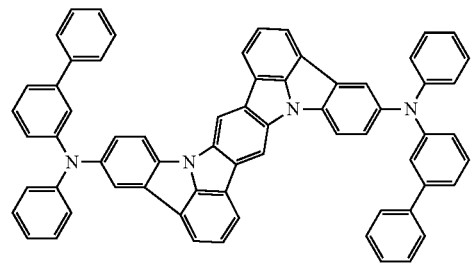
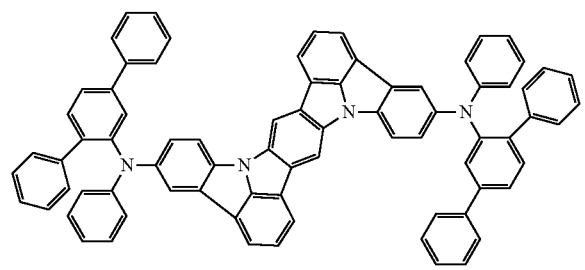
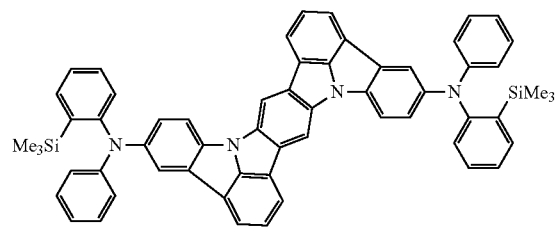
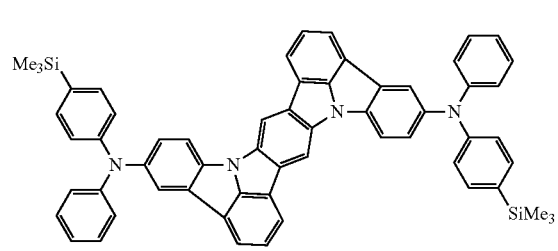
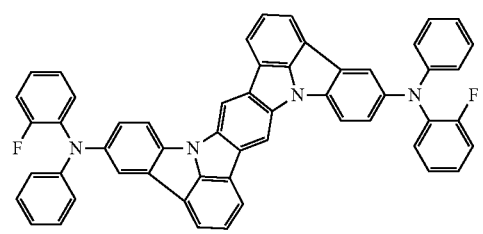
344
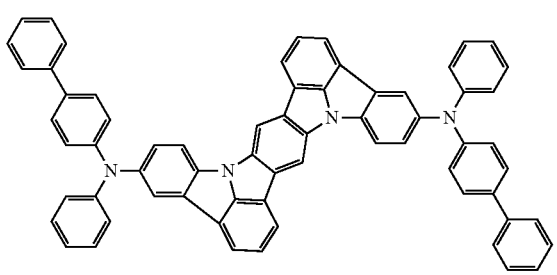
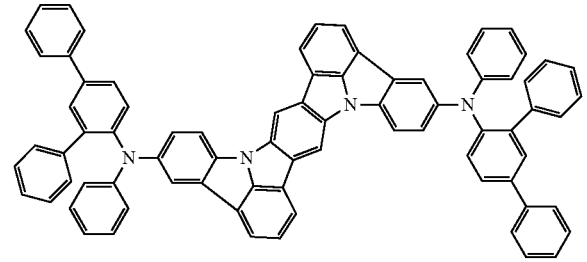
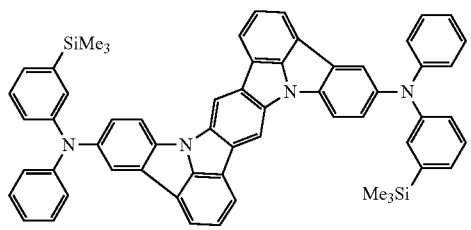
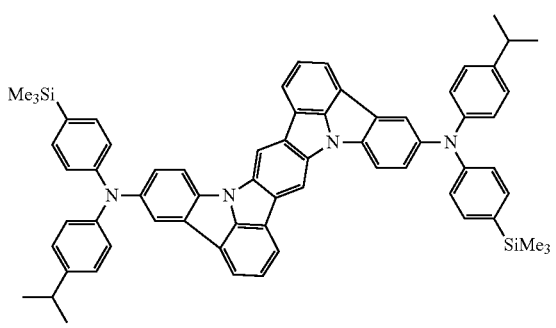
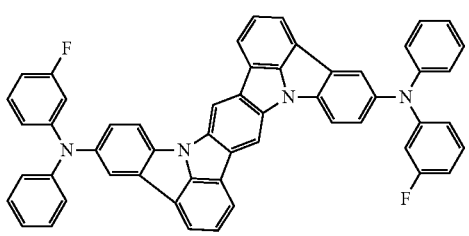

345 346
-continued
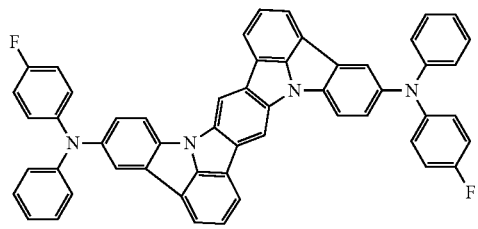 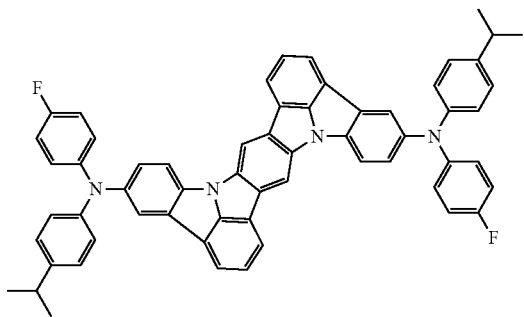
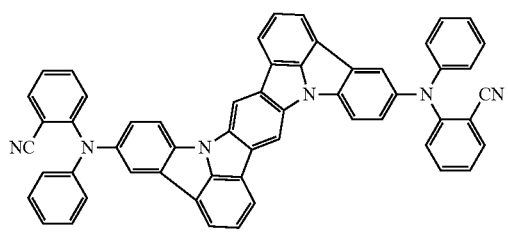 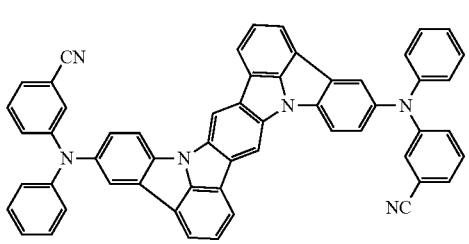
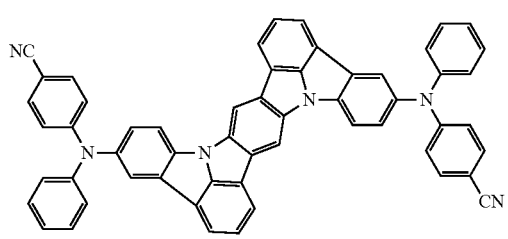 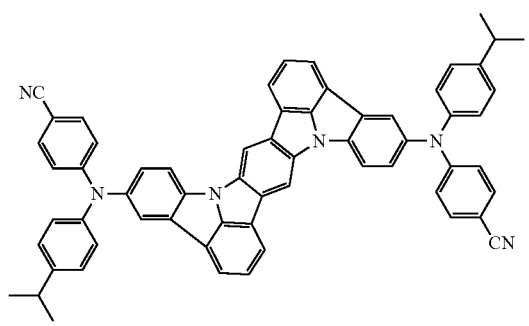
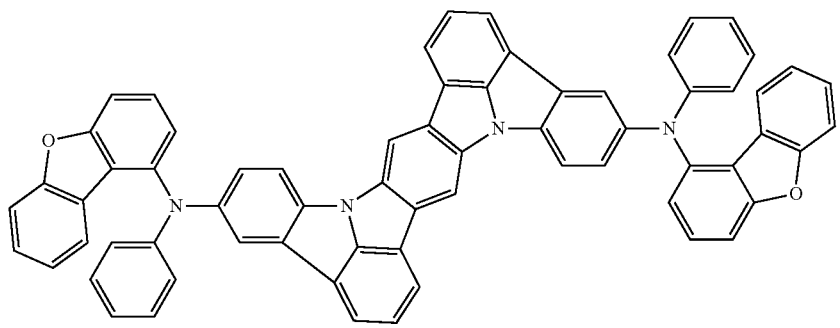
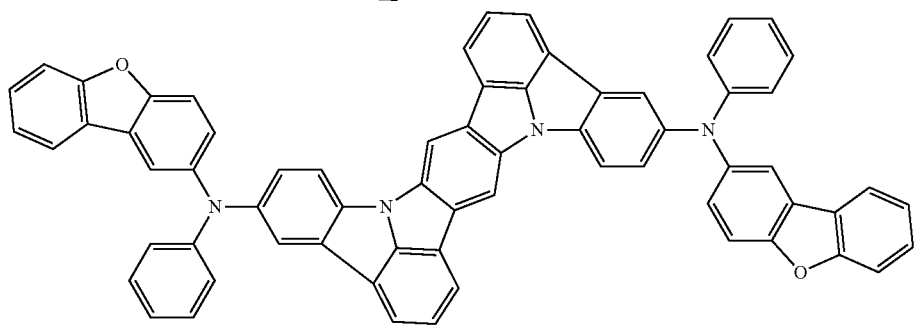

-continued
347 348
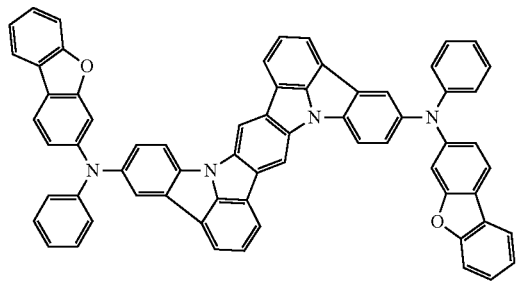
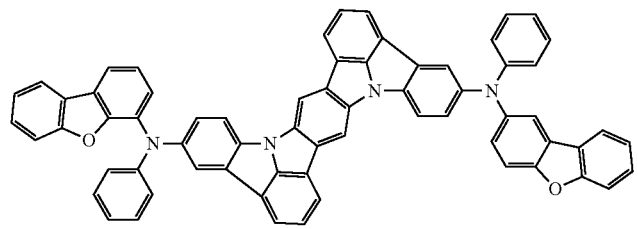
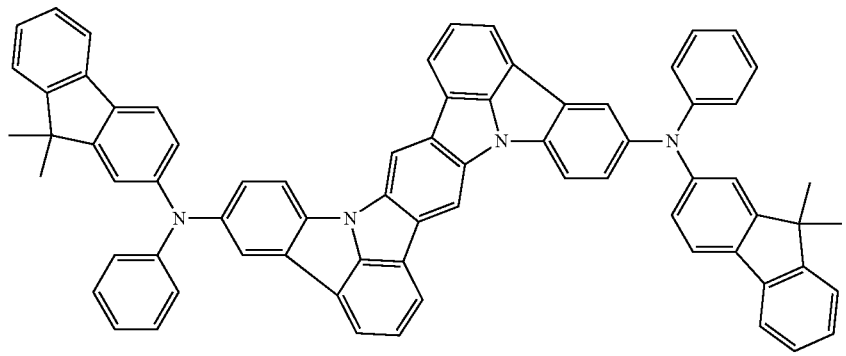
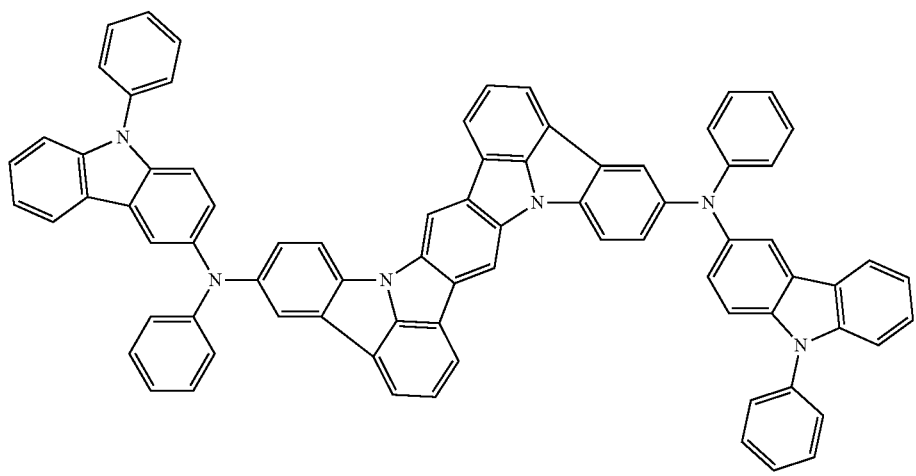
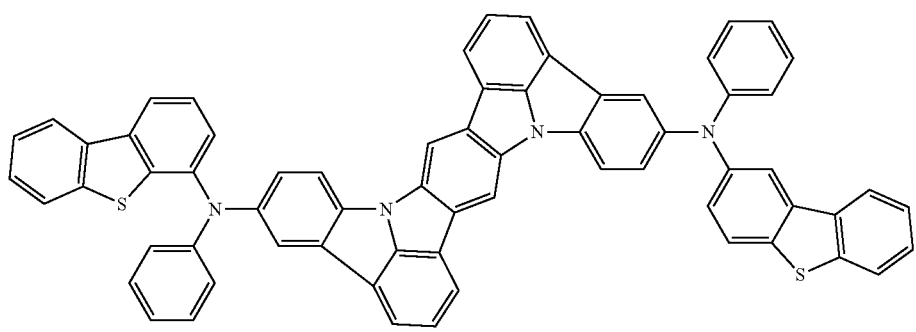

-continued
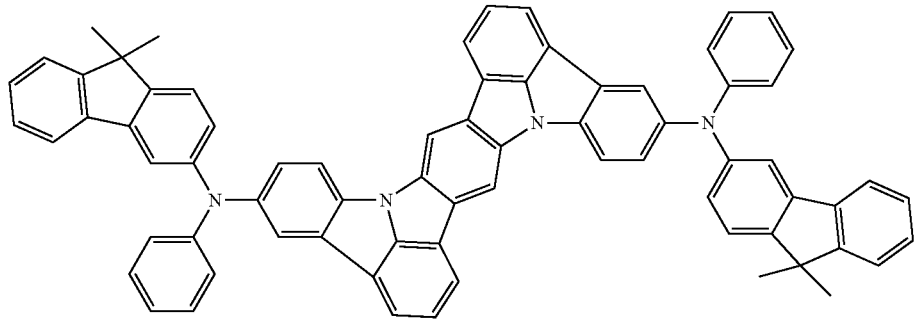
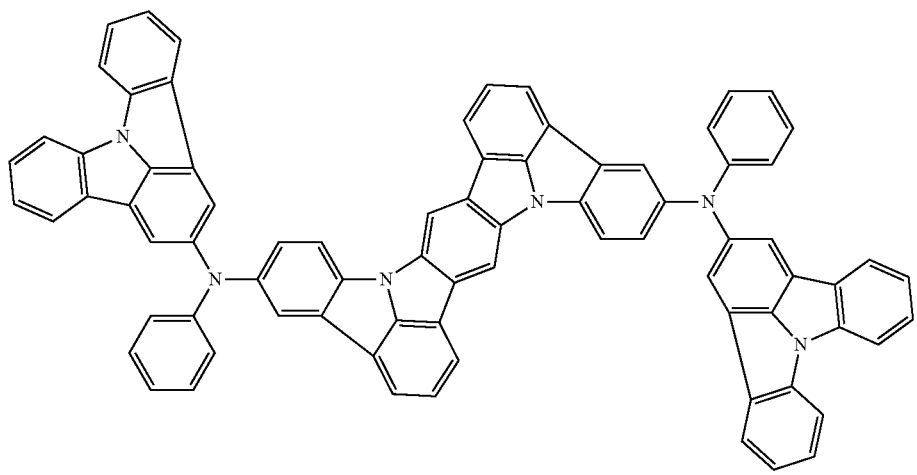
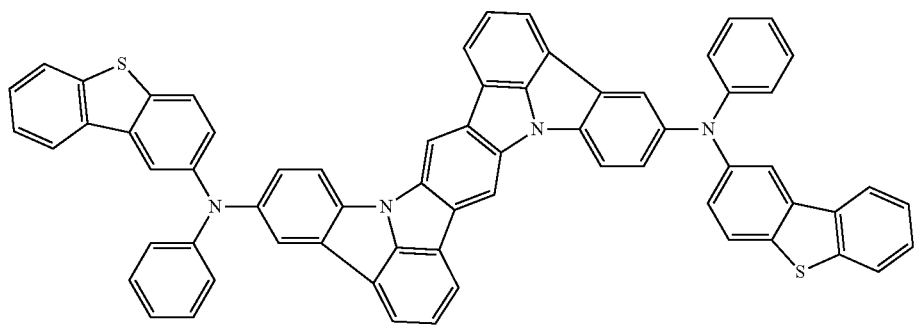
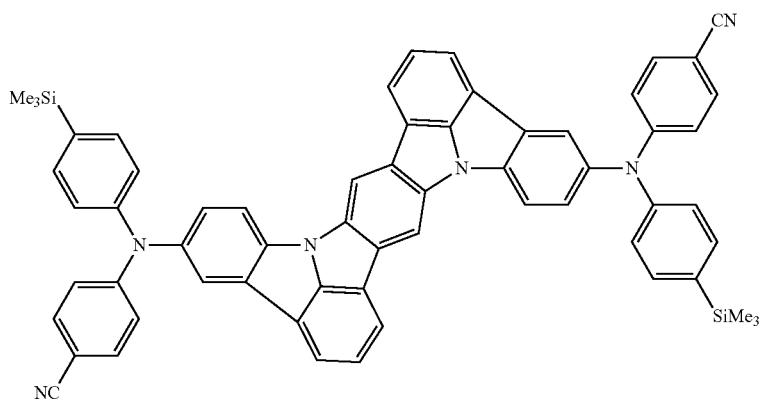

-continued
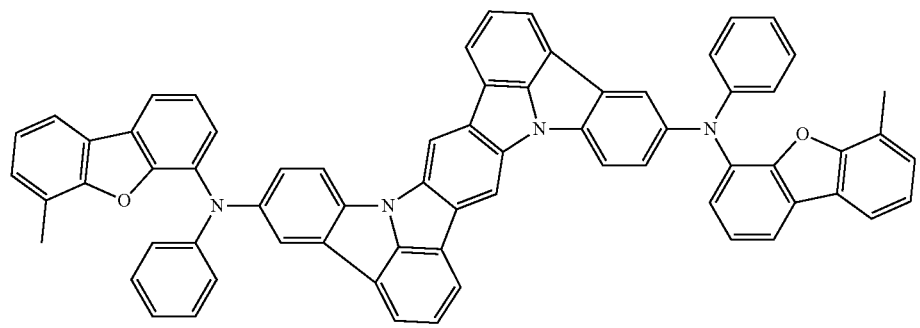
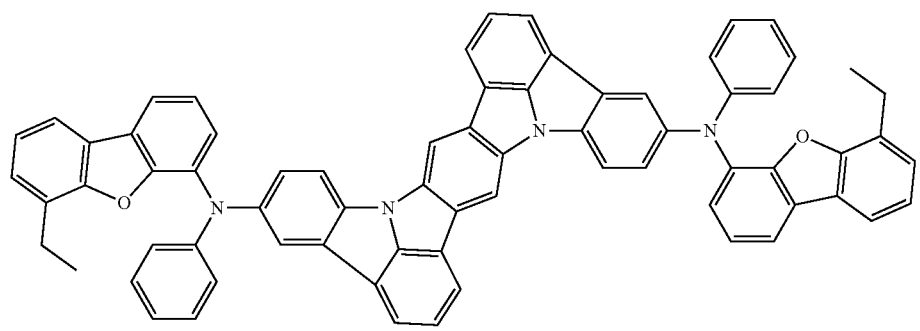
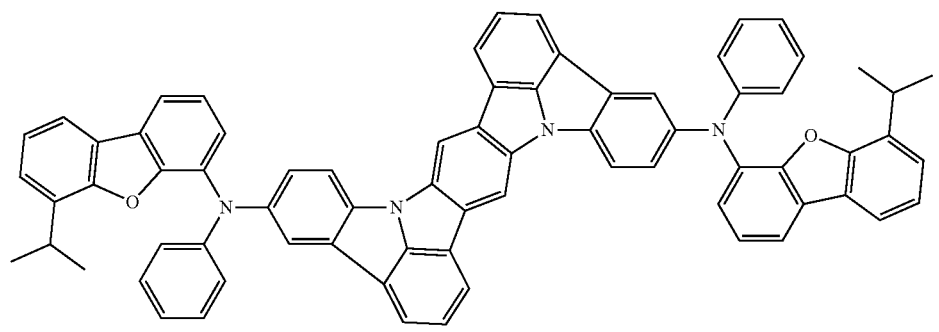
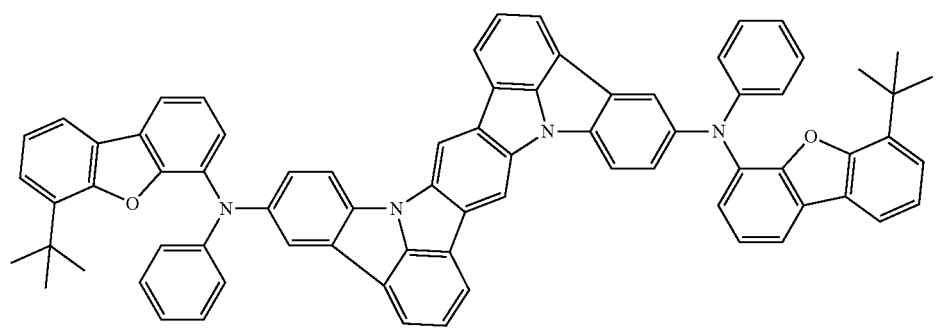
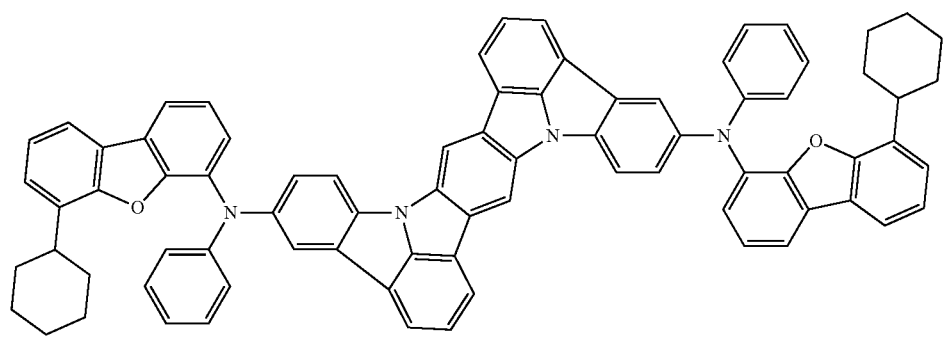

-continued
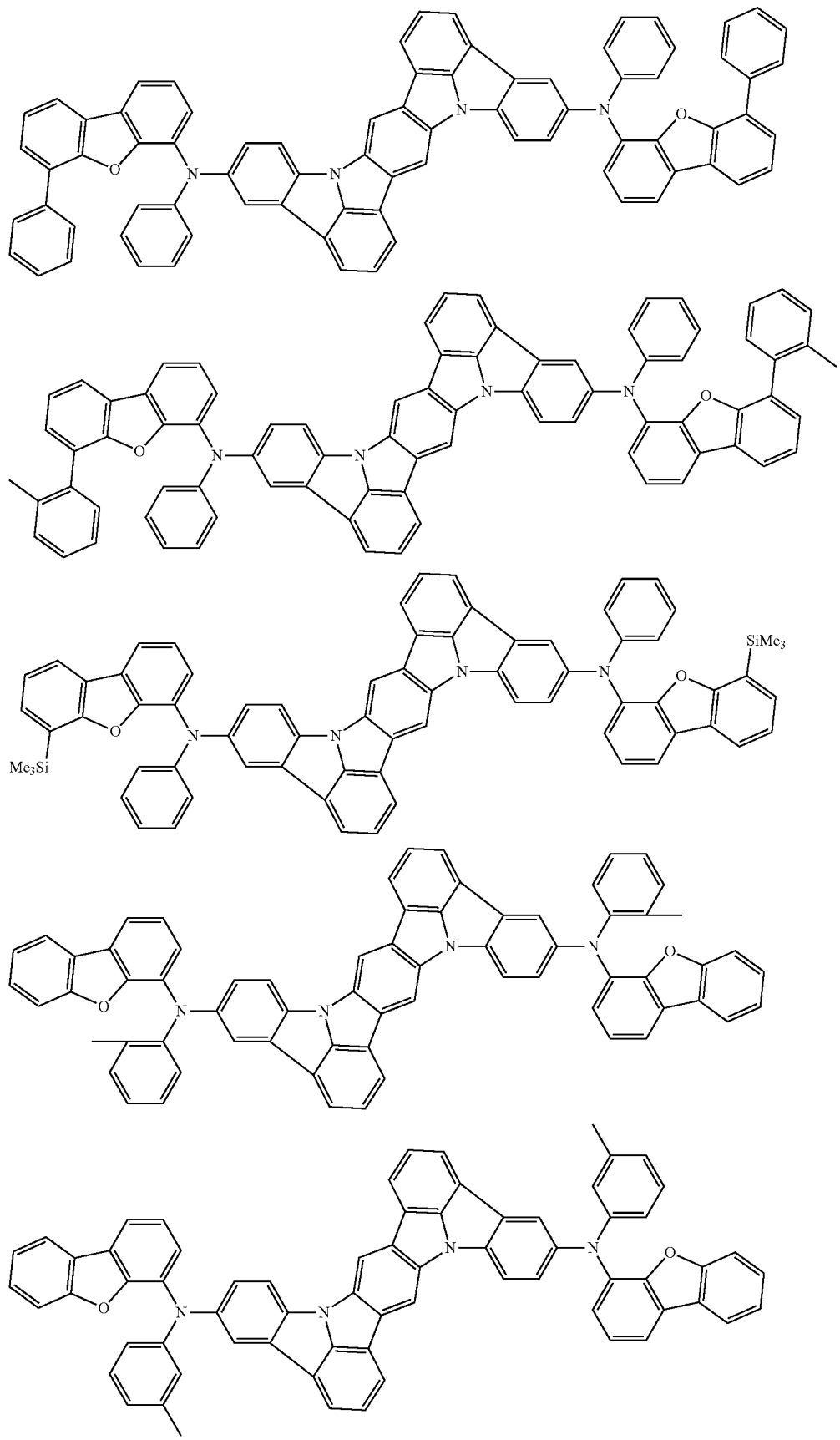

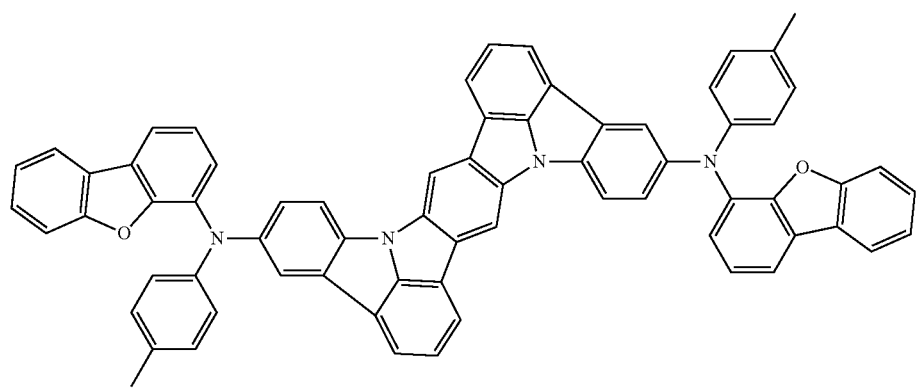
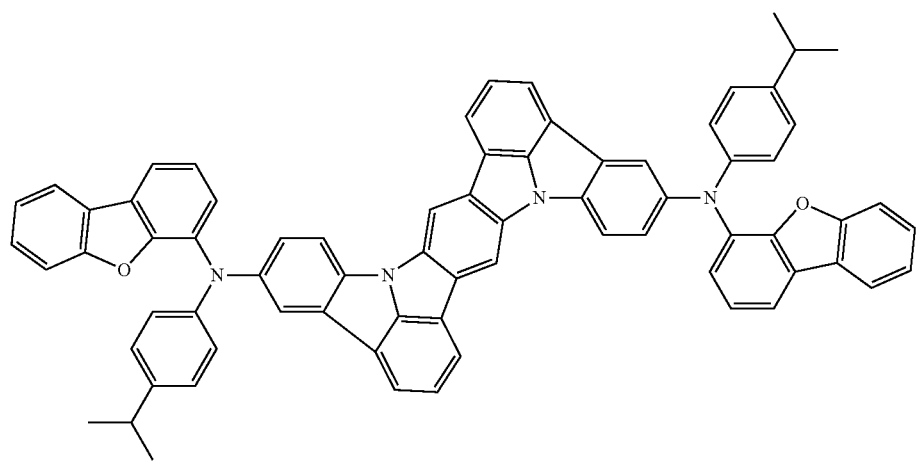
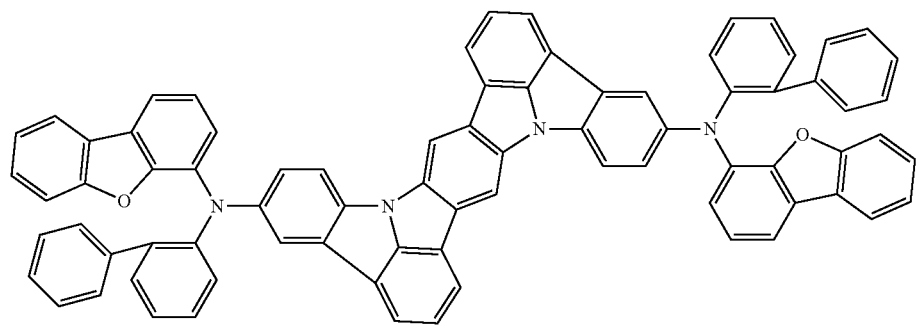
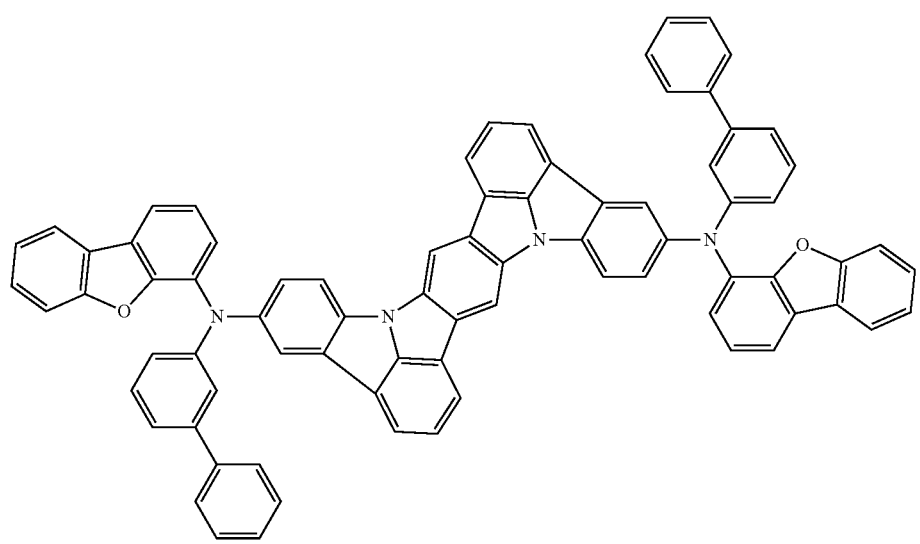

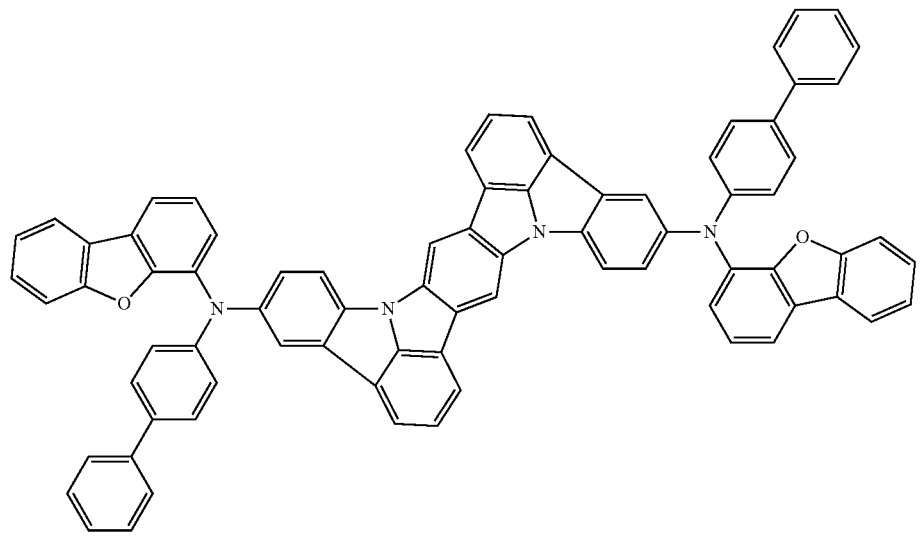
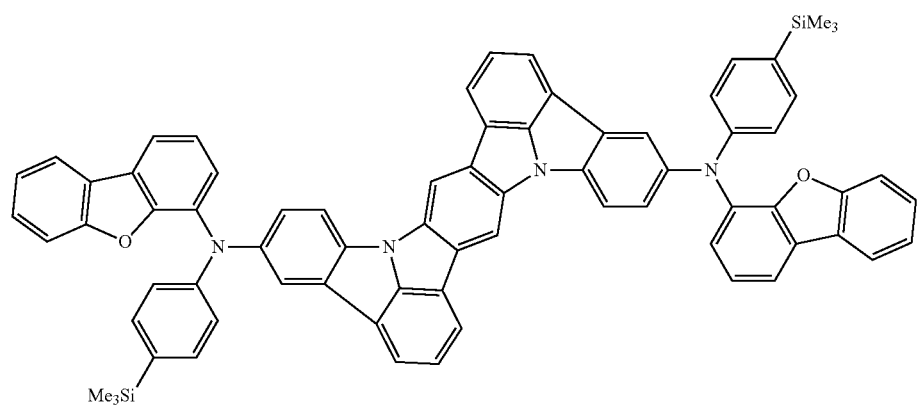
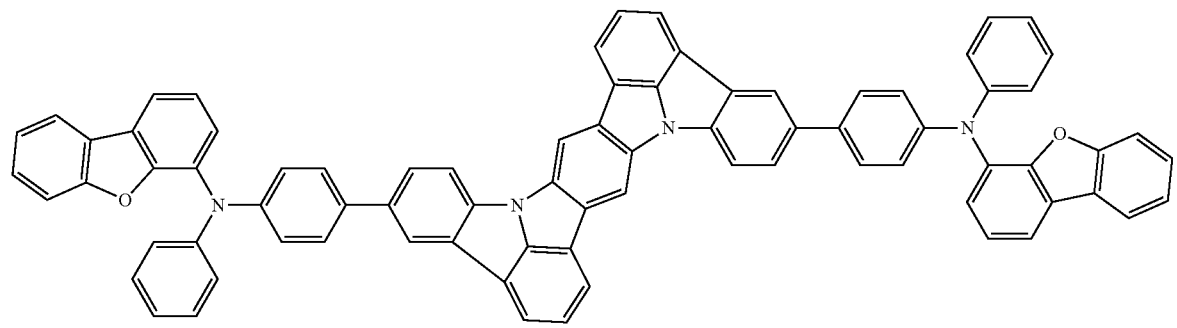
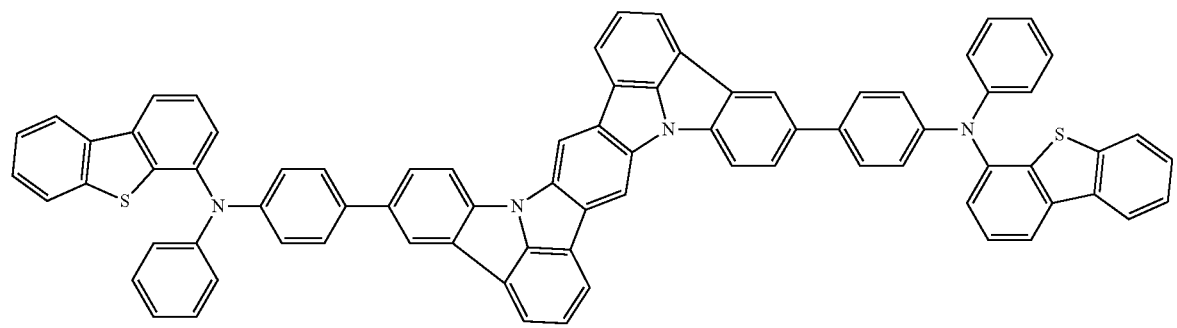

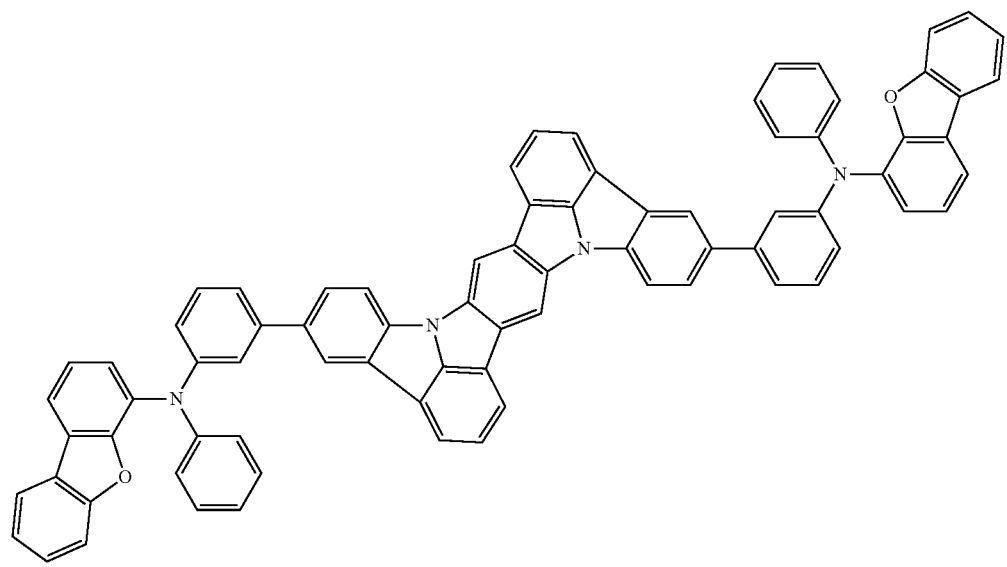
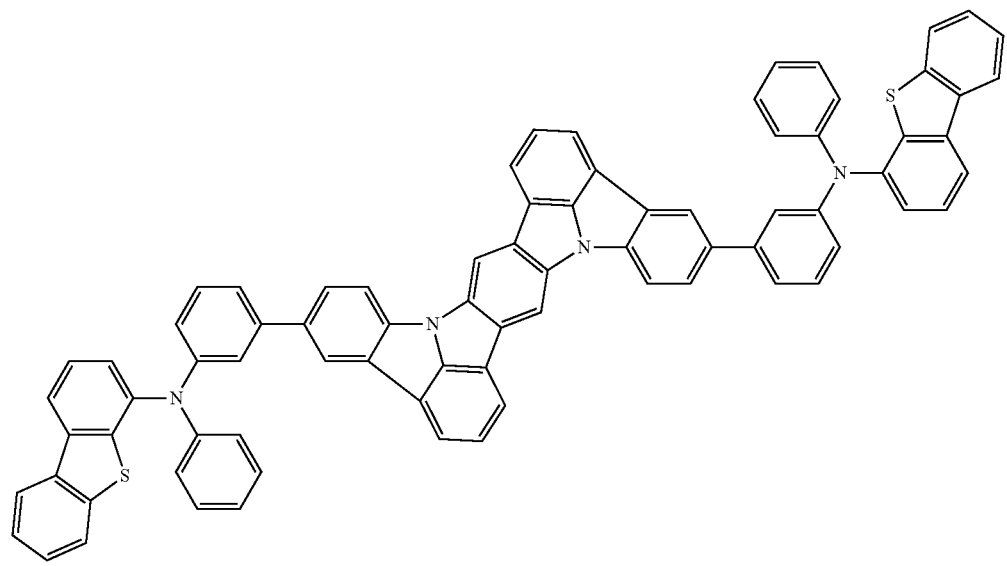
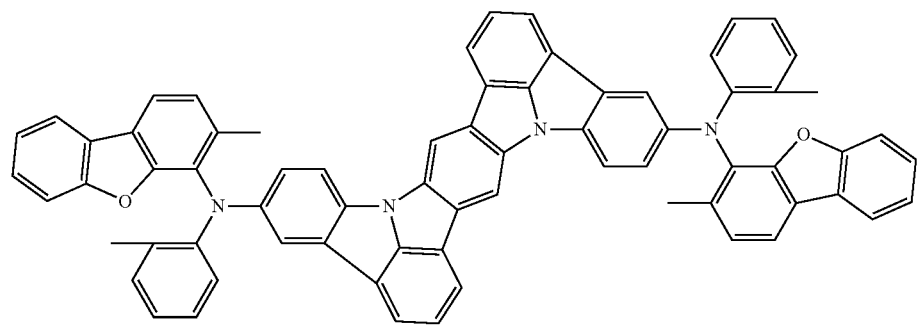

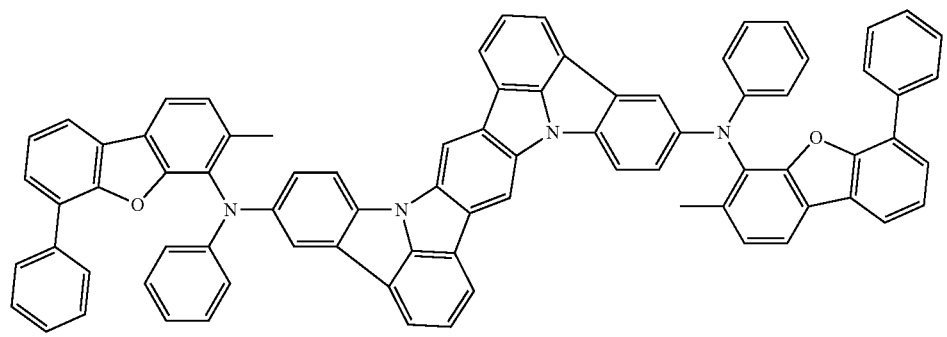
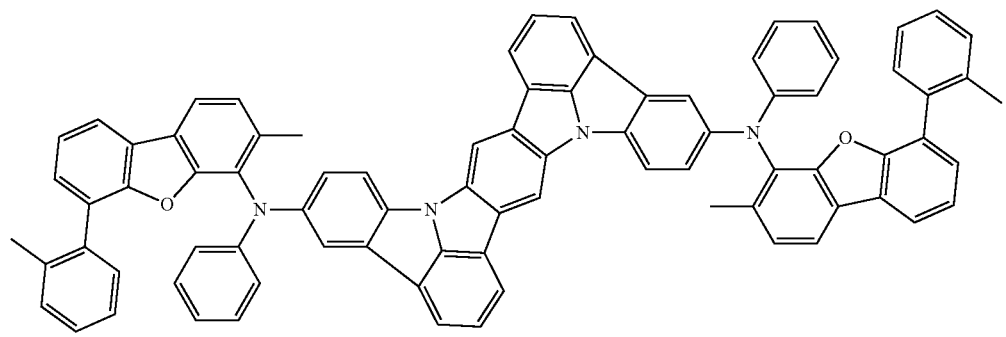
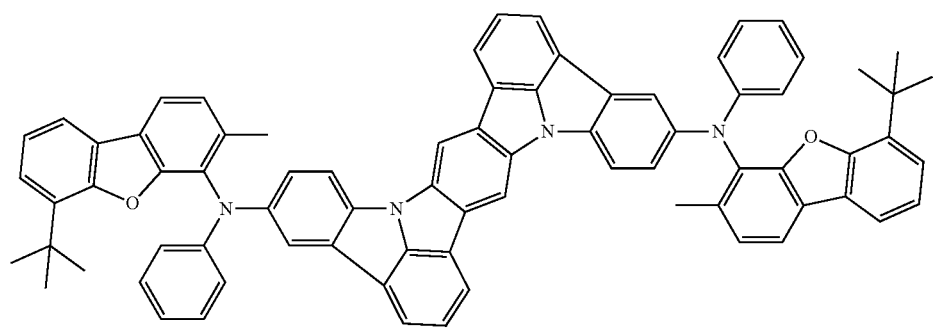
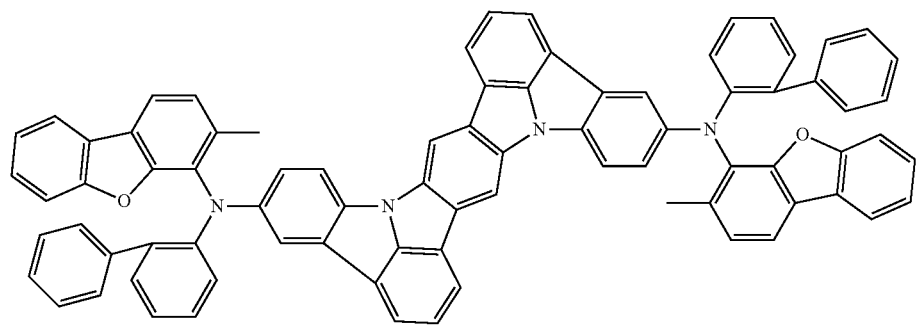

-continued
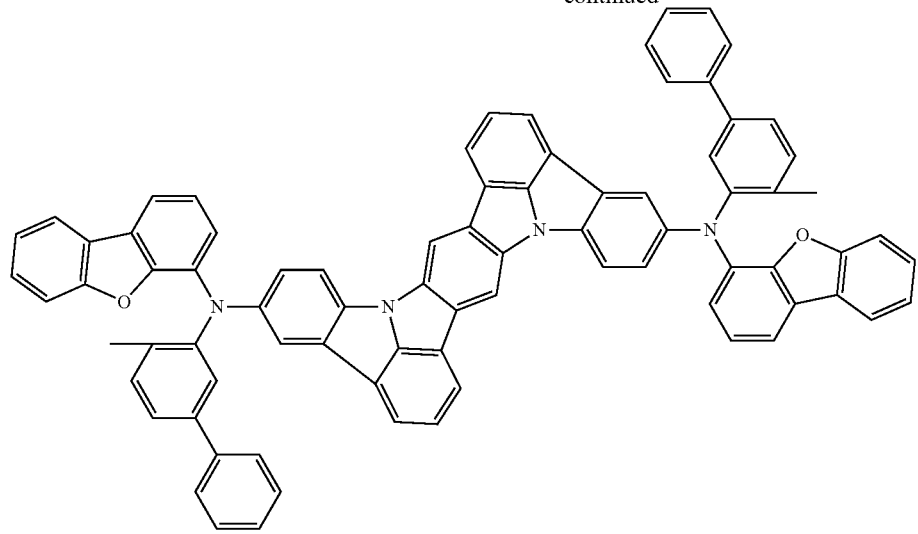
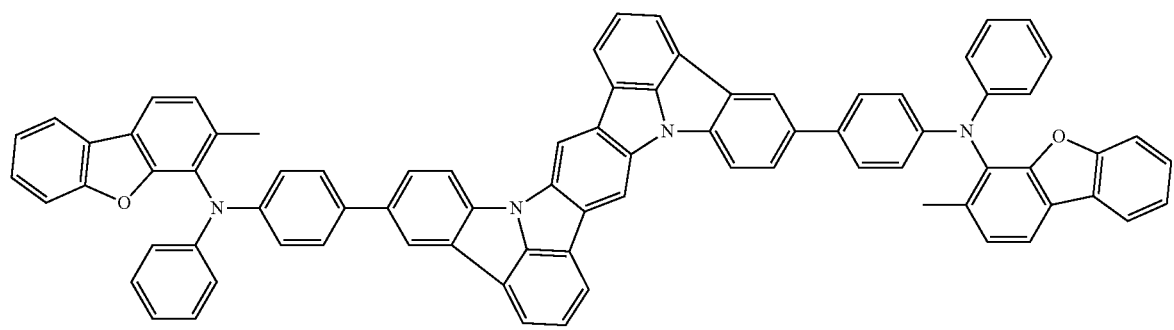
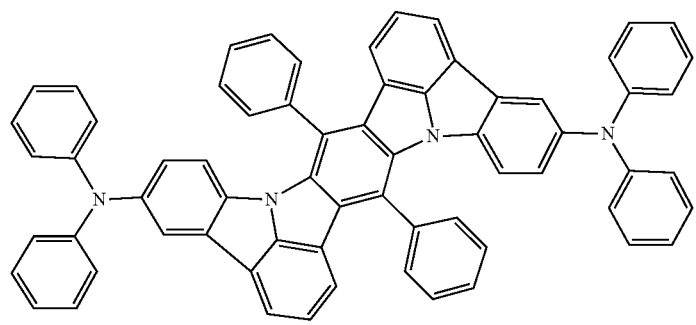
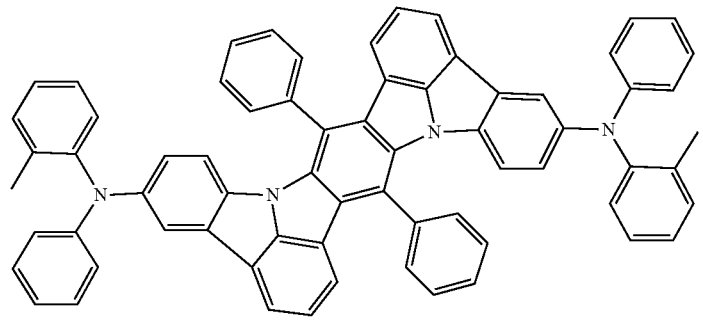

-continued
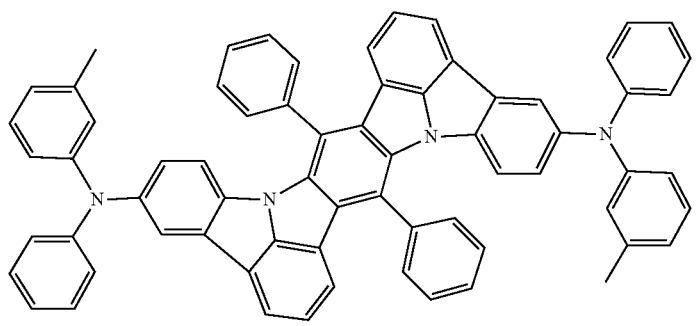
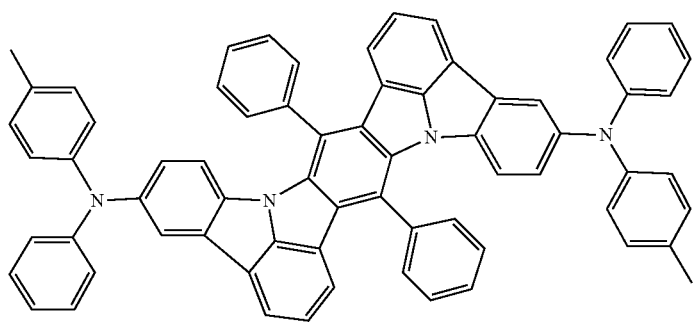
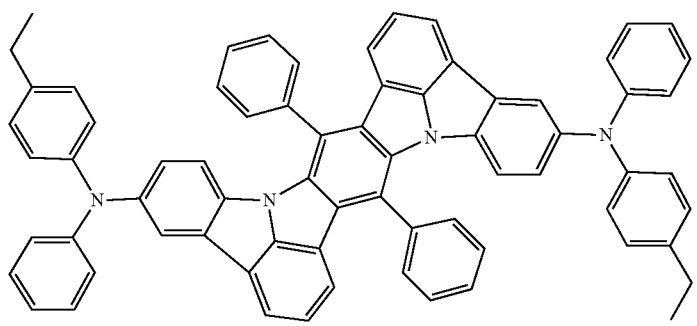
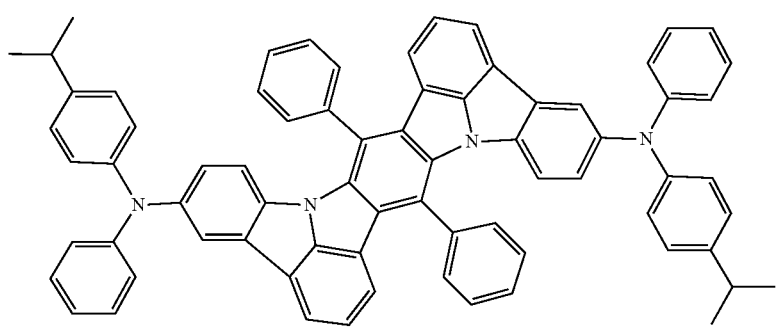
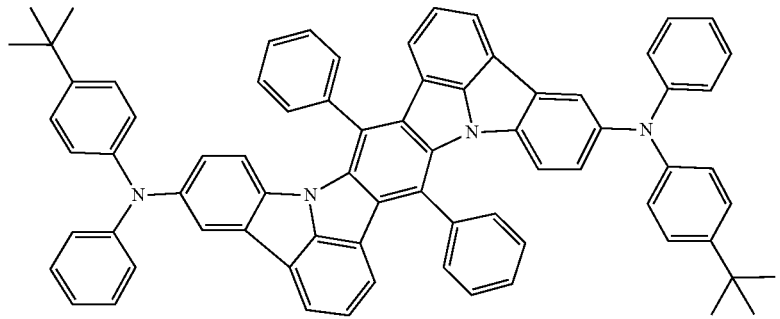

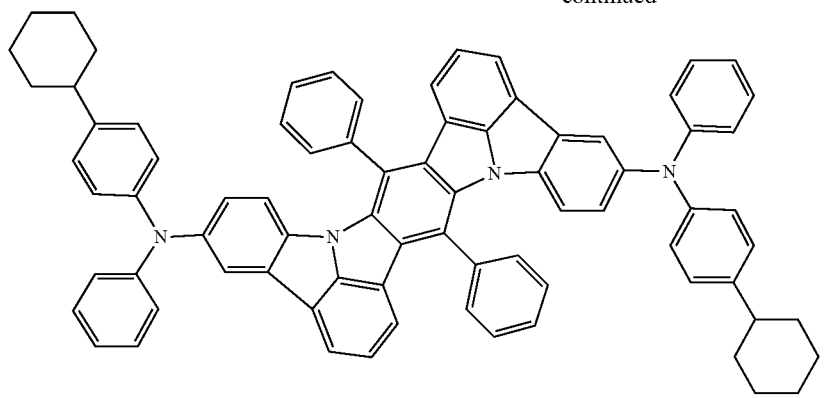
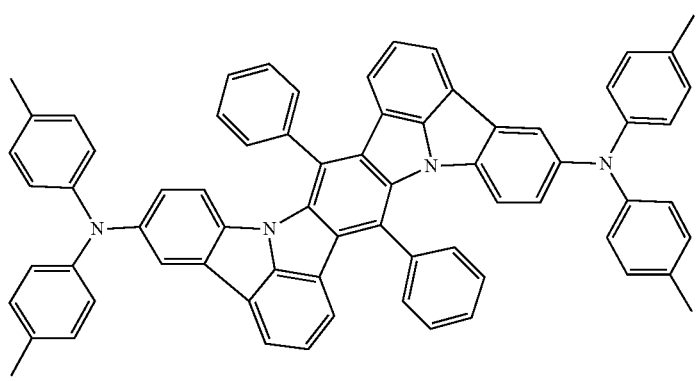
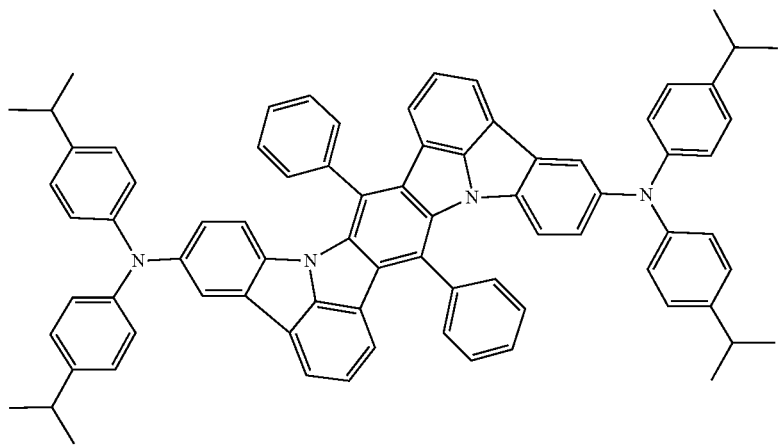
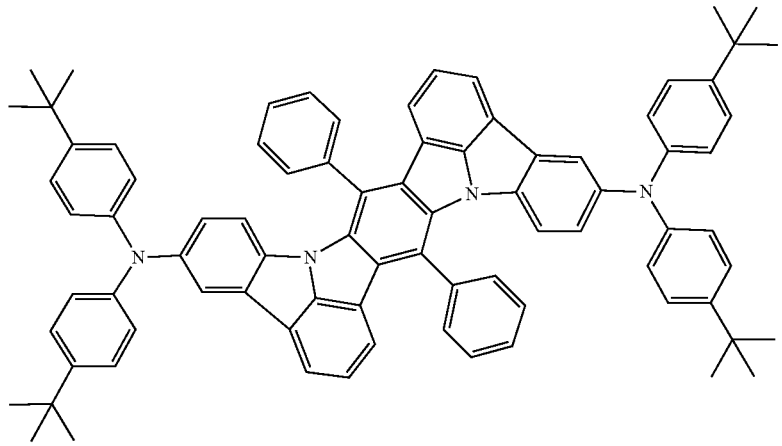

-continued
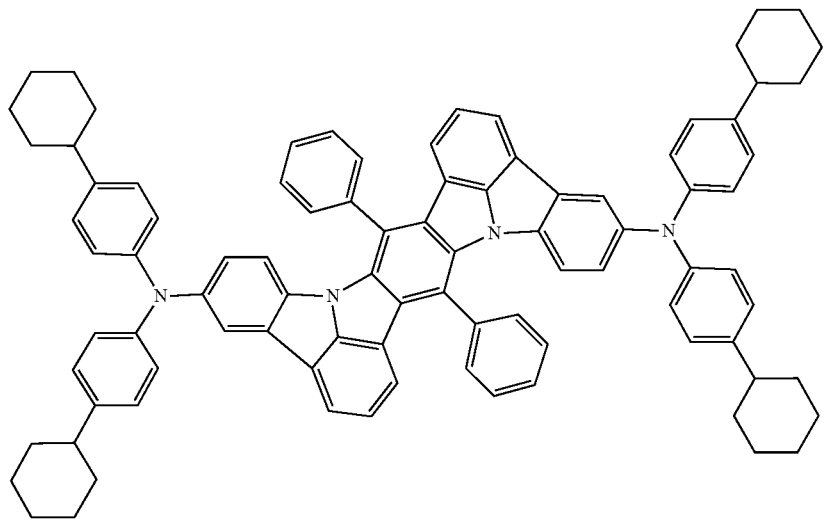
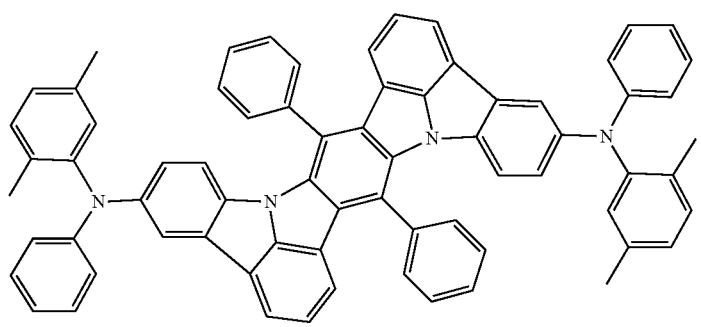
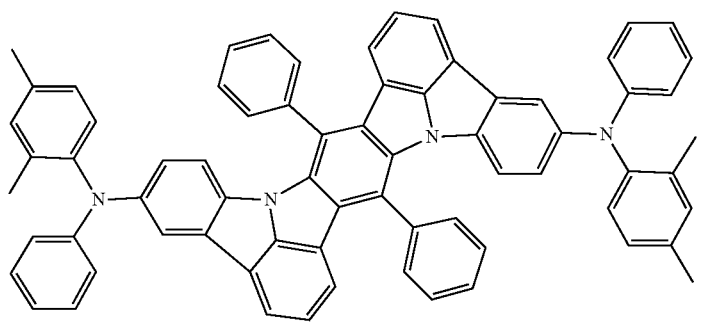
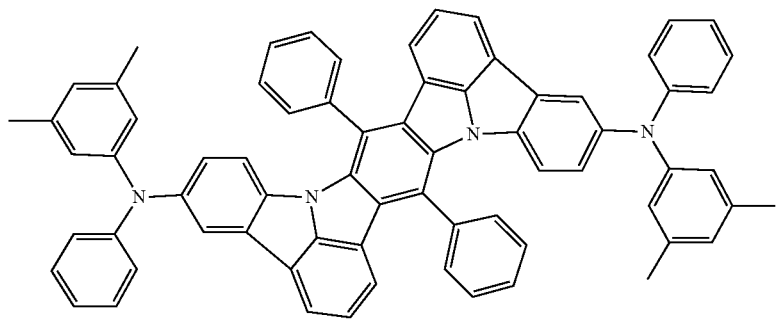

-continued
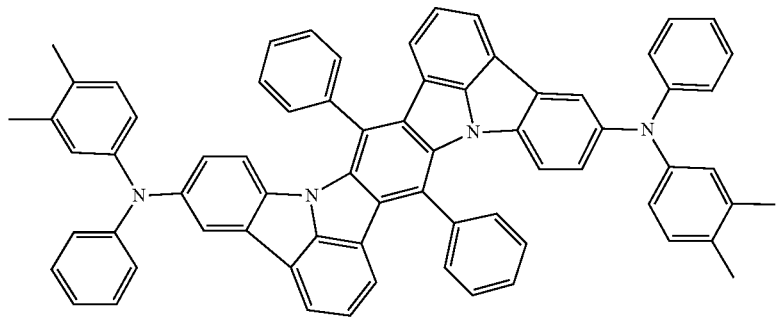
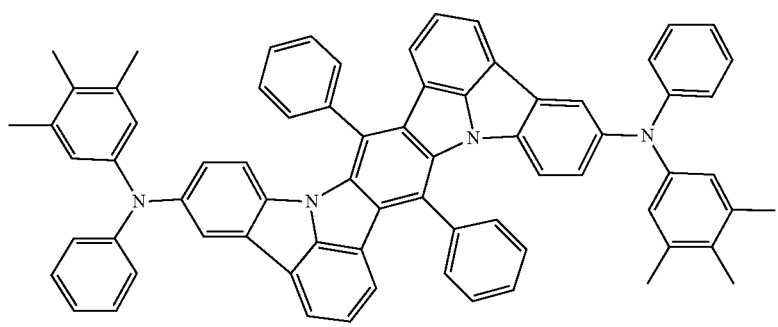
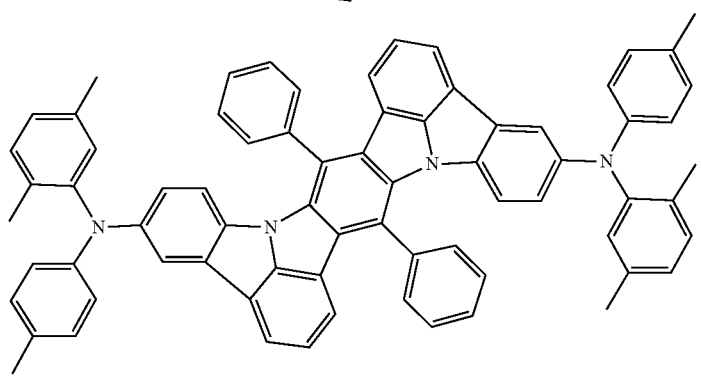
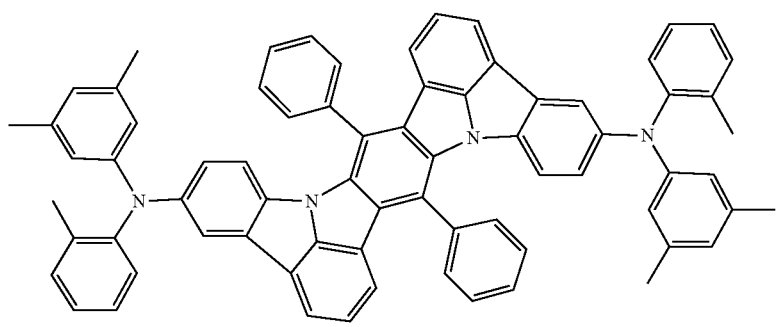
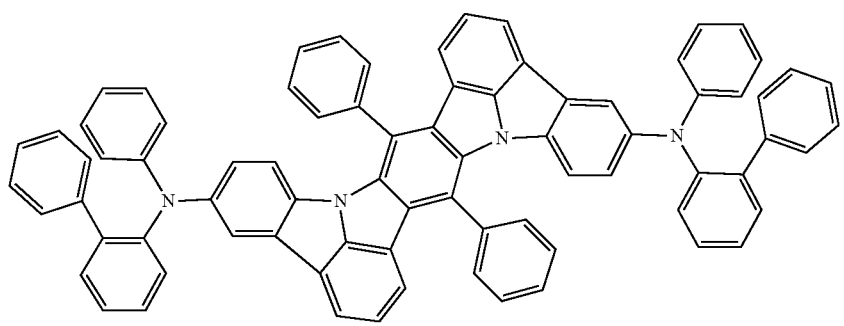

-continued
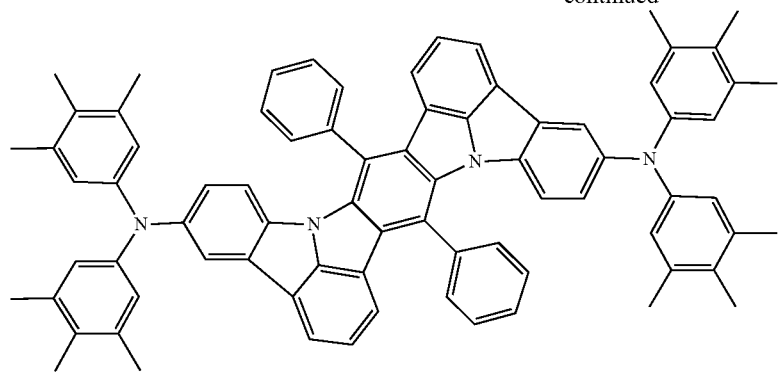
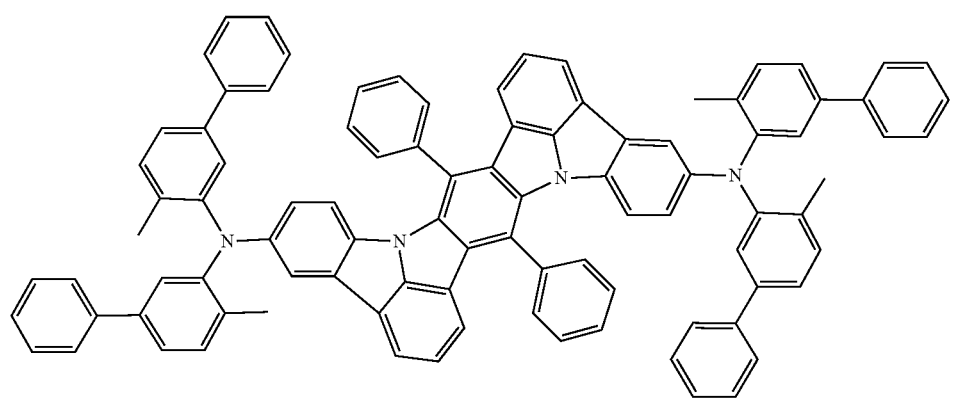
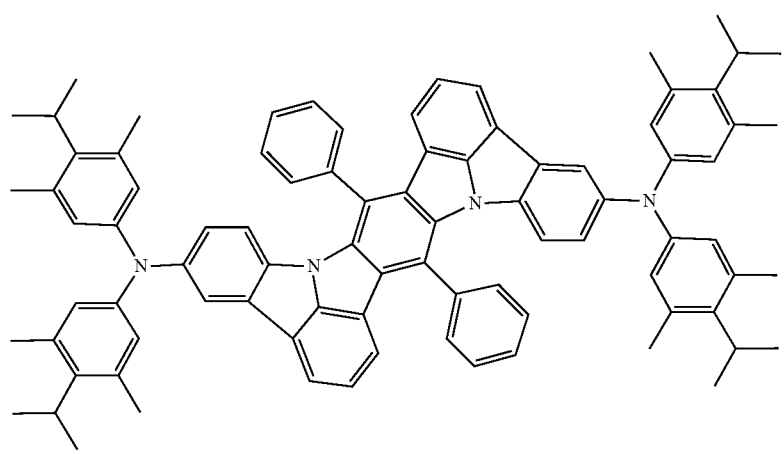
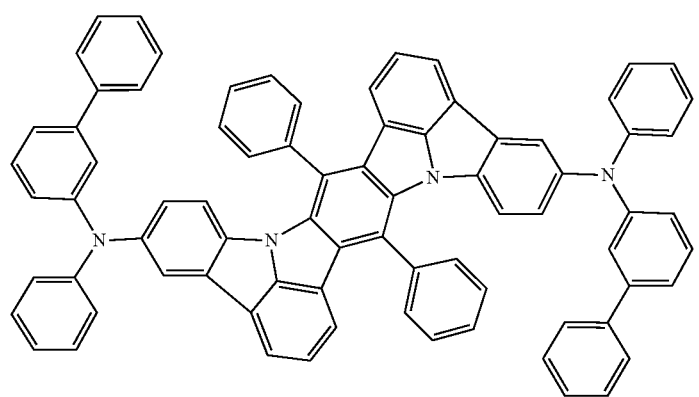

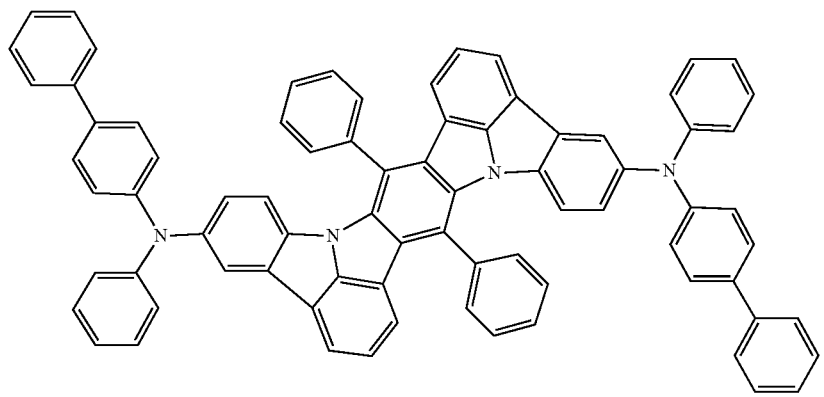
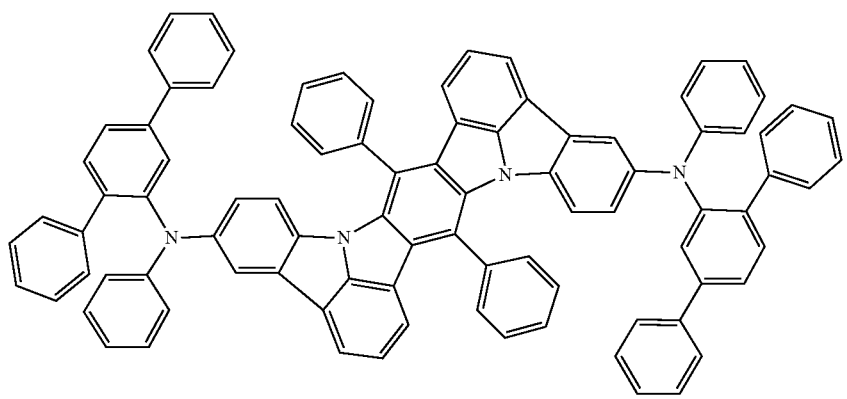
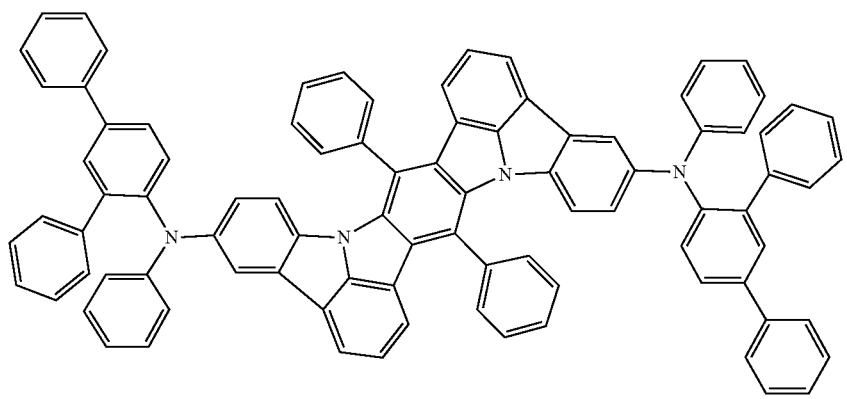
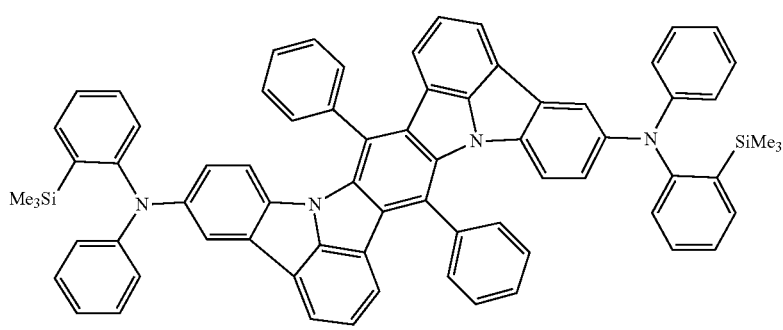

-continued
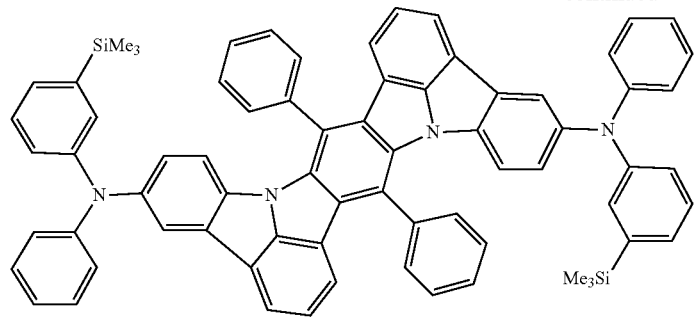
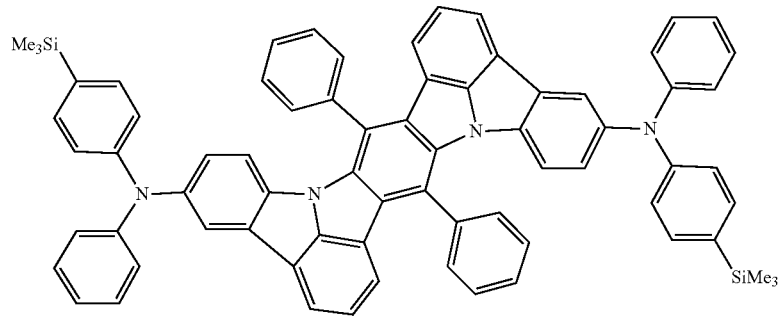
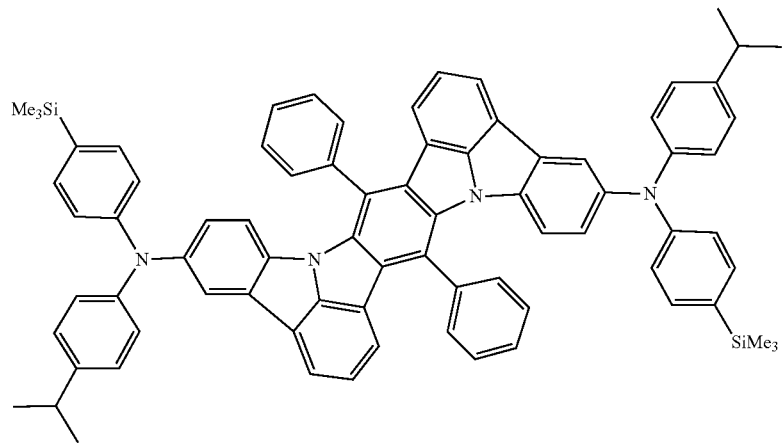
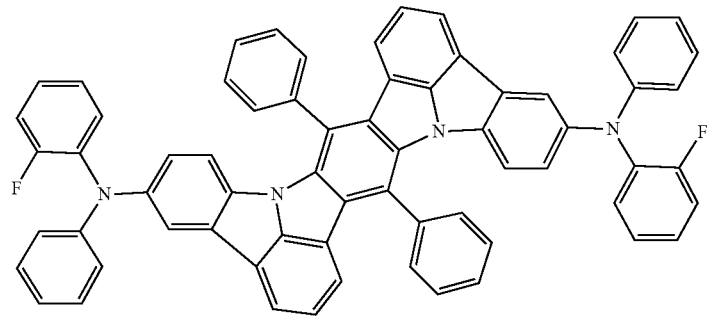
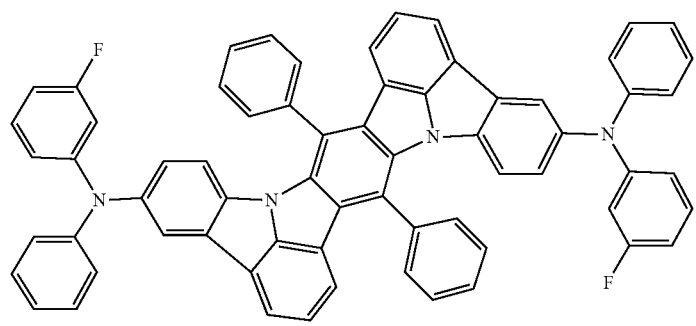

-continued
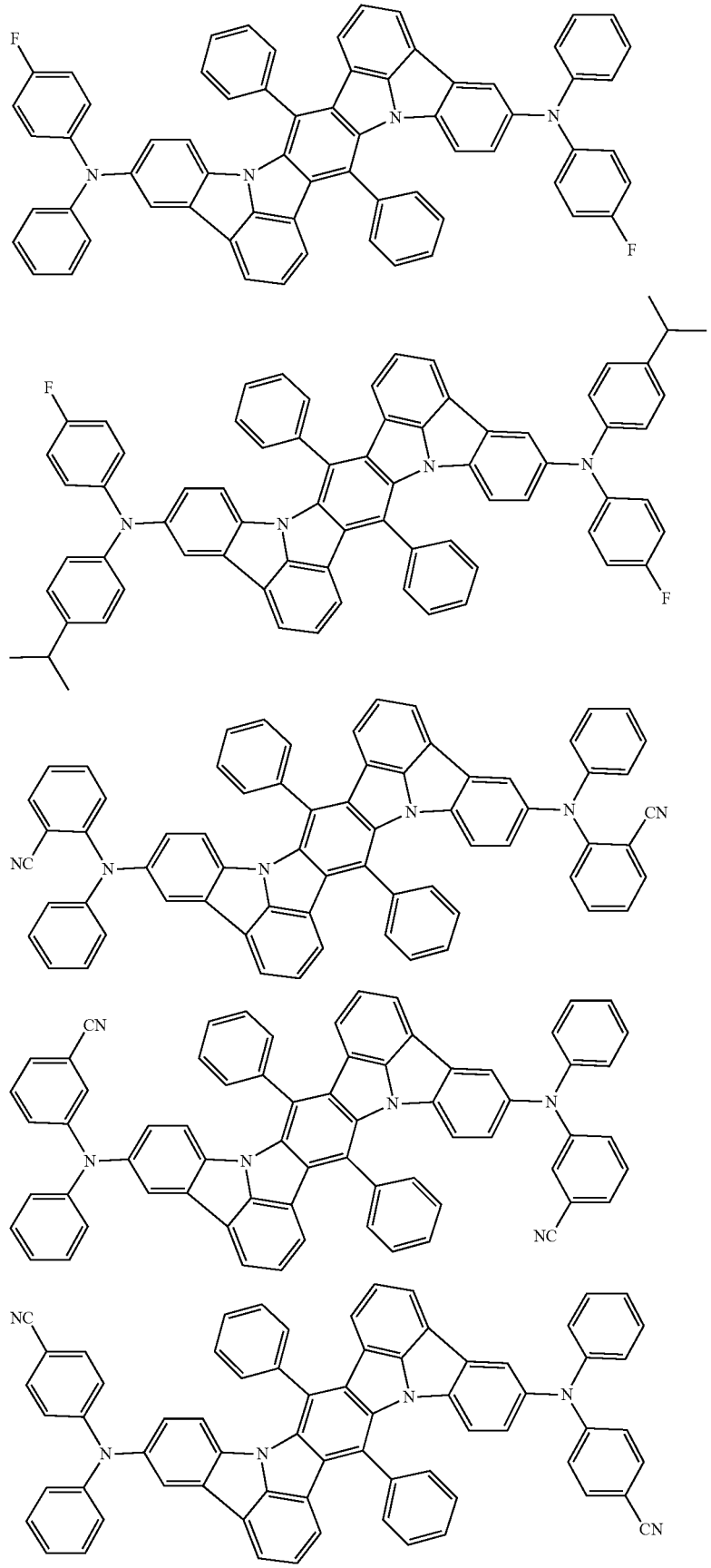

-continued
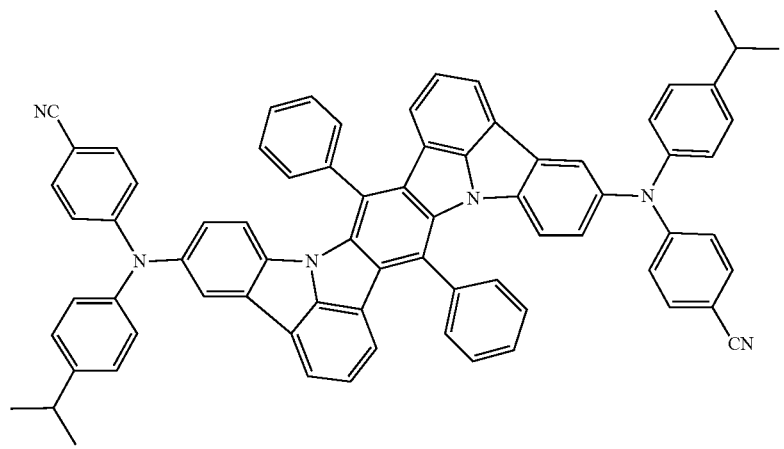
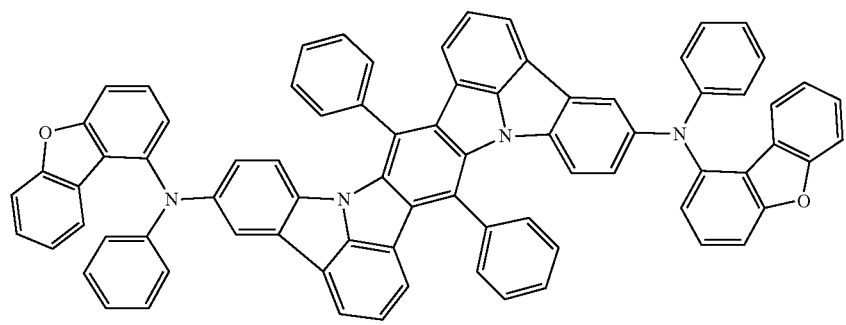
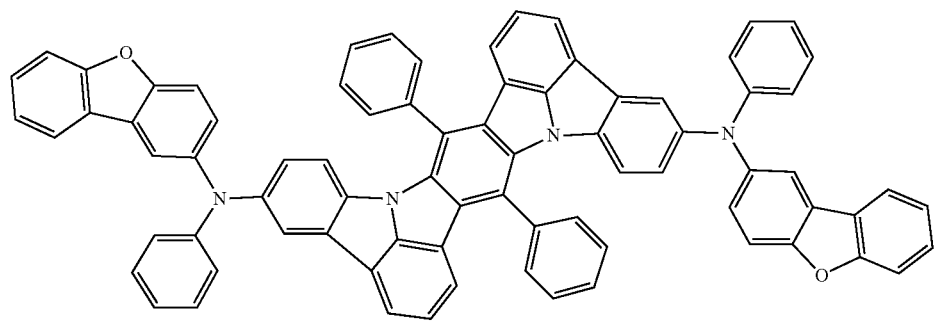
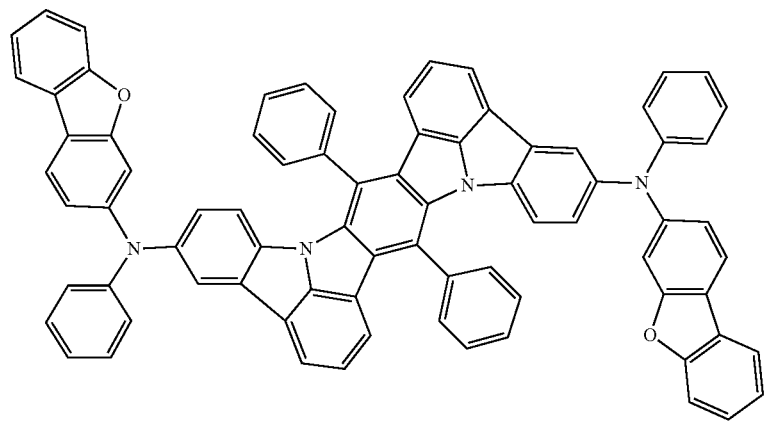

-continued
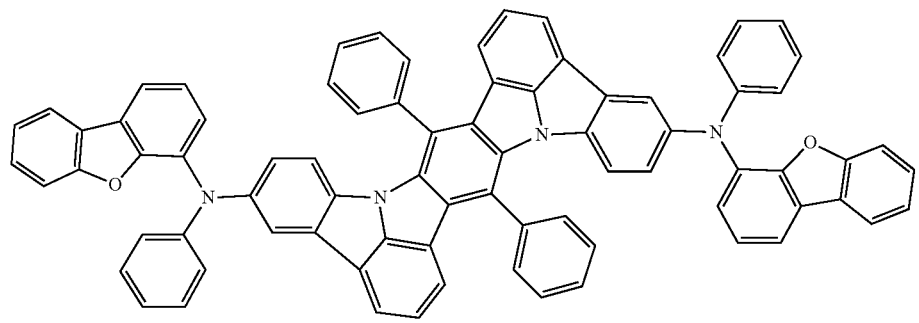
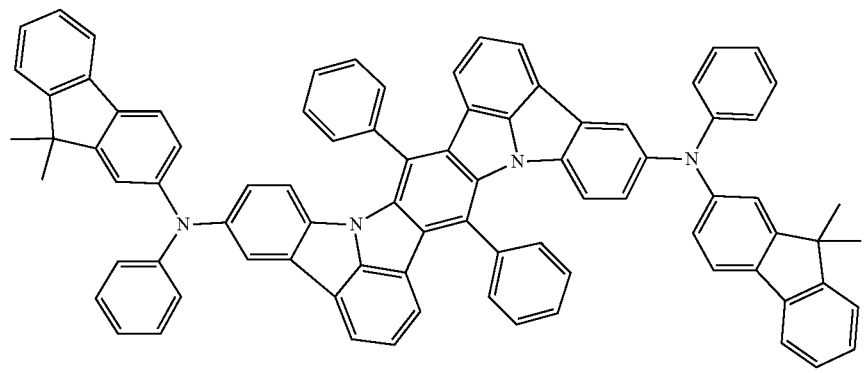
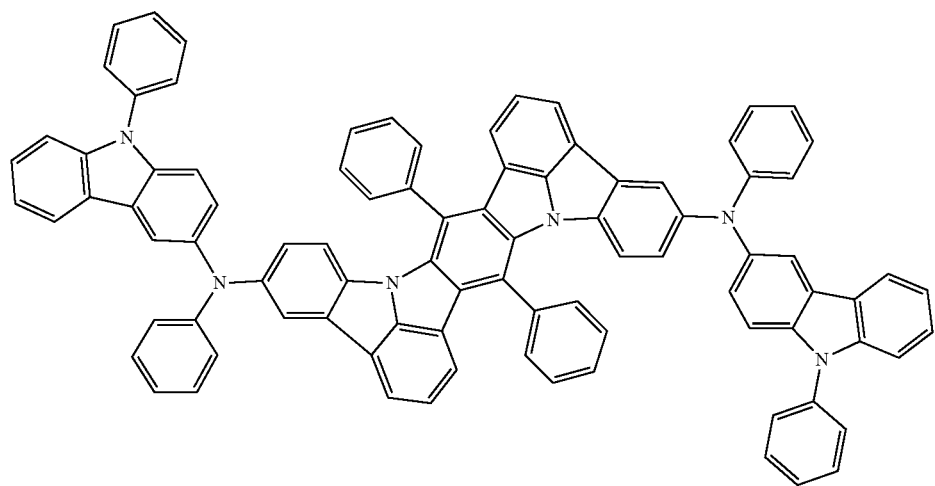
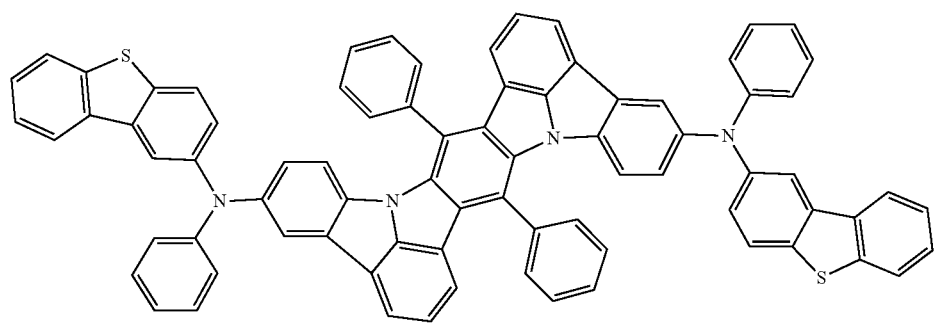

-continued
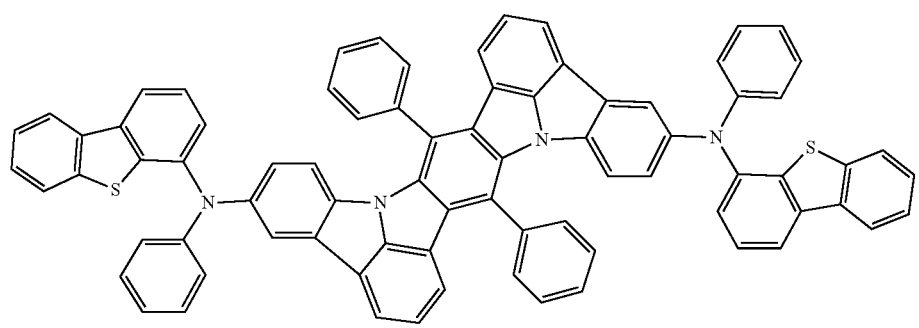
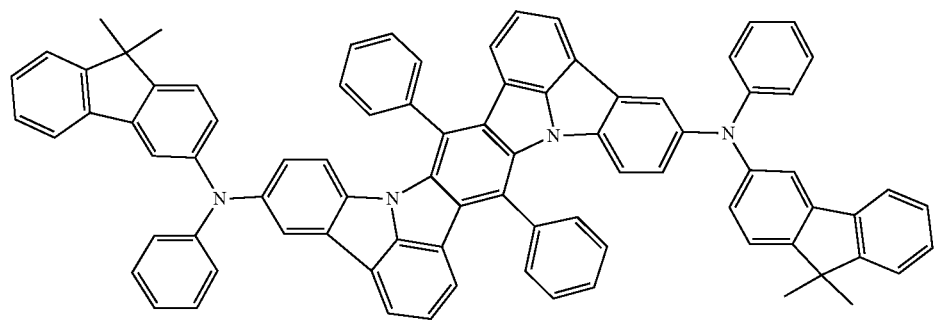
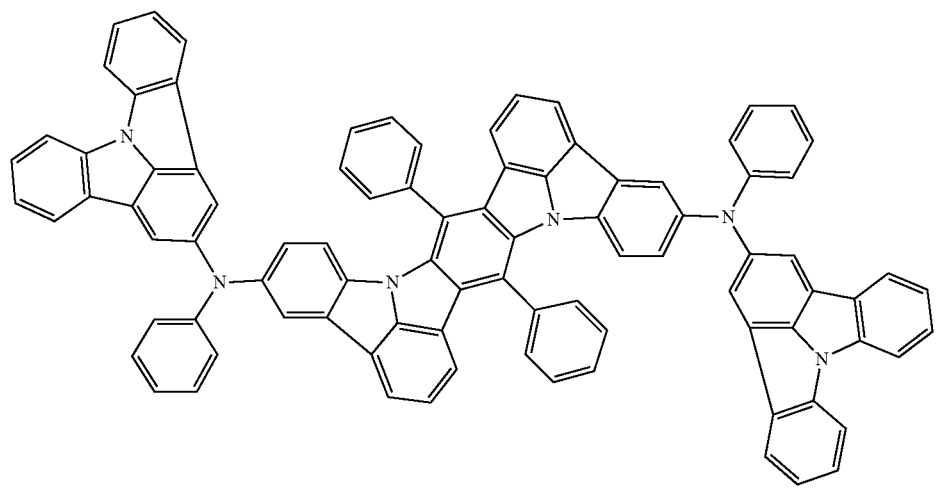
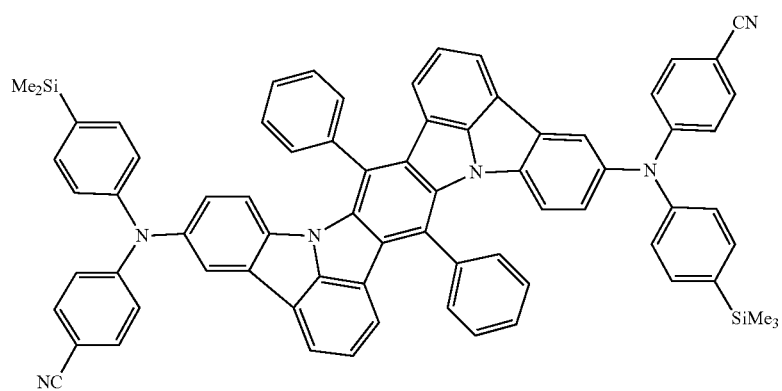

-continued
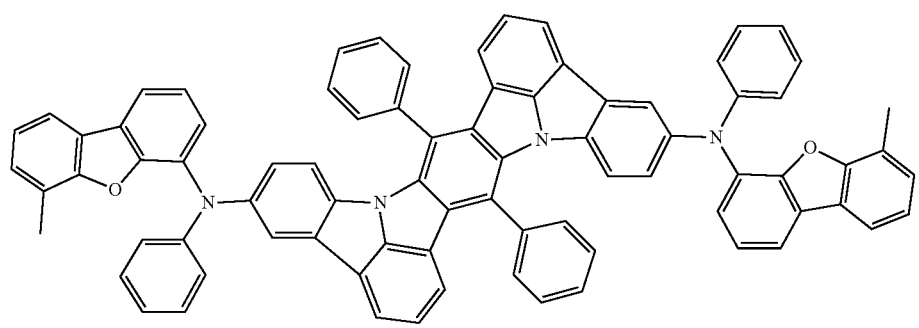
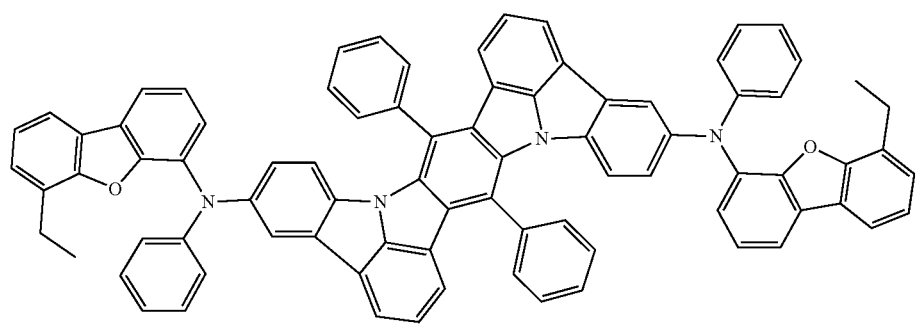
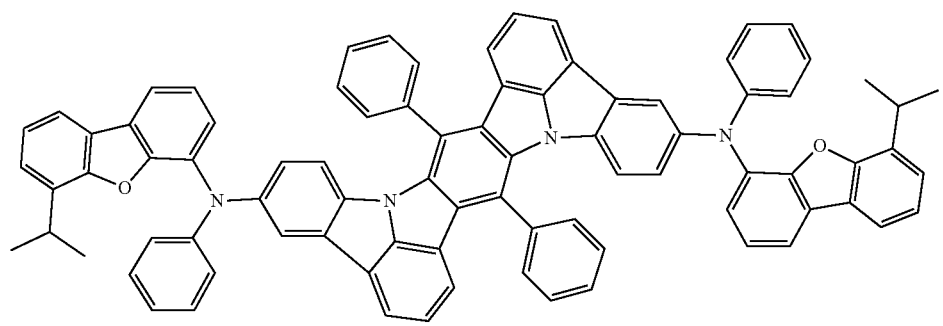
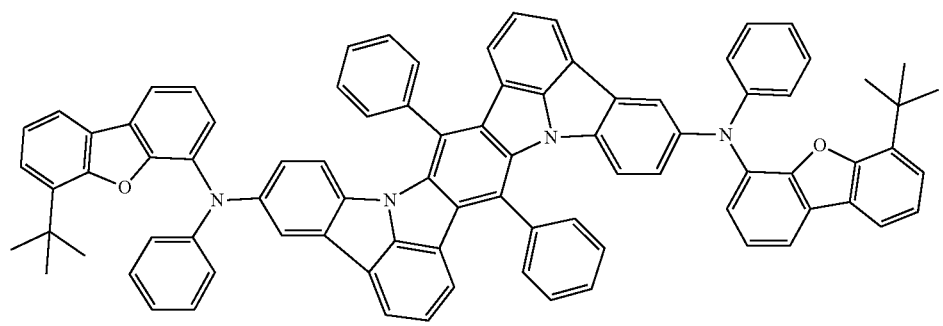
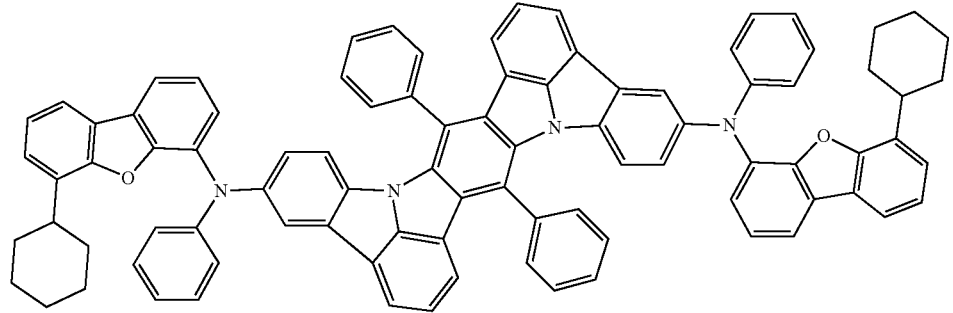

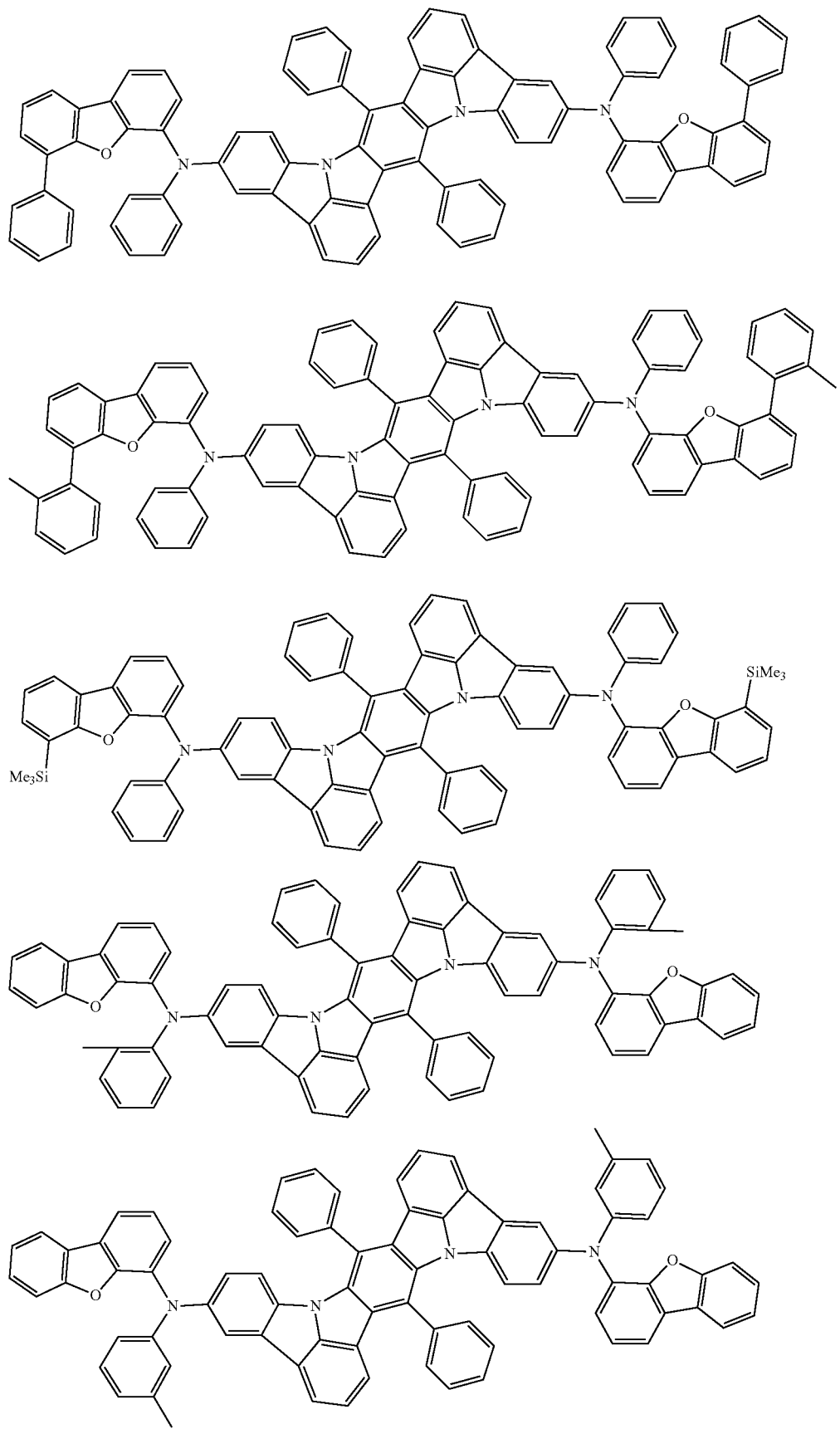

-continued
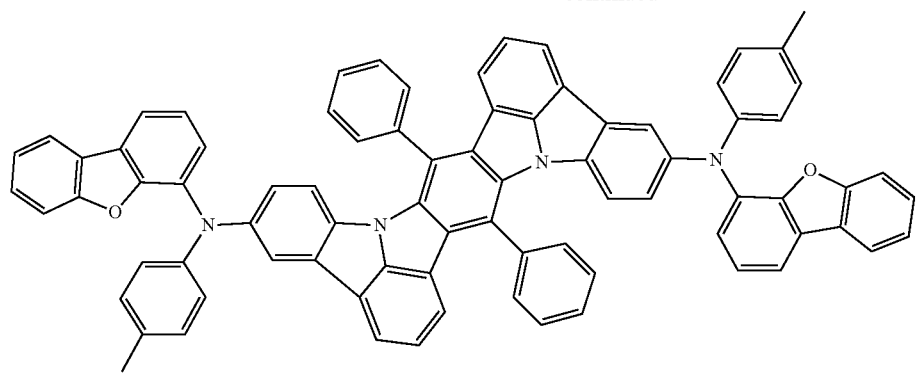
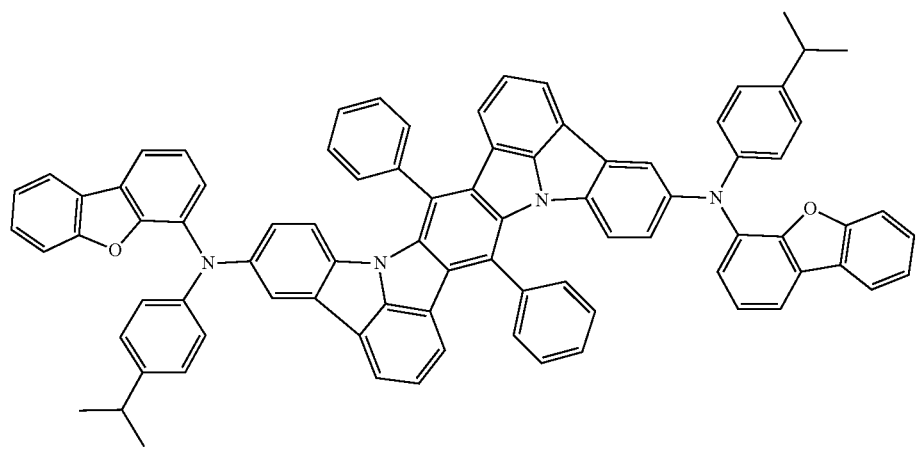
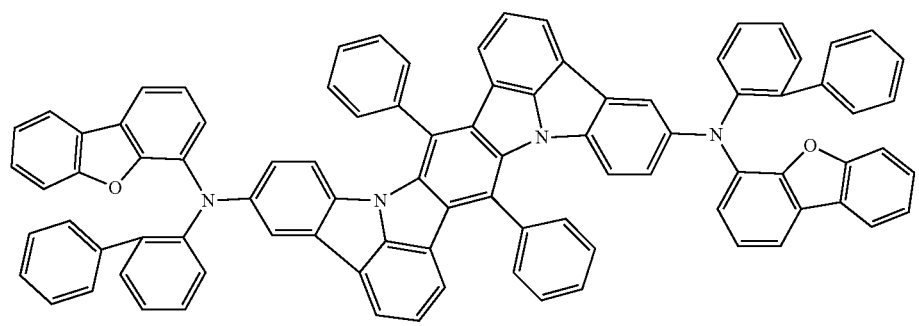
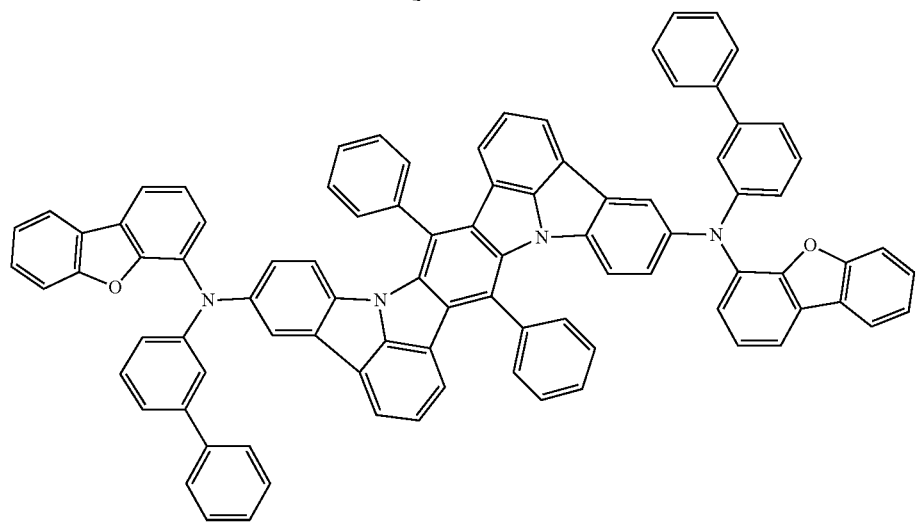

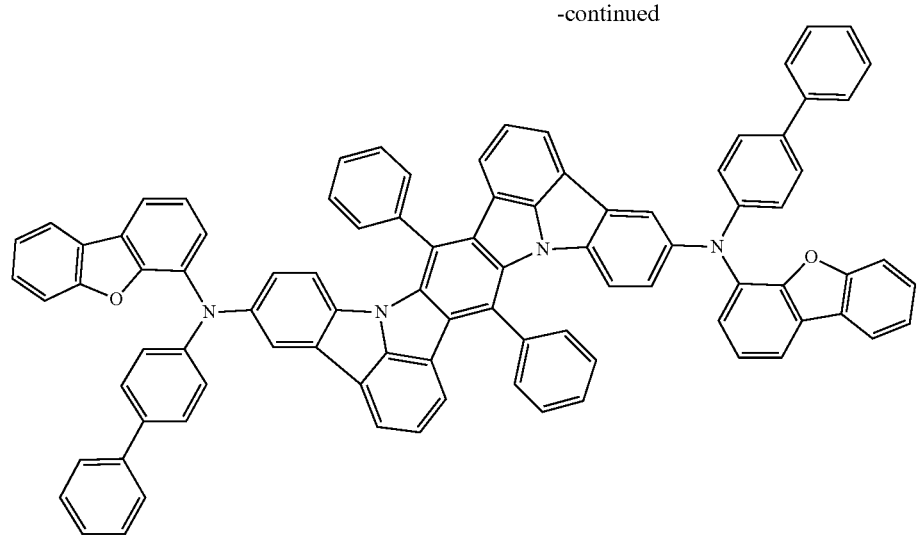
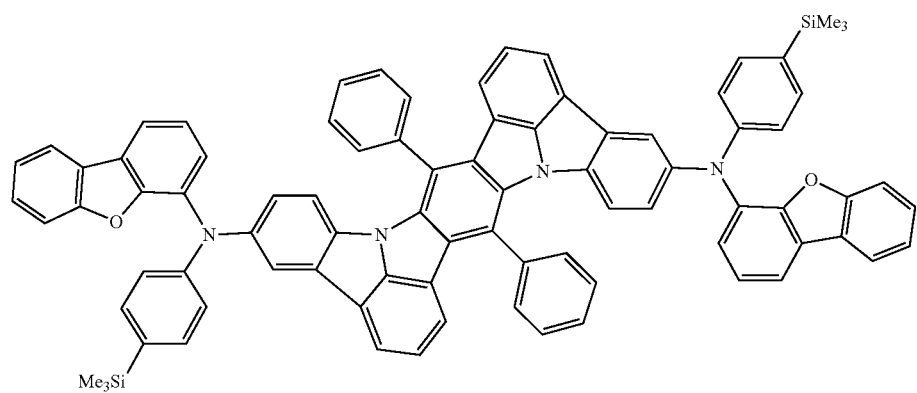
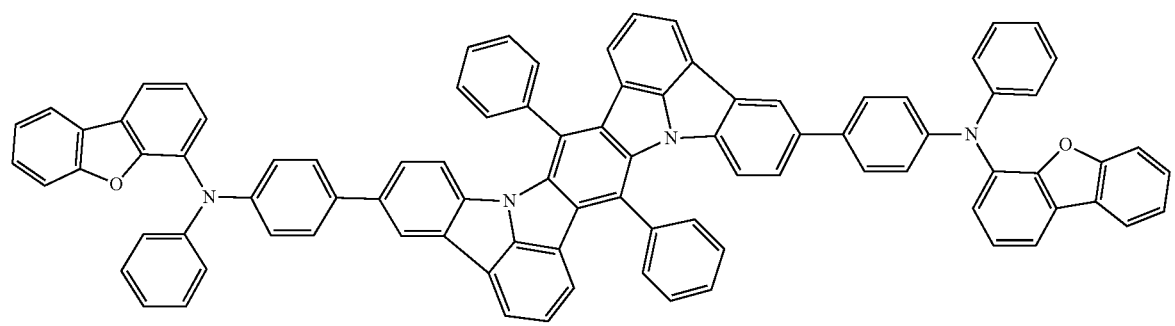
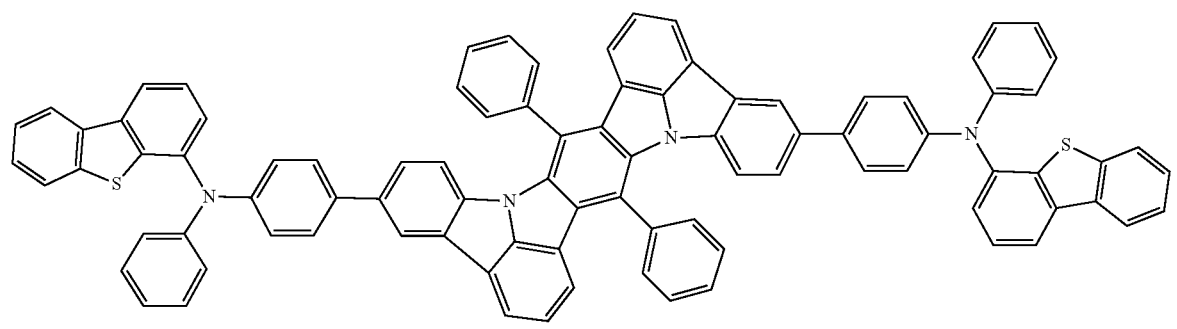

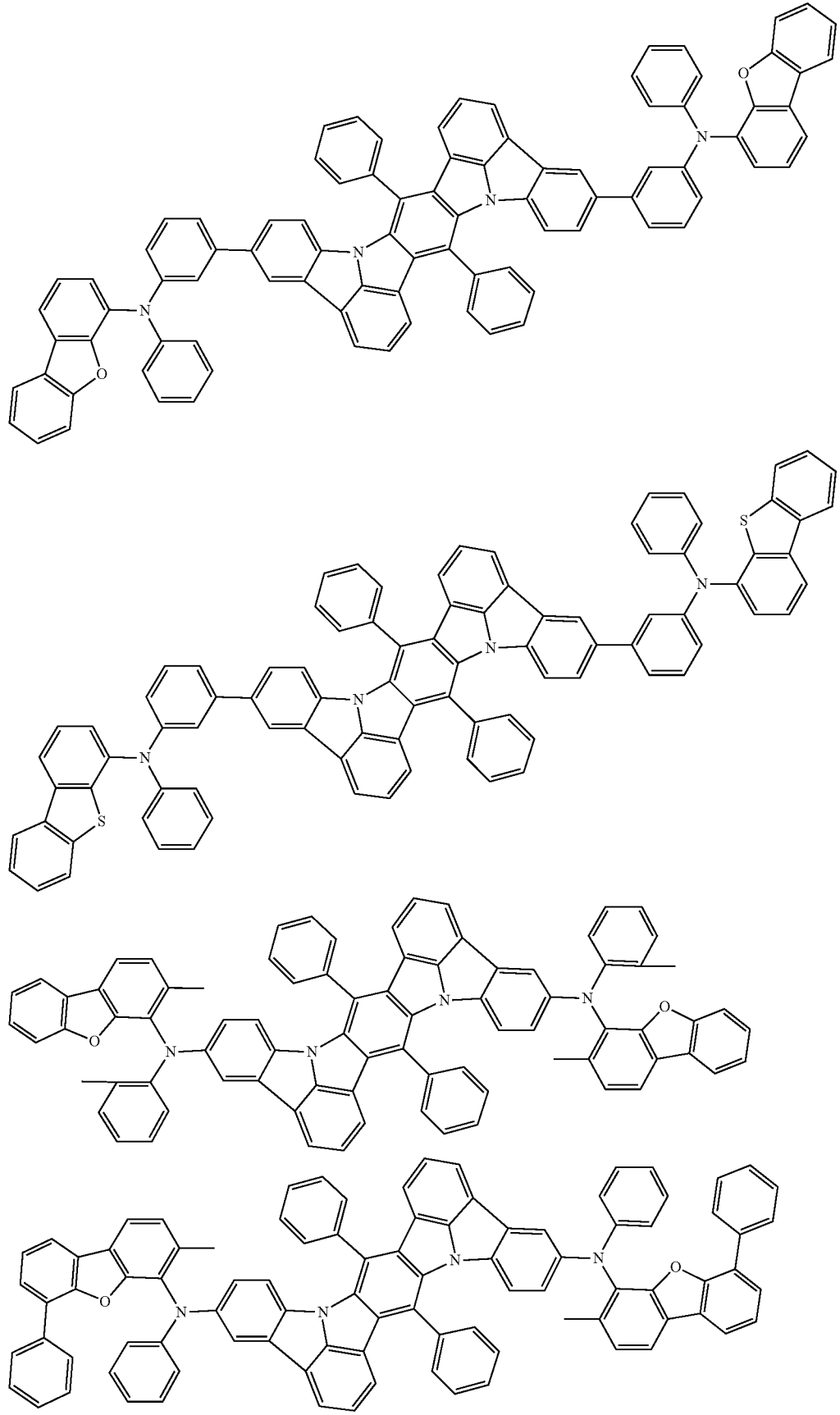

-continued
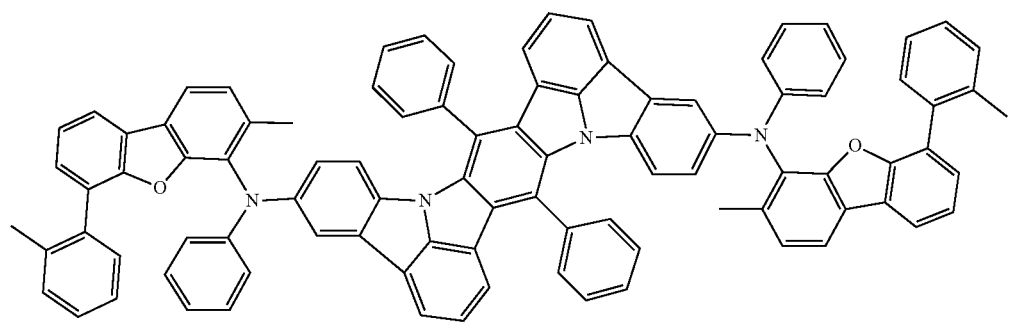
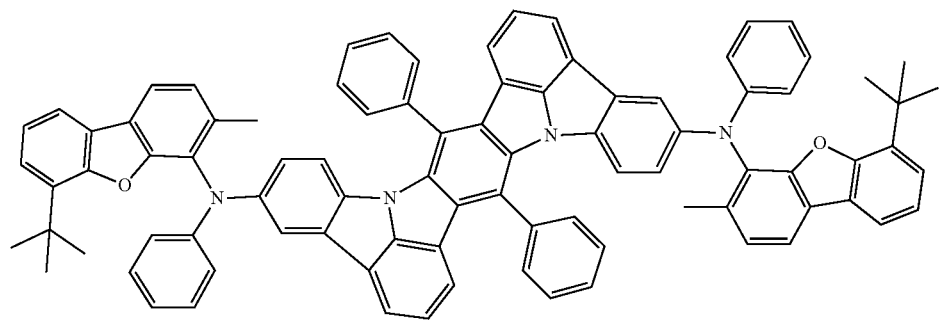
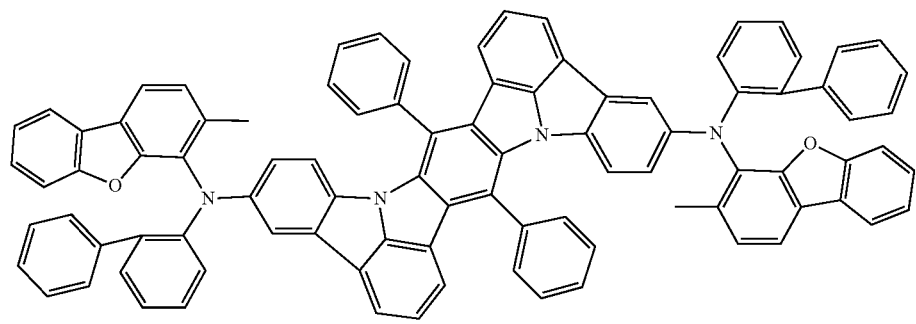
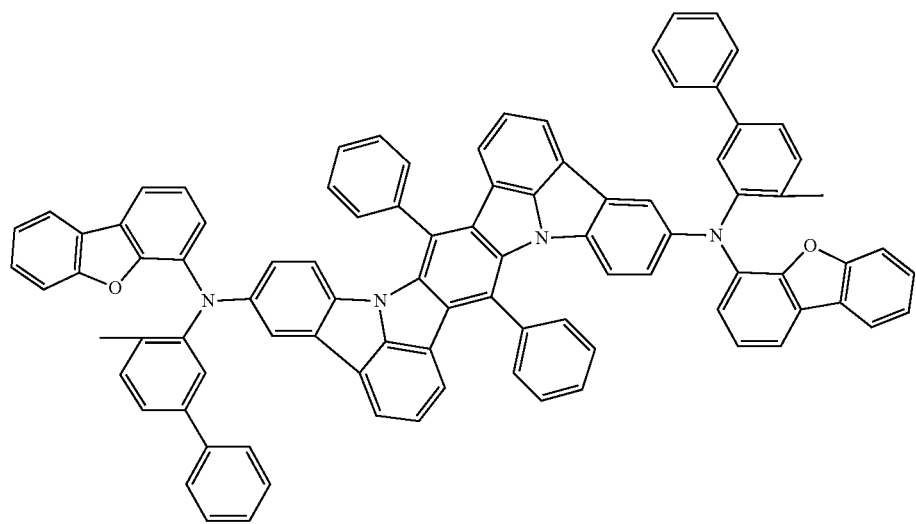

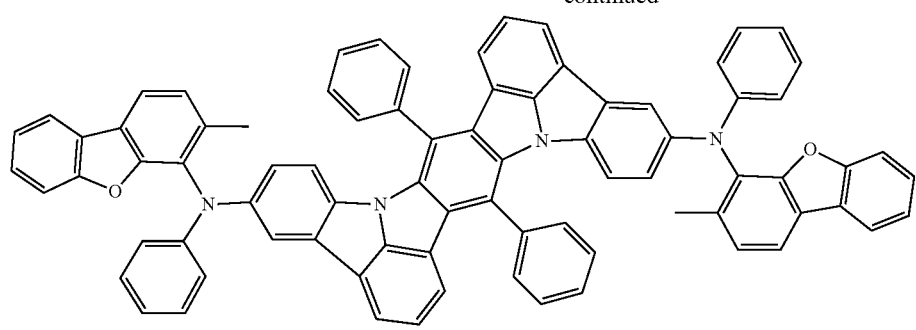
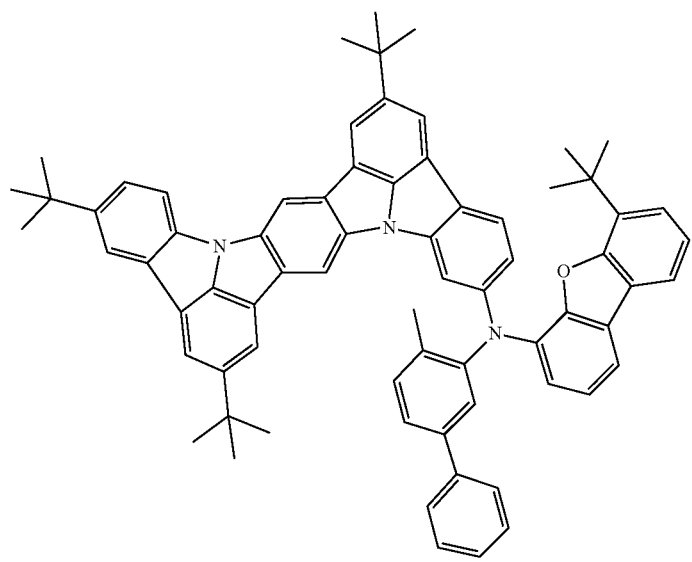
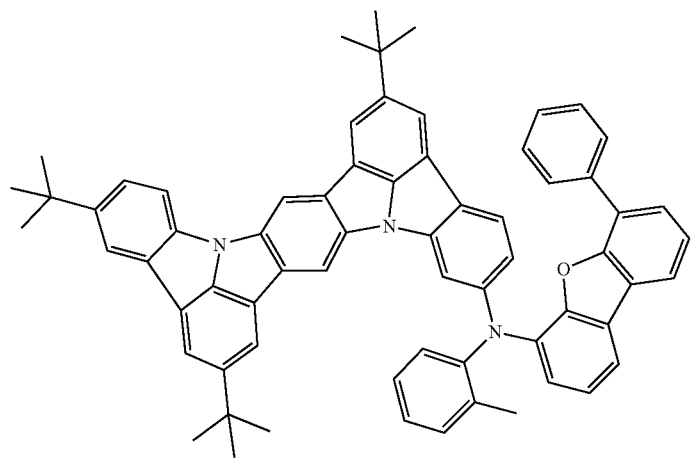

-continued
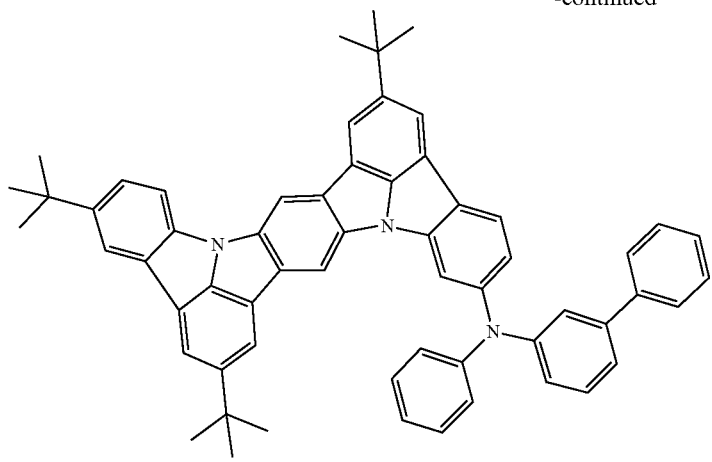
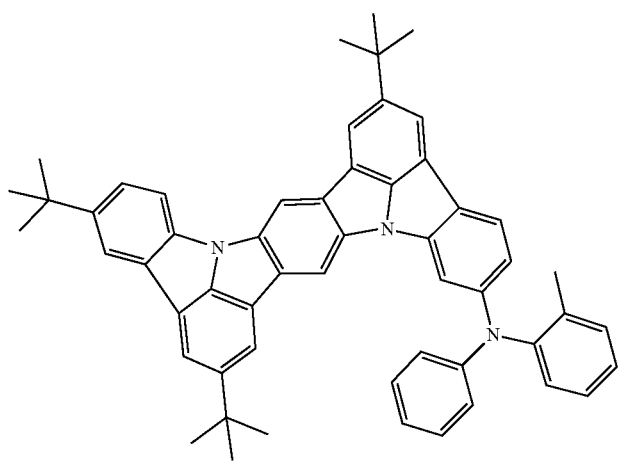
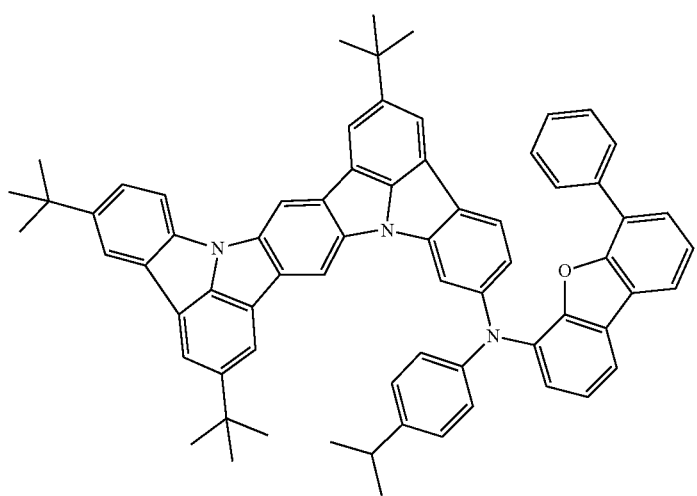

403
404
-continued
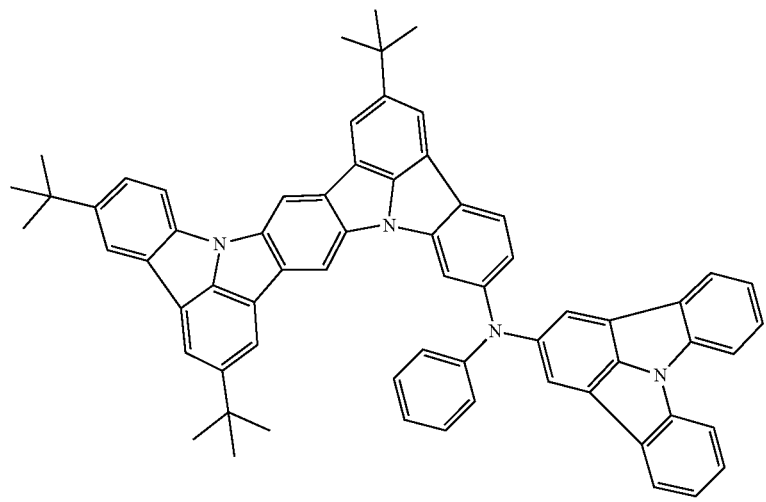
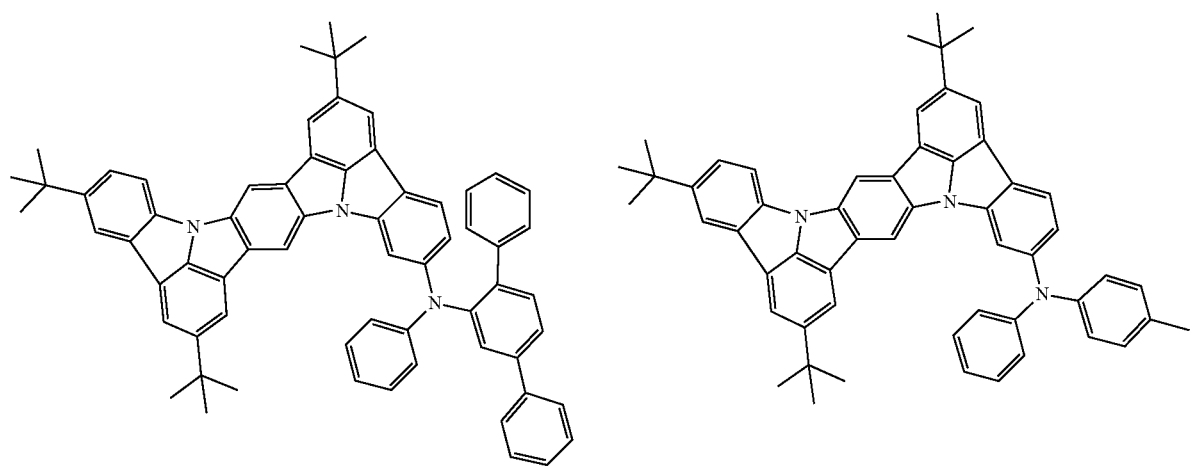 [SMILES: CC(C)(C)c1ccc2c(c1)c1cc(C(C)(C)C)cc3c4cc5c(cc4n2c13)c1cc(C(C)(C)C)cc2c3ccc(N(c4ccccc4)c4cc(-c6ccccc6)ccc4-c4ccccc4)cc3n5c21 ; Cc1ccc(N(c2ccccc2)c2ccc3c4cc(C(C)(C)C)cc5c6cc7c(cc6n(c3c2)c45)c2cc(C(C)(C)C)cc3c4cc(C(C)(C)C)ccc4n7c32)cc1]
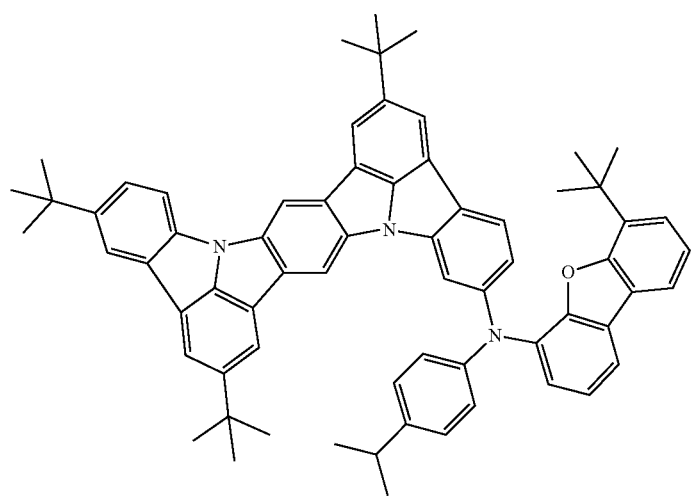 [SMILES: CC(C)c1ccc(N(c2ccc3c4cc(C(C)(C)C)cc5c6cc7c(cc6n(c3c2)c45)c2cc(C(C)(C)C)cc3c4cc(C(C)(C)C)ccc4n7c32)c2cccc3c2oc2c(C(C)(C)C)cccc23)cc1]

-continued
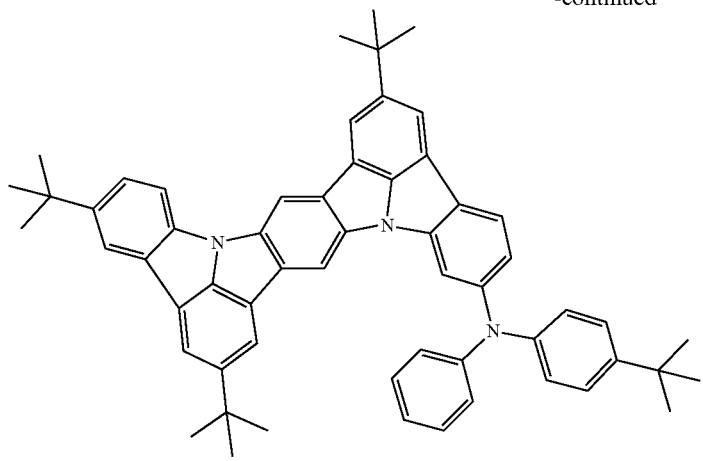
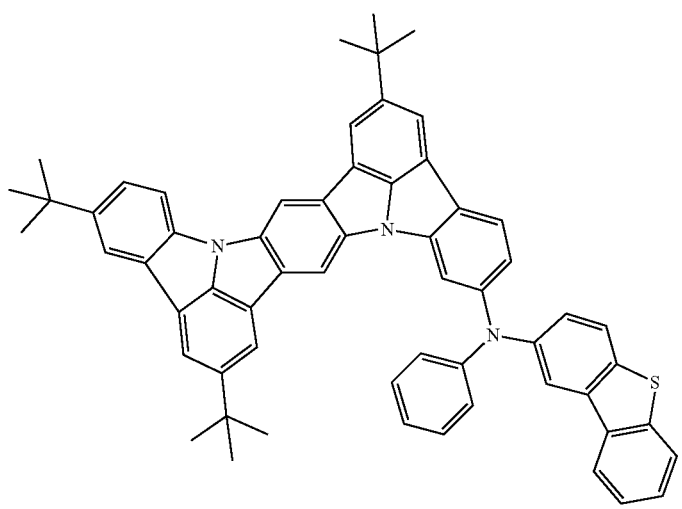
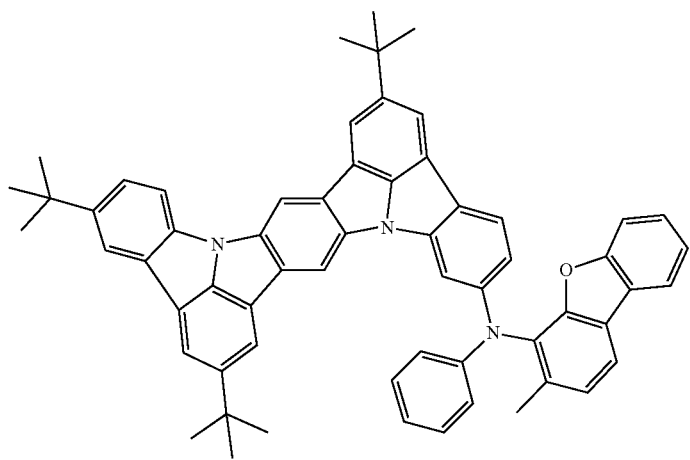

-continued
407
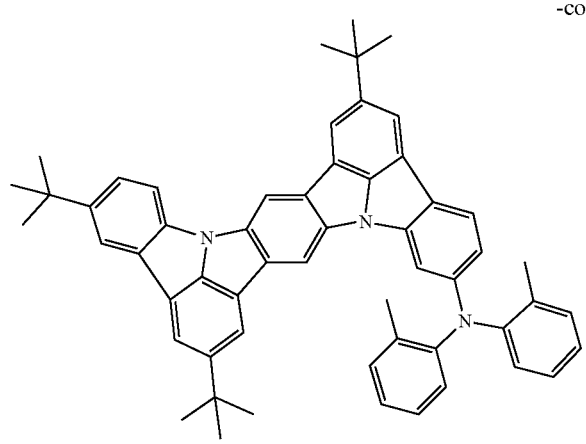
408
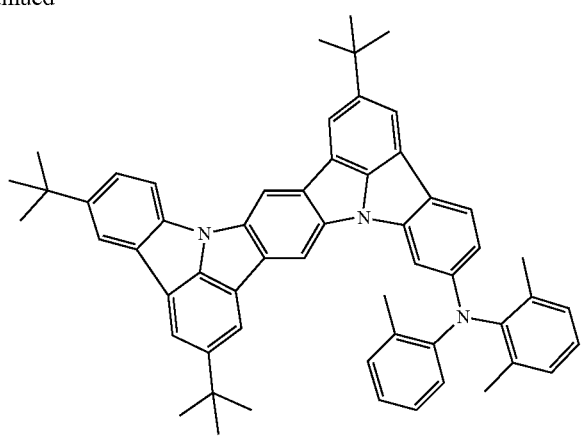
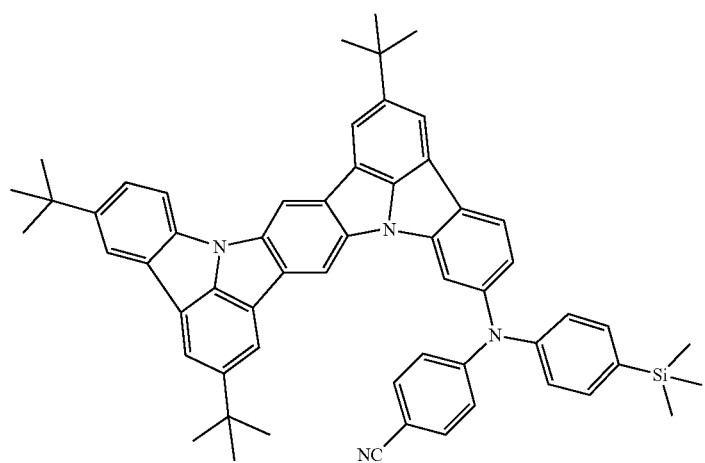
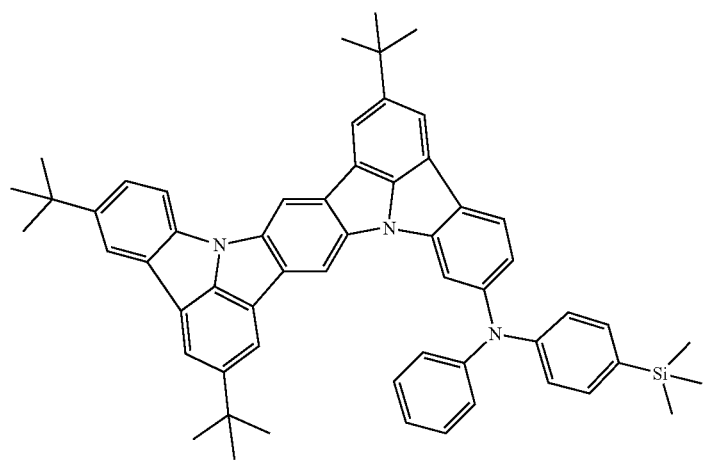

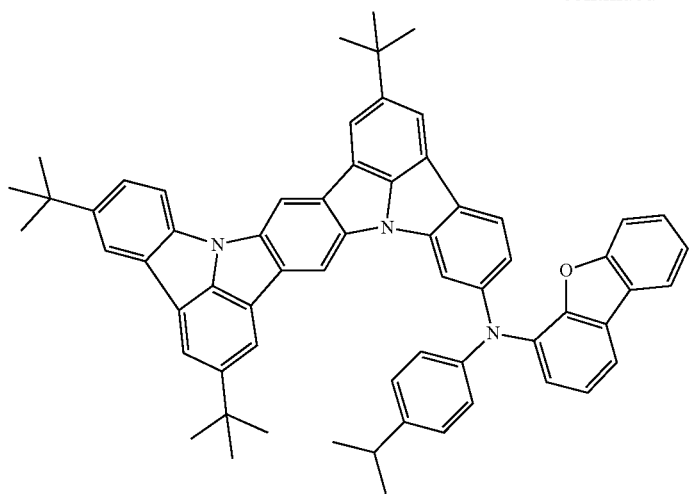
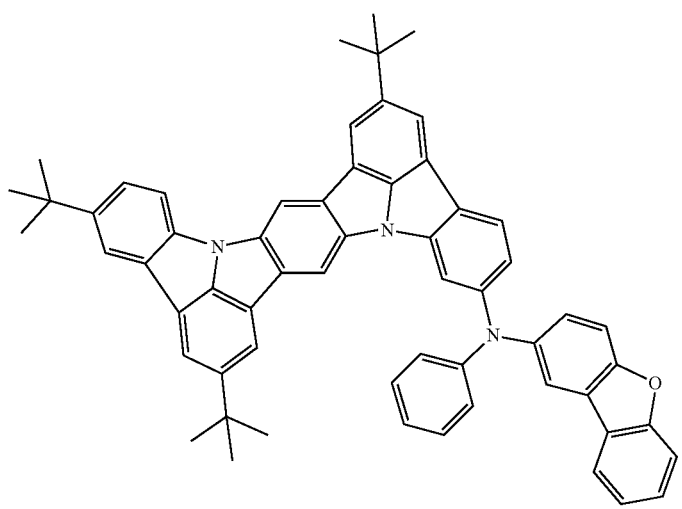
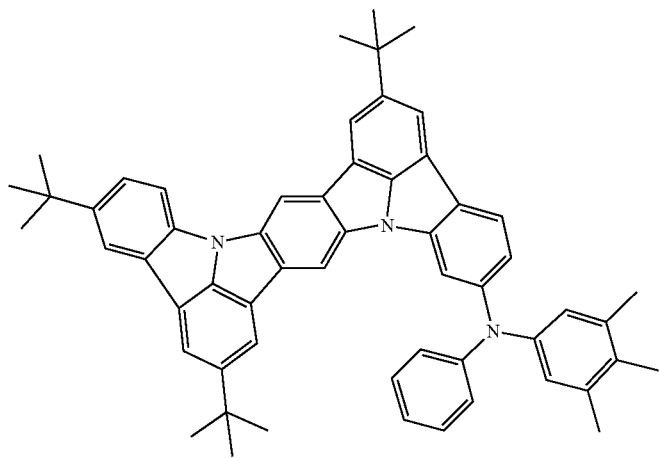

-continued
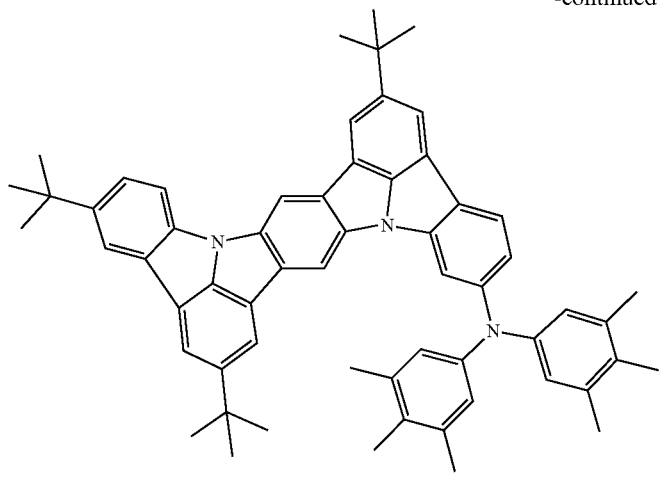
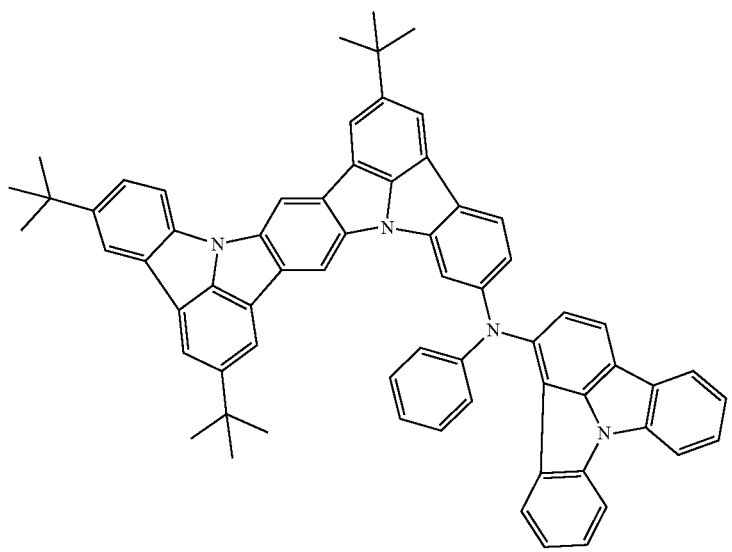
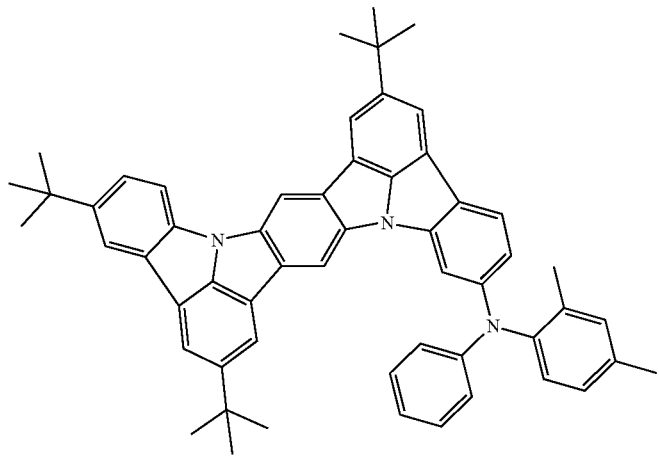

413
414
-continued
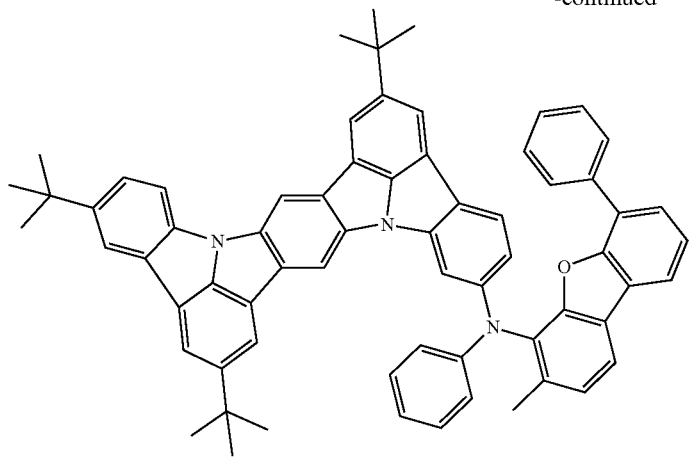
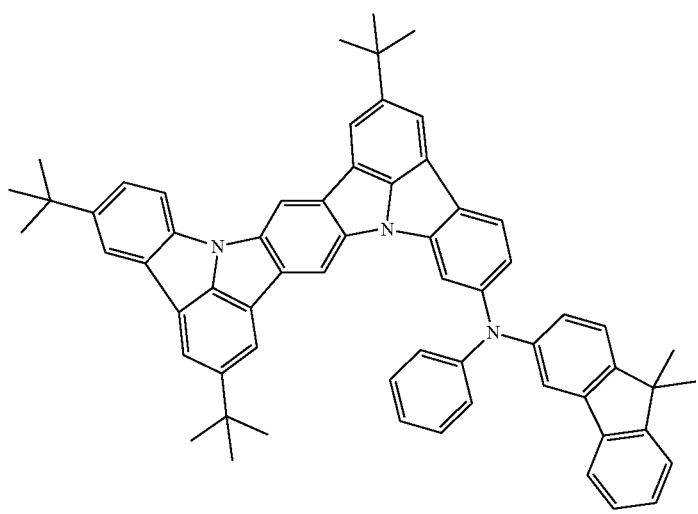
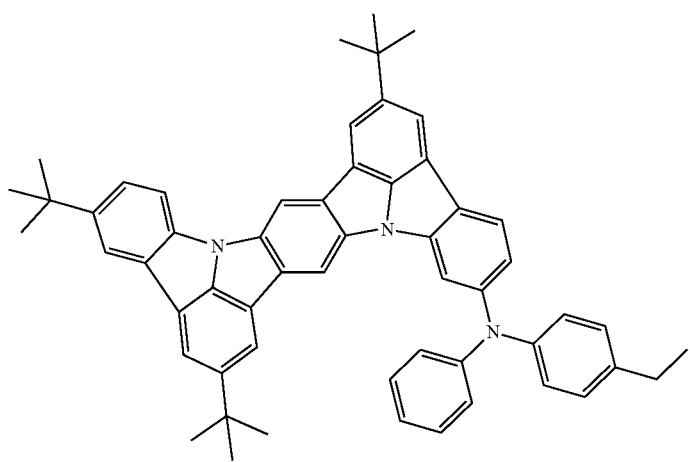

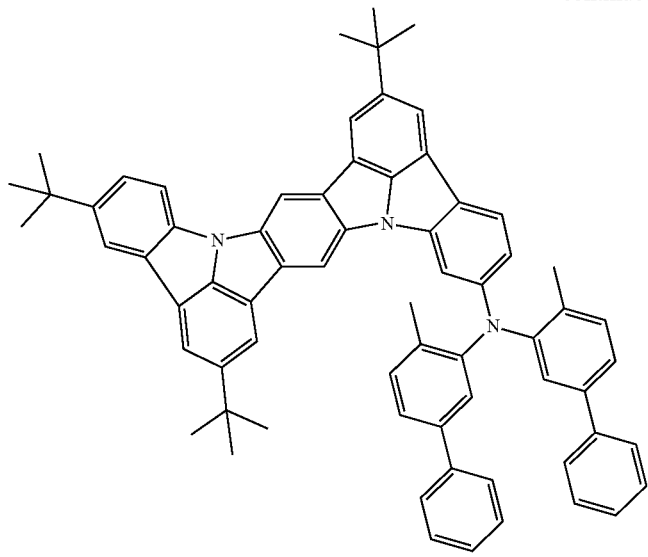
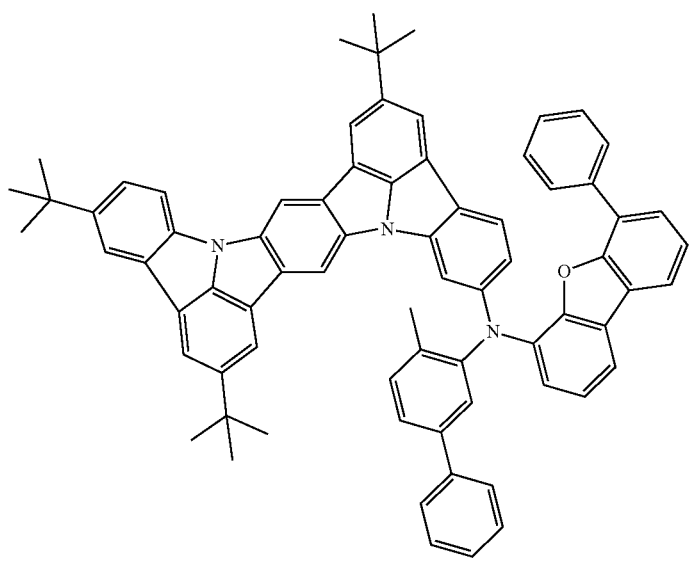
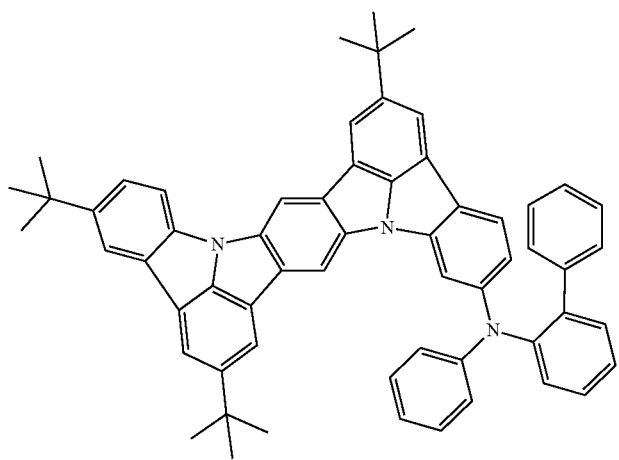

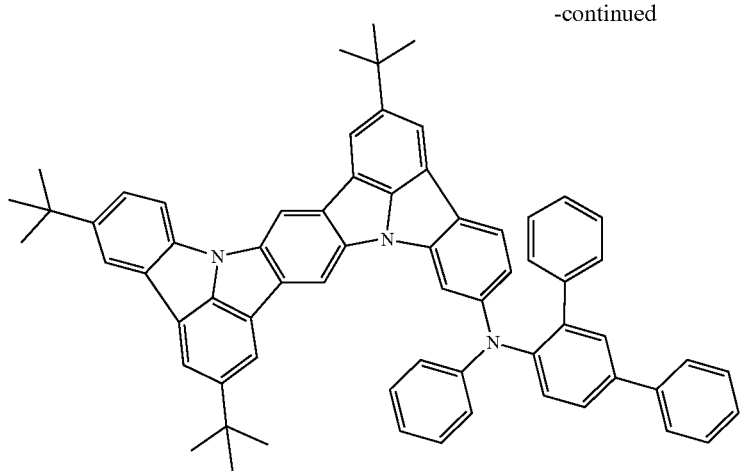
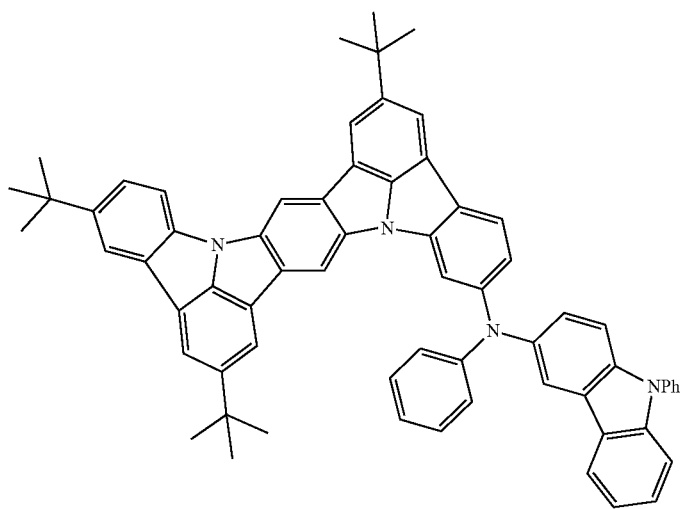
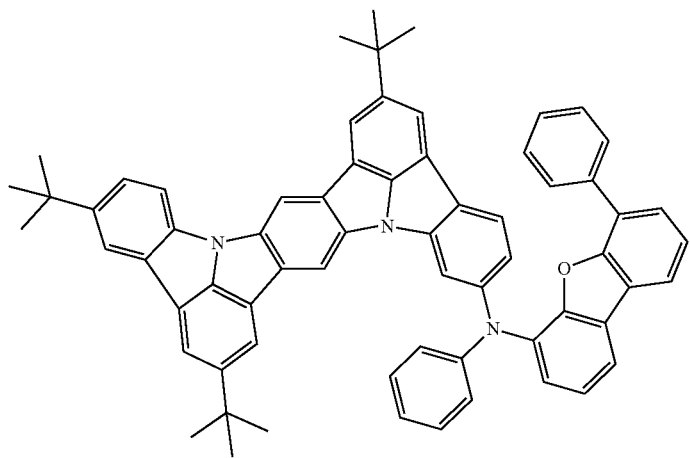

-continued
419
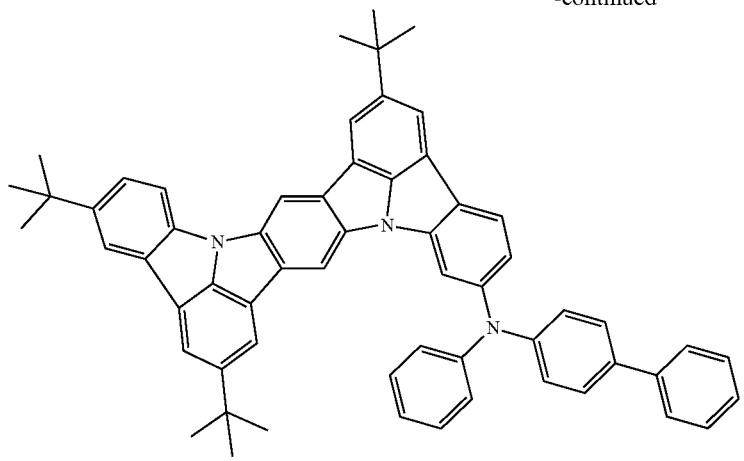
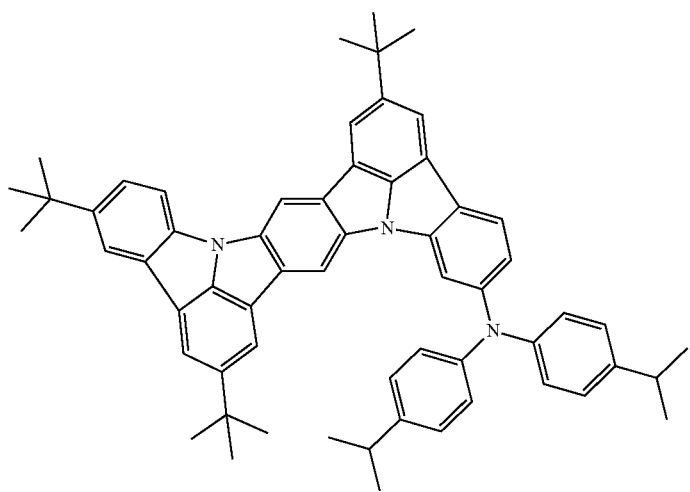
420
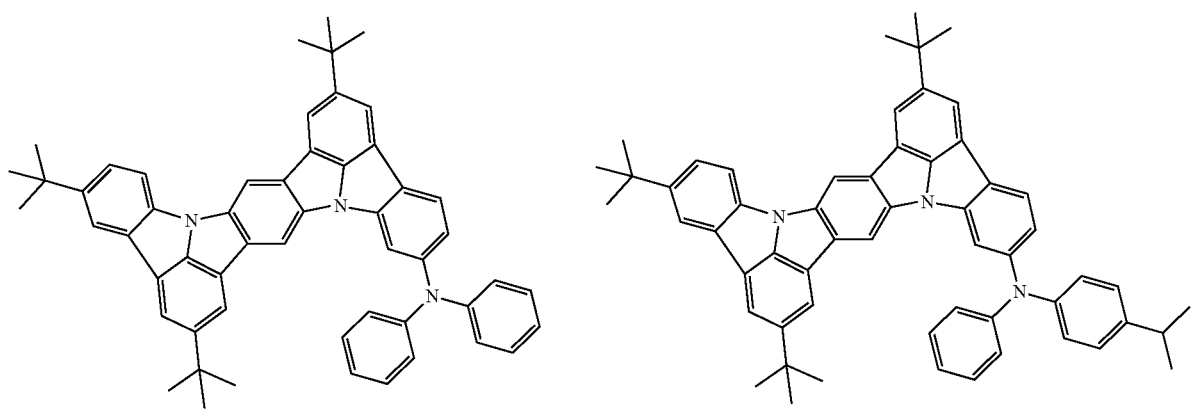

421
422
-continued
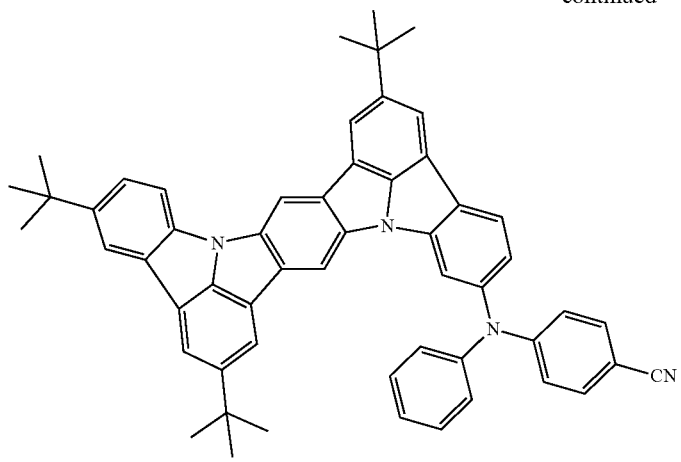
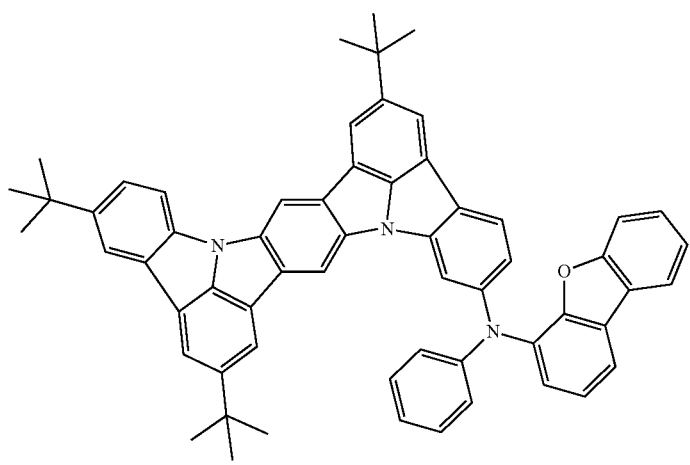
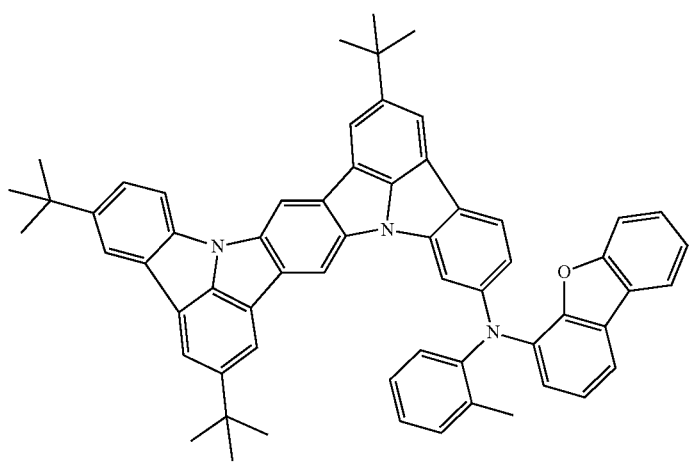

423
424
-continued
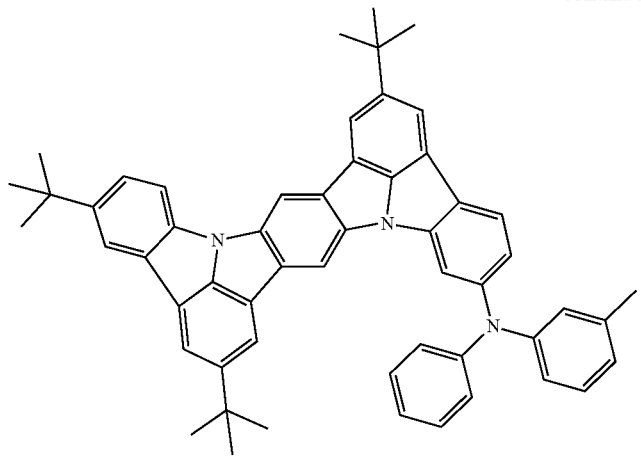
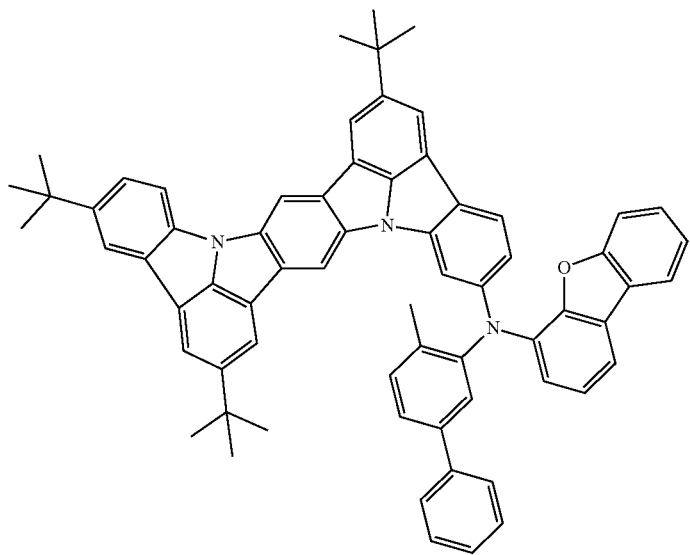
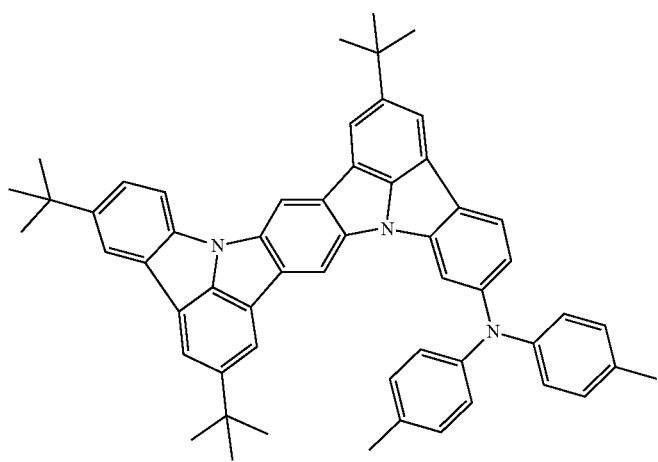

425
426
-continued
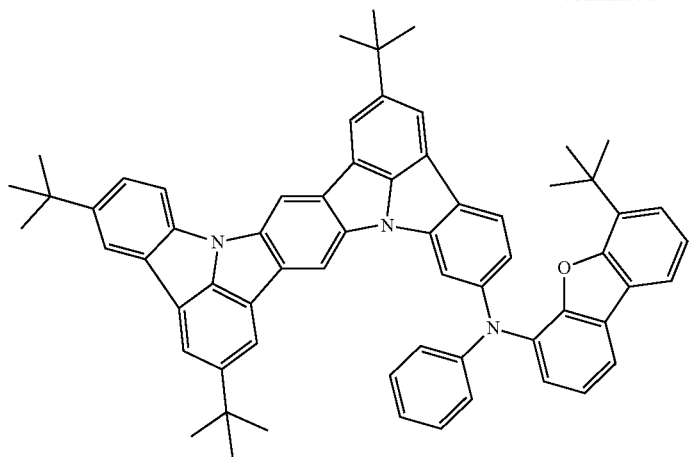
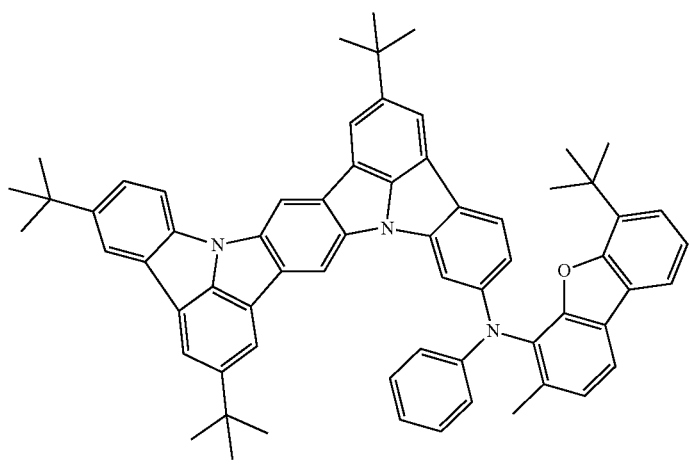
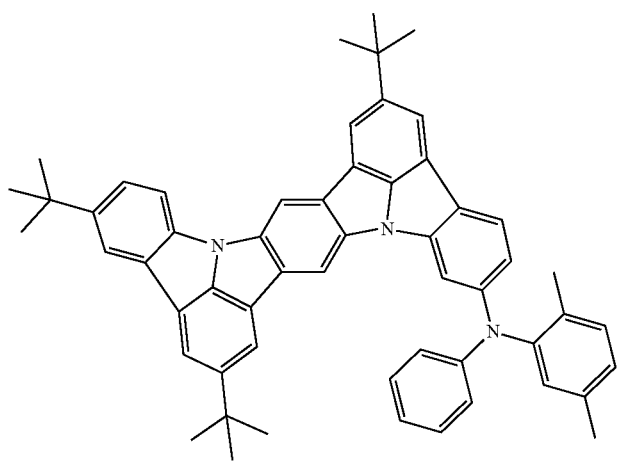

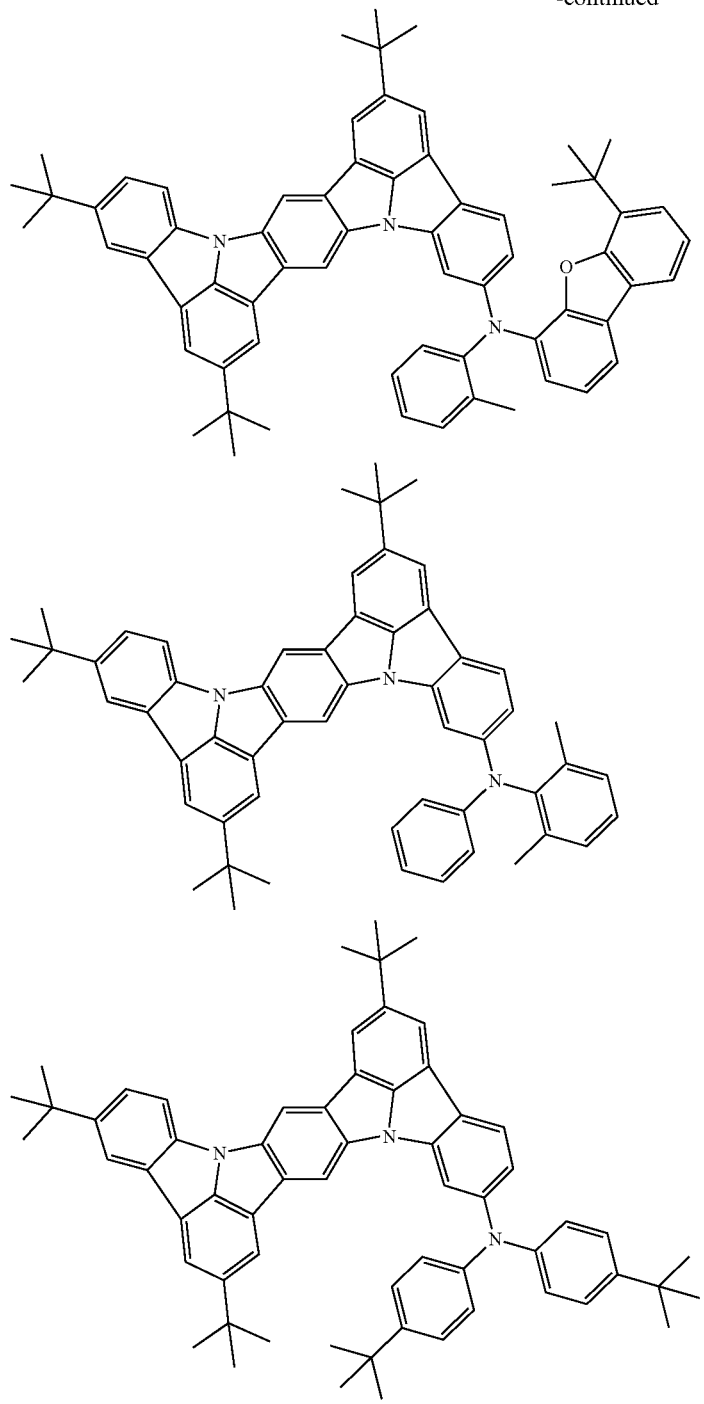

In the present specification, regarding "at least one organic layer disposed between the cathode and the anode", if only one organic layer is present between the cathode and the anode, it means the layer, and if plural organic layers are present between the cathode and the anode, it means at least one layer thereof.

Further, regarding "the at least one organic layer comprises an emitting layer", if only one organic layer is present between the cathode and the anode, it means that the layer is an emitting layer, and if plural organic layers are present, it means that at least one of these layers is an emitting layer.

In one embodiment, the organic EL device has a hole-transporting layer between the anode and the emitting layer.

In one embodiment, the organic EL device has an electron-transporting layer between the cathode and the emitting layer.

In the present specification, regarding the "at least one layer between the emitting layer and the anode", if only one organic layer is present between the emitting layer and the anode, it means that layer, and if plural organic layers are present, it means at least one layer thereof. For example, if two or more organic layers are present between the emitting layer and the anode, an organic layer nearer to the emitting layer is called the "hole-transporting layer", and an organic layer nearer to the anode is called the "hole-injecting layer". Each of the "hole-transporting layer" and the "hole-injecting layer" may be a single layer or may be formed of two or more layers. One of these layers may be a single layer and the other may be formed of two or more layers.

Similarly, regarding the "at least one layer between the emitting layer and the cathode", if only one organic layer is present between the emitting layer and the cathode, it means that layer, and if plural organic layers are present, it means at least one layer thereof. For example, if two or more organic layers are present between the emitting layer and the cathode, an organic layer nearer to the emitting layer is called the "electron-transporting layer", and an organic layer nearer to the cathode is called the "electron-injecting layer". Each of the "electron-transporting layer" and the "electron-injecting layer" may be a single layer or may be formed of two or more layers. One of these layers may be a single layer and the other may be formed of two or more layers.

In one embodiment, the "at least one organic layer" mentioned above comprises the emitting layer, the emitting layer comprises a compound represented by the formulas (1-1) and (1-3) or a compound represented by the formulas (1-2) and (1-3). The compound represented by the formulas (1-1) and (1-3) or a compound represented by the formulas (1-2) and (1-3) can function as a fluorescent emitting material and can enhance the luminous efficiency of the organic EL device.

In one embodiment, the "at least one organic layer" mentioned above comprises the emitting layer, and the emitting layer comprises a compound represented by the formula (3-11). The compound represented by the formula (3-11) can function as a fluorescent emitting material and can enhance the luminous efficiency of the organic EL device.

In one embodiment, the "at least one organic layer" mentioned above comprises the emitting layer, the emitting layer comprises a compound represented by the formula (3-21). The compound represented by the formula (3-21) can function as a fluorescent emitting material and can enhance the luminous efficiency of the organic EL device.

In one embodiment, the "at least one organic layer" mentioned above comprises the emitting layer, the emitting layer comprises a compound represented by the formula (3-31) or (3-32). The compound represented by the formula (3-31) or (3-32) can function as a fluorescent emitting material and can enhance the luminous efficiency of the organic EL device.

In one embodiment, the "at least one organic layer" mentioned above comprises a compound represented by the formulas (1-1) and (1-3) or a compound represented by the formulas (1-2) and (1-3). The compound represented by the formulas (1-1) and (1-3) or the compound represented by the formulas (1-2) and (1-3) can function as a fluorescent emitting material and can enhance the luminous efficiency of the organic EL device.

In one embodiment, the "at least one organic layer" mentioned above comprises a compound represented by formula (3-11). The compound represented by the formula (3-11) is comprised as an emitting material and can enhance the luminous efficiency of the organic EL device.

In one embodiment, the "at least one organic layer" mentioned above comprises a compound represented by formula (3-21). The compound represented by the formula (3-21) is comprised as an emitting material and can enhance the luminous efficiency of the organic EL device.

In one embodiment, the "at least one organic layer" mentioned above comprises a compound represented by formula (3-31) or (3-32). The compound represented by the formula (3-31) or (3-32) is comprised as an emitting material and can enhance the luminous efficiency of the organic EL device.

In one embodiment, the emitting layer further comprises a compound represented by the following formula (10) (hereinafter may be referred to as the compound (10)):

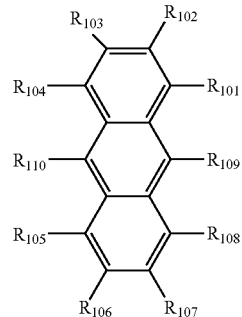

(10)

wherein the formula (10),
one or more pairs of two or more adjacent $R_{101}$ to $R_{110}$ may form a substituted or unsubstituted, saturated or unsaturated ring;

$R_{101}$ to $R_{110}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylene group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{121}$)($R_{122}$)($R_{123}$), —C(=O)$R_{124}$, —COO$R_{125}$, —N($R_{126}$)($R_{127}$), a halogen atom, a cyano group, a nitro group, a substituted or unsubstituted aryl group including 6 to 50 ring carbon atoms, a substituted or unsubstituted monovalent heterocyclic group including 5 to 50 ring atoms, or a group represented by the following formula (31);

$R_{121}$ to $R_{127}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms; when each of $R_{121}$ to $R_{127}$ is present in plural, each of the plural $R_{121}$ to $R_{127}$ may be the same or different;

provided that at least one of $R_{101}$ to $R_{110}$ that do not form the substituted or unsubstituted, saturated or unsaturated ring is a group represented by the following formula (31). If two or more groups represented by the formula (31) are present, each of these groups may be the same or different;

$$-L_{101}-Ar_{101} \quad (31)$$

wherein in the formula (31), $L_{101}$ is a single bond, a substituted or unsubstituted arylene group including 6 to 30 ring carbon atoms or a substituted or unsubstituted divalent heterocyclic group including 5 to 30 ring atoms;

$Ar_{101}$ is a substituted or unsubstituted aryl group including 6 to 50 ring carbon atoms or a substituted or unsubstituted monovalent heterocyclic group including 5 to 50 ring atoms.

Specific examples of each substituent, substituents for "substituted or unsubstituted" and the halogen atom in the compound (10) are the same as those mentioned above.

An explanation will be given on "one or more pairs of two or more adjacent $R_{101}$ to $R_{110}$ may form a substituted or unsubstituted, saturated or unsaturated ring".

The "one pair of two or more adjacent $R_{101}$ to $R_{110}$" is a combination of $R_{101}$ and $R_{102}$, $R_{102}$ and $R_{103}$, $R_{103}$ and $R_{104}$, $R_{105}$ and $R_{106}$, $R_{106}$ and $R_{107}$, $R_{107}$ and $R_{108}$, $R_{108}$ and $R_{10}$, $R_{101}$ and $R_{102}$ and $R_{103}$ or the like, for example.

The substituent in "substituted" in the "substituted or unsubstituted" for the saturated or unsaturated ring is the same as those for "substituted or unsubstituted" mentioned in the formula (10).

The "saturated or unsaturated ring" means, when $R_{101}$ and $R_{102}$ form a ring, for example, a ring formed by a carbon atom with which $R_{101}$ is bonded, a carbon atom with which $R_{102}$ is bonded and one or more arbitrary elements. Specifically, when a ring is formed by $R_{101}$ and $R_{102}$, when an unsaturated ring is formed by a carbon atom with which $R_{101}$ is bonded, a carbon atom with $R_{102}$ is bonded and four carbon atoms, the ring formed by $R_{101}$ and $R_{102}$ is a benzene ring.

The "arbitrary element" is preferably a C element, a N element, an O element and a S element. In the arbitrary element (C element or N element, for example), atomic bondings that do not form a ring may be terminated by a hydrogen atom, or the like.

The "one or more arbitrary element" is preferably 2 or more and 15 or less, more preferably 3 or more and 12 or less, and further preferably 3 or more and 5 or less arbitrary elements.

For example, $R_{101}$ and $R_{102}$ may form a ring, and simultaneously, $R_{105}$ and $R_{106}$ may form a ring. In this case, the compound represented by the formula (10) is a compound represented by the following formula (10A), for example:

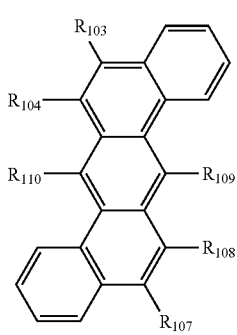

(10A)

In one embodiment, $R_{101}$ to $R_{110}$ are independently a hydrogen atom, a substituted or unsubstituted alkyl group including 1 to 50 carbon atoms, a substituted or unsubstituted aryl group including 6 to 50 ring carbon atoms, a substituted or unsubstituted heterocyclic group including 5 to 50 ring atoms or a group represented by the formula (31).

In one embodiment, $R_{101}$ to $R_{110}$ are independently a hydrogen atom, a substituted or unsubstituted aryl group including 6 to 50 ring carbon atoms, a substituted or unsubstituted heterocyclic group including 5 to 50 ring atoms or a group represented by the formula (31).

In one embodiment, $R_{101}$ to $R_{110}$ are independently a hydrogen atom, a substituted or unsubstituted aryl group including 6 to 18 ring carbon atoms, a substituted or unsubstituted heterocyclic group including 5 to 18 ring atoms or a group represented by the formula (31).

In one embodiment, at least one of $R_{109}$ and $R_{110}$ is a group represented by the formula (31).

In one embodiment, $R_{109}$ and $R_{110}$ are independently a group represented by the formula (31).

In one embodiment, the compound (10) is a compound represented by the following formula (10-1):

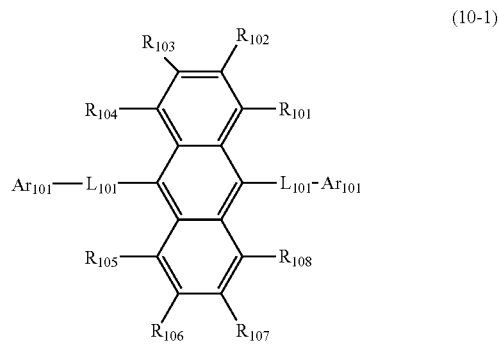

(10-1)

wherein in the formula (10-1), $R_{101}$ to $R_{108}$, $L_{101}$ and $Ar_{101}$ are as defined in the formula (10).

In one embodiment, the compound (10) is a compound represented by the following formula (10-2):

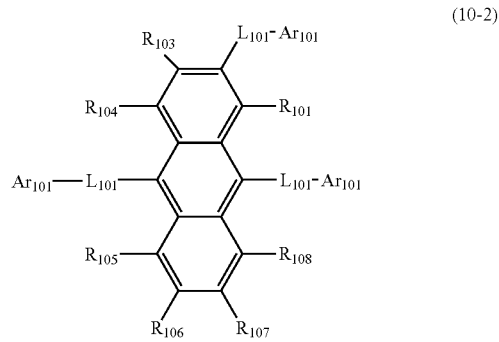

(10-2)

wherein in the formula (10-2), $R_{101}$, $R_{103}$ to $R_{108}$, $L_{101}$ and $Ar_{101}$ are as defined in the formula (10).

In one embodiment, the compound (10) is a compound represented by the following formula (10-3):

(10-3)

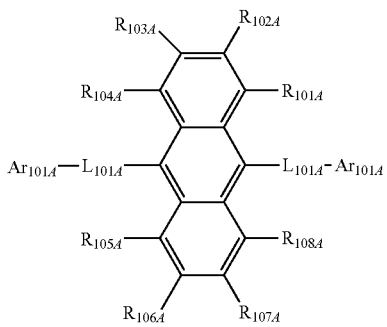

wherein in the formula (10-3), $R_{101A}$ to $R_{108A}$ are independently a hydrogen atom or a substituted or unsubstituted aryl group including 6 to 50 ring carbon atoms;

$L_{101A}$ is a single bond or a substituted or unsubstituted arylene group including 6 to 30 ring carbon atoms, and the two $L_{101A}$s may be the same or different;

$Ar_{101A}$ is a substituted or unsubstituted aryl group including 6 to 50 ring carbon atoms, and the two $Ar_{101A}$s may be the same or different.

In one embodiment, the compound (10) is a compound represented by the following formula (10-4):

(10-4)

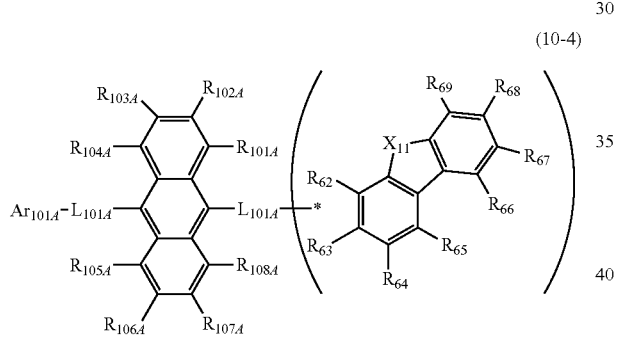

wherein in the formula (10-4), $L_{101}$ and $Ar_{101}$ are as defined in the formula (10);

$R_{101A}$ to $R_{108A}$ are independently a hydrogen atom or a substituted or unsubstituted aryl group including 6 to 50 ring carbon atoms;

$X_{11}$ is O, S, or $N(R_{61})$;

$R_{61}$ is a hydrogen atom, a substituted or unsubstituted alkyl group including 1 to 50 carbon atoms or a substituted or unsubstituted aryl group including 6 to 50 ring carbon atoms;

one of $R_{62}$ to $R_{69}$ is an atomic bonding that is bonded with $L_{101}$;

one or more pairs of adjacent $R_{62}$ to $R_{69}$ that are not bonded with $L_{101}$ may be bonded with each other to form a substituted or unsubstituted, saturated or unsaturated ring; and $R_{62}$ to $R_{69}$ that are not bonded with $L_{101}$ and do not form the substituted or unsubstituted, saturated or unsaturated ring are independently a hydrogen atom, a substituted or unsubstituted alkyl group including 1 to 50 carbon atoms or a substituted or unsubstituted aryl group including 6 to 50 ring carbon atoms.

In one embodiment, the compound (10) is a compound represented by the following formula (10-4A):

(10-4A)

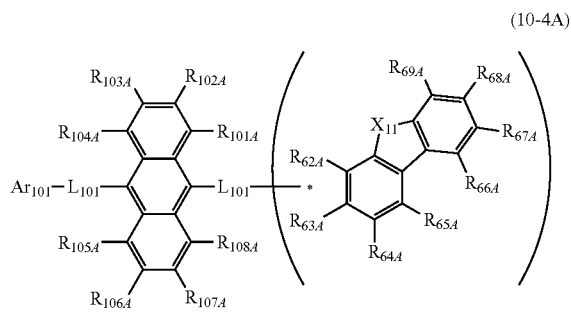

wherein in the formula (10-4A), $L_{101}$ and $Ar_{101}$ are as defined in the formula (10);

$R_{101A}$ to $R_{108A}$ are independently a hydrogen atom or a substituted or unsubstituted aryl group including 6 to 50 ring carbon atoms;

$X_{11}$ is O, S or $N(R_{61})$;

$R_{61}$ is a hydrogen atom, a substituted or unsubstituted alkyl group including 1 to 50 carbon atoms or a substituted or unsubstituted aryl group including 6 to 50 ring carbon atoms; one or more pairs of adjacent two or more of $R_{62A}$ to $R_{69A}$ may form a substituted or unsubstituted, saturated or unsaturated ring, and adjacent two of $R_{62A}$ to $R_{69A}$ form a ring represented by the following formula (10-4A-1); and $R_{62A}$ to $R_{69A}$ that do not form a substituted or unsubstituted, saturated or unsaturated ring are independently a hydrogen atom, a substituted or unsubstituted alkyl group including 1 to 50 carbon atoms or a substituted or unsubstituted aryl group including 6 to 50 ring carbon atoms.

(10-4A-1)

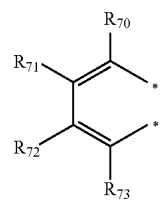

wherein in the formula (10-4A-1), each of the two atomic bondings * is bonded with adjacent two of $R_{62A}$ to $R_{69A}$;

one of $R_{70}$ to $R_{73}$ is an atomic bonding that is bonded with $L_{101}$; and $R_{70}$ to $R_{73}$ that are not bonded with $L_{101}$ are independently a hydrogen atom, a substituted or unsubstituted alkyl group including 1 to 50 carbon atoms or a substituted or unsubstituted aryl group including 6 to 50 ring carbon atoms.

In one embodiment, the compound (10) is a compound represented by the following formula (10-6):

(10-6)

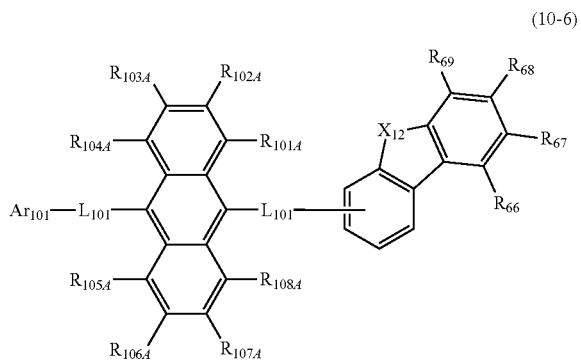

wherein in the formula (10-6),
$L_{101}$ and $Ar_{101}$ are as defined in the formula (10);
$R_{101A}$ to $R_{108A}$ are as defined in the formula (10-4);
$R_{66}$ to $R_{69}$ are as defined in the formula (10-4); and
$X_{12}$ is O or S.

In one embodiment, the compound represented by the formula (10-6) is a compound represented by the following formula (10-6H):

(10-6H)

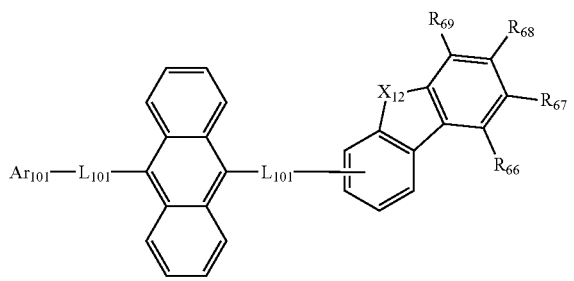

wherein in the formula (10-6H),
$L_{101}$ and $Ar_{101}$ are as defined in the formula (10);
$R_{66}$ to $R_{69}$ are as defined in the formula (10-4); and
$X_{12}$ is O or S.

In one embodiment, the compound represented by the formulas (10-6) and (10-6H) is a compound represented by the following formula (10-6Ha):

(10-6Ha)

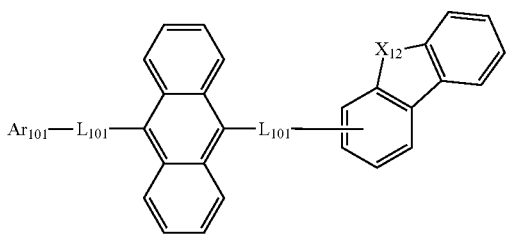

wherein in the formula (10-6Ha),
$L_{101}$ and $Ar_{101}$ are as defined in the formula (10); and
$X_{12}$ is O or S.

In one embodiment, the compound represented by the formulas (10-6), (10-6H) and (10-6Ha) is a compound represented by the following formula (10-6Ha-1) or (10-6Ha-2):

(10-6Ha-1)

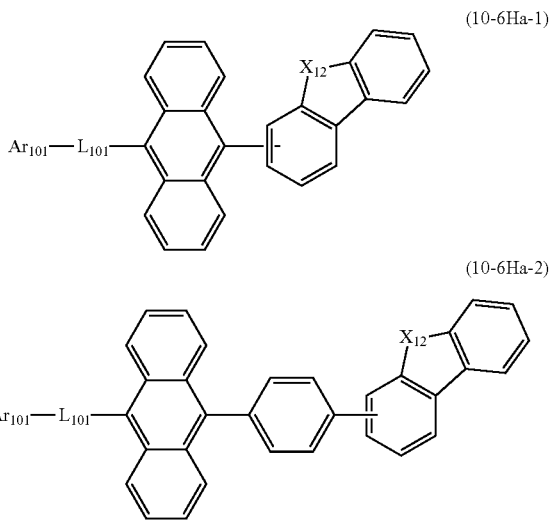

(10-6Ha-2)

wherein in the formula (10-6Ha-1) and (10-6Ha-2),
$L_{101}$ and $Ar_{101}$ are as defined in the formula (10); and
$X_{12}$ is O or S.

In one embodiment, the compound (10) is a compound represented by the following formula (10-7):

(10-7)

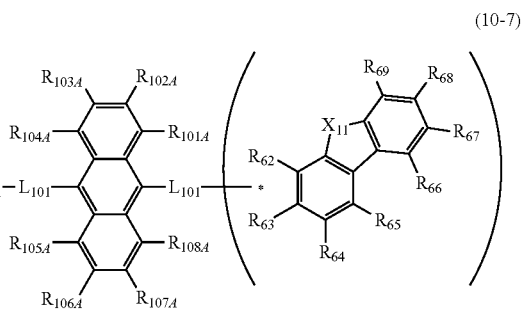

wherein in the formula (10-7),
$L_{101}$ and $Ar_{101}$ are as defined in the formula (10);
$R_{101A}$ to $R_{108A}$ are as defined in the formula (10-4);
$X_{11}$ is as defined in the formula (10-4); and
$R_{62}$ to $R_{69}$ are as defined in the formula (10-4), provided that any one pair of $R_{66}$ and $R_{67}$, $R_{67}$ and $R_{68}$, and $R_{68}$ and $R_{69}$ are bonded with each other to form a substituted or unsubstituted, saturated or unsaturated ring.

In one embodiment, the compound (10) is a compound represented by the following formula (10-7H):

(10-7H)

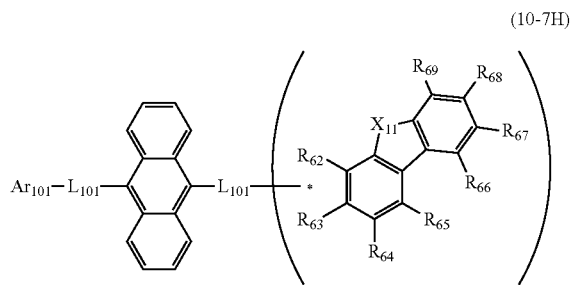

wherein in the formula (10-7H),
$L_{101}$ and $Ar_{101}$ are as defined in the formula (10);
$X_{11}$ is as defined in the formula (10-4); and $R_{62}$ to $R_{69}$ are as defined in the formula (10-4), provided that any one pair of $R_{66}$ and $R_{67}$, $R_{67}$ and $R_{68}$, and $R_{68}$ and $R_{69}$ are bonded with each other to form a substituted or unsubstituted, saturated or unsaturated ring.

In one embodiment, the compound (10) is a compound represented by the following formula (10-8):

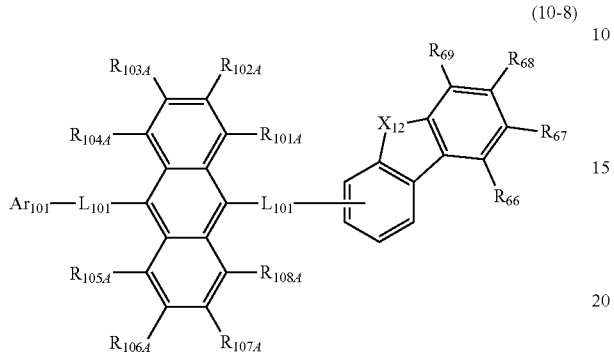

(10-8)

wherein in the formula (10-8), $L_{101}$ and $Ar_{101}$ are as defined in the formula (10);

$R_{101A}$ to $R_{108A}$ are as defined in the formula (10-4);

$X_{12}$ is O or S; and $R_{66}$ to $R_{69}$ are as defined in the formula (10-4), provided that any one pair of $R_{66}$ and $R_{67}$, $R_{67}$ and $R_{68}$, as well as $R_{68}$ and $R_{69}$ are bonded with each other to form a substituted or unsubstituted, saturated or unsaturated ring.

In one embodiment, the compound represented by the formula (10-8) is a compound represented by the following formula (10-8H):

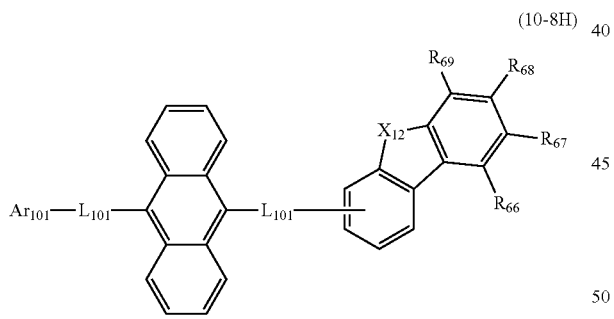

(10-8H)

In the formula (10-8H), $L_{101}$ and $Ar_{101}$ are as defined in the formula (10).

$R_{66}$ to $R_{69}$ are as defined in the formula (10-4), provided that any one pair of $R_{66}$ and $R_{67}$, $R_{67}$ and $R_{68}$, as well as $R_{68}$ and $R_{69}$ are bonded with each other to form a substituted or unsubstituted, saturated or unsaturated ring. Any one pair of $R_{66}$ and $R_{67}$, $R_{67}$ and Rea, as well as $R_{68}$ and $R_{69}$ may preferably be bonded with each other to form an unsubstituted benzene ring; and $X_{12}$ is O or S.

In one embodiment, as for the compound represented by the formula (10-7), (10-8) or (10-8H), any one pair of $R_{66}$ and $R_{67}$, $R_{67}$ and Rea, as well as $R_{68}$ and $R_{69}$ are bonded with each other to form a ring represented by the following formula (10-8-1) or (10-8-2), and $R_{66}$ to $R_{69}$ that do not form the ring represented by the formula (10-8-1) or (10-8-2) do not form a substituted or unsubstituted, saturated or unsaturated ring.

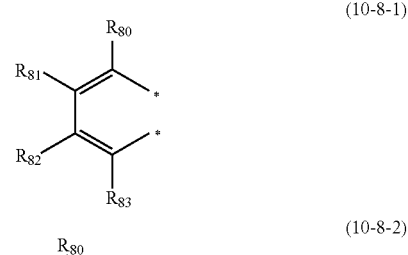

(10-8-1)

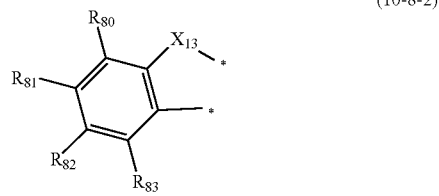

(10-8-2)

wherein in the formulas (10-8-1) and (10-8-2), the two atomic bondings * are independently bonded with one pair of $R_{66}$ and $R_{67}$, $R_{67}$ and $R_{68}$, or $R_{68}$ and $R_{69}$;

$R_{80}$ to $R_{83}$ are independently a hydrogen atom, a substituted or unsubstituted alkyl group including 1 to 50 carbon atoms or a substituted or unsubstituted aryl group including 6 to 50 ring carbon atoms; and $X_{13}$ is O or S.

In one embodiment, the compound (10) is a compound represented by the following formula (10-9):

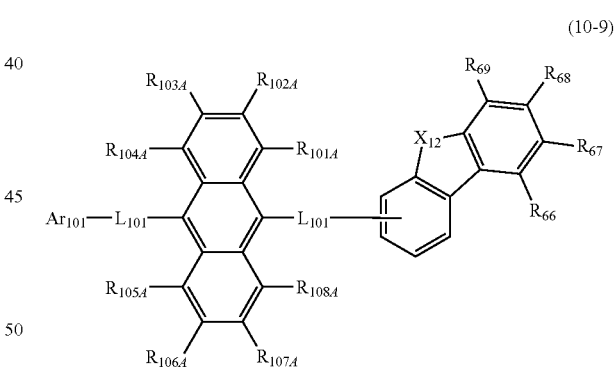

(10-9)

wherein in the formula (10-9), $L_{101}$ and $Ar_{101}$ are as defined in the formula (10);

$R_{101A}$ to $R_{108A}$ are as defined in the formula (10-4);

$R_{66}$ to $R_{69}$ are as defined in the formula (10-4), provided that $R_{66}$ and $R_{67}$, $R_{67}$ and $R_{68}$, as well as $R_{68}$ and $R_{69}$ are not bonded with each other and do not form a substituted or unsubstituted, saturated or unsaturated ring; and $X_{12}$ is O or S.

In one embodiment, the compound (10) is selected from the group consisting of compounds represented by the following formulas (10-10-1) to (10-10-4).

(10-10-1)

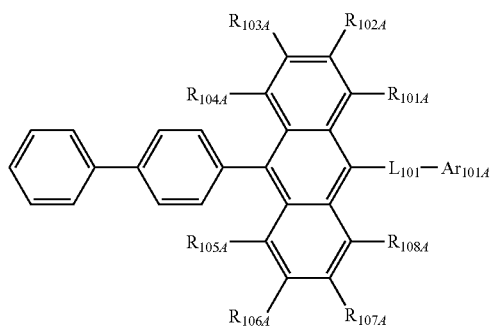

(10-10-2)

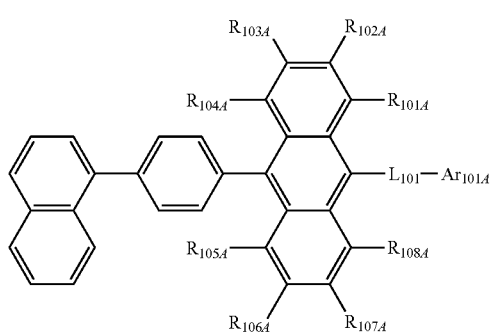

(10-10-3)

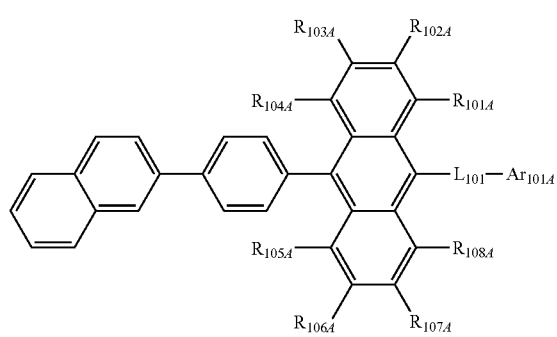

(10-10-4)

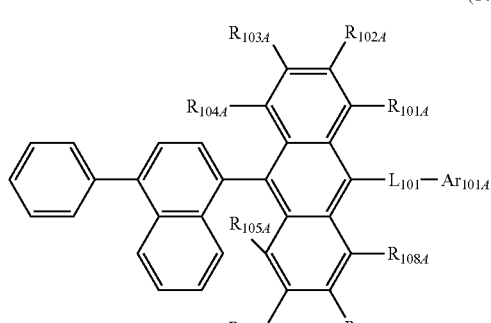

In the formulas (10-10-1) to (10-10-4), $L_{101A}$, $Ar_{101A}$ and $R_{101A}$ to $R_{108A}$ are as defined in the formula (10-3).

In one embodiment, the compound represented by the above formulas (10-10-1) to (10-10-4) is a compound represented by the following formulas (10-10-1H) to (10-10-4H):

(10-10-1H)

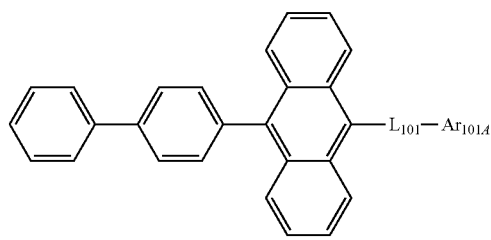

(10-10-2H)

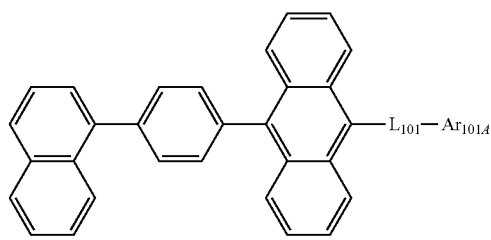

(10-10-3H)

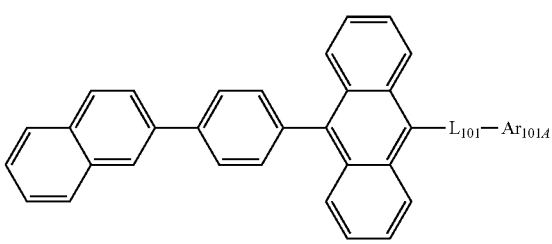

(10-10-4H)

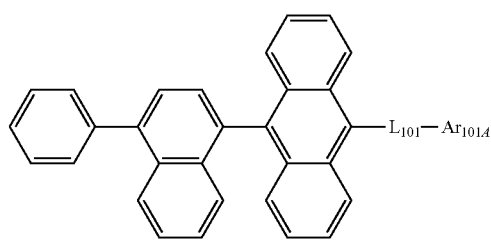

In the formulas (10-10-1H) to (10-10-4H), $L_{101A}$ and $Ar_{101A}$ are as defined in the formula (10-3).

As for the compound represented by the formula (10), the following compounds can be given as specific examples.

441
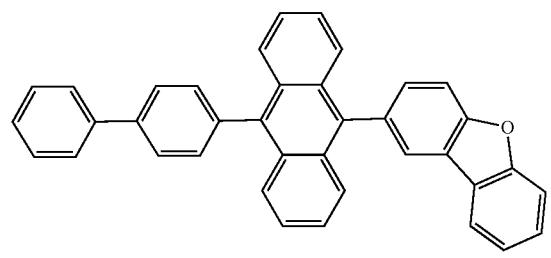
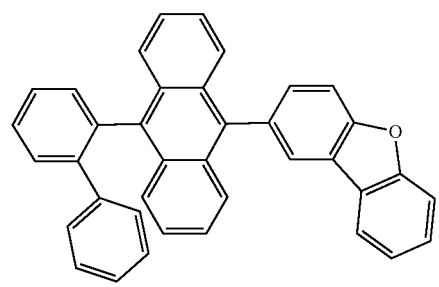
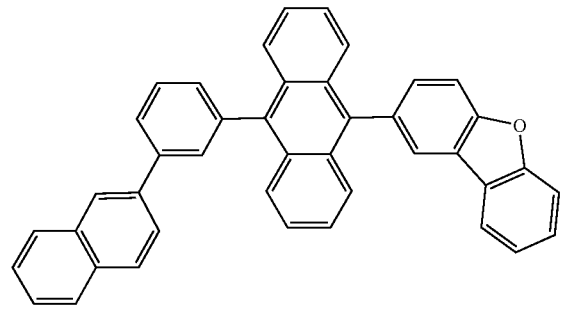
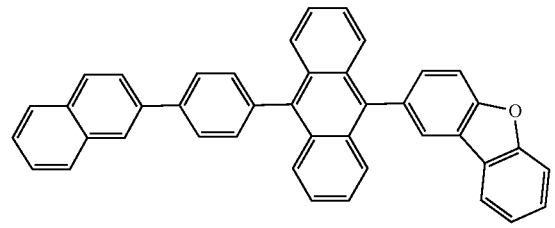
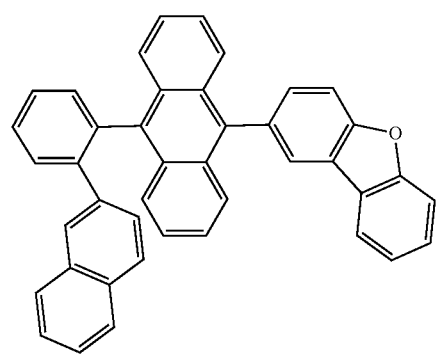
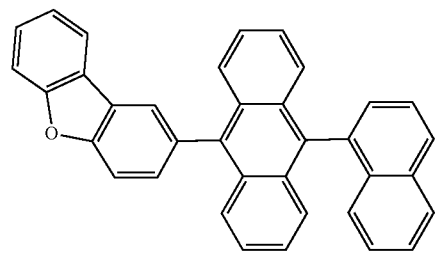
442
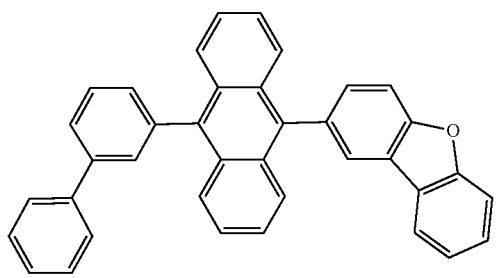
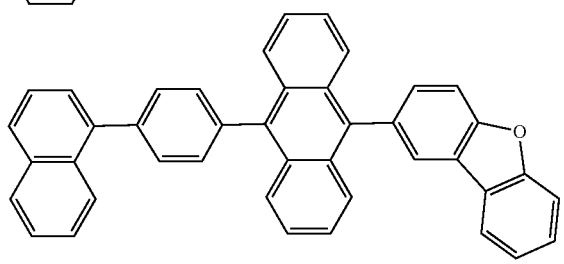
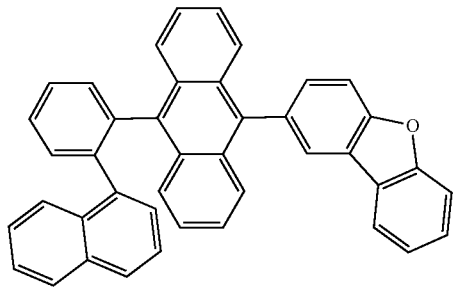
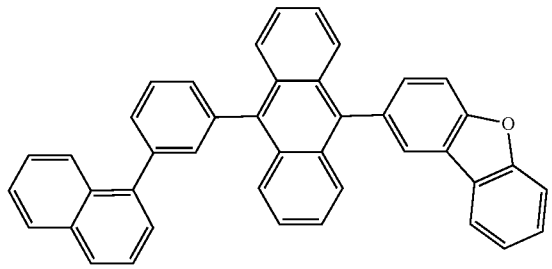
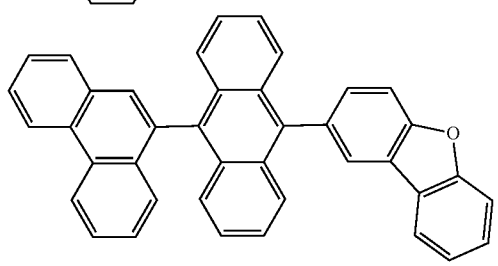
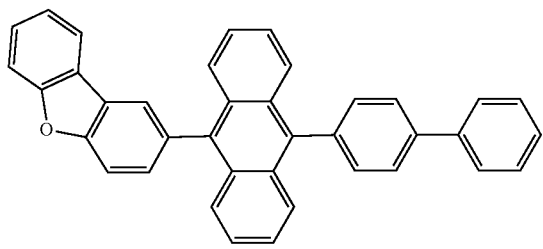

443
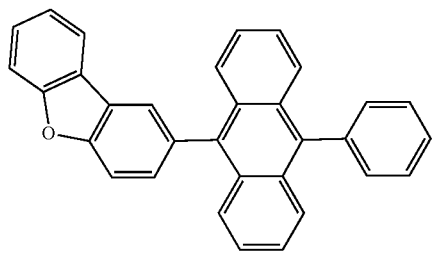
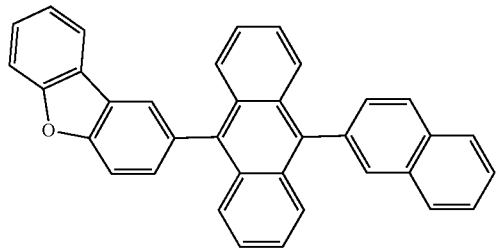
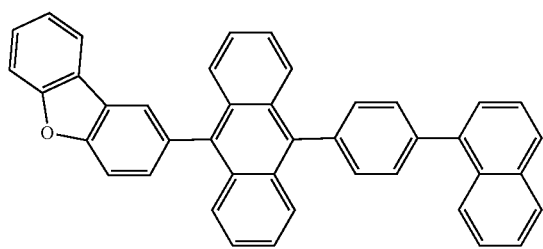
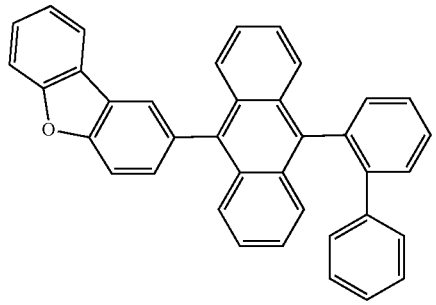
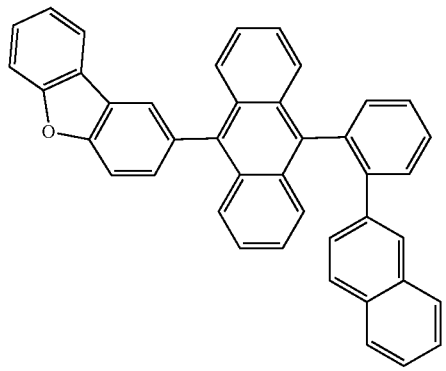
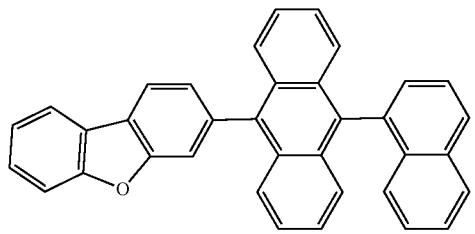
444
-continued
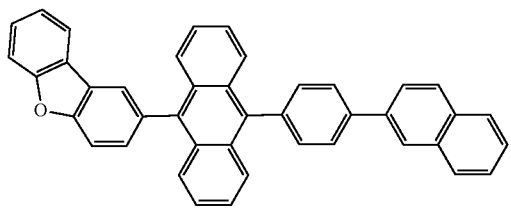
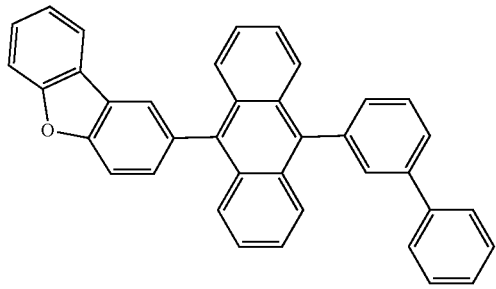
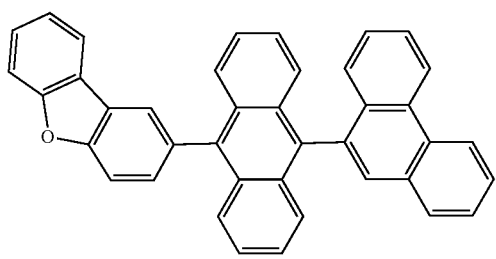
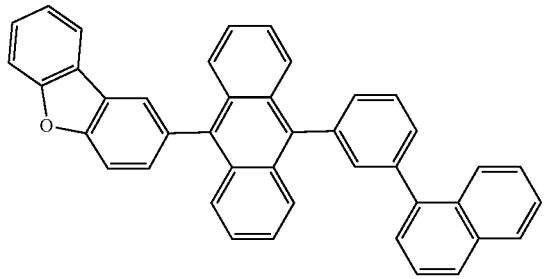
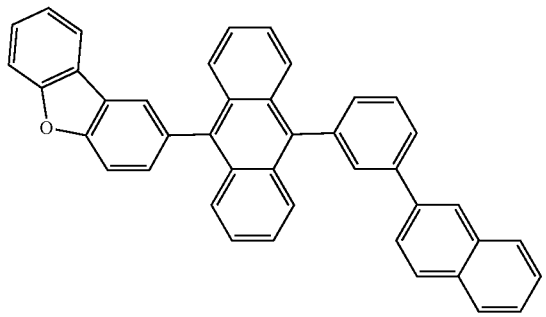
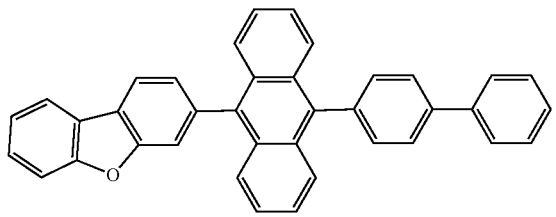

-continued
445
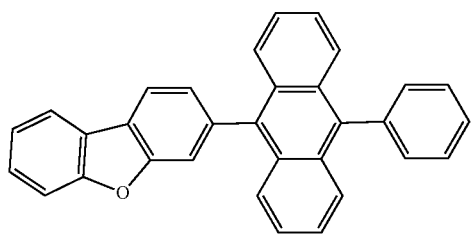
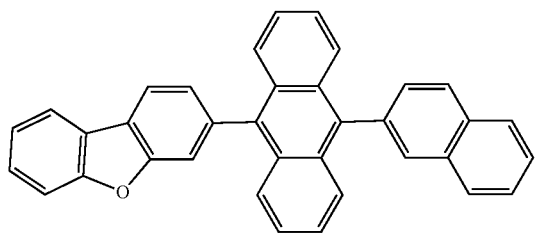
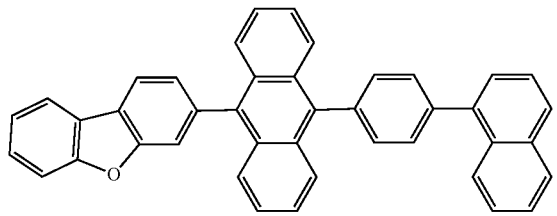
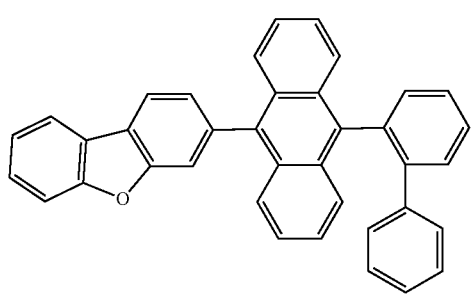
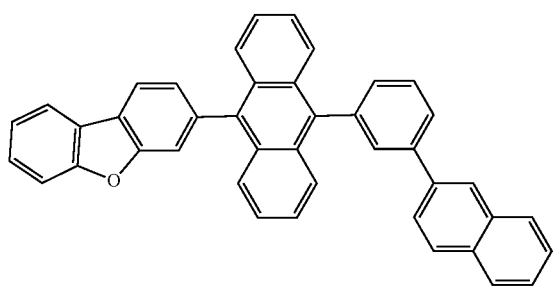
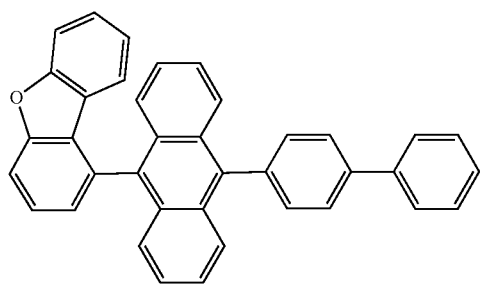
446
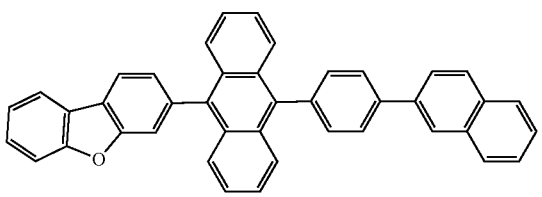
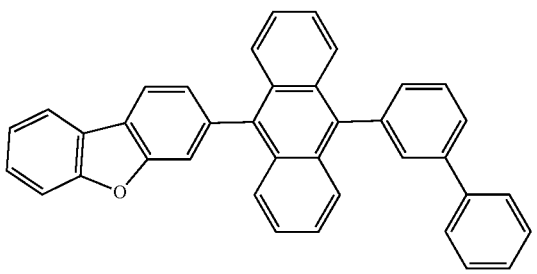
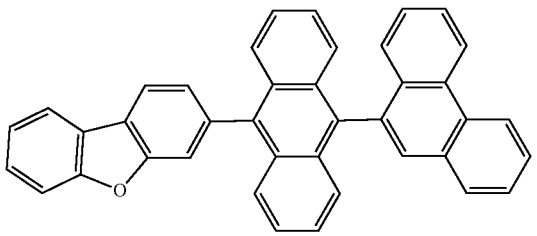
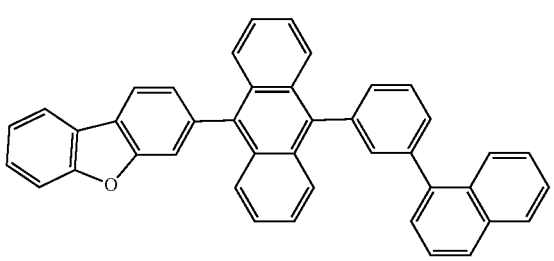
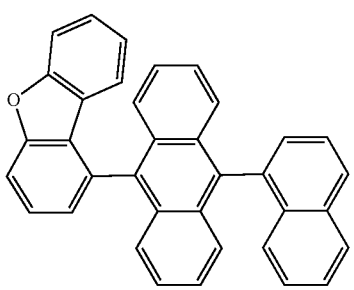
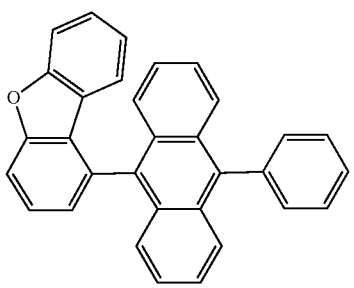

447
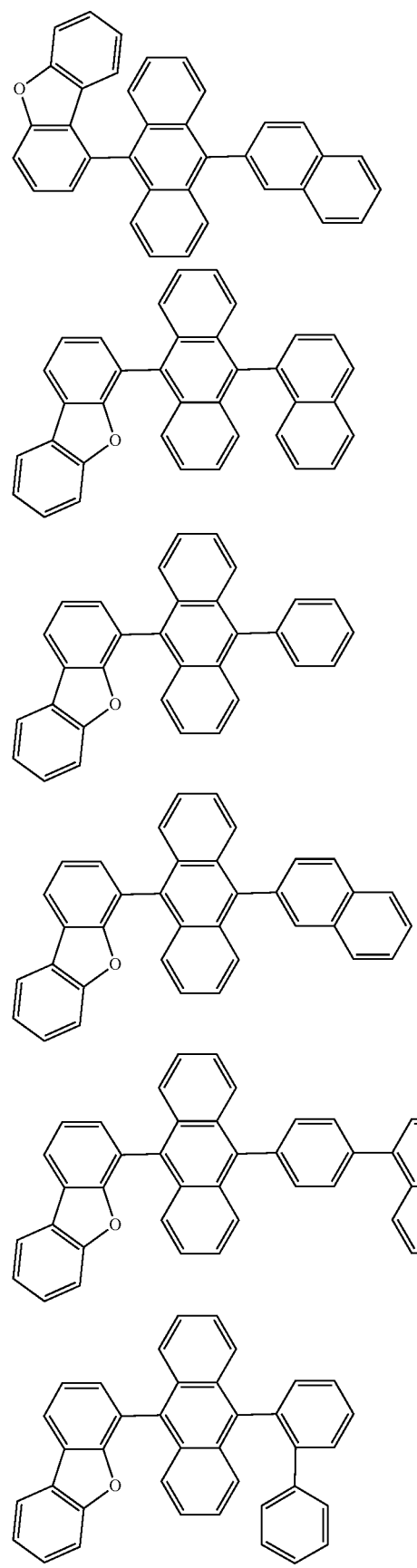
448
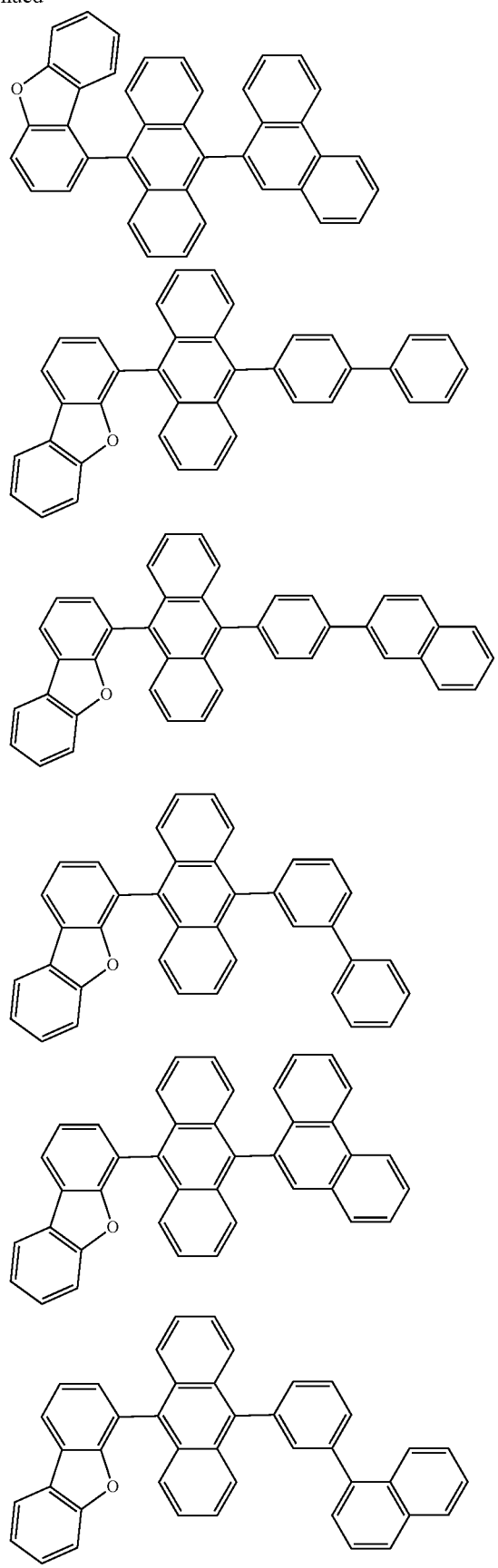

-continued
449
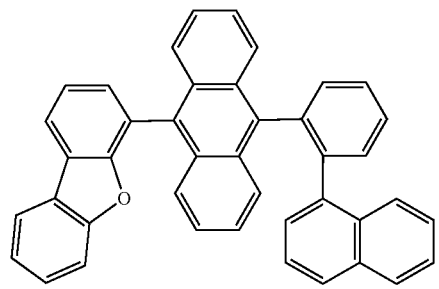
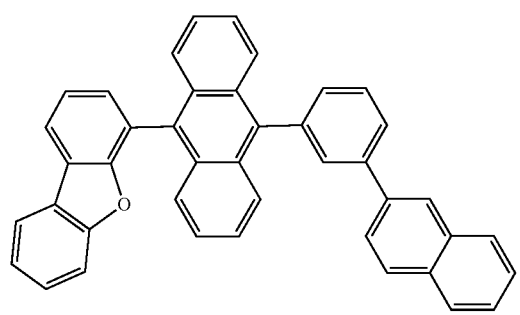
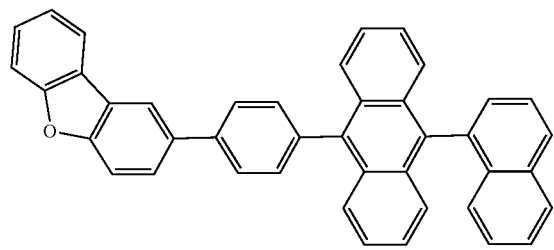
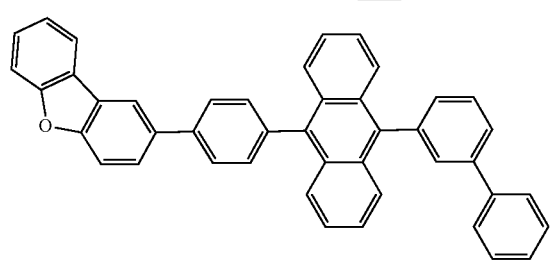
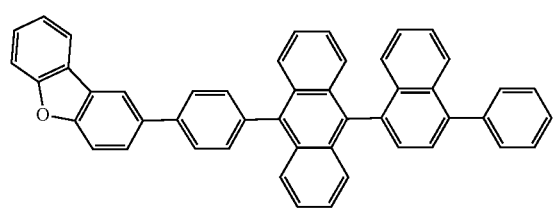
450
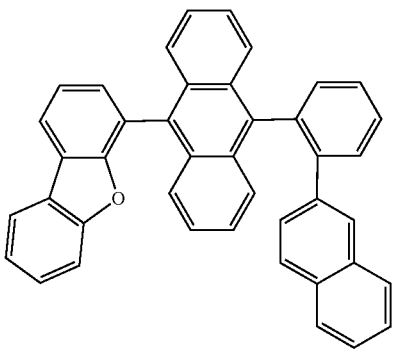
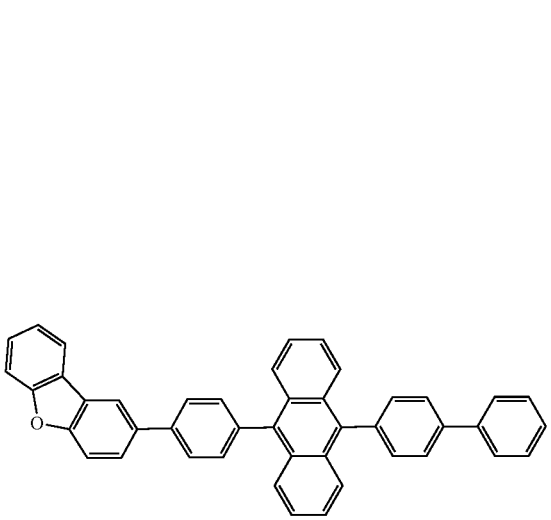
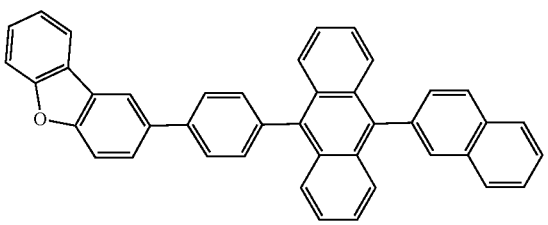
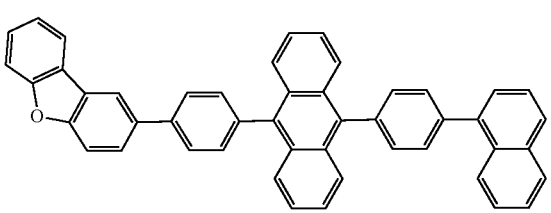
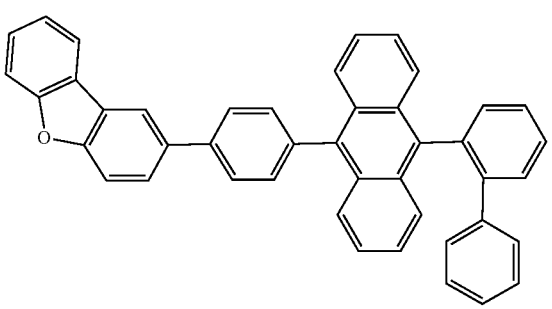

451 452
-continued
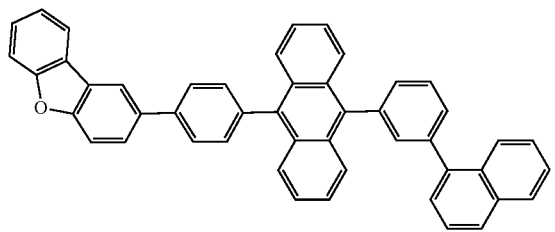 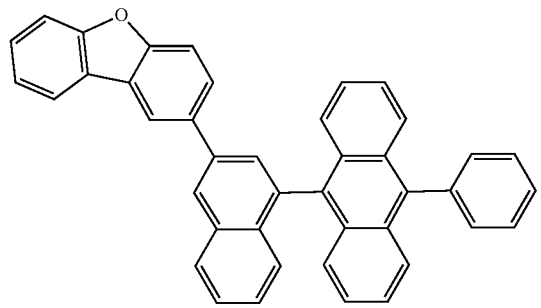
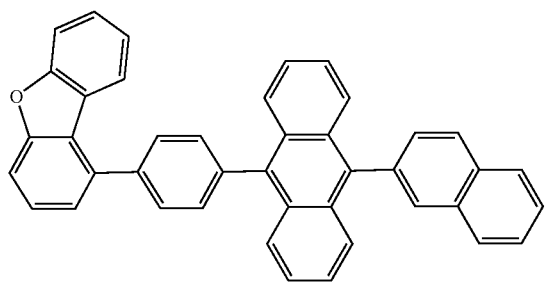 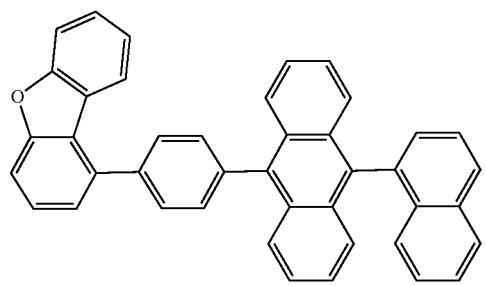
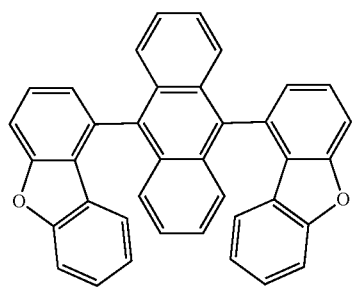 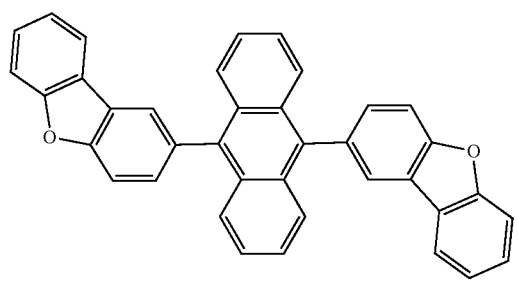
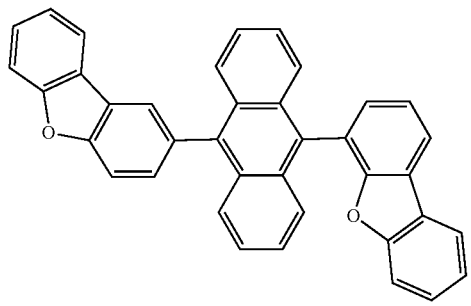
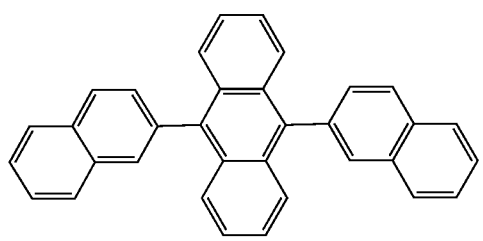 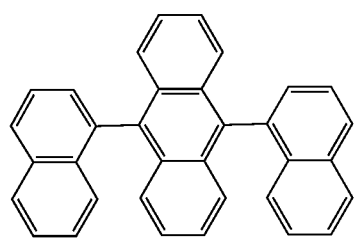
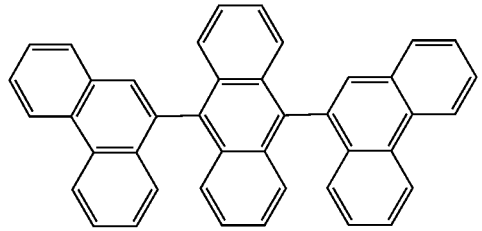 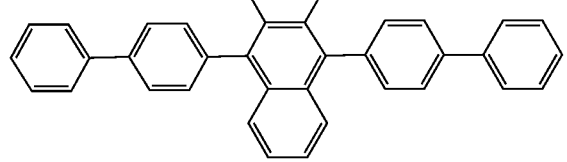

-continued
| 453 | 454 |
|---|---|
| 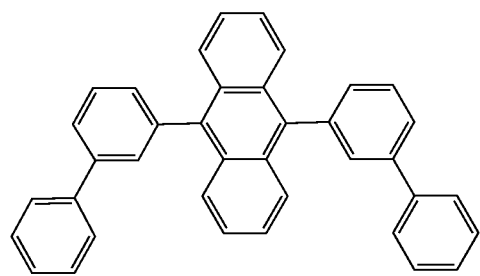 | 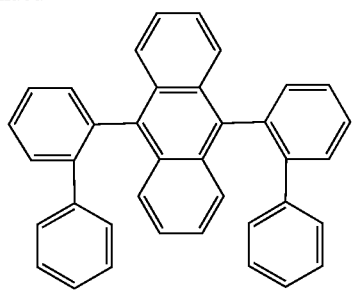 |
| 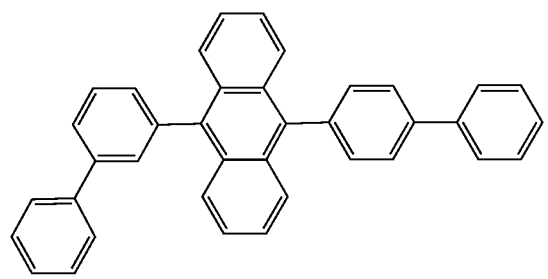 | |
| 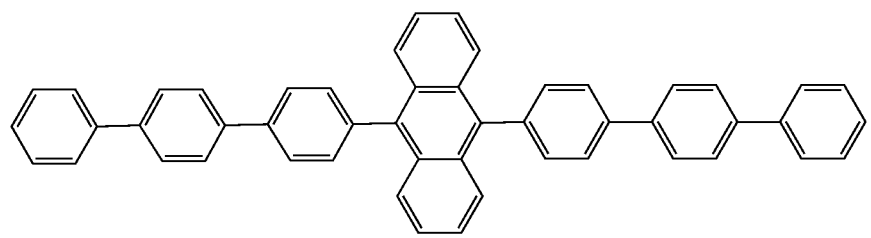 | |
| 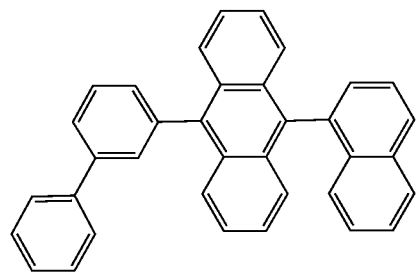 | 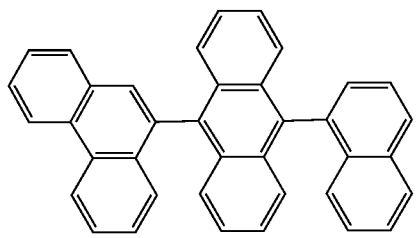 |
| 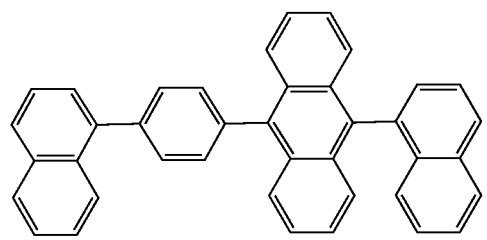 | 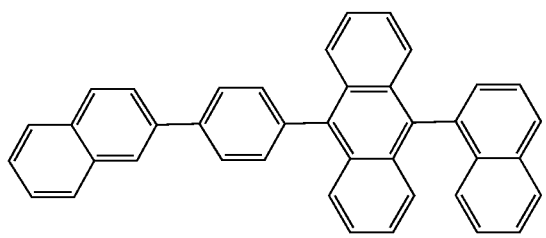 |
| 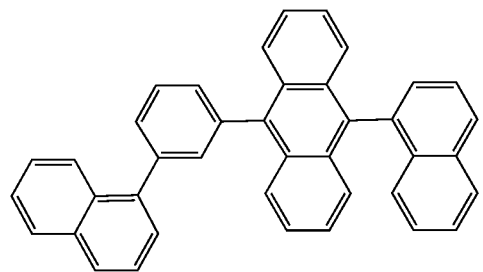 | 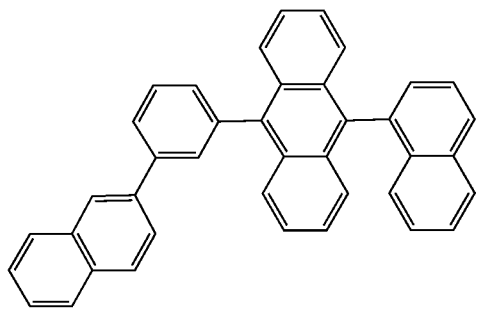 |

455 456
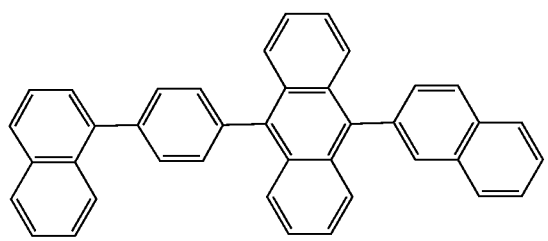 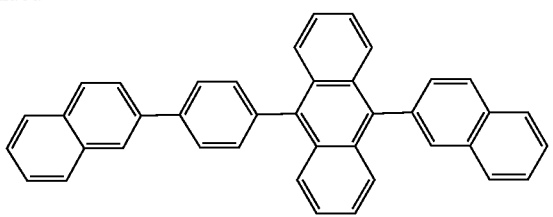
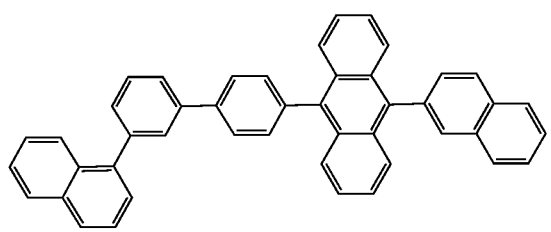 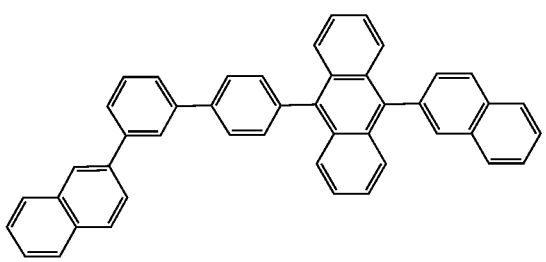
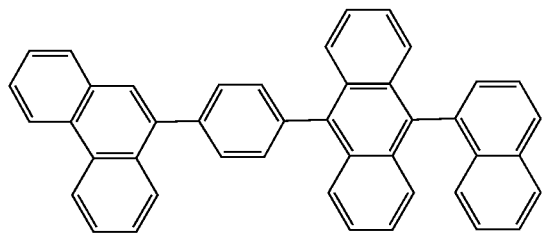 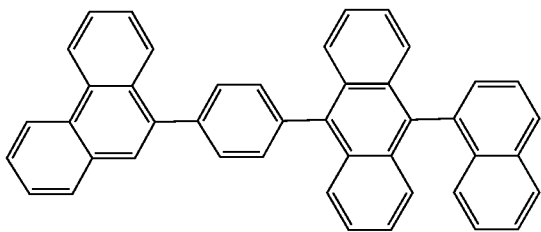
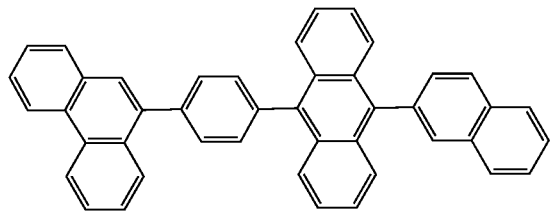 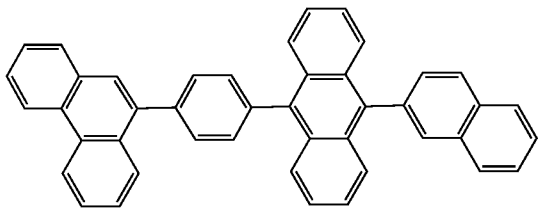
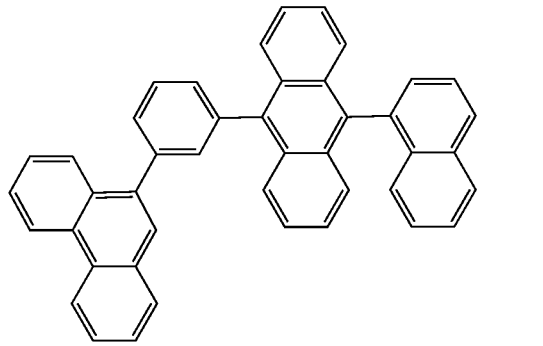 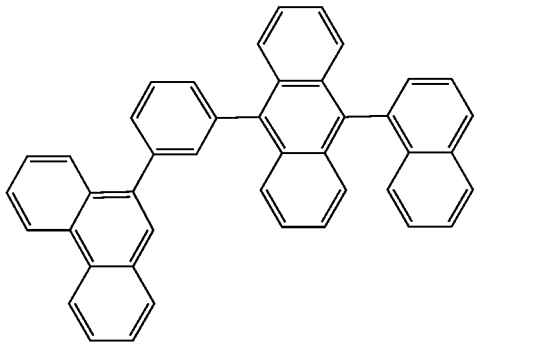
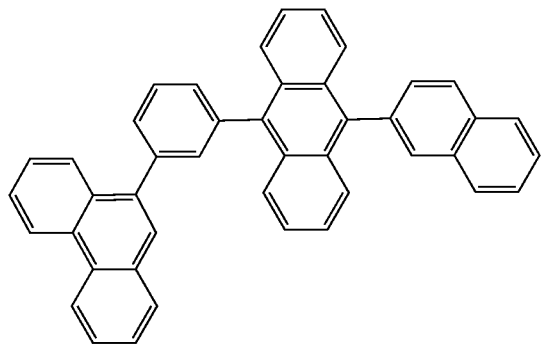 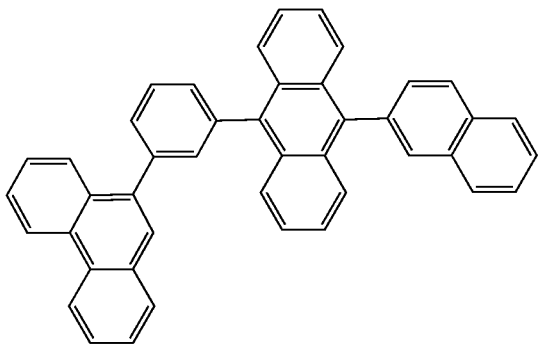

-continued
| 457 | 458 |
|---|---|
| 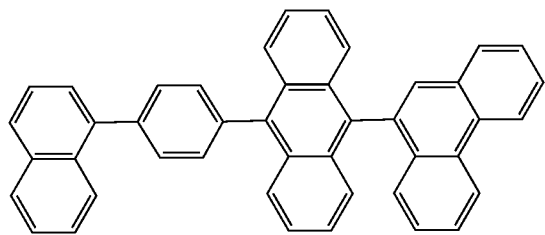 | 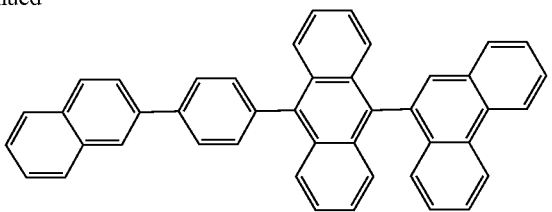 |
| 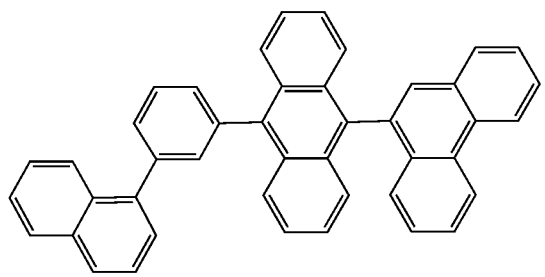 | 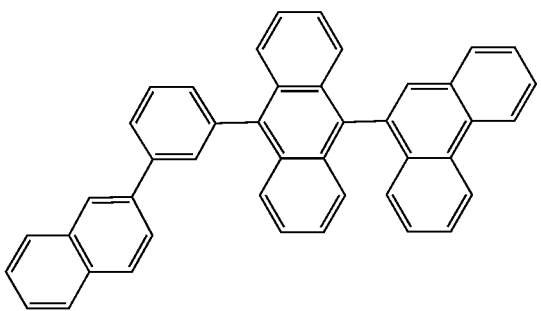 |
| 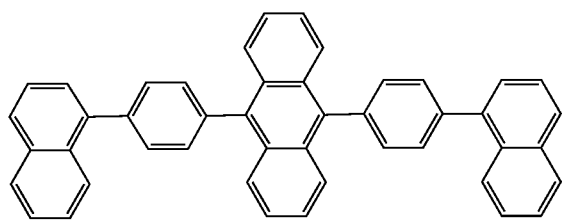 | 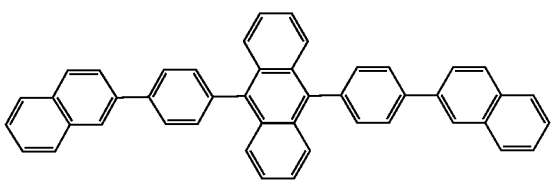 |
| 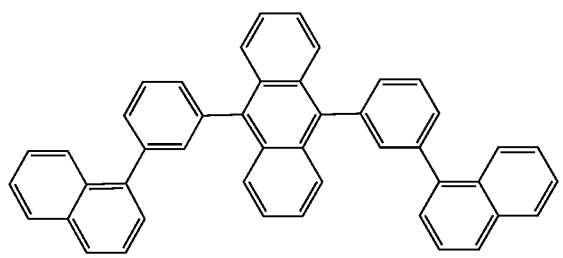 | 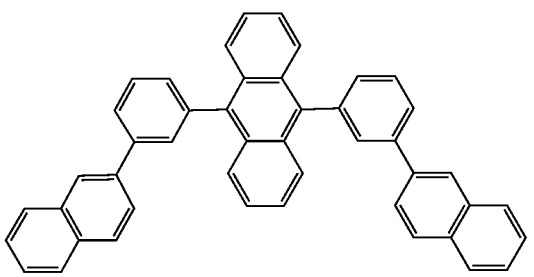 |
| 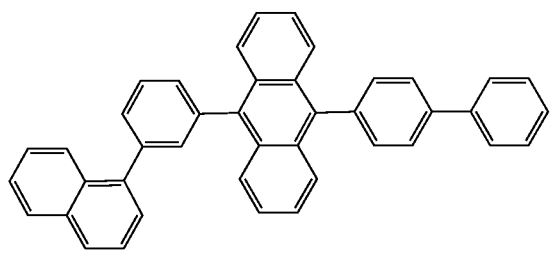 | 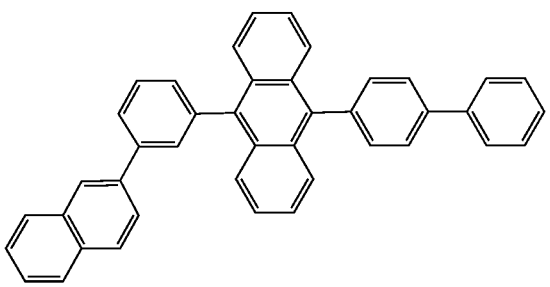 |
| 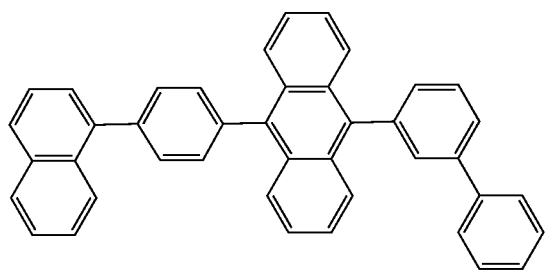 | 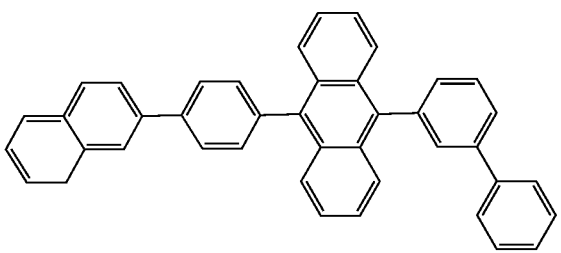 |

459
460
-continued
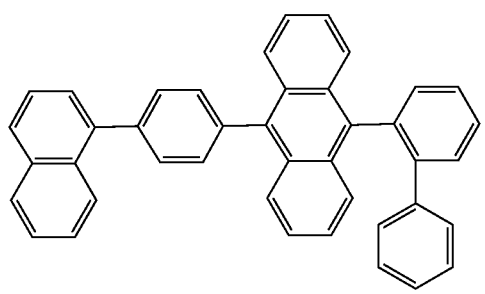
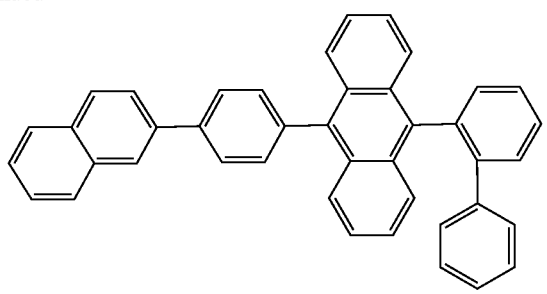
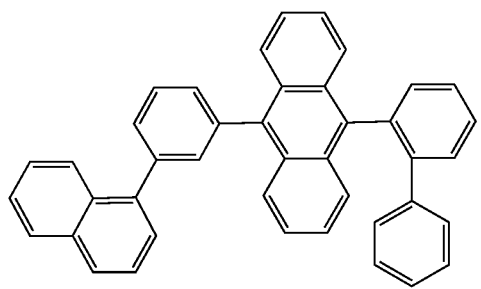
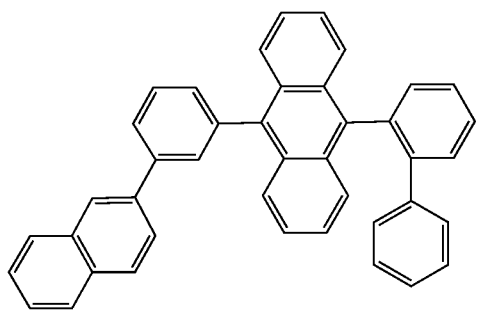
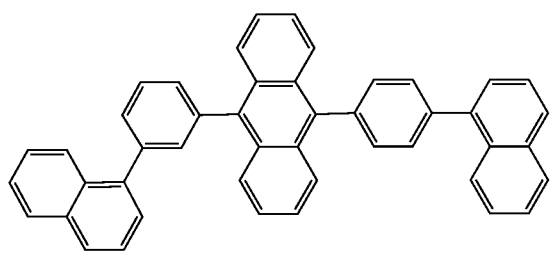
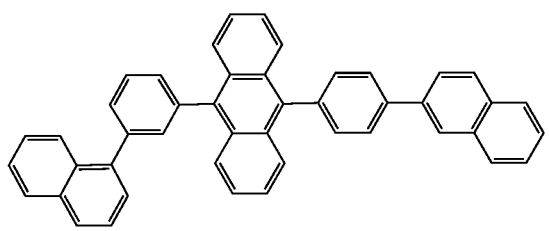
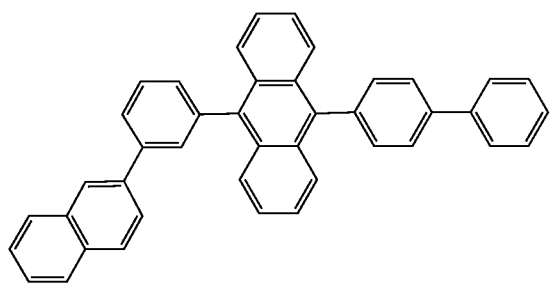
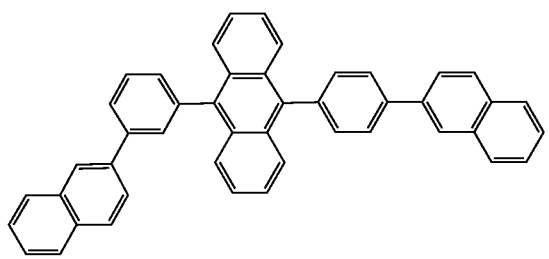
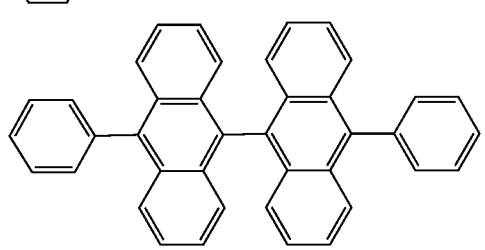
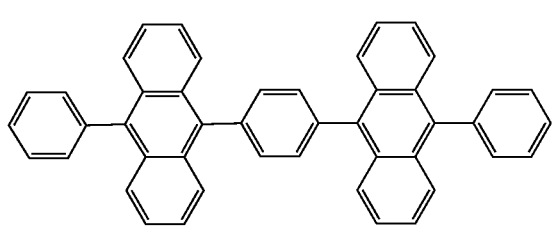
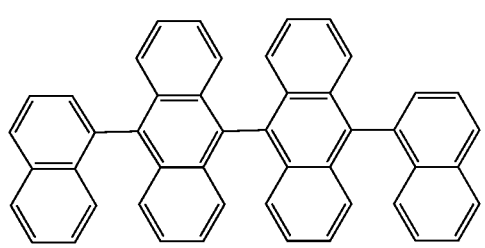
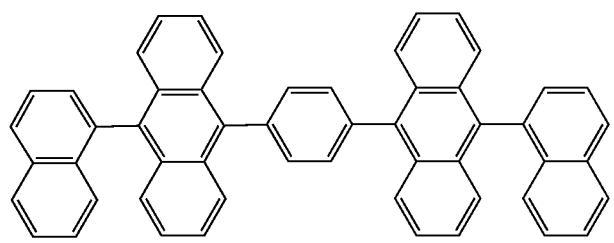

-continued
461
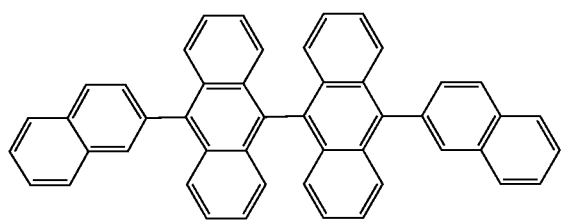
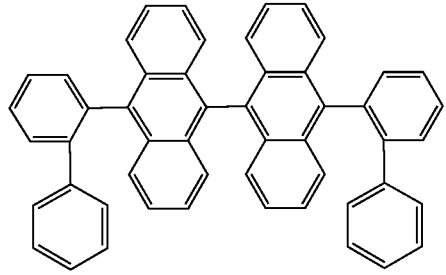
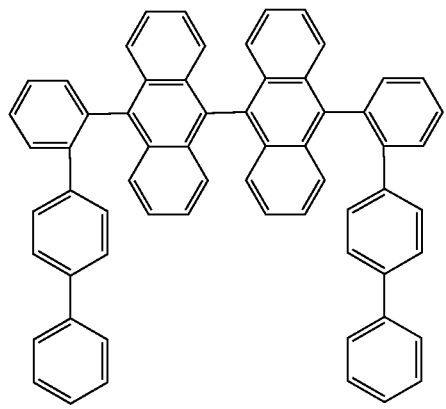
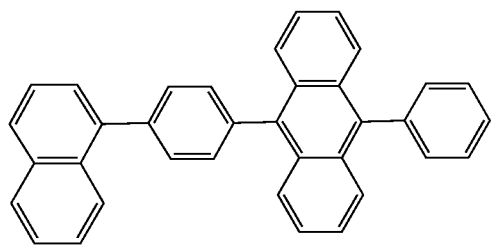
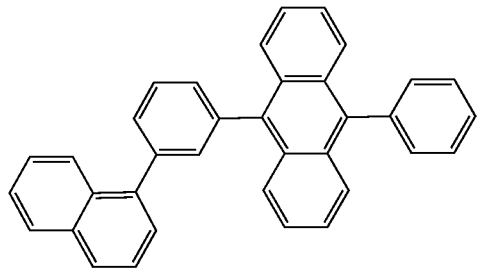
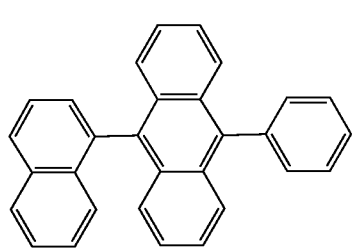
462
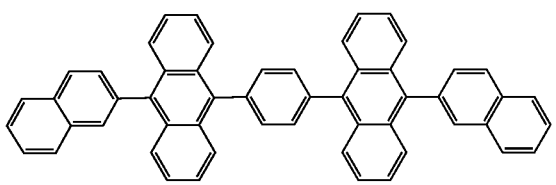
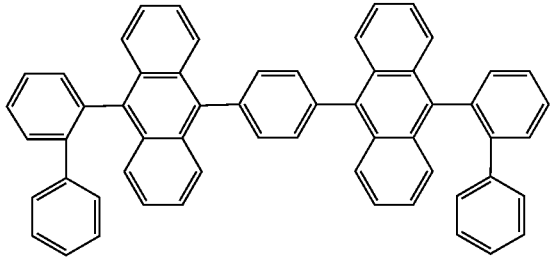
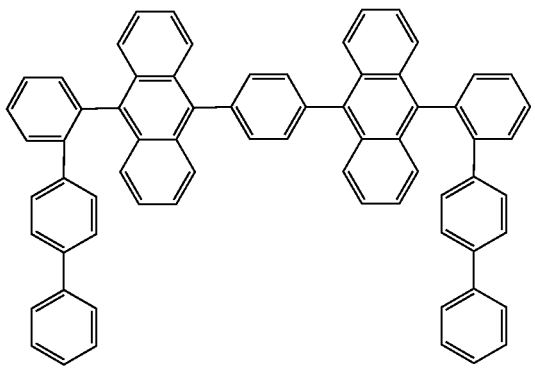
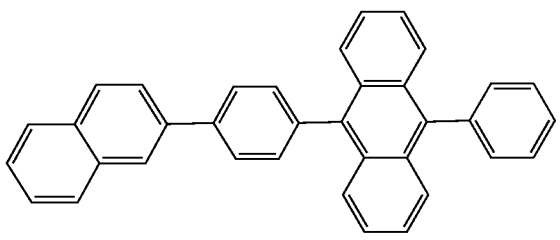
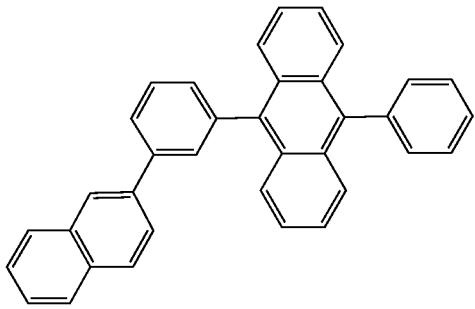
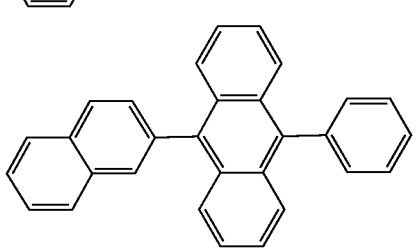

-continued
| 463 | 464 |
|---|---|
| 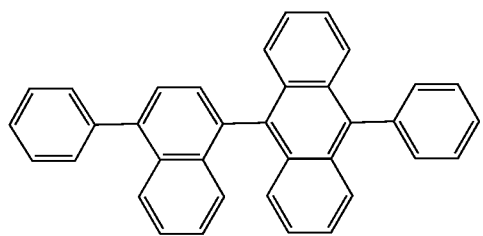 | 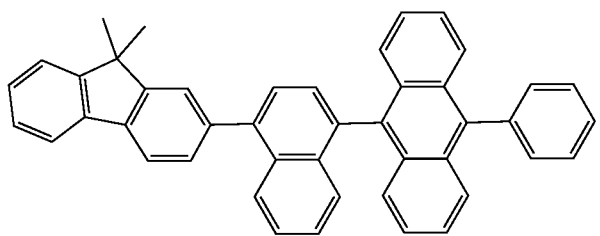 |
| 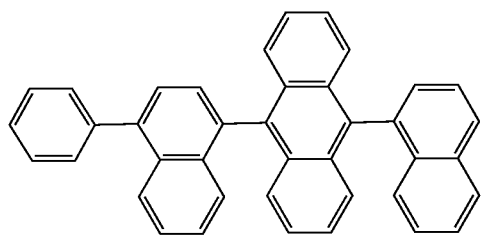 | 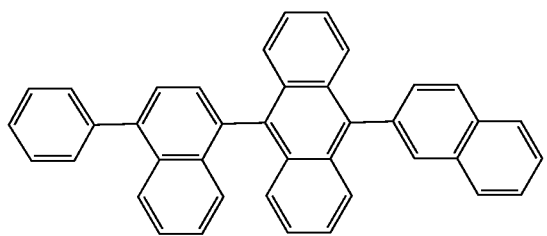 |
| 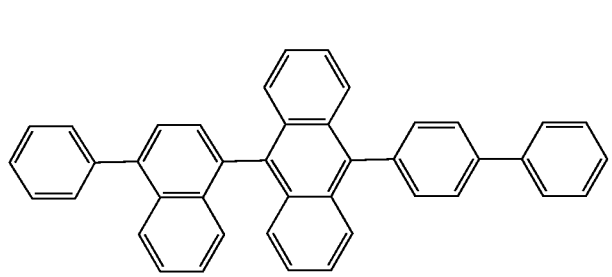 | 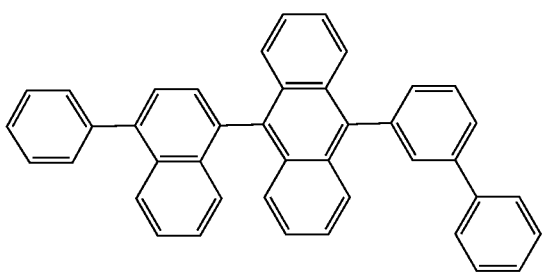 |
| 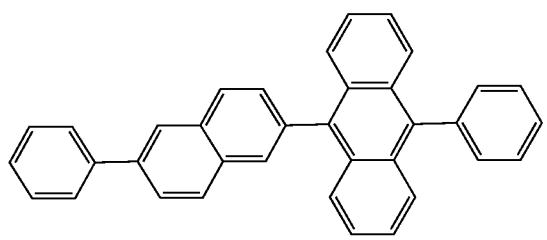 | 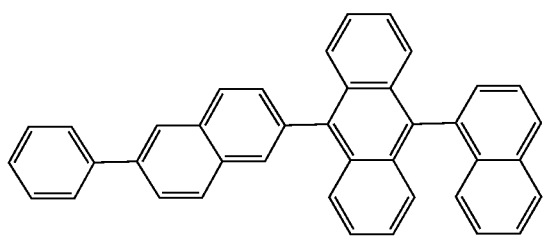 |
| 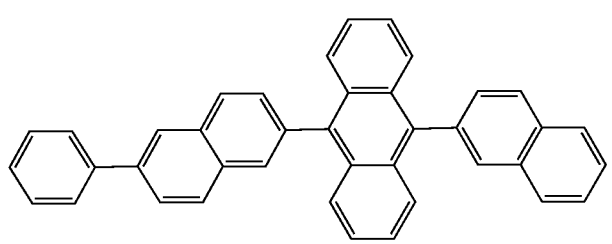 | 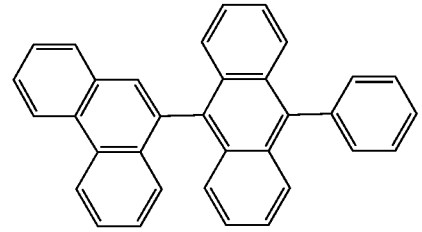 |
| 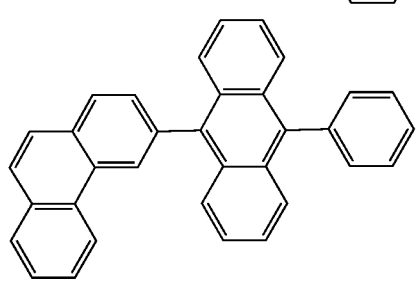 | 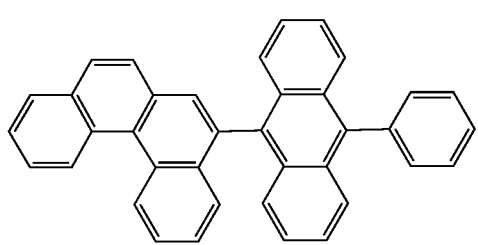 |

| 465 | 466 |
|---|---|
| 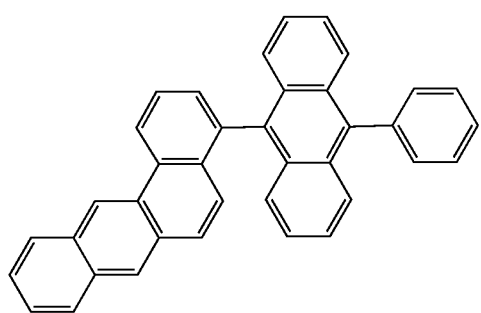 | 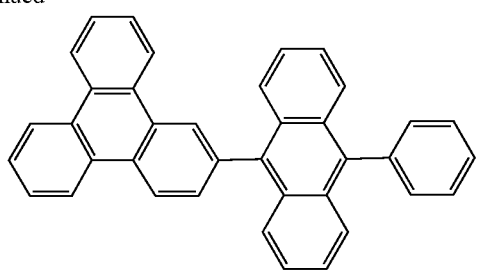 |
| 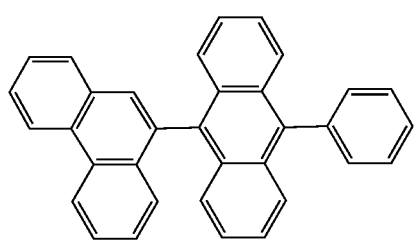 | 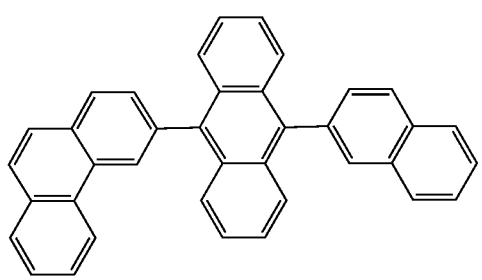 |
| 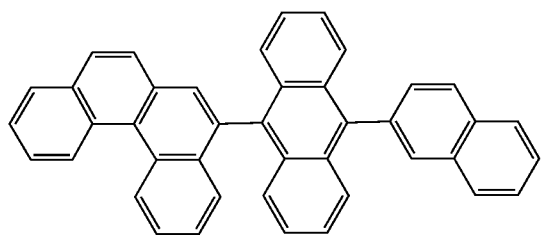 | 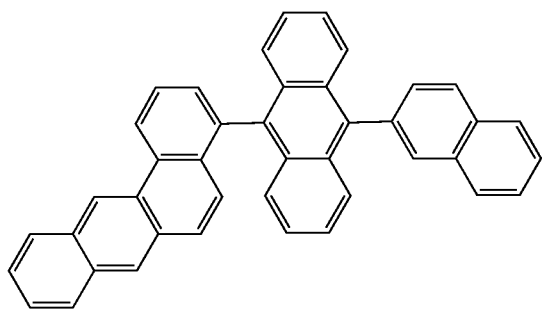 |
| 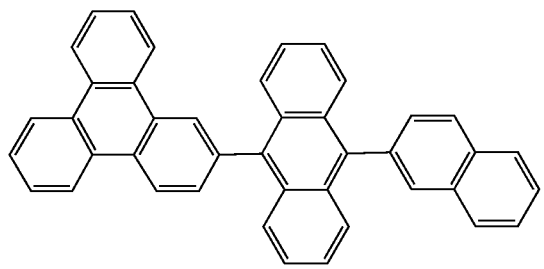 | 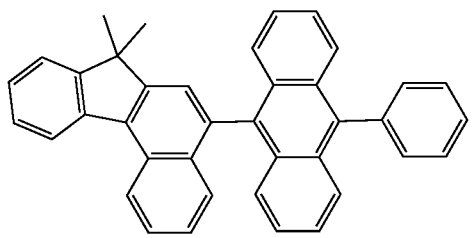 |
| 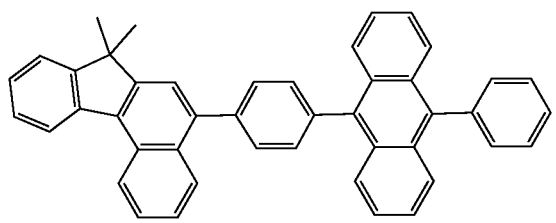 | 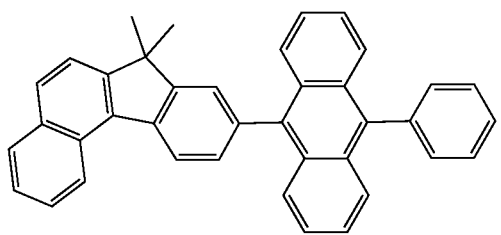 |
| 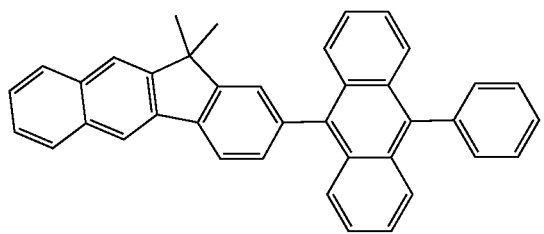 | 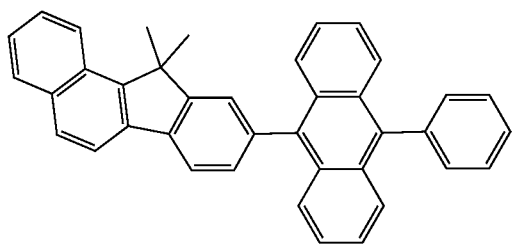 |

-continued
| 467 | 468 |
|---|---|
| 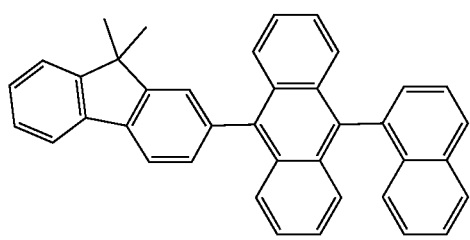 | 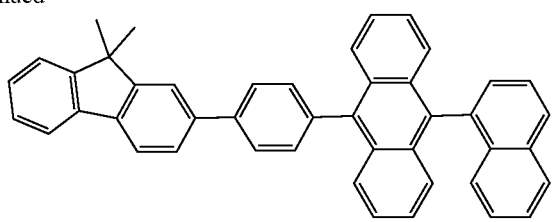 |
| 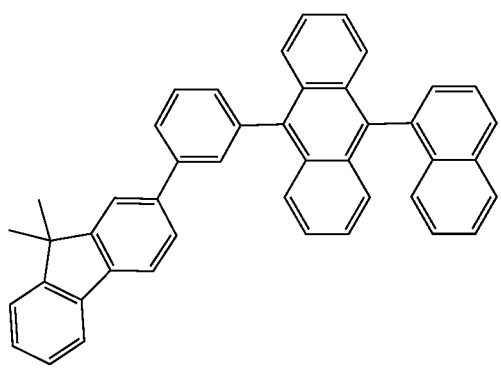 | 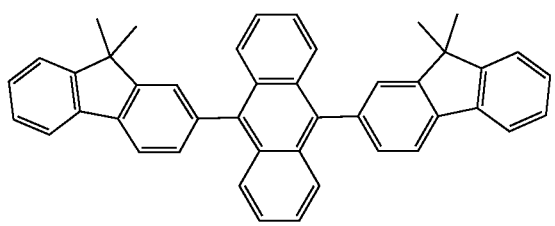 |
| 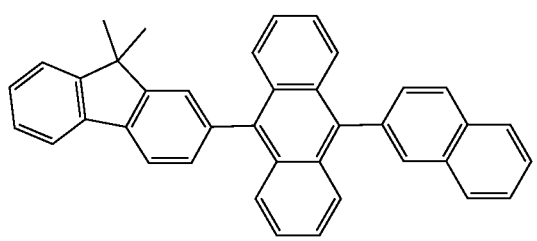 | 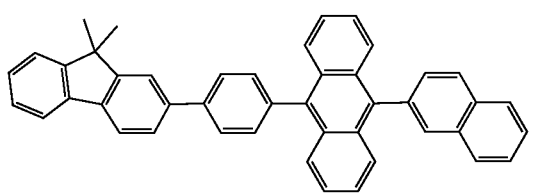 |
| 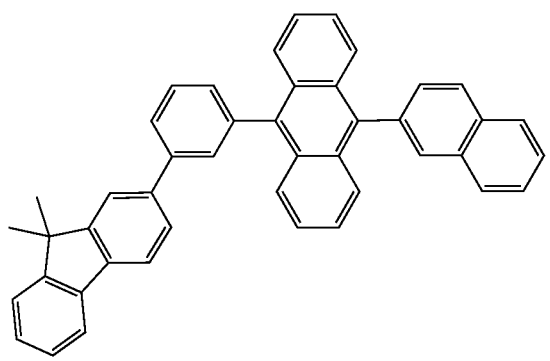 | 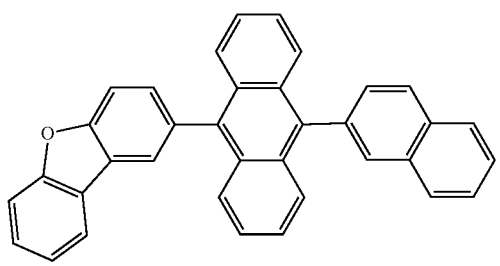 |
| 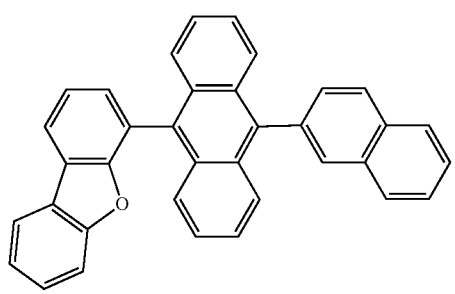 | 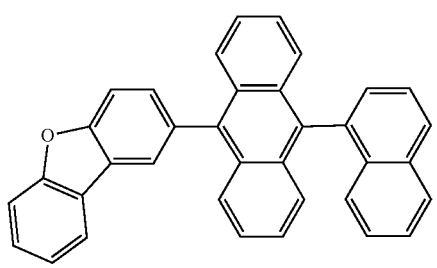 |

-continued
| 469 | 470 |
|---|---|
| 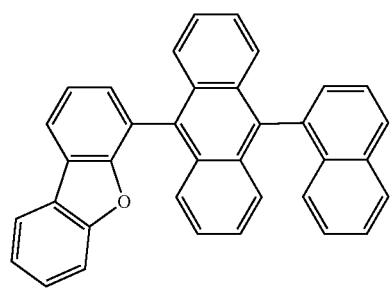 | 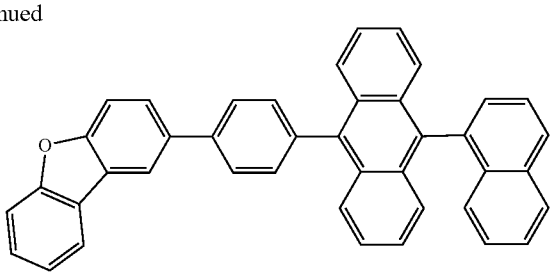 |
| 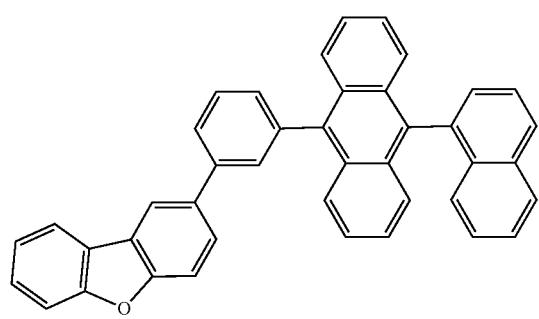 | 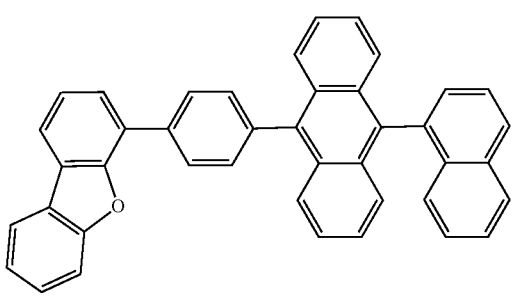 |
| 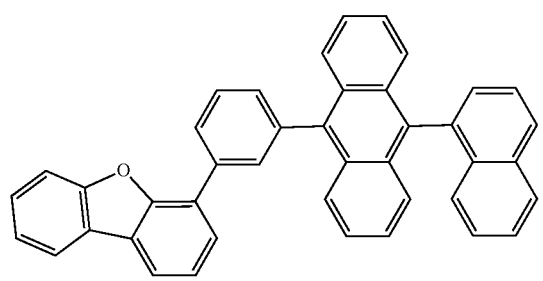 | |
| 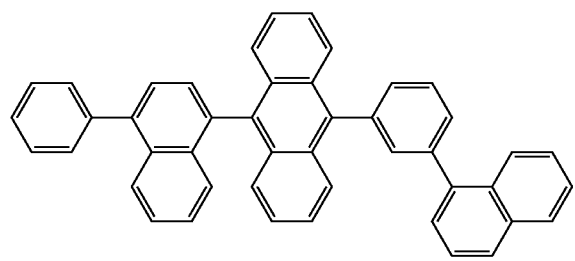 | 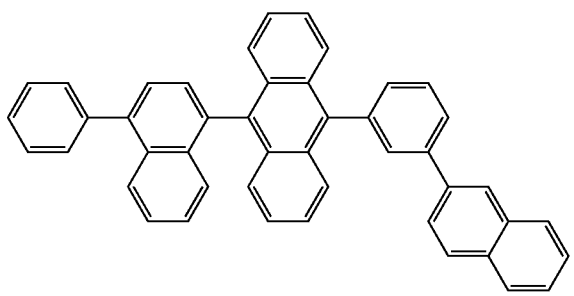 |
| 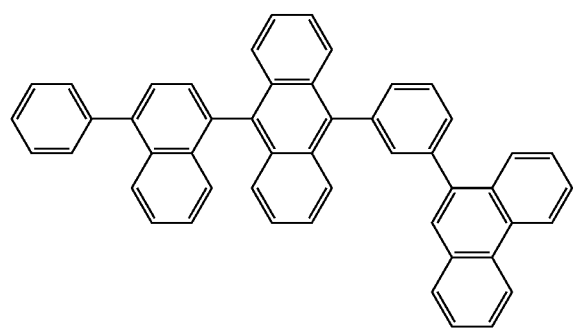 | 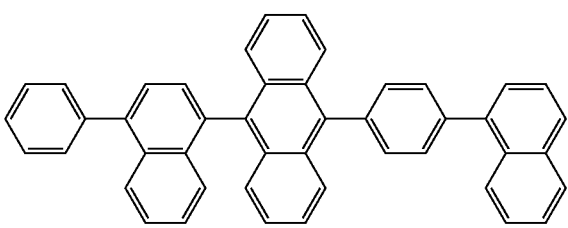 |

471 472
-continued
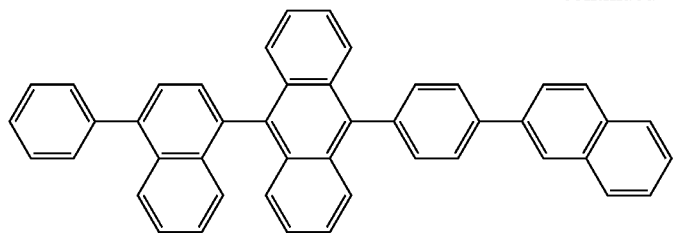

-continued
| 473 | 474 |
|---|---|
| 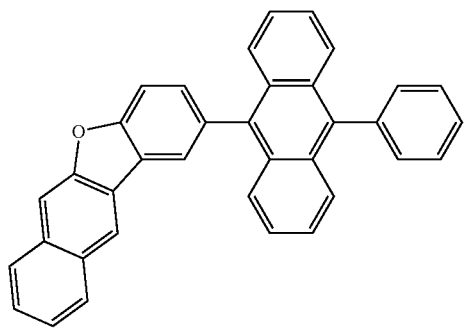 | 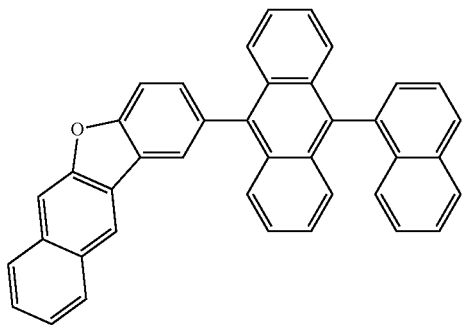 |
| 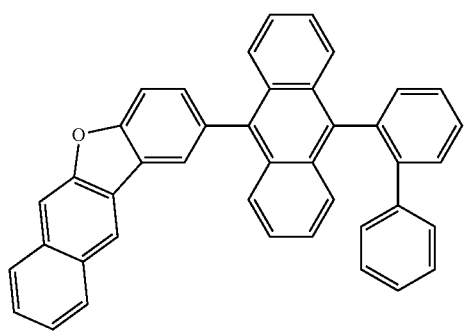 | 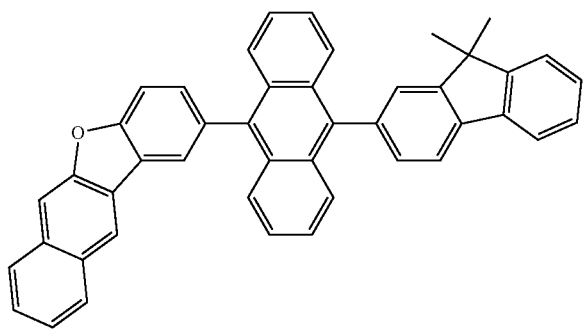 |
| 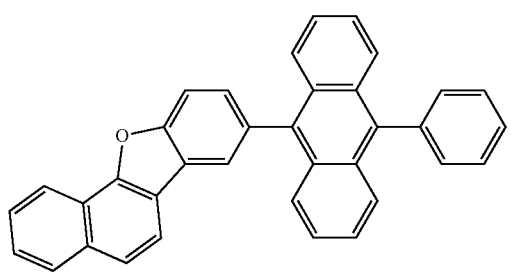 | 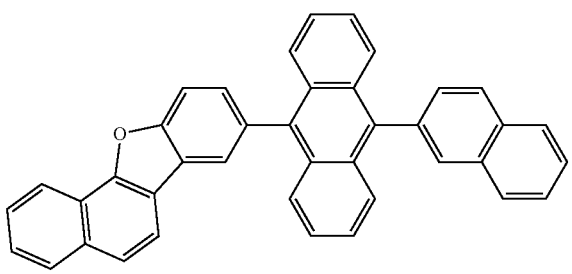 |
| 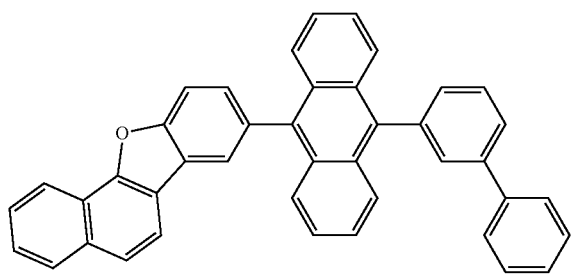 | |
| 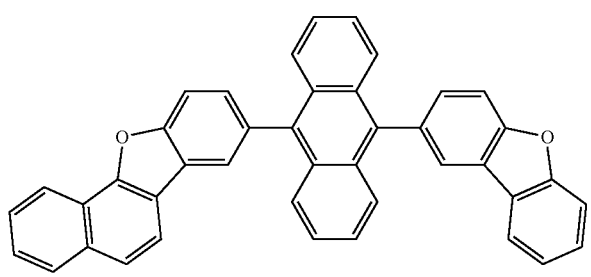 | 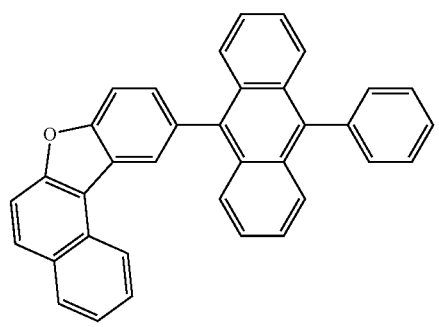 |

475
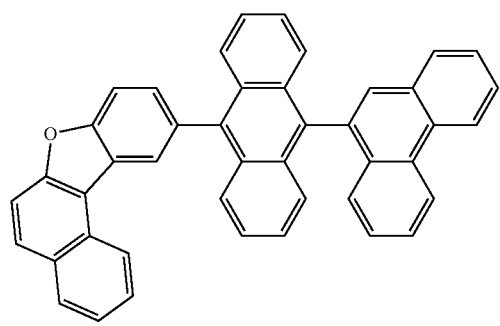
-continued
476
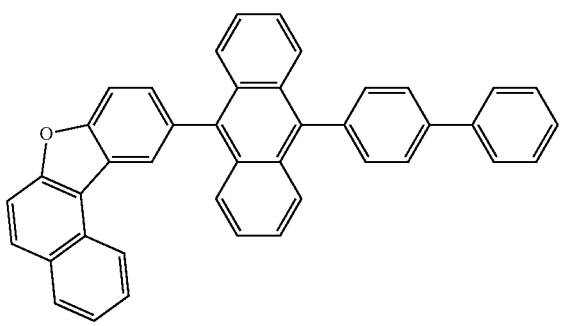
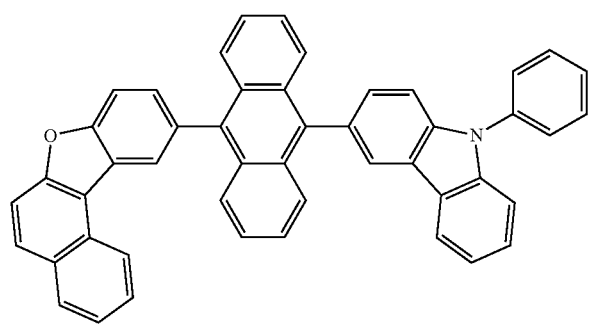
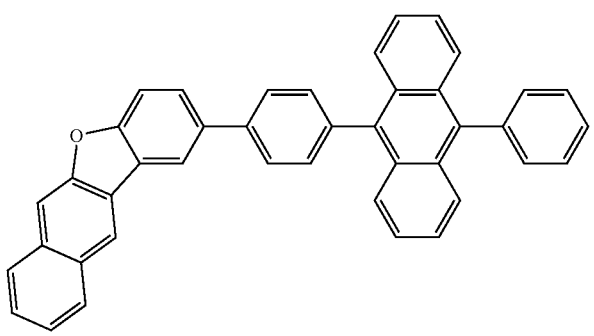
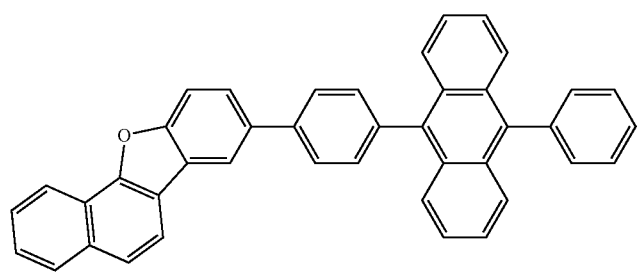
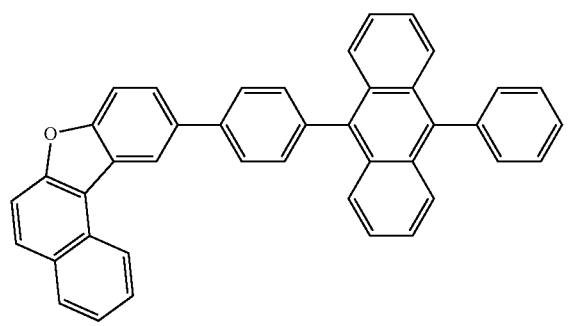
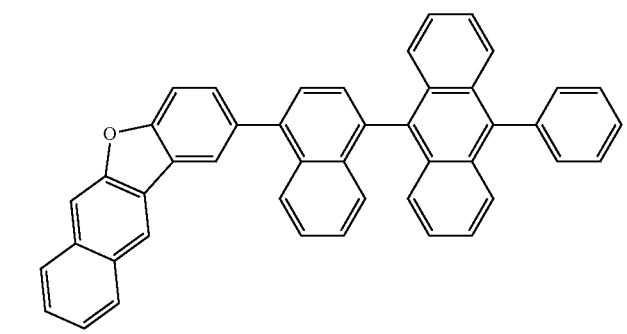
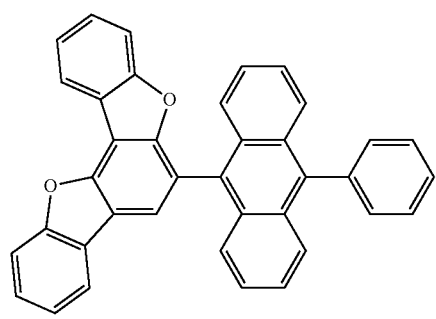
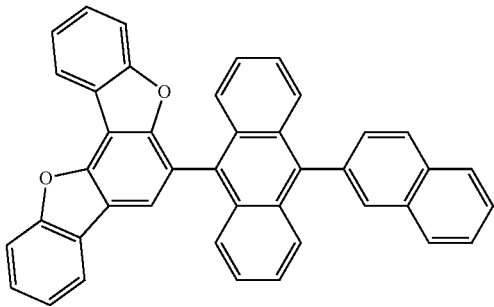

| 477 | 478 |
|---|---|
| 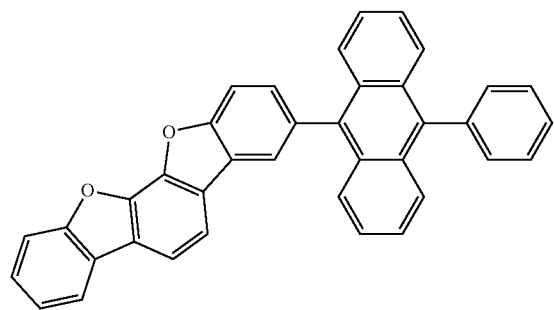 | 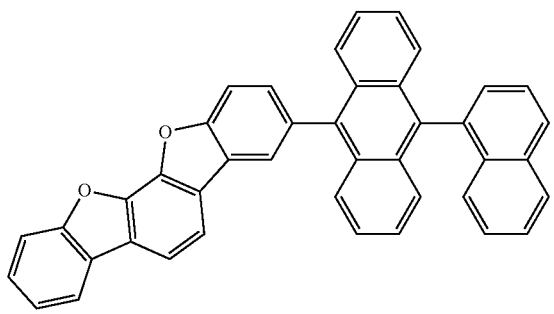 |
| 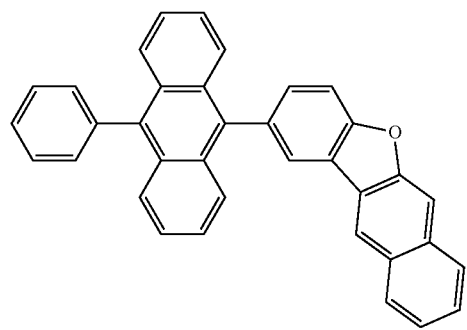 | 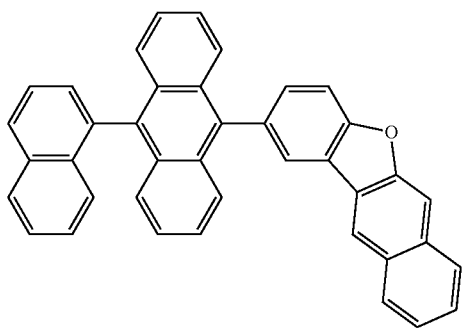 |
| 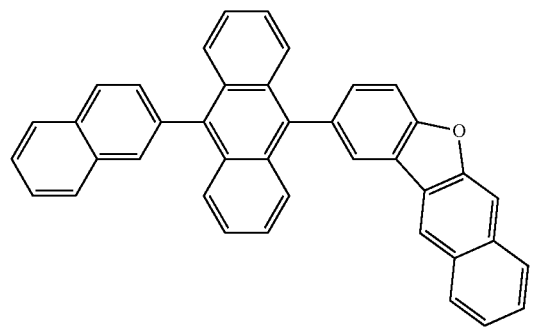 | 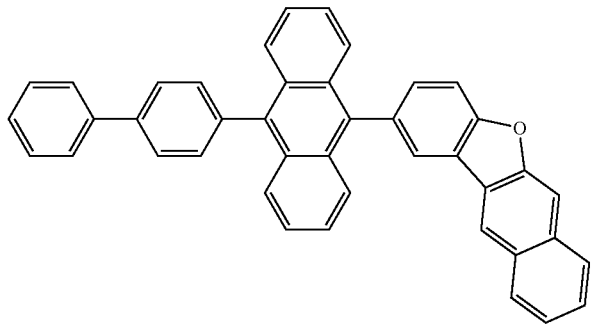 |
| 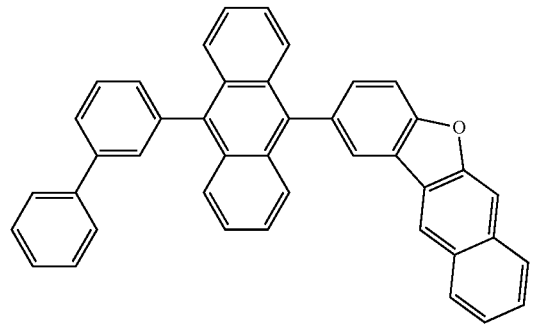 | 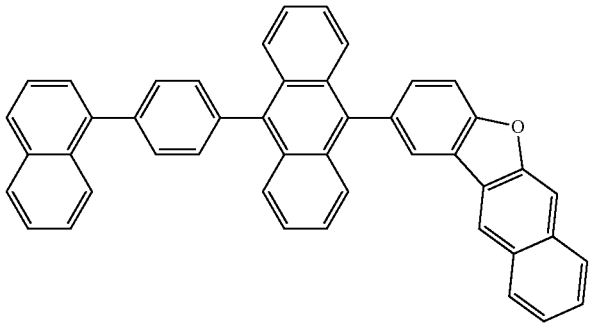 |
| 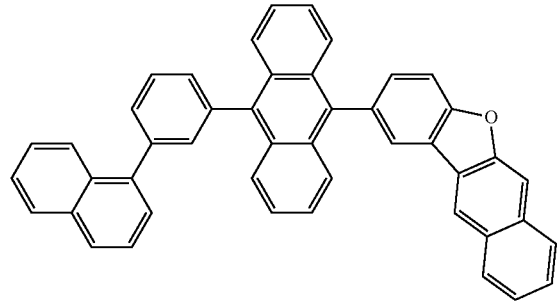 | 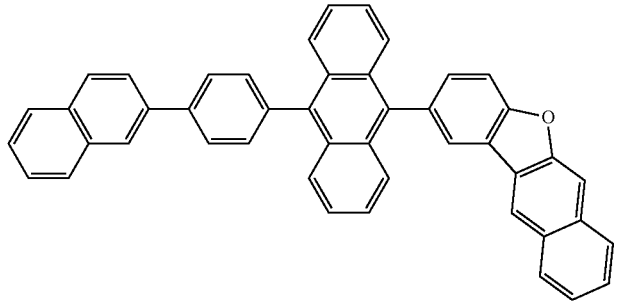 |

479 480
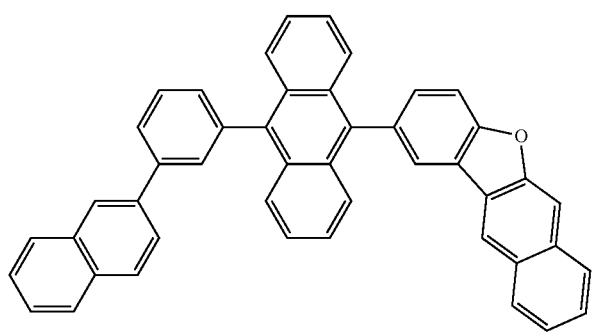 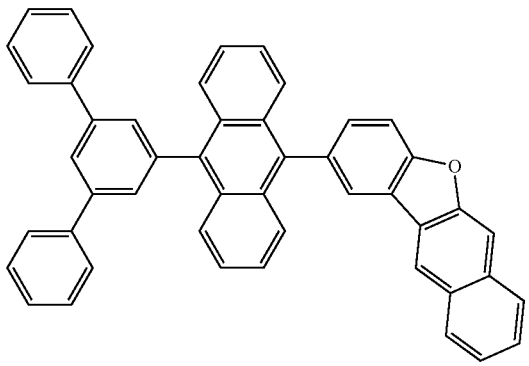
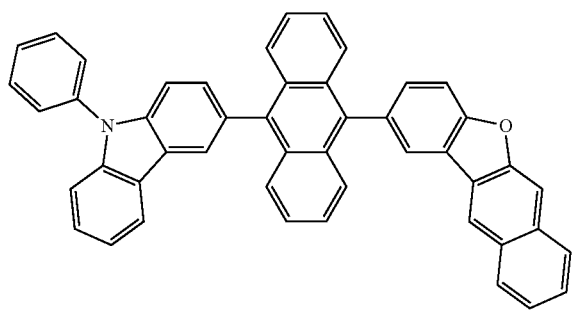 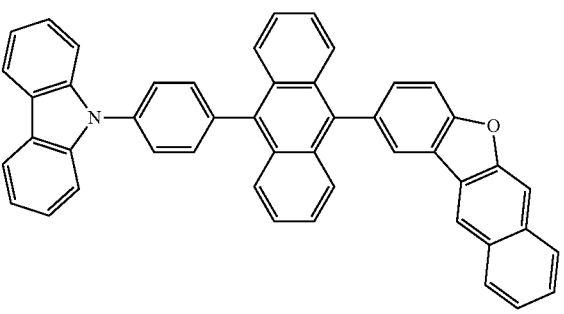
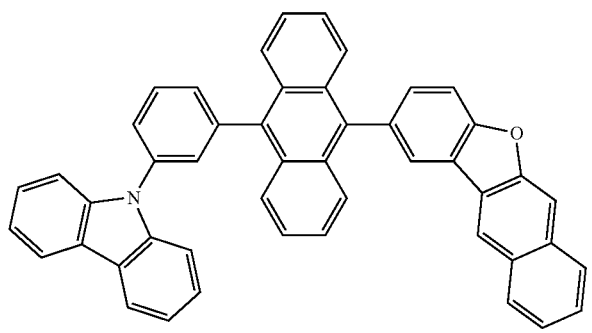 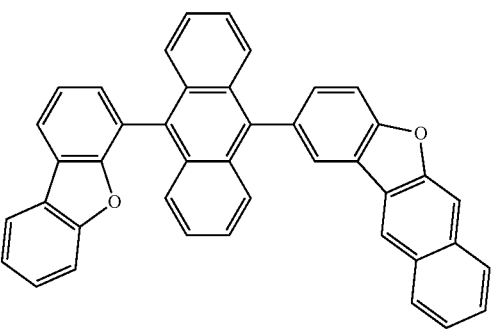
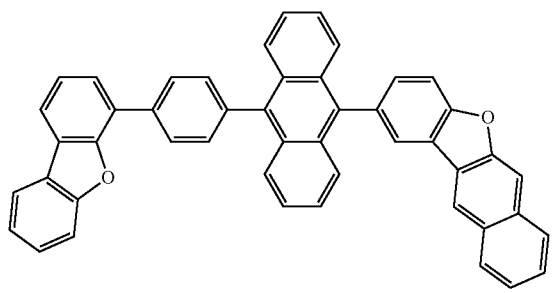 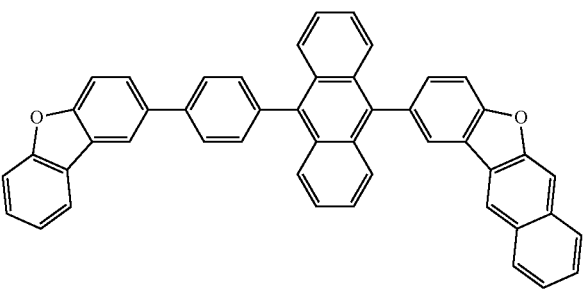
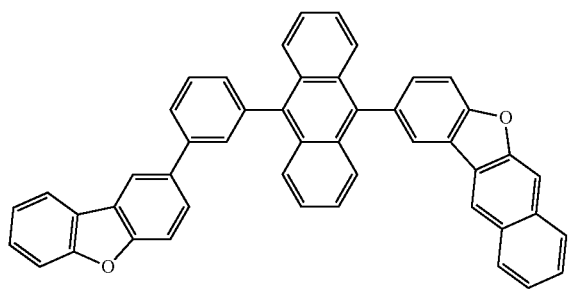 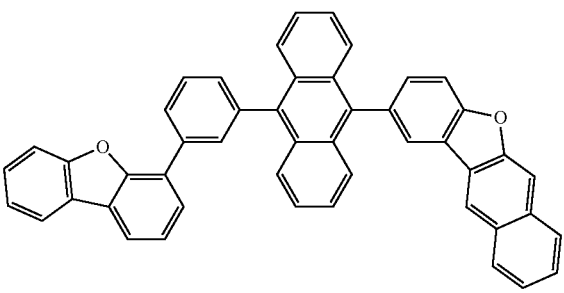

| 481 | 482 |
|---|---|
| 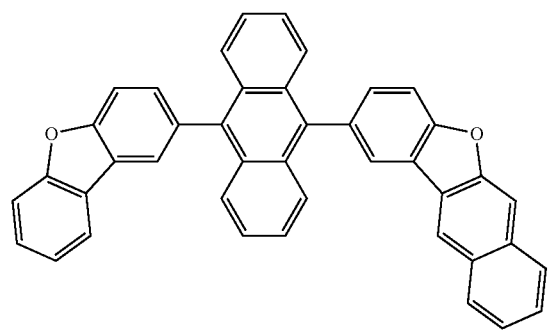 | 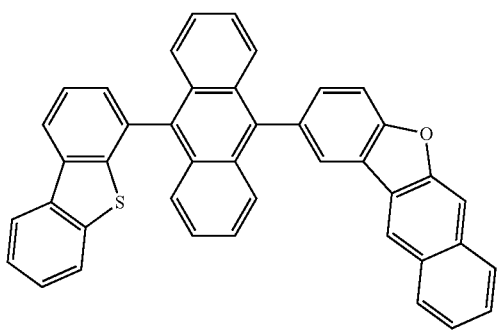 |
| 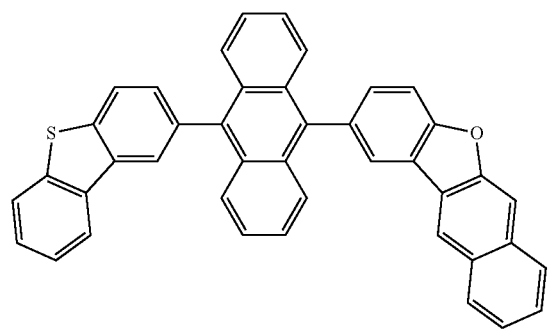 | 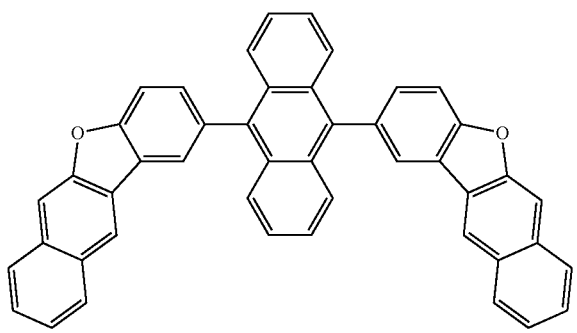 |
| 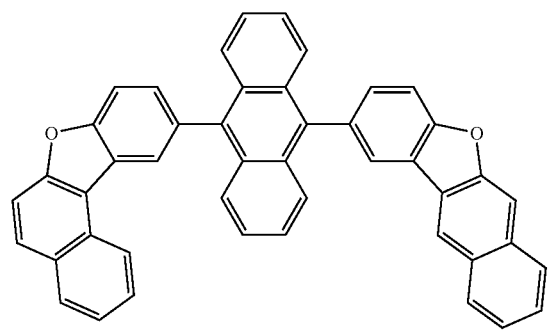 | 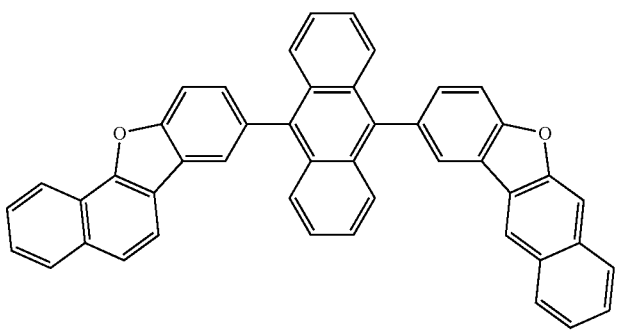 |
| 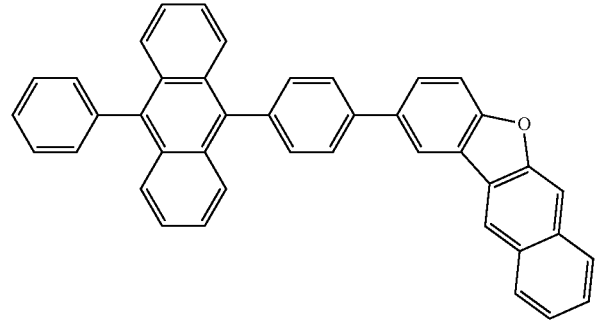 | 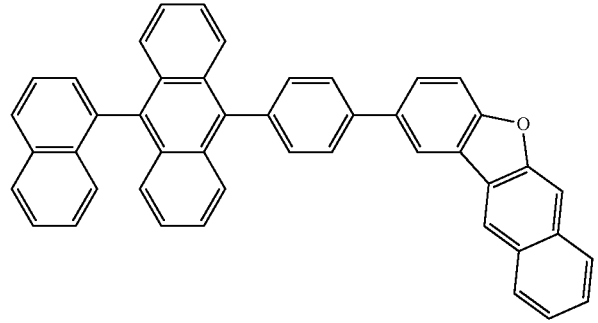 |
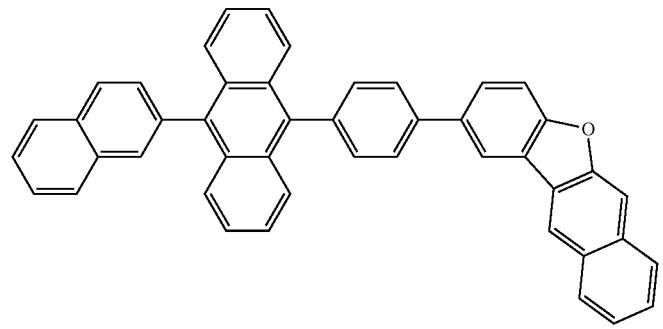

-continued
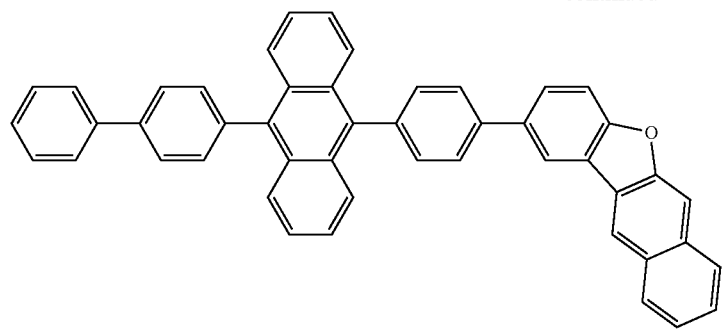
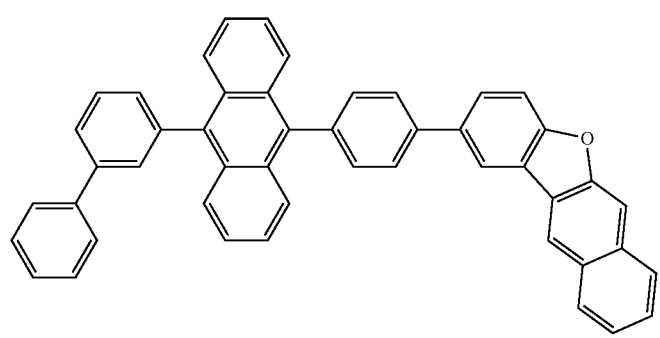
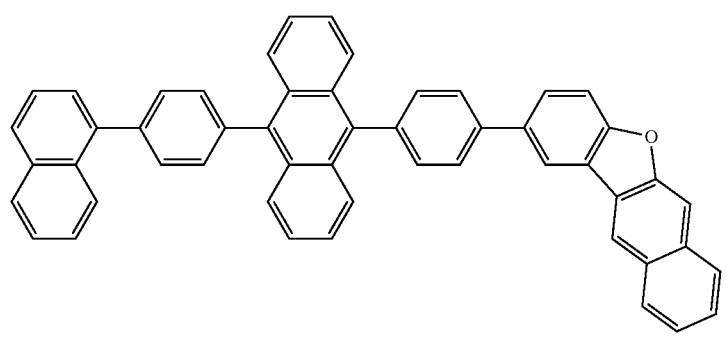
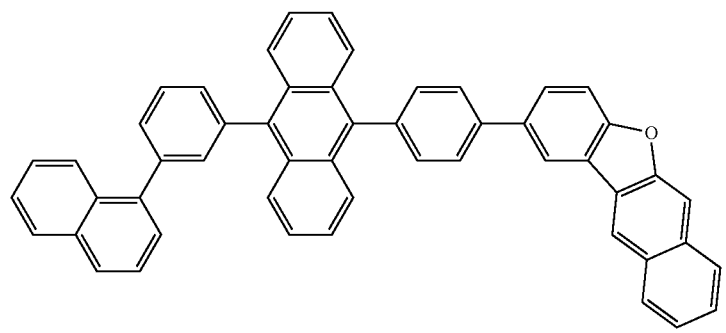
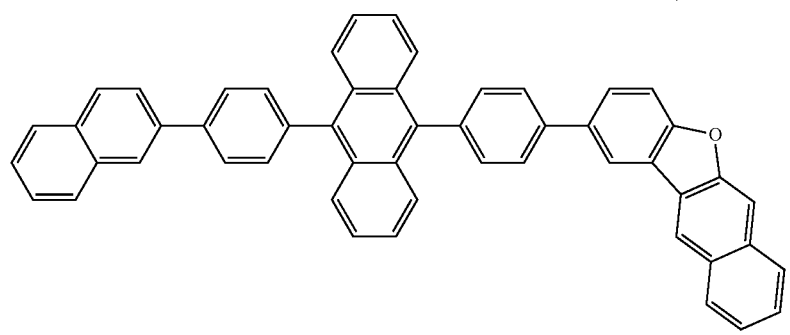

485 486
-continued
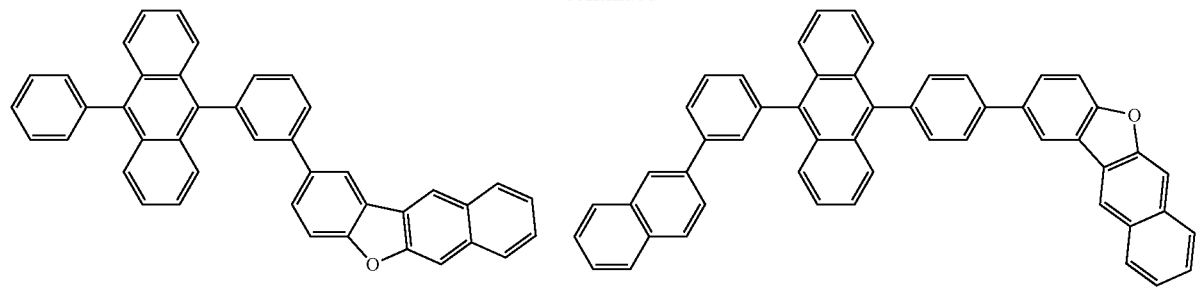
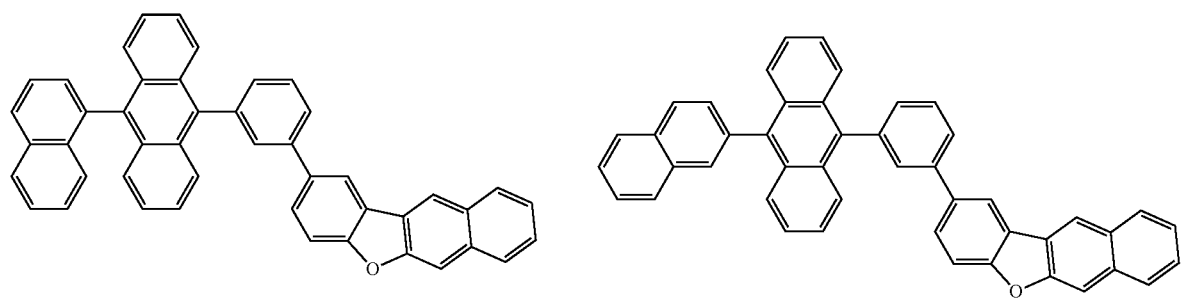
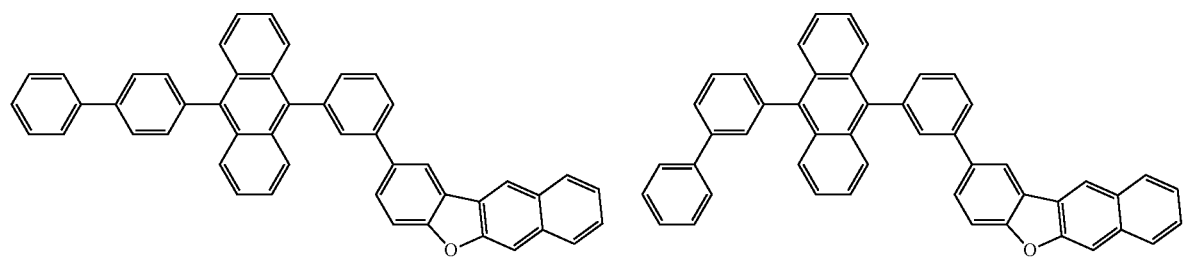
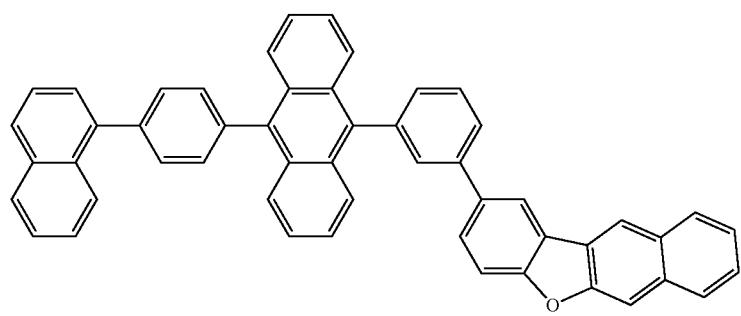
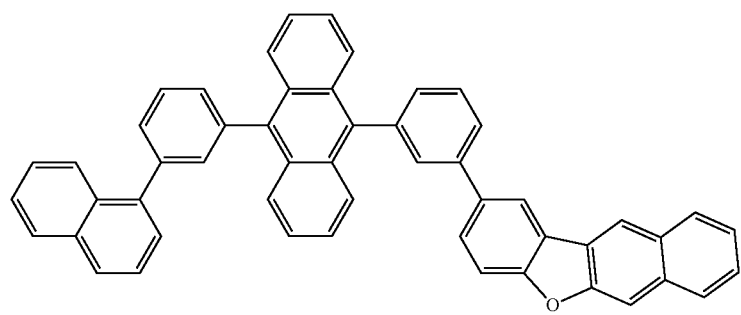

-continued
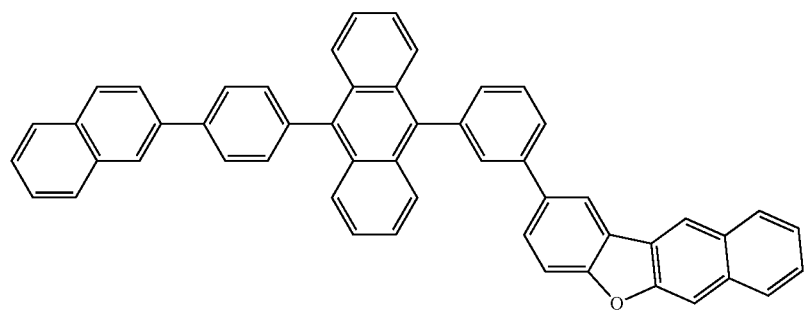

489   490
-continued
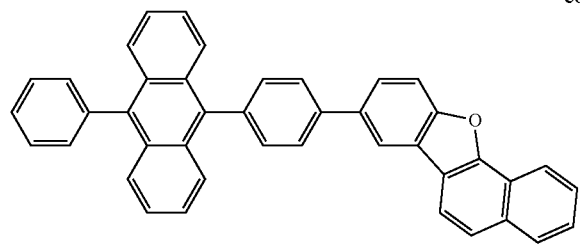
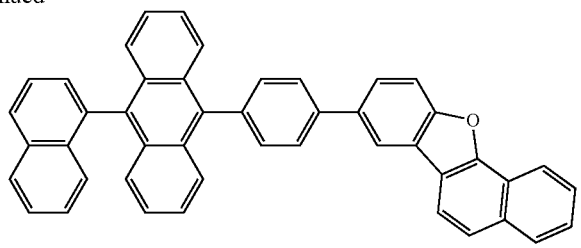
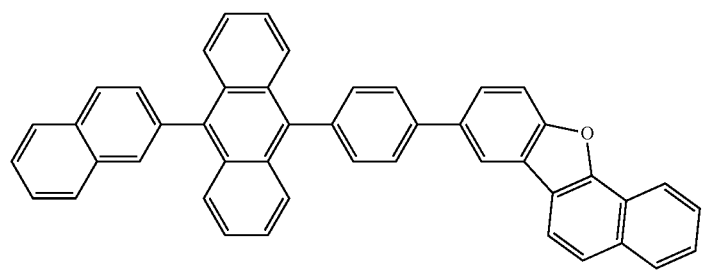
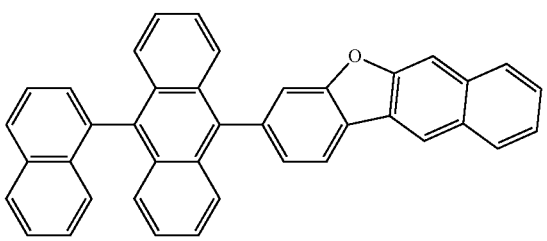
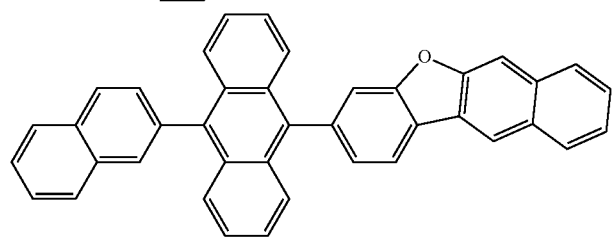
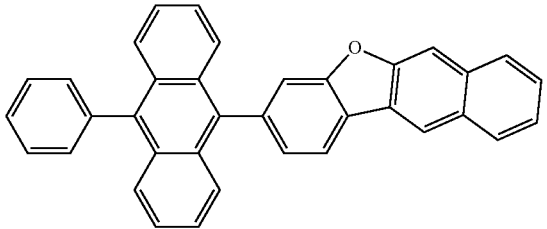
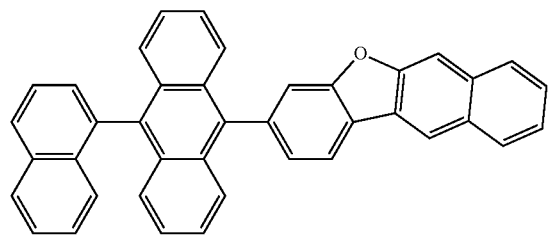
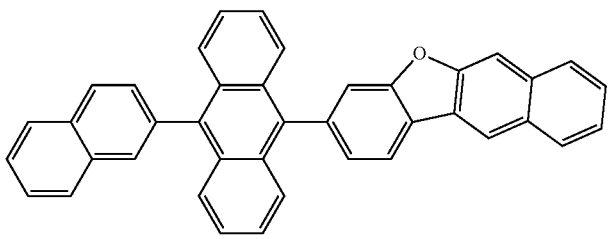
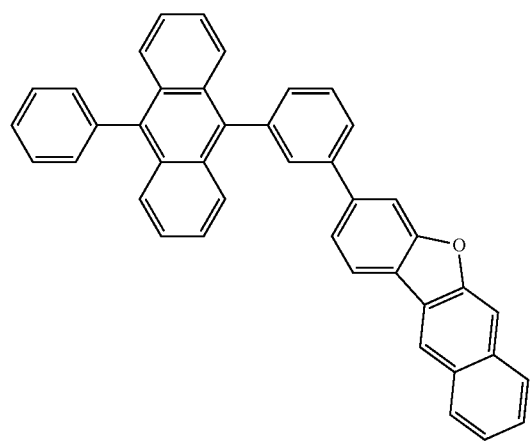
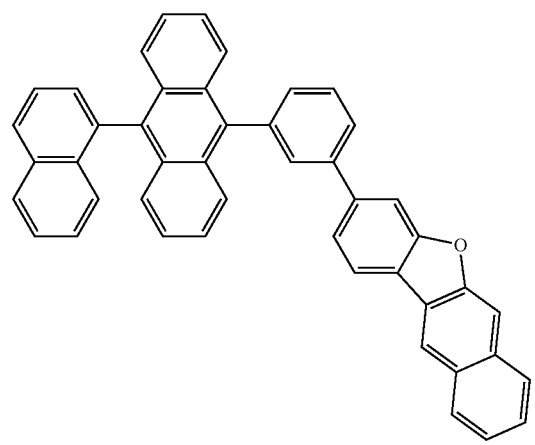

-continued
| 491 | 492 |
|---|---|
| 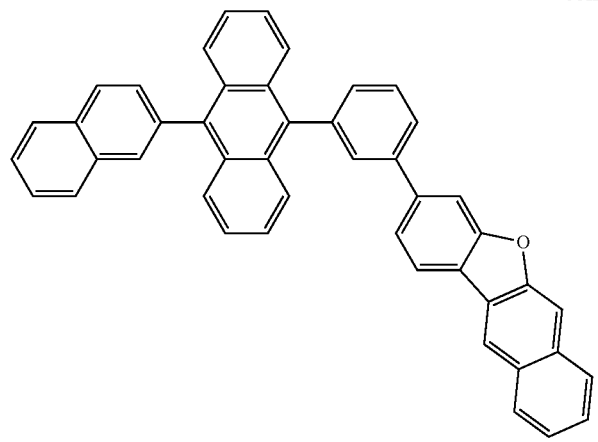 | 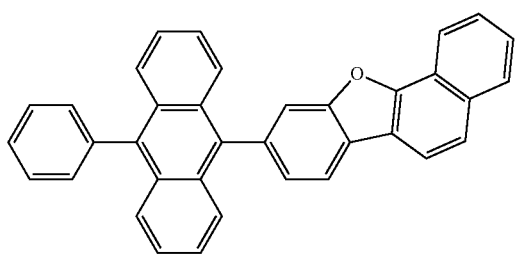 |
| 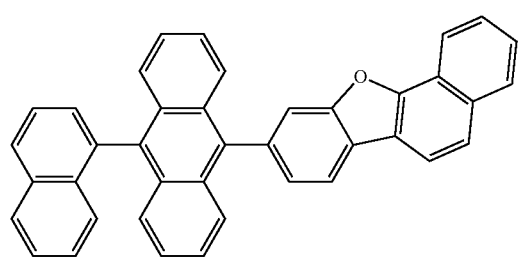 | 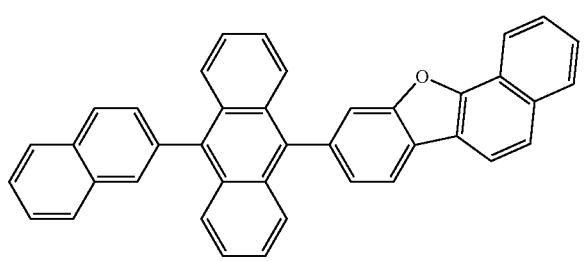 |
| 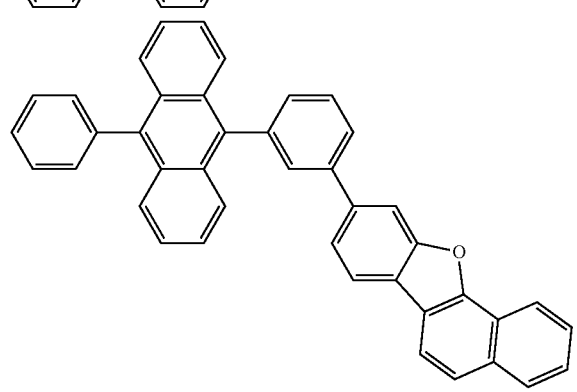 | 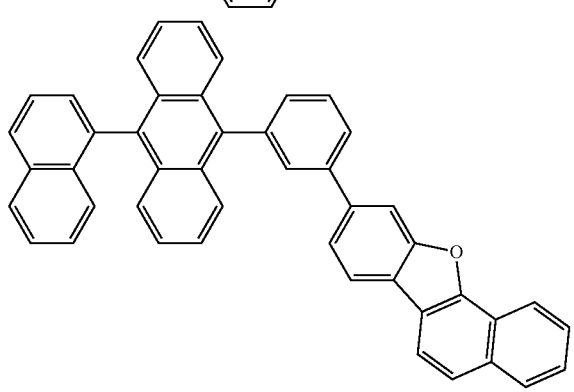 |
| 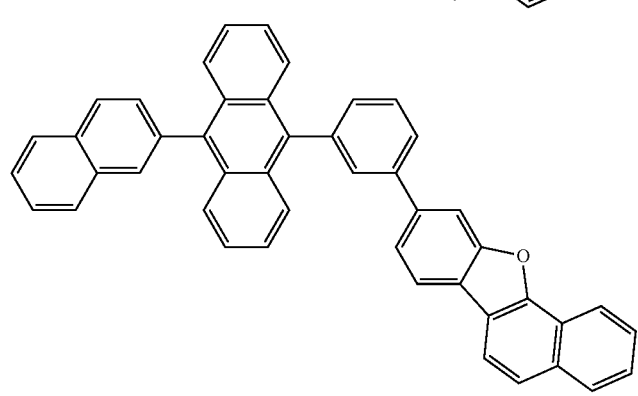 | 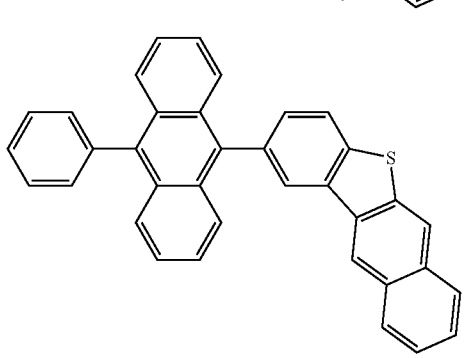 |
| 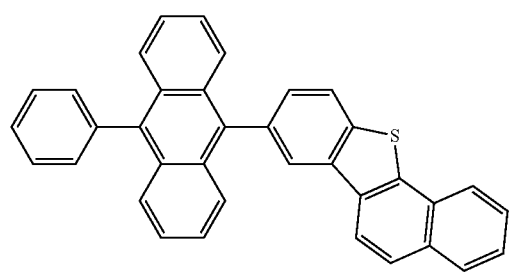 | 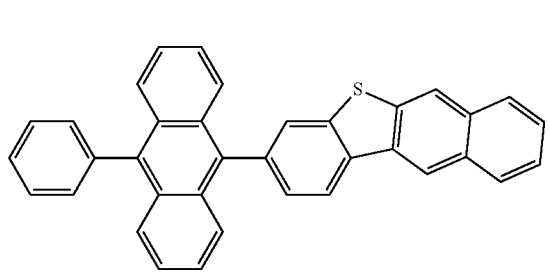 |

493
494
-continued
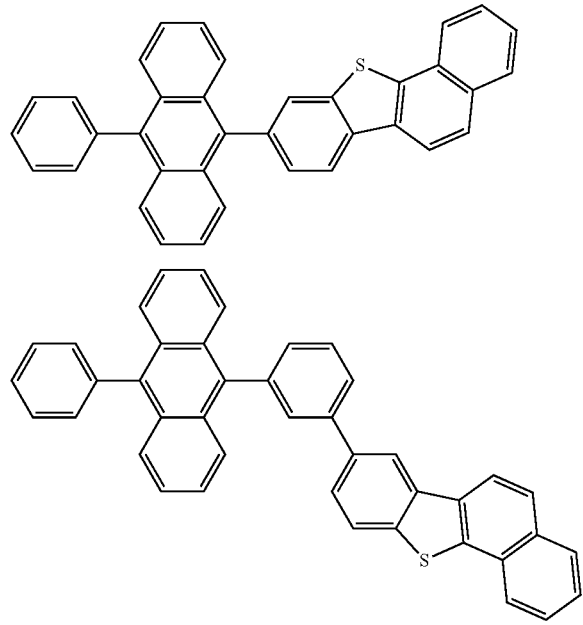
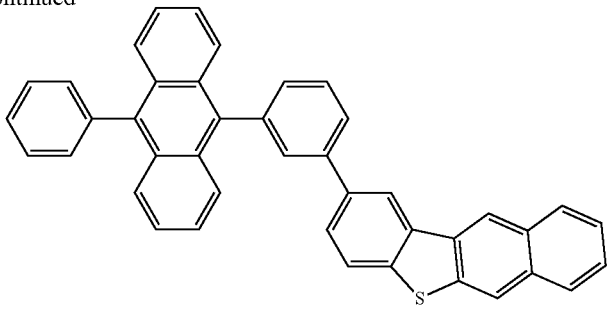
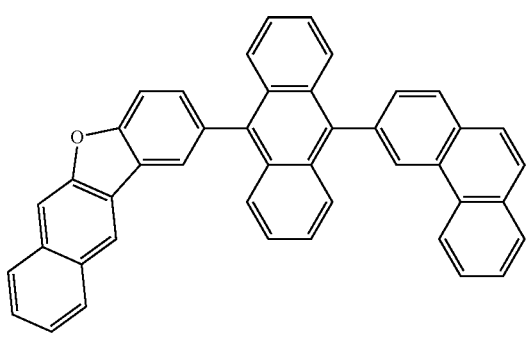
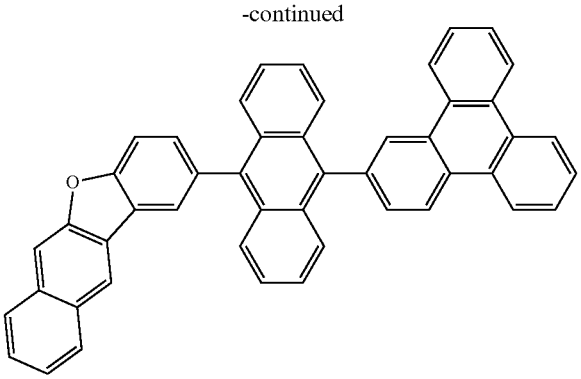
-continued
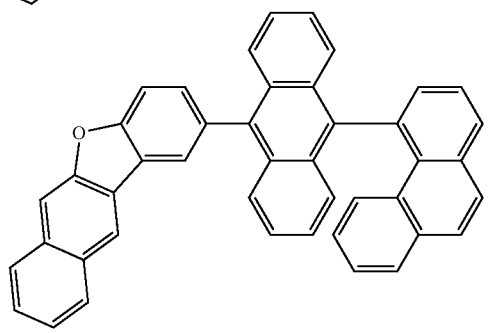
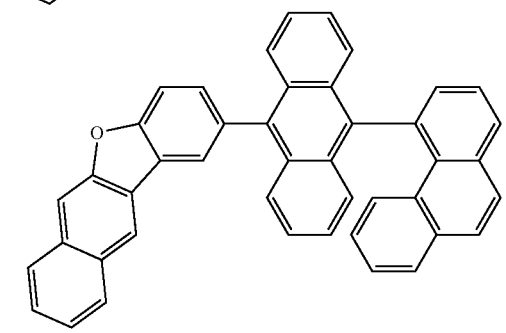
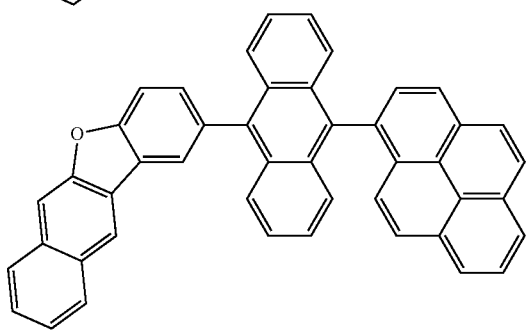
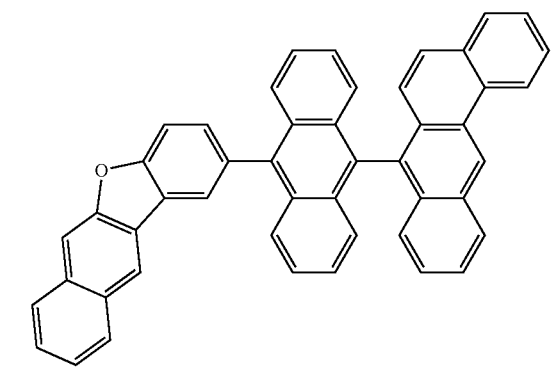

495
-continued
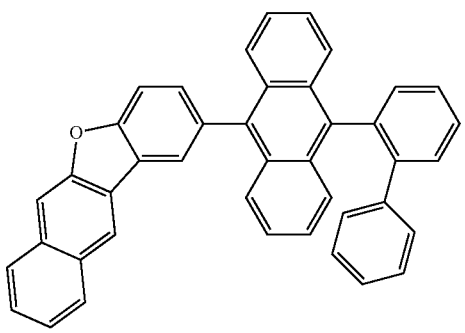
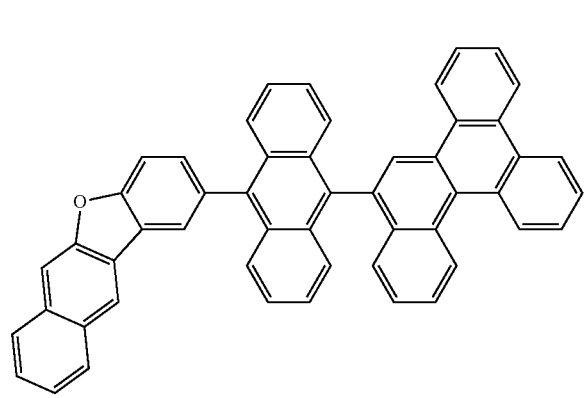
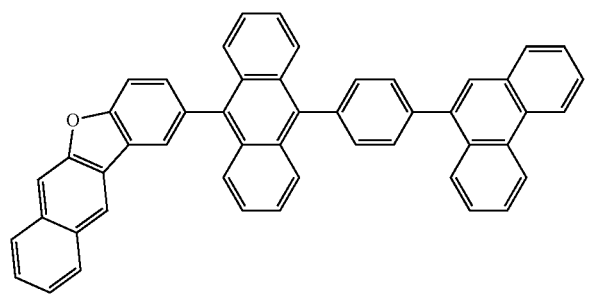
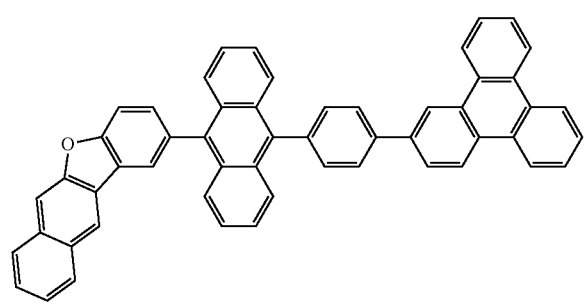
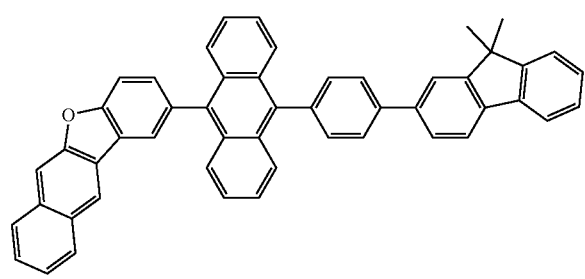
496
-continued
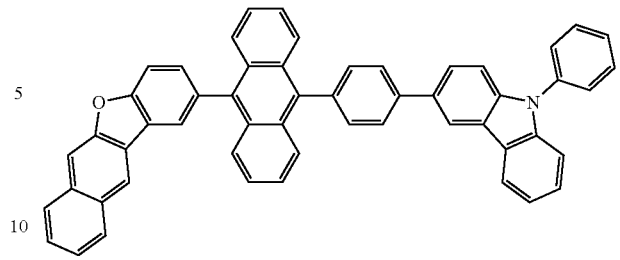
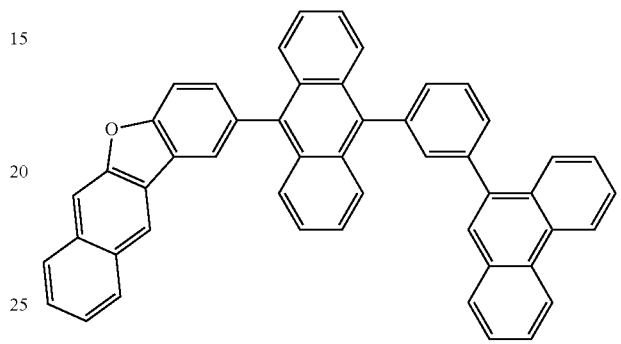
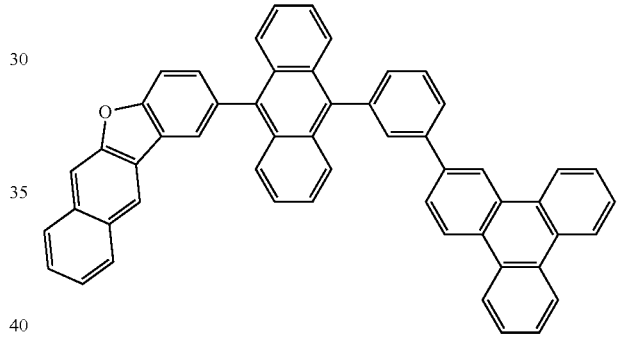
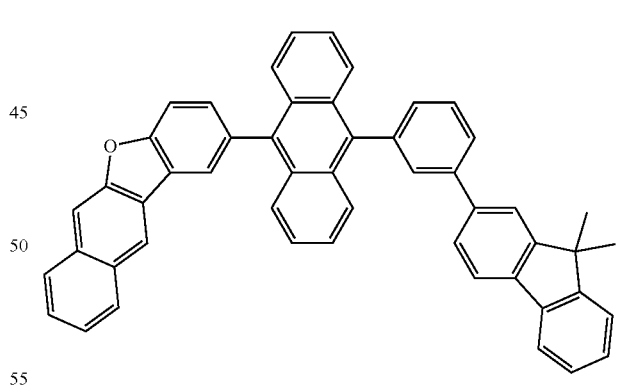
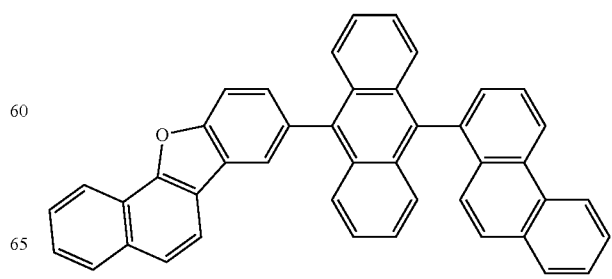

497
-continued
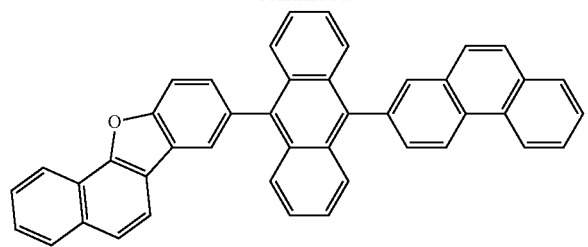
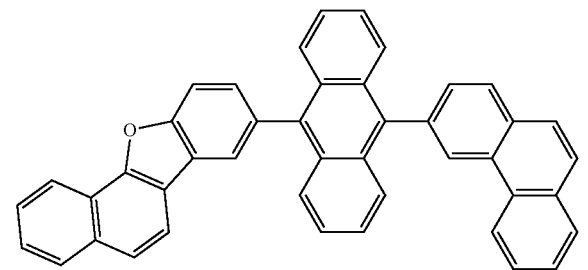
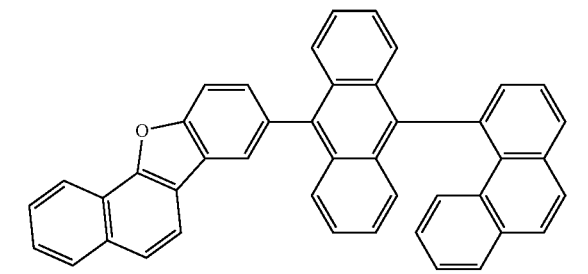
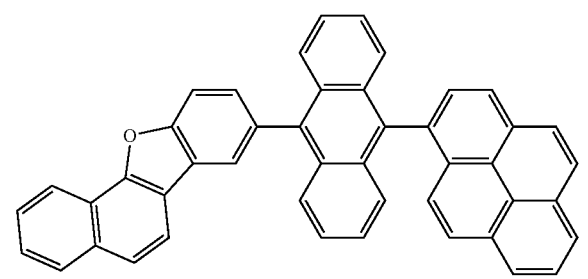
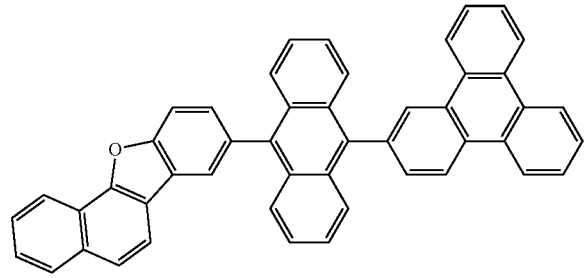
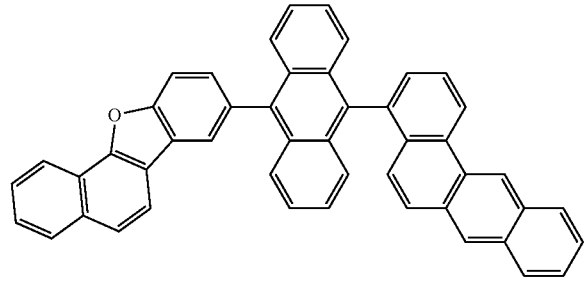
498
-continued
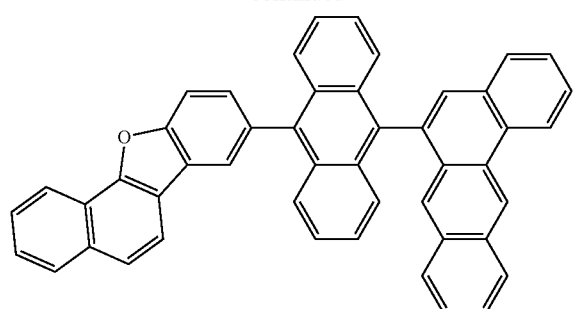
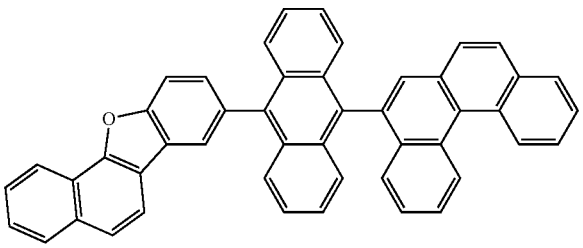
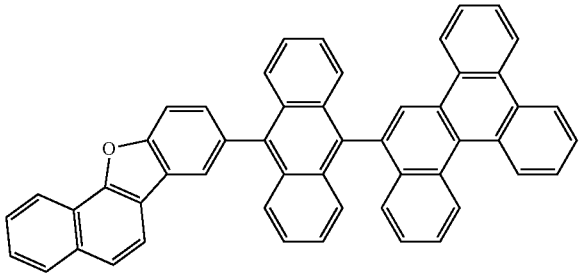
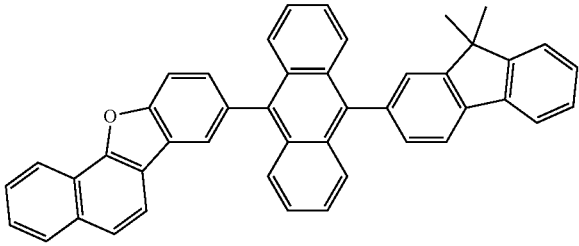
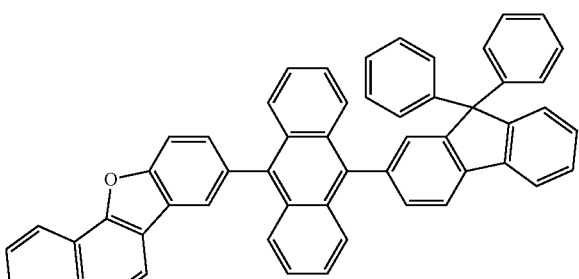
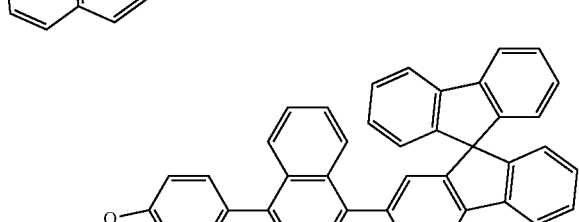

499
-continued
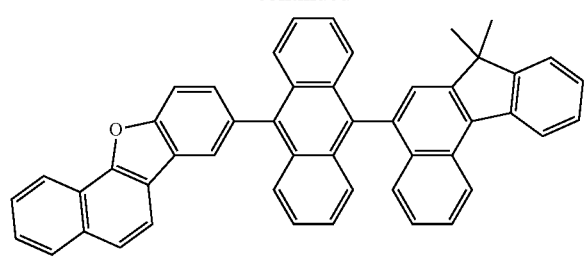
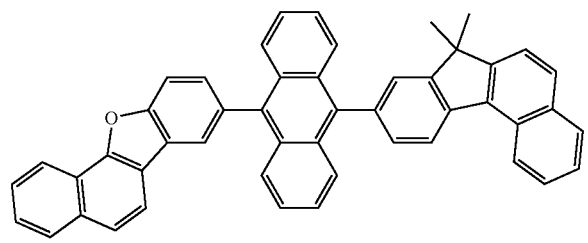
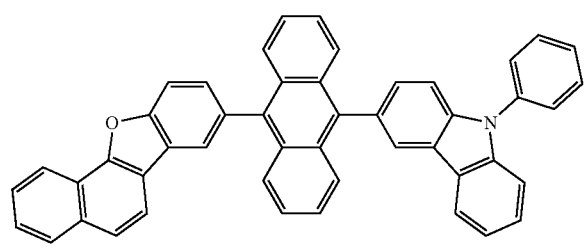
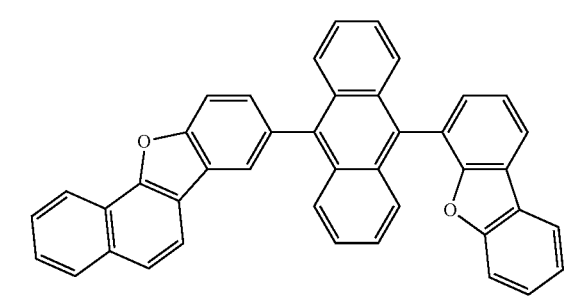
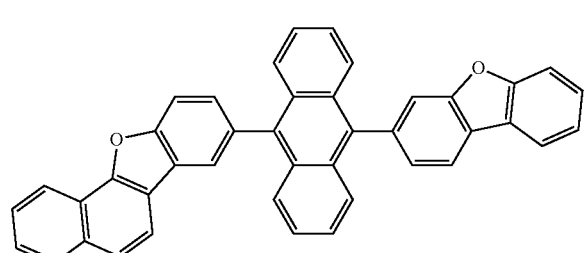
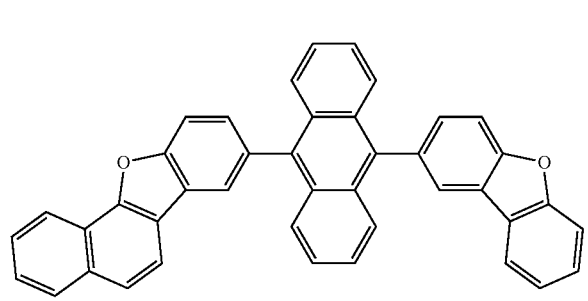
500
-continued
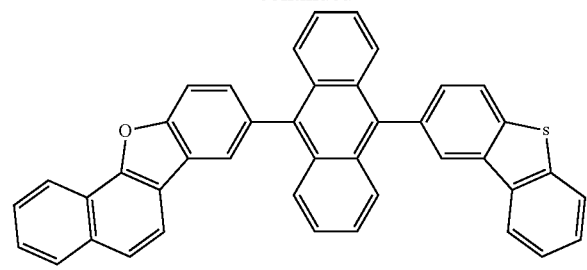
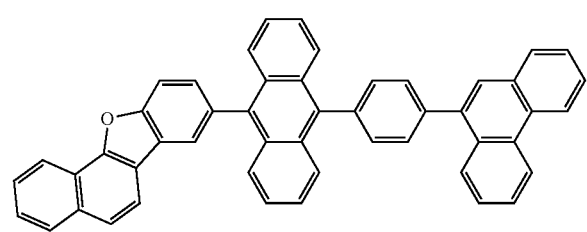
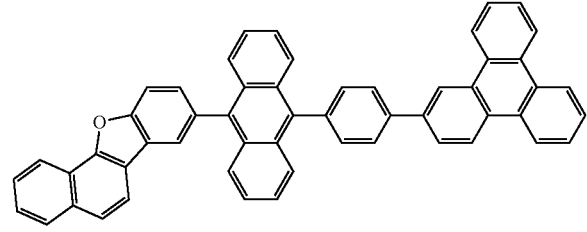
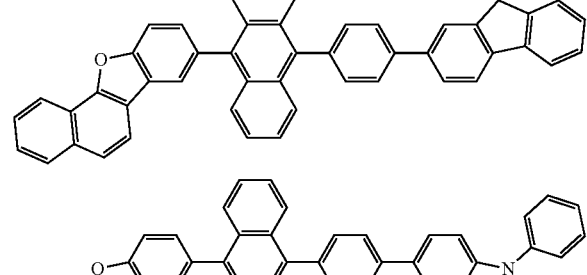
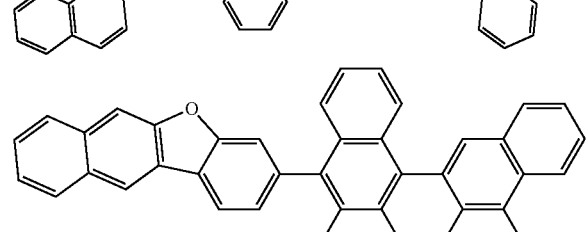
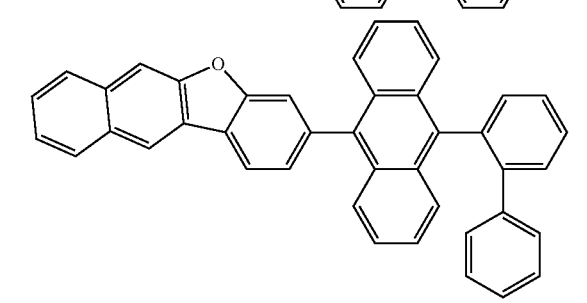

501
-continued
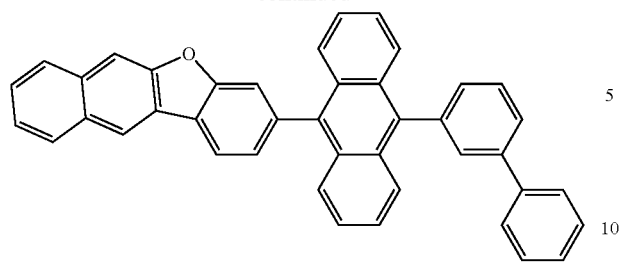
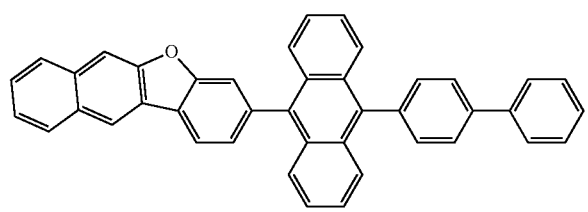
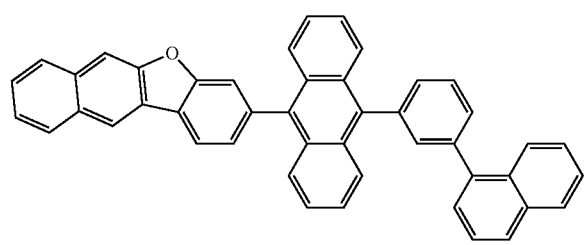
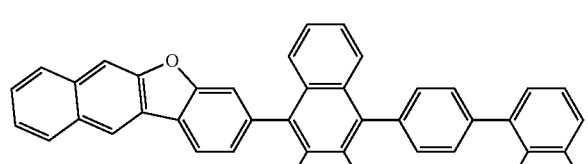
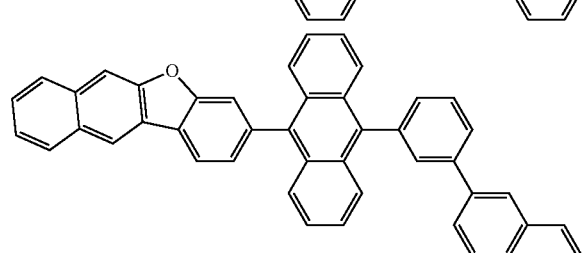
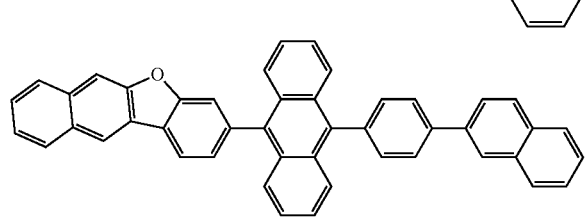
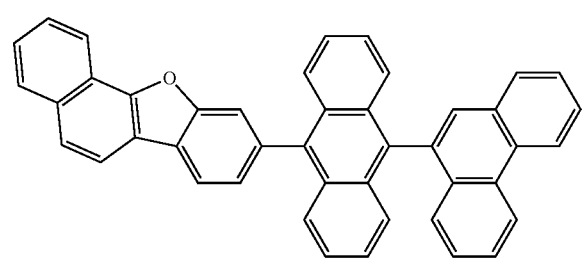
502
-continued
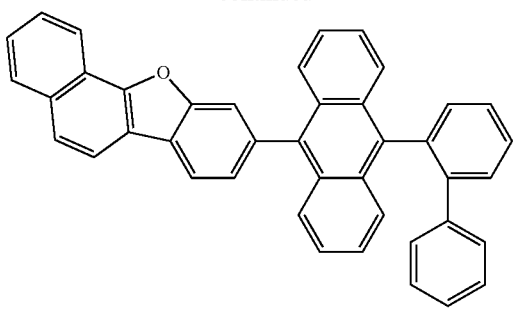
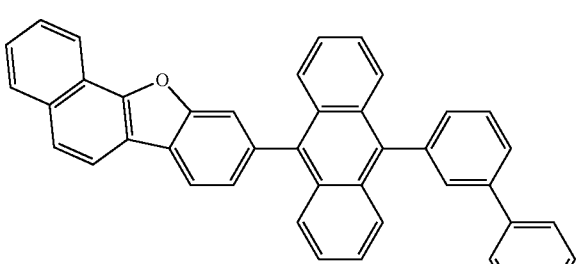
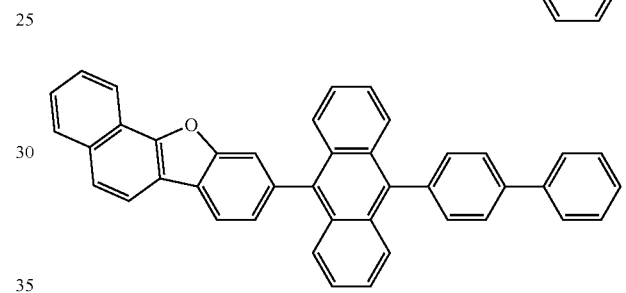
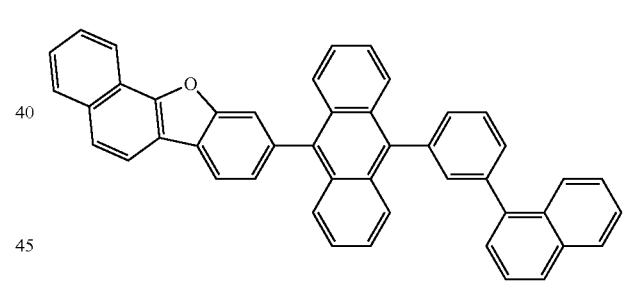
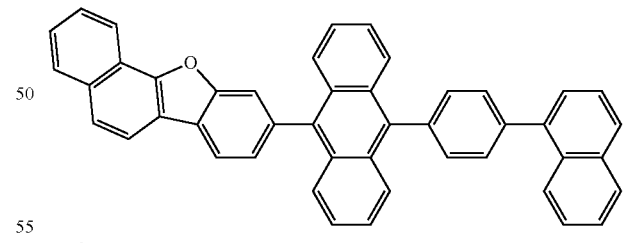
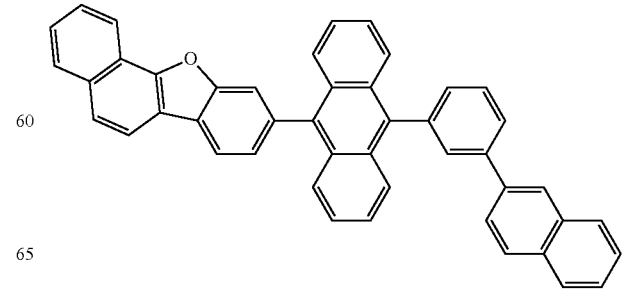

503
-continued
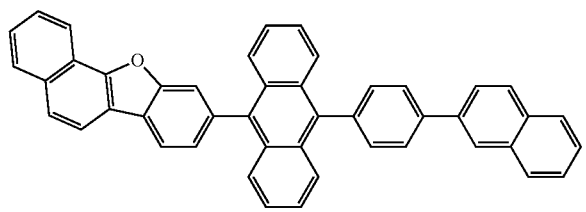
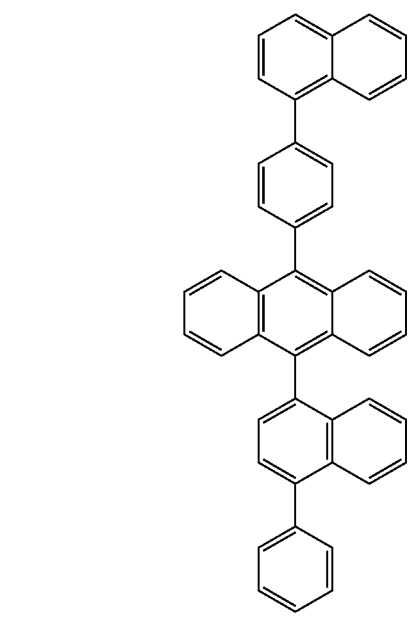
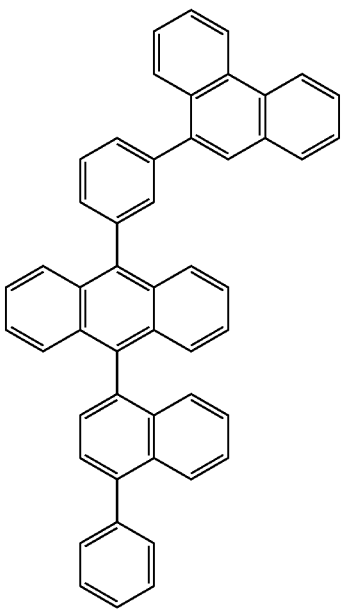
504
-continued
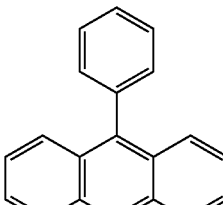
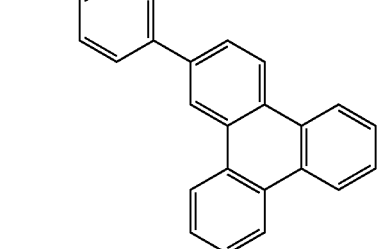

505
-continued
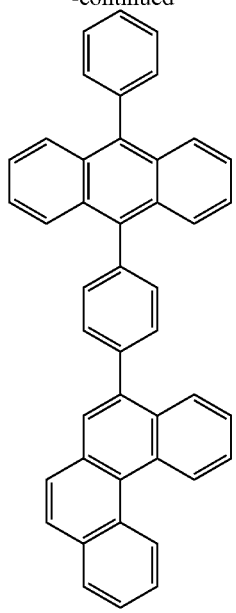
506
-continued
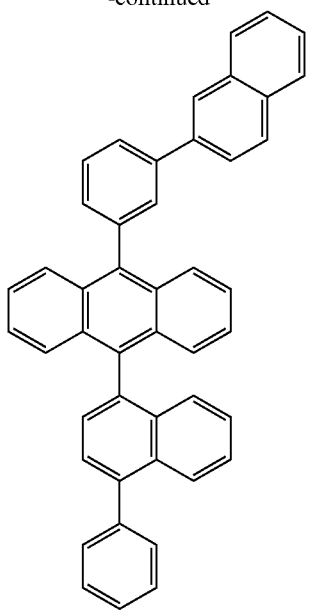
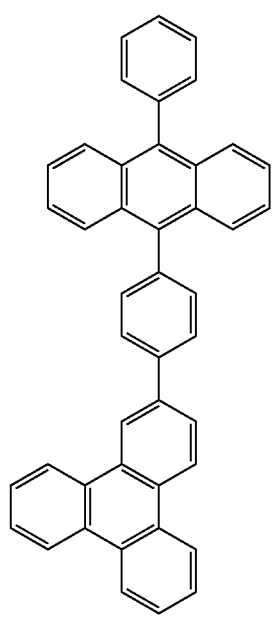
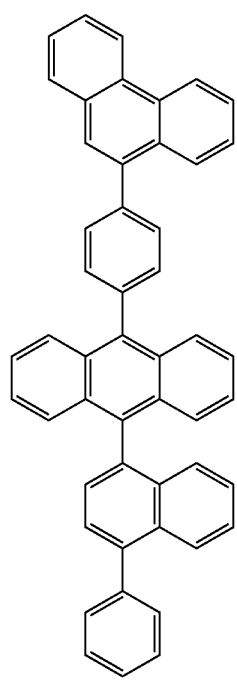

507
-continued
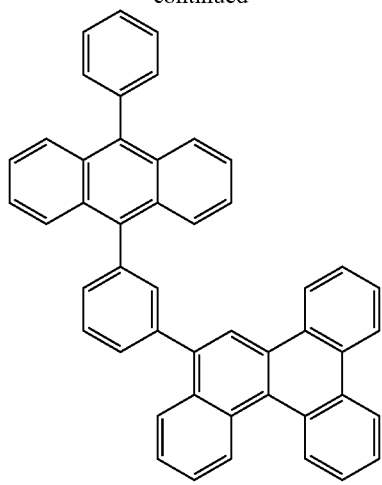
508
-continued
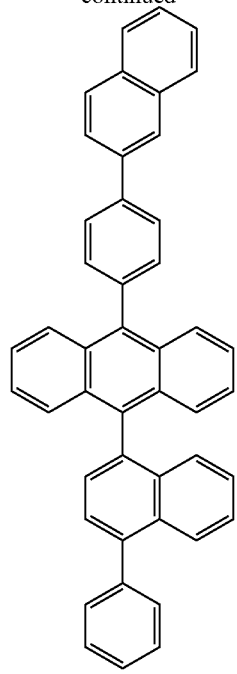
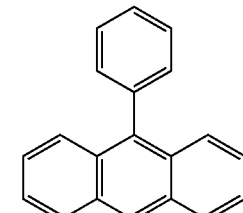
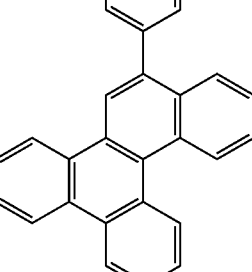
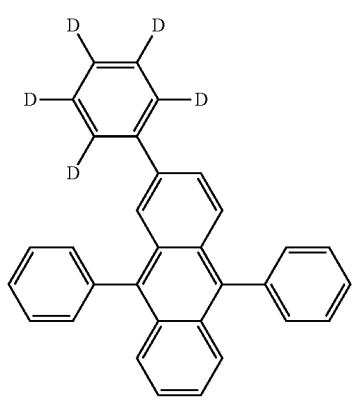

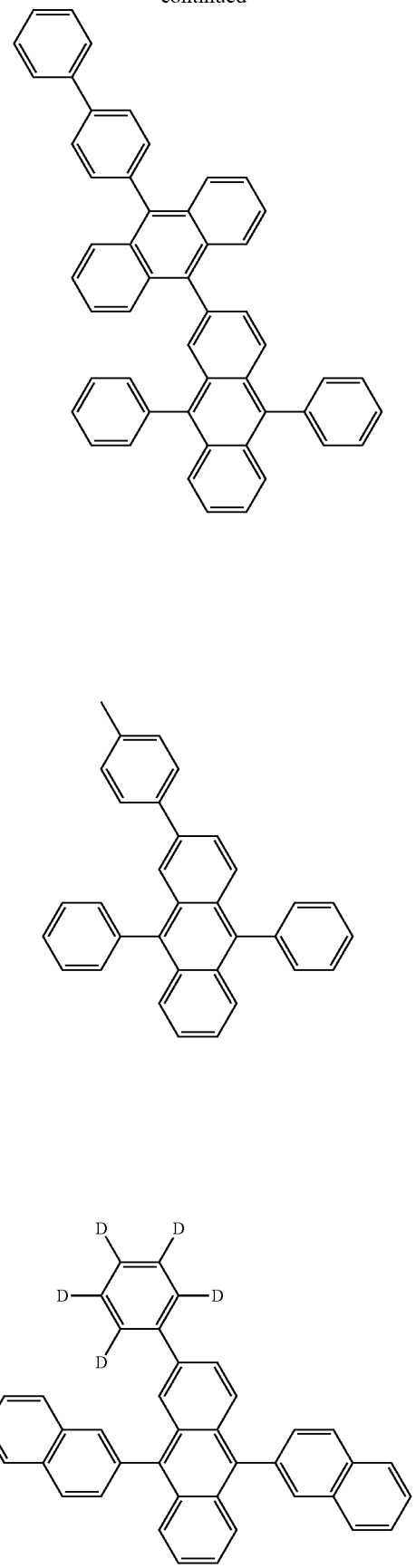

511
-continued
512
-continued
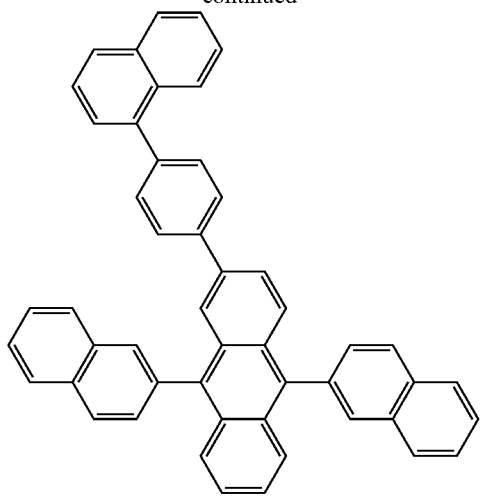
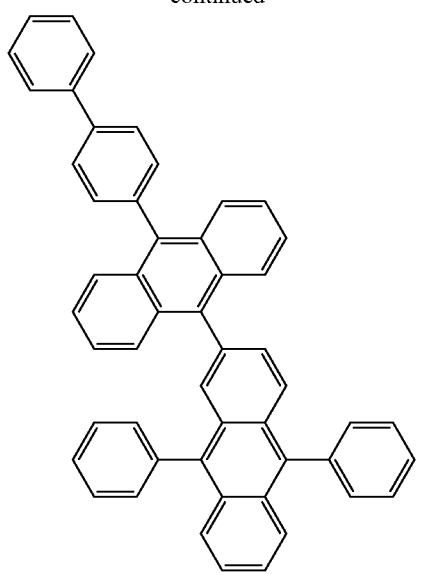
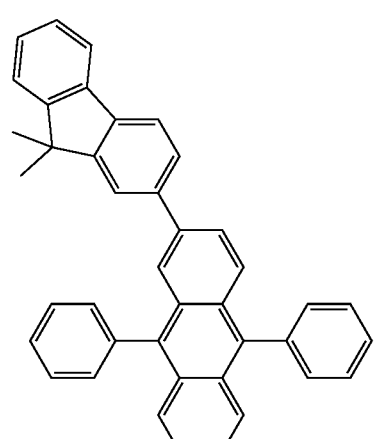
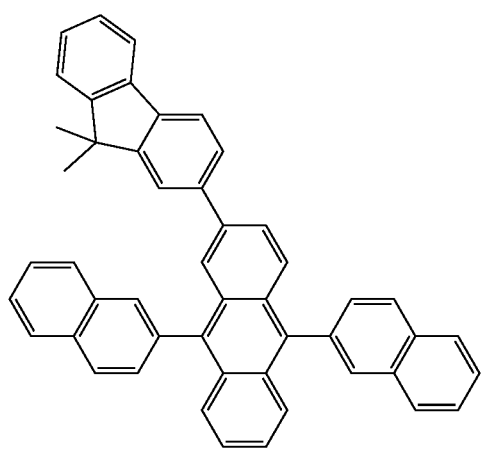
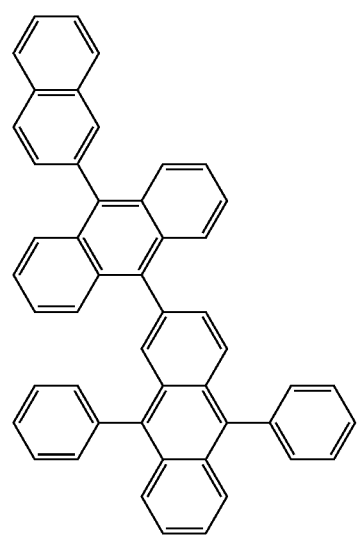
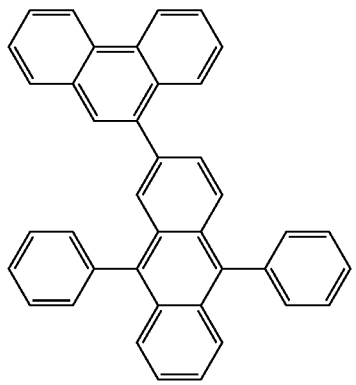

513
-continued
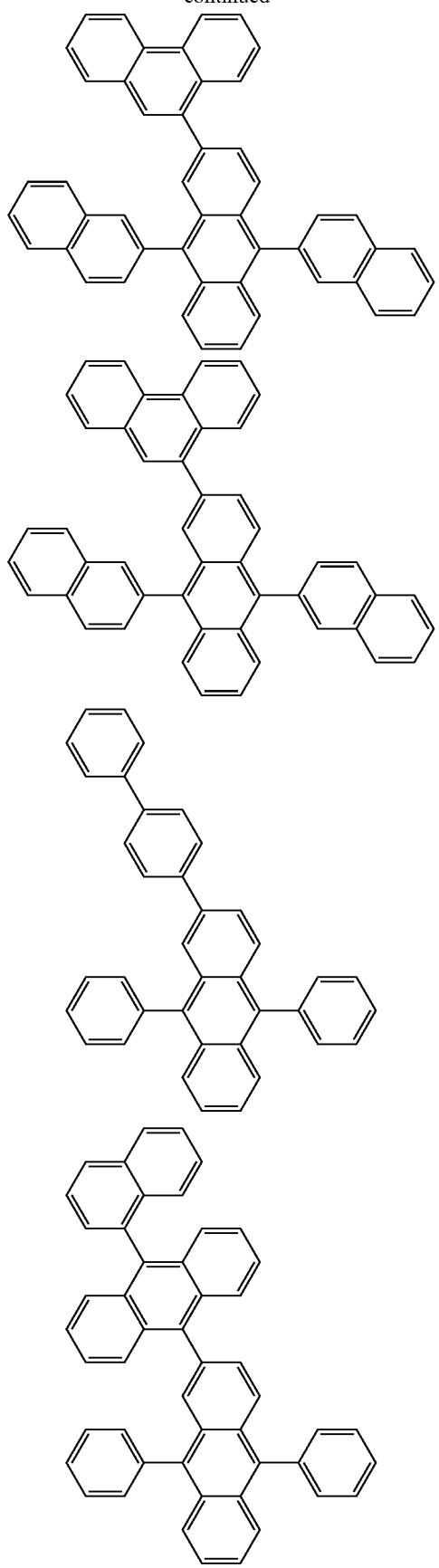
514
-continued
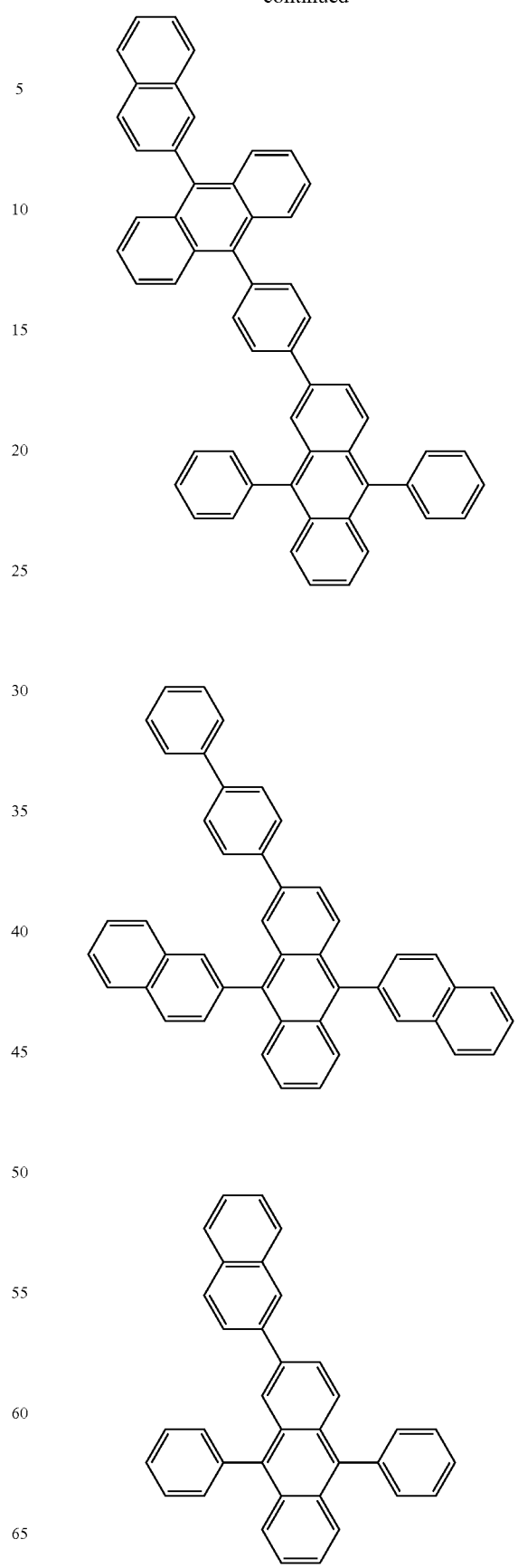

515
-continued
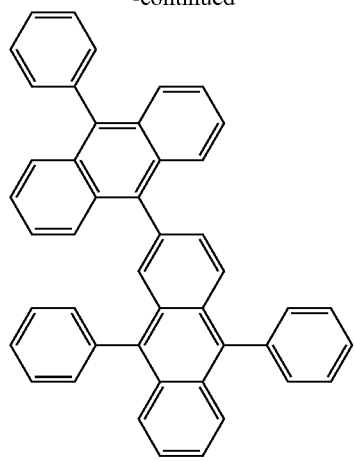
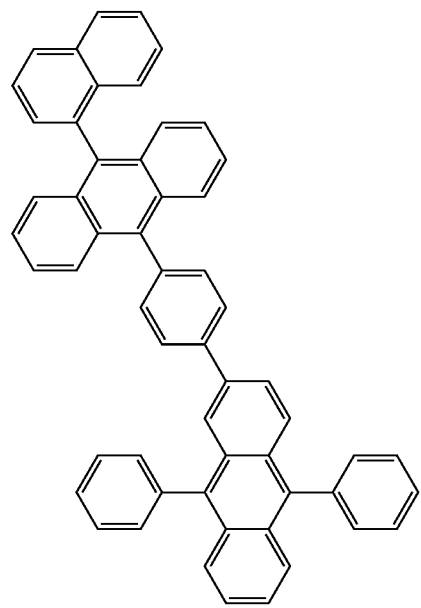
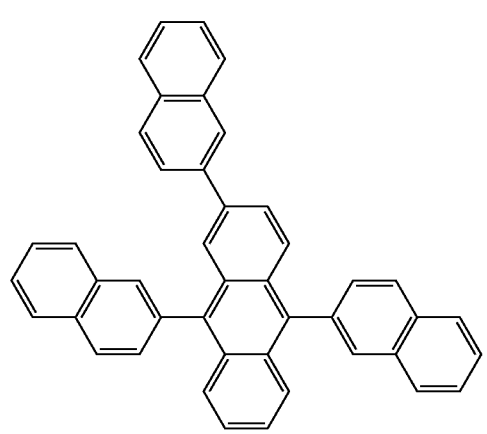
516
-continued
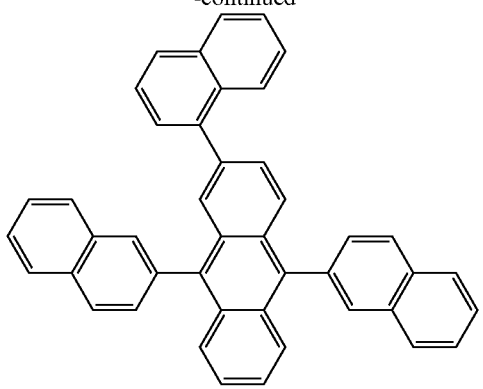
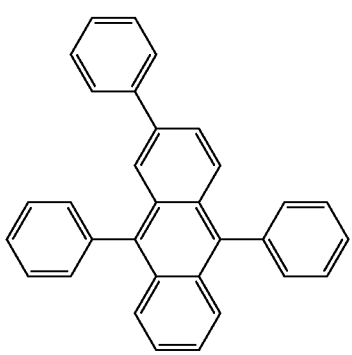
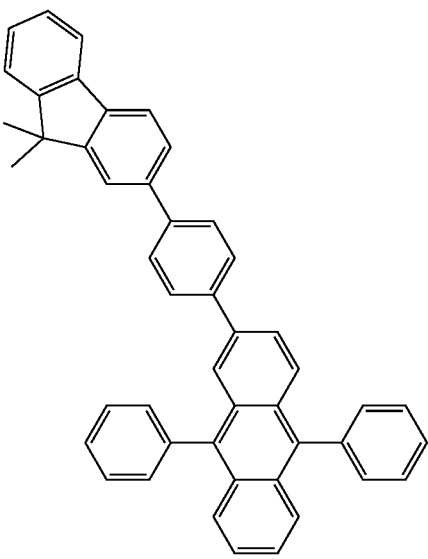

517
-continued
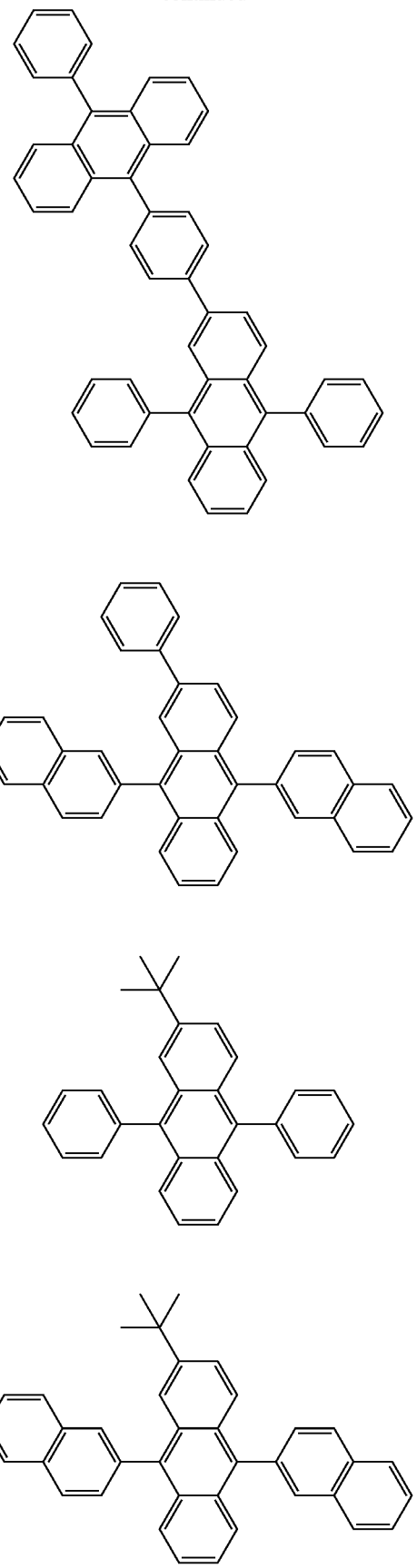
518
-continued
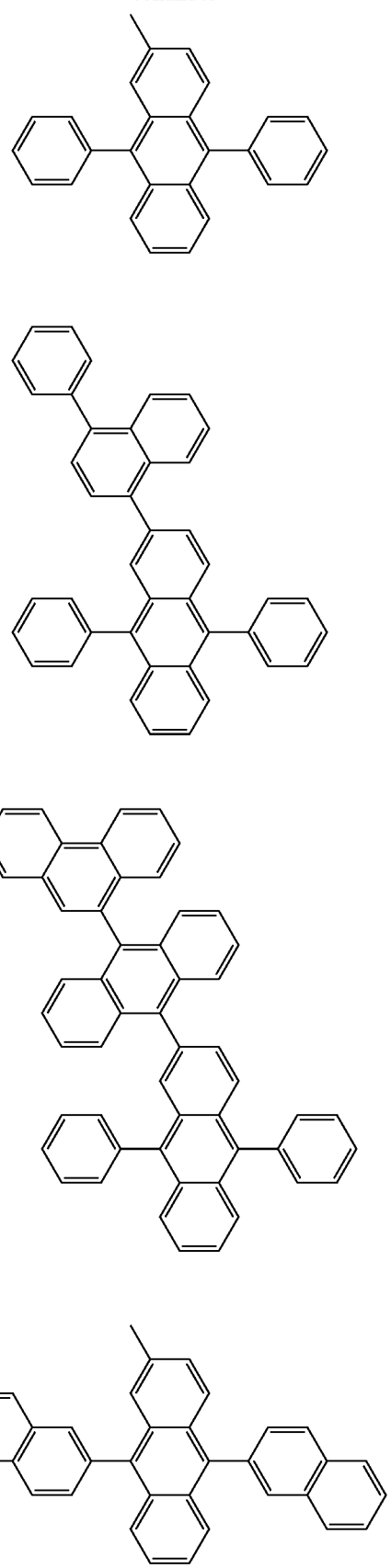

519
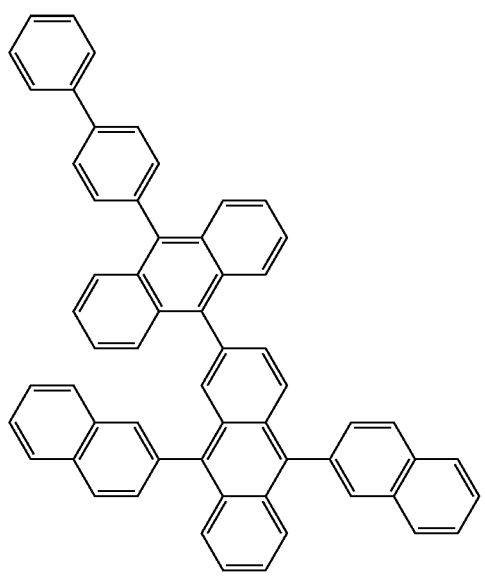
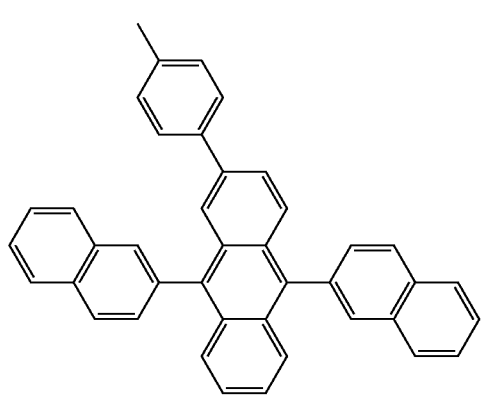
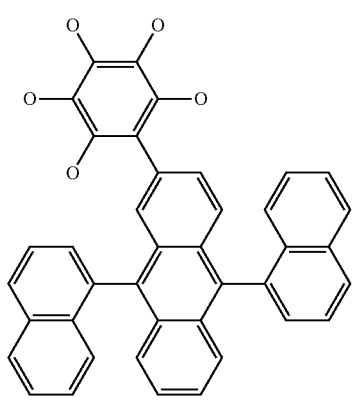
520
-continued
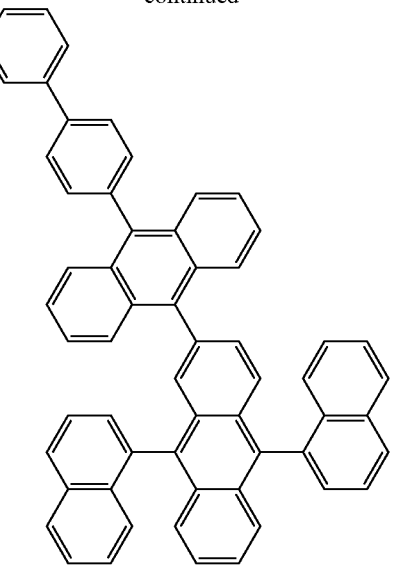
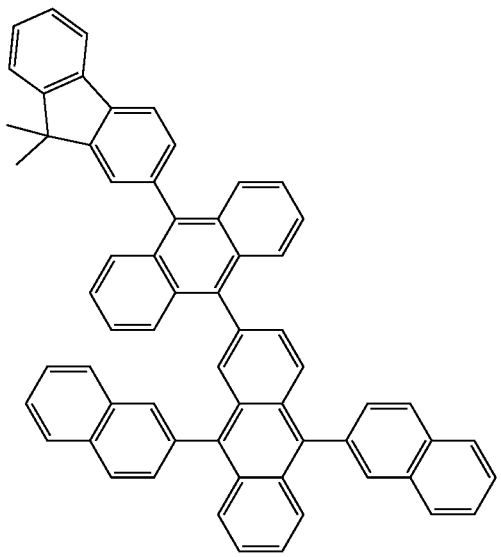

521
-continued
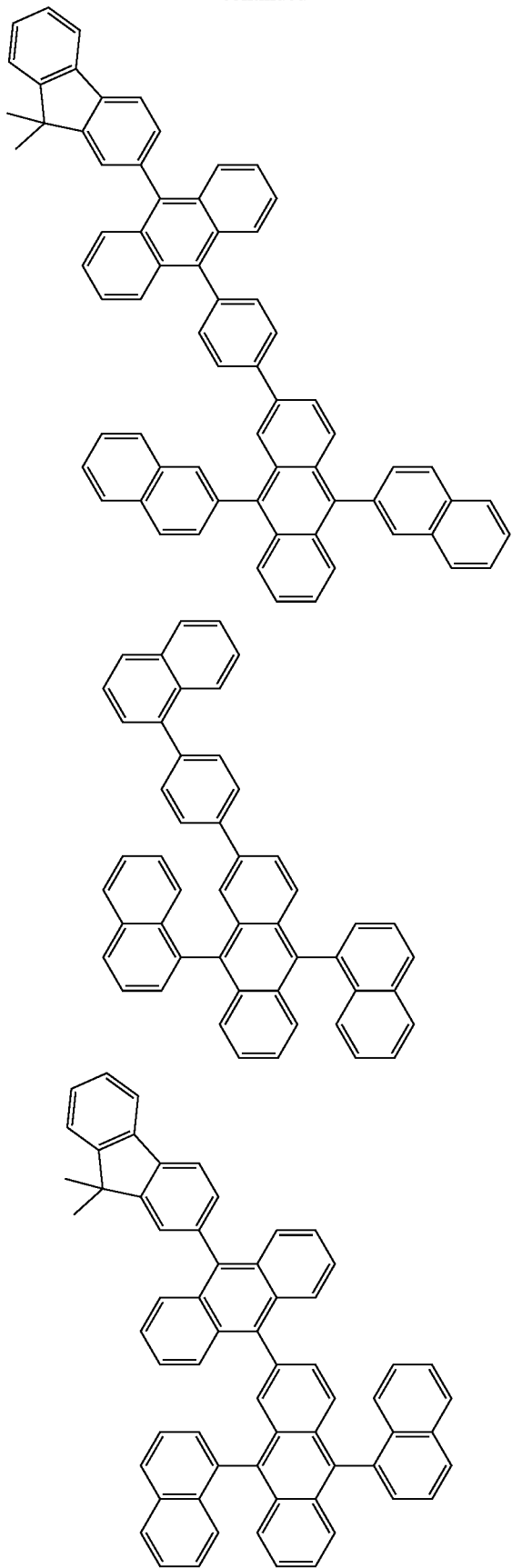
522
-continued
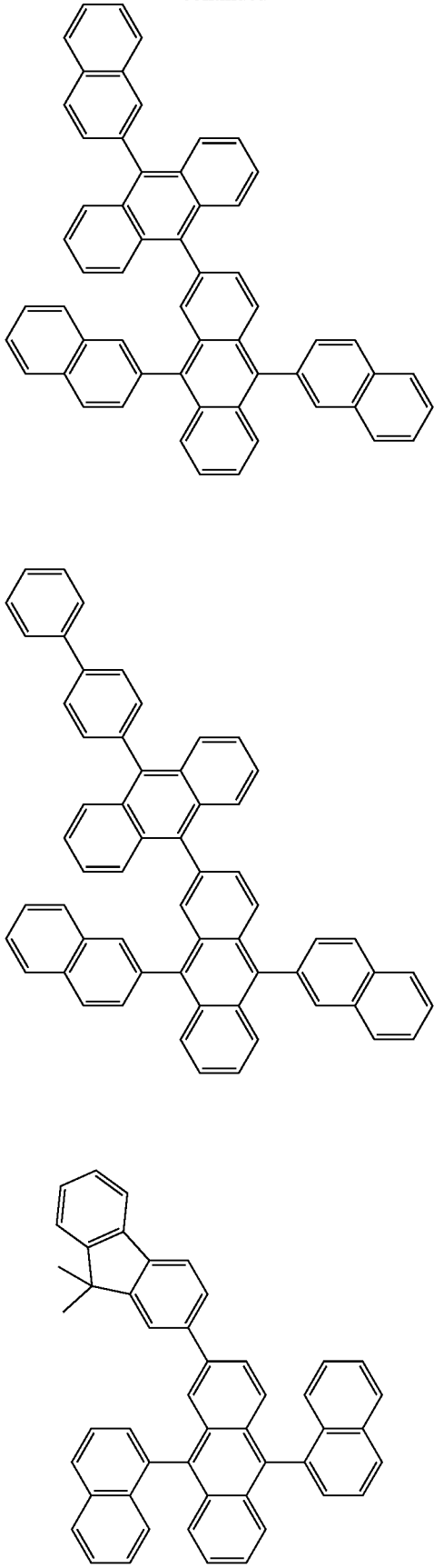

523
-continued
524
-continued
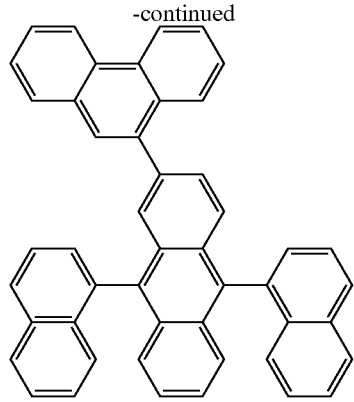

525
-continued
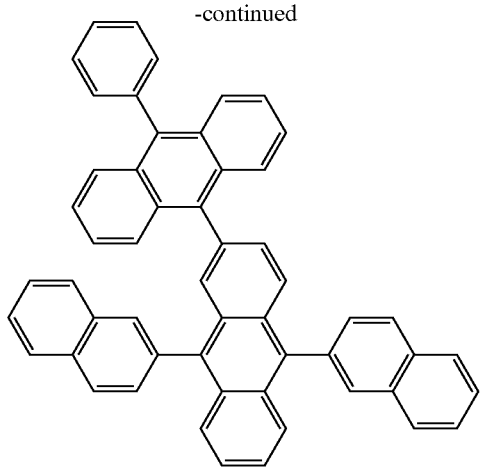
526
-continued
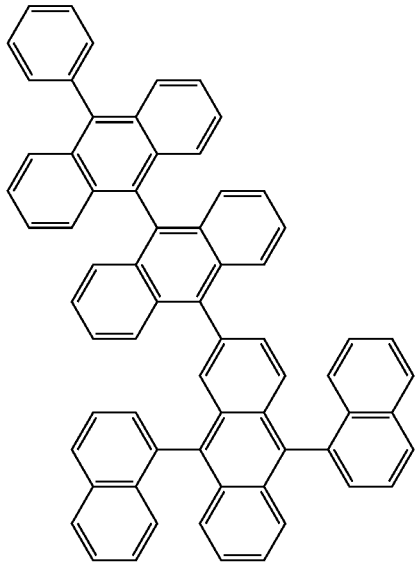
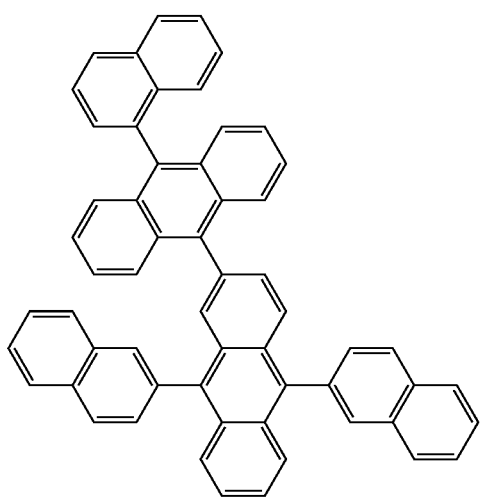
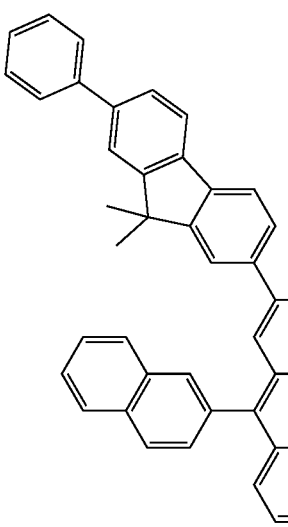
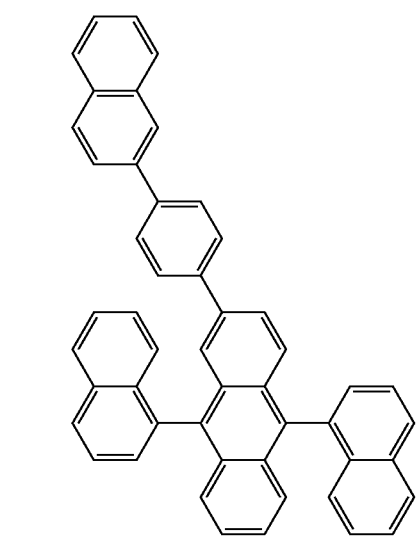
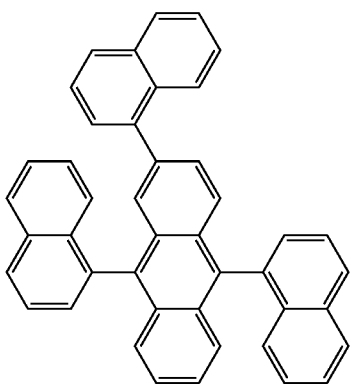

527
-continued
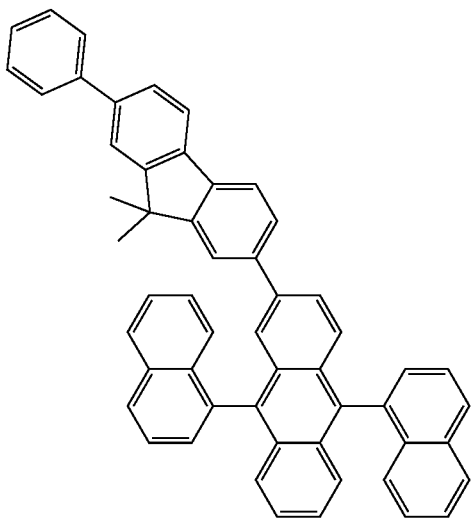
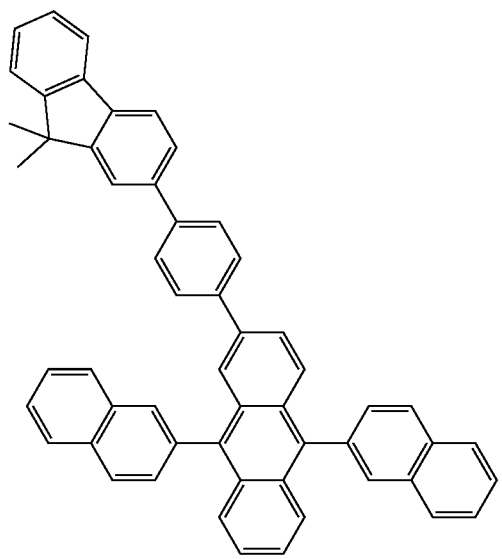
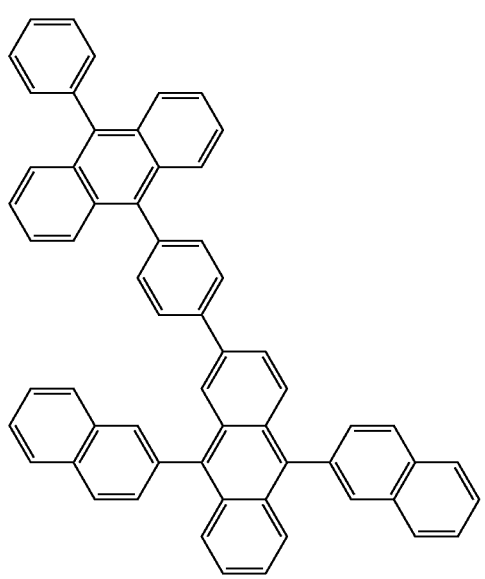
528
-continued
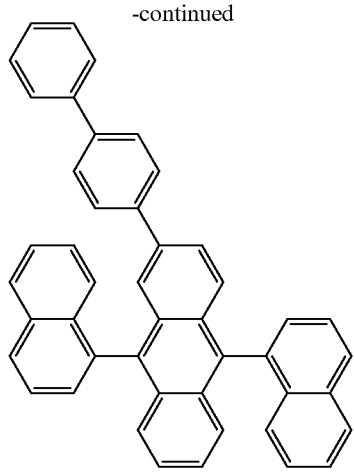
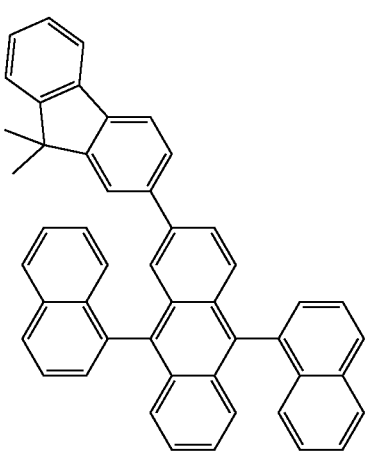
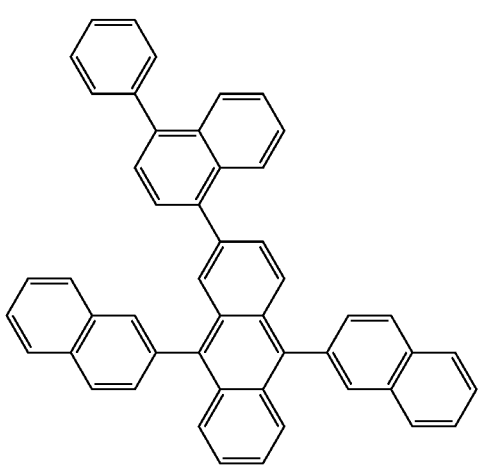

529
-continued
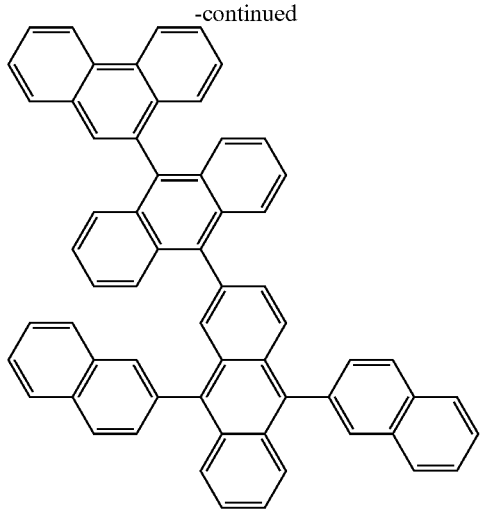
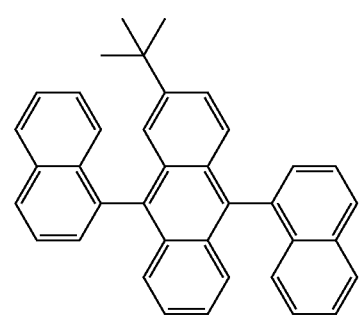
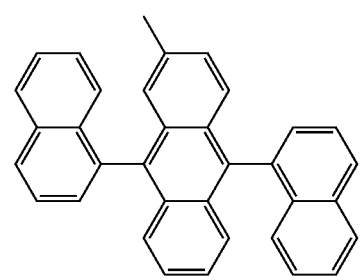
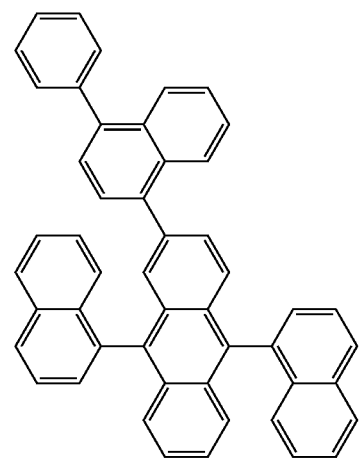
530
-continued
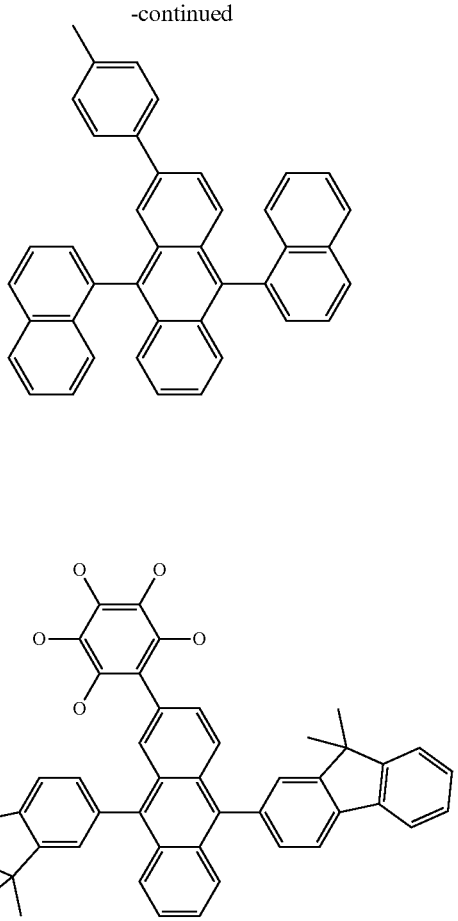
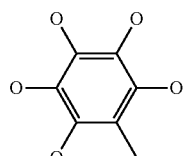
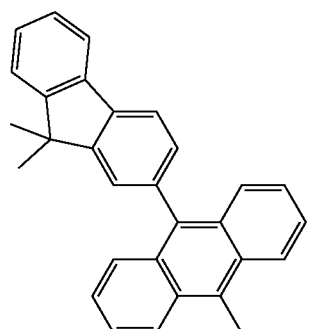
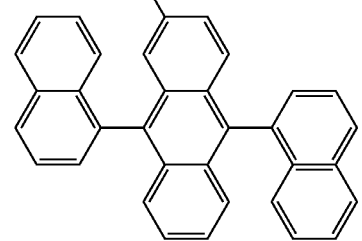

| 531 | 532 |
|---|---|
| -continued | -continued |
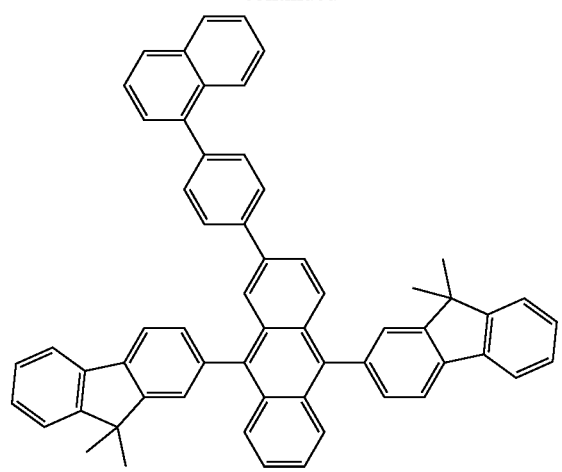
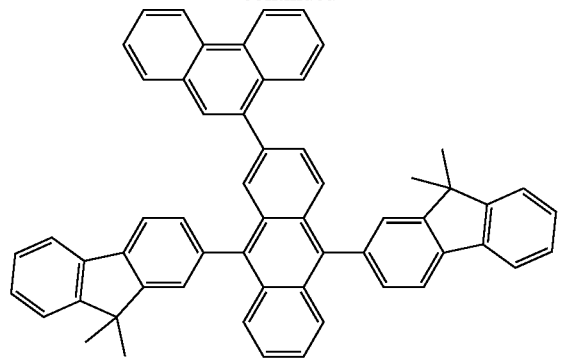
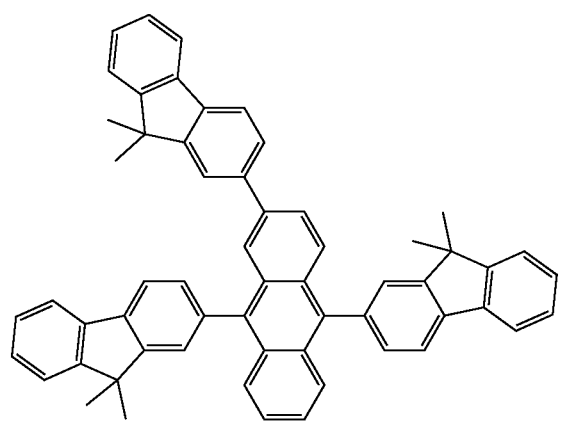

533
-continued
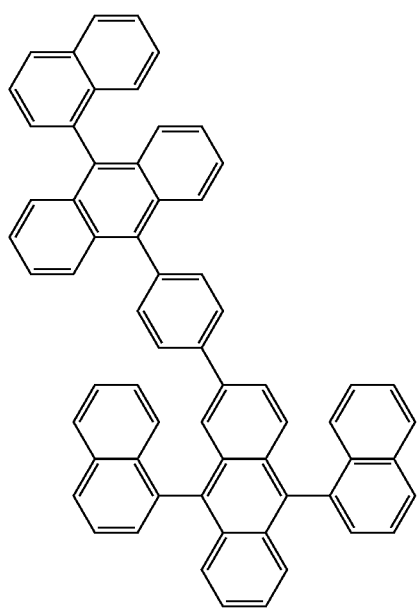
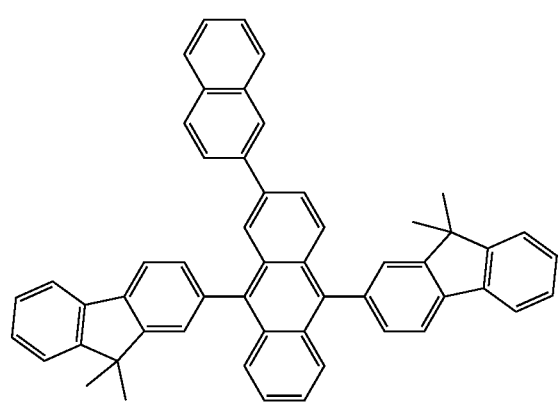
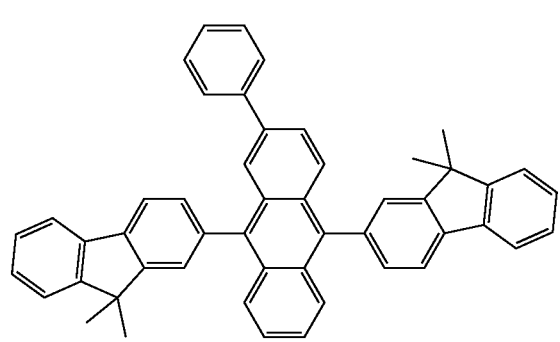
534
-continued
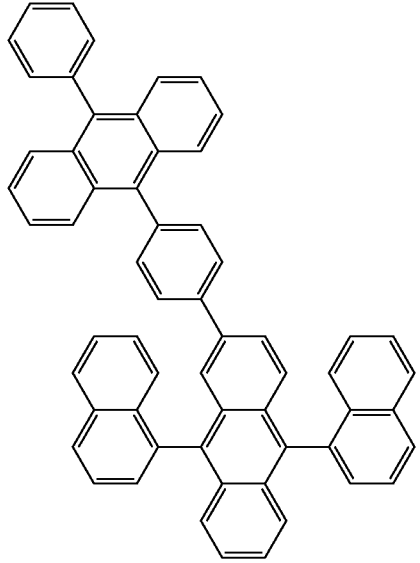
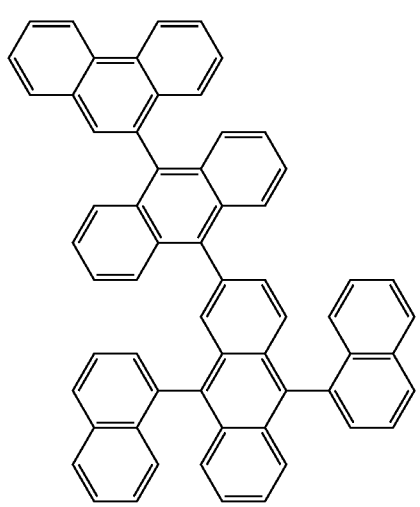
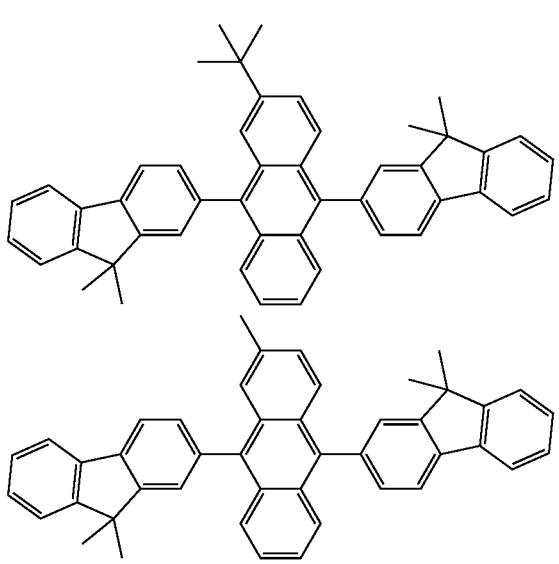

535
-continued
536
-continued
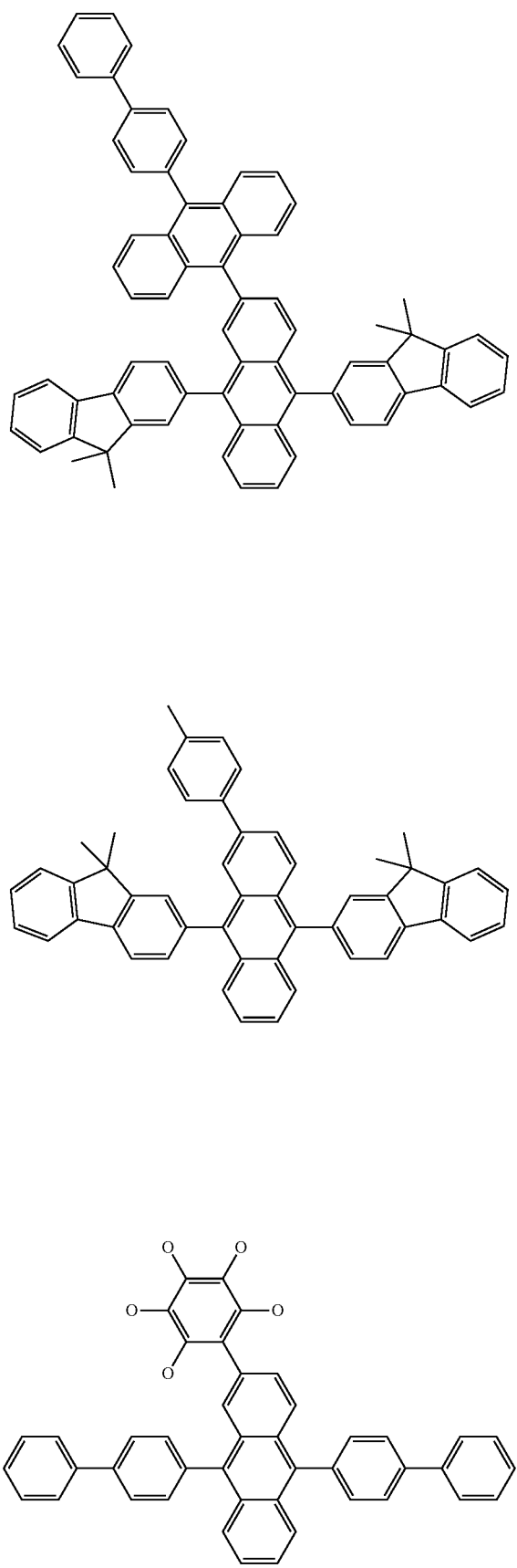
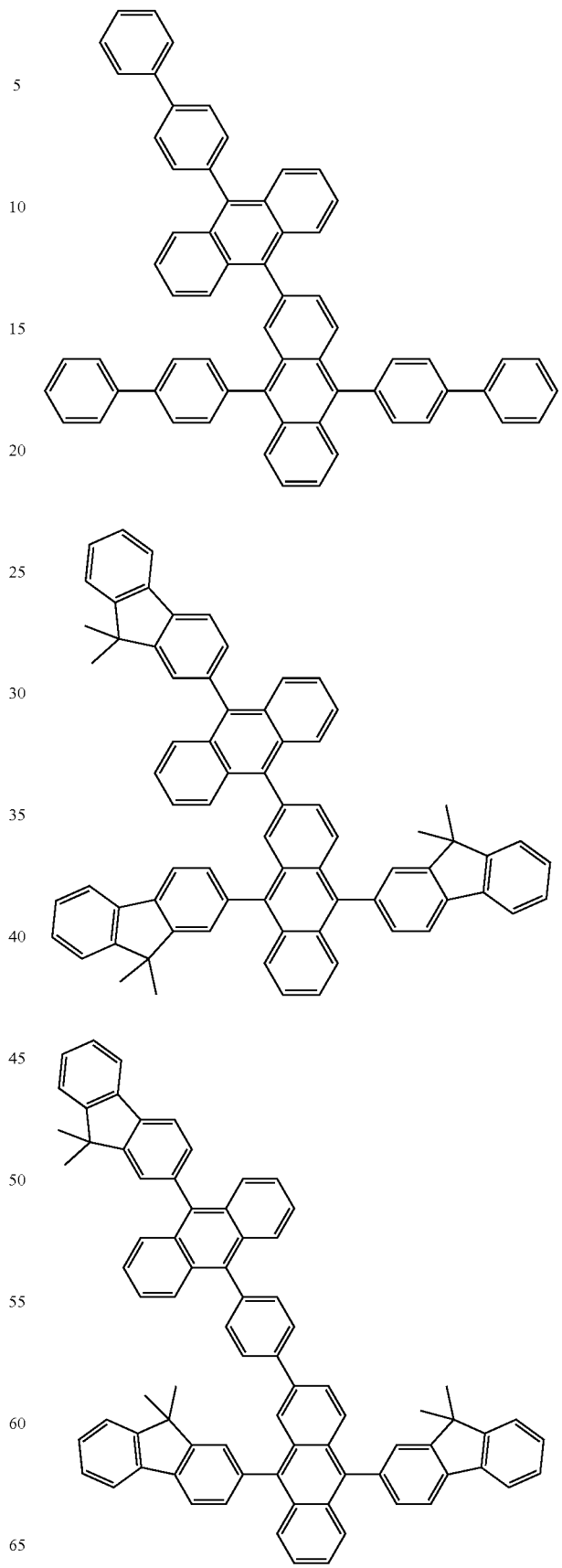

537
-continued
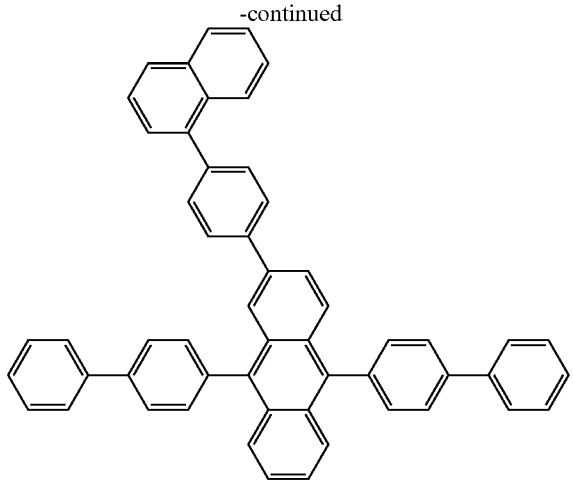
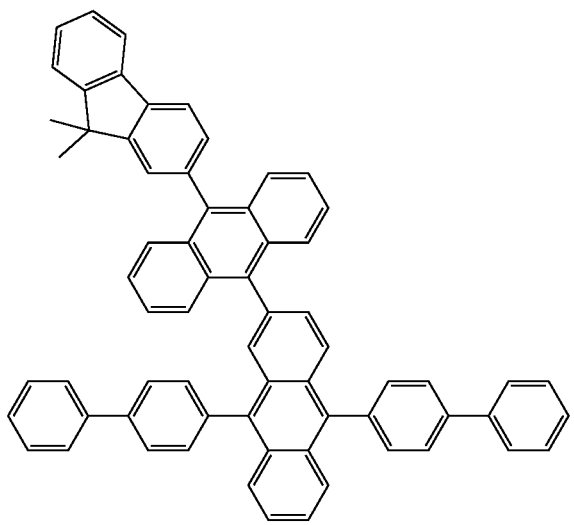
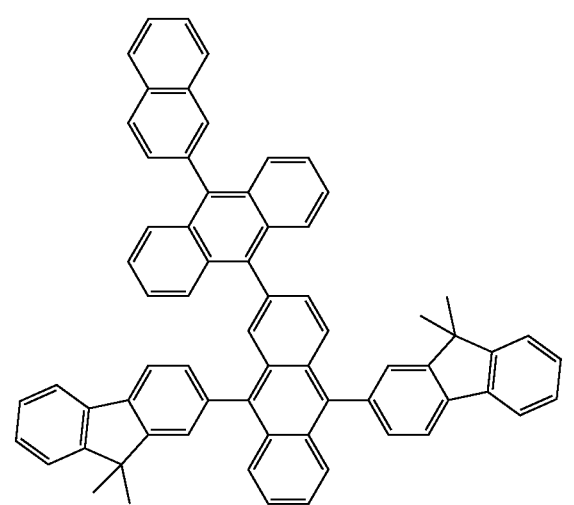
538
-continued
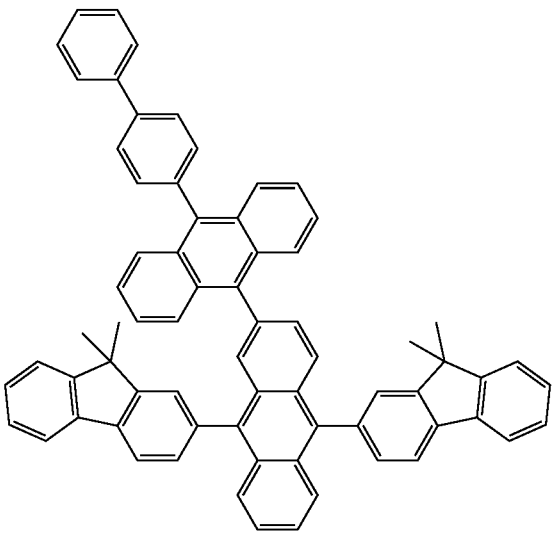
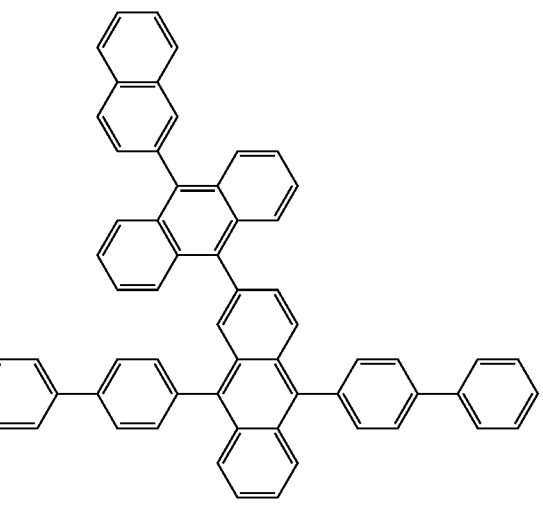

539
-continued
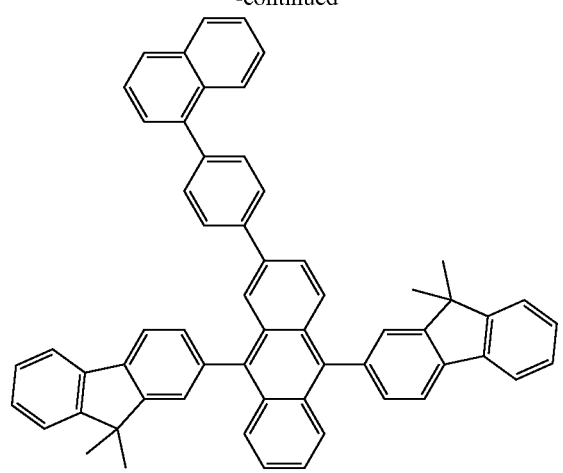
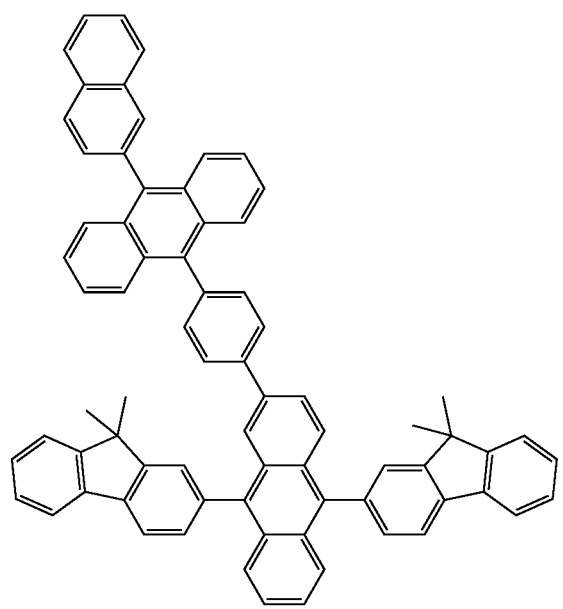
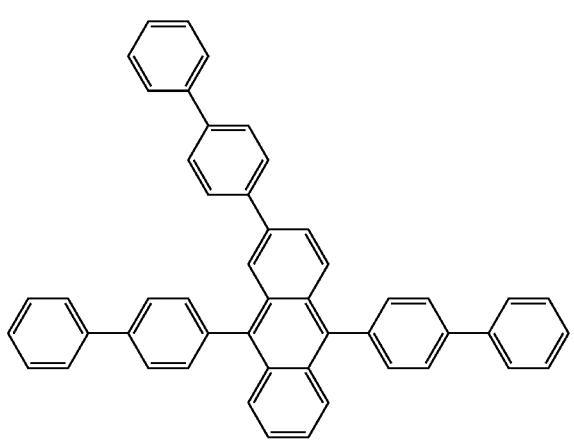
540
-continued
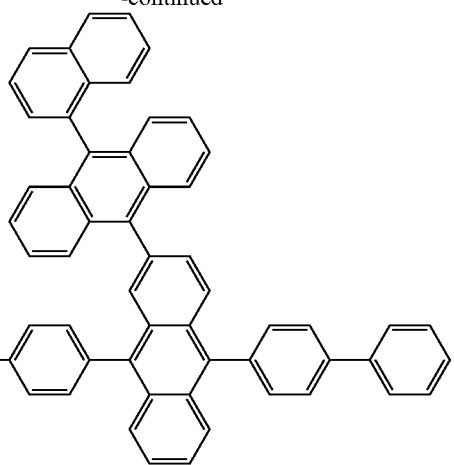
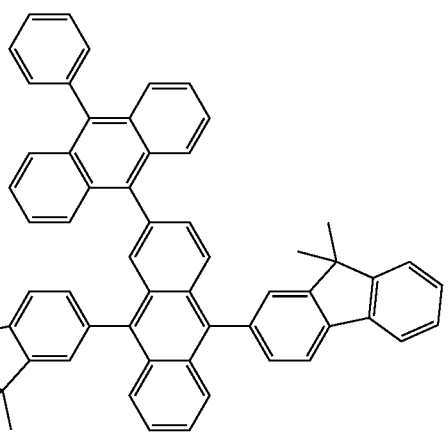
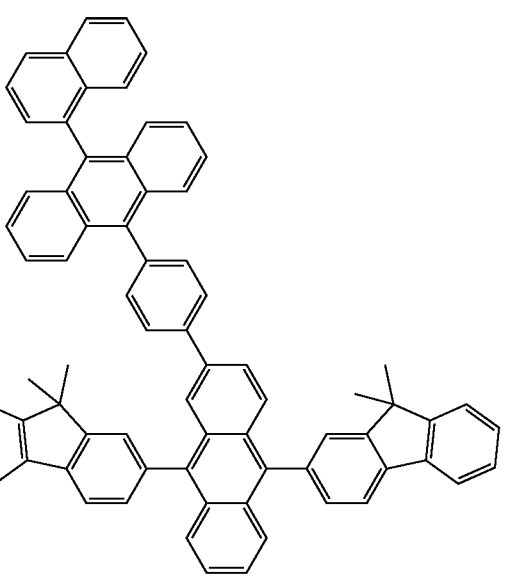

541
-continued
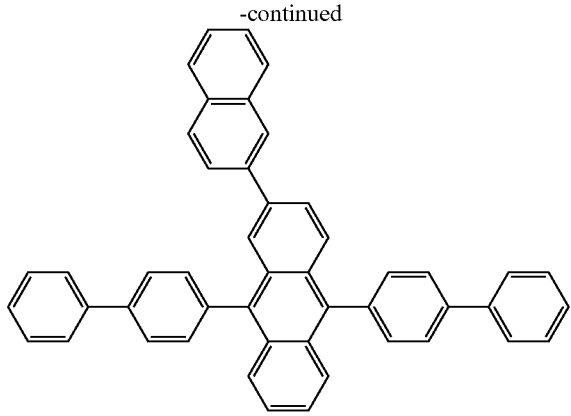
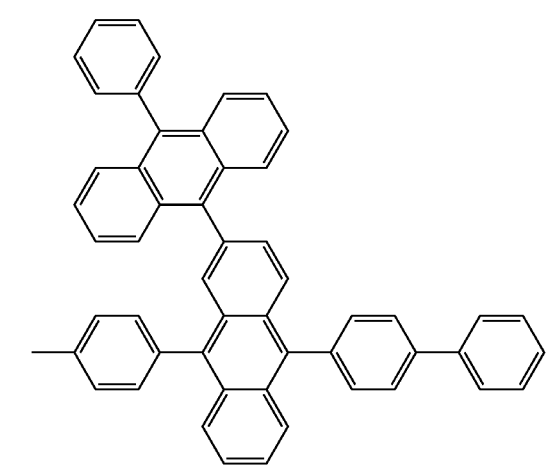
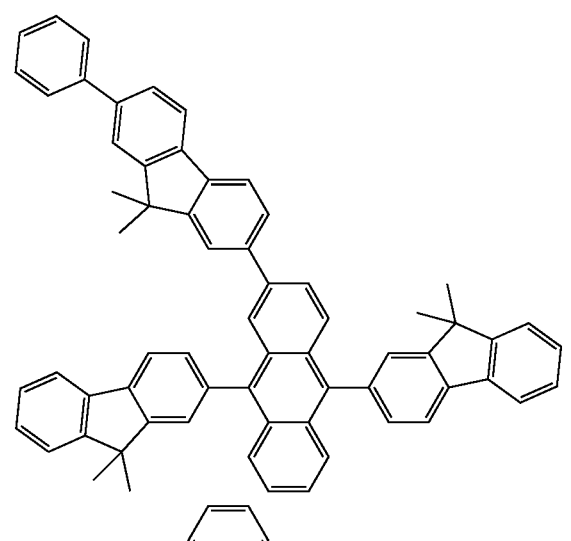
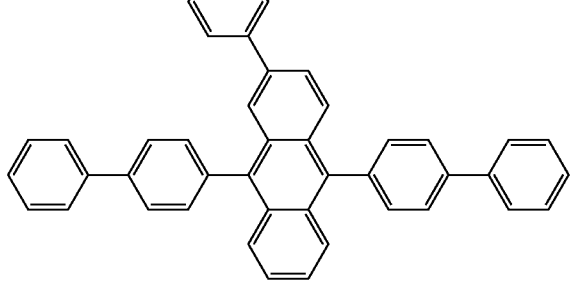
542
-continued
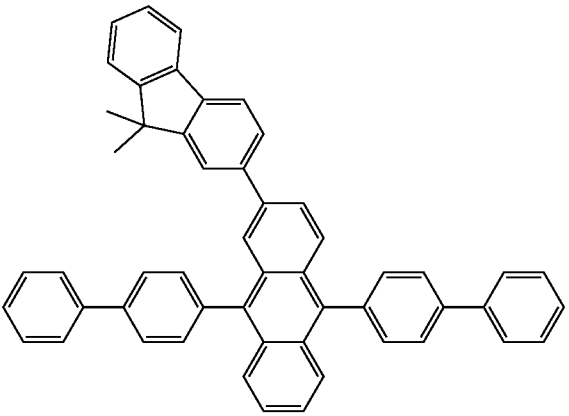
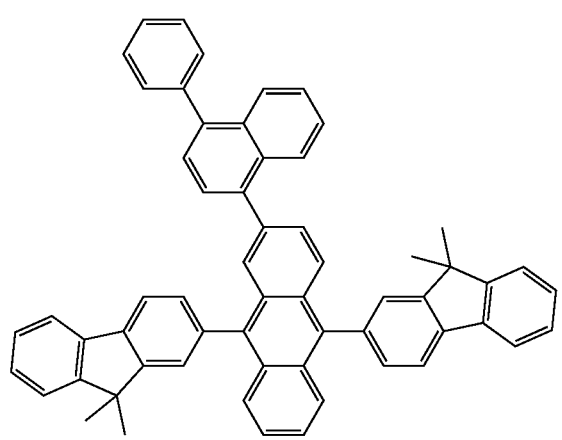
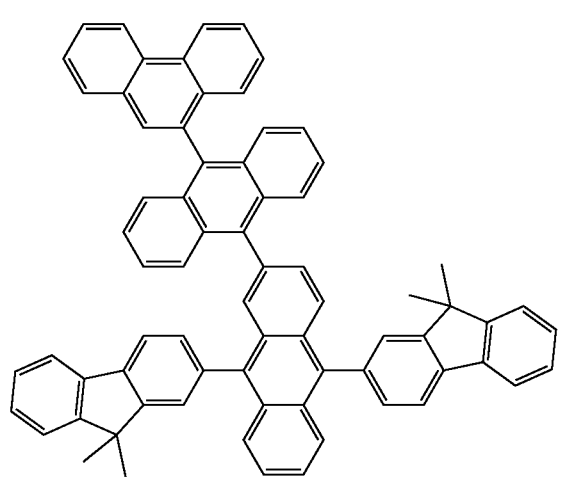
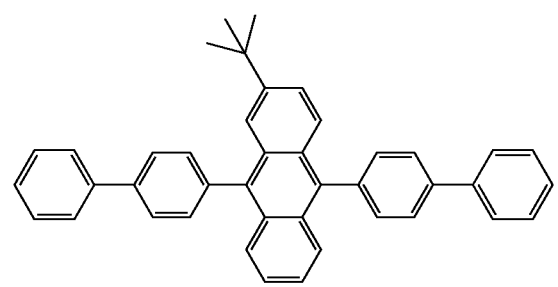

543
-continued
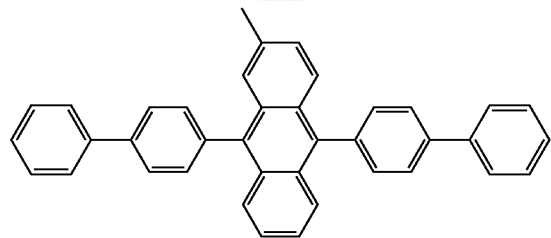
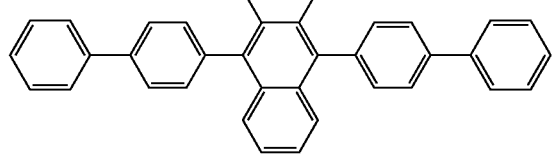
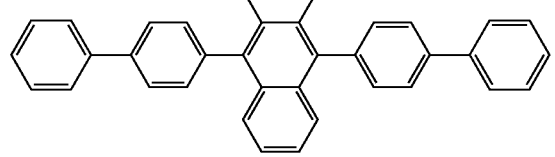
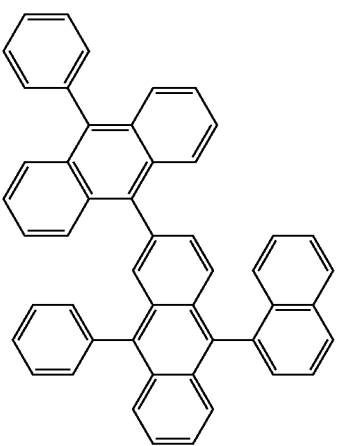
544
-continued
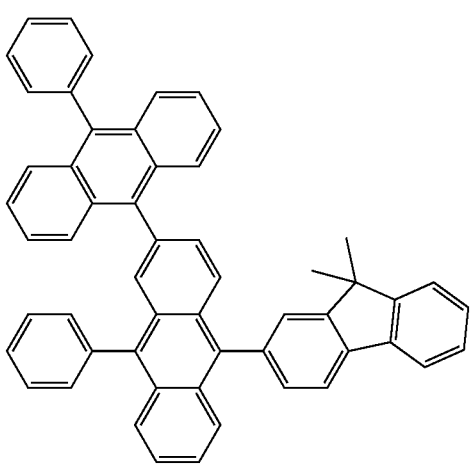
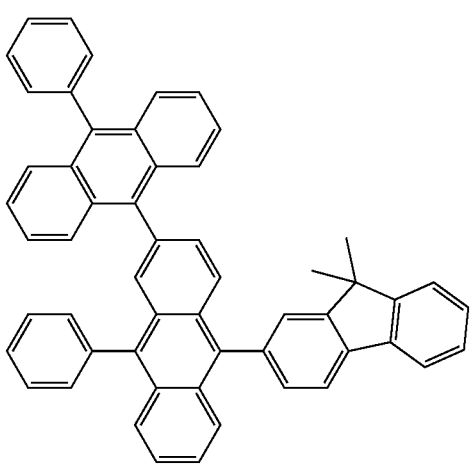
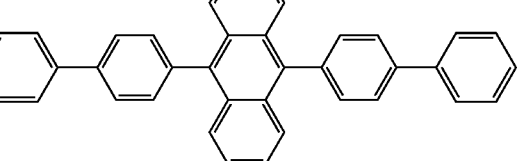

545
-continued
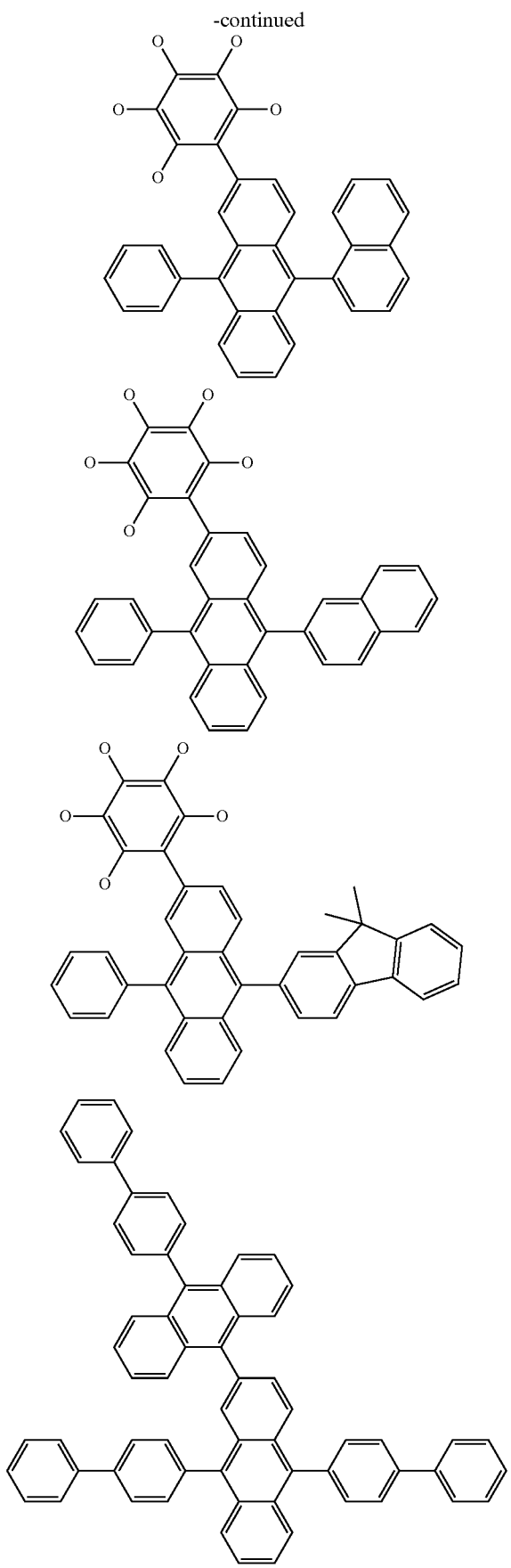
546
-continued
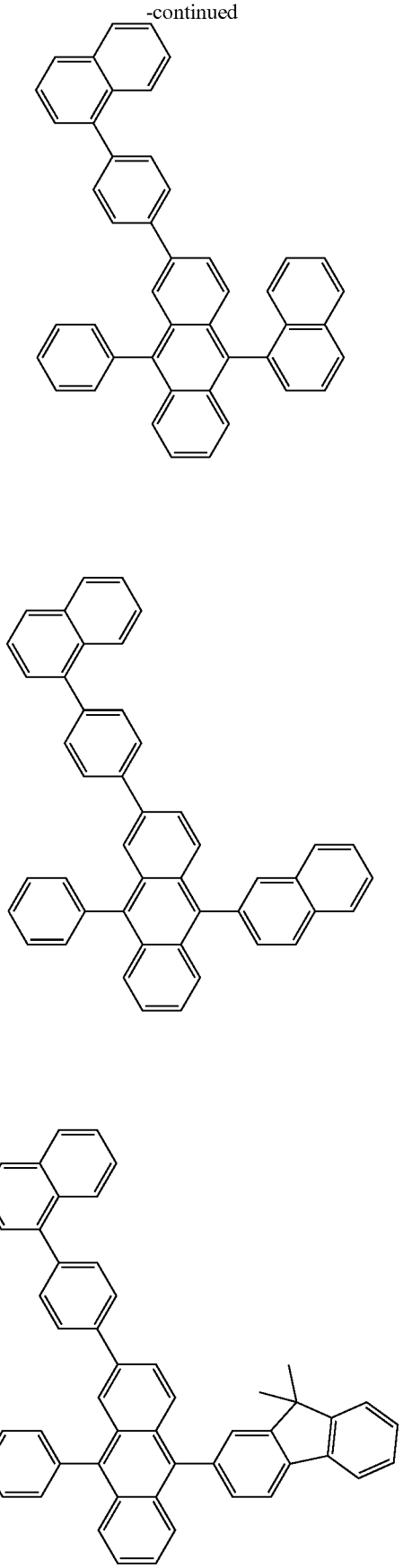

547
-continued
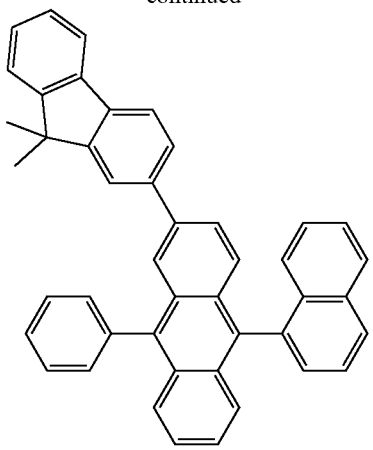
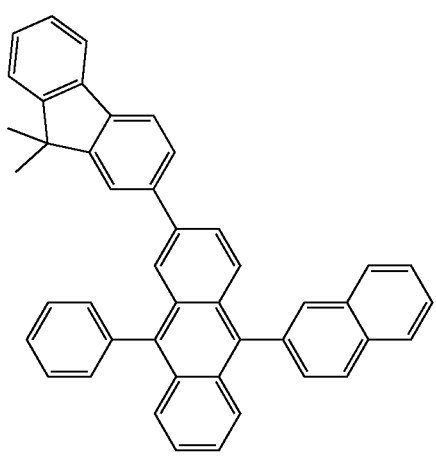
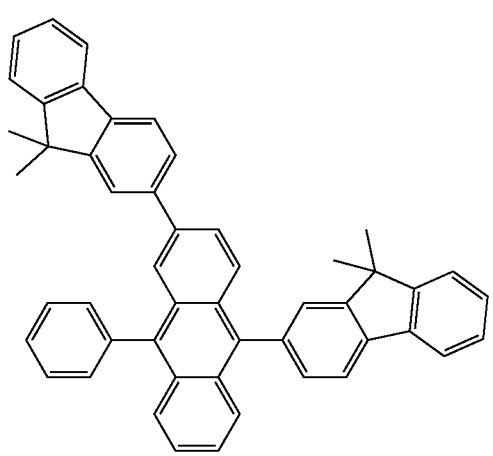
548
-continued
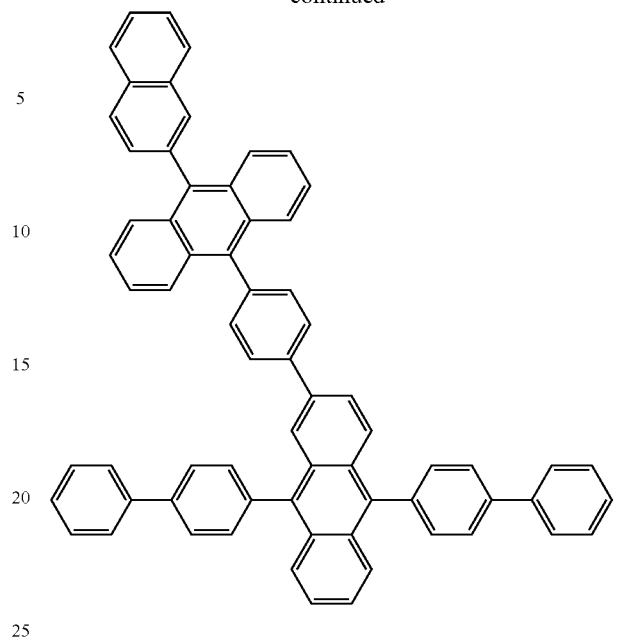
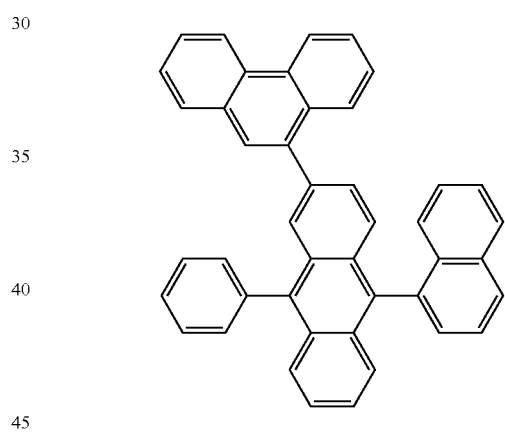
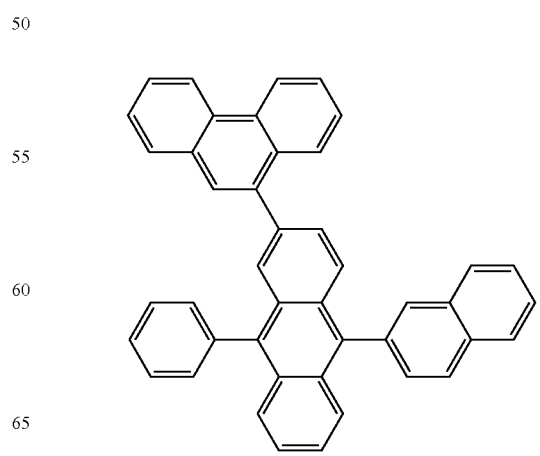

549
-continued
550
-continued
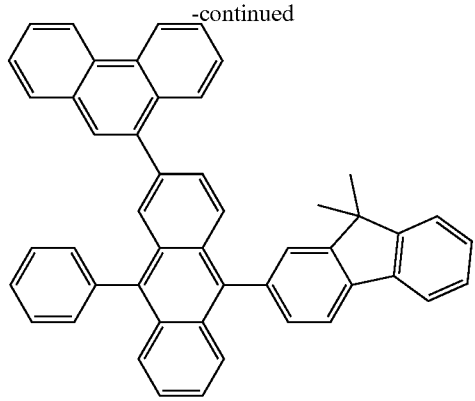
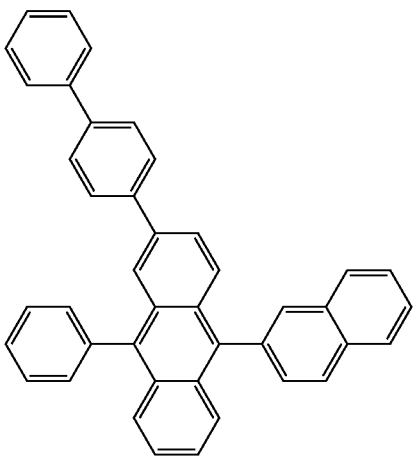
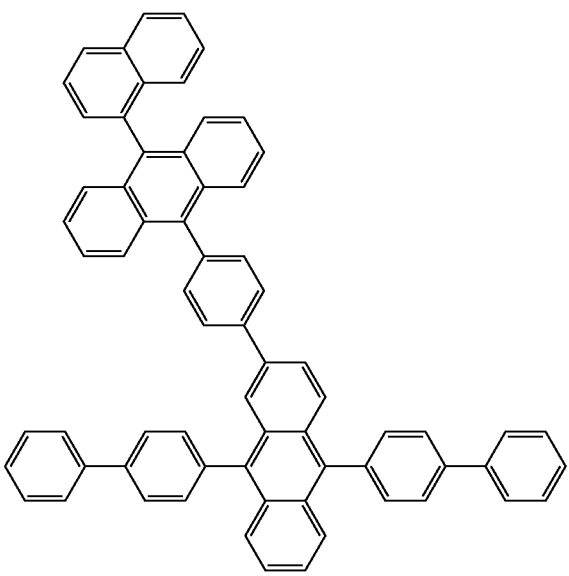
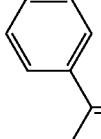
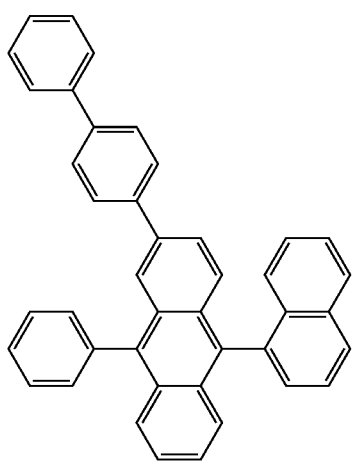
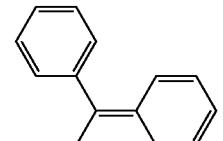
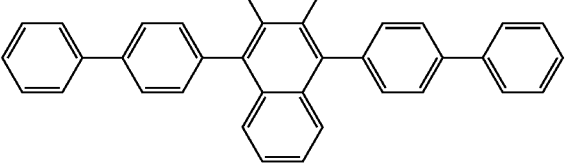

551
-continued
552
-continued
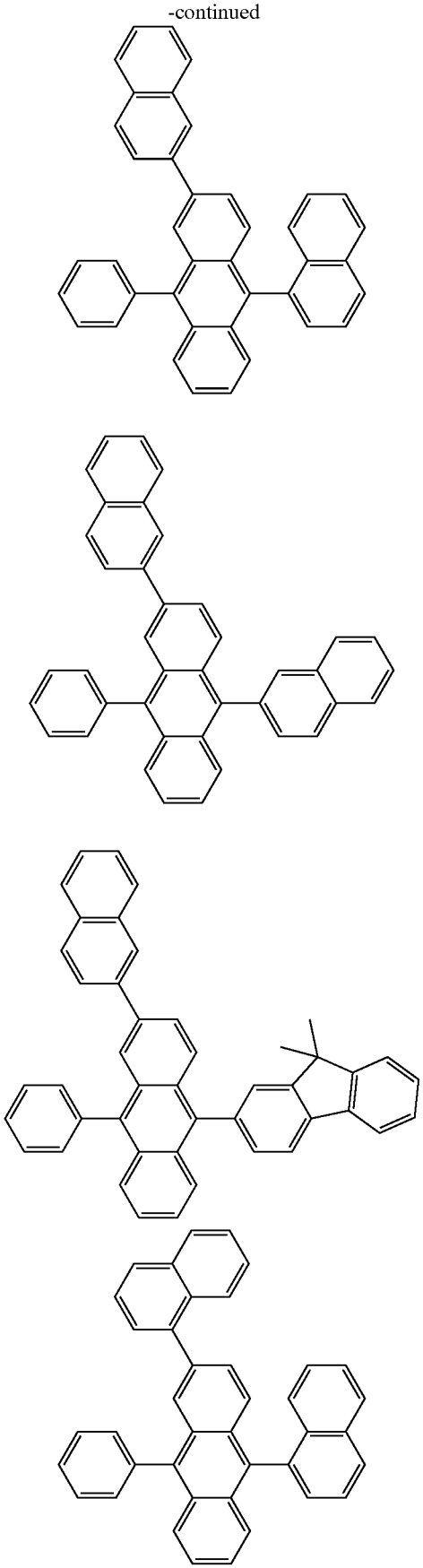
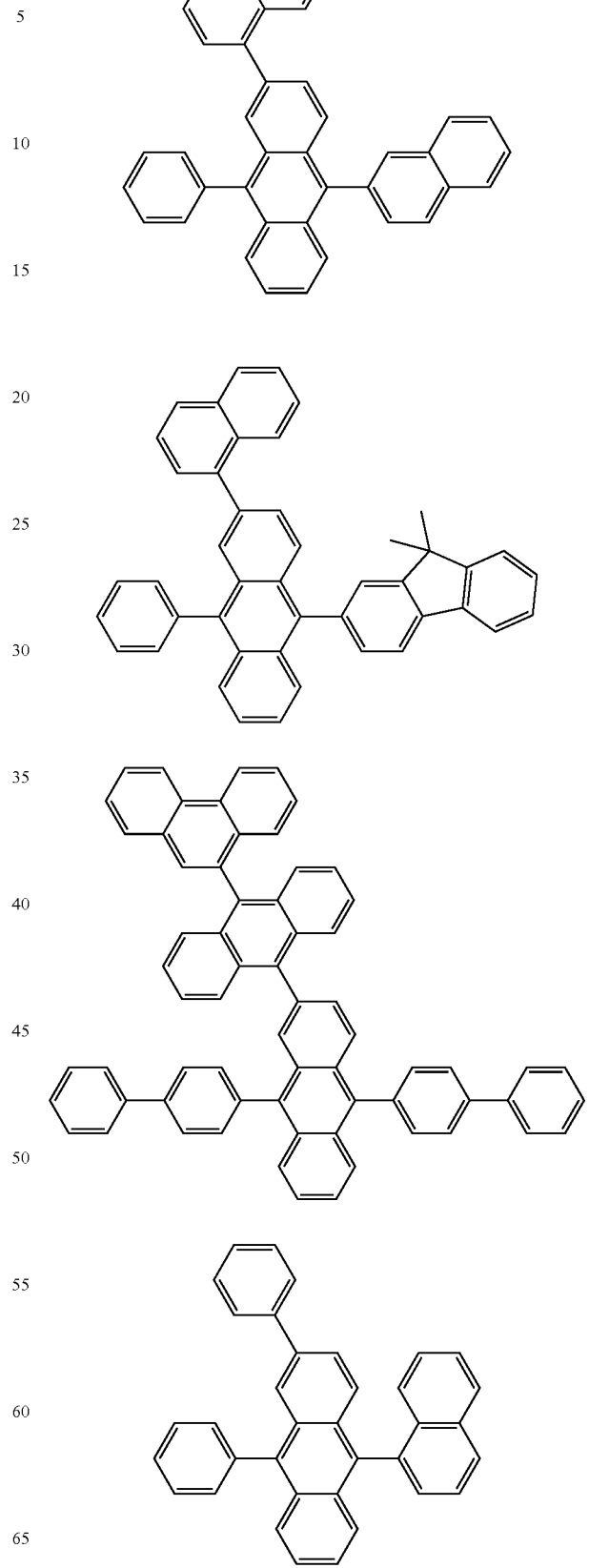

553
-continued
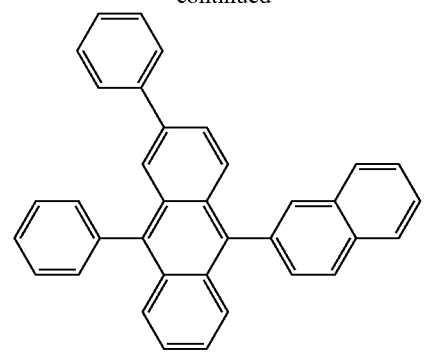
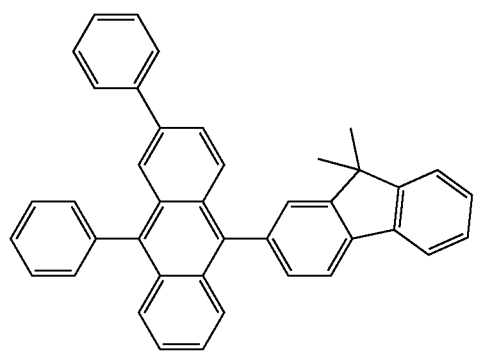
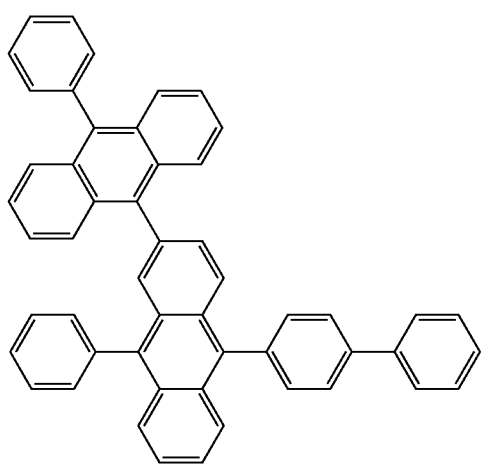
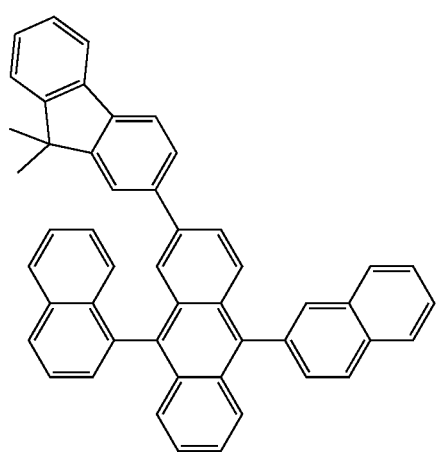
554
-continued
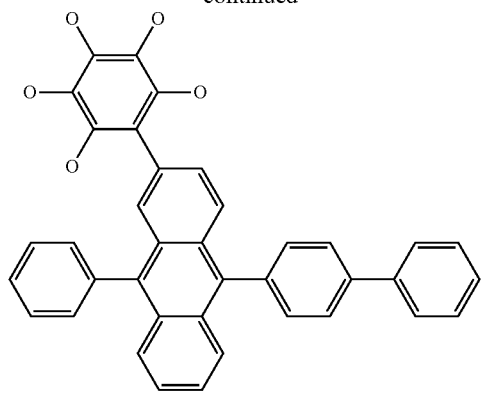
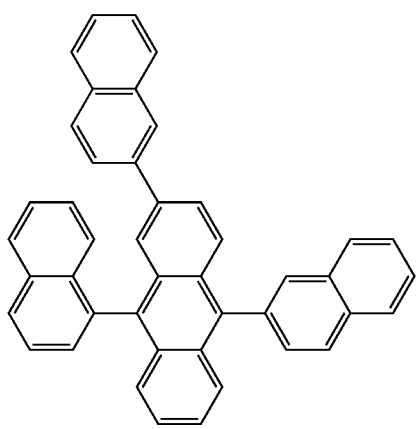
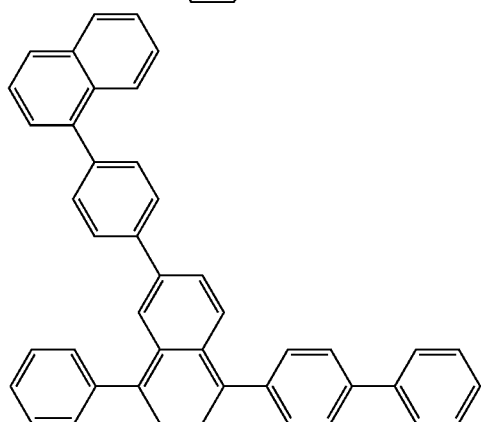
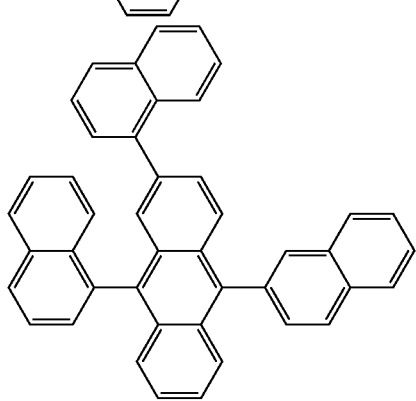

555
-continued
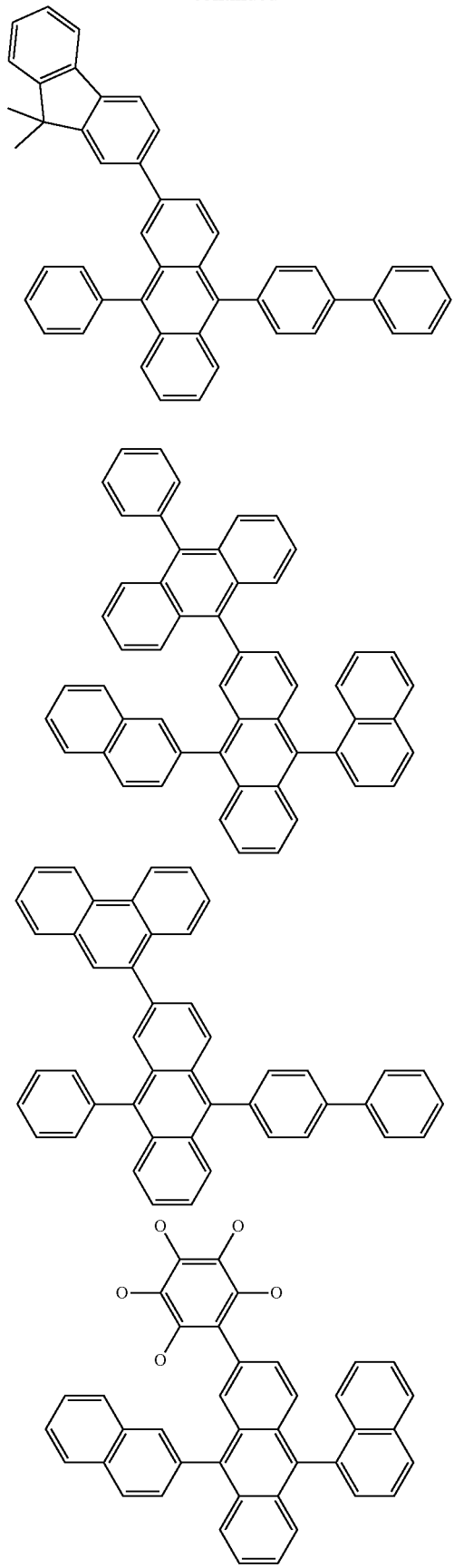
556
-continued
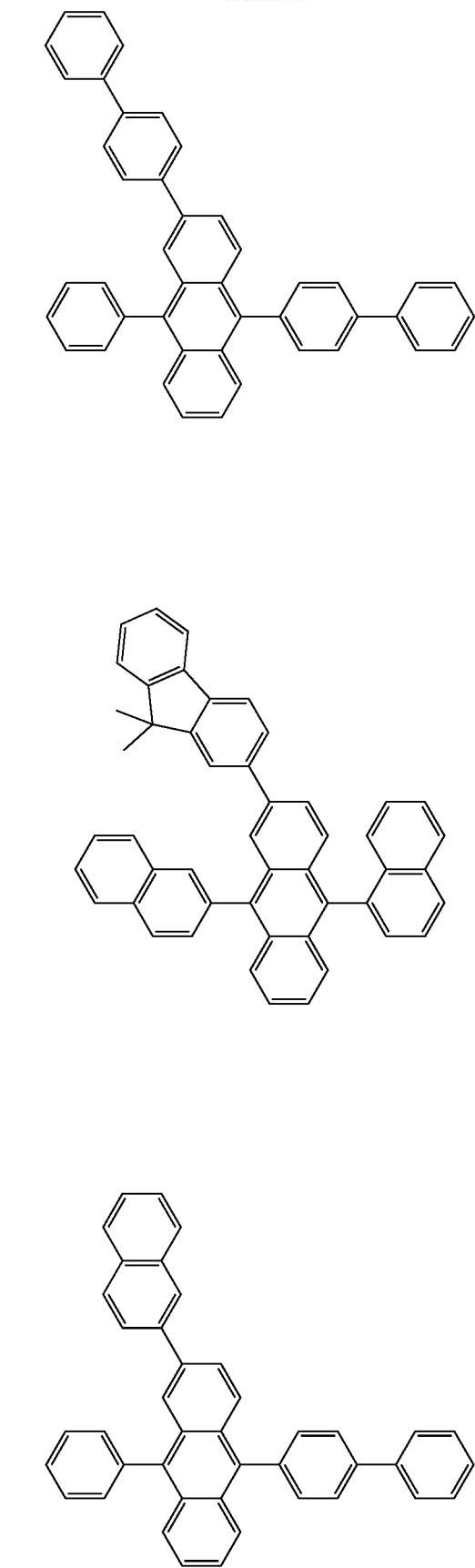

557
-continued
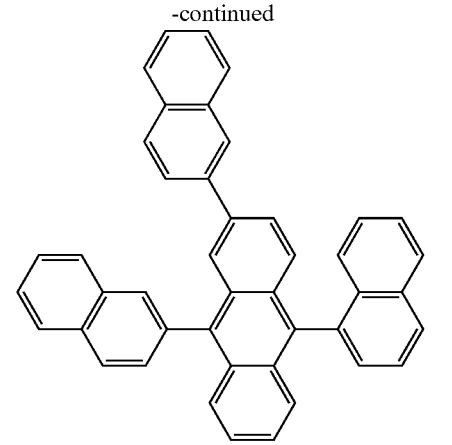
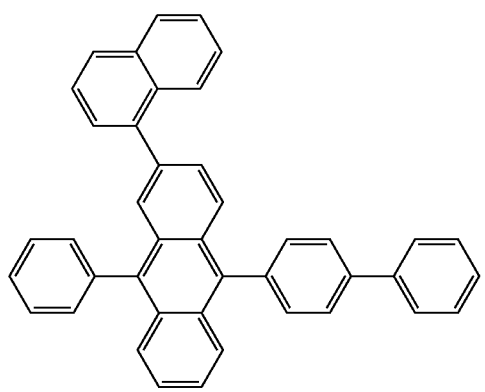
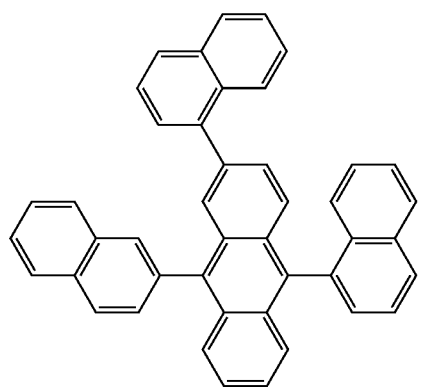
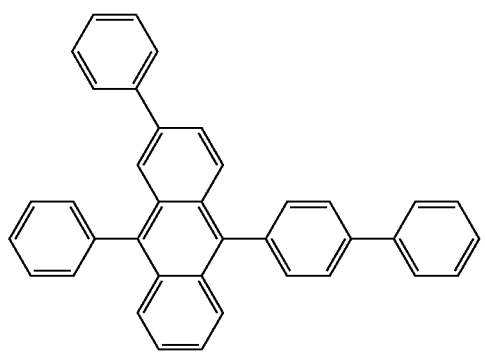
558
-continued
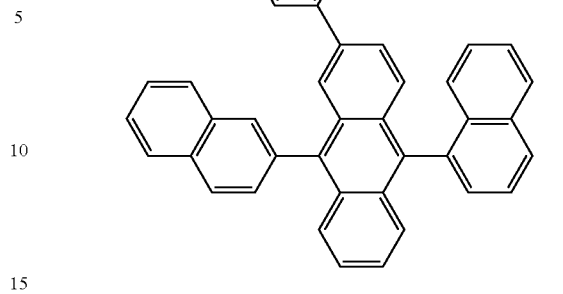
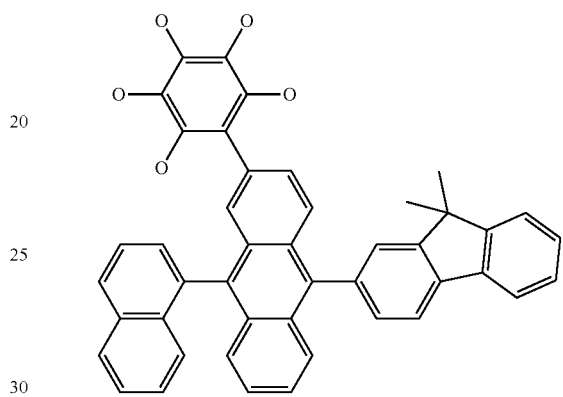
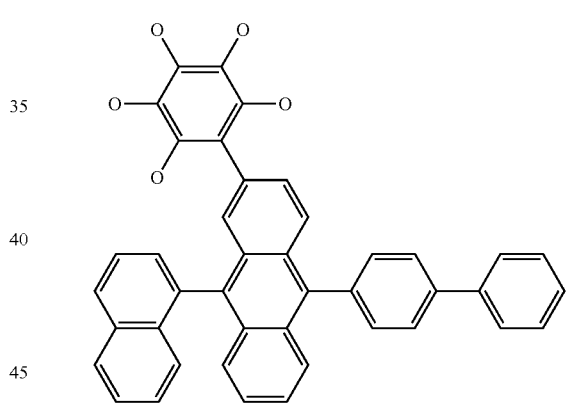
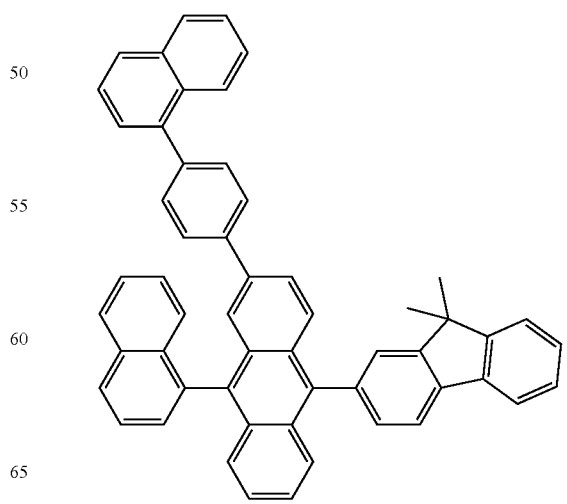

559
-continued
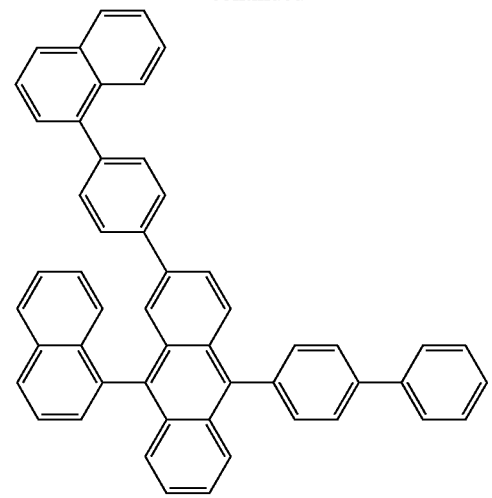
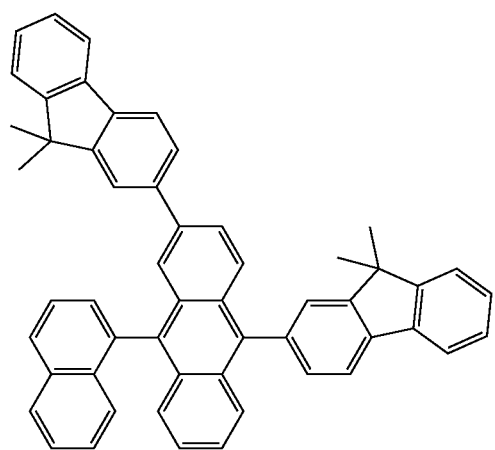
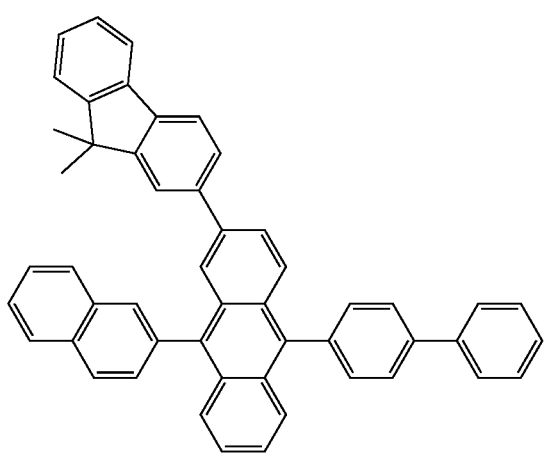
560
-continued
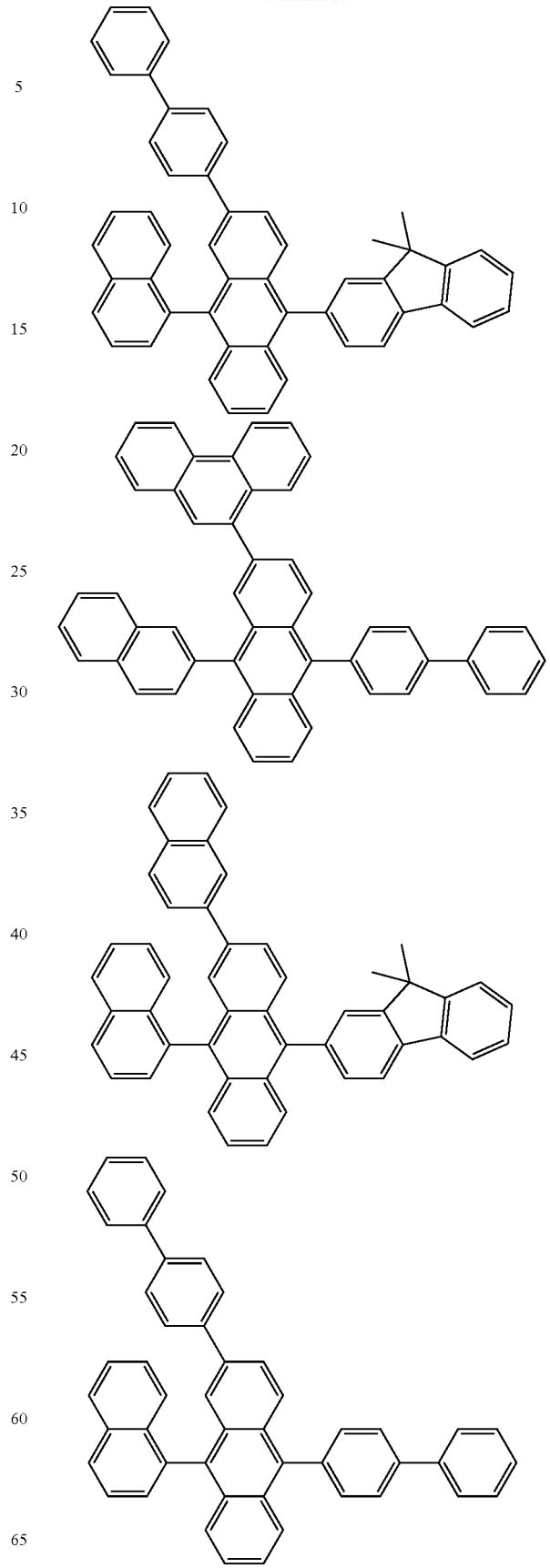

561
-continued
562
-continued
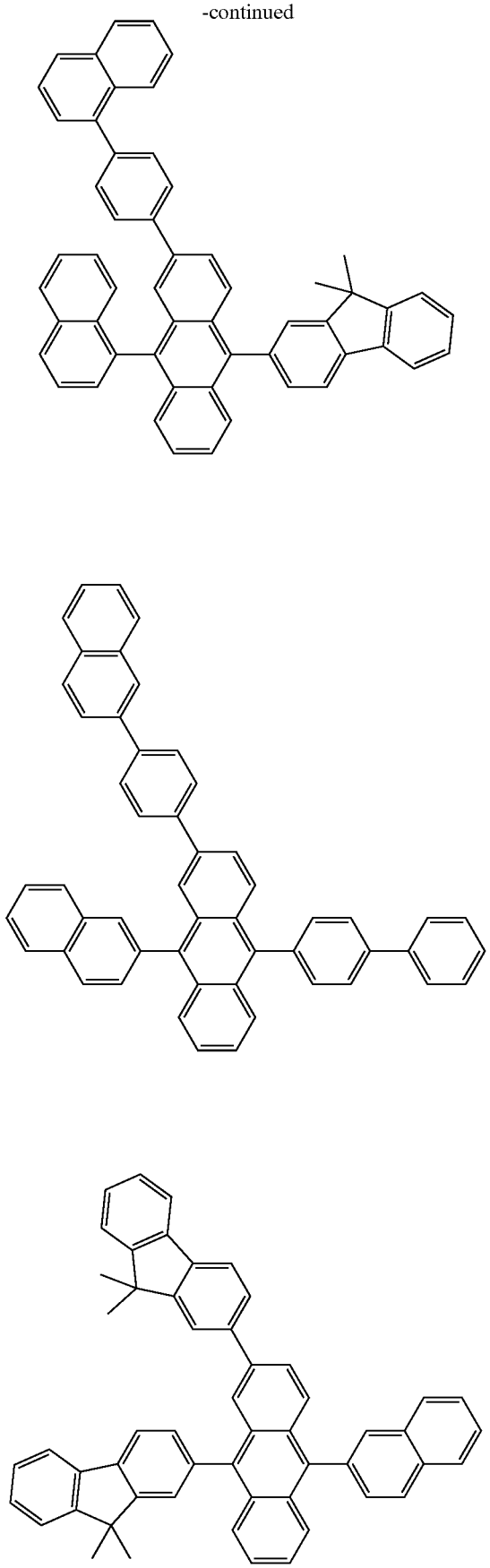
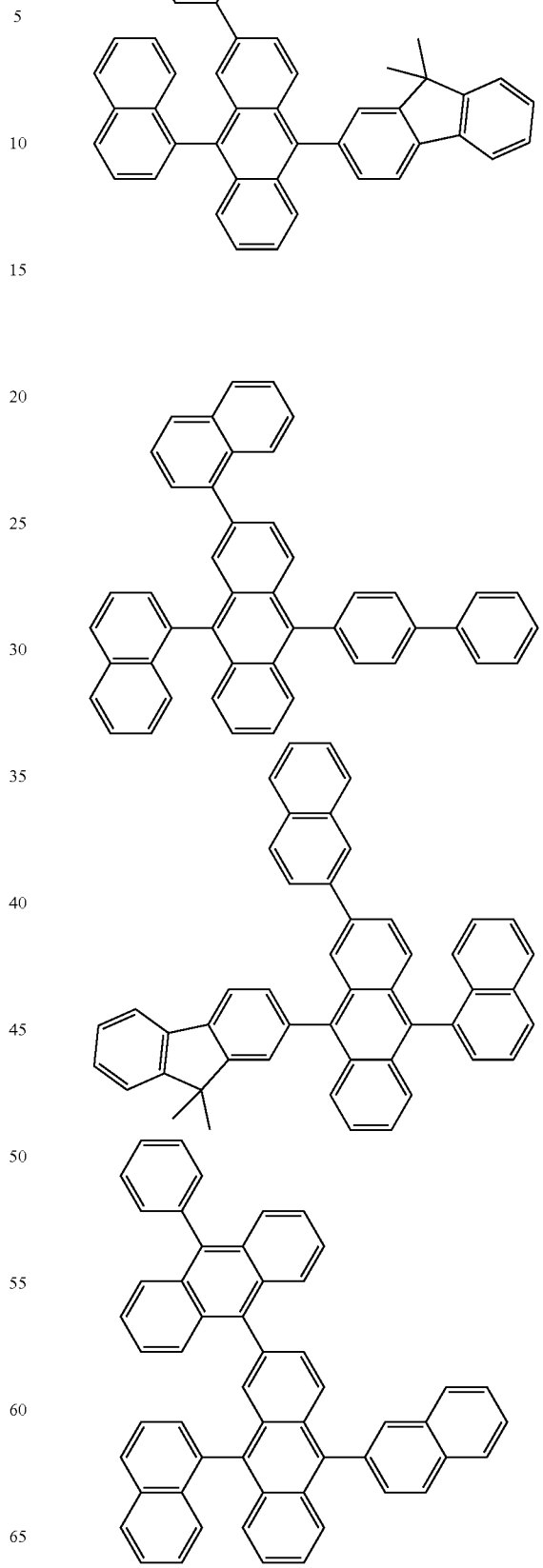

563
-continued
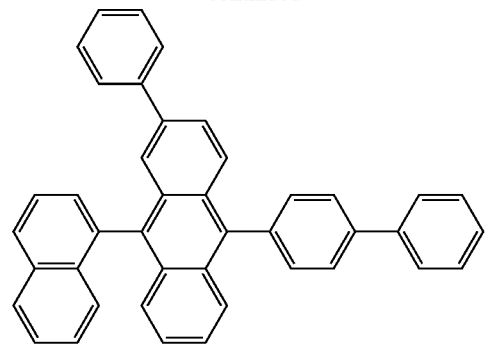
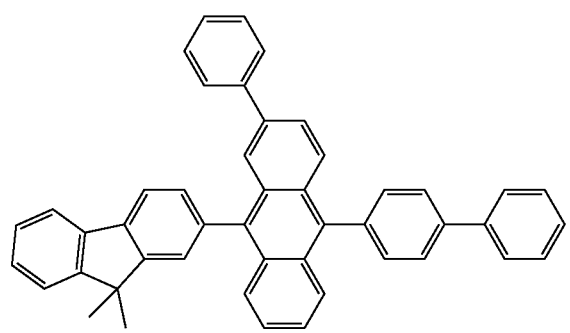
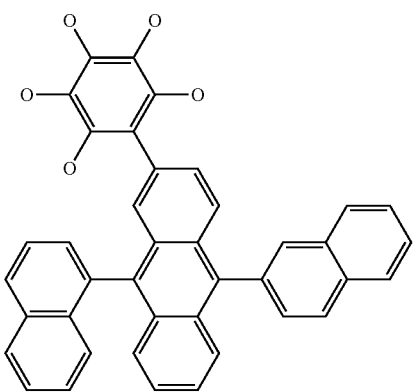
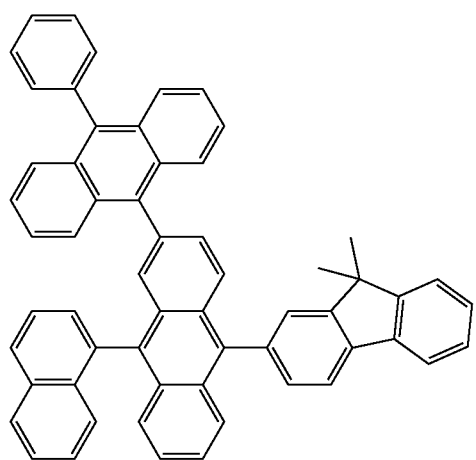
564
-continued
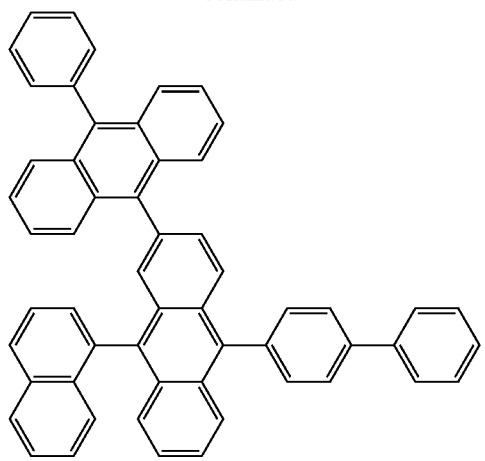
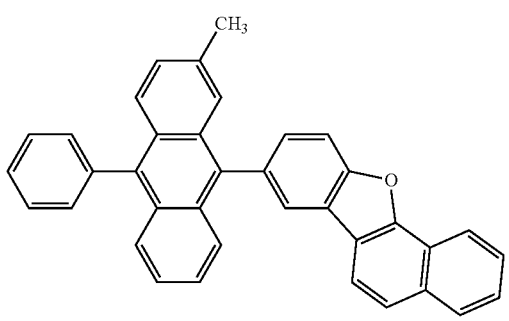
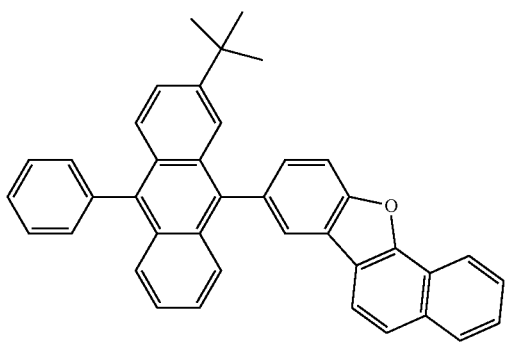
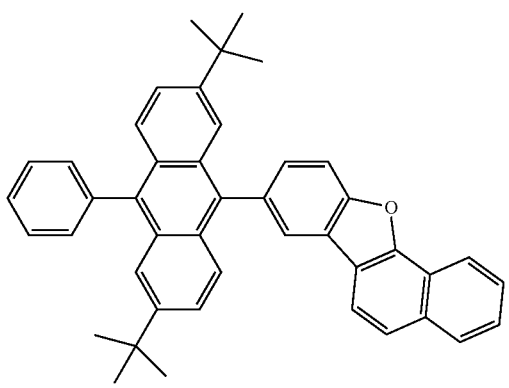

565
-continued
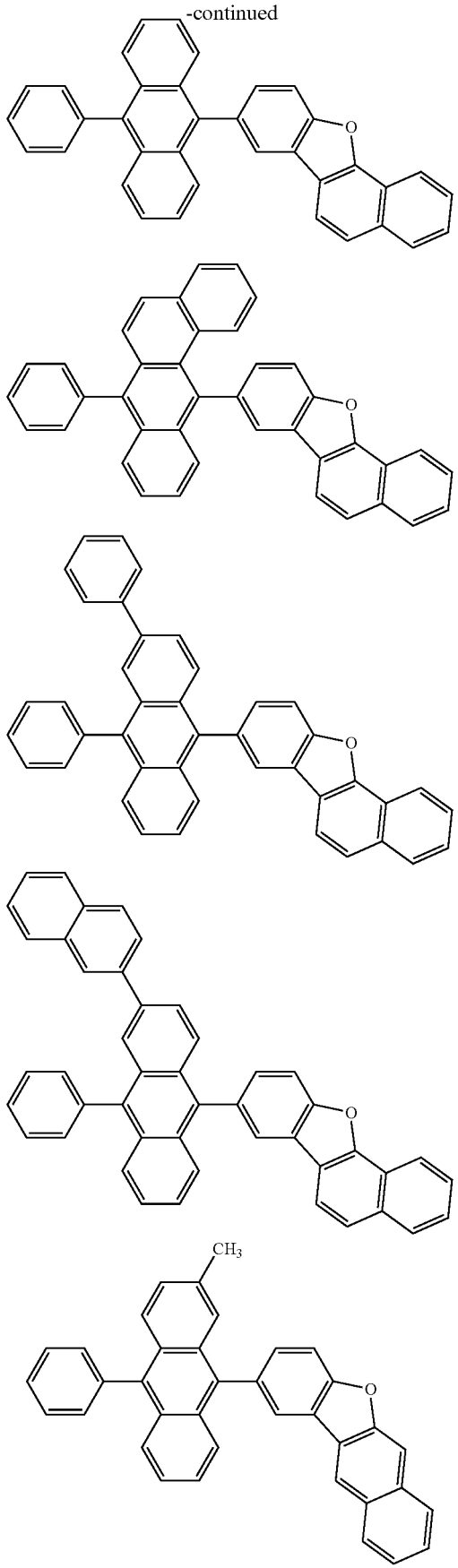
566
-continued
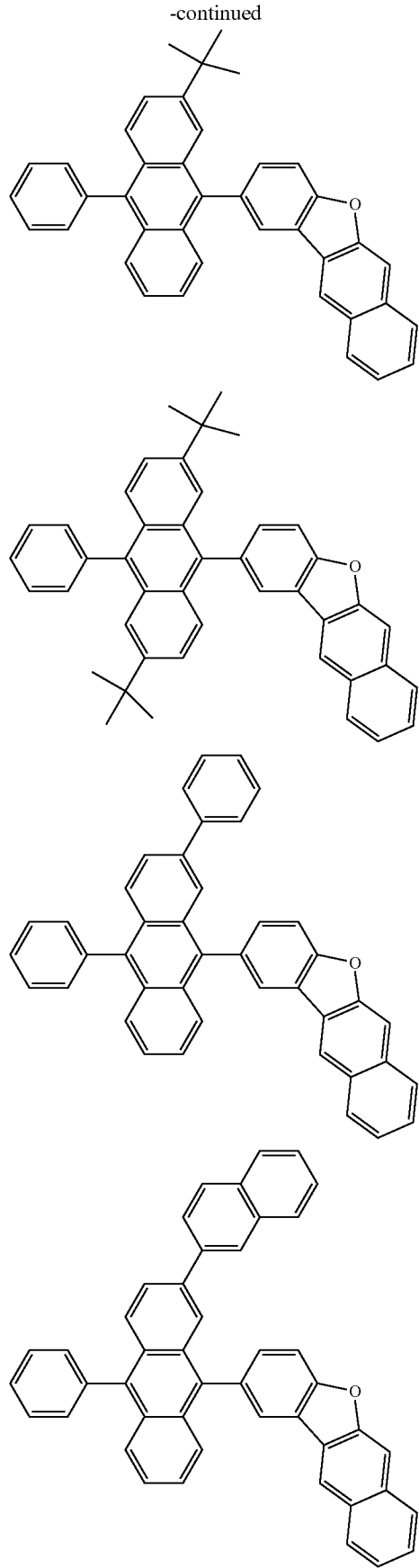

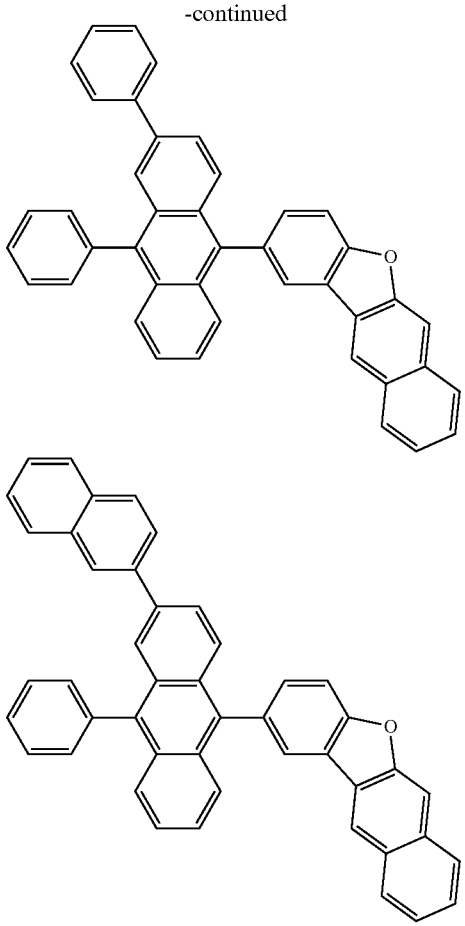

In one embodiment, when the emitting layer comprises the compound represented by the formulas (1-1) and (1-3) or the compound represented by the formulas (1-2) and (1-3) and the compound represented by the formula (10), the content of the compound represented by the formulas (1-1) and (1-3) or the compound represented by the following formulas (1-2) and (1-3) is preferably 1 mass % or more and 20 mass % or less relative to the entire emitting layer.

In one embodiment, when the emitting layer comprises the compound represented by the formulas (1-1) and (1-3) or the compound represented by the formulas (1-2) and (1-3) and the compound represented by the formula (10), the content of the compound represented by the formula (10) is preferably 80 mass % or more and 99 mass % or less relative to the entire emitting layer.

In one embodiment, when the emitting layer comprises the compound represented by the formula (3-11) and the compound represented by the formula (10), the content of the compound represented by the formula (3-11) is preferably 1 mass % or more and 20 mass % or less relative to the entire emitting layer.

In one embodiment, when the emitting layer comprises the compound represented by the formula (3-11) and the compound represented by the formula (10), the content of the compound represented by the formula (10) is preferably 80 mass % or more and 99 mass % or less relative to the entire emitting layer.

In one embodiment, when the emitting layer comprises the compound represented by the formula (3-21) and the compound represented by the formula (10), the content of the compound represented by the formula (3-21) is preferably 1 mass % or more and 20 mass % or less relative to the entire emitting layer.

In one embodiment, when the emitting layer comprises the compound represented by the formula (3-21) and the compound represented by the formula (10), the content of the compound represented by the formula (10) is preferably 80 mass % or more and 99 mass % or less relative to the entire emitting layer.

In one embodiment, when the emitting layer comprises the compound represented by the formula (3-31) or (3-32), and the compound represented by the formula (10), the content of the compound represented by the formula (3-31) or (3-32) is preferably 1 mass % or more and 20 mass % or less relative to the entire emitting layer.

In one embodiment, when the emitting layer comprises the compound represented by the formula (3-31) or (3-32) and the compound represented by the formula (10), the content of the compound represented by the formula (10) is preferably 80 mass % or more and 99 mass % or less relative to the entire emitting layer.

An explanation will be made on the layer configuration of the organic EL device according to one aspect of the invention.

An organic EL device according to one aspect of the invention comprises an organic layer between a pair of electrodes consisting of a cathode and an anode. The organic layer comprises at least one layer composed of an organic compound. Alternatively, the organic layer is formed by laminating a plurality of layers composed of an organic compound. The organic layer may further comprise an inorganic compound in addition to the organic compound.

In one embodiment, at least one of the organic layers is an emitting layer. The organic layer may be constituted, for example, as a single emitting layer, or may comprise other layers which can be adopted in the layer structure of the organic EL device. The layer that can be adopted in the layer structure of the organic EL device is not particularly limited, but examples thereof include a hole-transporting zone (a hole-transporting layer, a hole-injecting layer, an electron-blocking layer, an exciton-blocking layer, etc.), an emitting layer, a spacing layer, and an electron-transporting zone (electron-transporting layer, electron-injecting layer, hole-blocking layer, etc.) provided between the cathode and the emitting layer.

The organic EL device according to one aspect of the invention may be, for example, a fluorescent or phosphorescent monochromatic light emitting device or a fluorescent/phosphorescent hybrid white light emitting device. Further, it may be a simple type device having a single emitting unit or a tandem type device having a plurality of emitting units.

The "emitting unit" in the specification is the smallest unit that comprises organic layers, in which at least one of the organic layers is an emitting layer and light is emitted by recombination of injected holes and electrons.

In addition, the "emitting layer" described in the present specification is an organic layer having an emitting function. The emitting layer is, for example, a phosphorescent emitting layer, a fluorescent emitting layer or the like, and may be a single layer or a stack of a plurality of layers.

The emitting unit may be a stacked type unit having a plurality of phosphorescent emitting layers or fluorescent emitting layers. In this case, for example, a spacing layer for preventing excitons generated in the phosphorescent emitting layer from diffusing into the fluorescent emitting layer may be provided between the respective light-emitting layers.

As the simple type organic EL device, a device configuration such as anode/emitting unit/cathode can be given.

The representative layer structure of the emitting unit is shown below. The layers in parentheses are provided arbitrarily.

(a) (Hole-injecting layer/) Hole-transporting layer/Fluorescent emitting layer (/Electron-transporting layer/Electron-injecting layer)
(b) (Hole-injecting layer/) Hole-transporting layer/Phosphorescent emitting layer (/Electron-transporting layer/Electron-injecting layer)
(c) (Hole-injecting layer/) Hole-transporting layer/First fluorescent emitting layer/Second fluorescent emitting layer (/Electron-transporting layer/Electron-injecting layer)
(d) (Hole-injecting layer/) Hole-transporting layer/First phosphorescent layer/Second phosphorescent layer (/Electron-transporting layer/Electron-injecting layer)
(e) (Hole-injecting layer/) Hole-transporting layer/Phosphorescent emitting layer/Spacing layer/Fluorescent emitting layer (/Electron-transporting layer/Electron-injecting layer)
(f) (Hole-injecting layer/) Hole-transporting layer/First phosphorescent emitting layer/Second phosphorescent emitting layer/Spacing layer/Fluorescent emitting layer (/Electron-transporting layer/Electron-injecting layer)
(g) (Hole-injecting layer/) Hole-transporting layer/First phosphorescent layer/Spacing layer/Second phosphorescent emitting layer/Spacing layer/Fluorescent emitting layer (/Electron-transporting layer/Electron-injecting layer)
(h) (Hole-injecting layer/) Hole-transporting layer/Phosphorescent emitting layer/Spacing layer/First fluorescent emitting layer/Second fluorescent emitting layer (/Electron-transporting Layer/Electron-injecting Layer)
(i) (Hole-injecting layer/) Hole-transporting layer/Electron-blocking layer/Fluorescent emitting layer (/Electron-transporting layer/Electron-injecting layer)
(j) (Hole-injecting layer/) Hole-transporting layer/Electron-blocking layer/Phosphorescent emitting layer (/Electron-transporting layer/Electron-injecting layer)
(k) (Hole-injecting layer/) Hole-transporting layer/Exciton-blocking layer/Fluorescent emitting layer (/Electron-transporting layer/Electron-injecting layer)
(l) (Hole-injecting layer/) Hole-transporting layer/Exciton-blocking layer/Phosphorescent emitting layer (/Electron-transporting layer/Electron-injecting layer)
(m) (Hole-injecting layer/) First hole-transporting Layer/Second hole-transporting Layer/Fluorescent emitting layer (/Electron-transporting layer/electron-injecting Layer)
(n) (Hole-injecting layer/) First hole-transporting layer/Second hole-transporting layer/fluorescent emitting layer (/First electron-transporting layer/Second electron-transporting layer/Electron-injection layer)
(o) (Hole-injecting layer/) First hole-transporting layer/Second hole-transporting layer/Phosphorescent emitting layer (/Electron-transporting layer/Electron-injecting Layer)
(p) (Hole-injecting layer/) First hole-transporting layer/Second hole-transporting layer/Phosphorescent emitting layer (/First electron-transporting Layer/Second electron-transporting layer/Electron-injecting layer)
(q) (Hole-injecting layer/) Hole-transporting layer/Fluorescent emitting layer/Hole-blocking layer (/Electron-transporting layer/Electron-injecting layer)
(r) (Hole-injecting layer) Hole-transporting layer/Phosphorescent emitting layer/Hole-blocking layer(/Electron-transport layer/Electron-injecting layer)
(s) (Hole-injecting layer/) Hole-transporting layer/Fluorescent emitting layer/Exciton-blocking layer (/Electron-transporting layer/Electron-injecting layer)
(t) (Hole-injecting layer/) Hole-transporting layer/Phosphorescent emitting layer/Exciton-blocking layer (/Electron-transporting layer/Electron-injecting layer)

The layer structure of the organic EL device according to one aspect of the invention is not limited thereto. For example, when the organic EL device has a hole-injecting layer and a hole-transporting layer, it is preferred that a hole-injecting layer be provided between the hole-transporting layer and the anode. Further, when the organic EL device has an electron-injecting layer and an electron-transporting layer, it is preferred that an electron-injecting layer be provided between the electron-transporting layer and the cathode. Further, each of the hole-injecting layer, the hole-transporting layer, the electron-transporting layer and the electron-injecting layer may be formed of a single layer or be formed of a plurality of layers.

The plurality of phosphorescent emitting layers, and the plurality of the phosphorescent emitting layer and the fluorescent emitting layer may be emitting layers that emit mutually different colors. For example, the emitting unit (f) may include a hole-transporting layer/first phosphorescent layer (red light emission)/second phosphorescent emitting layer (green light emission)/spacing layer/fluorescent emitting layer (blue light emission)/electron-transporting layer.

An electron-blocking layer may be provided between each light emitting layer and the hole-transporting layer or the spacing layer. Further, a hole-blocking layer may be provided between each emitting layer and the electron-transporting layer. By providing the electron-blocking layer or the hole-blocking layer, it is possible to confine electrons or holes in the emitting layer, thereby to improve the recombination probability of carriers in the emitting layer, and to improve light emitting efficiency.

As a representative device configuration of a tandem type organic EL device, for example, a device configuration such as anode/first emitting unit/intermediate layer/second emitting unit/cathode can be given.

The first emitting unit and the second emitting unit are independently selected from the above-mentioned emitting units, for example.

The intermediate layer is also generally referred to as an intermediate electrode, an intermediate conductive layer, a charge generating layer, an electron withdrawing layer, a connecting layer, a connector layer, or an intermediate insulating layer. The intermediate layer is a layer that supplies electrons to the first emitting unit and holes to the second emitting unit, and can be formed from known materials.

FIG. 1 shows a schematic view of one example of the layer structure of the organic EL device. An organic EL device 1 has a substrate 2, an anode 3, a cathode 4, and an emitting unit (organic layer) 10 arranged between the anode 3 and the cathode 4. The emitting unit 10 has at least one emitting layer 5.

A hole-transporting zone (hole-injecting layer, hole-transporting layer, etc.) 6 may be formed between the emitting layer 5 and the anode 3, and an electron-transporting zone (electron-injecting layer, electron-transporting layer, etc.) 7 may be formed between the emitting layer 5 and the cathode 4. An electron-blocking layer (not shown) may be provided on the anode 3 side of the emitting layer 5, and a hole-blocking layer (not shown) may be provided on the cathode 4 side of the emitting layer 5. Due to such a configuration, electrons or holes are confined in the emitting layer 5, whereby efficiency of formation of excitons in the emitting layer 5 can be further enhanced.

Figure 2:
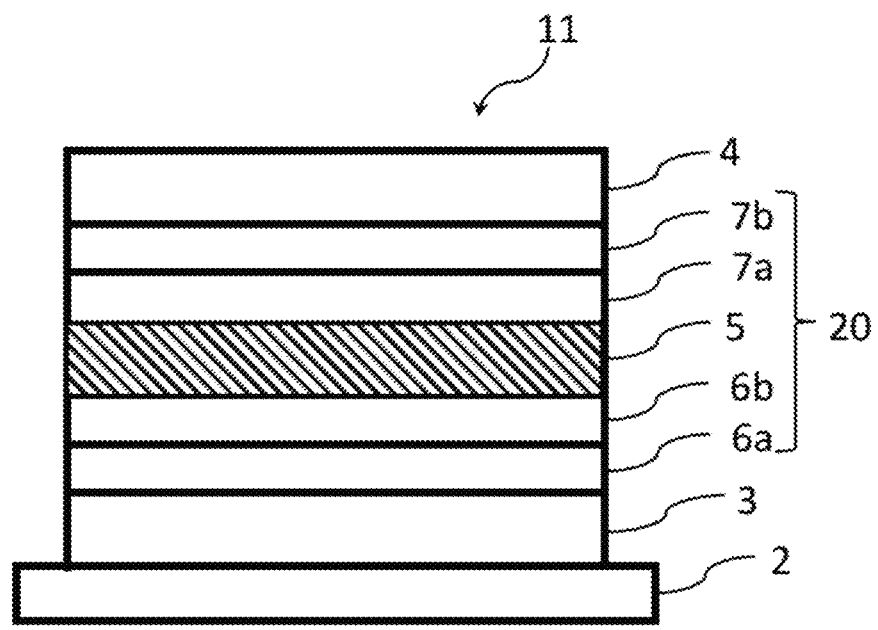
FIG. 2 is a view showing a schematic configuration of another embodiment of the organic EL device of the invention.

FIG. 2 shows a schematic view of another example of the layer configuration of the organic EL device. In an organic EL device 11 shown in FIG. 2, in an emitting unit 20, the hole-transporting layer in the hole-transporting zone 6 and the electron-transporting layer in the electron-transporting zone 7 of the emitting unit 10 of the organic EL device 1 in FIG. 1 are respectively composed of two layers. The hole-transporting zone 6 has a first hole-transporting layer 6a on the anode side and a second hole-transporting layer 6b on the cathode side. The electron-transporting zone 7 has a first electron-transporting layer 7a on the anode side and a second hole-transporting layer 7b on the cathode side. As for the other numerical references, since they are the same as those in FIG. 1, an explanation is omitted.

Hereinbelow, an explanation will be made on function, materials, etc. of each layer constituting the organic EL device described in the present specification.

(Substrate)

The substrate is used as a support of the organic EL device. The substrate preferably has a light transmittance of 50% or more in the visible light region with a wavelength of 400 to 700 nm, and a smooth substrate is preferable. Examples of the material of the substrate include soda-lime glass, aluminosilicate glass, quartz glass, plastic and the like. As a substrate, a flexible substrate can be used. The flexible substrate means a substrate that can be bent (flexible), and examples thereof include a plastic substrate and the like. Specific examples of the material for forming the plastic substrate include polycarbonate, polyallylate, polyether sulfone, polypropylene, polyester, polyvinyl fluoride, polyvinyl chloride, polyimide, polyethylene naphthalate and the like. Also, an inorganic vapor deposited film can be used.

(Anode)

As the anode, for example, it is preferable to use a metal, an alloy, a conductive compound, a mixture thereof or the like and having a high work function (specifically, 4.0 eV or more). Specific examples of the material of the anode include indium oxide-tin oxide (ITO: Indium Tin Oxide), indium oxide-tin oxide containing silicon or silicon oxide, indium oxide-zinc oxide, indium oxide containing tungsten oxide or zinc oxide, graphene and the like. In addition, it is also possible to use gold, silver, platinum, nickel, tungsten, chromium, molybdenum, iron, cobalt, copper, palladium, titanium, and nitrides of these metals (e.g. titanium oxide).

The anode is normally formed by depositing these materials on the substrate by a sputtering method. For example, indium oxide-zinc oxide can be formed by a sputtering method by using a target in which 1 to 10 mass % zinc oxide is added relative to indium oxide. Further, indium oxide containing tungsten oxide or zinc oxide can be formed by a sputtering method by using a target in which 0.5 to 5 mass % of tungsten oxide or 0.1 to 1 mass % of zinc oxide is added relative to indium oxide.

As the other methods for forming the anode, a vacuum deposition method, a coating method, an inkjet method, a spin coating method or the like can be given. When silver paste or the like is used, it is possible to use a coating method, an inkjet method or the like.

The hole-injecting layer formed in contact with the anode is formed by using a material that allows easy hole injection regardless of the work function of the anode. For this reason, in the anode, it is possible to use a common electrode material, e.g. a metal, an alloy, a conductive compound and a mixture thereof. Specifically, a material having a small work function such as alkaline metals such as lithium and cesium; alkaline earth metals such as calcium and strontium; alloys containing these metals (for example, magnesium-silver and aluminum-lithium); rare earth metals such as europium and ytterbium; and an alloy containing rare earth metals.

(Hole-Injecting Layer)

A hole-injecting layer is a layer that contains a substance having high hole-injection property and has a function of injecting holes from the anode to the organic layer. As the substance having high hole-injection property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, an electron-attracting (acceptor) compound or a polymeric compound (oligomer, dendrimer, polymer, etc.) or the like can be used. Among these, a compound such as an aromatic amine compound and an acceptor compound are preferable, with an acceptor compound being more preferable.

As specific examples of an aromatic amine compound, 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1) or the like can be given.

As the acceptor compound, for example, a heterocyclic derivative having an electron attracting group, a quinone derivative having an electron attracting group, an aryl borane derivative, a heteroaryl borane derivative and the like are preferable. As specific examples, hexacyanohexaazatriphenylene, 2,3,5,6-tetrafluoro-7,7,8,8-tetracyanoquinodimethane (abbreviation: F4TCNQ), 1,2,3-tris[(cyano)(4-cyano-2,3,5,6-tetrafluorophenyl)methylene]cyclopropane or the like can be given.

When the acceptor compound is used, it is preferred that the hole-injecting layer further comprise a matrix material. As the matrix material, a material known as the material for an organic EL device can be used. For example, an electron-donating (donor) compound can be used. More preferably, the above-mentioned aromatic amine compound can be used.

(Hole-Transporting Layer)

The hole-transporting layer is a layer that comprises a high hole-transporting property, and has a function of transporting holes from the anode to the organic layer.

As the substance having a high hole-transporting property, a material having a hole mobility of $10^{-6}$ cm$^2$/(V·s) or more is preferable. For example, aromatic amine compounds, carbazole derivatives, anthracene derivatives, polymeric compounds, and the like can be given, for example.

Specific examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluorene-2-yl)-N-phenylamino]biphenyl (abbreviation: BSPB) or the like.

Specific examples of the carbazole derivatives include 4,4'-di(9-carbazolyl)biphenyl (abbreviation: CBP), 9-[4-(9-carbazolyl)phenyl]-10-phenylanthracene (abbreviation: CzPA), 9-phenyl-3-[4-(10-phenyl-9-anthryl)phenyl]-9H-carbazole (abbreviation: PCzPA) or the like.

Specific examples of the anthracene derivative include 2-t-butyl-9,10-di(2-naphthyl) anthracene (abbreviation: t-BuDNA), 9,10-di(2-naphthyl)anthracene (abbreviation: DNA) 9,10-diphenylanthracene (abbreviation: DPAnth) or the like.

Specific examples of the polymeric compound include poly(N-vinylcarbazole) (abbreviation: PVK) and poly(4-vinyltriphenylamine) (abbreviation: PVTPA).

As long as it is a compound having a higher hole-transporting property as compared with electron-transporting property, other substances than those mentioned above can be used.

The hole-transporting layer may be a single layer or may be a stacked layer of two or more layers. In this case, it is preferred that a layer that contains a substance having a larger energy gap among substances having higher hole-transporting property be arranged on a side nearer to the emitting layer.

(Emitting Layer)

The emitting layer is a layer containing a substance having a high emitting property (dopant material). As the dopant material, various materials can be used. For example, a fluorescent emitting compound (fluorescent dopant), a phosphorescent emitting compound (phosphorescent dopant) or the like can be used. A fluorescent emitting compound is a compound capable of emitting light from the singlet excited state, and an emitting layer containing a fluorescent emitting compound is called a fluorescent emitting layer. Further, a phosphorescent emitting compound is a compound capable of emitting light from the triplet excited state, and an emitting layer containing a phosphorescent emitting compound is called a phosphorescent emitting layer.

The emitting layer normally comprises a dopant material and a host material that allows it to emit light efficiently. In some literatures, a dopant material is called a guest material, an emitter or an emitting material. In some literatures, a host material is called a matrix material.

A single emitting layer may comprise plural dopant materials and plural host materials. Further, plural emitting layers may be present.

In the present specification, a host material combined with the fluorescent dopant is referred to as a "fluorescent host" and a host material combined with the phosphorescent dopant is referred to as the "phosphorescent host". Note that the fluorescent host and the phosphorescent host are not classified only by the molecular structure. The phosphorescent host is a material for forming a phosphorescent emitting layer containing a phosphorescent dopant, but does not mean that it cannot be used as a material for forming a fluorescent emitting layer. The same can be applied to the fluorescent host.

In one embodiment, it is preferred that the emitting layer comprise the compound represented by the formulas (1-1) and (1-3) or the compound represented by the formulas (1-2) and (1-3) (hereinafter, these compounds may be referred to as the "compound (1)"). More preferably, it is contained as a dopant material. Further, it is preferred that the compound (1) be contained in the emitting layer as the fluorescent dopant.

In one embodiment, no specific restrictions are imposed on the content of the compound (1) as the dopant material in the emitting layer. In respect of sufficient emission and concentration quenching, the content is preferably 0.1 to 70 mass %, more preferably 0.1 to 30 mass %, further preferably 1 to 30 mass %, still further preferably 1 to 20 mass %, and particularly preferably 1 to 10 mass %.

In one embodiment, it is preferred that the emitting layer comprise the compound represented by the formula (3-11). More preferably, it is contained as a dopant material. Further, it is preferred that the compound (3-11) be contained in the emitting layer as the fluorescent dopant.

In one embodiment, no specific restrictions are imposed on the content of the compound represented by the formula (3-11) as the dopant material in the emitting layer. In respect of sufficient emission and concentration quenching, the content is preferably 0.1 to 70 mass %, more preferably 0.1 to 30 mass %, further preferably 1 to 30 mass %, still further preferably 1 to 20 mass %, and particularly preferably 1 to 10 mass %.

In one embodiment, it is preferred that the emitting layer comprise the compound represented by the formula (3-21). More preferably, it is contained as a dopant material. Further, it is preferred that the compound (3-21) be contained in the emitting layer as the fluorescent dopant.

In one embodiment, no specific restrictions are imposed on the content of the compound represented by the formula (3-21) as the dopant material in the emitting layer. In respect of sufficient emission and concentration quenching, the content is preferably 0.1 to 70 mass %, more preferably 0.1 to 30 mass %, further preferably 1 to 30 mass %, still further preferably 1 to 20 mass %, and particularly preferably 1 to 10 mass %.

In one embodiment, it is preferred that the emitting layer comprise the compound represented by the formula (3-31) or (3-32). More preferably, it is contained as a dopant material. Further, it is preferred that the compound (3-31) or (3-32) be contained in the emitting layer as the fluorescent dopant.

In one embodiment, no specific restrictions are imposed on the content of the compound (3-31) or (3-32) as the dopant material in the emitting layer. In respect of sufficient emission and concentration quenching, the content is preferably 0.1 to 70 mass %, more preferably 0.1 to 30 mass %, further preferably 1 to 30 mass %, still further preferably 1 to 20 mass %, and particularly preferably 1 to 10 mass %.

(Fluorescent Dopant)

As the fluorescent dopant other than the compound (1), the compound represented by the formula (3-11), the compound represented by the formula (3-21) and the compound represented by the formula (3-31) or (3-32), a fused polycyclic aromatic derivative, a styrylamine derivative, a fused ring amine derivative, a boron-containing compound, a pyrrole derivative, an indole derivative, a carbazole derivative can be given, for example. Among these, a fused ring amine derivative, a boron-containing compound, carbazole derivative is preferable.

As the fused ring amine derivative, a diaminopyrene derivative, a diaminochrysene derivative, a diaminoanthracene derivative, a diaminofluorene derivative, a diaminofluorene derivative with which one or more benzofuro skeletons are fused, or the like can be given.

As the boron-containing compound, a pyrromethene derivative, a triphenylborane derivative or the like can be given.

As the blue fluorescent dopant, pyrene derivatives, styrylamine derivatives, chrysene derivatives, fluoranthene derivatives, fluorene derivatives, diamine derivatives, triarylamine derivatives and the like can be given, for example. Specifically, N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenyamine (abbreviation: YGAPA), 4-(10-phenyl-9-anthryl)-4'-(9-phenyl-9H-carbazole-3-yl)triphenylamine (abbreviation: PCBAPA) or the like can be given.

As the green fluorescent dopant, an aromatic amine derivative or the like can be given, for example. Specifically, N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), N,N,9-triphenylanthracene-9-amine (abbreviation: DPhAPhA) or the like can be given, for example.

As the red fluorescent dopant, a tetracene derivative, a diamine derivative or the like can be given. Specifically, N,N,N',N'-tetrakis(4-methylphenyl)tetracene-5,11-diamine (abbreviation: p-mPhTD), 7,14-diphenyl-N,N,N',N'-tetrakis (4-methylphenyl)acenaphtho[1,2-a]fluoranthene-3,10-diamine (abbreviation: p-mPhAFD) or the like can be given.

(Phosphorescent Dopant)

As the phosphorescent dopant, a phosphorescent emitting heavy metal complex and a phosphorescent emitting rare earth metal complex can be given.

As the heavy metal complex, an iridium complex, an osmium complex, a platinum complex or the like can be given. As the heavy metal complex, an ortho-metalated complex of a metal selected from iridium, osmium and platinum.

Examples of rare earth metal complexes include terbium complexes, europium complexes and the like. Specifically, tris(acetylacetonate)(monophenanthroline)terbium(III) (abbreviation: Tb(acac)$_3$(Phen)), tris(1,3-diphenyl-1,3-propandionate)(monophenanthroline)europium(III) (abbreviation: Eu(DBM)$_3$(Phen)), tris[1-(2-thenoyl)-3,3,3-trifluoroacetonate](monophenanthroline)europium(III) (abbreviation: Eu(TTA)$_3$(Phen)) or the like can be given. These rare earth metal complexes are preferable as phosphorescent dopants since rare earth metal ions emit light due to electronic transition between different multiplicity.

As the blue phosphorescent dopant, an iridium complex, an osmium complex, a platinum complex, or the like can be given, for example. Specifically, bis[2-(4',6'-difluorophenyl)pyridinate-N,C2']iridium(III) tetrakis(1-pyrazolyl)borate (abbreviation: Fir6), bis[2-(4',6'-difluorophenyl)pyridinate-N,C2']iridium(III) picolinate (abbreviation: Flrpic), bis[2-(3',5'-bistrifluoromethylphenyl) pyridinato-N,C2']iridium (III) picolinate (abbreviation: Ir(CF$_3$ppy)$_2$(pic)), bis[2-(4',6'-difluorophenyl)pyridinato-N,C2']iridium(III) acetylacetonate (abbreviation: Flracac) or the like can be given.

As the green phosphorescent dopant, an iridium complex or the like can be given, for example. Specifically, tris(2-phenylpyridinato-N,C2') iridium(III) (abbreviation: Ir(ppy)$_3$), bis(2-phenylpyridinato-N,C2')iridium(III) acetylacetonate (abbreviation: Ir(ppy)$_2$(acac)), bis(1,2-diphenyl-1H-benzimidazolato)iridium(III) acetylacetonate (abbreviation: Ir(pbi)$_2$(acac)), bis(benzo[h]quinolinato)iridium(III) acetylacetonate (abbreviation: Ir(bzq)$_2$(acac)) or the like can be given.

As the red phosphorescent dopant, an iridium complex, a platinum complex, a terbium complex, an europium complex or the like can be given. Specifically, bis[2-(2'-benzo[4,5-a]thienyl)pyridinato-N,C3']iridium(III) acetylacetonate (abbreviation: Ir(btp)$_2$(acac)), bis(1-phenylisoquinolinato-N,C2')iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), 2,3,7,8,12,13,17,18-octaethyl-21H,23H-porphyrin platinum(II) (abbreviation PtOEP) or the like can be given.

(Host Material)

As the host material, metal complexes such as aluminum complexes, beryllium complexes and zinc complexes; heterocyclic compounds such as indole derivatives, pyridine derivatives, pyrimidine derivatives, triazine derivatives, quinoline derivatives, isoquinoline derivatives, quinazoline derivatives, dibenzofuran derivatives, dibenzothiophene derivatives, oxadiazole derivatives, benzimidazole derivatives, phenanthroline derivatives; fused aromatic compounds such as a naphthalene derivative, a triphenylene derivative, a carbazole derivative, an anthracene derivative, a phenanthrene derivative, a pyrene derivative, a chrysene derivative, a naphthacene derivative, a fluoranthene derivative; and aromatic amine compound such as triarylamine derivatives and fused polycyclic aromatic amine derivatives can be given, for example. Plural types of host materials can be used in combination.

As specific examples of the metal complex, tris(8-quinolinato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato]zinc(II) (abbreviation: ZnPBO), bis[2-(2-benzothiazolyl)phenolate]zinc(II) (abbreviation: ZnBTZ) or the like can be given.

As specific examples of the heterocyclic compound, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzoimidazole)(abbreviation: TPBI), bathophenanthroline (abbreviation: BPhen), bathocuproin (abbreviation: BCP) or the like can be given.

As specific examples of the fused aromatic compound, 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di (2-naphthyl)anthracene (abbreviation: DNA), 2-tert-butyl-9,10-di(2-naphthyl)anthracene (abbreviation: t-BuDNA), 9,9'- bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyene (abbreviation: TPB3), 9,10-diphenylanthracene (abbreviation: DPAnth), 6,12-dimethoxy-5,11-diphenylcrysene or the like can be given.

As specific examples of the aromatic amine compound, N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluorene-2-yl)-N-phenylamino]biphenyl (abbreviation: DFLDPBi), 4,4'-bis[N-(spiro-9,9'-bifluorene-2-yl)-N-phenylamino]biphenyl (abbreviation: BSPB) or the like can be given.

As the fluorescent host, a compound having a higher singlet energy level than a fluorescent dopant is preferable. For example, a heterocyclic compound, a fused aromatic compound or the like can be given. As the fused aromatic compound, an anthracene derivative, a pyrene derivative, a chrysene derivative, a naphthacene derivative or the like are preferable.

As the phosphorescent host, a compound having a higher triplet energy level as compared with a phosphorescent dopant is preferable. For example, a metal complex, a heterocyclic compound, a fused aromatic compound or the like can be given. Among these, an indole derivative, a carbazole derivative, a pyridine derivative, a pyrimidine derivative, a triazine derivative, a quinolone derivative, an isoquinoline derivative, a quinazoline derivative, a dibenzofuran derivative, a dibenzothiophene derivative, a naphthalene derivative, a triphenylene derivative, a phenanthrene derivative, a fluoranthene derivative or the like can be given.

(Electron-Transporting Layer)

An electron-transporting layer is a layer that comprises a substance having high electron-transporting property. As the substance having high electron-transporting property, a substance having an electron mobility of $10^{-6}$ cm$^2$N/s or more is preferable. For example, a metal complex, an aromatic heterocyclic compound, an aromatic hydrocarbon compound, a polymeric compound or the like can be given.

As the metal complex, an aluminum complex, a beryllium complex, a zinc complex or the like can be given. Specifically, tris(8-quinolinolate)aluminum(III) (abbreviation: Alq), tris(4-methyl-8-quinolinolate)aluminum (abbreviation: Almq3), bis(10-hydroxybenzo[h]quinolinolate)beryllium (abbreviation: BeBq2), bis(2-methyl-8-quinollinolate)(4-phenylphenolate)aluminum(III) (abbreviation: BAlq), bis(8-quinolinolate)zinc(II) (abbreviation: Znq), bis[2-(2-benzoxazolyl)phenolato]zinc(II) (abbreviation: ZnPBO), bis[2-(2-benzothiazolyl)phenolato]zinc(II) (abbreviation: ZnBTZ) or the like can be given, for example.

As the aromatic heterocyclic compound, imidazole derivatives such as benzimidazole derivatives, imidazopyridine derivatives and benzimidazophenanthridine derivatives; azine derivatives such as pyrimidine derivatives and triazine derivatives; a compound containing a nirogen-containing six-membered ring structure such as quinoline derivatives, isoquinoline derivatives, and phenanthroline derivatives (including one having a phosphine oxide-based substituent on the heterocyclic ring) or the like can be given. Specifically, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), 4,4'-bis(5-methylbenzoxazol-2-yl)stilbene (abbreviation: BzOs) or the like can be given.

As the aromatic hydrocarbon compound, an anthracene derivative, a fluoranthene derivative or the like can be given, for example.

As specific examples of the polymeric compound, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)] (abbreviation: PF-BPy) or the like can be given.

As long as it is a compound having a higher electron-transporting property as compared with hole-transporting property, such a compound may be used in the electron-transporting layer in addition to the substances mentioned above.

The electron-transporting layer may be a single layer, or a stacked layer of two or more layers. In this case, it is preferable to arrange a layer that includes a substance having a larger energy gap, among substances having a high electron-transporting capability, on the side nearer to the emitting layer.

For example, as shown in FIG. 2, a configuration including the first electron-transporting layer 7a on the anode side and the second electron-transporting layer 7b on the cathode side may be employed.

The electron-transporting layer may contain a metal such as an alkali metal, magnesium, an alkaline earth metal, or an alloy containing two or more of these metals; a metal compound such as an alkali metal compound such as 8-quinolinolato lithium (Liq), or an alkaline earth metal compound.

When a metal such as an alkali metal, magnesium, an alkaline earth metal, or an alloy containing two or more of these metals is contained in the electron-transporting layer, the content of the metal is not particularly limited, but is preferably from 0.1 to 50 mass %, more preferably from 0.1 to 20 mass %, further preferably from 1 to 10 mass %.

When a metal compound such as an alkali metal compound or an alkaline earth metal compound is contained in the electron-transporting layer, the content of the metal compound is preferably 1 to 99 mass %, more preferably from 10 to 90 mass %. When the electron-transporting layer is formed of plural layers, a layer on the emitting layer side can be formed only from these metal compounds.

(Electron-Injecting Layer)

The electron-injecting layer is a layer that includes a substance that has a high electron-injecting capability, and has the function of efficiently injecting electrons from a cathode to an emitting layer. Examples of the substance that has a high electron-injecting capability include an alkali metal, magnesium, an alkaline earth metal, and a compound thereof. Specific examples thereof include lithium, cesium, calcium, lithium fluoride, cesium fluoride, calcium fluoride, lithium oxide, and the like. In addition, an electron-transporting substance having electron-transporting property in which is incorporated with an alkali metal, magnesium, an alkaline earth metal, or a compound thereof is incorporated, for example, Alq incorporated with magnesium, may also be used.

Alternatively, a composite material that includes an organic compound and a donor compound may also be used in the electron-injecting layer. Such a composite material is excellent in the electron-injecting capability and the electron-transporting capability since the organic compound receives electrons from the donor compound.

The organic compound is preferably a material excellent in transporting capability of the received electrons, and specifically, for example, a metal complex, an aromatic heterocyclic compound, or the like, which is a substance that has a high electron-transporting capability mentioned above, can be used.

Any material capable of donating its electron to the organic compound can be used as the donor compound. Examples thereof include an alkali metal, magnesium, an alkaline earth metal, and a rare earth metal. Specific examples thereof include lithium, cesium, magnesium, calcium, erbium, and ytterbium. Further, an alkali metal oxide and an alkaline earth metal oxide are preferred, and examples thereof include lithium oxide, calcium oxide, and barium oxide. In addition, a Lewis base such as magnesium oxide can be used. Moreover, an organic compound such as tetrathiafulvalene (abbreviation: TTF) can also be used.

(Cathode)

For the cathode, a metal, an alloy, an electrically conductive compound, and a mixture thereof, each having a small work function (specifically, a work function of 3.8 eV or less) are preferably used. Specific examples of the material for such a cathode include an alkali metal such as lithium and cesium; magnesium; an alkaline earth metal such as calcium, and strontium; an alloy containing these metals (for example, magnesium-silver, aluminum-lithium); a rare earth metal such as europium and ytterbium; and an alloy containing a rare earth metal.

The cathode is usually formed by a vacuum vapor deposition or a sputtering method. Further, in the case of using a silver paste or the like, a coating method, an inkjet method, or the like can be employed.

Moreover, when the electron-injecting layer is provided, various electrically conductive materials such as aluminum, silver, ITO, graphene, indium oxide-tin oxide containing silicon or silicon oxide, selected independently from the work function, can be used to form a cathode. These electrically conductive materials are made into films using a sputtering method, an inkjet method, a spin coating method, or the like.

(Insulating Layer)

In the organic EL device, pixel defects based on leakage or a short circuit are easily generated since an electric field is applied to a thin film. In order to prevent this, it is preferred to insert an insulating thin layer between a pair of electrodes.

Examples of materials used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture thereof may be used in the insulating layer, and a laminate of a plurality of layers that include these materials can be also used for the insulating layer.

(Spacing Layer)

The spacing layer is a layer provided between the fluorescent emitting layer and the phosphorescent emitting layer when the fluorescent emitting layer and the phosphorescent emitting layer are stacked in order to prevent diffusion of excitons generated in the phosphorescent emitting layer to the fluorescent emitting layer or in order to adjust the carrier balance. Further, the spacing layer can be provided between the plural phosphorescent emitting layers.

Since the spacing layer is provided between the emitting layers, the material used for the spacing layer is preferably a material having both electron-transporting capability and hole-transporting capability. In order to prevent diffusion of the triplet energy in adjacent phosphorescent emitting layers, it is preferred that the spacing layer have a triplet energy of 2.6 eV or more.

As the material used for the spacing layer, the same materials as those used in the above-mentioned hole-transporting layer can be given.

(Electron-Blocking Layer, Hole-Blocking Layer, Exciton-Blocking Layer)

An electron-blocking layer, a hole-blocking layer, an exciton (triplet)-blocking layer, and the like may be provided in adjacent to the emitting layer.

The electron-blocking layer has a function of preventing leakage of electrons from the emitting layer to the hole-transporting layer. The hole-blocking layer has a function of preventing leakage of holes from the emitting layer to the electron-transporting layer. The exciton-blocking layer has a function of preventing diffusion of excitons generated in the emitting layer to the adjacent layers and confining the excitons within the emitting layer.

(Method for Forming a Layer)

The method for forming each layer of the organic EL device of the invention is not particularly limited unless otherwise specified. A known film-forming method such as a dry film-forming method, a wet film-forming method or the like can be used. Specific examples of the dry film-forming method include a vacuum deposition method, a sputtering method, a plasma method, an ion plating method, and the like. Specific examples of the wet film-forming method include various coating methods such as a spin coating method, a dipping method, a flow coating method, an inkjet method, and the like.

(Film Thickness)

The film thickness of each layer of the organic EL device of the invention is not particularly limited unless otherwise specified. If the film thickness is too small, defects such as pinholes are likely to occur to make it difficult to obtain a sufficient luminance. If the film thickness is too large, a high driving voltage is required to be applied, leading to a lowering in efficiency. In this respect, the film thickness is preferably 5 nm to 10 μm, and more preferably 10 nm to 0.2 μm.

[Electronic Apparatus]

The electronic apparatus according to one aspect of the invention includes the above-described organic EL device according to one aspect of the invention. Examples of the electronic apparatus include display parts such as an organic EL panel module; display devices of television sets, mobile phones, smart phones, and personal computer, and the like; and emitting devices of a lighting device and a vehicle lighting device.

[Novel Compound]

The novel compound according to one aspect of the invention is a compound represented by the following formulas (1-1) and (1-3), or the compound represented by the following formulas (1-2) and (1-3):

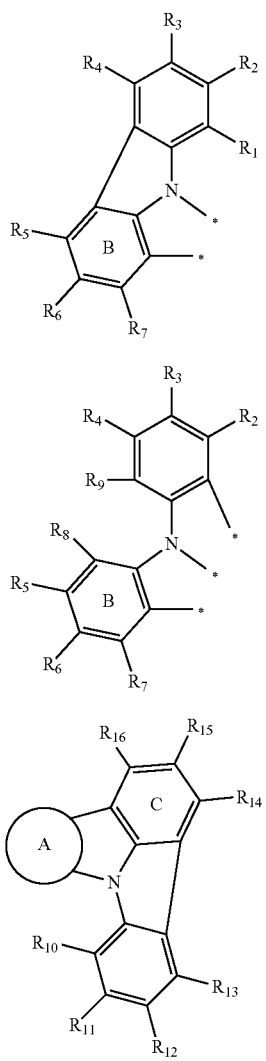

(1-1)

(1-2)

(1-3)

wherein in the formulas (1-1), (1-2) and (1-3),
ring A is a substituted or unsubstituted fused aryl ring including 10 to 50 ring carbon atoms, a substituted or unsubstituted fused heterocyclic ring including 8 to 50 ring atoms or a benzene ring represented by the following formula (2);
two atomic bondings * in the formula (1-1) are respectively bonded with a ring carbon atom of the fused aryl ring of the ring A, a ring atom of the fused heterocyclic ring of the ring A, or a ring carbon atom of the benzene ring represented by the formula (2) of the ring A;
three atomic bondings * in the formula (1-2) are respectively bonded with a ring carbon atom of the fused aryl ring of the ring A, a ring atom of the fused heterocyclic ring of the ring A, or a ring carbon atom of the benzene ring represented by the formula (2) of the ring A;
one or more pairs of adjacent two or more of $R_1$ to $R_{16}$ may form a substituted or unsubstituted, saturated or unsaturated ring;
$R_1$ to $R_{16}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;
$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms;
when the ring A is a benzene ring represented by the formula (2), at least one of $R_1$ to $R_{17}$ is a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms; or at least one pair of adjacent two or more of $R_1$ to $R_{16}$ forms a substituted or unsubstituted, saturated or unsaturated ring; and
when each of $R_{31}$ to $R_{37}$ is present in plural, each of the plural $R_{31}$s to $R_{37}$s may be the same or different;

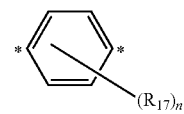

(2)

wherein in the formula (2), at one of the two ring carbon atoms indicated by the atomic bonding extending from the benzene ring B in the formula (1-1) or the formula (1-2) is bonded, and at the other of the two ring carbon atoms indicated by *, the atomic bonding extending from the benzene ring C in the formula (1-3) is bonded;
$R_{17}$ is a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms;

when each of $R_{31}$ to $R_{37}$ is present in plural, each of the plural $R_{31}$s to $R_{37}$s may be the same or different; and n is an integer of 1 or 2, and when n is 2, two $R_{17}$s may be the same or different.

In the above-mentioned novel compound, if the ring A is a benzene ring represented by the formula (2), at least one of $R_1$ to $R_{17}$ is a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms; or at least one pair of adjacent two or more of $R_1$ to $R_{16}$ forms a substituted or unsubstituted, saturated or unsaturated ring.

In this respect, the novel compound according to this aspect is different from the compound represented by the formulas (1-1) and (1-3) and the compound represented by the formula (1-2) and (1-3) contained in the organic layer of the organic electroluminescence device according to one aspect of the invention described above. On the other hand, the novel compound according to this aspect is the same except for this respect.

Therefore, structures, each substituent, preparation methods in other embodiments of the novel compound according to this aspect are the same as those of the compound represented by the formulas (1-1) and (1-3) and the compound represented by the formula (1-2) and (1-3) contained in the organic layer of the organic electroluminescence device according to one aspect of the invention. Furthermore, specific examples thereof include the same compounds except for the following compounds.

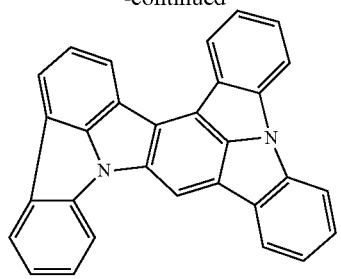

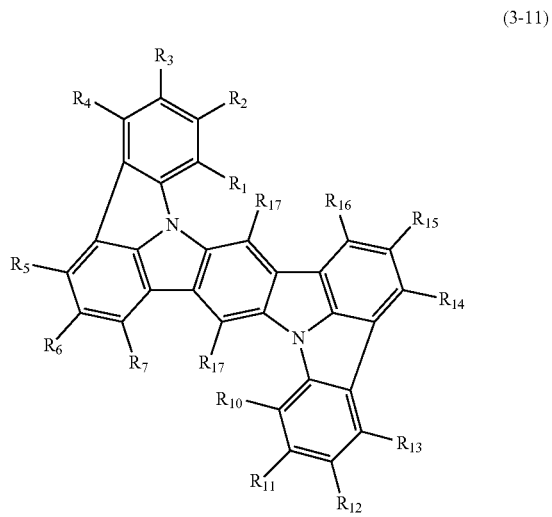

The novel compound according to another aspect of the invention is a compound represented by the following formula (3-11):

(3-11)

wherein in the formula (3-11), one or more pairs of adjacent two or more of $R_1$ to $R_7$ and $R_{10}$ to $R_{16}$ may form a substituted or unsubstituted, saturated or unsaturated ring;

$R_1$ to $R_7$ and $R_{10}$ to $R_{16}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O) $R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms, provided that at least one of $R_1$ to $R_7$ and $R_{10}$ to $R_{16}$ is —N($R_{36}$)($R_{37}$);

$R_{17}$ is a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;

two $R_{17}$s may be the same or different;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms; and when each of $R_{31}$ to $R_{37}$ is present in plural, each of the plural $R_{31}$s to $R_{37}$s may be the same or different.

The above-mentioned novel compound is the same as the compound represented by the formula (3-11) contained in the organic layer of the organic electroluminescence device according to one aspect of the invention described above.

Therefore, structures, each substituent, and preparation methods in other embodiments of the novel compound according to this aspect are the same as those of the compound represented by the formula (3-11) contained in the organic layer of the organic electroluminescence device according to one aspect of the invention. Furthermore, the same can be applied to the specific examples of the compound represented by the formula (3-11).

In one embodiment, the compound represented by the formula (3-11) is compound represented by the following formula (3-13):

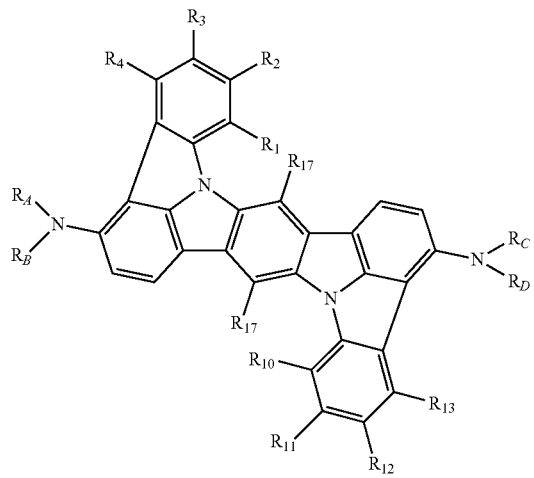

(3-13)

wherein in the formula (3-13), one or more pairs of adjacent two or more of $R_1$ to $R_4$ and $R_{10}$ to $R_{13}$ may form a substituted or unsubstituted, saturated or unsaturated ring;

$R_1$ to $R_4$, $R_{10}$ to $R_{13}$, and $R_{17}$ that do not form the substituted or unsubstituted, saturated or unsaturated ring are independently a hydrogen atom, a substituted or unsubstituted aryl group including 6 to 18 ring carbon atoms or a substituted or unsubstituted monovalent heterocyclic group including 5 to 18 ring atoms;

two $R_{17}$s may be the same or different; and $R_A$, $R_B$, $R_C$ and $R_D$ are independently a substituted or unsubstituted aryl group including 6 to 18 ring carbon atoms or a substituted or unsubstituted monovalent heterocyclic group including 5 to 18 ring atoms.

The above-mentioned novel compound is the same as the compound represented by the formula (3-13) contained in the organic layer of the organic electroluminescence device according to one aspect of the invention described above.

Therefore, structures, each substituent, and preparation methods in other embodiments of the novel compound according to this aspect are the same as those of the compound represented by the formula (3-13) contained in the organic layer of the organic electroluminescence device according to one aspect of the invention. Furthermore, the same can be applied to the specific examples of the compound represented by the formula (3-13).

The novel compound according to another aspect of the invention is a compound represented by the following formula (3-21):

(3-21)

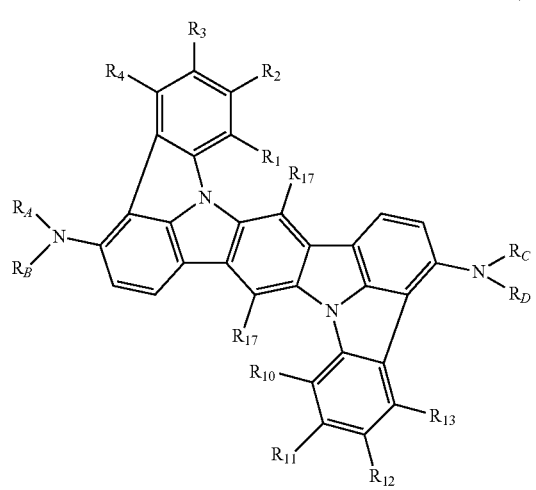

wherein in the formula (3-21), one or more pairs of adjacent two or more of $R_1$ to $R_4$ and $R_{10}$ to $R_{13}$ may form a substituted or unsubstituted, saturated or unsaturated ring; $R_{17}$, and $R_1$ to $R_4$ and $R_{10}$ to $R_{13}$ that do not form the substituted or unsubstituted, saturated or unsaturated ring are independently a hydrogen atom, a substituted or unsubstituted aryl group including 6 to 20 ring carbon atoms or a substituted or unsubstituted monovalent heterocyclic group including 5 to 20 ring atoms;

two $R_{17}$s may be the same or different; and $R_A$, $R_B$, $R_C$ and $R_D$ are independently a substituted or unsubstituted aryl group including 6 to 20 ring carbon atoms.

The above-mentioned novel compound is the same as the compound represented by the formula (3-21) contained in the organic layer of the organic electroluminescence device according to one aspect of the invention described above.

Therefore, structures, each substituent, and preparation methods in other embodiments of the novel compound according to this aspect are the same as those of the compound represented by the formula (3-21) contained in the organic layer of the organic electroluminescence device according to one aspect of the invention. Furthermore, the same can be applied to the specific examples of the compound represented by the formula (3-21).

The novel compound according to another aspect of the invention is a compound represented by the following formula (3-31) or (3-32):

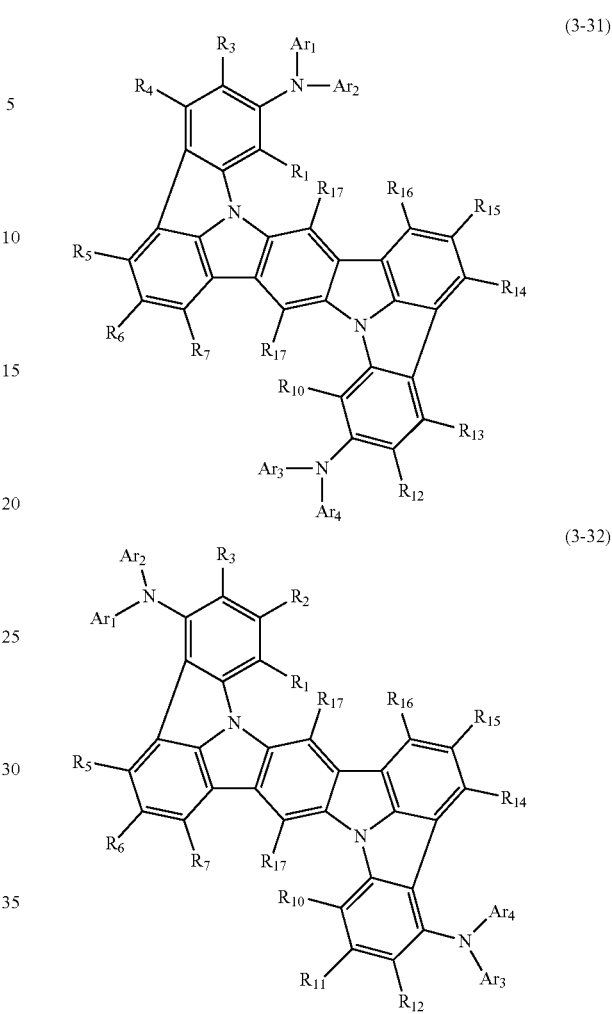

wherein in the formula (3-31) and (3-32), one or more pairs of adjacent two or more of $R_1$ to $R_7$ and $R_{10}$ to $R_{16}$ may form a substituted or unsubstituted, saturated or unsaturated ring; $R_{17}$, and $R_1$ to $R_7$ and $R_{10}$ to $R_{16}$ that do not form the substituted or unsubstituted, saturated or unsaturated ring are independently a hydrogen atom, a substituted or unsubstituted aryl group including 6 to 20 ring carbon atoms or a substituted or unsubstituted monovalent heterocyclic group including 5 to 20 ring atoms;

two $R_{17}$s may be the same or different; and $Ar_1$ to $Ar_4$ are independently a substituted or unsubstituted aryl group including 6 to 20 ring carbon atoms.

The above-mentioned novel compound is the same as the compound represented by the formula (3-31) and (3-32) contained in the organic layer of the organic electroluminescence device according to one aspect of the invention described above.

Therefore, structures, each substituent, and preparation methods in other embodiments of the novel compound according to this aspect are the same as those of the compound represented by the formula (3-31) and (3-32) contained in the organic layer of the organic electroluminescence device according to one aspect of the invention. Furthermore, the same can be applied to the specific examples of the compound represented by the formula (3-31) and (3-32).

The novel compounds according to the above aspects are useful as a material for organic electroluminescent devices. The novel compounds according to the above aspects are useful as a material of an emitting layer of an organic electroluminescent device, and is particularly useful as a fluorescent emitting material (also referred to as a fluorescent dopant) of an emitting layer. The novel compounds according to the above aspects can enhance the luminous efficiency of the organic EL device.

EXAMPLES

Next, the invention will be explained in more detail in accordance with the following synthesis examples, examples, and comparative examples, which should not be construed as limiting the scope of the invention.

Example 1-1

(Fabrication of Organic EL Device)

A glass substrate of 25 mm by 75 mm by 1.1 mm thick with an ITO transparent electrode (anode) (manufactured by GEOMATEC Co., Ltd.) was subjected to ultrasonic cleaning with isopropyl alcohol for 5 minutes, and then subjected to UV-ozone cleaning for 30 minutes. The thickness of ITO was 130 nm.

The cleaned glass substrate with a transparent electrode was mounted in a substrate holder of a vacuum vapor deposition apparatus. First, compound HI was deposited on the surface where the transparent electrode was formed so as to cover the transparent electrode, thereby to form a compound HI film having a thickness of 5 nm. This HI film functioned as a hole-injecting layer.

Subsequent to the formation of the HI film, compound HT1 was deposited to form an HT1 film in a thickness of 80 nm on the HI film. This HT1 film functioned as a first hole-transporting layer.

Subsequent to the formation of the HT1 film, compound HT2 was deposited to form an HT2 film in a thickness of 10 nm on the HT1 film. This HT2 film functioned as a second hole-transporting layer.

Compound BH-1 (host material) and compound BD-1 (dopant material) were co-deposited on the HT2 film so that the ratio (weight ratio) of compound BD-1 was 4% to form an emitting layer having a thickness of 25 nm.

Compound HBL was deposited on the emitting layer to form an electron-transporting layer having a thickness of 10 nm. Compound ET (electron-transporting material) was deposited on the electron-transporting layer to form an electron-injecting layer having a thickness of 15 nm. LiF was deposited on the electron-injecting layer to form a LiF film having a thickness of 1 nm. Al metal was deposited on the LiF film to form a metal cathode having a thickness of 80 nm.

An organic EL device was thus fabricated. The compounds used to fabricate the organic EL device are shown below.

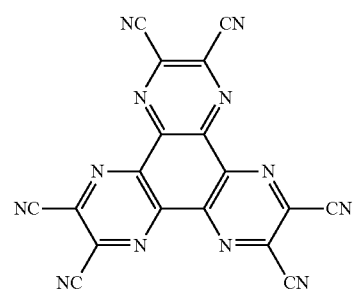

HI

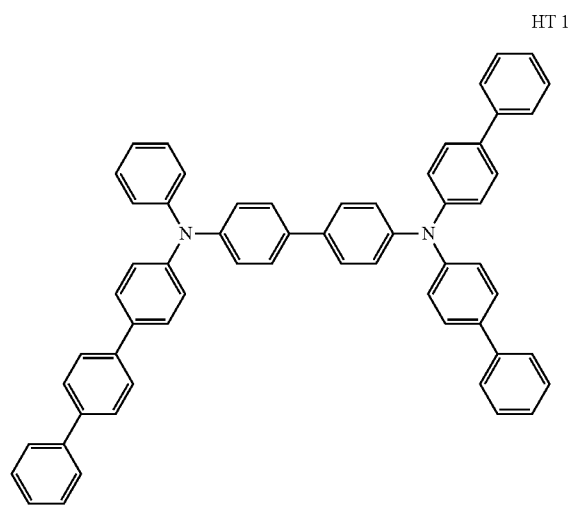

HT1

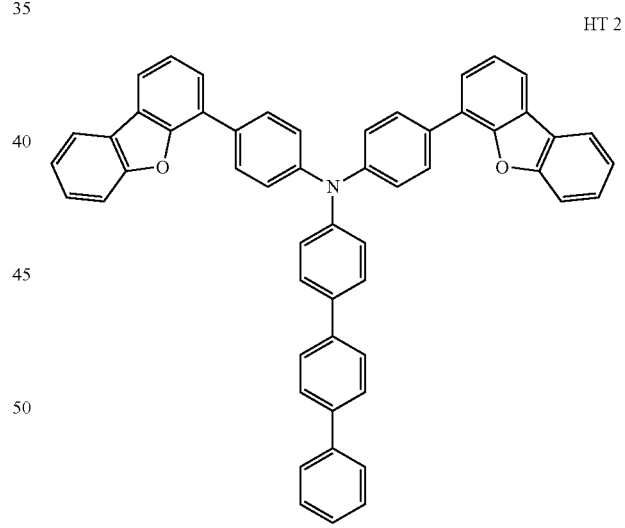

HT2

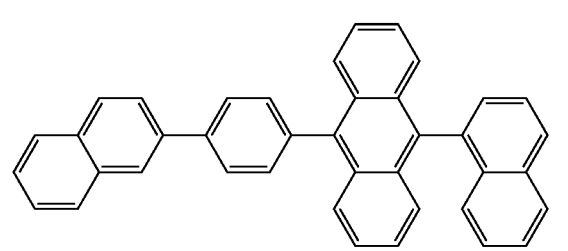

BH-1

-continued

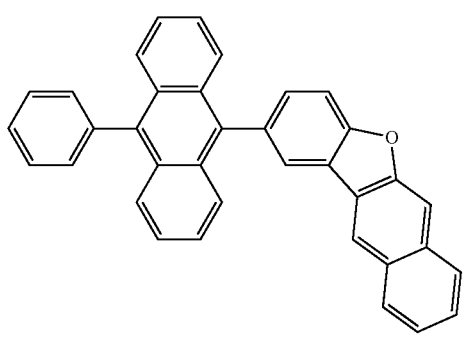
BH-2

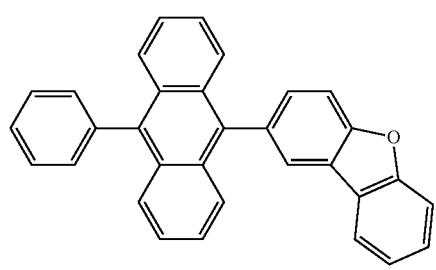
BH-3

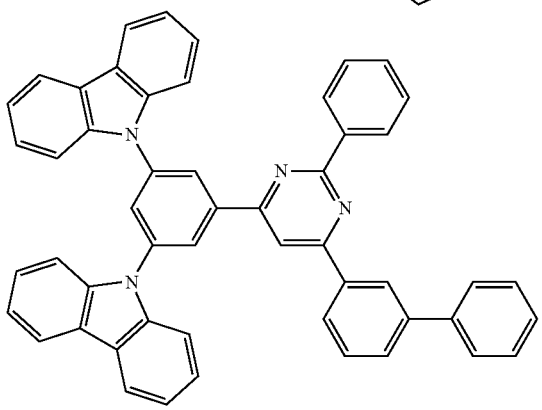
HBL

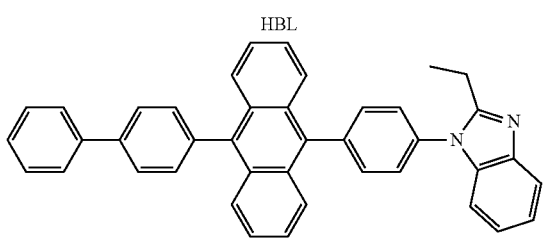
ET (Evaluation of Organic EL Device)

The initial characteristics of the obtained organic EL device were measured at room temperature at 10 mA/cm² of DC (direct current) constant current driving. The measurement results of the voltage are shown in Table 1.

Furthermore, a voltage was applied to the organic EL device so that the current density was 10 mA/cm², and the EL emission spectrum was measured using a spectroradiometer "CS-1000" (manufactured by Konica Minolta, Inc.). The external quantum efficiency (EQE) (%) was calculated from the resulting spectral radiance spectrum. The results are shown in Table 1. The numerical values in Table 1 are relative values with the values of Comparative Examples 1-1, 1-2 and 1-3 being each taken to be 100%.

Further, a voltage was applied to the organic EL device so that the current density was 50 mA/cm², and the time (lifetime LT95) until the luminance reached 95% with respect to the initial luminance was measured. The results of the lifetime LT 95 are shown in Table 1.

Examples 1-2 to 1-22 and Comparative Examples 1-1 to 1-3

Using combinations of the dopant materials and the host materials shown in Table 1, organic EL devices were fabricated and evaluated in the same manner as in Example 1-1. The results are shown in Table 1.

The compounds used are shown below. The compound BD-1 and the compound BD-2 were synthesized according to the synthesis method described in Dibenzo[2,3:5,6]pyrrolizino[1,7-bc]indolo[1,2,3-Im]carbazole: a new electron donor, New J. Chem., 2010, 34, 1243-1246. Compounds BD-4, BD-9 and BD-11 to BD-14 were synthesized by the method described below

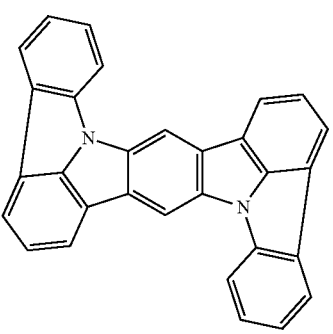
BD-1

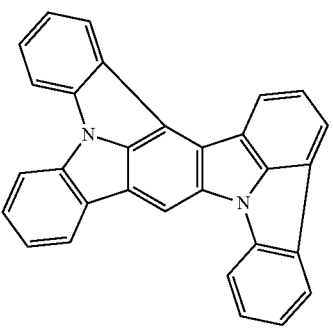
BD-2

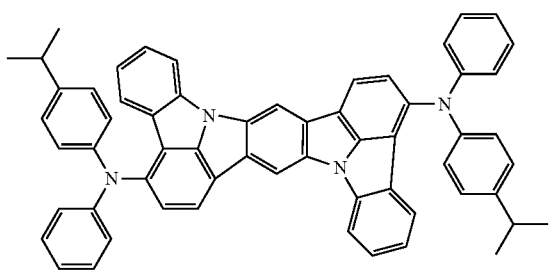
BD-4

BD-9
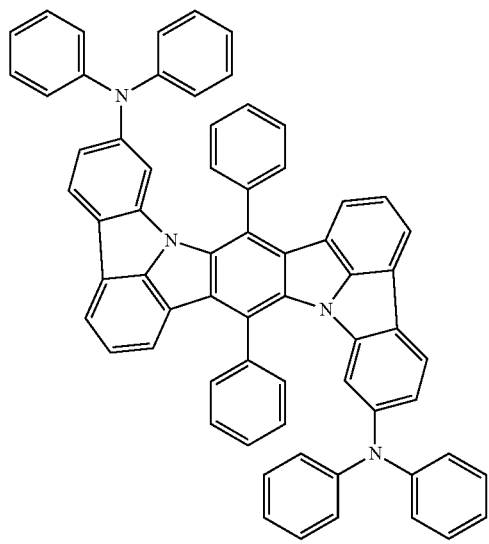
BD-11
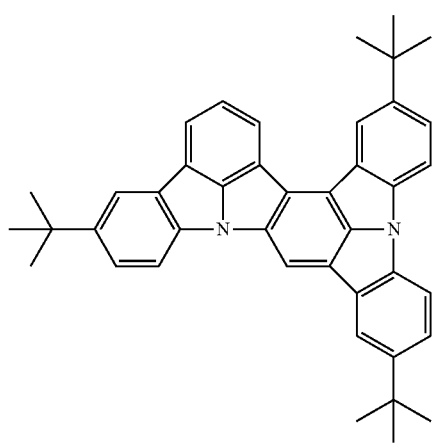
BD-12
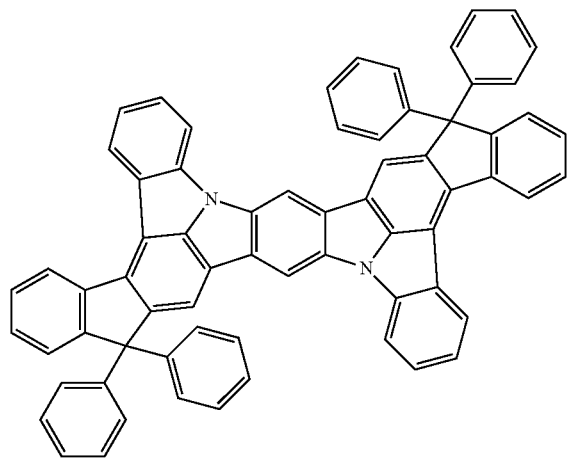
BD-13
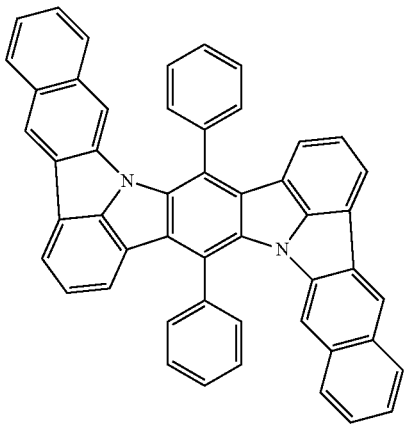
BD-14
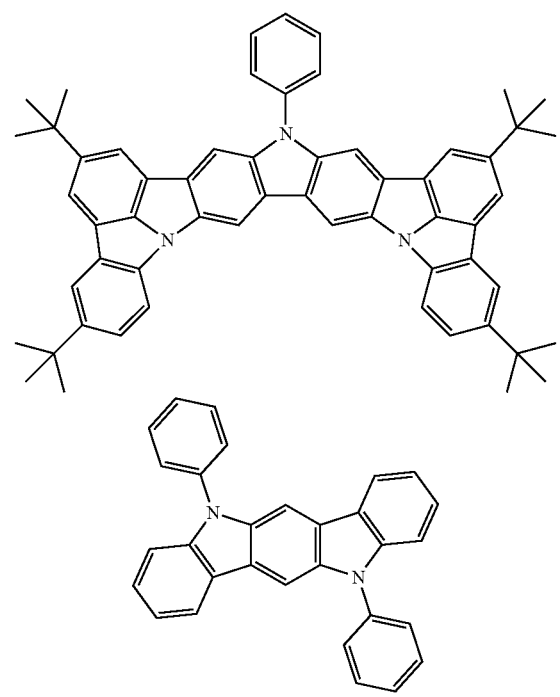
BD-COM
TABLE 1
|  | Host | Dopant | Driving Voltage (V) | EQE (%) | LT95 (hr) |
|---|---|---|---|---|---|
| Example 1-1 | BH-1 | BD-1 | 3.7 | 135 | 92 |
| Example 1-2 |  | BD-2 | 3.7 | 133 | 81 |
| Example 1-3 |  | BD-4 | 3.6 | 146 | 87 |
| Example 1-4 |  | BD-9 | 3.7 | 140 | 108 |
| Example 1-5 |  | BD-11 | 3.7 | 131 | 95 |
| Example 1-6 |  | BD-12 | 3.7 | 140 | 80 |
| Example 1-7 |  | BD-13 | 3.7 | 129 | 94 |
| Example 1-8 |  | BD-14 | 3.6 | 125 | 130 |
| Comp. Ex. 1-1 |  | BD-COM | 3.7 | 100 | 66 |
| Example 1-9 | BH-2 | BD-1 | 3.3 | 144 | 105 |
| Example 1-10 |  | BD-2 | 3.3 | 144 | 94 |
| Example 1-11 |  | BD-4 | 3.3 | 150 | 85 |
| Example 1-12 |  | BD-9 | 3.3 | 147 | 102 |
| Example 1-13 |  | BD-11 | 3.3 | 145 | 93 |
| Example 1-14 |  | BD-12 | 3.3 | 154 | 90 |
| Example 1-15 |  | BD-13 | 3.3 | 140 | 99 |

TABLE 1-continued

| | Host | Dopant | Driving Voltage (V) | EQE (%) | LT95 (hr) |
|---|---|---|---|---|---|
| Example 1-16 | | BD-14 | 3.3 | 141 | 105 |
| Comp. Ex. 1-2 | | BD-COM | 3.3 | 100 | 75 |
| Example 1-17 | BH-3 | BD-4 | 3.7 | 143 | 95 |
| Example 1-18 | | BD-9 | 3.7 | 132 | 122 |
| Example 1-19 | | BD-11 | 3.7 | 127 | 100 |
| Example 1-20 | | BD-12 | 3.7 | 129 | 103 |
| Example 1-21 | | BD-13 | 3.7 | 124 | 105 |
| Example 1-22 | | BD-14 | 3.6 | 119 | 139 |
| Comp. Ex. 1-3 | | BD-COM | 3.7 | 100 | 70 |

From the results shown in Table 1, it can be said that BD-1, BD-2, BD-4, BD-9 and BO-11 to BD-14 were ring-fused, and hence, deactivation of excitons due to thermal vibration of the compound was suppressed. As a result, the stability of the compound also increased, so that the compound had higher efficiency and longer life than those of BD-COM.

Example 2-1

Compound 1 was synthesized by the following synthesis route.

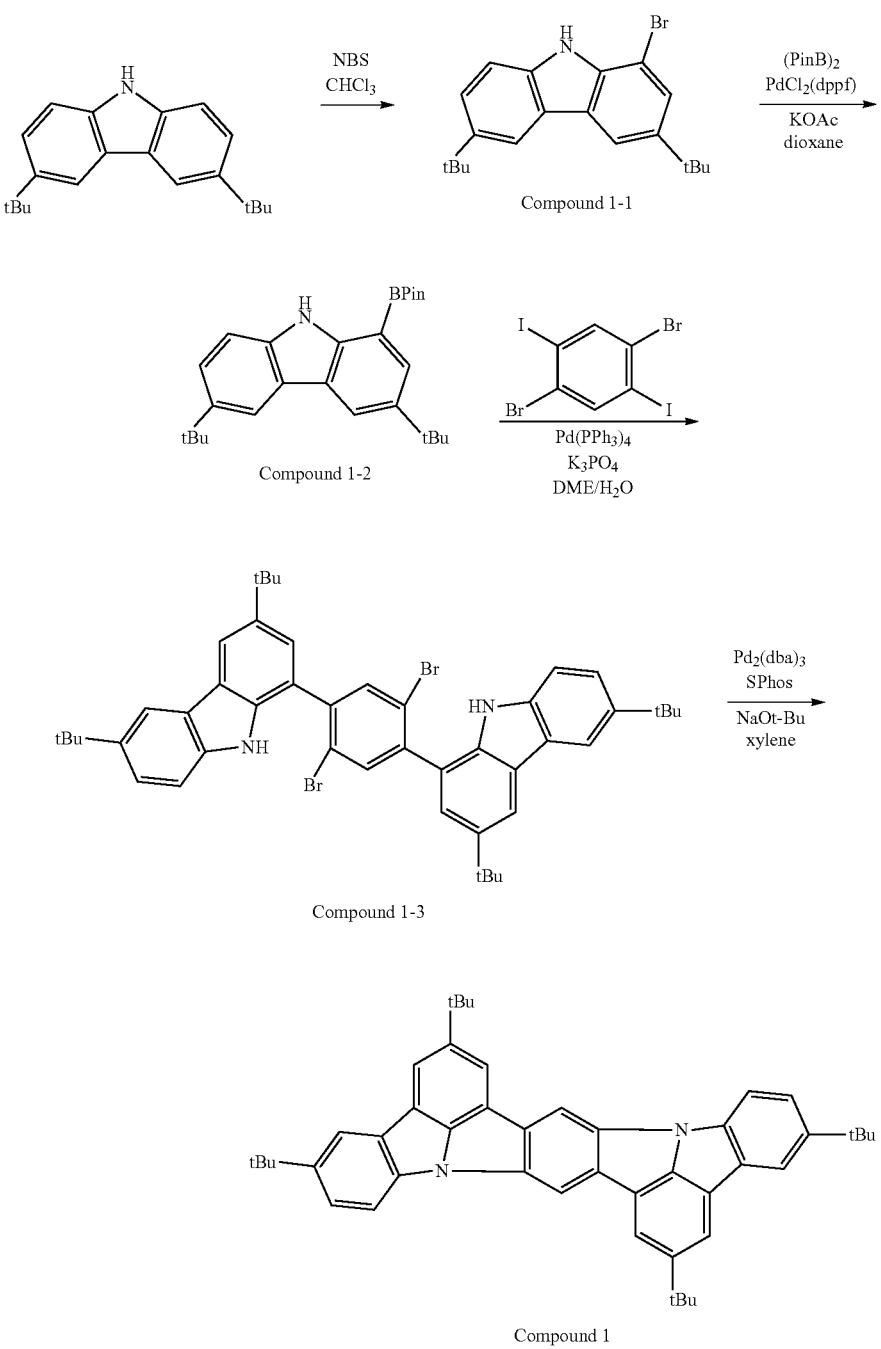

Compound 1

Synthesis of Compound 1-1

Under an argon atmosphere, 3,6-di-tert-butylcarbazole (11.2 g, 40 mmol) was dissolved in chloroform (200 mL), and n-bromosuccinimide (7.12 g) was added thereto, and the mixture was stirred at room temperature for 5 hours. After completion of the reaction, the solvent was concentrated, and the residues were purified by column chromatography, whereby obtaining an amorphous solid (14.4 g). The obtained solid was compound 1-1, which is an intended product, and by mass spectrum analysis, it was confirmed that it had an m/e value of 358 with respect to a molecular weight of 358.

Synthesis of Compound 1-2

Under an argon atmosphere, compound 1-1 (14.4 g), bis(pinacolato)diboron (15.2 g, 60 mmol, 1.5 eq.), $PdCl_2$(dppf) (1.46 g, 2.0 mmol, 5% Pd), and potassium acetate (7.85 g, 80 mmol) were suspended in dioxane (200 mL), and the mixture was refluxed for 7 hours. After completion of the reaction, the solvent was concentrated by passing through short pass silica gel column chromatography. The resulting solid was recrystallized from hexane/ethyl acetate (9:1) to obtain a white solid (12.1 g, yield: 75%). The obtained solid was compound 1-2, which is an intended product, and by mass spectrum analysis, it was confirmed that it had an m/e value of 405 with respect to a molecular weight of 405.

Synthesis of Compound 1-3

Under an argon atmosphere, dibromodiiodobenzene (4.00 g, 8.20 mmol), compound 1-2 (6.81 g, 16.8 mmol, 1.05 eq.), and $Pd(PPh_3)_4$(474 mg, 0.41 mmol, 5% Pd) were dissolved in 1,2-dimethoxyethane (800 mL) and water (200 mL) in which $K_3PO_4$ (10.4 g, 49.2 mmol) was dissolved was added thereto, and the mixture was stirred with heating at 50° C. for 24 hours. After completion of the reaction, extraction with ethyl acetate was conducted, and the solvent was concentrated. The resulting solid was purified by column chromatography, whereby obtaining a white solid (5.0 g, yield: 77%). The obtained solid was compound 1-3, which is an intended product, and by mass spectrum analysis, it was confirmed that it had an m/e value of 790 with respect to a molecular weight of 790.

Synthesis of Compound 1

Under an argon atmosphere, compound 1-3 (2.00 g), $Pd_2(dba)_3$ (232 mg), SPhos (415 mg), and NaOt-Bu (973 mg) were suspended in xylene (200 mL), and the mixture was refluxed for 8 hours. After completion of the reaction, the resulting mixture was purified by silica gel column chromatography, whereby obtaining a yellow solid (450 mg, yield: 28%). The obtained solid was compound 1, which is an intended product, and by mass spectrum analysis, it was confirmed that it had an m/e value of 628 with respect to a molecular weight of 628.

Example 2-2

Compound BD-4 was synthesized by the following synthesis route.

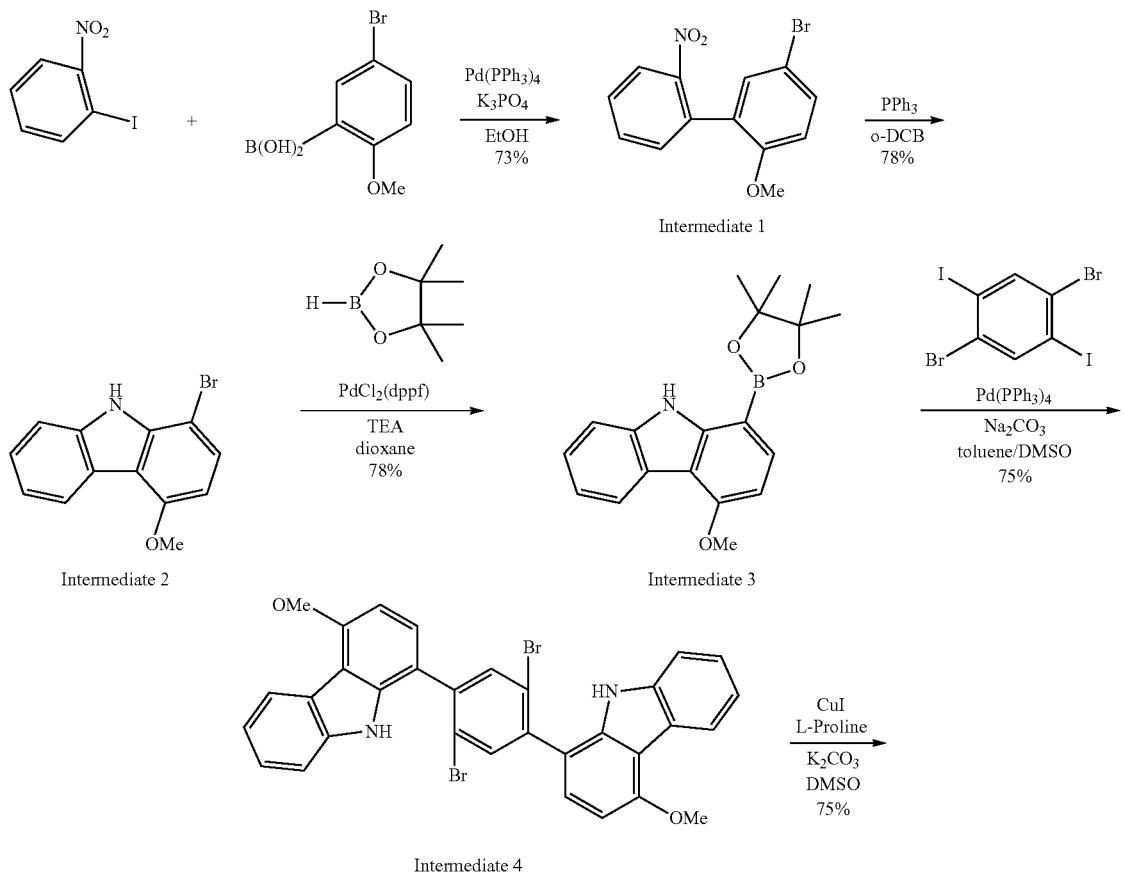

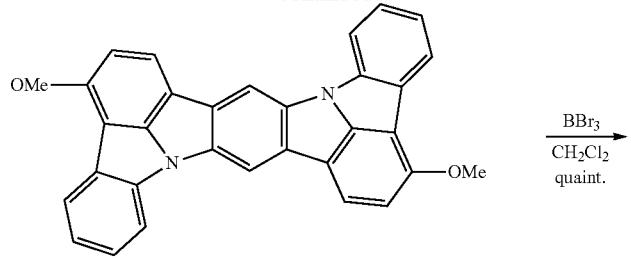

Intermediate 5

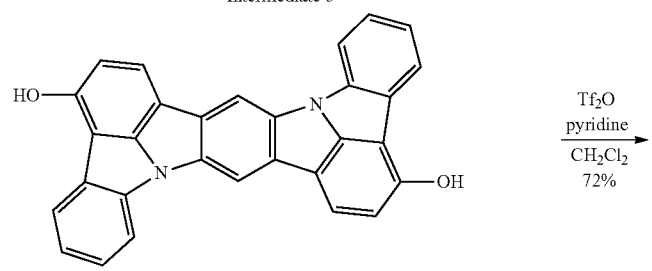

Intermediate 6

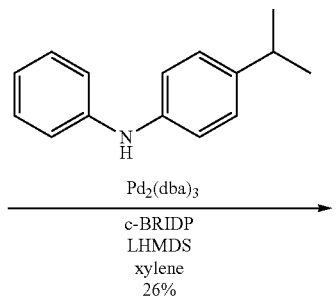

Intermediate 7

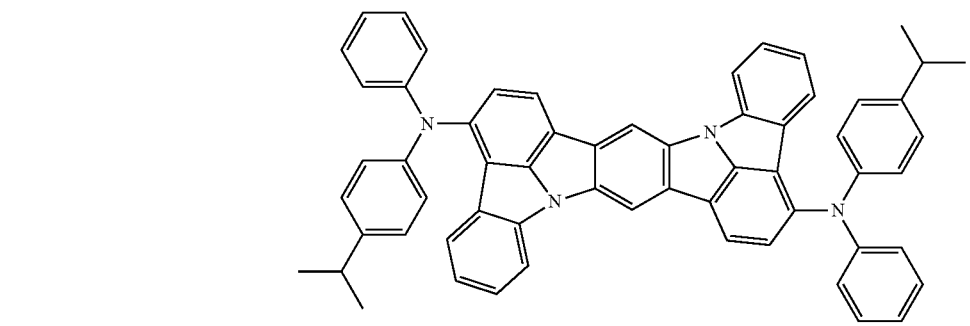

BD-4

Synthesis of Intermediate 1

Under an argon atmosphere, 2-iodonitrobenzene (9.7 g, 39 mmol), 5-bromo-2-methoxyphenylboronic acid (9.2 g, 40 mmol), tetrakis(triphenylphosphine)palladium(0) (Pd(PPh$_3$)$_4$, 1.1 g, 0.975 mmol), and K$_3$PO$_4$ (21 g, 97 mmol) was dissolved in ethanol (95 mL), and the mixture was refluxed for 8 hours. After completion of the reaction, the solvent was concentrated, and the residues were purified by column chromatography, whereby obtaining a yellow solid (8.8 g, yield: 73%). The obtained solid was Intermediate 1, which is an intended product, and by mass spectrum analysis, it was confirmed that it had an r/e value of 308 with respect to a molecular weight of 308.

Synthesis of Intermediate 2

Intermediate 1 (7.00 g, 22.7 mmol) was dissolved in o-dichlorobenzene (80 mL), triphenylphosphine (14.9 g, 56.8 mmol) was added thereto, and the mixture was refluxed for 12 hours. After completion of the reaction, the solvent was concentrated, and the residues were purified by column chromatography, whereby obtaining a white solid (5.7 g, yield: 78%). The obtained solid was Intermediate 2, which is an intended product, and by mass spectrum analysis, it was confirmed that it had an m/e value of 276 with respect to a molecular weight of 276.

Synthesis of Intermediate 3

Under an argon atmosphere, Intermediate 2 (5.7 g, 21 mmol), pinacolborane (7.9 g, 62 mmol), and dichloro[1,1'-bis(diphenylphosphino)ferrocene]palladium (PdCl$_2$(dppf), 1.5 g, 2.0 mmol) was dissolved in dioxane (250 mL), triethylamine (11.5 mL, 83 mmol) was added thereto, and the mixture was refluxed for 5 hours. After completion of the reaction, the solvent was concentrated, and the residues were purified by column chromatography, whereby obtaining a yellow solid (5.0 g, yield: 75%). The obtained solid was Intermediate 3, which is an intended product, and by mass spectrum analysis, it was confirmed that it had an m/e value of 323 with respect to a molecular weight of 323.

Synthesis of Intermediate 4

Under an argon atmosphere, dibromodiiodobenzene (2.5 g, 5.1 mmol), Intermediate 3 (4.97 g, 15.4 mmol), and Pd(PPh$_3$)$_4$(237 mg, 0.205 mmol) were dissolved in toluene (250 mL) and dimethylsulfoxide (DMSO, 50 mL), 2 M Na$_2$CO$_3$ aqueous solution (13 mL) was added thereto, and the mixture was stirred with heating at 90° C. for 24 hours. After completion of the reaction, toluene was removed under reduced pressure, and the precipitated solid was filtered off. This solid was washed with methanol and ethyl acetate, whereby obtaining a white solid (2.5 g, yield: 75%). The obtained solid was Intermediate 4, which is an intended product, and by mass spectrum analysis, it was confirmed that it had an m/e value of 626 with respect to a molecular weight of 626.

Synthesis of Intermediate 5

Under an argon atmosphere, Intermediate 4 (2.5 g, 3.99 mmol), CuI (76 mg, 0.40 mmol), L-proline (92 mg, 0.80 mmol), and K$_2$CO$_3$ (1.38 g, 10 mmol) were suspended in DMSO (80 mL), and the mixture was stirred with heating at 150° C. for 6 hours. After completion of the reaction, the precipitated solid was filtered off. This solid was washed with methanol and ethyl acetate, whereby obtaining a brown solid (1.4 g, yield: 75%). The obtained solid was Intermediate 5, which is an intended product, and by mass spectrum analysis, it was confirmed that it had an m/e value of 464 with respect to a molecular weight of 464.

Synthesis of Intermediate 6

Intermediate 5 (1.4 g, 3.0 mmol) was dissolved in dichloromethane (150 mL), dichloromethane solution of 1 M BBr$_3$(15 mL, 15 mmol) was added thereto, and the mixture was refluxed for 8 hours. After completion of the reaction, ice water (50 mL) was added, and the precipitate was filtered off. This solid was washed with methanol, whereby obtaining a white solid (1.4 g). The obtained solid was Intermediate 6, which is an intended product, and by mass spectrum analysis, it was confirmed that it had an m/e value of 436 with respect to a molecular weight of 436.

Synthesis of Intermediate 7

Intermediate 6 (1.4 g, 3.2 mmol) was suspended in dichloromethane (75 mL) and pyridine (75 mL), anhydrous triflate (3.8 mL, 22.5 mmol) was added thereto, and the mixture was stirred for 8 hours. After completion of the reaction, water (50 mL) was added, and the precipitate was filtered off. This solid was washed with methanol and ethyl acetate, whereby obtaining a white solid (1.8 g, yield: 72%). The obtained solid was Intermediate 7, which is an intended product, and by mass spectrum analysis, it was confirmed that it had an m/e value of 700 with respect to a molecular weight of 700.

Synthesis of BD-4

Under an argon atmosphere, Intermediate 7 (1.00 g, 1.43 mmol), 4-iPr-N-phenylaniline (754 mg, 3.57 mmol), tris(dibenzylideneacetone)dipalladium(0) (Pd$_2$(dba)$_3$, 26 mg, 0.029 mmol), and di-tert-butyl(1-methyl-2,2-diphenylcyclopropyl)phosphine (40 mg, 0.11 mmol) were dissolved in xylene (120 mL), tetrahydrofuran solution of 1 M lithium bis(trimethylsilyl)amide (3.6 mL, 3.6 mmol) was added thereto, and the mixture was refluxed for 8 hours.
After completion of the reaction, the mixture was filtered through celite, and the solvent was distilled off. The obtained solid was purified by column chromatography, whereby obtaining a yellow solid (300 mg, yield: 26%). The obtained solid was BD-4, which is an intended product, and by mass spectrum analysis, it was confirmed that it had an m/e value of 823 with respect to a molecular weight of 823.

Example 2-3

Compound BD-5 was synthesized by the following synthesis route.

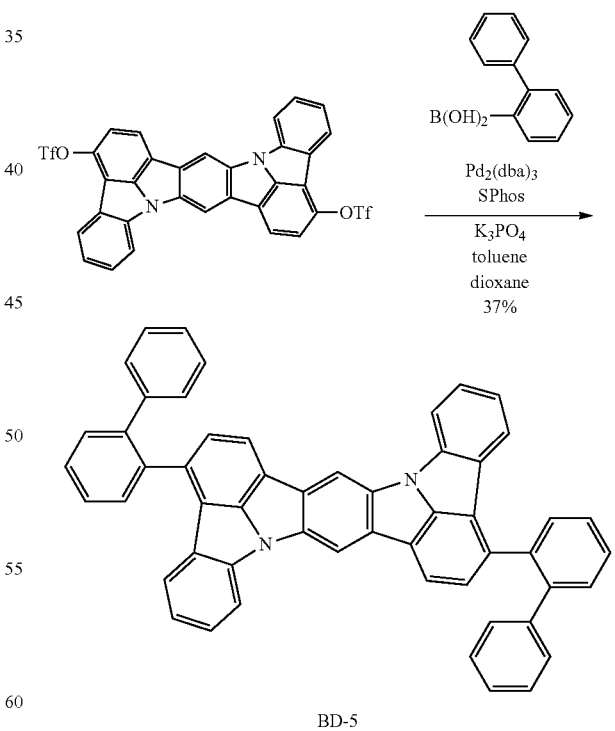

BD-5

Synthesis of BD-5

Under an argon atmosphere, Intermediate 7 (50 mg, 0.071 mmol), 2-biphenylboronic acid (113 mg, 0.571 mmol), Pd$_2$(dba)$_3$ (2.6 mg, 0.0028 mmol), 2-dicyclohexylphosphino-2',6'-dimethoxybiphenyl (SPhos, 4.7 mg, 0.011 mmol) and K$_3$PO$_4$ (151 mg, 0.714 mmol) were dissolved in toluene (3 mL) and dioxane (3 mL) and the mixture was stirred with heating at 90° C. for 6 hours. After completion of the reaction, heated chlorobenzene was added, the mixture was filtered through celite, and the solvent was distilled off. The obtained solid was washed with dimethoxyethane, whereby obtaining a yellow solid (18.5 mg, yield: 37%). The obtained solid was BD-5, which is an intended product, and by mass spectrum analysis, it was confirmed that it had an m/e value of 708 with respect to a molecular weight of 708.

Example 2-4

Compound BD-6 was synthesized by the following synthesis route.

Synthesis of Intermediate 8

Under an argon atmosphere, 2-chloroaniline (10.0 g, 46.2 mmol), 3-bromo-4-chlorobenzonitrile (5.89 g, 46.2 mmol), (4,5-bis(diphenylphosphino)-9,9-dimethylxanthene)(allyl) palladium chloride (352 mg, 0.462 mmol) and sodium tert-butoxide (4.44 g, 46.2 mmol) were suspended in dioxane (250 mL), and the mixture was stirred with heating at 100° C. for 8 hours. After completion of the reaction, the mixture was filtered through celite and the solvent was distilled off. The obtained residue was purified by column chromatography, whereby obtaining a white solid (6.8 g, yield: 56%). The obtained solid was Intermediate 8, which is an intended product, and by mass spectrum analysis, it was confirmed that it had an m/e value of 263 with respect to a molecular weight of 263.

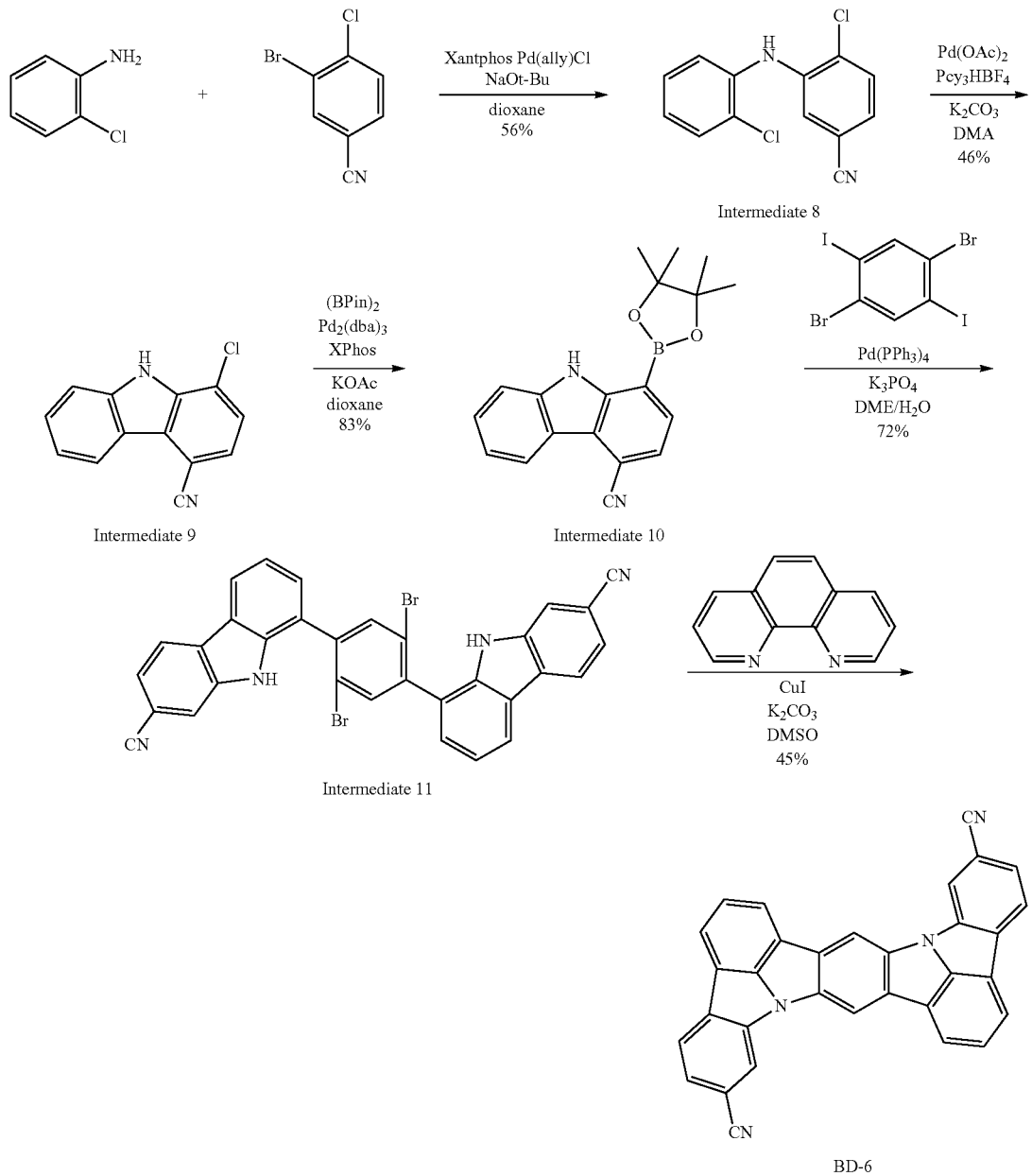

BD-6

Synthesis of Intermediate 9

Under an argon atmosphere, Intermediate 8 (6.50 g, 24.7 mmol), palladium acetate (277 mg, 1.24 mmol), tricyclohexylphosphonium tetrafluoroborate (910 mg, 2.47 mmol), and potassium carbonate ($K_2CO_3$, 6.83 g, 49.4 mmol) were suspended in N,N-dimethylacetamide (DMA, 250 mL), and the mixture was stirred with heating at 140° C. for 5 hours. After completion of the reaction, the mixture was filtered through celite and the solvent was distilled off. The obtained residue was purified by column chromatography, whereby obtaining a white solid (2.5 g, yield: 45%). The obtained solid was Intermediate 9, which is an intended product, and by mass spectrum analysis, it was confirmed that it had an m/e value of 226 with respect to a molecular weight of 226.

Synthesis of Intermediate 10

Under an argon atmosphere, Intermediate 9 (1.30 g, 5.74 mmol), bis(pinacolato)diboron (2.91 g, 11.5 mmol), $Pd_2(dba)_3$ (105 mg, 0.115 mmol), 2-dicyclohexylphosphino-2',4',6'-triisopropylbiphenyl (XPhos, 0.219 g, 0.459 mmol) and potassium acetate (1.69 g, 17.2 mmol) were dissolved in dioxane (250 mL), and the mixture was stirred with heating at 100° C. for 5 hours. After completion of the reaction, the solvent was distilled off through a short pass column chromatography, and the obtained residue was recrystallized with hexane, whereby obtaining a white solid (1.52 g, yield: 83%). The obtained solid was Intermediate 10, which is an intended product, and by mass spectrum analysis, it was confirmed that it had an m/e value of 318 with respect to a molecular weight of 318.

Synthesis of Intermediate 11

Under an argon atmosphere, dibromodiiodobenzene (400 mg, 0.820 mmol), Intermediate 10 (535 mg, 1.68 mmol), $Pd(PPh_3)_4$ (47 mg, 0.041 mmol) and potassium phosphate (1.05 g, 4.92 mmol) were dissolved in dimethoxyethane (80 mL) and water (20 mL), and the mixture was stirred with heating at 50° C. for 24 hours. After completion of the reaction, the precipitate was filtered off. This solid was washed with water and methanol, whereby obtaining a white solid (365 mg, yield: 72%). The obtained solid was Intermediate 11, which is an intended product, and by mass spectrum analysis, it was confirmed that it had an m/e value of 616 with respect to a molecular weight of 616.

Synthesis of BD-6

Under an argon atmosphere, Intermediate 11 (150 mg, 0.243 mmol), CuI (9 mg, 0.05 mmol), 1,10-phenanthroline monohydrate (48 mg, 0.24 mmol) and $K_2CO_3$ (135 mg, 0.974 mmol) were suspended in dimethylsulfoxide (20 mL), and the mixture was stirred with heating at 150° C. for 8 hours. After completion of the reaction, the precipitated solid was filtered off. This solid was washed with methanol and ethyl acetate, whereby obtaining a yellow solid (50 mg, yield: 45%). The obtained solid was BD-6, which is an intended product, and by mass spectrum analysis, it was confirmed that it had an m/e value of 454 with respect to a molecular weight of 454.

Example 2-5

Compound GD-1 was synthesized by the following synthesis route.

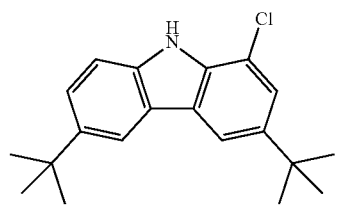
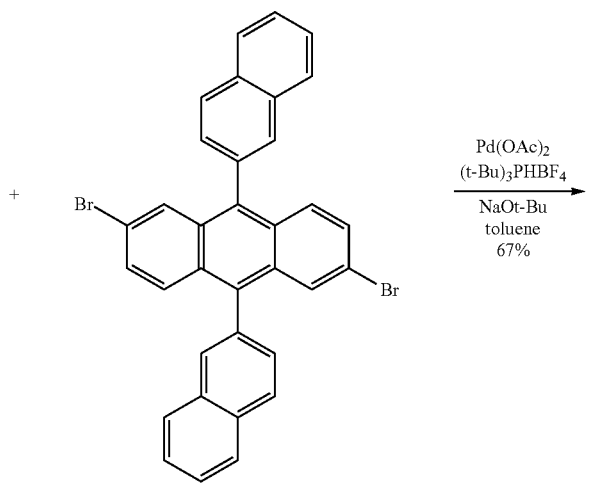

-continued

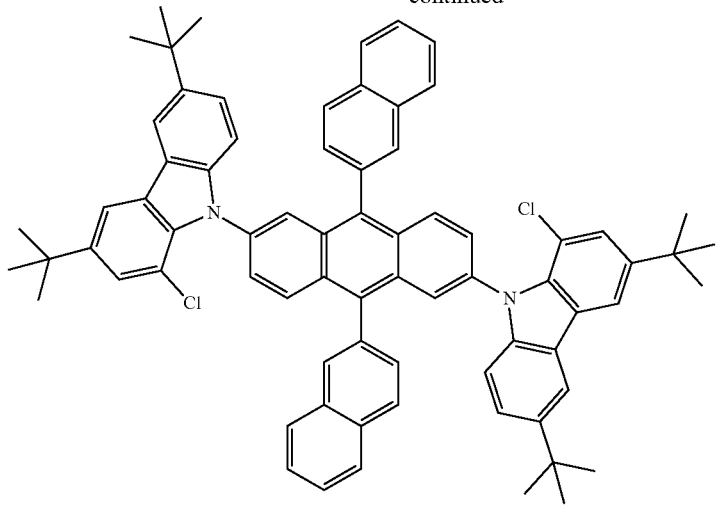

Intermediate 12

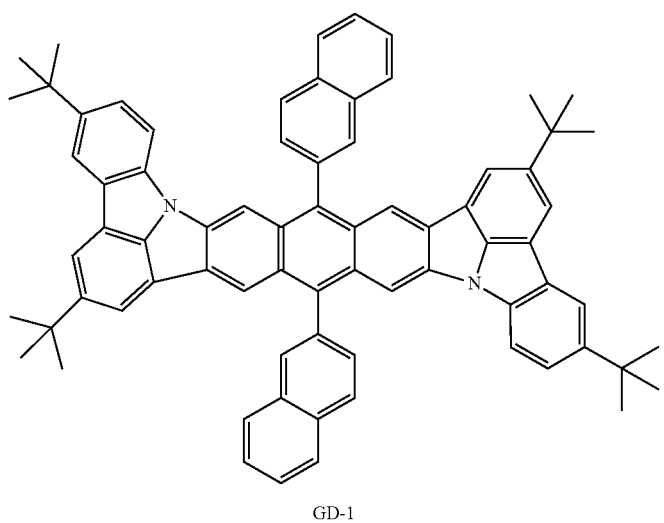

GD-1

Synthesis of Intermediate 12

Under an argon atmosphere, 2,6-dibromo-9,10-bis(2-naphthyl)anthracene (3.30 g, 5.61 mmol), 3,6-di-tert-butyl-1-chloro-9H-carbazole (3.70 g, 11.8 mmol), palladium acetate (63 mg, 0.28 mmol), tri-tert-butylphosphonium tetrafluoroborate (163 mg, 0.561 mmol) and sodium tert-butoxide (2.16 g, 22.4 mmol) were suspended in toluene (80 mL), and the mixture was stirred with heating at 100° C. for 8 hours. After completion of the reaction, the mixture was filtered through celite and the solvent was distilled off. The obtained residue was purified by column chromatography, whereby obtaining a yellow solid (3.95 g, yield: 67%). The obtained solid was Intermediate 12, which is an intended product, and by mass spectrum analysis, it was confirmed that it had an m/e value of 1054 with respect to a molecular weight of 1054.

Synthesis of GD-1

Under an argon atmosphere, Intermediate 12 (3.50 g, 3.32 mmol), palladium acetate (37 mg, 0.166 mmol), tricyclohexylphosphonium tetrafluoroborate (122 mg, 0.332 mmol) and potassium carbonate (1.84 g, 13.3 mmol) was suspended in N,N-dimethylacetamide (170 mL), and the mixture was stirred with heating at 140° C. for 8 hours. After completion of the reaction, the precipitate was filtered off. This solid was washed with heated chlorobenzene, whereby obtaining an orange solid (2.1 g, yield: 65%). The obtained solid was GD-1, which is an intended product, and by mass spectrum analysis, it was confirmed that it had an m/e value of 981 with respect to a molecular weight of 981.

Example 2-6

Compound BD-7 was synthesized by the following synthesis route.

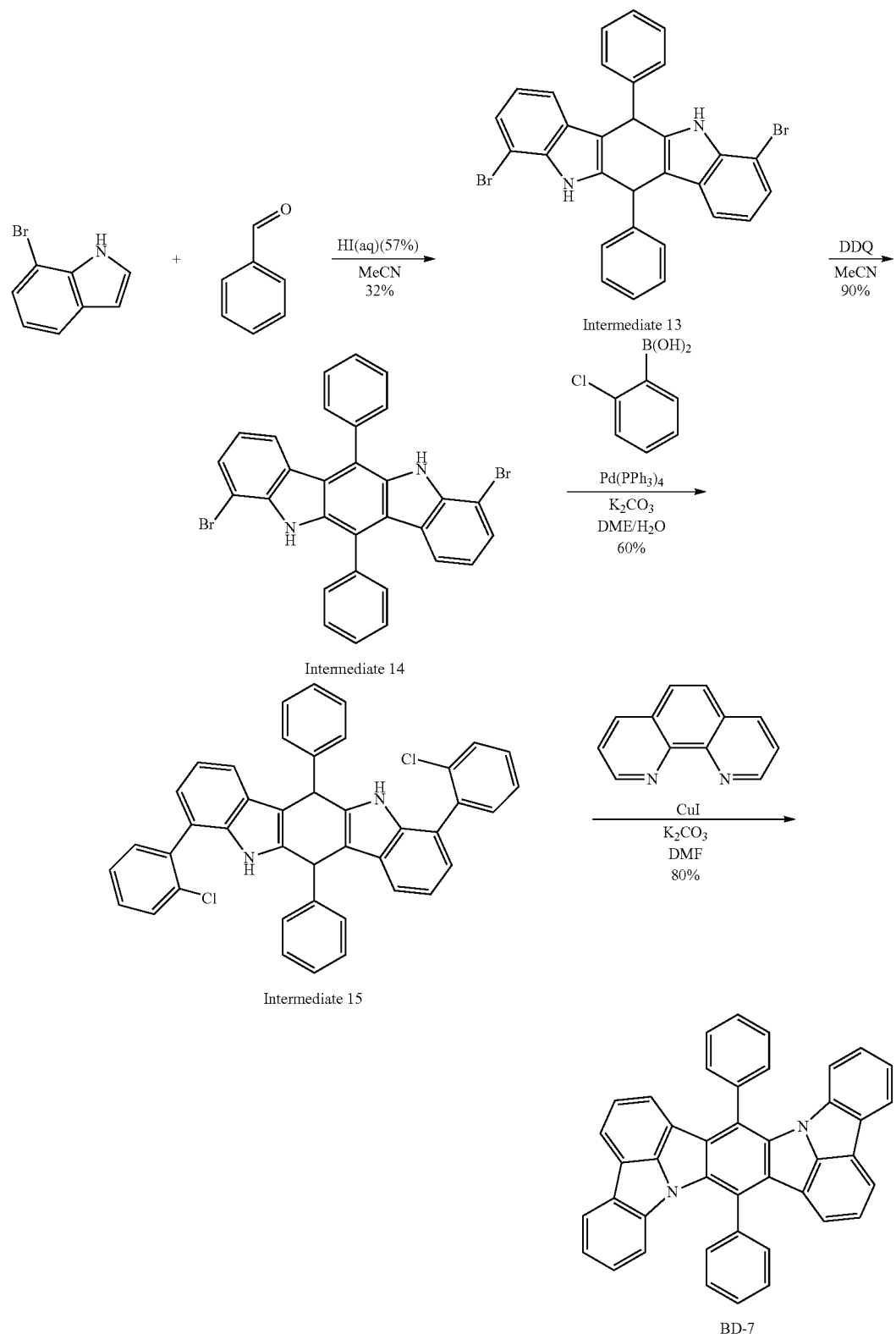
Synthesis of Intermediate 13
7-Bromo-1H-indole (10.0 g, 51.0 mmol) and benzaldehyde (5.41 g, 51.0 mmol) were dissolved in acetonitrile (200 mL), 57% hydroiodic acid (2 mL) was added dropwise with stirring, and the mixture was stirred with heating at 80° C. for 8 hours. After completion of the reaction, the precipitated solid was filtered off and washed with acetonitrile, whereby obtaining a pale-yellow solid (4.60 g, yield: 32%). The obtained solid was Intermediate 13, which is an intended product, and by mass spectrum analysis, it was confirmed that it had an m/e value of 568 with respect to a molecular weight of 568.

Synthesis of Intermediate 14

Intermediate 13 (4.50 g, 7.92 mmol) was suspended in acetonitrile and 2,3-dichloro-5,6-dicyano-p-benzoquinone (DDQ, 4.49 g, 19.8 mmol) was added with stirring, and the mixture was stirred with heating at 80° C. for 6 hours. After completion of the reaction, the precipitate was filtered off. This solid was washed with acetonitrile, whereby obtaining a yellow solid (4.02 g, yield: 90%). The obtained solid was Intermediate 14, which is an intended product, and by mass spectrum analysis, it was confirmed that it had an m/e value of 566 with respect to a molecular weight of 566.

Synthesis of Intermediate 15

Under an argon atmosphere, Intermediate 14 (1.50 g, 2.65 mmol), 2-chlorophenylboronic acid (1.24 g, 7.95 mmol), Pd(PPh$_3$)$_4$ (153 mg, 0.132 mmol) and potassium carbonate (2.20 g, 15.9 mmol) were dissolved in dimethoxyethane (20 mL) and water (5 mL), and the mixture was stirred with heating at 80° C. for 8 hours. After completion of the reaction, the precipitate was filtered off. This solid was suspended in toluene with heating and washed, whereby obtaining a pale-yellow solid (1.00 g, yield: 60%). The obtained solid was Intermediate 15, which is an intended product, and by mass spectrum analysis, it was confirmed that it had an m/e value of 629 with respect to a molecular weight of 629.

Synthesis of BD-7

Under an argon atmosphere, Intermediate 15 (900 mg, 1.43 mmol), CuI (136 mg, 0.715 mmol), 1,10-phenanthroline monohydrate (142 mg, 0.715 mmol) and K$_2$CO$_3$ (790 mg, 5.72 mmol) were suspended in N,N-dimethylformamide (30 mL), and the mixture was stirred with heating at 150° C. for 8 hours. After completion of the reaction, short pass column chromatography was carried out. After distilling off the solvent, the obtained solid was recrystallized with cyclohexanone, whereby obtaining a yellow solid (505 mg, yield: 63%). The obtained solid was BD-7, which is an intended product, and by mass spectrum analysis, it was confirmed that it had an m/e value of 556 with respect to a molecular weight of 556.

Example 2-7

Compound BD-8 was synthesized by the following synthesis route.

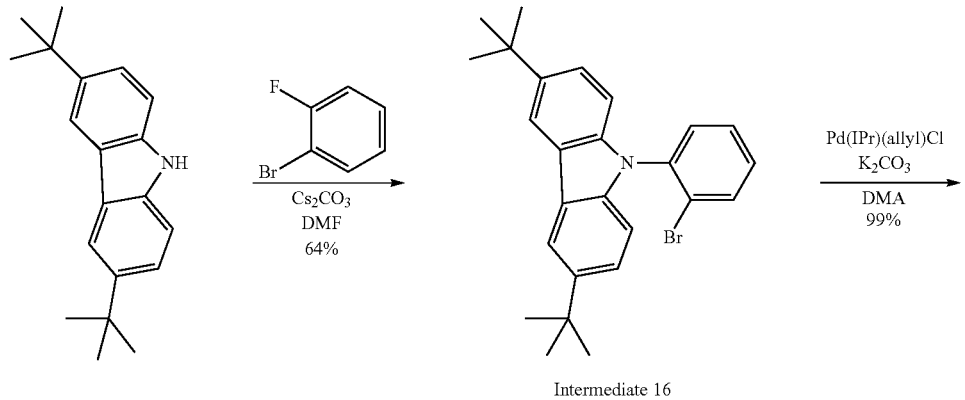

Intermediate 16

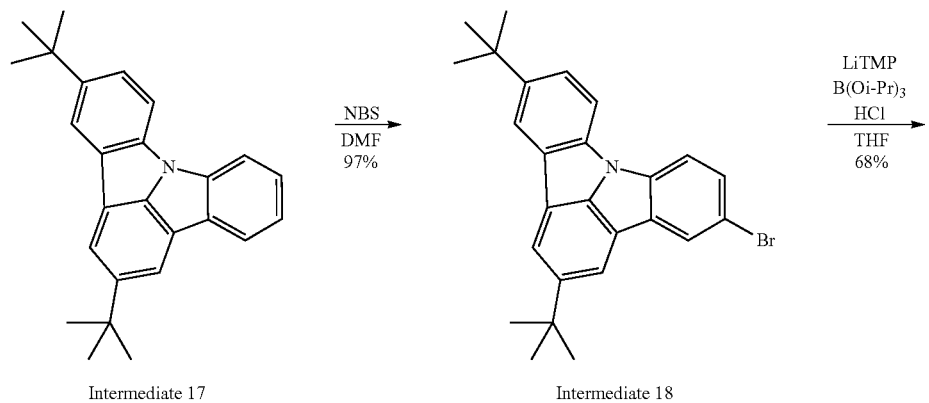

Intermediate 17

Intermediate 18

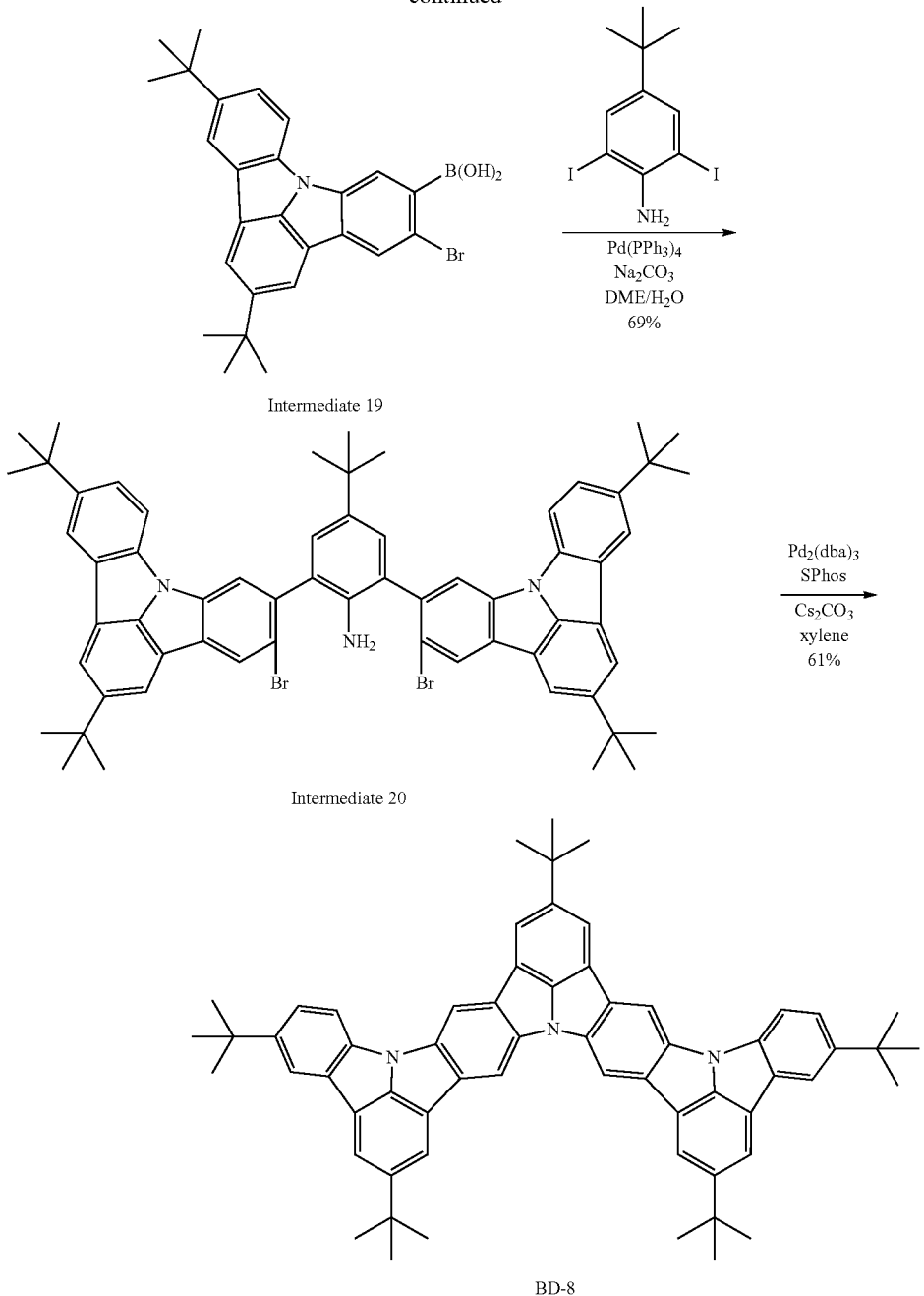

Intermediate 19

Intermediate 20

BD-8

Synthesis of Intermediate 16

3,6-di-tert-butyl-9H-carbazole (15.0 g, 53.7 mmol), 1-bromo-2-fluorobenzene (18.8 g, 107 mmol) and cesium carbonate (35.0 g, 107 mmol) were suspended in N,N-dimethylformamide (190 mL), and the mixture was stirred with heating at 150° C. for 22 hours. After completion of the reaction, water was added and the precipitate was filtered off. This solid was purified by column chromatography, whereby obtaining a white solid (21.7 g, yield: 93%). The obtained solid was Intermediate 16, which is an intended product, and by mass spectrum analysis, it was confirmed that it had an m/e value of 434 with respect to a molecular weight of 434.

Synthesis of Intermediate 17

Under an argon atmosphere, Intermediate 16 (21.7 g, 50.0 mmol), allylchloro[1,3-bis(2,6-diisopropylphenyl)imidazol-2-ylidene]palladium (570 mg, 0.996 mmol) and potassium carbonate (13.8 g, 100 mmol) was suspended in N,N-dimethylacetamide (250 mL), and the mixture was stirred with heating at 130° C. for 11 hours. After completion of the reaction, water was added and the precipitate was filtered off. This solid was purified by column chromatography, whereby obtaining a white solid (15.5 g, yield: 88%). The obtained solid was Intermediate 17, which is an intended product, and by mass spectrum analysis, it was confirmed that it had an m/e value of 353 with respect to a molecular weight of 353.

Synthesis of Intermediate 18

Intermediate 17 (4.10 g, 11.6 mmol) was dissolved in N,N-dimethylformamide, N-bromosuccinimide (NBS, 2.20 g, 12.36 mmol) was added with stirring, and the mixture was stirred at room temperature for 10 hours. After completion of the reaction, the precipitate was filtered off. This solid was purified by column chromatography, whereby obtaining a white solid (4.87 g, yield: 97%). The obtained solid was Intermediate 18, which is an intended product, and by mass spectrum analysis, it was confirmed that it had an m/e value of 432 with respect to a molecular weight of 432.

Synthesis of Intermediate 19

2,2,6,6-tetramethylpiperidine (3.20 g, 22.7 mmol) was dissolved in tetrahydrofuran, and n-butyllithium hexane solution (1.55 M, 14.6 mL) was added with stirring at −50° C. to obtain lithium tetramethylpiperidide (LiTMP). After stirring at the same temperature for 20 minutes, it was cooled to −73° C. and triisopropyl borate (8.00 mL, 34.7 mmol) was added. After stirring this solution for 5 minutes, a tetrahydrofuran solution of Intermediate 18 (4.83 g, 11.2 mmol) (30 mL) was added dropwise. After stirring for 10 hours while gradually raising the temperature to room temperature, 10% hydrochloric acid (100 mL) was added and the mixture was stirred for 30 minutes. After the completion of the reaction, ethyl acetate was added for extraction, and the organic layer was collected and the solvent was distilled off. The obtained residues were purified by column chromatography, whereby obtaining a yellow solid (3.62 g, yield: 68%). The obtained solid was Intermediate 19, which is an intended product, and by mass spectrum analysis, it was confirmed that it had an m/e value of 476 with respect to a molecular weight of 476.

Synthesis of Intermediate 20

Under an argon atmosphere, 4-tert-butyl-2,6-diiodoaniline (1.39 g, 3.47 mmol), Intermediate 19 (3.62 g, 7.60 mmol), Pd(PPh$_3$)$_4$ (400 mg, 0.346 mmol) and sodium bicarbonate (2.30 g, 27.4 mmol) were dissolved in dimethoxyethane (50 mL) and water (25 mL), and the mixture was stirred with heating at 80° C. for 10 hours. After completion of the reaction, the mixture was extracted with methylene chloride, and the organic layer was dried with magnesium sulfate. The solid was removed by filtration, and the solvent was distilled off. The obtained residue was purified by column chromatography, whereby obtaining a yellow solid (2.41 g, yield: 69%). The obtained solid was Intermediate 20, which is an intended product, and by mass spectrum analysis, it was confirmed that it had an m/e value of 1010 with respect to a molecular weight of 1010.

Synthesis of BD-8

Under an argon atmosphere, Intermediate 20 (2.41 g, 2.39 mmol), Pd$_2$(dba)$_3$ (90 mg, 0.098 mmol), SPhos (16 mg, 0.39 mmol) and cesium carbonate (4.7 g, 14.4 mmol) was suspended in xylene (240 mL), and the mixture was stirred with heating at 140° C. for 10 hours. After completion of the reaction, the precipitated solid was filtered off and washed with water and methanol. This solid was purified by column chromatography, whereby obtaining a yellow solid (1.24 g, yield: 61%). The obtained solid was BD-8, which is an intended product, and by mass spectrum analysis, it was confirmed that it had an m/e value of 848 with respect to a molecular weight of 848.

Example 2-8

Compound BD-9 was synthesized by the following synthesis route.

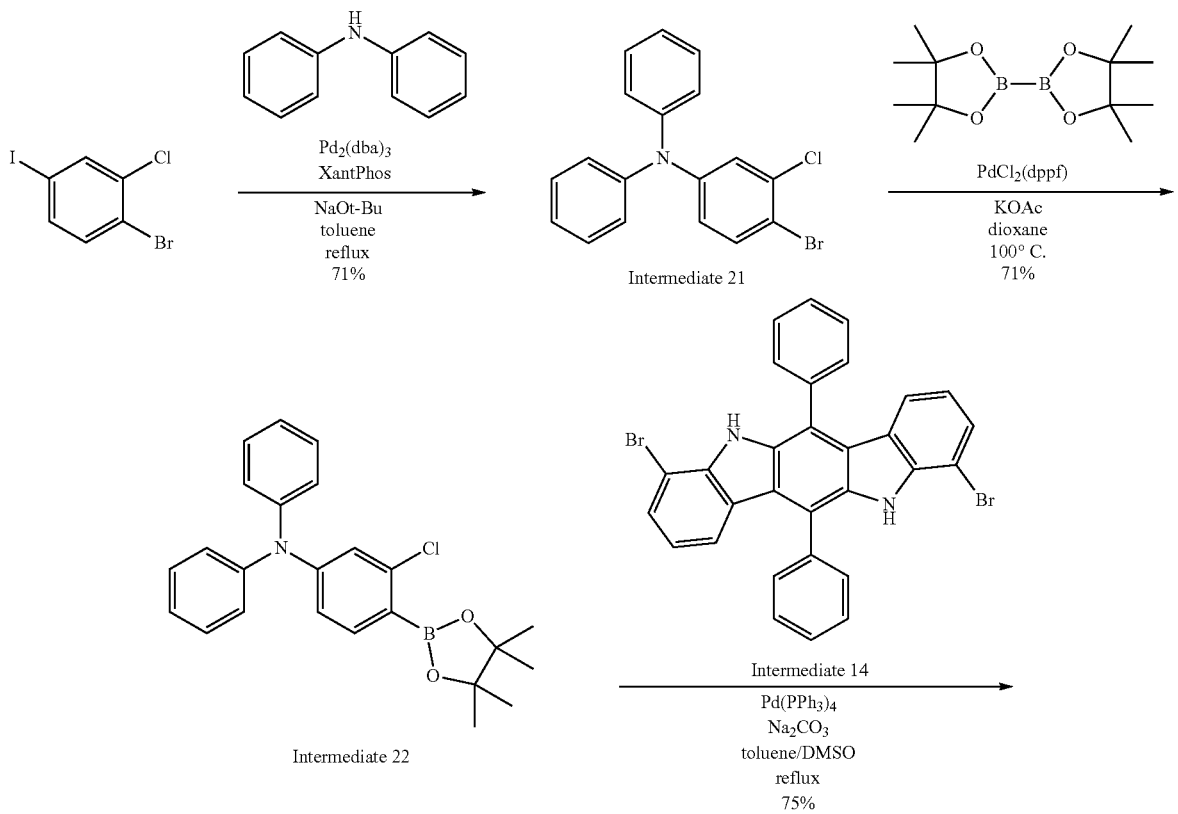

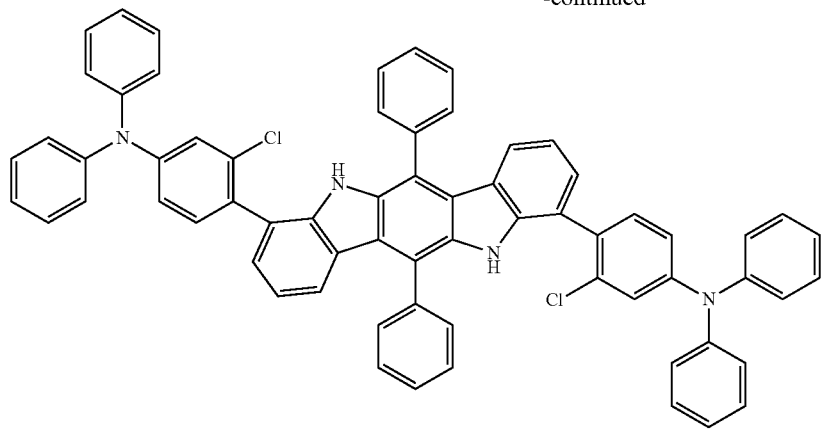

Intermediate 23

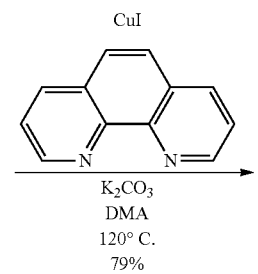

K₂CO₃
DMA
120° C.
79%

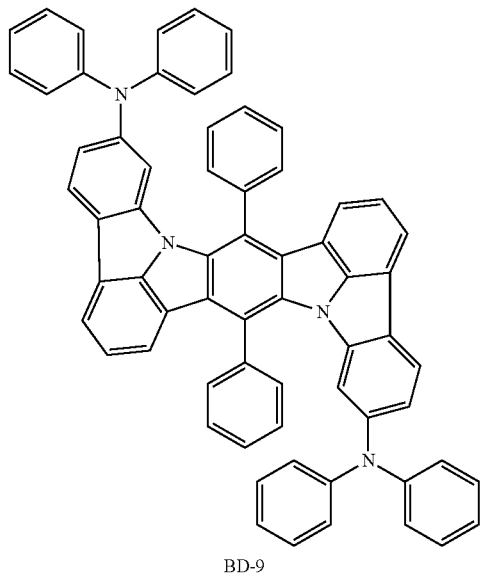 [SMILES: c1ccc(-c2c3c4cccc5c6ccc(N(c7ccccc7)c7ccccc7)cc6n(c3c(-c3ccccc3)c3c6cccc7c8ccc(N(c9ccccc9)c9ccccc9)cc8n(c23)c76)c54)cc1 ; "BD-9"]

BD-9

Synthesis of Intermediate 21

Under an argon atmosphere, 1-bromo-2-chloro-4-iodo-benzene (17.0 g, 53.6 mmol), diphenyl amine (9.07 g, 53.6 mmol), Pd$_2$(dba)$_3$ (981 mg, 1.07 mmol), 4,5'-bis(diphenylphosphino)-9,9'-dimethylxanthene (XantPhos, 1.24 g, 2.14 mmol), and NaOt-Bu (5.15 g, 53.6 mmol) were refluxed in toluene (500 mL) for 8 hours. After completion of the reaction, the mixture was filtered through celite, and concentrated. The obtained residue was purified by silica gel column chromatography, whereby a white solid was obtained (13.6 g, yield: 71%). The obtained solid was Intermediate 21, which is an intended product, and by mass spectrum analysis, it was confirmed that it had an m/e value of 359 with respect to a molecular weight of 358.6.

Synthesis of Intermediate 22

Under an argon atmosphere, Intermediate 21 (13.6 g, 38.0 mmol), bis(pinacolato)diboron (19.3 g, 76.0 mmol), PdCl$_2$(dppf) (621 mg, 0.761 mmol), and potassium acetate (7.46 g, 76 mmol) were suspended in dioxane (400 mL) and refluxed for 7 hours. After completion of the reaction, the solvent was concentrated by passing through short pass silica gel column chromatography. The obtained solid was washed with methanol, whereby a white solid was obtained (18.5 mg, yield: 71%). The obtained solid was Intermediate 22, which is an intended product, and by mass spectrum analysis, it was confirmed that it had an m/e value of 406 with respect to a molecular weight of 405.7.

Synthesis of Intermediate 23

Under an argon atmosphere, dibromo-modification (Intermediate 14) (5.00 g, 8.83 mmol), a boronic acid ester (Intermediate 22) (10.8 g, 26.5 mmol), and Pd(PPh$_3$)$_4$ (1.02 g, 0.883 mmol) were dissolved in toluene (250 mL) and dimethylsulfoxide (500 mL), and 2 M Na$_2$CO$_3$ (130 mL) was added thereto, and the mixture was stirred with heating at 100° C. for 6 hours. After completion of the reaction, the solvent was concentrated by passing through short pass silica gel column chromatography. The obtained residue was washed with ethyl acetate and toluene, whereby a yellow solid was obtained (6.39 g, yield: 75%). The obtained solid was Intermediate 23, which is an intended product, and by mass spectrum analysis, it was confirmed that it had an m/e value of 965 with respect to a molecular weight of 964.0.

Synthesis of BD-9

Under argon atmosphere, Intermediate 23 (6.24 g, 6.47 mmol), copper(I) iodide (1.48 g, 7.77 mmol), 1,10-phenanthroline (1.40 g, 7.77 mmol), and potassium carbonate (7.16 g, 51.8 mmol) were suspended in N,N-dimethylacetamide (1.2 L), and the mixture was stirred with heating at 120° C. for 15 hours. After completion of the reaction, the solvent was concentrated by passing through short pass silica gel column chromatography. The obtained residue was recrystallized with chlorobenzene and washed with toluene and methanol, whereby a yellow solid was obtained (4.54 g, yield: 79%). The obtained solid was BD-9, which is an intended product, and by mass spectrum analysis, it was confirmed that it had an m/e value of 892 with respect to a molecular weight of 891.1.

Example 2-9

Compound BD-10 was synthesized by the following synthesis route.

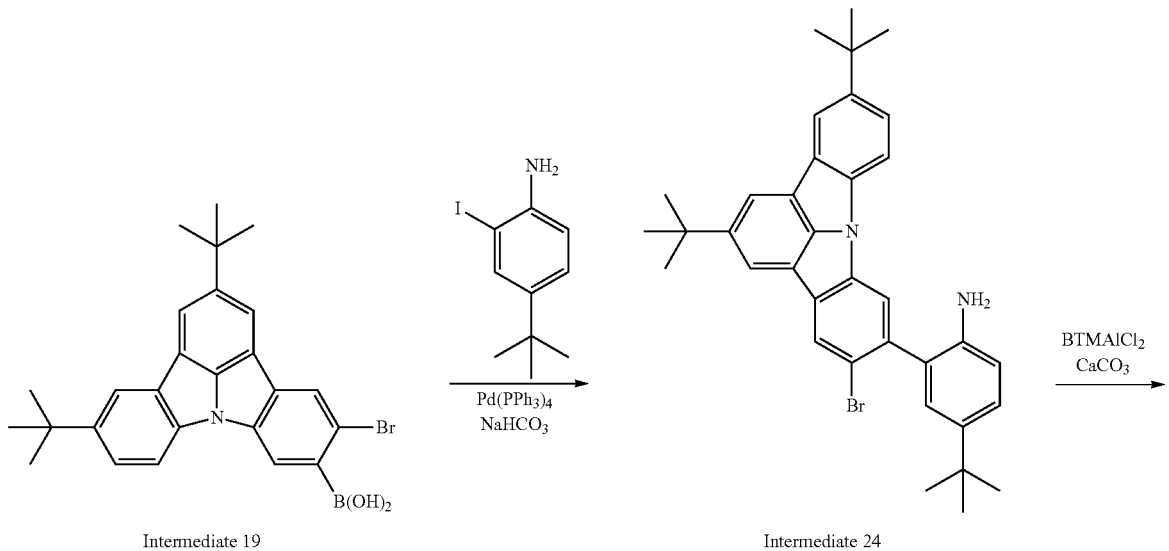

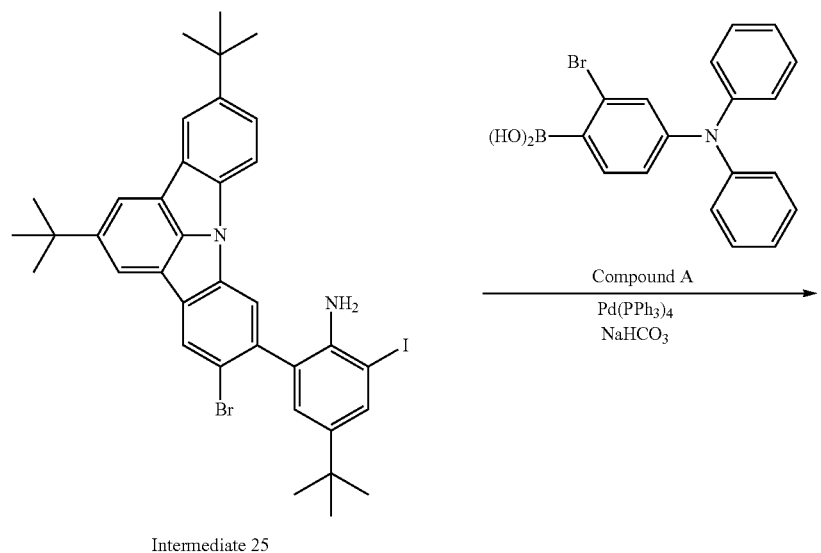

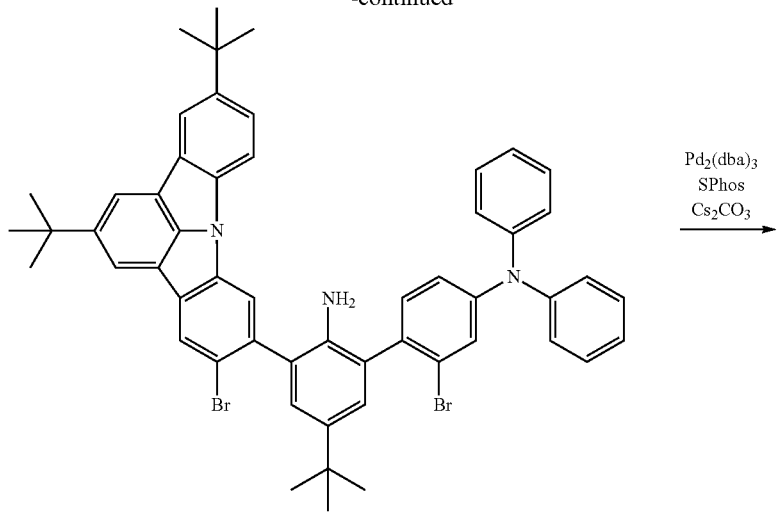

Intermediate 26

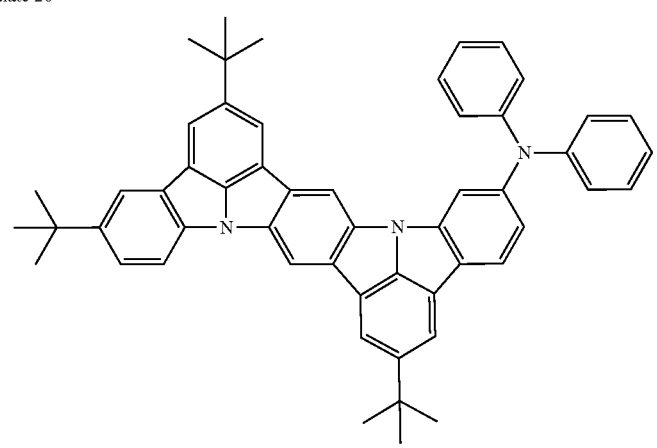

BD-10

Synthesis of Intermediate 24

Under an argon atmosphere, 4-tert-butyl-2-iodoaniline (2.00 g, 7.27 mmol), Intermediate 19 (3.00 g, 6.30 mmol), Pd (PPh$_3$)$_4$ (420 mg, 0.364 mmol), and sodium hydrogen carbonate (1.90 g, 22.6 mmol) were dissolved in dimethoxyethane (40 mL) and water (20 mL), and the mixture was stirred with heating at 80° C. for 10 hours. After completion of the reaction, the mixture was extracted with methylene chloride, and the organic phase was dried with magnesium sulfate. The solid was removed by filtration, and the solvent was distilled off. The obtained residue was purified by column chromatography, whereby obtaining a white solid (2.95 g, yield: 81%). The obtained solid was Intermediate 24, which is an intended product, and by mass spectrum analysis, it was confirmed that it had an m/e value of 580 with respect to a molecular weight of 579.6.

Synthesis of Intermediate 25

Intermediate 24 (2.95 g, 5.09 mmol) was dissolved in methylene chloride (50 mL) and methanol (20 mL), and calcium carbonate (0.80 g, 8.0 mmol) and benzyltrimethylammonium dichloro iodide (1.80 g, 5.17 mmol) were added with stirring, and the mixture was stirred at room temperature for 10 hours. After completion of the reaction, a saturated aqueous sodium thiosulfate solution was added, the mixture was slightly stirred, and then extracted with methylene chloride. The organic phase was concentrated and the obtained solid was purified by column chromatography, whereby obtaining a white solid (3.16 g, yield: 88%). The obtained solid was Intermediate 25, which is an intended product, and by mass spectrum analysis, it was confirmed that it had an m/e value of 706 with respect to a molecular weight of 705.5.

Synthesis of Intermediate 26

Under an argon atmosphere, iodine intermediate (Intermediate 25) (3.16 g, 4.48 mmol), boronic acid compound A (2.00 g, 5.43 mmol), Pd(PPh$_3$)$_4$ (260 mg, 0.225 mmol), and sodium hydrogen carbonate (1.60 g, 19.1 mmol) were dissolved in dimethoxyethane (40 mL) and water (20 mL), and the mixture was stirred with heating at 80° C. for 10 hours. After completion of the reaction, extraction was performed with methylene chloride, and the organic phase was dried over magnesium sulfate. The solid was removed by filtration, and the solvent was distilled off. The obtained residue was purified by column chromatography, whereby obtaining a yellow solid (3.93 g, yield 97%). The obtained solid was Intermediate 26, which is an intended product, and by mass spectrum analysis, it was confirmed that it had an m/e value of 902 with respect to a molecular weight of 901.8.

Synthesis of BD-10

Under argon atmosphere, Intermediate 26 (3.93 g, 2.39 mmol), $Pd_2(dba)_3$ (160 mg, 0.175 mmol), SPhos (290 mg, 0.706 mmol), and cesium carbonate (8.4 g, 26 mmol) were suspended in xylene (360 mL), and the mixture was stirred with heating at 140° C. for 10 hours. After completion of the reaction, the precipitated solid was filtered off and washed with water and methanol. This solid was purified by column chromatography, whereby obtaining a yellow solid (1.35 g, yield: 42%). The obtained solid was BD-10, which is an intended product, and by mass spectrum analysis, it was confirmed that it had an m/e value of 741 with respect to a molecular weight of 740.0.

Example 2-10

Compound BD-11 was synthesized by the following synthesis route.

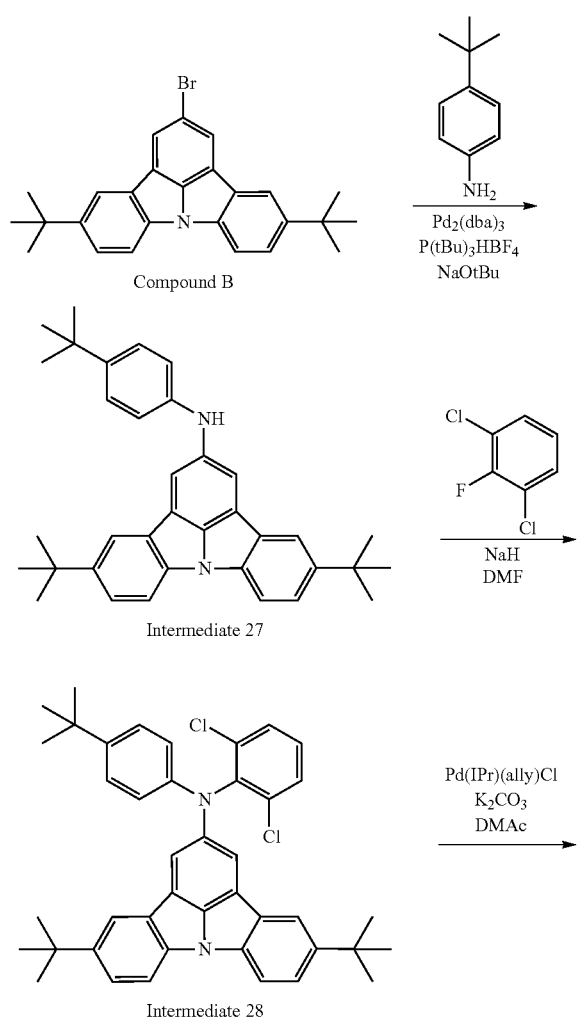

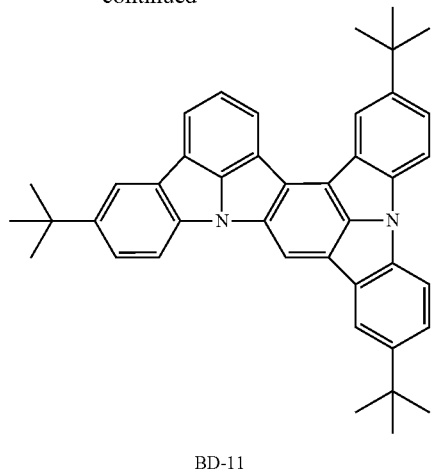

BD-11

Synthesis of Intermediate 27

Under argon atmosphere, Compound B (3.00 g, 6.94 mmol), 4-tert-butyl-aniline (1.20 g, 8.04 mmol), $Pd_2(dba)_3$ (60 mg, 0.066 mmol), tri-tert-butyl phosphonium tetrafluoroborate (80 mg, 0.276 mmol), and sodium tert-butoxide (0.94 g, 9.8 mmol) were suspended in toluene (25 mL), and the mixture was stirred with heating at 100° C. for 10 hours. After completion of the reaction, the mixture was filtered through celite and the solvent was distilled off. The obtained residue was purified by column chromatography, whereby obtaining a yellow solid (3.20 g, yield: 92%). The obtained solid was Intermediate 27, which is an intended product, and by mass spectrum analysis, it was confirmed that it had an m/e value of 508 with respect to a molecular weight of 500.7.

Synthesis of Intermediate 28

Intermediate 27 (3.20 g, 6.39 mmol) was dissolved in N,N-dimethylformamide (20 mL), and about 60% sodium hydride (0.77 g, 19 mmol) dispersed in liquid paraffin was added thereto, and the mixture was stirred for 20 minutes. 1,3-dichloro-2-fluorobenzene (1.6 g, 9.7 mmol) was added to this solution and the mixture was stirred with heating at 50° C. for 10 hours. After completion of the reaction, the precipitated solid was filtered off and washed with methanol. This solid was purified by column chromatography, whereby obtaining a yellow solid (3.44 g, yield: 79%). The obtained solid was Intermediate 28, which is an intended product, and by mass spectrum analysis, it was confirmed that it had an m/e value of 646 with respect to a molecular weight of 645.7.

Synthesis of BD-11

Under argon atmosphere, Intermediate 28 (3.44 g, 5.33 mmol), allyl[1,3-bis(2,6-diisopropylphenyl)imidazol-2-ylidene]chloropalladium (120 mg, 0.210 mmol), and potassium carbonate (2.94 g, 21.5 mmol) were suspended in N,N-dimethylacetamide (30 mL), and the mixture was stirred with heating at 150° C. for 10 hours. After completion of the reaction, water was added and the solid was filtered off. The obtained solid was purified by column chromatography and recrystallization, whereby obtaining a yellow solid (1.87 g, yield 61%). The obtained solid was BD-11, which is an intended product, and by mass spectrum analysis, it was confirmed that it had an m/e value of 573 with respect to a molecular weight of 572.8.

Example 2-11

Compound BD-12 was synthesized by the following synthesis route.

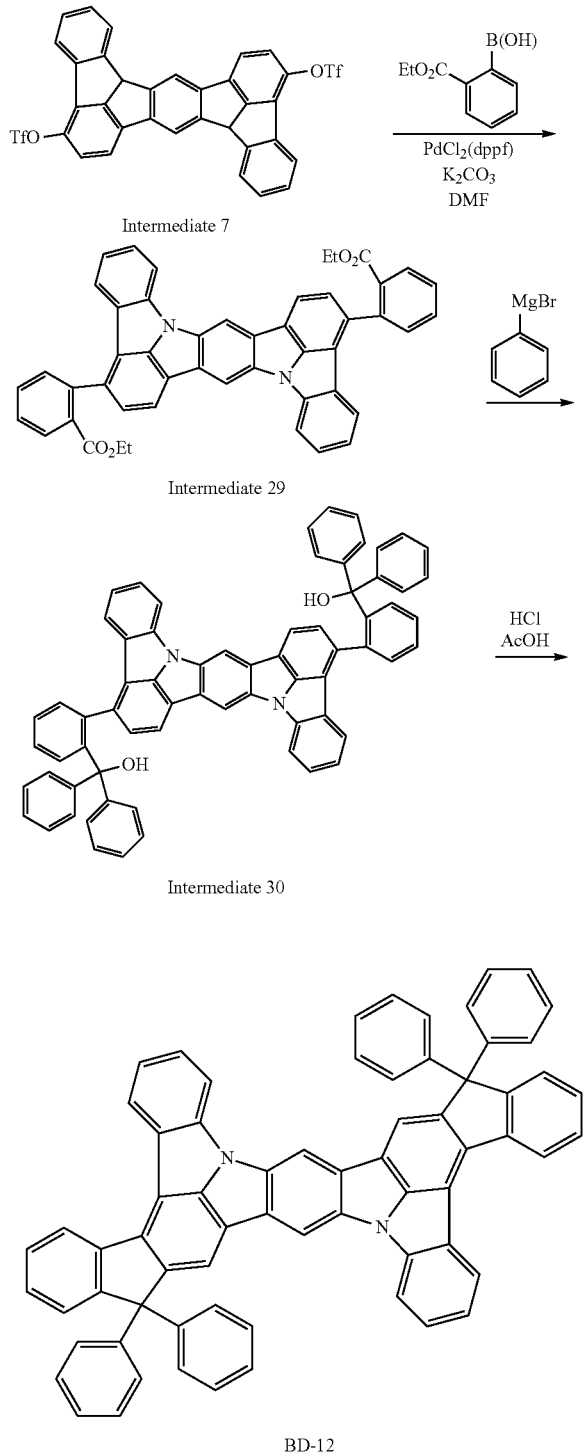

Synthesis of Intermediate 29

Under argon atmosphere, Intermediate 7 (3.00 g, 4.28 mmol), 2-(ethoxycarbonyl) phenylboronic acid (2.50 g, 12.9 mmol), [1,1'-bis(diphenylphosphino)ferrocene]dichloropalladium (157 mg, 0.214 mmol), and potassium carbonate (2.37 g, 17.1 mmol) were suspended in N,N-dimethylformamide (200 mL), and the mixture was stirred with heating at 130° C. for 8 hours. After completion of the reaction, water was added and the precipitate was filtered off and washed with methanol. The obtained solid was purified by column chromatography, whereby obtaining a yellow solid (2.40 g, yield: 80%). The obtained solid was Intermediate 29, which is an intended product, and by mass spectrum analysis, it was confirmed that it had an m/e value of 701 with respect to a molecular weight of 700.8.

Synthesis of Intermediate 30

Under an argon atmosphere, Intermediate 29 (2.35 g, 3.35 mmol) was dissolved in tetrahydrofuran (300 mL), and 1 M phenylmagnesium bromide/THF solution (30 mL, 30 mmol) was added dropwise at 0° C. After completion of the dropwise addition, the mixture was heated to room temperature and stirred for 5 hours. After completion of the reaction, water was added and extraction was performed with ethyl acetate. The organic layer was concentrated and the obtained solid was purified by column chromatography, whereby obtaining a yellow solid (2.10 g, yield: 68%). The obtained solid was Intermediate 30, which is an intended product, and by mass spectrum analysis, it was confirmed that it had an m/e value of 922 with respect to a molecular weight of 921.1.

Synthesis of BD-12

Acetic acid (50 mL) and concentrated hydrochloric acid (3 mL) were added to Intermediate 30 (2.00 g, 2.17 mmol), and the mixture was stirred with heating at 100° C. for 6 hours. After completion of the reaction, water was added and the solid was filtered off. The obtained solid was purified by column chromatography, whereby obtaining a yellow solid (0.82 g, yield 43%). The obtained solid was BD-12, which is an intended product, and by mass spectrum analysis, it was confirmed that it had an m/e value of 886 with respect to a molecular weight of 885.1.

Example 2-12

Compound BD-13 was synthesized by the following synthesis route.

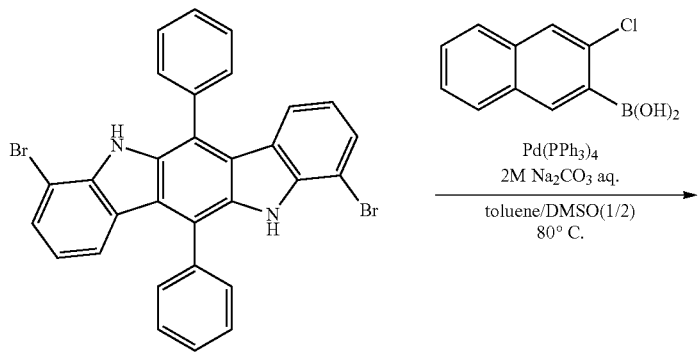

Intermediate 13

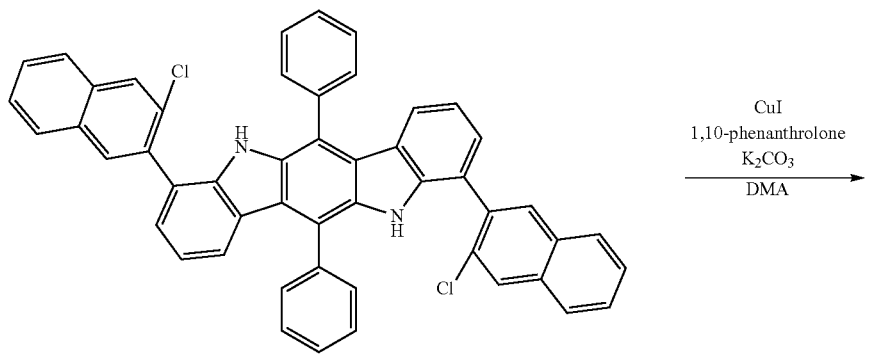

Intermediate 31

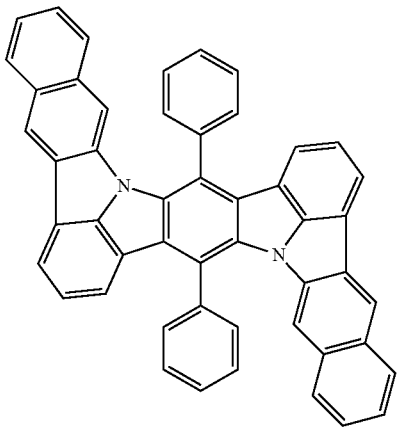

BD-13

Synthesis of Intermediate 31

Under an argon atmosphere, dibromo-modification (Intermediate 13) (500 mg, 0.88 mmol), boronic acid compound C (380 mg, 1.85 mmol), and Pd(PPh$_3$)$_4$ (40 mg, 0.035 mmol) were dissolved in toluene (5 mL) and dimethylsulfoxide (10 mL), and 2 M Na$_2$CO$_3$ (2 mL) was added thereto, and the mixture was stirred with heating at 80° C. for 6 hours. After completion of the reaction, the solvent was concentrated by passing through short pass silica gel column chromatography. The obtained residue was washed with ethyl acetate and toluene, whereby a yellow solid was obtained (320 mg, yield: 50%). The obtained solid was Intermediate 31, which is an intended product, and by mass spectrum analysis, it was confirmed that it had an m/e value of 730 with respect to a molecular weight of 729.7.

Synthesis of BD-13

Under argon atmosphere, Intermediate 31 (300 mg, 0.411 mmol), copper (I) iodide (94 mg, 0.49 mmol), 1,10-phenanthroline (89 mg, 0.49 mmol), and potassium carbonate (450 mg, 3.29 mmol) were suspended in N,N-dimethylacetamide (20 mL), and the mixture was stirred with heating at 120° C. for 15 hours. After completion of the reaction, the solvent was concentrated by passing through short pass silica gel column chromatography. The obtained residue was washed with toluene and methanol, whereby a yellow solid was obtained (148 mg, yield: 55%). The obtained solid was BD-13, which is an intended product, and by mass spectrum analysis, it was confirmed that it had an m/e value of 657 with respect to a molecular weight of 656.8.

Example 2-13
Compound BD-14 was synthesized by the following synthesis route.
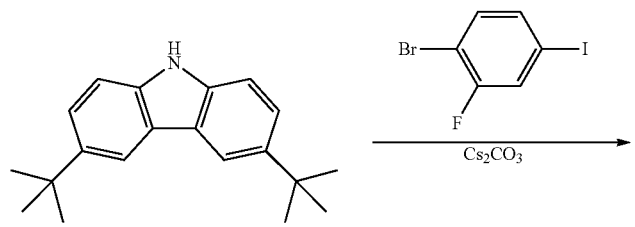
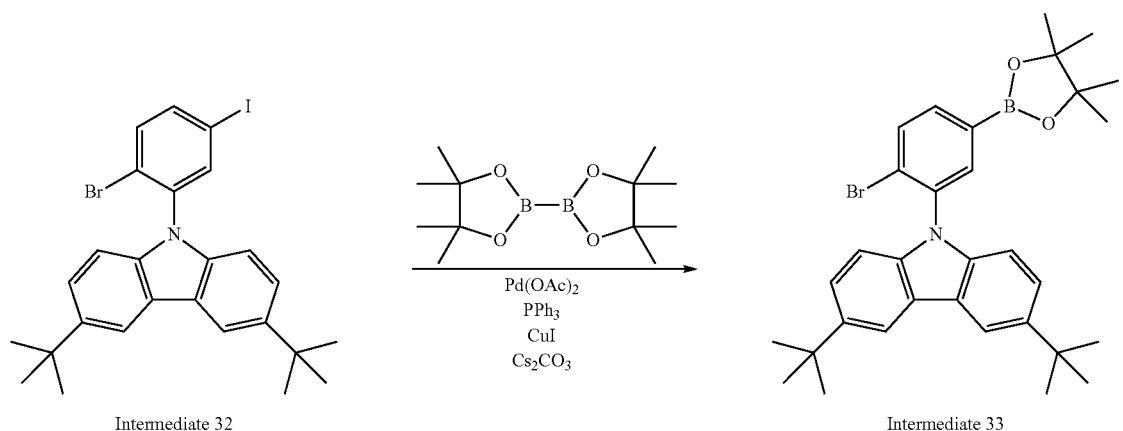
Intermediate 32
Intermediate 33
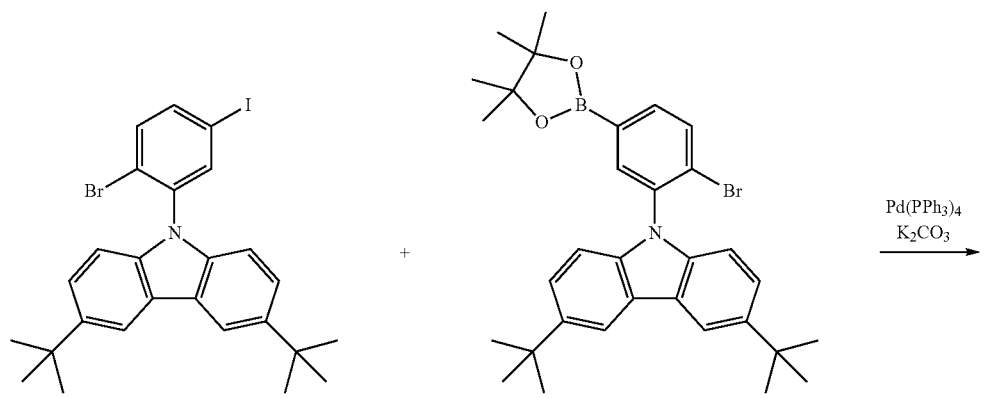
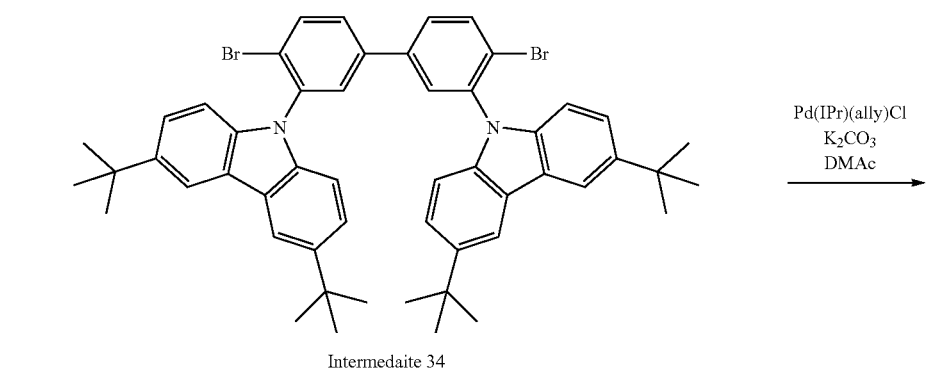
Intermedaite 34

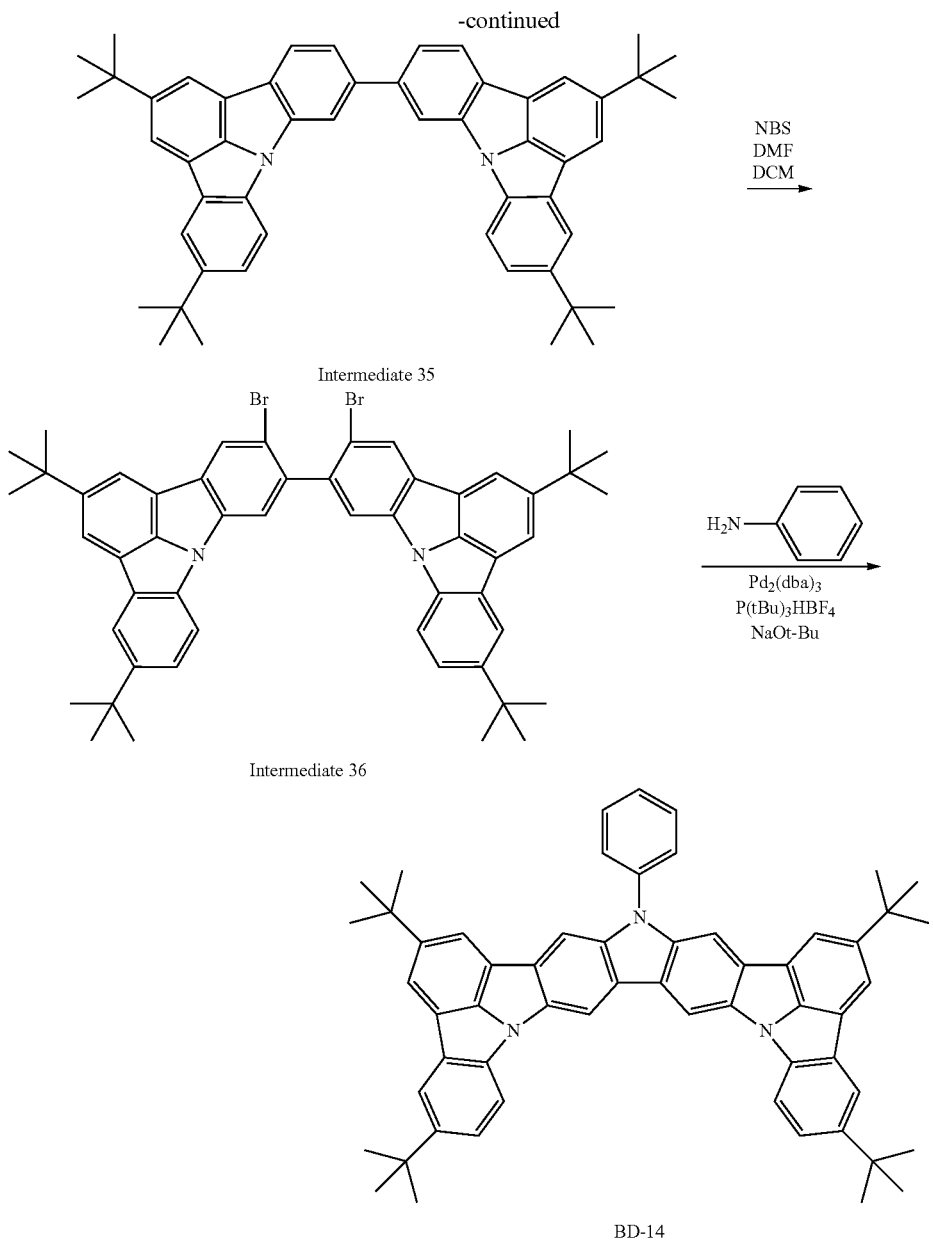

Synthesis of Intermediate 32

Under argon atmosphere, 3,6-di-tert-butyl-9H-carbazole (11.6 g, 41.5 mmol), 1-bromo-2-fluoro-4-iodobenzene (25 g, 83 mmol), and cesium carbonate (27 g, 83 mmol) were suspended in N,N-dimethylformamide (145 mL), and the mixture was stirred with heating at 150° C. for 22 hours. After completion of the reaction, water was added and the precipitate was filtered off. The obtained solid was purified by column chromatography, whereby obtaining a white solid (21.5 g, yield: 92%). The obtained solid was Intermediate 32, which is an intended product, and by mass spectrum analysis, it was confirmed that it had an m/e value of 561 with respect to a molecular weight of 560.3.

Synthesis of Intermediate 33

Under argon atmosphere, Intermediate 32 (5.00 g, 8.92 mmol), bis(pinacolato)diboron (3.40 g, 13.4 mmol), palladium acetate (40 mg, 0.18 mmol), triphenylphosphine (50 mg, 0.19 mmol), copper iodide (0.34 g, 1.79 mmol), and cesium carbonate (4.4 g, 13.5 mmol) were suspended in acetonitrile (50 mL), and the mixture was stirred at room temperature for 20 hours. After completion of the reaction, the mixture was filtered through celite and the solvent was concentrated. The obtained solid was purified by column chromatography, whereby obtaining a white solid (3.84 g, yield: 77%). The obtained solid was Intermediate 33, which is an intended product, and by mass spectrum analysis, it was confirmed that it had an m/e value of 561 with respect to a molecular weight of 560.4.

Synthesis of Intermediate 34

Under an argon atmosphere, iodine intermediate 32 (3.49 g, 6.23 mmol), boronic acid intermediate 33 (3.84 g, 6.85 mmol), Pd(PPh$_3$)$_4$ (360 mg, 0.312 mmol), and potassium carbonate (2.60 g, 18.8 mmol) were dissolved in tetrahydrofuran (90 mL) and water (20 mL), and the mixture was stirred with heating at 80° C. for 10 hours. After completion of the reaction, extraction was performed with methylene chloride, and the organic layer was dried over magnesium sulfate. The solid was removed by filtration, and the solvent was distilled off. The obtained residue was purified by column chromatography, whereby obtaining a white solid (5.33 g, yield 99%). The obtained solid was Intermediate 34, which is an intended product, and by mass spectrum analysis, it was confirmed that it had an m/e value of 867 with respect to a molecular weight of 866.8.

Synthesis of Intermediate 35

Under argon atmosphere, Intermediate 34 (5.33 g, 6.15 mmol), allyl[1,3-bis(2,6-diisopropylphenyl)imidazol-2-ylidene]chloropalladium (140 mg, 0.245 mmol), and potassium carbonate (3.40 g, 24.6 mmol) were suspended in N,N-dimethylacetamide (30 mL), and the mixture was stirred with heating at 130° C. for 11 hours. After completion of the reaction, water was added and the precipitate was filtered off. The obtained solid was purified by column chromatography, whereby obtaining a yellow solid (3.0 g, yield: 69%). The obtained solid was Intermediate 35, which is an intended product, and by mass spectrum analysis, it was confirmed that it had an m/e value of 706 with respect to a molecular weight of 705.0.

Synthesis of Intermediate 36

Intermediate 35 (3.00 g, 4.26 mmol) was dissolved in N,N-dimethylformamide (50 mL) and methylene chloride (150 mL), and N-bromosuccinimide (1.67 g, 9.38 mmol) was added with stirring, and the mixture was stirred at room temperature for 11 hours. After completion of the reaction, methylene chloride was distilled off, and water was added thereto, and the solid was filtered off. The obtained solid was purified by column chromatography, whereby obtaining a white solid (3.51 g, yield: 95%). The obtained solid was Intermediate 36, which is an intended product, and by mass spectrum analysis, it was confirmed that it had an m/e value of 863 with respect to a molecular weight of 862.8.

Synthesis of BD-14

Under argon atmosphere, Intermediate 36 (3.50 g, 4.06 mmol), $Pd_2(dba)_3$ (190 mg, 0.207 mmol), tri-tert-butylphosphonium tetrafluoroborate (240 mg, 0.828 mmol), and sodium tert-butoxide (1.56 g, 16.3 mmol) were suspended in toluene (40 mL), and aniline (0.37 mL, 4.1 mmol) was added thereto. The mixture was stirred with heating at 80° C. for 22 hours. After completion of the reaction, the precipitated solid was filtered and washed with toluene and methanol, whereby obtaining a yellow solid (2.46 g, yield: 76%). The obtained solid was BD-14, which is an intended product, and by mass spectrum analysis, it was confirmed that it had an m/e value of 795 with respect to a molecular weight of 794.1.

Several embodiments and/or examples of the present invention have been described in detail above. However, without substantially departing from novel teachings and effects of the present invention, the person skilled in the art can readily make a number of modifications to the embodiments and/or examples which are exemplifications of these teachings and effects. Thus, these modifications are included in the scope of the present invention.

The documents described in this specification and the contents of the application that serves as the basis of priority claim under Paris convention are incorporated herein by reference in its entirety.

The invention claimed is:

1. A compound represented by a formula selected from the group consisting of the following formulas (3), (4), (5), (6-2) to (6-4) and (6-8) to (6-10):

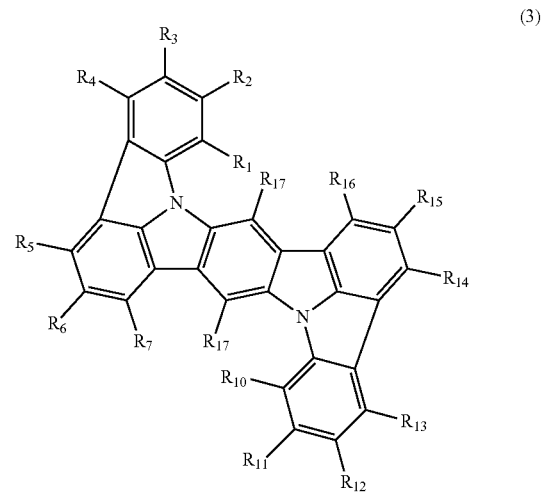

(3)

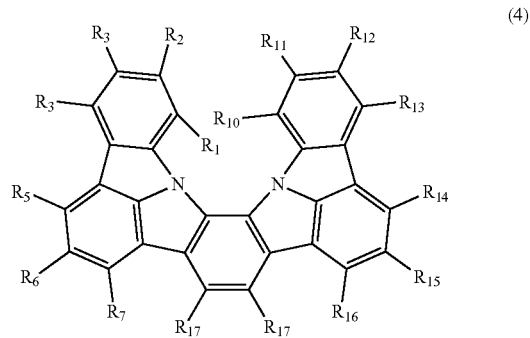

(4)

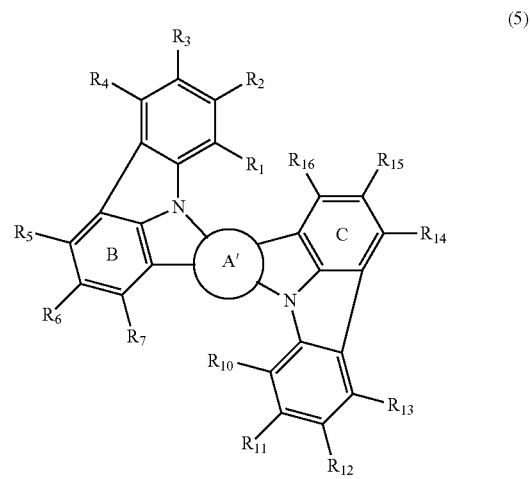

(5)

(6-2)

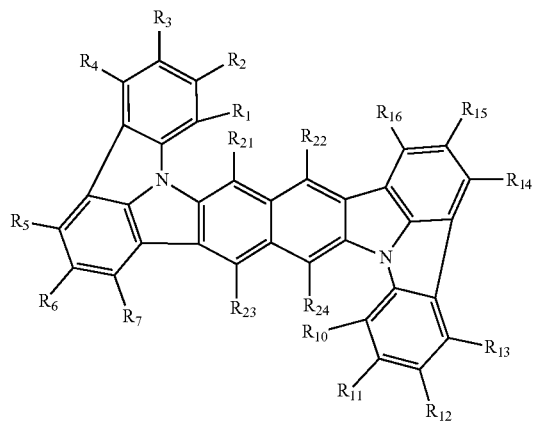

(6-3)

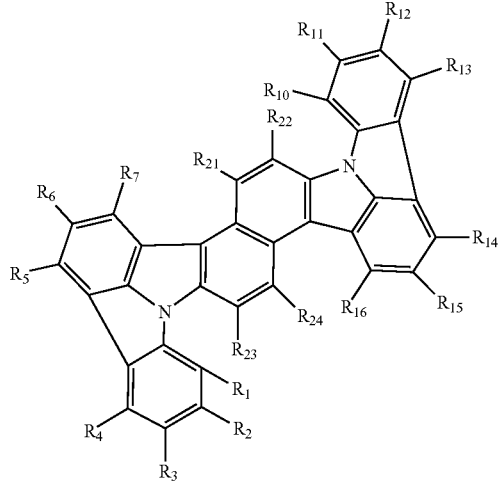

(6-4)

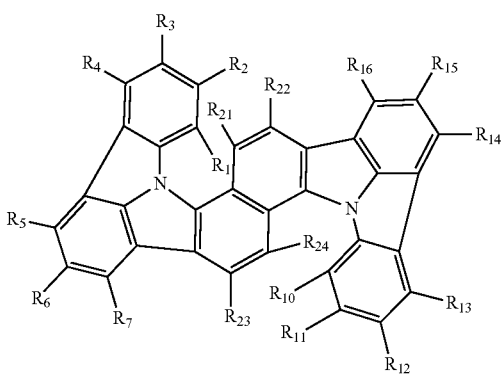

(6-8)

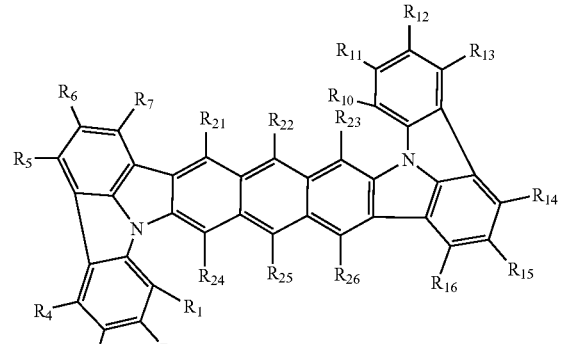

(6-9)

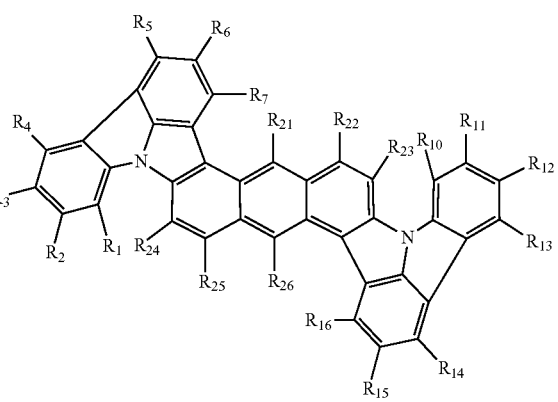

(6-10)

wherein in the formulas (3), (4), (5), (6-2) to (6-4) and (6-8) to (6-10), the ring A' is a substituted or unsubstituted fused heterocycle including 8 to 50 ring atoms;

one or more pairs of adjacent two or more of $R_1$ to $R_7$, $R_{10}$ to $R_{16}$ and $R_{21}$ to $R_{26}$ may form a substituted or unsubstituted, saturated or unsaturated ring;

$R_1$ to $R_7$, $R_{10}$ to $R_{16}$ and $R_{21}$ to $R_{26}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;

$R_{17}$ is a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms;

two $R_{17}$s may be the same as or different from each other;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms or a substituted or unsubstituted monovalent heterocyclic group including 5 to 50 ring atoms; and when a plurality of each of $R_{31}$ to $R_{37}$ is present, the plurality of each of $R_{31}$s to $R_{37}$s may be the same as or different from each other.

2. The compound according to claim 1, being selected from the group consisting of compounds represented by the following formulas (6-1) to (6-6):

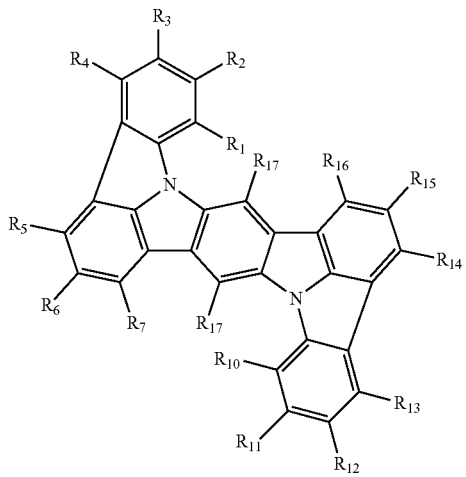

(6-1)

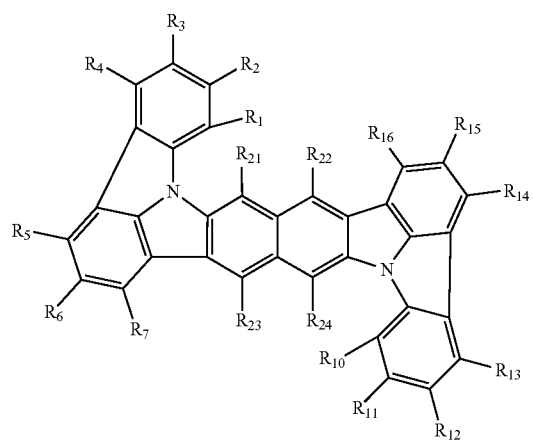

(6-2)

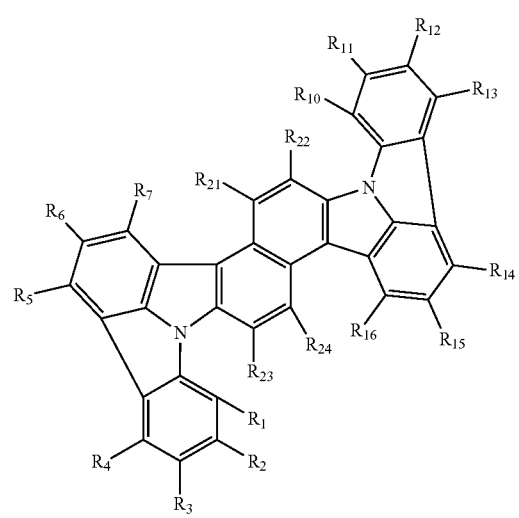

(6-3)

-continued

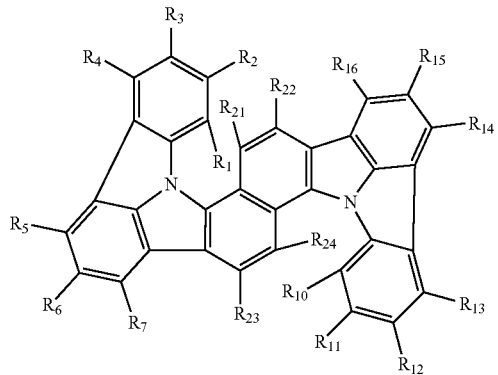

(6-4)

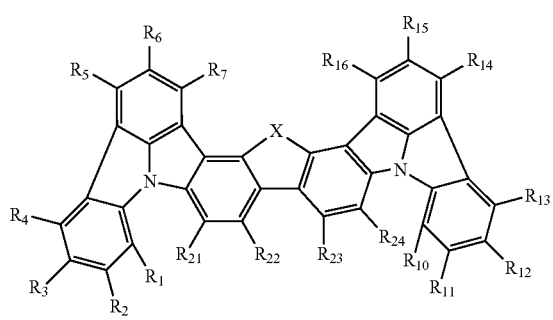

(6-5)

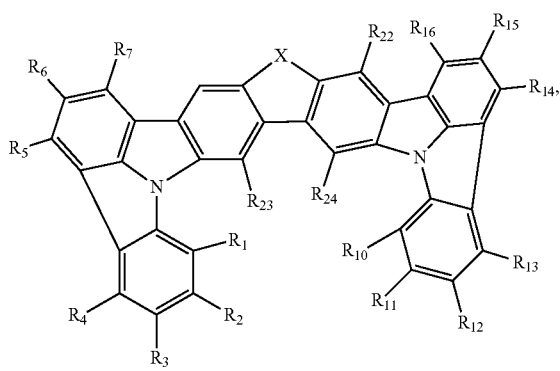

(6-6)

wherein in the formulas (6-1) to (6-6), $R_1$ to $R_7$ and $R_{10}$ to $R_{17}$ are as defined in the formulas (3), (4) and (5);

X is O, $NR_{25}$ or $C(R_{26})(R_{27})$;

one or more pairs of adjacent two or more of $R_{21}$ to $R_{27}$ may form a substituted or unsubstituted, saturated or unsaturated ring;

$R_{21}$ to $R_{27}$ that do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms or a substituted or unsubstituted monovalent heterocyclic group including 5 to 50 ring atoms; and $R_{31}$ to $R_{37}$ are as defined in the formulas (3), (4) and (5).

3. The compound according to claim 1, wherein $R_1$ to $R_7$, $R_{10}$ to $R_{16}$ and $R_{21}$ to $R_{26}$ are independently selected from the group consisting of a hydrogen atom, a substituted or unsubstituted aryl group including 6 to 50 ring carbon atoms and a substituted or unsubstituted heterocyclic group including 5 to 50 ring atoms.

4. The compound according to claim 1, wherein $R_1$ to $R_7$, $R_{10}$ to $R_{16}$ and $R_{21}$ to $R_{26}$ are independently selected from the group consisting of a hydrogen atom, a substituted or unsubstituted aryl group including 6 to 18 ring carbon atoms and a substituted or unsubstituted heterocyclic group including 5 to 18 ring atoms.

5. The compound according to claim 1, wherein a substituent in the "substituted or unsubstituted" is selected from the group consisting of an alkyl group including 1 to 50 carbon atoms, a haloalkyl group including 1 to 50 carbon atoms, a alkenyl group including 2 to 50 carbon atoms, a alkynyl group including 2 to 50 carbon atoms, a cycloalkyl group including 3 to 50 ring carbon atoms, a alkoxy group including 1 to 50 carbon atoms, a alkylthio group including 1 to 50 carbon atoms, a aryloxy group including 6 to 50 ring carbon atoms, a arylthio group including 6 to 50 ring carbon atoms, a aralkyl group including 7 to 50 carbon atoms, —Si($R_{41}$)($R_{42}$)($R_{43}$), —C(=O)$R_{44}$, —COO$R_{45}$, —S(=O)$_2$$R_{46}$, —P(=O)($R_{47}$)($R_{48}$), —Ge($R_{49}$)($R_{50}$)($R_{51}$), —N($R_{52}$)($R_{53}$), a hydroxyl group, a halogen atom, a cyano group, a nitro group, an aryl group including 6 to 50 ring carbon atoms, and a monovalent heterocyclic group including 5 to 50 ring atoms;

$R_{41}$ to $R_{53}$ are independently a hydrogen atom, an alkyl group including 1 to 50 carbon atoms, an aryl group including 6 to 50 ring carbon atoms or a monovalent heterocyclic group including 5 to 50 ring atoms; and when a plurality of each of $R_{41}$s to $R_{53}$s is present, the plurality of each of $R_{41}$s is to $R_{53s}$ may be the same as or different from each other.

6. The compound according to claim 1, wherein a substituent in the "substituted or unsubstituted" is an alkyl group including 1 to 50 carbon atoms, an aryl group including 6 to 50 ring carbon atoms, or a monovalent heterocyclic group including 5 to 50 ring atoms.

7. The compound according to claim 1, wherein a substituent in the "substituted or unsubstituted" is an alkyl group including 1 to 18 carbon atoms, an aryl group including 6 to 18 ring carbon atoms, or a monovalent heterocyclic group including 5 to 18 ring atoms.

8. A compound represented by the following formula (3-13):

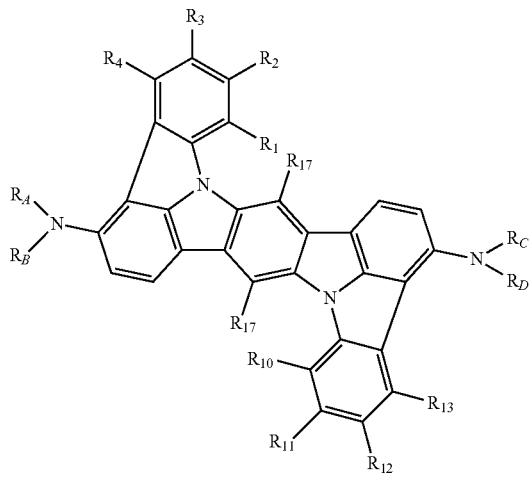

(3-13)

wherein in the formula (3-13),
one or more pairs of adjacent two or more of $R_1$ to $R_4$ and $R_{10}$ to $R_{13}$ may form a substituted or unsubstituted, saturated or unsaturated ring;

$R_1$ to $R_4$, and $R_{10}$ to $R_{13}$ that do not form the substituted or unsubstituted, saturated or unsaturated ring are independently a hydrogen atom, a substituted or unsubstituted aryl group including 6 to 18 ring carbon atoms or a substituted or unsubstituted monovalent heterocyclic group including 5 to 18 ring atoms; and $R_A$, $R_B$, $R_C$ and $R_D$ are independently a substituted or unsubstituted phenyl group; and two $R_{17}$s are hydrogen atoms.

9. A material for an organic electroluminescence device comprising the compound according to claim 1.

10. An organic electroluminescence device comprising:
a cathode,
an anode, and
at least one organic layer disposed between the cathode and the anode, wherein
at least one layer of the at least one organic layer comprises the compound according to claim 1.

11. An electronic apparatus provided with the organic electroluminescence device according to claim 10.

12. The compound according to claim 1, being selected from the group consisting of compounds represented by the formulas (3), (4), and (5).

13. The compound according to claim 1, being selected from the group consisting of compounds represented by the formulas (3) and (4).

* * * * *

UNITED STATES PATENT AND TRADEMARK OFFICE
CERTIFICATE OF CORRECTION

PATENT NO. : 12,262,634 B2
APPLICATION NO. : 18/079612
DATED : March 25, 2025
INVENTOR(S) : Ryota Takahashi et al.

Page 1 of 2

It is certified that error appears in the above-identified patent and that said Letters Patent is hereby corrected as shown below:

In the Claims

In Claim 1, Column 634, please replace formula drawing (4) with:

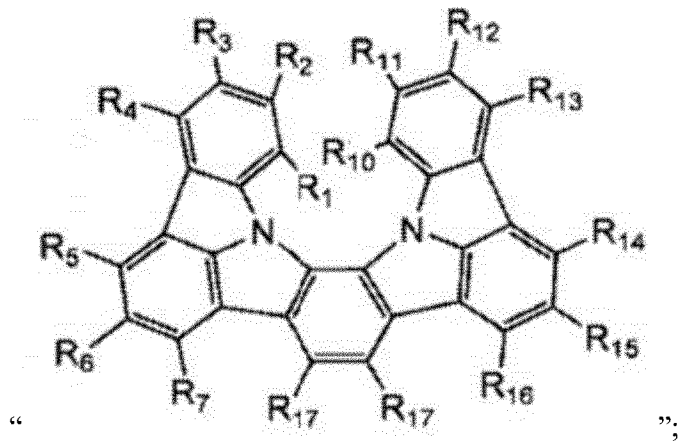
" ";

In Claim 2, Column 639, please replace formula drawing (6-6) with:

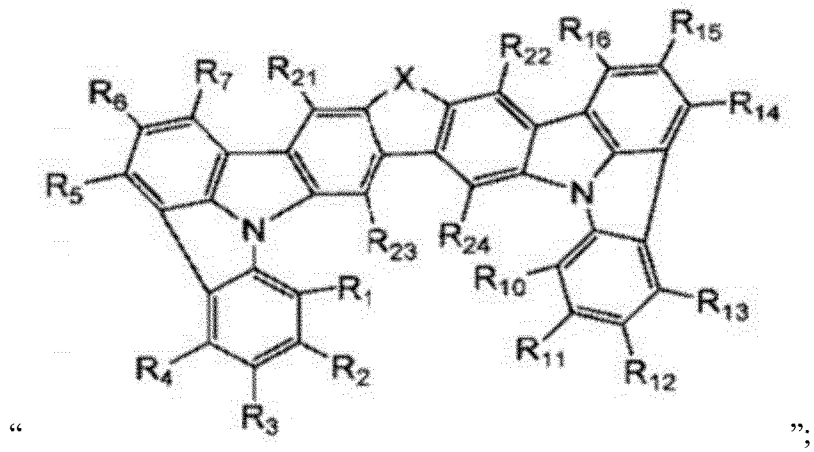
" ";

Signed and Sealed this
Fifteenth Day of July, 2025

Coke Morgan Stewart
*Acting Director of the United States Patent and Trademark Office*

In Claim 5, Column 640, Line 54, please replace "$R_{41s}$ s" with "$R_{41s}$";

In Claim 5, Column 640, Line 55, please replace "$R_{53s}$" with "$R_{53s}$".